United States Patent
O'Neill et al.

(10) Patent No.: US 11,819,476 B2
(45) Date of Patent: Nov. 21, 2023

(54) RAPAMYCIN ANALOGS AND USES THEREOF

(71) Applicant: Janssen Pharmaceutica NV, Beerse (BE)

(72) Inventors: David John O'Neill, Arlington, MA (US); Eddine Saiah, Brookline, MA (US); Seong Woo Anthony Kang, Somerville, MA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/111,674

(22) Filed: Dec. 4, 2020

(65) Prior Publication Data
US 2021/0186935 A1    Jun. 24, 2021

Related U.S. Application Data

(60) Provisional application No. 62/944,166, filed on Dec. 5, 2019.

(51) Int. Cl.
| | | |
|---|---|---|
| C07D 498/18 | (2006.01) | |
| A61K 31/436 | (2006.01) | |
| A61K 31/4985 | (2006.01) | |
| C07D 519/00 | (2006.01) | |

(52) U.S. Cl.
CPC ........ A61K 31/436 (2013.01); A61K 31/4985 (2013.01); C07D 498/18 (2013.01); C07D 519/00 (2013.01)

(58) Field of Classification Search
CPC .......................... C07D 498/18; A61K 31/436
USPC ........................................ 540/456; 514/392
See application file for complete search history.

(56) References Cited

U.S. PATENT DOCUMENTS

| | | | |
|---|---|---|---|
| 5,362,735 A | 11/1994 | Luengo | |
| 5,583,139 A | 12/1996 | Or et al. | |
| 5,639,600 A | 6/1997 | McGrath et al. | |
| 5,728,710 A | 3/1998 | Luengo | |
| 5,912,253 A | 6/1999 | Cottens et al. | |
| 5,922,730 A | 7/1999 | Hu et al. | |
| 6,342,507 B1 | 1/2002 | Naicker et al. | |
| 6,552,065 B2 | 4/2003 | Remiszewski et al. | |
| 7,067,526 B1 | 6/2006 | Yang et al. | |
| 7,087,648 B1 | 8/2006 | McGrath | |
| 7,390,799 B2 | 6/2008 | Bruncko et al. | |
| 8,138,347 B2 | 3/2012 | Knight et al. | |
| 10,117,945 B2 | 11/2018 | Shokat et al. | |
| 10,683,308 B2 * | 6/2020 | Saiah .................. | C07D 498/18 |
| 10,980,784 B2 | 4/2021 | Salah et al. | |
| 2005/0131008 A1 | 6/2005 | Betts et al. | |
| 2006/0025356 A1 | 2/2006 | Yang et al. | |
| 2006/0189551 A1 | 8/2006 | Heitman et al. | |
| 2007/0203168 A1 | 8/2007 | Zhao | |
| 2008/0188511 A1 | 8/2008 | Beckmann et al. | |
| 2010/0305093 A1 | 12/2010 | Anand et al. | |
| 2012/0232011 A1 | 9/2012 | Kneissel et al. | |
| 2013/0184661 A1 | 7/2013 | Beaton et al. | |
| 2014/0271897 A1 | 9/2014 | Pathak | |
| 2016/0008367 A1 | 1/2016 | Borland et al. | |
| 2016/0279108 A1 | 9/2016 | Forrest et al. | |
| 2019/0031683 A1 * | 1/2019 | Saiah .................. | C07D 498/18 |
| 2019/0388401 A1 | 12/2019 | Saiah et al. | |

FOREIGN PATENT DOCUMENTS

| | | | | |
|---|---|---|---|---|
| CA | 2257803 A1 | 1/1998 | | |
| CN | 1087913 A | 6/1994 | | |
| CN | 1137797 A | 12/1996 | | |
| ES | 2527530 T3 | 1/2015 | | |
| JP | 07-509246 A | 10/1995 | | |
| JP | 09-505299 A | 5/1997 | | |
| JP | 09-506604 A | 6/1997 | | |
| JP | 2002-514165 A | 5/2002 | | |
| JP | 3934705 B2 * | 6/2007 | ............. | A61K 31/71 |
| WO | 94/02136 A1 | 2/1994 | | |

(Continued)

OTHER PUBLICATIONS

Alvero et al., "Targeting the mitochondria activates two independent cell death pathways in ovarian cancer stem cells," Mol. Cancer Ther. 2011;10(8):1385-93.

Apsel et al., "Targeted polypharmacology: discovery of dual inhibitors of tyrosine and phosphoinositide kinases," Nat. Chem. Biol. 2008;4(11):691-699.

Awad et al., "Altered TFEB-mediated lysosomal biogenesis in Gaucher disease iPSC-derived neuronal cells," Hum. Mol. Genet. 2015;24(20):5775-88.

Berge et al., "Pharmaceutical Salts", J. Pharmaceutical Sciences, vol. 66, No. 1, Jan. 1977 (pp. 1-19).

Bonne and Quijano-Roy, "Emery-Dreifuss muscular dystrophy, laminopathies, and other nuclear envelopathies," Handb. Clin. Neurol. 2013;113:1367-76.

(Continued)

*Primary Examiner* — Jeffrey H Murray
(74) *Attorney, Agent, or Firm* — BakerHostetler

(57) ABSTRACT

The present invention provides compounds of formula I, compositions thereof, and methods of using the same as mTORC1 inhibitors.

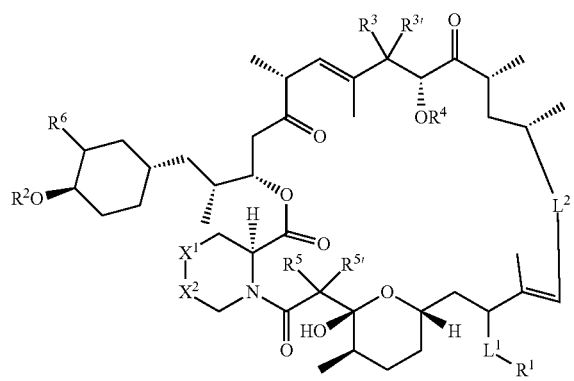

12 Claims, 2 Drawing Sheets

(56) References Cited

FOREIGN PATENT DOCUMENTS

| WO | 94/11380 A1 | 5/1994 |
|---|---|---|
| WO | 94/25072 A1 | 11/1994 |
| WO | WO-1995014023 A1 | 5/1995 |
| WO | WO-1995016691 A1 | 6/1995 |
| WO | 96/41807 A1 | 12/1996 |
| WO | WO-1996041865 A1 | 12/1996 |
| WO | 98/09970 A2 | 3/1998 |
| WO | 2001/014387 A1 | 3/2001 |
| WO | 01/23395 A2 | 4/2001 |
| WO | WO-2001042246 A2 | 6/2001 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006078846 A1 | 7/2006 |
| WO | WO-2006122806 A2 | 11/2006 |
| WO | WO-2007016176 A2 | 2/2007 |
| WO | WO-2007044729 A2 | 4/2007 |
| WO | WO-2007044813 A1 | 4/2007 |
| WO | WO-2007053452 A1 | 5/2007 |
| WO | WO-2007061737 A2 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2007133249 A2 | 11/2007 |
| WO | WO-2007136940 A2 | 11/2007 |
| WO | WO-2008014446 A2 | 1/2008 |
| WO | WO-2008032162 A1 | 3/2008 |
| WO | WO-2008039218 A2 | 4/2008 |
| WO | WO-2008070740 A1 | 6/2008 |
| WO | WO-2008109943 A1 | 9/2008 |
| WO | WO-2008110491 A2 | 9/2008 |
| WO | WO-2008118802 A1 | 10/2008 |
| WO | WO-2009114512 A1 | 9/2009 |
| WO | 2009/122176 A2 | 10/2009 |
| WO | WO-2009143313 A1 | 11/2009 |
| WO | WO-2009153597 A2 | 12/2009 |
| WO | WO-2010062571 A1 | 6/2010 |
| WO | WO-2010106211 A1 | 9/2010 |
| WO | WO-2010110685 A2 | 9/2010 |
| WO | WO-2010114484 A1 | 10/2010 |
| WO | WO-2011090760 A1 | 7/2011 |
| WO | WO-2012007926 A1 | 1/2012 |
| WO | WO-2012097039 A1 | 7/2012 |
| WO | WO-2015051043 A1 | 4/2015 |
| WO | 2015116904 A1 | 8/2015 |
| WO | WO-2017044720 A1 | 3/2017 |
| WO | 2018/204416 A1 | 11/2018 |
| WO | WO 2019/064182 A1 | 4/2019 |
| WO | WO-2020076738 A2 | 4/2020 |
| WO | WO 2020/128861 A1 | 6/2020 |
| WO | WO-2020154447 A1 | 7/2020 |
| WO | WO 2020/194209 A1 | 10/2020 |
| WO | WO 2021/195599 A1 | 9/2021 |
| WO | WO 2022/020522 A2 | 1/2022 |
| WO | WO 2022/020522 A3 | 1/2022 |

OTHER PUBLICATIONS

Chang et al., "Novel phosphoinositide 3-kinase/mTOR dual inhibitor, NVP-BGT226, displays potent growth-inhibitory activity against human head and neck cancer cells in vitro and in vivo," Clin. Cancer Res. 2011;17(22):7116-26.
Chen et al., "Rapamycin ameliorates kidney fibrosis by inhibiting the activation of mTOR signaling in interstitial macrophages and myofibroblasts," PLoS One. 2012;7(3):E33626.
Choo et al., "Rapamycin differentially inhibits S6Ks and 4E-BP1 to mediate cell-type-specific repression of mRNA translation," Proc. Natl. Acad. Sci. USA. 2008;105(45):17414-9.

Cortes et al., "Polyglutamine-expanded androgen receptor interferes with TFEB to elicit autophagy defects in SBMA," Nat. Neurosci. 2014;17(9):1180-9.
Decressac et al., "TFEB-mediated autophagy rescues midbrain dopamine neurons from ?-synuclein toxicity," Proc. Natl. Acad. Sci. USA. 2013;110(19):E1817-26.
Di Paolo et al., "Chronic Inhibition of Mammalian Target of Rapamycin Signaling Downregulates Insulin Receptor Substrates 1 and 2 and AKT Activation: A Crossroad between Cancer and Diabetes?" JASN. 2006;17(8):2236-2244.
Di Rosa et al., "Autophagy in Diabetic Retinopathy," Curr. Neuropharmacol. 2016;14(8):810-425.
Eleftheriadis et al., "Differential effects of the two amino acid sensing systems, the GCN2 kinase and the mTOR complex 1, on primary human alloreactive CD4+ T-cells," Int. J. Mol. Med., vol. 37, No. 5, 2016, (pp. 1412-1420).
Feldman et al., "Active-site inhibitors of mTOR target rapamycin-resistant outputs of mTORCI and mTORC2," PLoS Biology, vol. 7, No. 2, Feb. 2009 (13 pages).
Fok et al., "Combined treatment of rapamycin and dietary restriction has a larger effect on the transcriptome and metabolome of liver," Aging Cell, vol. 13, No. 2, Apr. 2014 (pp. 311-319).
Franz and Weiss, "Molecular therapies for tuberous sclerosis and neurofibromatosis," Currently Neurology and Neuroscience Reports, vol. 12, No. 3, Jun. 2012 (pp. 294-301).
Fujii et al., "Insufficient autophagy promotes bronchial epithelial cell senescence in chronic obstructive pulmonary disease," Oncoimmunology. 2012;1(5):630-41.
Garcia-Martinez et al., "Ku-0063794 is a specific inhibitor of the mammalian target of rapamycin (mTOR)," Biochemical Journal, vol. 421, No. 1, Jun. 2009 (pp. 29-42).
Grinfeld et al., "Acid catalyzed functionalization of rapamycin," Tet. Lett. 1994;35(37):6835-38.
Gross et al., "Abstract 4484: AR-mTOR-26—A potent, selective mTORC 1/2 kinase inhibitor for the treatment of malignancy," 101 st Animal Meeting of the American Association of Cancer Research (AACR), Apr. 17-21, 2010, Washington, D.C. (2 pages).
Guertin and Sabatini, "Defining the role of mTOR in cancer," Cancer Cell. 2007;12(1):9-22.
Gupta et al., "Identification of Selective Inhibitors of Cancer Stem Cells by High-Throughput Screening," Cell, vol. 138, No. 4, Aug. 2009 (pp. 645-659).
Howell et al., "A growing role for mTOR in promoting anabolic metabolism," Biochem. Soc. Trans. 2013;41(4):906-12.
Hua et al., "Rapamycin inhibition of eosinophil differentiation attenuates allergic airway inflammation in mice," Respirology, vol. 20, No. 7, Oct. 2015 (pp. 1055-1065).
Ilagen et al., "Emerging role of mTOR in the response to cancer therapeutics," Trends Cancer, vol. 2, No. 5, May 2016 (pp. 241-251).
International Search Report and Written Opinion issued by the United States Patent and Trademark Office as International Searching Authority for International Application No. PCT/US2016/050913, dated Jan. 10, 2017 (9 pages).
International Search Report and Written Opinion issued by the United States Patent and Trademark Office as International Searching Authority for International Application No. PCT/US2019/037507 dated Nov. 13, 2019 (19 pages).
Jacinto et al., "Mammalian TOR complex 2 controls the actin cytoskeleton and is rapamycin insensitive," Nat. Cell Biol. 2004;6(11):1122-8.
Jiang et al., "Rheb/mTORC1 Signaling Promotes Kidney Fibroblast Activation and Fibrosis," Journal of the American Society of Nephrology, vol. 24, No. 7, Jun. 2013 (pp. 1114-1126).
Johnson et al., "MTOR inhibition alleviates mitochondrial disease in a mouse model of Leigh syndrome," Science, vol. 342, No. 6165, 2013 (pp. 1524-1528).
Kaeberlein, "mTOR Inhibition: From Aging to Autism and Beyond," Scientifica, vol. 2013, Oct. 2013 (17 pages).
Kashiyama et al., "Antitumor Activity and Induction of TP53-Dependent Apoptosis toward Ovarian Clear Cell Adenocarcinoma by the Dual Pl3K/mTOR Inhibitor DS-7423," PLoS One, vol. 9, No. 2, Feb. 2014 (12 pages).

(56) References Cited

OTHER PUBLICATIONS

Kennedy et al., "The mechanistic Target of Rapamycin: The grand educTOR of metabolism and aging," Cell Metab. 2016;23(6):990-1003.
Kim et al., "Nutrient regulation of the mTOR complex 1 signaling pathway," Mol. Cells. 2013;35(6):463-73.
Kolosova et al., "Prevention of Age-Related Macular Degeneration-Like Retinopathy by Rapamycin in Rats," Am. J. Path. 2012;181(2):472-7.
Laberge et al., "MTOR regulates the pro-tumorigenic senescence-associated secretory phenotype by promoting IL1A translation," Nature Cell Biology, vol. 17, No. 8, Aug. 2015 (pp. 1049-1061).
Lamming et al., "Rapamycin-induced insulin resistance is mediated by mTORC2 loss and uncoupled from longevity," Science, vol. 335, Mar. 2012 (pp. 1638-1643).
LaPlante and Sabatini, "mTOR Signaling in Growth Control and Disease," Cell, vol. 149, No. 2, Apr. 2012 (pp. 274-293).
Lee et al., "Abstract C270: In vitro and in vivo antitumor activity of DCBCI0901, a potent PI3K/mTORC1/mTORC2 inhibitor," Molecular Cancer Therapeutics, vol. 12, No. 11 (Supp), Nov. 2013 (2 pages).
Li et al., "Rapamycin: one drug, many effects," Cell Metab. 2014;19(3):373-9.
Liberies et al., "Inducible gene expression and protein translocation using nontoxic ligands identified by a mammalian three-hybrd screen," PNAS. 1997; 94(15):7825-7830.
Liu et al., "Characterization of Torin2, an ATP-Competitive Inhibitor of mTOR, ATM, and ATR," Cancer Res. 2013;73(8):2574-86.
Liu et al., "Kinome-wide selectivity profiling of ATP-competitive mammalian target of rapamycin (mTOR) inhibitors and characterization of their binding kinetics," J. Biol. Chem. 2012;287(13):9742-52.
Liu et al., "Rapamycin reduces renal hypoxia, interstitial inflammation and fibrosis in a rat model of unilateral ureteral obstruction," Clinical and Investigative Medicine, vol. 37, No. 3, Jun. 2014 (pp. E142-E153).
Luengo et al., "Structure-activity studies of rapamycin analogs: evidence that the C-7 methoxy group is part of the effector domain and positioned at the FKBP12-FRAP interface," Chem. Biol. 1995;2(7):471-81.
Ma et al., "Rapamycin reduced pulmonary vascular remodelling by inhibiting cell proliferation via Akt/mTOR signalling pathway downregulation in the carotid artery-jugular vein shunt pulmonary hypertension rat model," Interact. Cardiovasc. Thorac. Surg. 2017;25(2):206-11.
Mannick et al., "mTOR inhibition improves immune function in the elderly," Science Translational Medicine, vol. 6, No. 268, Dec. 2014 (8 pages).
Mannick et al., "TORC1 inhibition enhances immune function and reduces infections in the elderly," Sci. Trans. Med. 2018;10(449):eaaq1564.
Medina et al., "Transcriptional Activation of Lysosomal Exocytosis Promotes Cellular Clearance," Developmental Cell, vol. 21, No. 3, Sep. 2011 (pp. 421-430).
Mercer et al., "Exploration of a potent PI3 kinase/mTOR inhibitor as a novel anti-fibrotic agent in IPF," Thorax, vol. 71, No. 8, Aug. 2016 (pp. 701-711).
Miller et al., "322 Poster mTORC1/mTORC2 selective inhibitors: Identification and characterization of novel small molecules with anti-tumor activity," European Journal of Cancer Supplements, vol. 6, No. 12, Oct. 2008 (pp. 102-103).
Mitra et al., "Dual mTOR Inhibition Is Required to Prevent TGF-?-Mediated Fibrosis: Implications for Scleroderma," J Invest Dermatol. 2015;135(11):2873-6.
Mori et al., "The mTOR pathway is highly activated in diabetic nephropathy and rapamycin has a strong therapeutic potential," Biochem. Res. Commun. 2009;384(4):471-5.
Nacarelli et al., "Mitochondrial stress induces cellular senescence in an mTORCI-dependent manner," Free Radical Biology and Medicine, vol. 95, Jun. 2016 (pp. 133-154).

Navarro et al., "Targeting Tumor Mitochondrial Metabolism Overcomes Resistance to Antiangiogenics," Cell Reports, vol. 15, No. 12, Jun. 2016 (pp. 2705-2718).
Okamoto et al., "The Neuroprotective Effect of Rapamycin as a Modulator of the mTOR-NF-?B Axis during Retinal Inflammation," Plos One. 2016;11(1):e0146517.
Pal et al., "mTOR: A Potential Therapeutic Target in Osteoarthritis?" Drugs R&D. 2015;15(1):27-36.
Pastore et al., "Gene transfer of master autophagy regulator TFEB results in clearance of toxic protein and correction of hepatic disease in alpha-1-anti-trypsin deficiency," EMBO Molecular Medicine, vol. 5, No. 3, Mar. 2013 (pp. 397-412).
Patel et al., "Autophagy in Idiopathic Pulmonary Fibrosis," PLoS One, vol. 7, No. 7, Jul. 2012 (pp. E41394).
PCT International Seach Report and Written Opinion from PCT/US2020/063351, dated Mar. 15, 2021.
Pereira et al., "MTOR inhibition with rapamycin causes impaired insulin signalling and glucose uptake in human subcutaneous and omental adipocytes," Mol. Cel.1 Endocrinol. 2012;355(1):96-105.
Polito et al., "Selective clearance of aberrant tau proteins and rescue of neurotoxicity by transcription factor EB," EMBO Molecular Medicine, vol. 6, No. 9, Sep. 2014 (pp. 1142-1160).
Porter et al., "Autophagic dysregulation in glaucomatous trabecular meshwork cells," Biochim. Biophys. Acta. 2014;1852(3):379-85.
Pubchem, Compound Summary for CID 23376689, (1R,9S,12S,15R,16E,18R,21R,23S,24Z,26E,28E,30S,32S,35R)-1,18-Dihydroxy-12-[(2R)-1-[(1S,3R,4R)-4-hydroxy-3-methoxycyclohexyl]propan-2-yl]-19-methoxy-15,17,21,23,29,35-hexamethyl-30-pent-2-ynoxy-11,36-dioxa-4-azatricyclo[30.3.1,04.9]hexatriaconta-16,24,26,28-tetraene-2,3,10,14,20-pentone, Dec. 5, 2007 (4 pages).
Pubchem, Rapamycin, SID 341826803, Sep. 13, 2017 (8pages).
Puri and Chandra, "Autophagy modulation as a potential therapeutic target for liver diseases," Journal of Clinical and Experimental Hepatology, vol. 4, No. 1, Mar. 2014 (pp. 51-59).
Ramos et al., "Rapamycin Reverses Elevated mTORC1 Signaling in Lamin A/C-Deficient Mice, Rescues Cardiac and Skeletal Muscle Function, and Extends Survival," Science Translational Medicine, vol. 4, No. 144, Jul. 2012 (pp. 144ra103).
Sarbassov et al., "Prolonged rapamycin treatment inhibits mTORC2 assembly and Akt/PKB," Molecular Cell, vol. 22, No. 2, Apr. 2006 (pp. 159-168).
Sarbassov et al., "Rictor, a novel binding partner of mTOR, defines a rapamycin-insensitive and raptor-independent pathway that regulates the cytoskeleton," Current Biology, vol. 14, No. 14, Jul. 2004 (pp. 1296-1302).
Sardiello, "Transcription factor EB: from master coordinator of lysosomal pathways to candidate therapeutic target in degenerative storage diseases," Annals of The New York Academy of Sciences, vol. 1371, No. 1, May 2016 (pp. 3-14).
Sciarretta et al., "New Insights Into the Role of mTOR Signaling in the Cardiovascular System," Circ. Res. 2018;122(3):489-505.
Shum et al., "Pharmacological inhibition of S6K1 increases glucose metabolism and Akt signalling in vitro and in diet-induced obese mice," Diabetologia, vol. 59, No. 3, Mar. 2016 (pp. 592-603).
Spampanato et al., "Transcription factor EB (TFEB) is a new therapeutic target for Pompe disease," EMBO Molecular Medicine, vol. 5, No. 5, May 2013 (pp. 691-706).
Syed et al., "Keloid disease can be inhibited by antagonizing excessive mTOR signaling with a novel dual TORC1/2 inhibitor," American Journal of Pathology, vol. 181, No. 5, Nov. 2012 (pp. 1642-1658).
Taveira-Dasilva et al., "Clinical features, epidemiology, and therapy of lymphangioleiomyomatosis," Journal of Clinical Epidemiology, vol. 7, Apr. 2015 (pp. 249-257).
Thoreen et al., "An ATP-competitive mammalian target of rapamycin inhibitor reveals rapamycin-resistant functions of mTORC1," J. Biol. Chem. 2009;284(12):8023-32.
Torres et al., "Prospects for mTOR inhibitor use in patients with polycystic kidney disease and hamartomatous diseases," Clin. J. Am. Soc. Nephrol. 2010;5(7):1312-29.

(56) References Cited

OTHER PUBLICATIONS

Tsunemi et al., "PGC-1a rescues Huntington's disease proteotoxicity by preventing oxidative stress and promoting TFEB function," Science Translational Medicine, vol. 4, No. 142, Jul. 2012 (pp. 142ra97).

Varin et al., "Dual mTORC1/2 inhibition induces anti-proliferative effect in NF1-associated plexiform neurofibroma and malignant peripheral nerve sheath tumor cells," Oncotarget, vol. 7, No. 24, Jan. 2016 (pp. 35753-35767).

Wallace et al., "Abstract B267: AR-mTOR-1: A potent, selective mTORC 1/2 kinase inhibitor for the treatment of malignancy," AACR, International Conference: Molecular Targets and Cancer Therapeutics, Nov. 15-19, 2009, Boston, Massachusetts (2 pages).

Wander et al., "Next-generation mTOR inhibitors in clinical oncology: how pathway complexity informs therapeutic strategy," The Journal of Clinical Investigation, vol. 121, Apr. 2011 (pp. 1231-1241).

Wu et al., "Rapamycin attenuates unilateral ureteral obstruction-induced renal fibrosis," Kidney International, vol. 69, No. 11, Jun. 2006 (pp. 2029-2036).

Yano et al., "Clinical impact of myocardial mTORCI activation in nonischemic dilated cardiomyopathy," Journal of Molecular and Cellular Cardiology, vol. 91, Feb. 2016 (pp. 6-9).

Yu et al., "Biochemical, Cellular, and in vivo Activity of Novel ATP-Competitive and Selective Inhibitors of the Mammalian Target of Rapamycin," Cancer Res. 2009;69(15):6232-6240.

Yu et al., "Rapamycin and Dietary Restriction Induce Metabolically Distinctive Changes in Mouse Liver," The Journals of Gerontology: Series A, vol. 70, No. 4, Apr. 2015 (pp. 410-420).

Zhao and Vollrath, "mTOR pathway activation in age-related retinal disease," Aging. 2011;3(4):346-347.

Zschiedrich et al., "Targeting mTOR Signaling Can Prevent the Progression of FSGS," JASN. 2017;28(7):2144-2157.

Kallen et al., "X-ray Crystal Structure of 28-O-Methylrapamycin complexed with FKBP12: Is the Cyclohexyl Moiety Part of the Effector Domain of Rapamycin?," J. Am. Chem. Soc. 1996; 118(25):5857-5861.

PubChem, Compound Summary for CID 58100814, "(1R,9S,12S, 15R,16E,18R,19R,21R,23S,24E,26E,28E,30S,32S,35R)-1,18-dihydroxy-30-(hydroxymethyl)-12-[(2R)-1-[(1R,3R,4S)-3-(hydroxymethyl)-4-methylcyclohexyl]propan-2-yl]-19-methoxy-15,17,21,23,29,35-hexamethyl-11,36-dioxa-4-azatricyclo[30.3.1. 04,9]hexatriaconta-16,24,26,28-tetraene-2,3,10,14,20-pentone", created Aug. 19, 2012.

"What is polycystic kidney disease ?—NIDDK", https://www.niddk.nih.gov/health-information/kidney-disease/polycystic-kidney-disease/what-is-pkd#, last reviewed Jan. 2017, accessed Apr. 3, 2023, specifically "Can I prevent PKD".

Benjamin et al., "Rapamycin passes the torch: a new generatio11 of mTOR inhibitors", Nature Reviews: Drug Discovery, 2011, 10, 868-880.

Devita et al., Hellman, Principles Of Radiation Therapy, Cancer, In Principles And Practice Of Oncology, Eds., 4th Edition, vol. 1, 1993, pp. 248-275.

Sun et al., "Recent Advances of Curcumin in the Prevention and Treatment of Renal Fibrosis", BioMed Research International, 2017, article ID 2418671, pp. 1-9.

\* cited by examiner

RAPAMYCIN ANALOGS AND USES THEREOF

CROSS REFERENCE TO RELATED APPLICATIONS

This application claims the benefit of U.S. Provisional App. No. 62/944,166, filed on Dec. 5, 2019, the content of which is hereby incorporated by reference.

TECHNICAL FIELD OF THE INVENTION

The present invention relates to compounds and methods useful for modulating mTORC1 activity. The invention also provides pharmaceutically acceptable compositions comprising provided compounds of the present invention and methods of using such compositions in the treatment of various disorders.

BACKGROUND OF THE INVENTION mTOR complex 1 (mTORC1) positively regulates cell growth and proliferation by promoting many anabolic processes, including biosynthesis of proteins, lipids and organelles, and by limiting catabolic processes such as autophagy. Much of the knowledge about mTORC1 function comes from the use of the bacterial macrolide rapamycin. Upon entering the cell, rapamycin binds to FK506-binding protein of 12 kDa (FKBP12) and interacts with the FKBP12-rapamycin binding domain (FRB) of mTOR, thus inhibiting mTORC1 functions (Guertin, D. A. & Sabatini, D. M. Cancer Cell 12(1): 9-22 (2007)). In contrast to its effect on mTORC1, FKBP12-rapamycin cannot physically interact with or acutely inhibit mTOR complex 2 (mTORC2) (Janinto, E. et al., Nat. Cell Bio., 6(11): 1122-8 (2004); Sarbassov, D. D. et al., Curr. Biol. 14(14): 1296-302 (2004)). On the basis of these observations, mTORC1 and mTORC2 have been respectively characterized as the rapamycin-sensitive and rapamycin-insensitive complexes. However, this paradigm might not be entirely accurate, as chronic rapamycin treatment can, in some cases, inhibit mTORC2 activity by blocking its assembly (Sarbassov, D. D. et al., Mol. Cell, 22(2): 159-68 (2006)). In addition, recent reports suggest that important mTORC1 functions are resistant to inhibition by rapamycin (Choo, A. Y. et al., Proc. Natl. Acad. Sci., 105(45): 17414-9 (2008); Feldman, M. E. et al., PLoS Biol., 7(2):e38 (2009); Garcia-Martinez, J. M. et al., Biochem J., 421(1): 29-42 (2009); Thoreen, C. C. et al., J. Biol. Chem., 284(12): 8023-32 (2009)). Therefore, selective inhibition of mTORC1 would enable the treatment of diseases that involve dysregulation of protein synthesis and cellular metabolism. Furthermore, this detailed understanding of regulating mTORC1 activation pathways will permit the discovery of new strategies for regulating abnormal disease processes by modulating mTORC1 activity across its spectrum of function.

Many diseases are associated with abnormal cellular responses triggered by events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

The mechanistic target of rapamycin complex 1 (mTORC1) is a master growth regulator that senses diverse environmental cues, such as growth factors, cellular stresses, and nutrient and energy levels. When activated, mTORC1 phosphorylates substrates that potentiate anabolic processes, such as mRNA translation and lipid synthesis, and limits catabolic ones, such as autophagy. mTORC1 dysregulation occurs in a broad spectrum of diseases, including diabetes, epilepsy, neurodegeneration, immune response, suppressed skeletal muscle growth, and cancer among others (Howell, J. J. et al., Biochem. Soc. Trans., 41: 906-12 (2013); Kim, S. G. et al., Molecular and cells, 35(6): 463-73 (2013); Laplante, M. & Sabatini, D. M., Cell, 149(2): 274-93 (2012)).

Rapamycin was initially discovered as an antifungal metabolite produced by *Streptomyces hygroscopicus* from a soil sample of Easter Island. Subsequently, rapamycin was found to possess immunosuppressive and antiproliferative properties in mammalian cells, spurring an interest in identifying the mode of action of rapamycin. Rapamycin was shown to be a potent inhibitor of S6K1 phosphorylation. Concurrently, the target of rapamycin (TOR) was identified in yeast and animal cells. Rapamycin forms a gain-of-function complex with the 12 kDa FK506-binding protein (FKBP12), and this complex binds and specifically acts as an allosteric inhibitor of mammalian TOR (mTOR, also known as mechanistic TOR) complex 1 (mTORC1).

Biochemical and genetic analysis of mTOR has demonstrated that it is present in two functionally distinct complexes. The core components of mTORC1 consist of mTOR, mammalian lethal with sec-13 protein 8 (mLST8), and regulatory-associated protein of TOR (Raptor). Additional components include DEP-domain-containing mTOR-interacting protein (DEPTOR) and Proline-rich Akt substrate 40 kDa (PRAS40).

The mTOR complex 2 (mTORC2) core is composed of mTOR, rapamycin insensitive companion of mTOR (Rictor), stress-activated protein kinase-interacting protein 1 (mSIN1), and mLST8. Protein observed with rictor 1/2 (protor 1/2) and DEPTOR are additional regulatory components. S6 kinase 1 (S6K1) and eukaryotic inhibition factor eIF4E binding protein 1 (4E-BP1) are two well-characterized substrates of mTORC1 while AKT is a well characterized substrate of mTORC2 (Li, J. et al., Cell Met., 19(3): 373-9 (2014)).

Because FKBP12-rapamycin does not bind to mTORC2, rapamycin was initially thought to inhibit only mTORC1 (Sarbassov, D. D. et al., Curr. Biol., 14(14): 1296-302 (2004)). However, in 2006 it was shown that rapamycin suppresses the assembly and function of mTORC2 and inhibits pAkt (Sarbassov, D. D. et al., Molecular Cell, 22(2): 159-68 (2006)). The effects of rapamycin on the phosphorylation of S473 of Akt (an mTORC2 substrate) and of T389 of S6K1 (an mTORC1 substrate) were compared in multiple cell lines. In PC3, HEK-293T, HeLa, and H460 cells, 1 or 24 hour treatments with rapamycin inhibited S6K1 phosphorylation, consistent with inhibition of mTORC1. Selective inhibition of S6K1 by rapamycin should lead to an increase in Akt phosphorylation, and, indeed, this is what is reported in HeLa cells. However, in PC3 cells, the drug strongly decreased Akt phosphorylation suggesting that rapamycin is not selective in this cell line. Partial inhibition of pAKT is observed in HEK-293T cells. In about one third of the cell lines, rapamycin caused a strong or partial inhibition of Akt phosphorylation, while the drug either did not affect or increased Akt phosphorylation in the others. The inhibition of pAKT after 24 hours is also observed in primary and non-transformed cell lines including endothelial and muscle cells. Rapamycin was also shown to inhibit pAkt in vivo, as mice treated daily for 1 week with the drug had decreased Akt phosphorylation in the thymus, adipose tissue, heart, and lung. These findings demonstrated that inhibition of Akt phosphorylation by rapamycin is common and occurs in normal cell lines, cancer cell lines as well as in vivo.

It was concluded by Sarbassov et al. that rapamycin and its analogs (CCI 779, RAD001 also known as Everolimus, AP23573) can inhibit mTORC2 function in certain cell lines and tissues. Rapamycin-mediated inhibition of Akt may help explain the side effects of the drug. For example, rapamycin strongly inhibits Akt phosphorylation in adipose tissue, a tissue type in which insulin-stimulated Akt activity plays an important role in suppressing lipolysis. Inhibition of Akt by rapamycin in adipocytes may allow lipolysis to remain high even in the presence of insulin, resulting in the accumulation of free fatty acids in the plasma that can be used by the liver to generate triglycerides, providing a molecular mechanism for the hyperlipidemia commonly seen in patients treated with rapamycin.

Pereira et al. (Mol Cell Endocrinol., 355(1): 96-105 (2012)) explored rapamycin effects on glucose uptake and insulin signaling proteins in adipocytes obtained via fat biopsies in human donors. At therapeutic concentration (0.0 µM) rapamycin reduced AKT (PKB) Ser473 phosphorylation and reduced glucose uptake in human adipocytes through impaired insulin signaling.

Lamming et al. (Science., 335(6076): 1638-1643 (2012)) demonstrated that rapamycin disrupted mTORC2 in vivo and that mTORC2 was required for the insulin-mediated suppression of hepatic gluconeogenesis.

Similar results were shown in human. Di Paolo et al. published similar findings in human (JASN, 17(8): 2236-2244 (2006)). The main objective of their study was to ascertain the effect of chronic exposure to rapamycin on AKT activation, in view of its crucial role in the regulation of cell growth and survival, as well as in the cell response to nutrients and growth factors. They found that mTOR inhibition was associated with a marked downregulation of basal and insulin-induced AKT phosphorylation. AKT is responsible primarily for many of the metabolic actions of insulin and they concluded therefore that the depression of AKT activation significantly correlated with the increase of insulin resistance in renal transplant recipients.

Kennedy et al. reviewed recently the role of mTORC1 and mTORC2 in metabolism and aging (Cell Metab., 23(6): 990-1003 (2016)).

It has been surprisingly found that provided compounds inhibit mTORC1, but do not impact mTORC2 (as measured by their impact on pAKT) over extended periods of time (e.g., 8 hours, 24 hours, 30 hours, and 48 hours). This novel activity is predicated on the presence of a sufficiently large group at the C-7 position of rapamycin and its analogs. Small substitutions at this position such as OMe, as seen in rapamycin, OEt, OBn do not confer selectivity over mTORC2 at 24 hours. Medium length groups, such as OCH$_2$CH$_2$OH or OCH$_2$CH$_2$CH$_2$OH show partial selectivity over mTORC2 at 24 hours, but still show some level of inhibition. In comparison, larger groups, such as those of the present invention (e.g., I-19), provide a marked selectivity over mTORC2 as measured by the impact of pAKT.

The location of this substitution is also critical to the observed selectivity. Introduction of larger substitutions at position 43 for example does not lead to this unique selectivity profile claimed in this application.

For the purpose of clarity, the structure of Rapamycin is reproduced below with the C-7 and C-43 positions noted.

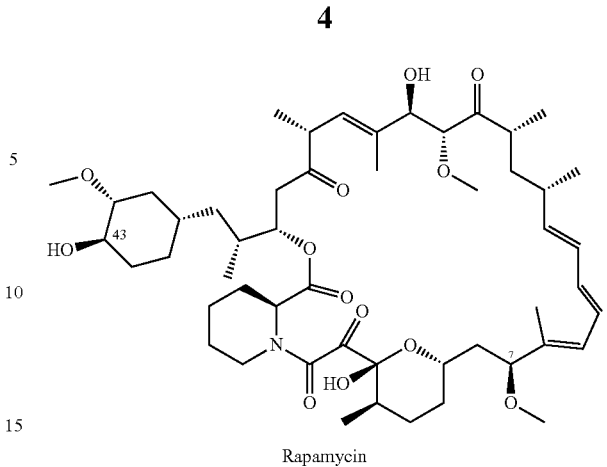

Rapamycin

In some embodiments, the present invention provides novel rapamycin analogues that are potent mTORC1 inhibitors as measured by pS6K. Unlike Rapamycin and Everolimus, these compounds do not inhibit pAKT at longer time points (e.g., 24 hours and 48 hours). These compounds also show improved solubility and improved pharmacokinetics comparing to Rapamycin.

The activity of a compound utilized in this invention as an inhibitor of mTORC1, may be assayed in vitro, in vivo or in a cell line. In vitro assays include assays that determine the inhibition of mTORC1. Detailed conditions for assaying a compound utilized in this invention as an inhibitor of mTORC1 are well known to one of ordinary skill in the art. Such methods are described in detail by Liu et al., Cancer Research, 73(8): 2574-86 (2013) and Liu et al., J. Biological Chemistry 287(13): 9742-52 (2012).

SUMMARY OF THE INVENTION

It has now been found that compounds of this invention, and pharmaceutically acceptable compositions thereof, are effective as inhibitors mTORC1 inhibitors. Such compounds have the general Formula I:

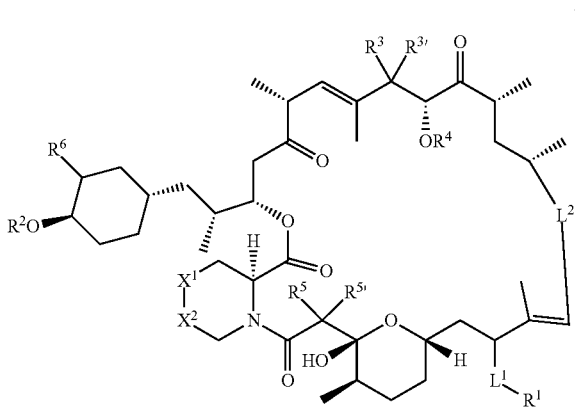

or a pharmaceutically acceptable salt thereof, wherein each of R, $R^1$, $R^2$, $R^3$, $R^{3'}$, $R^4$, $R^5$, $R^{5'}$, $R^6$, $L^1$, $L^2$, $X^1$, and $X^2$ is as defined and described herein.

Compounds of the present invention, and pharmaceutically acceptable compositions thereof, are useful for treating a variety of diseases, disorders or conditions, associated with mTORC1. Such diseases, disorders, or conditions include those described herein.

DETAILED DESCRIPTION OF CERTAIN EMBODIMENTS

Figure 1:
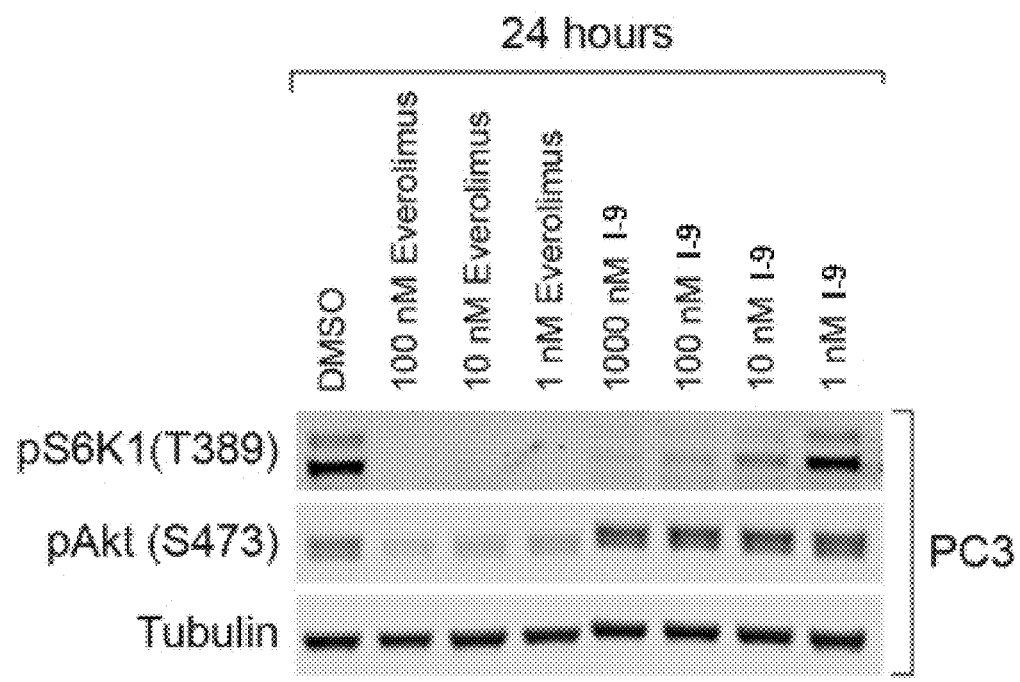
FIG. 1 shows a Western blot performed after treating PC3 cells with everolimus, or a compound of the present invention (I-9) for 24 hours. Staining indicates strong inhibition of the mTORC1 pathway for everolimus, and a moderate concentration dependent inhibition of the mTORC1 pathway for I-9. Significantly, these results demonstrate that compounds of the present invention do not inhibit mTORC2, as demonstrated by the lack of Akt phosphorylation inhibition.

1. General Description of Certain Embodiments of the Invention

In certain embodiments, the present invention provides a compound of Formula I:

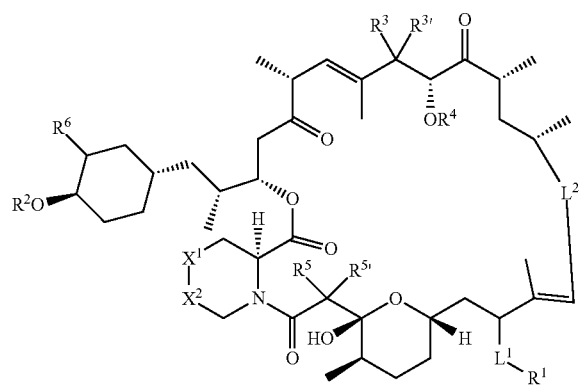

I or a pharmaceutically acceptable salt thereof, wherein:
L$^1$ is a covalent bond, or a C$_{1-30}$ bivalent straight or branched saturated or unsaturated hydrocarbon chain, wherein 1-10 methylene units of the chain are independently and optionally replaced with -Cy$_1$-, —O—, —S—, —S(O)$_2$—, —C(O)—, —C(S)—, —C(R)$_2$—, —CH(R)—, —CF$_2$—, —P(O)(R)—, —Si(R)$_2$—, —Si(OR)(R)—, or —NR—;
each -Cy$_1$- is independently an optionally substituted bivalent ring selected from phenylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;

each R is independently hydrogen, or an optionally substituted group selected from C$_{1-6}$ aliphatic, 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, or 5-6 membered heteroaryl ring having 1-4 heteroatoms independently selected from nitrogen, oxygen, or sulfur, or two R groups on the same atom are taken together with their intervening atoms to form a 4-7 membered saturated, partially unsaturated, or aryl ring having 0-3 heteroatoms, in addition to the same atom to which they are attached, independently selected from nitrogen, oxygen, or sulfur;

L$^2$ is a C$_{1-6}$ bivalent straight or branched saturated or unsaturated hydrocarbon chain, wherein 1-2 methylene units of the chain are independently and optionally replaced with -Cy$_1$-;

R$^1$ is hydrogen, halogen, —OR, —CN, —NO$_2$, —NR$_2$, or an optionally substituted group selected from a C$_{1-6}$ aliphatic, a 3-8 membered saturated or partially unsaturated monocyclic carbocyclic ring, a phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a 5-6 membered monocyclic heteroaromatic ring having 1-4 heteroatoms independently selected from nitrogen, oxygen, or sulfurs, or an 8-10 membered bicyclic heteroaromatic ring having 1-5 heteroatoms independently selected from nitrogen, oxygen, or sulfur, wherein -L$^1$-R$^1$ taken together do not form —OMe;

R$^2$ is

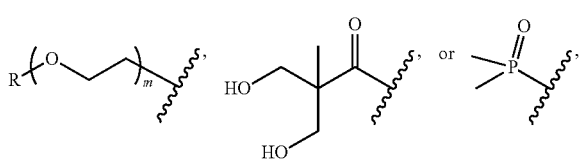

wherein m is 0, 1, 2, 3, or 4;
R$^3$ is hydrogen, halogen; —OR, or —OSiR$_3$;
R$^{3'}$ is hydrogen,
or R$^3$ and R$^{3'}$ are taken together to form =O or =S;
R$^4$ is hydrogen or an optionally substituted group selected from C$_{1-6}$ aliphatic;
R$^5$ and R$^{5'}$ are each hydrogen or taken together to form =O;
R$^6$ is hydrogen, —OMe, or halogen; and
X$^1$ and X$^2$ are each independently —CH$_2$—, —S—, or —S(O)—,
wherein at least one of X$^1$ and X$^2$ is —CH$_2$—,
provided the compound is other than a compound from Table 2.

In certain embodiments, the present invention provides a compound of Formula I other than those selected from:

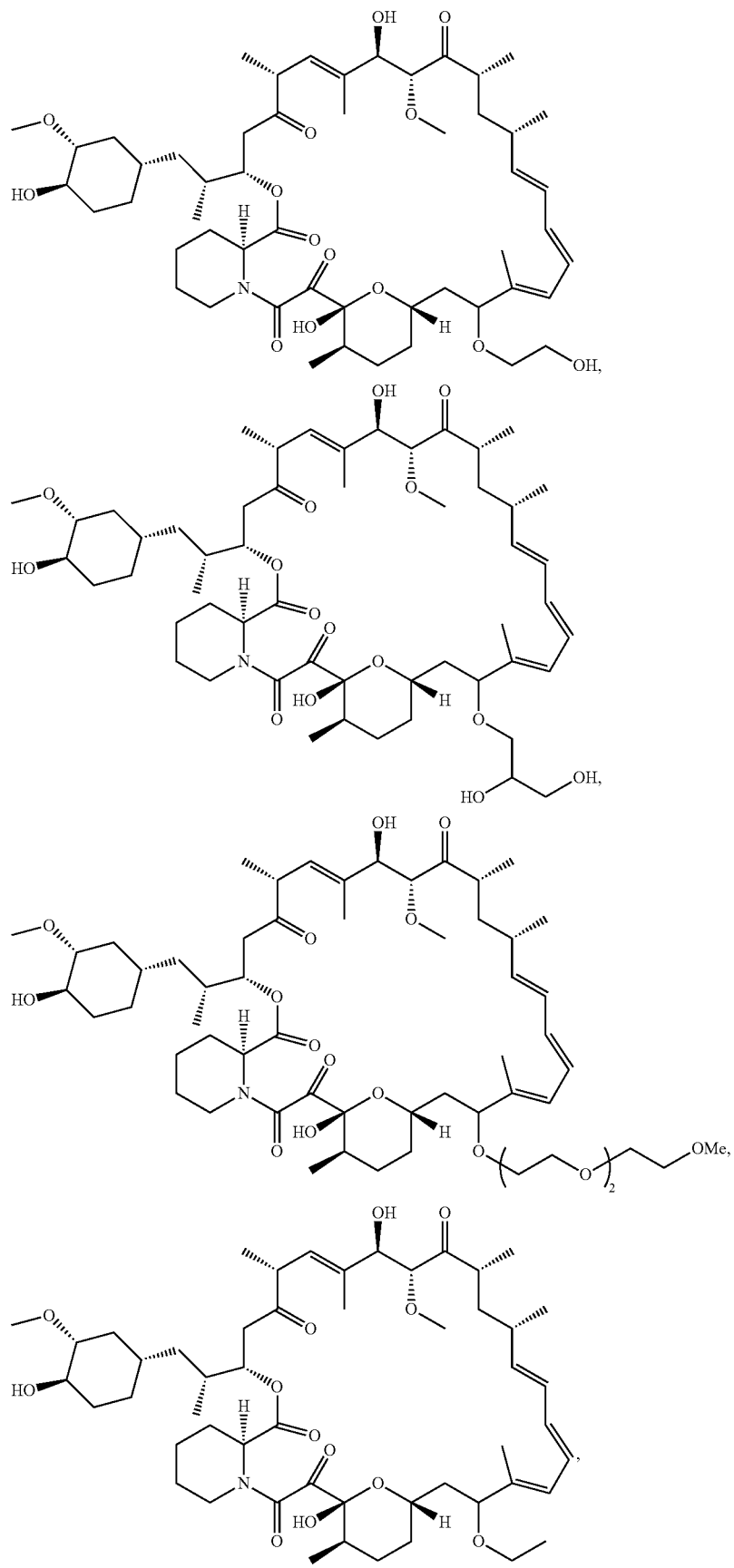

-continued
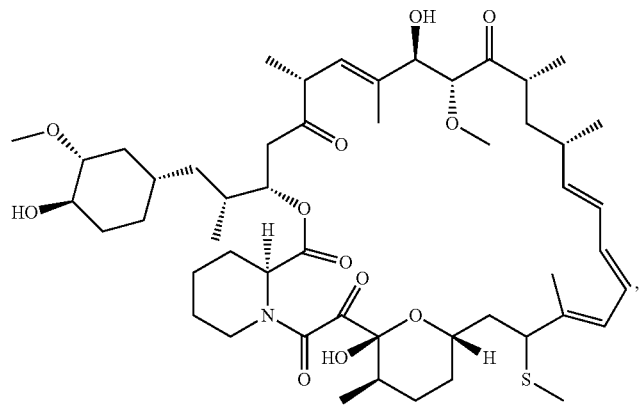
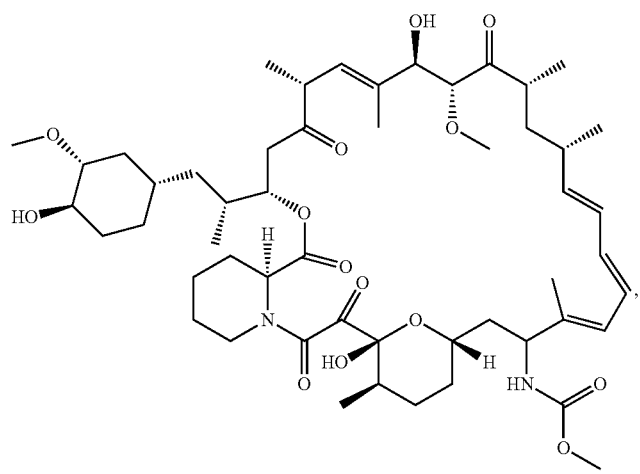
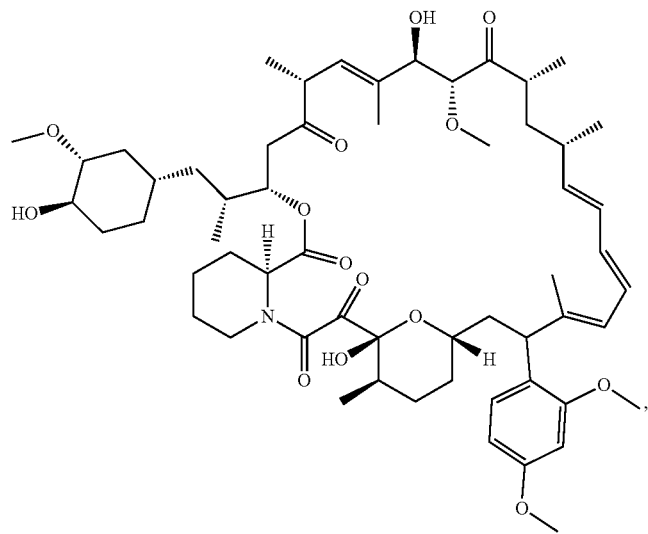

-continued
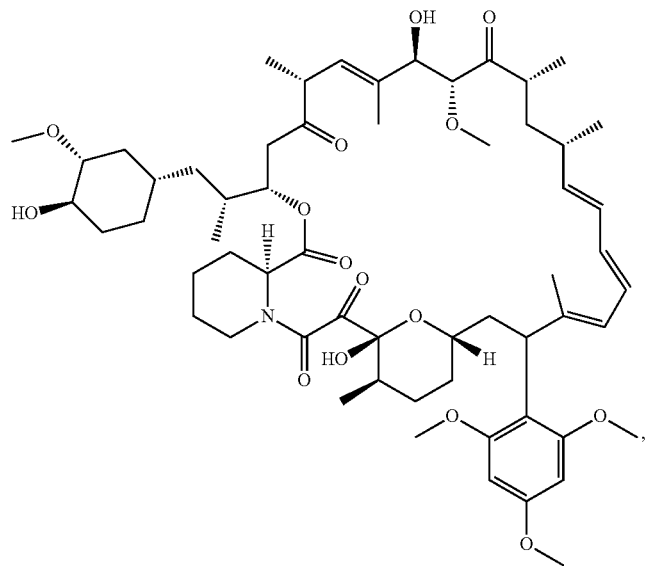
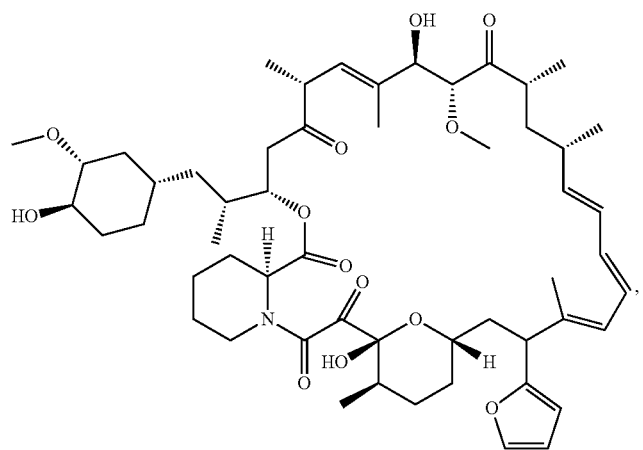
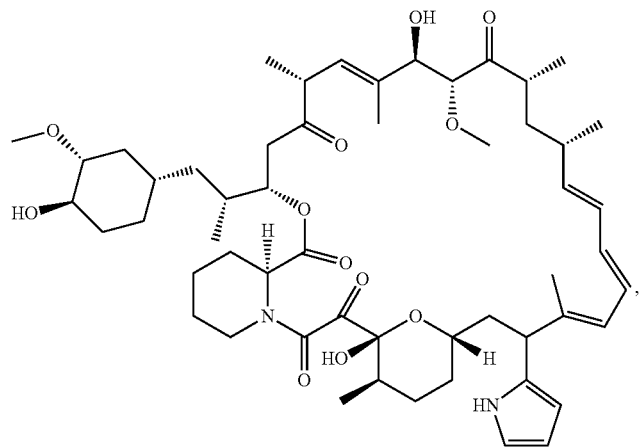

-continued
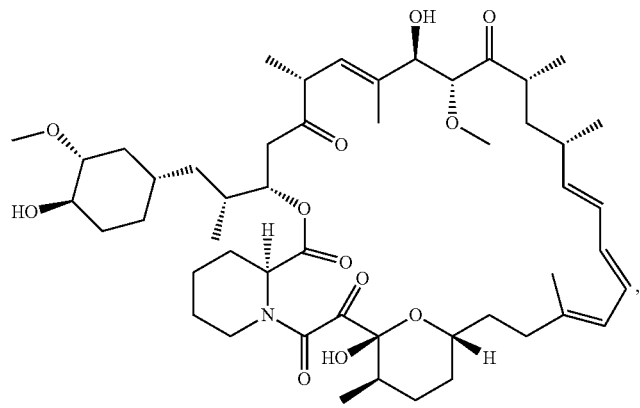
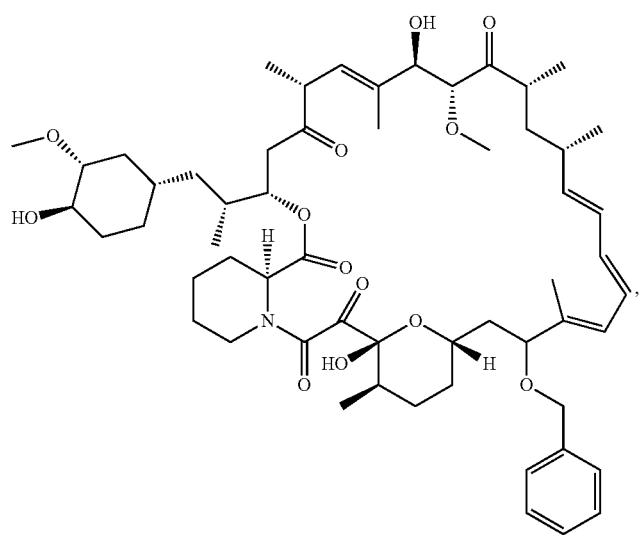
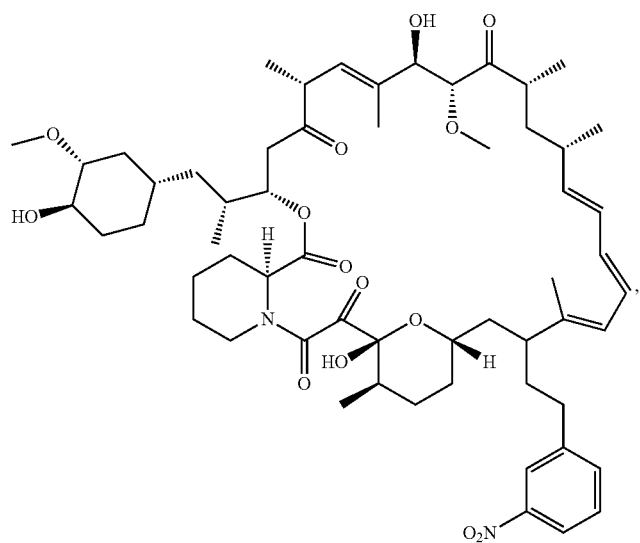

-continued
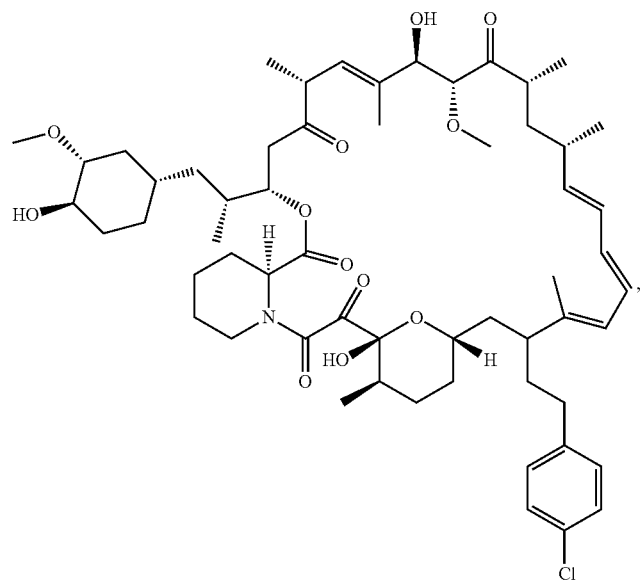
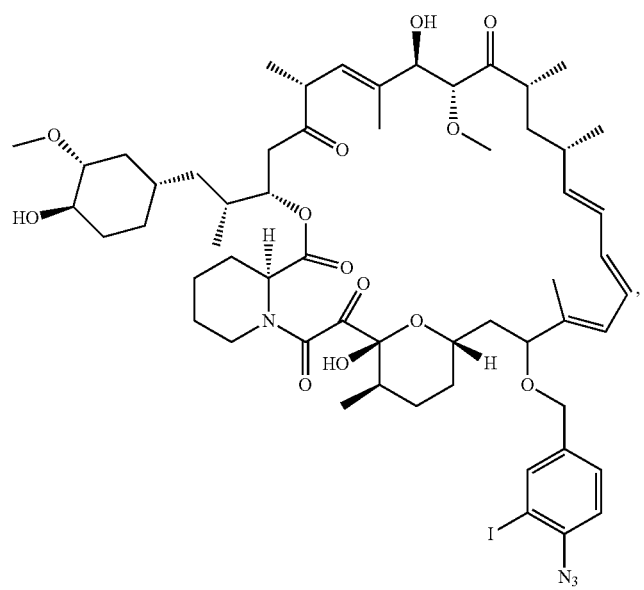
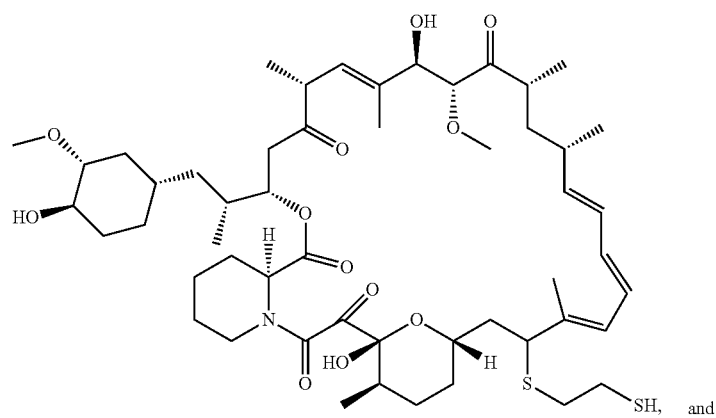
and

-continued

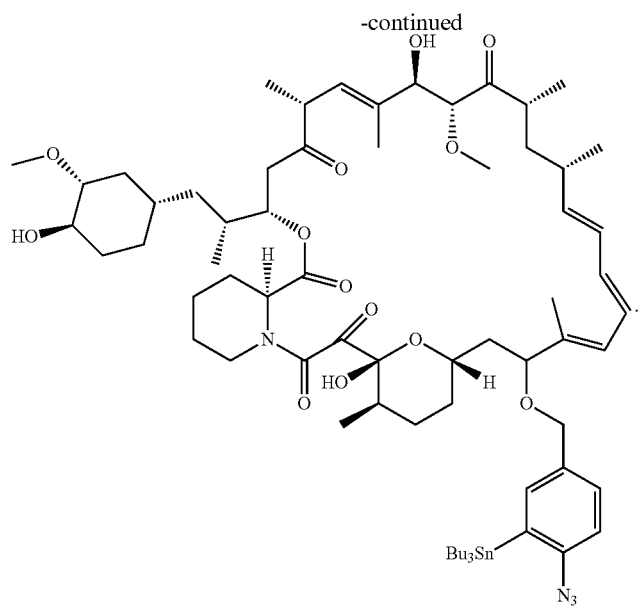

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted" means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}R°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR$—, SC(S)SR°; —$(CH_2)_{0-4}SC(O)R°$; —$(CH_2)_{0-4}C(O)NR°_2$; —C(S)NR°_2; —C(S)SR°; —SC(S)SR°, —$(CH_2)_{0-4}OC(O)NR°_2$; —C(O)N(OR°)R°; —C(O)C(O)R°; —C(O)CH_2C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —N(R°)S(O)_2NR°_2$; —N(R°)S(O)_2R°$; —N(OR°)R°; —C(NH)NR°_2$; —P(O)_2R°$; —P(O)R°_2$; —OP(O)R°_2$; —OP(O)(OR°)_2$; SiR°_3$; —($C_{1-4}$ straight or branched alkylene)O—N(R°)_2$; or —($C_{1-4}$ straight or branched alkylene)C(O)O—N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^{\bullet}$, -(haloR$^{\bullet}$), —$(CH_2)_{0-2}OH$, —$(CH_2)_{0-2}OR^{\bullet}$, —$(CH_2)_{0-2}CH(OR^{\bullet})_2$; —O(haloR$^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in mTORC1 activity between a sample comprising a compound of the present invention, or composition thereof, and mTORC1, and an equivalent sample comprising mTORC1 in the absence of said compound, or composition thereof.

3. Description of Exemplary Embodiments

As described above, in certain embodiments, the present invention provides a compound of Formula I:

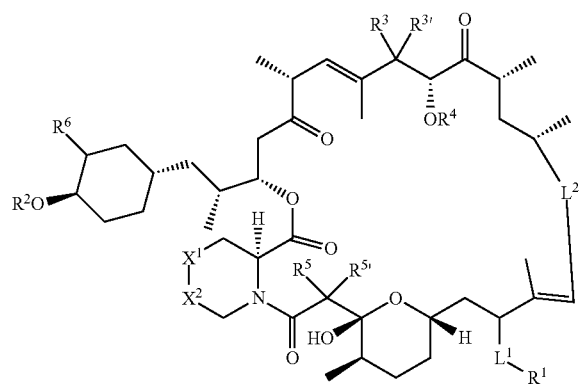

I or a pharmaceutically acceptable salt thereof, wherein:
L¹ is a covalent bond, or a C₁₋₃₀ bivalent straight or branched saturated or unsaturated hydrocarbon chain, wherein 1-10 methylene units of the chain are independently and optionally replaced with -Cy₁-, —O—, —S—, —S(O)₂—, —C(O)—, —C(S)—, —C(R)₂—, —CH(R)—, —CF₂—, —P(O)(R)—, —Si(R)₂—, —Si(OR)(R)—, or —NR—;
each -Cy₁- is independently an optionally substituted bivalent ring selected from phenylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur;
each R is independently hydrogen, or an optionally substituted group selected from C₁₋₆ aliphatic, 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, or 5-6 membered heteroaryl ring having 1-4 heteroatoms independently selected from nitrogen, oxygen, or sulfur, or
two R groups on the same atom are taken together with their intervening atoms to form a 4-7 membered saturated, partially unsaturated, or aryl ring having 0-3 heteroatoms, in addition to the same atom to which they are attached, independently selected from nitrogen, oxygen, or sulfur;
L² is a C₁₋₆ bivalent straight or branched saturated or unsaturated hydrocarbon chain, wherein 1-2 methylene units of the chain are independently and optionally replaced with -Cy₁-;
R¹ is hydrogen, halogen, —OR, —CN, —NO₂, —NR₂, or an optionally substituted group selected from a C₁₋₆ aliphatic, a 3-8 membered saturated or partially unsaturated monocyclic carbocyclic ring, a phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a 5-6 membered monocyclic heteroaromatic ring having 1-4 heteroatoms independently selected from nitrogen, oxygen, or sulfurs, or an 8-10 membered bicyclic heteroaromatic ring having 1-5 heteroatoms independently selected from nitrogen, oxygen, or sulfur,
wherein -L¹-R¹ taken together do not form —OMe;
R² is

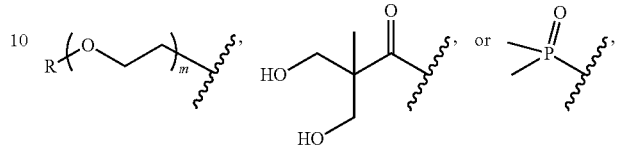

wherein m is 0, 1, 2, 3, or 4;
R³ is hydrogen, halogen; —OR, or —OSiR₃;
R³' is hydrogen,
or R³ and R³' are taken together to form =O or =S;
R⁴ is hydrogen or an optionally substituted group selected from C₁₋₆ aliphatic;
R⁵ and R⁵' are each hydrogen or taken together to form =O;
R⁶ is hydrogen, —OMe, or halogen; and
X¹ and X² are each independently —CH₂—, —S—, or —S(O)—,
wherein at least one of X¹ and X² is —CH₂—;
or a pharmaceutically acceptable salt thereof, provided the compound is other than a compound from Table 2.

In certain embodiments, the present invention provides a compound of Formula I wherein the stereochemistry is as shown below, thereby providing a compound of Formula I-a-1 or I-a-2:

I-a-1

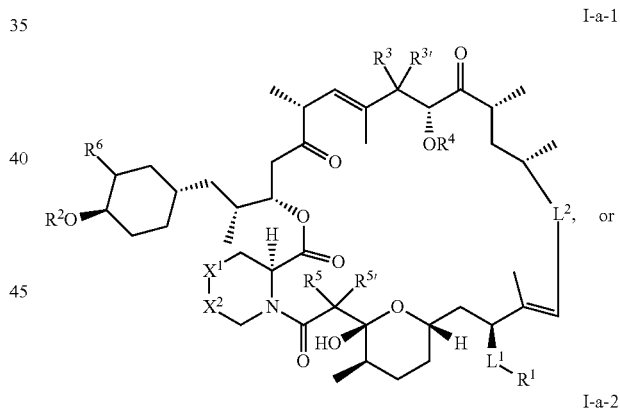

, or

I-a-2

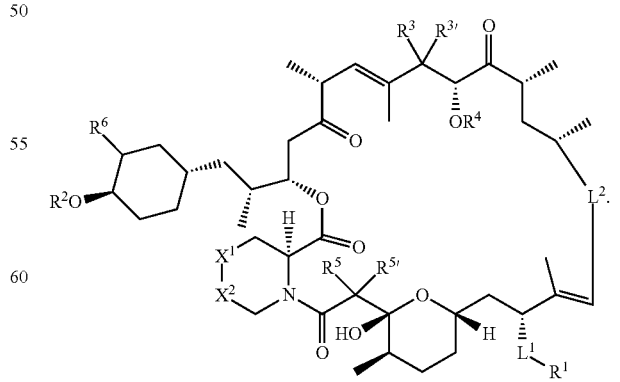

.

or a pharmaceutically acceptable salt thereof, wherein each of R¹, R², R³, R³', R⁴, R⁵, R⁵', R⁶, L¹, L², X¹, and X² is as defined and described herein, and provided the compound is other than a compound from Table 2.

It will be appreciated that the term "rapamycin", and structure thereof, recited throughout the specification is intended to encompass rapamycin and analogs thereof.

The herein recited analogs of rapamycin (i.e., rapalogs) are for exemplification and not intended to limit the current invention.

As defined above, $L^1$ is a covalent bond, or a $C_{1-30}$ bivalent straight or branched saturated or unsaturated hydrocarbon chain, wherein 1-10 methylene units of the chain are independently and optionally replaced with -Cy$_1$-, —O—, —S—, —S(O)$_2$—, —C(O)—, —C(S)—, —C(R)$_2$—, —CH(R)—, —CF$_2$—, —P(O)R—, —Si(R)$_2$—, —Si(OR)(R)—, or —NR—.

In some embodiments, $L^1$ is a covalent bond. In some embodiments, $L^1$ is $C_{1-30}$ bivalent straight saturated hydrocarbon chain, wherein 1-10 methylene units of the chain are independently and optionally replaced with -Cy$_1$-, —O—, —S—, —S(O)$_2$—, —C(O)—, —C(S)—, —C(R)$_2$—, —CH(R)—, —CF$_2$—, —P(O)(R)—, —Si(R)$_2$—, —Si(OR)(R)—, or —NR—.

In some embodiments, $L^1$ is —O—. In some embodiments, $L^1$ is —NH—. In some embodiments, $L^1$ is —O—CH$_2$—. In some embodiments, L is —O—(CH$_2$)$_2$—. In some embodiments, $L^1$ is —O—(CH$_2$)$_3$—. In some embodiments, $L^1$ is —O—(CH$_2$)$_4$—. In some embodiments, $L^1$ is —O—(CH$_2$)$_5$—. In some embodiments, $L^1$ is —O—(CH$_2$)$_2$—O—. In some embodiments, $L^1$ is —O—(CH$_2$)$_2$—O—(CH$_2$)$_2$—. In some embodiments, $L^1$ is —NH—CH$_2$—. In some embodiments, $L^1$ is —NH—C(O)—. In some embodiments, $L^1$ is —NH—C(O)O—. In some embodiments, $L^1$ is —NH—SO$_2$—. In some embodiments, $L^1$ is —NH—SO$_2$—(CH$_2$)$_2$—. In some embodiments, $L^1$ is —NH—SO$_2$—(CH$_2$)$_2$—O—(CH$_2$)$_2$—. In some embodiments, L is —O—(CH$_2$)$_2$—SO$_2$—(CH$_2$)$_2$—. In some embodiments, $L^1$ is —O—(CH$_2$)$_2$—SO$_2$—(CH$_2$)$_2$—SO$_2$—. In some embodiments, L is —O—(CH$_2$)$_2$—O—(CH$_2$)$_2$—O—(CH$_2$)$_2$—. In some embodiments, $L^1$ is

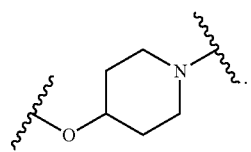 [SMILES: *OC1CCN(*)CC1]

In some embodiments, $L^1$ is selected from those depicted in Table 1, below.

As defined above, each -Cy$_1$- is independently an optionally substituted bivalent ring selected from phenylene, 4-7 membered saturated or partially unsaturated heterocyclylene having 1-2 heteroatoms independently selected from nitrogen, oxygen, or sulfur, or 5-6 membered heteroarylene having 1-4 heteroatoms independently selected from nitrogen, oxygen, or sulfur.

In some embodiments, each -Cy$_1$- is independently an optionally substituted bivalent phenylene. In some embodiments, each -Cy$_1$- is independently an optionally substituted 4-7 membered saturated heterocyclylene having 1-2 heteroatoms independently selected from nitrogen, oxygen, or sulfur. In some embodiments, each -Cy$_1$- is independently an optionally substituted 4-7 membered partially unsaturated heterocyclylene having 1-2 heteroatoms independently selected from nitrogen, oxygen, or sulfur. In some embodiments, each -Cy$_1$- is independently an optionally substituted 5-6 membered heteroarylene having 1-4 heteroatoms independently selected from nitrogen, oxygen, or sulfur.

In some embodiments, -Cy$_1$- is selected from those depicted in Table 1, below.

As defined above, each R is independently hydrogen, or an optionally substituted group selected from $C_{1-6}$ aliphatic, 3-8 membered saturated or partially unsaturated monocyclic carbocyclic ring, phenyl, 4-7 membered saturated or partially unsaturated heterocyclic ring having 1-2 heteroatoms independently selected from nitrogen, oxygen, or sulfur, or 5-6 membered heteroaryl ring having 1-4 heteroatoms independently selected from nitrogen, oxygen, or sulfur, or two R groups on the same atom are taken together with their intervening atoms to form a 4-7 membered saturated, partially unsaturated, or aryl ring having 0-3 heteroatoms, in addition to the atom, independently selected from nitrogen, oxygen, or sulfur In some embodiments, each R is independently hydrogen. In some embodiments, each R is an optionally substituted $C_{1-6}$ aliphatic. In some embodiments, each R is an optionally substituted 3-8 membered saturated monocyclic carbocyclic ring. In some embodiments, each R is an optionally substituted 3-8 membered partially unsaturated monocyclic carbocyclic ring. In some embodiments, each R is an optionally substituted phenyl. In some embodiments, each R is an optionally substituted 4-7 membered saturated heterocyclic ring having 1-2 heteroatoms independently selected from nitrogen, oxygen, or sulfur. In some embodiments, each R is an optionally substituted 4-7 membered partially unsaturated heterocyclic ring having 1-2 heteroatoms independently selected from nitrogen, oxygen, or sulfur. In some embodiments, each R is an optionally substituted 5-6 membered heteroaryl ring having 1-4 heteroatoms independently selected from nitrogen, oxygen, or sulfur. In some embodiments, two R groups on the same atom are taken together with their intervening atoms to form a 4-7 membered aryl ring having 0-3 heteroatoms, in addition to the atom to which they are attached, independently selected from nitrogen, oxygen, or sulfur. In some embodiments, two R groups on the same nitrogen atom are taken together with their intervening atoms to form a 4-7 membered partially unsaturated ring having 0-3 heteroatoms, in addition to the nitrogen atom to which they are attached, independently selected from nitrogen, oxygen, or sulfur.

In some embodiments, each R is selected from those depicted in Table 1, below.

As defined above, $L^2$ is a $C_{1-6}$ bivalent straight or branched saturated or unsaturated hydrocarbon chain, wherein 1-2 methylene units of the chain are independently and optionally replaced with -Cy$_1$-.

In some embodiments, $L^2$ is a $C_{1-6}$ bivalent straight saturated hydrocarbon chain, wherein 1-2 methylene units of the chain are independently and optionally replaced with -Cy$_1$-. In some embodiments, $L^2$ is a $C_{1-6}$ bivalent branched saturated hydrocarbon chain, wherein 1-2 methylene units of the chain are independently and optionally replaced with -Cy$_1$-.

In some embodiments, $L^2$ is

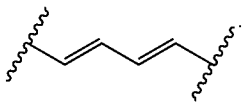

In some embodiments, $L^2$ is selected from those depicted in Table 1, below.

As defined above, $R^1$ is hydrogen, halogen, —OR, —CN, —NO$_2$, —NR$_2$, or an optionally substituted group selected from a $C_{1-6}$ aliphatic, a 3-8 membered saturated or partially unsaturated monocyclic carbocyclic ring, a phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a 5-6 membered monocyclic heteroaromatic ring having 1-4 heteroatoms independently selected from nitrogen, oxygen, or sulfurs, or an 8-10 membered bicyclic heteroaromatic ring having 1-5 heteroatoms independently selected from nitrogen, oxygen, or sulfur, wherein -L-R taken together do not form —OMe.

In some embodiments, $R^1$ is hydrogen. In some embodiments, $R^1$ is halogen. In some embodiments, $R^1$ is —OR, wherein -L$^1$-R$^1$ taken together do not form —OMe. In some embodiments, $R^1$ is —CN. In some embodiments, $R^1$ is —NO$_2$. In some embodiments, $R^1$ is —NR$_2$. In some embodiments, $R^1$ is an optionally substituted $C_{1-6}$ aliphatic, wherein -L$^1$-R$^1$ taken together do not form —OMe. In some embodiments, $R^1$ is an optionally substituted 3-8 membered saturated monocyclic carbocyclic ring. In some embodiments, $R^1$ is an optionally substituted 3-8 membered partially unsaturated monocyclic carbocyclic ring. In some embodiments, $R^1$ is an optionally substituted phenyl. In some embodiments, $R^1$ is an optionally substituted 8-10 membered bicyclic aromatic carbocyclic ring. In some embodiments, $R^1$ is an optionally substituted 4-8 membered saturated monocyclic heterocyclic ring having 1-2 heteroatoms independently selected from nitrogen, oxygen, or sulfur. In some embodiments, $R^1$ is an optionally substituted 4-8 membered partially unsaturated monocyclic heterocyclic ring having 1-2 heteroatoms independently selected from nitrogen, oxygen, or sulfur. In some embodiments, $R^1$ is an optionally substituted 7-10 membered saturated bicyclic heterocyclic ring having 1-3 heteroatoms independently selected from nitrogen, oxygen, or sulfur. In some embodiments, $R^1$ is an optionally substituted 7-10 membered partially unsaturated bicyclic heterocyclic ring having 1-3 heteroatoms independently selected from nitrogen, oxygen, or sulfur. In some embodiments, $R^1$ is an optionally substituted 5-6 membered monocyclic heteroaromatic ring having 1-4 heteroatoms independently selected from nitrogen, oxygen, or sulfurs. In some embodiments, R is an optionally substituted 8-10 membered bicyclic heteroaromatic ring having 1-5 heteroatoms independently selected from nitrogen, oxygen, or sulfur.

In some embodiments, $R^1$ is —OMe. In some embodiments, $R^1$ is —(CH$_2$)$_2$—OH. In some embodiments, $R^1$ is —CH$_2$CF$_3$. In some embodiments, $R^1$ is —(CH$_2$)$_2$—OMe. In some embodiments, $R^1$ is —SO$_2$—NH$_2$. In some embodiments, $R^1$ is —C(O)NH$_2$. In some embodiments, $R^1$ is —C(O)NMe$_2$. In some embodiments, $R^1$ is —OC(O)NHMe. In some embodiments, $R^1$ is —CO$_2$H. In some embodiments, $R^1$ is

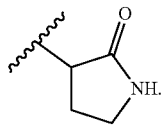 [SMILES: *C1CCNC1=O]

In some embodiments, $R^1$ is

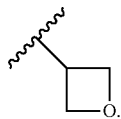

In some embodiments, $R^1$ is

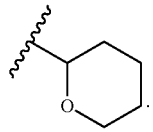

In some embodiments, $R^1$ is

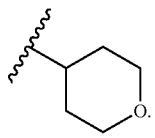 [SMILES: *C1CCOCC1]

In some embodiments, $R^1$ is

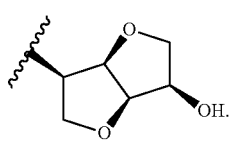 [SMILES: *[C@@H]1CO[C@H]2[C@@H]1OC[C@H]2O]

In some embodiments, $R^1$ is

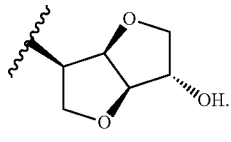 [SMILES: *[C@@H]1CO[C@H]2[C@@H]1OC[C@@H]2O]

In some embodiments, $R^1$ is

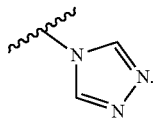

In some embodiments, $R^1$ is

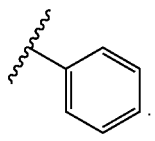 [SMILES: *c1ccccc1]

In some embodiments, R¹ is
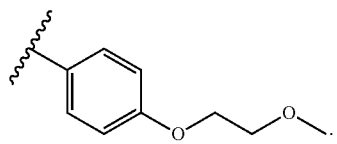 [SMILES: *c1ccc(OCCOC)cc1]
In some embodiments, R¹ is
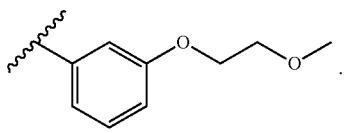 [SMILES: *c1cccc(OCCOC)c1]
In some embodiments, R¹ is
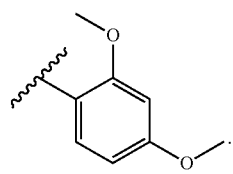 [SMILES: *c1ccc(OC)cc1OC]
In some embodiments, R¹ is
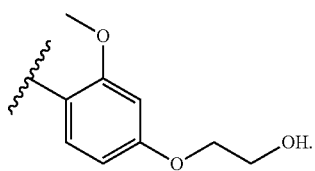 [SMILES: *c1ccc(OCCO)cc1OC]
In some embodiments, R¹ is
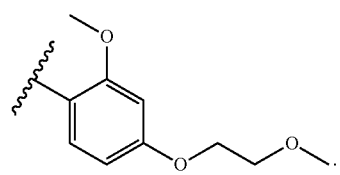 [SMILES: *c1ccc(OCCOC)cc1OC]
In some embodiments, R¹ is
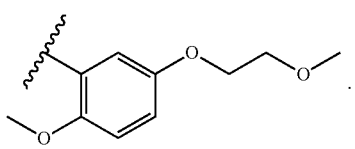
In some embodiments, R¹ is
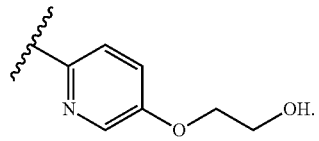 [SMILES: *c1ccc(OCCO)cn1]
In some embodiments, R¹ is
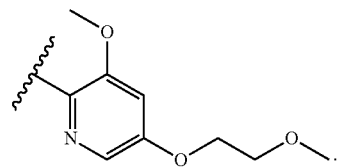 [SMILES: *c1ncc(OCCOC)cc1OC]
In some embodiments, R¹ is
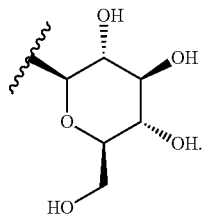 [SMILES: *[C@@H]1O[C@H](CO)[C@@H](O)[C@H](O)[C@H]1O]
In some embodiments, R¹ is
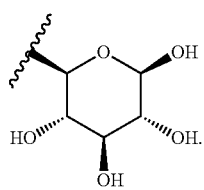 [SMILES: *[C@H]1O[C@@H](O)[C@H](O)[C@@H](O)[C@@H]1O]
In some embodiments, R¹ is
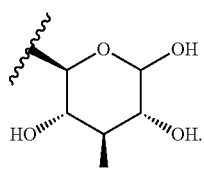
In some embodiments, R¹ is
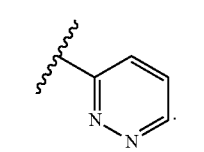

In some embodiments, $R^1$ is

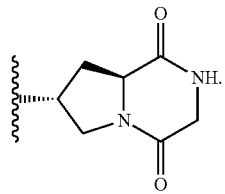 [SMILES: *[C@@H]1C[C@H]2C(=O)NCC(=O)N2C1]

In some embodiments, $R^1$ is

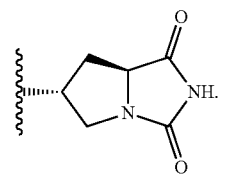 [SMILES: *[C@@H]1C[C@H]2C(=O)NC(=O)N2C1]

In some embodiments, $R^1$ is

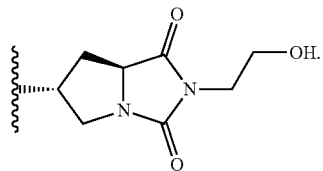 [SMILES: *[C@@H]1C[C@H]2C(=O)N(CCO)C(=O)N2C1]

In some embodiments, $R^1$ is

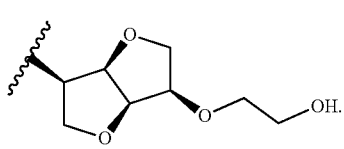 [SMILES: *[C@@H]1CO[C@H]2[C@@H]1OC[C@H]2OCCO]

In some embodiments, $R^1$ is

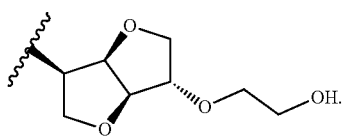 [SMILES: *[C@@H]1CO[C@H]2[C@@H]1OC[C@@H]2OCCO]

In some embodiments, $R^1$ is

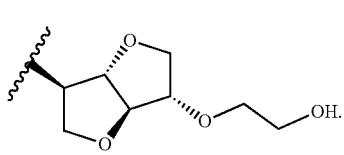 [SMILES: *[C@@H]1CO[C@H]2[C@H]1OC[C@@H]2OCCO]

In some embodiments, $R^1$ is

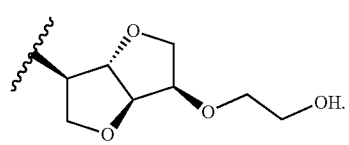 [SMILES: *[C@@H]1CO[C@H]2[C@H]1OC[C@H]2OCCO]

In some embodiments, $R^1$ is selected from those depicted in Table 1, below.

As defined above, $R^2$ is

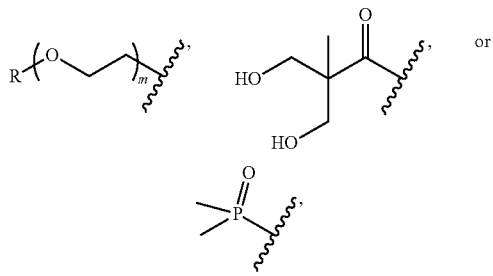

wherein m is 0, 1, 2, 3, or 4.

In some embodiments, $R^2$ is R. In some embodiments, $R^2$ is methyl. In some embodiments, $R^2$ is

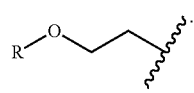

In some embodiments, $R^2$ is

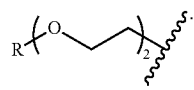

In some embodiments, $R^2$ is

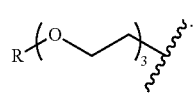

In some embodiments, $R^2$ is

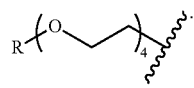

In some embodiments, $R^2$ is

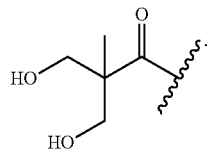

In some embodiments, $R^2$ is

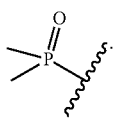

In some embodiments, $R^2$ is selected from those depicted in Table 1, below.

As defined above, $R^3$ is hydrogen, halogen; —OR, or —OSiR$_3$.

In some embodiments, $R^3$ is hydrogen. In some embodiments, $R^3$ is halogen. In some embodiments, $R^3$ is —OR. In some embodiments, $R^3$ is —OMe. In some embodiments, $R^3$ is —OSiR$_3$.

In some embodiments, $R^3$ is —OH.

In some embodiments, $R^3$ is selected from those depicted in Table 1, below.

As defined above, $R^{3'}$ is hydrogen or $R^3$ and $R^{3'}$ are taken together to form =O or =S.

In some embodiments, $R^{3'}$ is hydrogen. In some embodiments, or $R^3$ and $R^{3'}$ are taken together to form =O. In some embodiments, or $R^3$ and $R^{3'}$ are taken together to form =S.

In some embodiments, $R^{3'}$ is selected from those depicted in Table 1, below.

As defined above, $R^4$ is hydrogen or an optionally substituted group selected from $C_{1-6}$ aliphatic.

In some embodiments, $R^4$ is hydrogen. In some embodiments, $R^4$ is an optionally substituted group selected from $C_{1-6}$ aliphatic.

In some embodiments, $R^4$ is selected from those depicted in Table 1, below.

As defined above, $R^5$ and $R^{5'}$ are each hydrogen or taken together to form =O.

In some embodiments, $R^5$ and $R^{5'}$ are each hydrogen. In some embodiments, $R^5$ and $R^{5'}$ are taken together to form =O.

In some embodiments, $R^5$ and $R^{5'}$ are selected from those depicted in Table 1, below.

As defined above, $R^6$ is hydrogen, —OMe, or halogen.

In some embodiments, $R^6$ is hydrogen. In some embodiments, $R^6$ is —OMe. In some embodiments, $R^6$ is halogen.

In some embodiments, $R^6$ is selected from those depicted in Table 1, below.

As defined above, $X^1$ and $X^2$ are each independently —CH$_2$—, —S—, or —S(O)—, wherein at least one of $X^1$ and $X^2$ is —CH$_2$—.

In some embodiments, $X^1$ is —CH$_2$—. In some embodiments, $X^1$ is —S—. In some embodiments, $X^1$ is —S(O)—.

In some embodiments, $X^2$ is —CH$_2$—. In some embodiments, $X^2$ is —S—. In some embodiments, $X^2$ is —S(O)—.

In some embodiments, $X^1$ and $X^2$ are selected from those depicted in Table 1, below.

In certain embodiments, the present invention provides a compound of Formula I wherein $R^2$ is

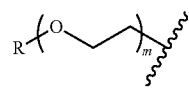

and the stereochemistry is as shown below, thereby providing a compound of Formula I-b-1 or I-b-2:

I-b-1

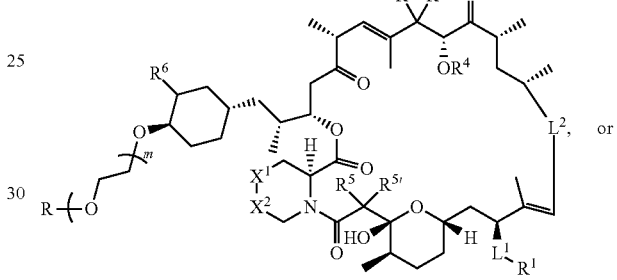

or

I-b-2

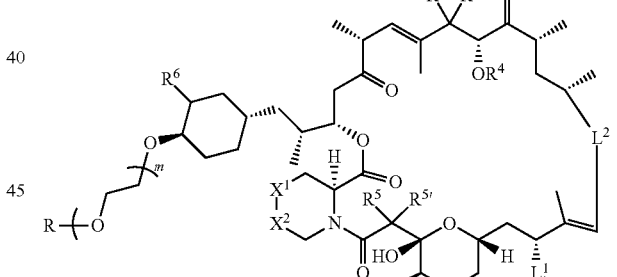

or a pharmaceutically acceptable salt thereof, wherein each of R, $R^1$, $R^3$, $R^{3'}$, $R^4$, $R^5$, $R^{5'}$, $R^6$, $L^1$, $L^2$, $X^1$, $X^2$, and m is as defined and described herein, provided the compound is other than a compound from Table 2.

In certain embodiments, the present invention provides a compound of Formula I wherein $R^2$ is

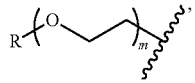

$R^3$ is —OH, $R^{3'}$ is hydrogen, $R^6$ is Me, $X^1$ is —CH$_2$—, $X^2$ is —CH$_2$—, and the stereochemistry is as shown below, thereby providing a compound of Formula I-c-1 or I-c-2:

I-c-1

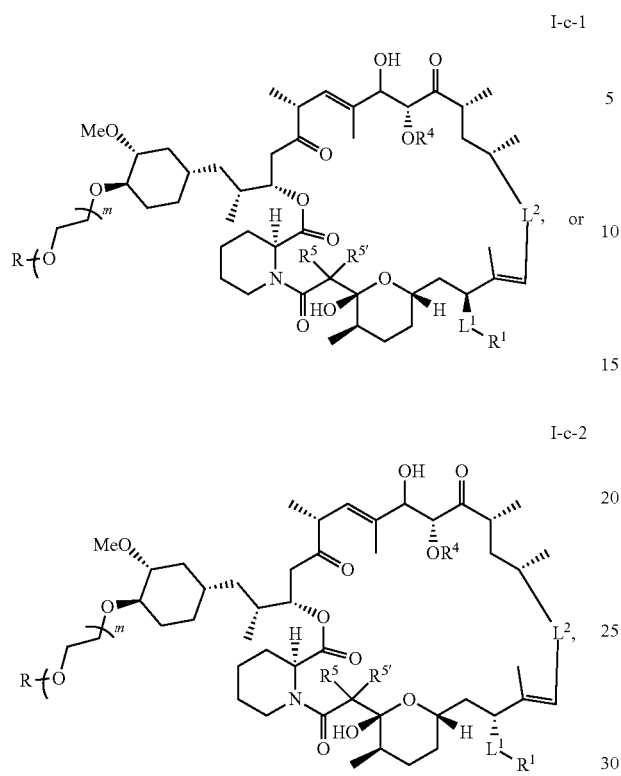

I-c-2

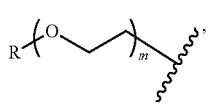

or a pharmaceutically acceptable salt thereof, wherein each of R, R$^1$, R$^4$, R$^5$, R$^{5'}$, L$^1$, L$^2$, and m is as defined and described herein, provided the compound is other than a compound from Table 2.

In certain embodiments, the present invention provides a compound of Formula I wherein R$^2$ is R$^3$ is —OH, R$^{3'}$ is hydrogen, R$^6$ is Me, L$^2$ is Cy$^1$, and the stereochemistry is as shown below, thereby providing a compound of Formula I-d-1 or I-d-2:

I-d-1

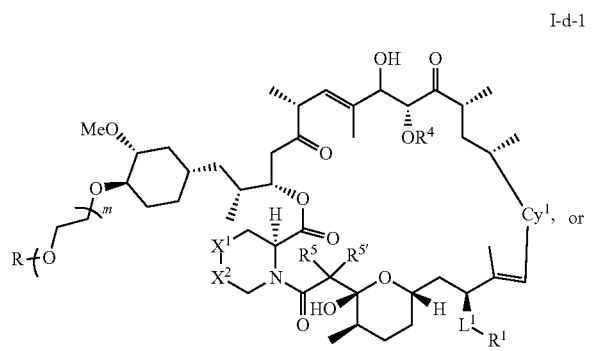

I-d-2

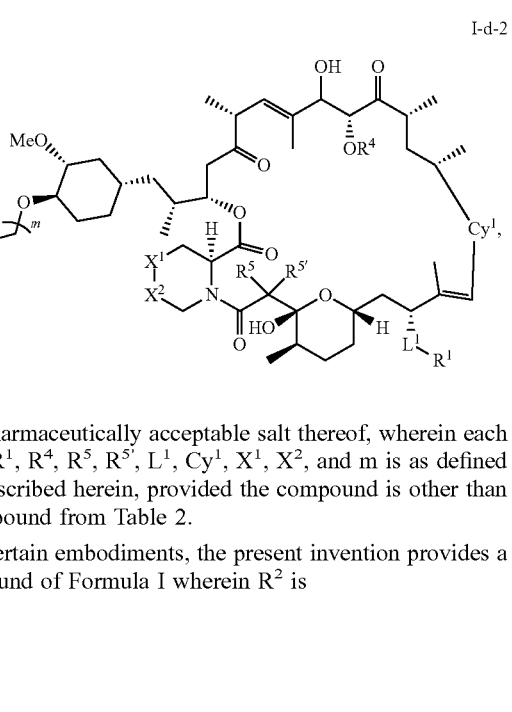

or a pharmaceutically acceptable salt thereof, wherein each of R, R$^1$, R$^4$, R$^5$, R$^{5'}$, L$^1$, Cy$^1$, X$^1$, X$^2$, and m is as defined and described herein, provided the compound is other than a compound from Table 2.

In certain embodiments, the present invention provides a compound of Formula I wherein R$^2$ is

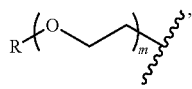

R$^6$ is Me, L$^2$ is

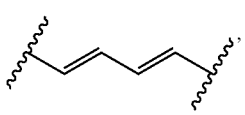 [SMILES: */C=C/C=C/*]

and the stereochemistry is as shown below, thereby providing a compound of Formula I-e-1 or I-e-2:

I-e-1

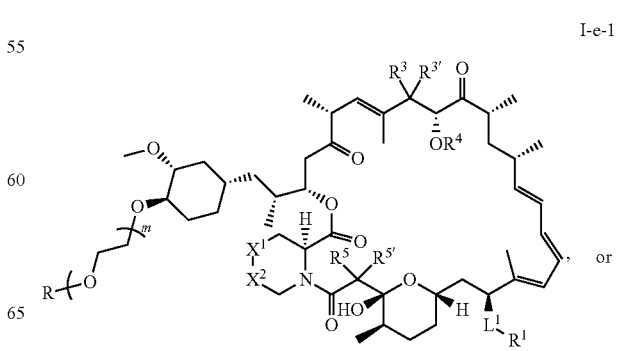

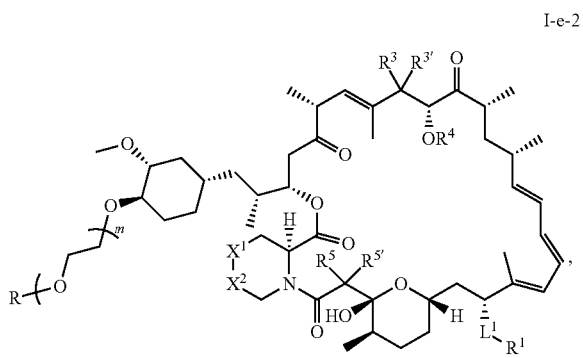

I-e-2

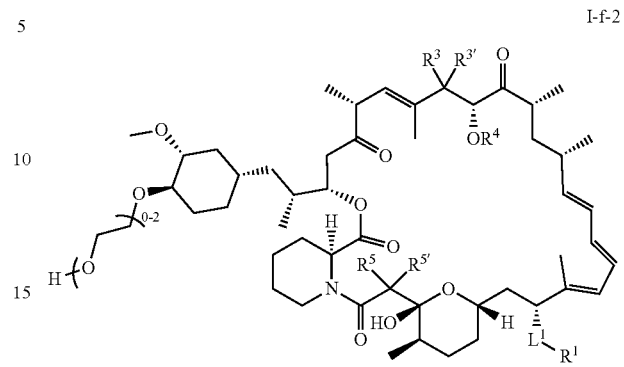

I-f-2 or a pharmaceutically acceptable salt thereof, wherein each of R, $R^1$, $R^3$, $R^{3'}$, $R^4$, $R^5$, $R^{5'}$, $L^1$, $X^1$, $X^2$, and m is as defined and described herein, provided the compound is other than a compound from Table 2.

In certain embodiments, the present invention provides a compound of Formula I wherein $R^2$ is

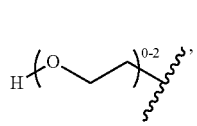

$R^6$ is Me, $X^1$ is —CH$_2$—, $X^2$ is —CH$_2$—, $L^2$ is

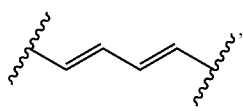 [SMILES: */C=C/C=C/*]

and the stereochemistry is as shown below, thereby providing a compound of Formula I-f-1 or I-f-2:

or a pharmaceutically acceptable salt thereof, wherein each of $R^1$, $R^3$, $R^{3'}$, $R^4$, $R^5$, $R^{5'}$, and $L^1$ is as defined and described herein, provided the compound is other than a compound from Table 2.

In certain embodiments, the present invention provides a compound of Formula I wherein $R^2$ is

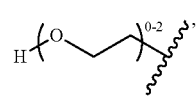

$X^1$ is —CH$_2$—, $X^2$ is —CH$_2$—, $R^5$ and $R^{5'}$ are =O, $L^2$ is

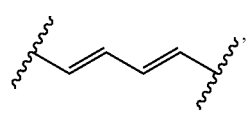 [SMILES: */C=C/C=C/*]

and the stereochemistry is as shown below, thereby providing a compound of Formula I-g-1 or I-g-2:

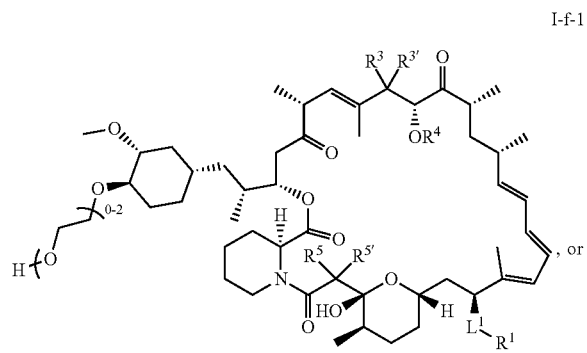

I-f-1

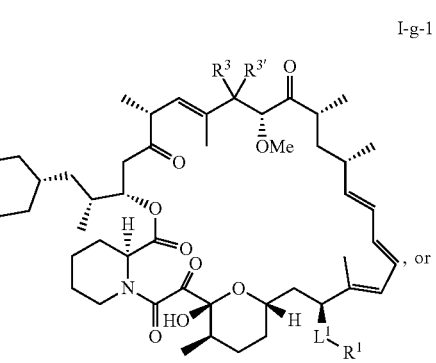

I-g-1

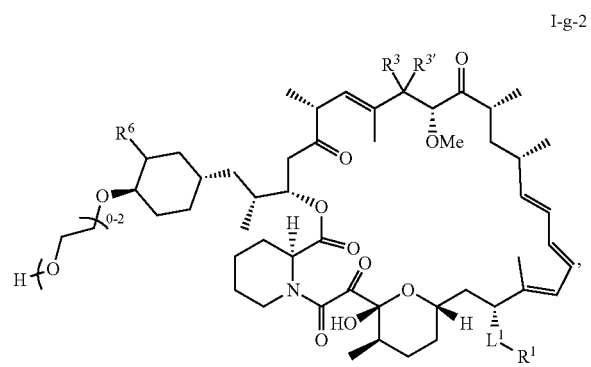

I-g-2 or a pharmaceutically acceptable salt thereof, wherein each of $R^1$, $R^3$, $R^{3'}$, $R^6$, and $L^1$ is as defined and described herein, provided the compound is other than a compound from Table 2.

In certain embodiments, the present invention provides a compound of Formula I wherein $R^2$ is

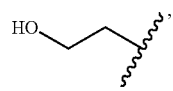

$X^1$ is —$CH_2$—, $X^2$ is —$CH_2$—, $R^5$ and $R^{5'}$ are =O, $L^2$ is

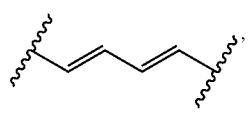 [SMILES: */C=C/C=C/*]

and the stereochemistry is as shown below, thereby providing a compound of Formula I-h-1 or I-h-2:

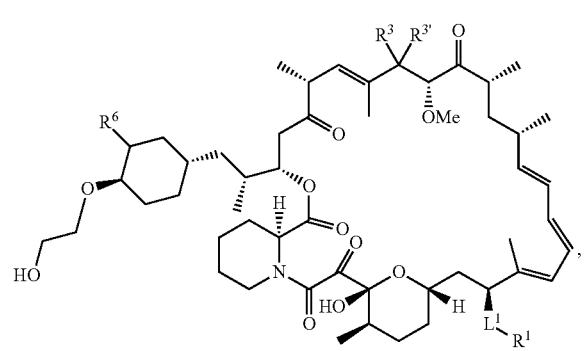

I-h-1

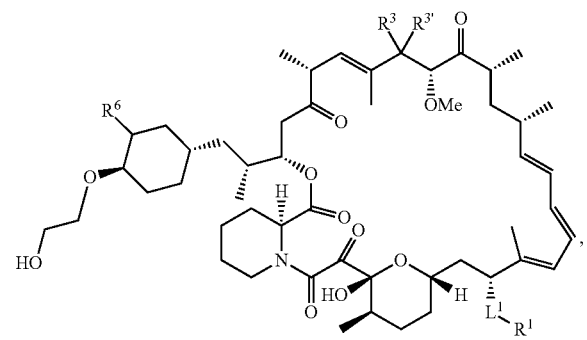

I-h-2 or a pharmaceutically acceptable salt thereof, wherein each of $R^1$, $R^3$, $R^{3'}$, $R^6$, and $L^1$ is as defined and described herein.

In certain embodiments, the present invention provides a compound of Formula I wherein $R^2$ is H, $X^1$ is —$CH_2$—, $X^2$ is —$CH_2$—, $R^5$ and $R^{5'}$ are =O, $L^2$ is and the stereochemistry is as shown below, providing a compound of Formula I-h-1 or I-h-2:

I-h-1

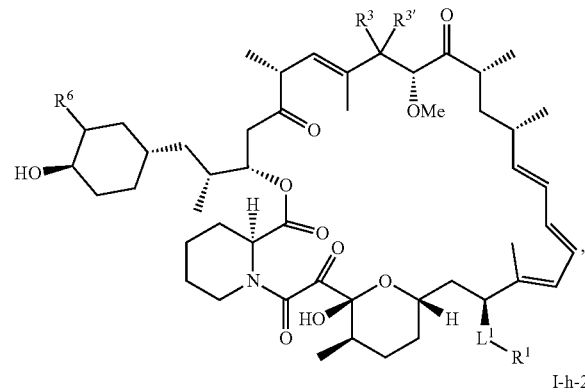

I-h-2

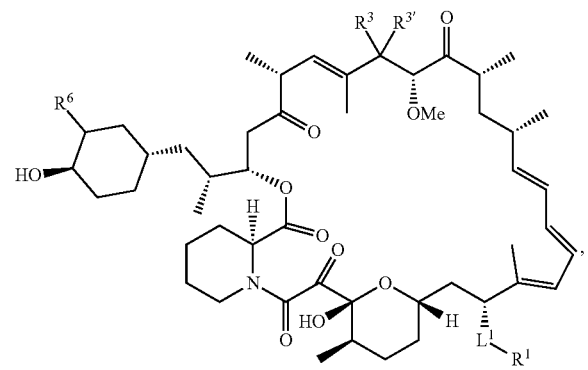

or a pharmaceutically acceptable salt thereof, wherein each of $R^1$, $R^3$, $R^{3'}$, $R^6$, and $L^1$ is as defined and described herein, provided the compound is other than a compound from Table 2.

In certain embodiments, the present invention provides a compound of Formula I wherein $R^2$ is

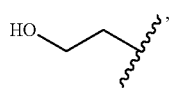

$X^1$ is —$CH_2$—, $X^2$ is —$CH_2$—, $R^4$ is Me, $R^5$ and $R^{5'}$ are =O, $L^2$ is

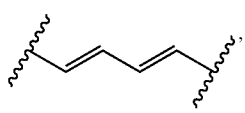 [SMILES: */C=C/C=C/*]

and the stereochemistry is as shown below, thereby providing a compound of Formula I-i-1 or I-i-2:

I-i-1

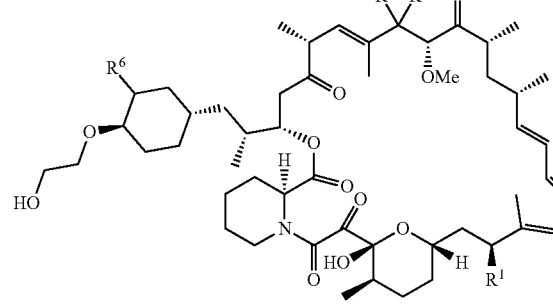

I-i-2

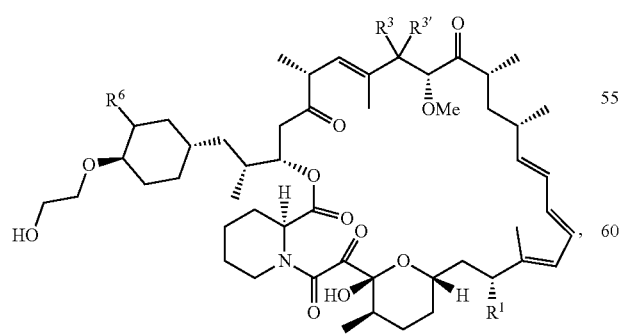

or a pharmaceutically acceptable salt thereof, wherein each of $R^1$, $R^3$, $R^{3'}$, and $R^6$ is as defined and described herein.

In certain embodiments the present invention provides a compound of Formula I wherein $R^2$ is H, $X^1$ is —$CH_2$—, $X^2$ is —$CH_2$—, $R^4$ is Me, $R^5$ and $R^{5'}$ are =O, $L^2$ is

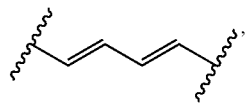 [SMILES: */C=C/C=C/*]

and the stereochemistry is as shown below, thereby providing a compound of Formula I-j-1 or I-j-2:

I-j-1

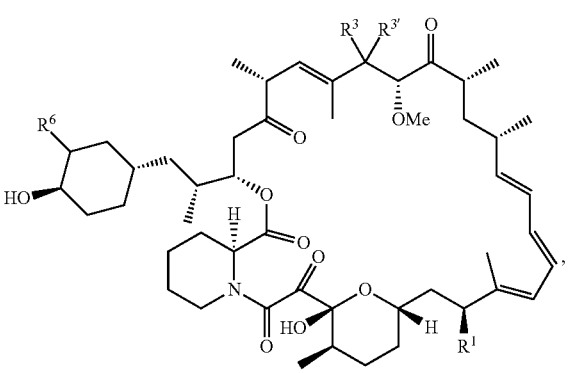

I-j-2 or a pharmaceutically acceptable salt thereof, wherein each of $R^1$, $R^3$, $R^{3'}$, and $R^6$ is as defined and described herein, provided the compound is other than a compound from Table 2.

In certain embodiments, the present invention provides a compound of Formula I wherein $R^2$ is

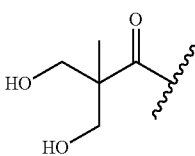

and the stereochemistry is as shown below, thereby providing a compound of Formula I-k-1 or I-k-2:

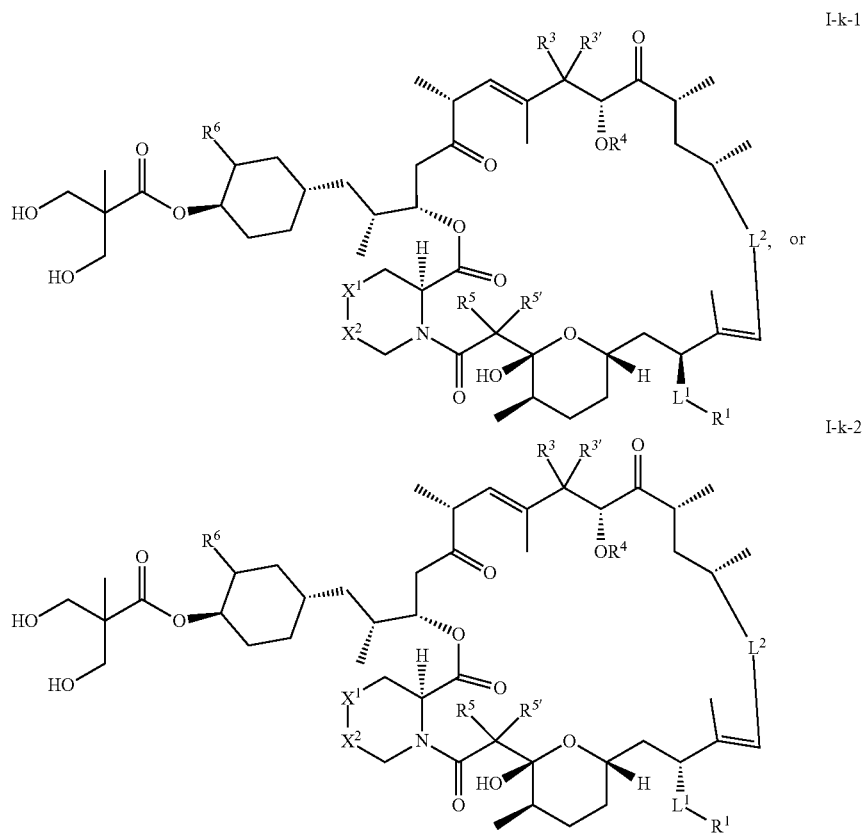

I-k-1, or

I-k-2 or a pharmaceutically acceptable salt thereof, wherein each of $R^1$, $R^3$, $R^{3'}$, $R^4$, $R^5$, $R^{5'}$, $R^6$, $L^1$, $L^2$, $X^1$, and $X^2$ is as defined and described herein.

In certain embodiments, the present invention provides a compound of Formula I wherein $R^2$ is

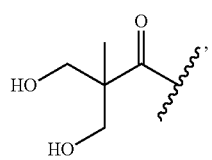

$R^3$ is —OH, $R^{3'}$ is hydrogen, $R^6$ is —OMe, $X^1$ is —CH$_2$—, $X^2$ is —CH$_2$—, and the stereochemistry is as shown below, thereby providing a compound of Formula I-l-1 or I-l-2:

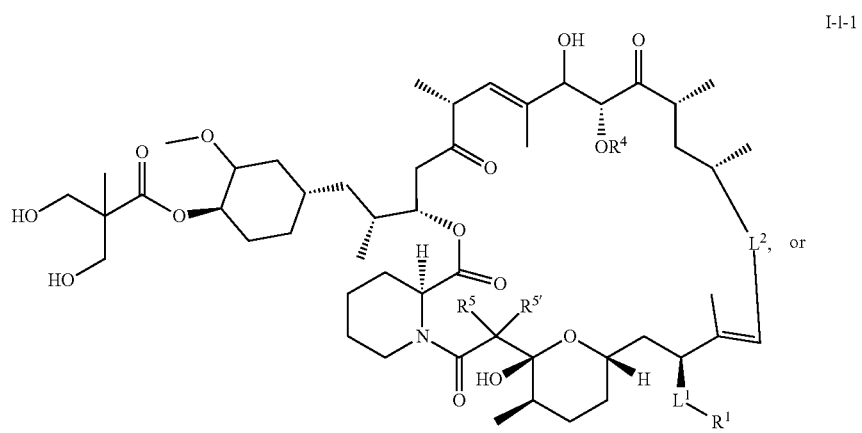

I-l-1, or

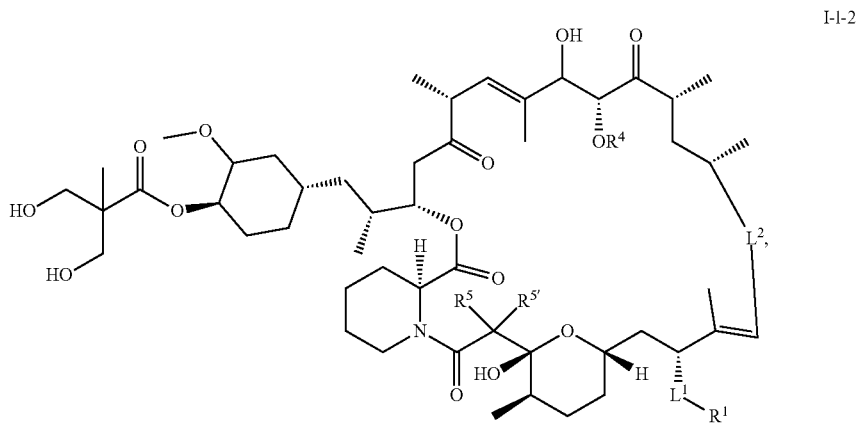

I-l-2 or a pharmaceutically acceptable salt thereof, wherein each of $R^1$, $R^4$, $R^5$, $R^{5'}$, $L^1$, and $L^2$ is as defined and described herein.

In certain embodiments, the present invention provides a compound of Formula I wherein $R^2$ is

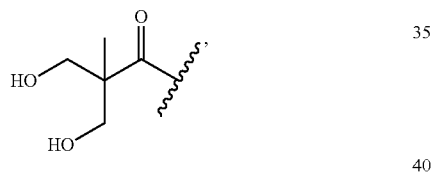

$R^3$ is —OH, $R^{3'}$ is hydrogen, $R^6$ is —OMe, $L^2$ is $Cy^1$, and the stereochemistry is as shown below, thereby providing a compound of Formula I-m-1 or I-m-2:

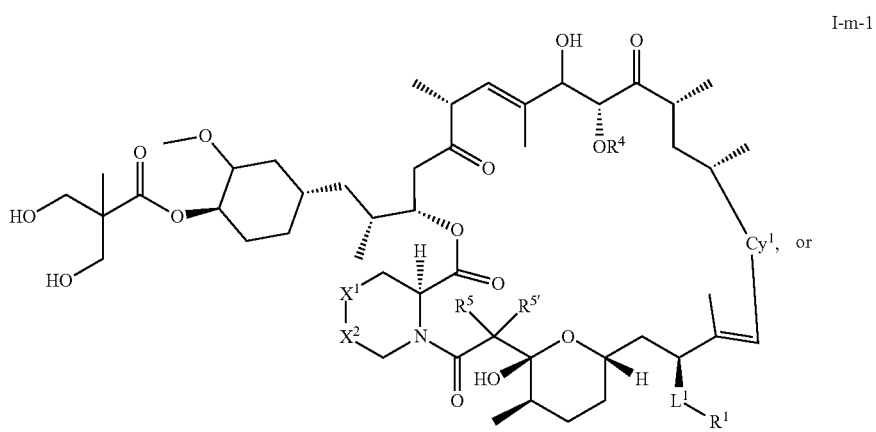

I-m-1

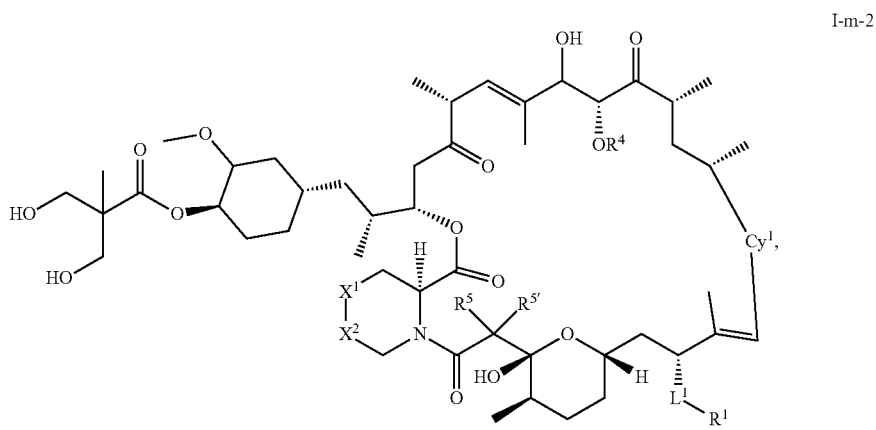

or a pharmaceutically acceptable salt thereof, wherein each of $R^1$, $R^4$, $R^5$, $R^{5'}$, $L^1$, $Cy^1$, $X^1$, and $X^2$ is as defined and described herein.

In certain embodiments, the present invention provides a compound of Formula I wherein $R^2$ is

$R^3$ is —OH, $R^{3'}$ is hydrogen, $R^6$ is —OMe, $L^2$ is and the stereochemistry is as shown below, thereby providing a compound of Formula I-n-1 or I-n-2:

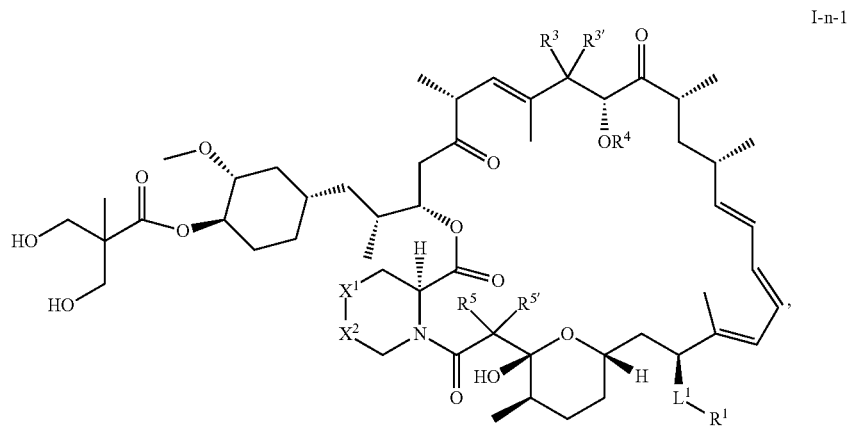

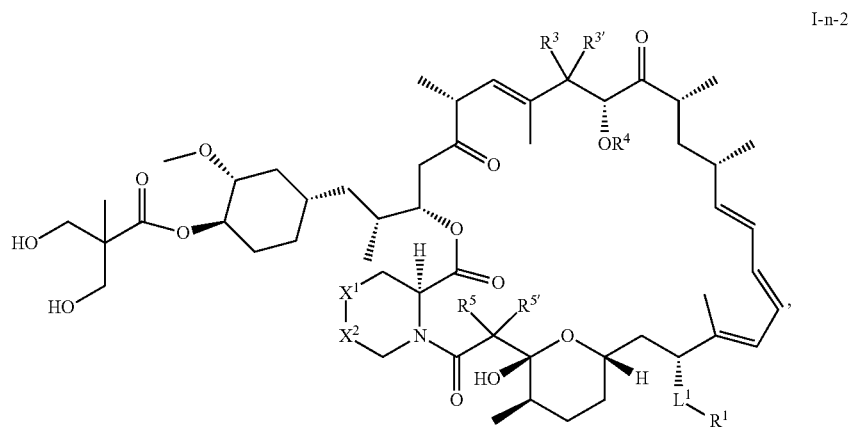

or a pharmaceutically acceptable salt thereof, wherein each of $R^1$, $R^3$, $R^{3'}$, $R^4$, $R^5$, $R^{5'}$, $L^1$, $X^1$, and $X^2$ is as defined and described herein.

In certain embodiments, the present invention provides a compound of Formula I wherein $R^2$ is

$R^6$ is —OMe, $X^1$ is —CH$_2$—, $X^2$ is —CH$_2$—, $L^2$ is and the stereochemistry is as shown below, thereby providing a compound of Formula I-o-1 or I-o-2:

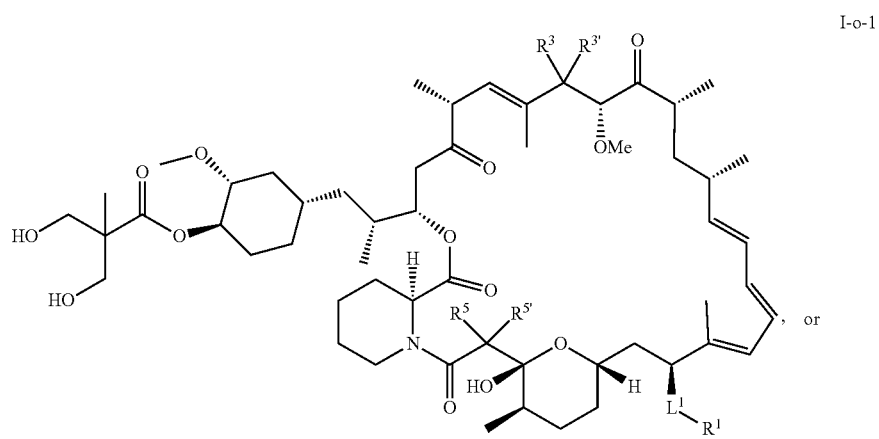

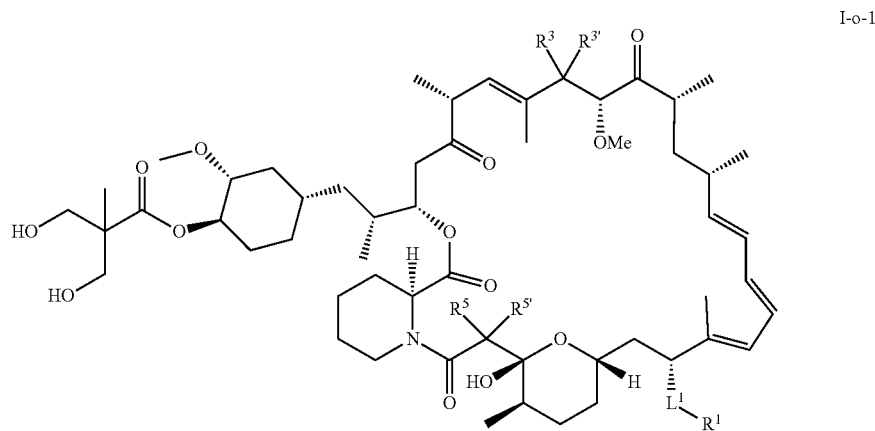
I-o-1 or a pharmaceutically acceptable salt thereof, wherein each of $R^1$, $R^3$, $R^{3'}$, $R^4$, $R^5$, $R^{5'}$, and $L^1$ is as defined and described herein.

In certain embodiments, the present invention provides a compound of Formula I wherein $R^2$ is

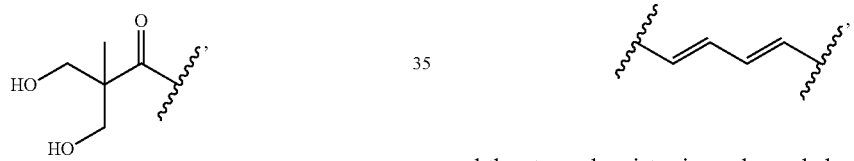

$R^4$ is Me, $R^5$ and $R^{5'}$ are =O, $X^1$ is —CH$_2$—, $L^2$ is and the stereochemistry is as shown below, thereby providing a compound of Formula I-p-1 or I-p-2:

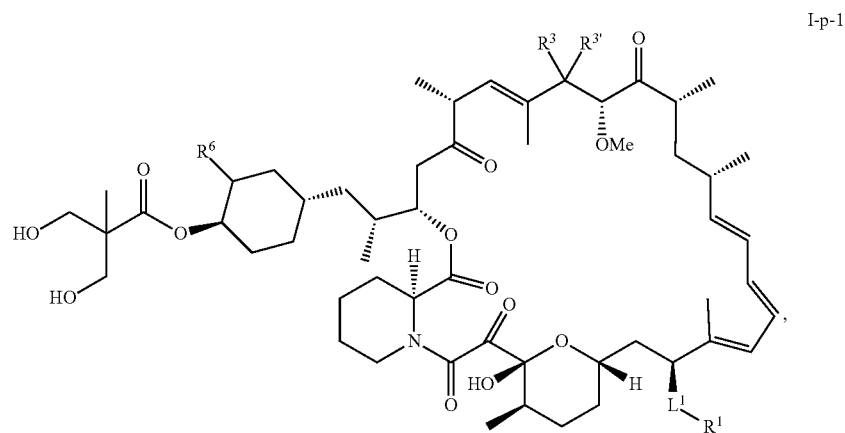
I-p-1

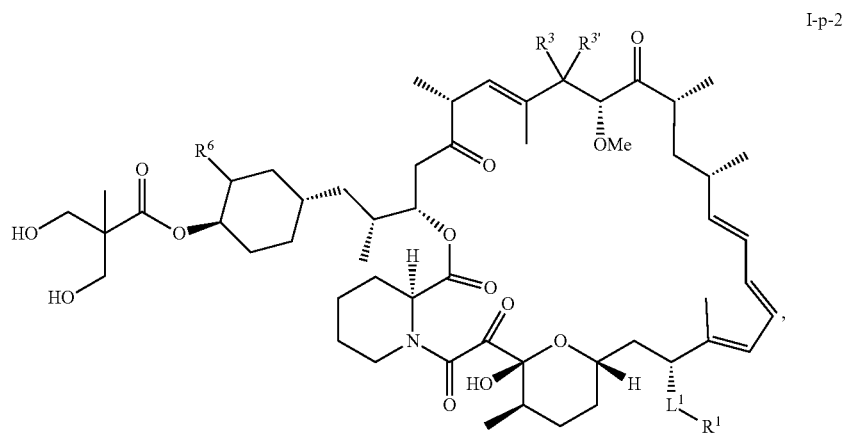

or a pharmaceutically acceptable salt thereof, wherein each of $R^1$, $R^3$, $R^{3'}$, $R^6$, and $L^1$ is as defined and described herein.

In certain embodiments, the present invention provides a compound of Formula I wherein $R^2$ is

$R^4$ is Me, $R^5$ and $R^{5'}$ are =O, $X^1$ is —$CH_2$—, $X^2$ is-$C_2$—, $L^2$ is

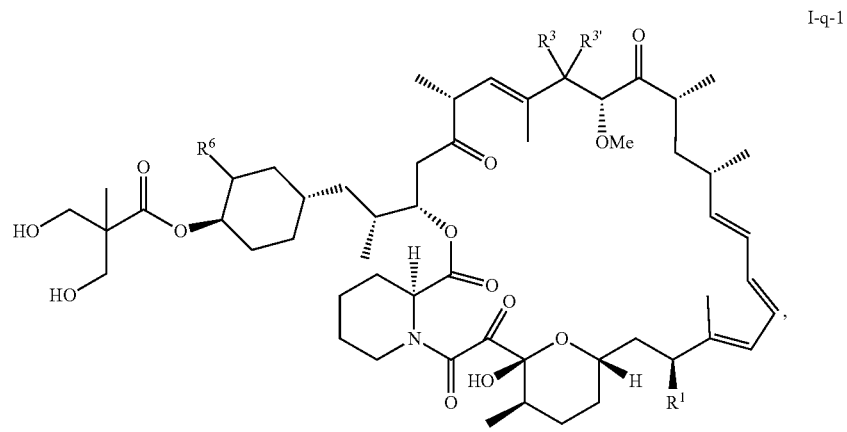

and the stereochemistry is as shown below, thereby providing a compound of Formula I-q-1 or I-q-2:

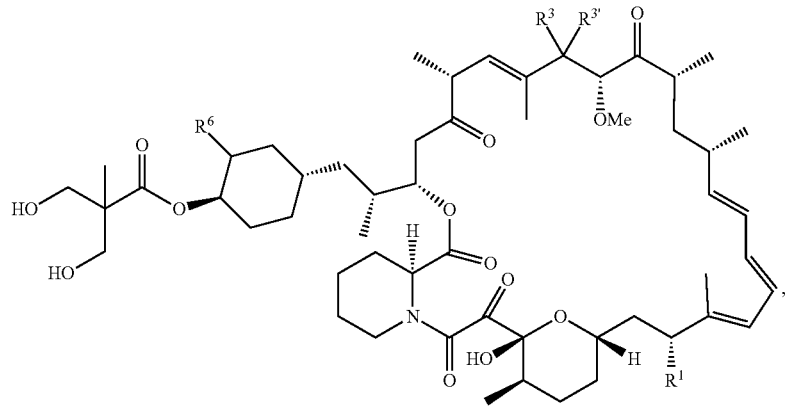

I-q-2 or a pharmaceutically acceptable salt thereof, wherein each of $R^1$, $R^3$, $R^{3'}$, and $R^6$ is as defined and described herein.

In certain embodiments, the present invention provides a compound of Formula I wherein $R^2$ is

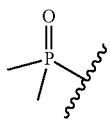

and the stereochemistry is as shown below, thereby providing a compound of Formula I-r-1 or I-r-2:

or a pharmaceutically acceptable salt thereof, wherein each of $R^1$, $R^3$, $R^{3'}$, $R^4$, $R^5$, $R^{5'}$, $R^6$, $L^1$, $L^2$, $X^1$, and $X^2$ is as defined and described herein.

In certain embodiments, the present invention provides a compound of Formula I wherein $R^2$ is

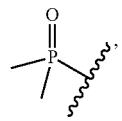

$R^3$ is —OH, $R^{3'}$ is hydrogen, $R^6$ is —OMe, $X^1$ is —CH$_2$—, $X^2$ is —CH$_2$—, and the stereochemistry is as shown below, thereby providing a compound of Formula I-s-1 or I-s-2:

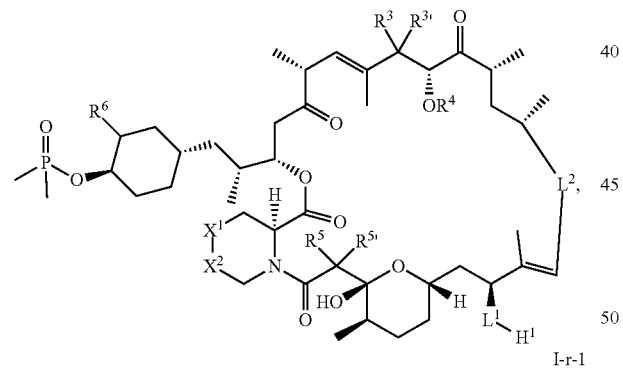

I-r-1

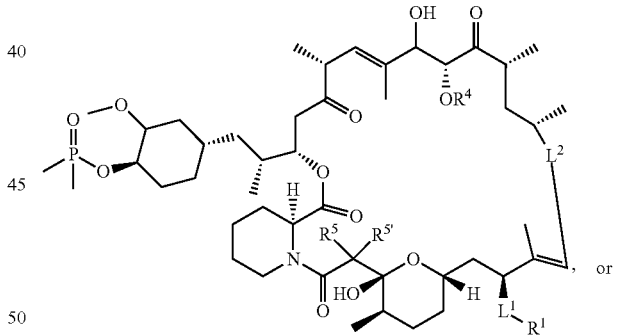

I-s-1

, or

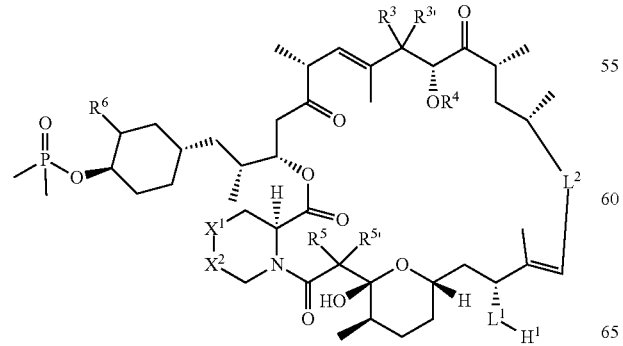

I-r-1

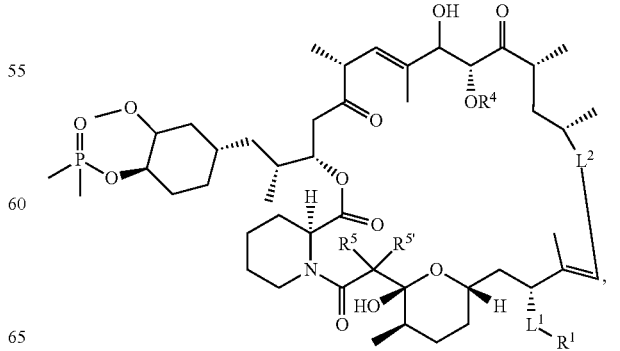

I-s-2 or a pharmaceutically acceptable salt thereof, wherein each of $R^1$, $R^4$, $R^5$, $R^{5'}$, $L^1$, and $L^2$ is as defined and described herein.

In certain embodiments, the present invention provides a compound of Formula I wherein $R^2$ is

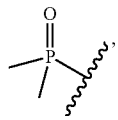

$R^3$ is —OH, $R^{3'}$ is hydrogen, $R^6$ is —OMe, $L^2$ is $Cy^1$, and the stereochemistry is as shown below, thereby providing a compound of Formula I-t-1 or I-t-2:

I-t-1

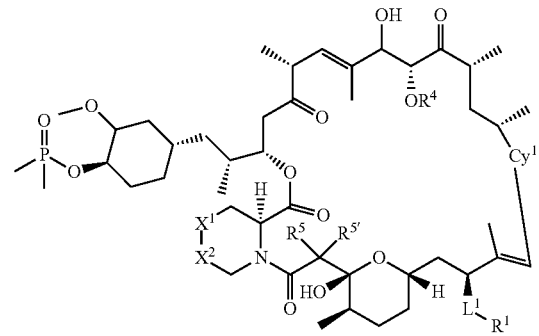

I-t-2

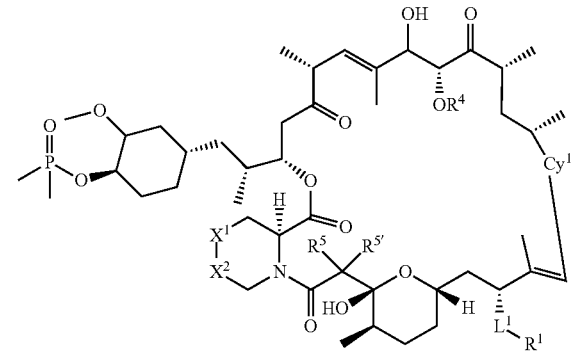

or a pharmaceutically acceptable salt thereof, wherein each of $R^1$, $R^4$, $R^5$, $R^{5'}$, $L^1$, $Cy^1$, $X^1$, and $X^2$ is as defined and described herein.

In certain embodiments, the present invention provides a compound of Formula I wherein $R^2$ is

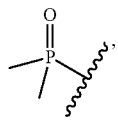

$R^6$ is —OMe, $L^2$ is

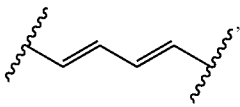

and the stereochemistry is as shown below, thereby providing a compound of Formula I-u-1 or I-u-2:

I-u-1

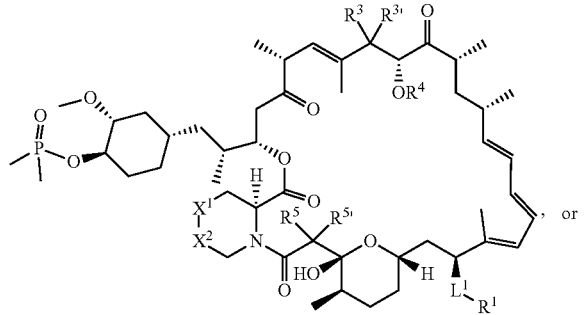

, or

I-u-2

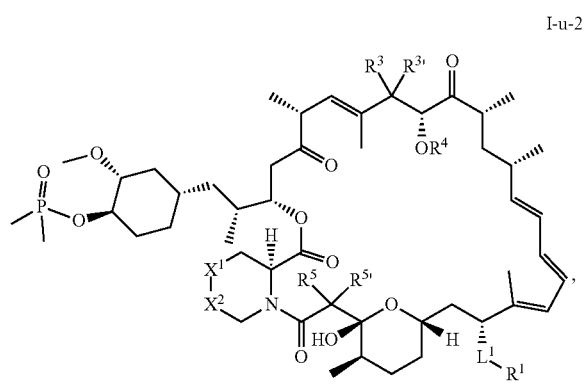

or a pharmaceutically acceptable salt thereof, wherein each of $R^1$, $R^3$, $R^{3'}$, $R^4$, $R^5$, $R^{5'}$, $L^1$, $X^1$, and $X^2$ is as defined and described herein.

In certain embodiments, the present invention provides a compound of Formula I wherein $R^2$ is

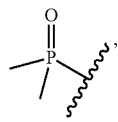

$R^6$ is —OMe, $X^1$ is —$CH_2$—, $X^2$ is —$CH_2$—, $L^2$ is $Cy^1$, $L^2$ is

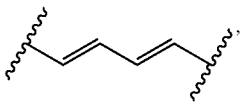 [SMILES: */C=C/C=C/*]

and the stereochemistry is as shown below, providing a compound of Formula I-v-1 or I-v-2:

and the stereochemistry is as shown below, providing a compound of Formula I-w-1 or I-w-2:

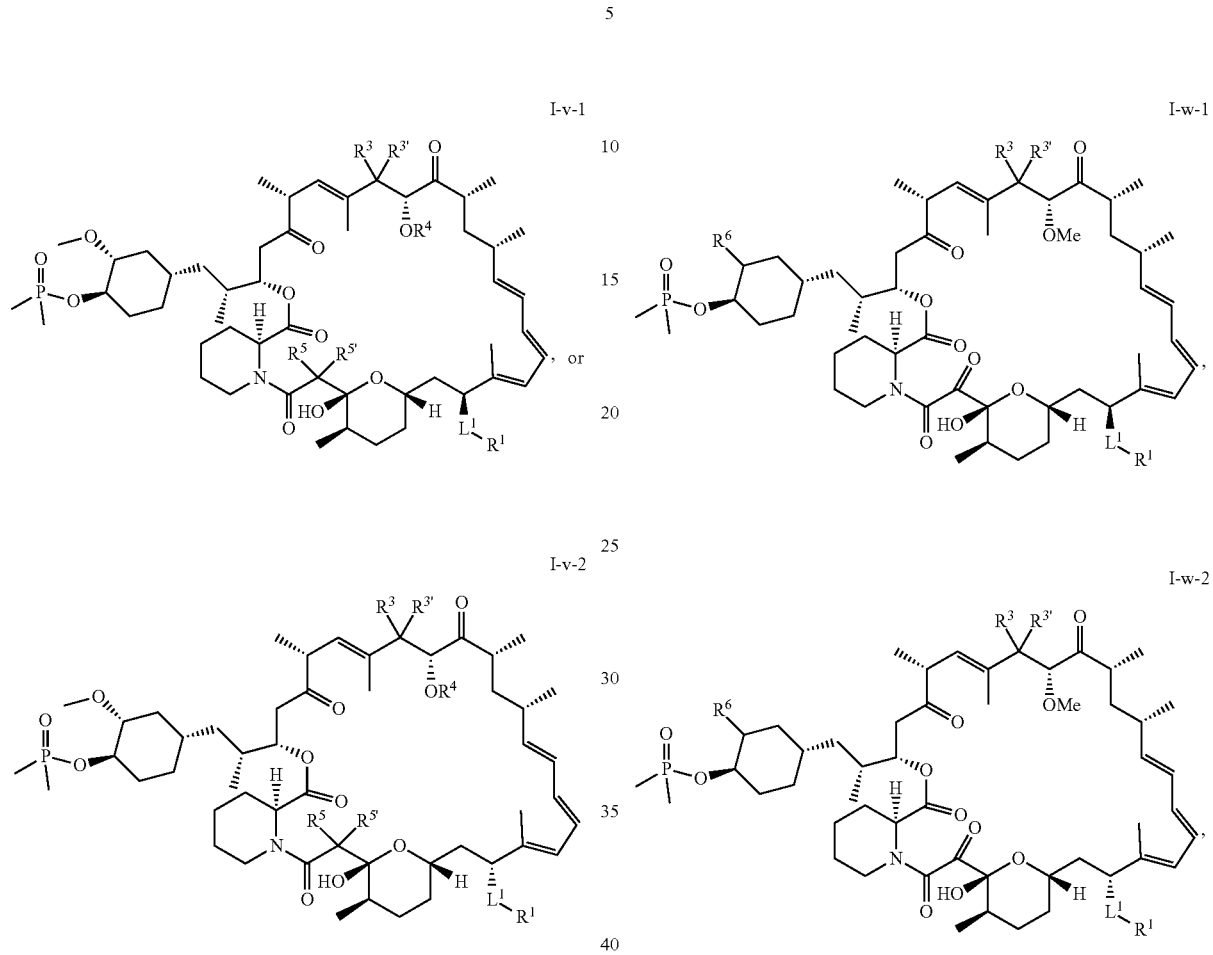

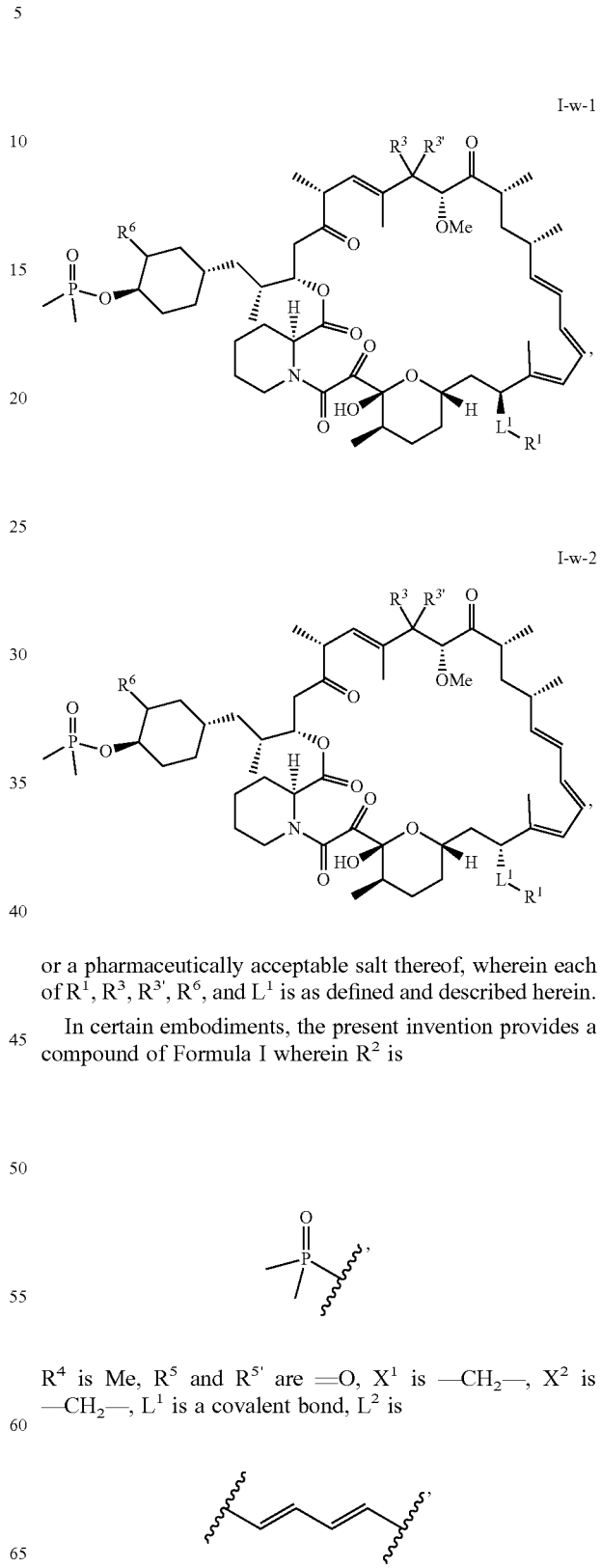

or a pharmaceutically acceptable salt thereof, wherein each of $R^1$, $R^3$, $R^{3'}$, $R^4$, $R^5$, $R^{5'}$, and $L^1$ is as defined and described herein.

In certain embodiments, the present invention provides a compound of Formula I wherein $R^2$ is or a pharmaceutically acceptable salt thereof, wherein each of $R^1$, $R^3$, $R^{3'}$, $R^6$, and $L^1$ is as defined and described herein.

In certain embodiments, the present invention provides a compound of Formula I wherein $R^2$ is $R^4$ is Me, $R^5$ and $R^{5'}$ are =O, $R^6$ is —OMe, $X^1$ is —CH$_2$—, $X^2$ is —CH$_2$—, $L^2$ is $R^4$ is Me, $R^5$ and $R^{5'}$ are =O, $X^1$ is —CH$_2$—, $X^2$ is —CH$_2$—, $L^1$ is a covalent bond, $L^2$ is and the stereochemistry is as shown below, thereby providing a compound of Formula I-x-1 or I-x-2:

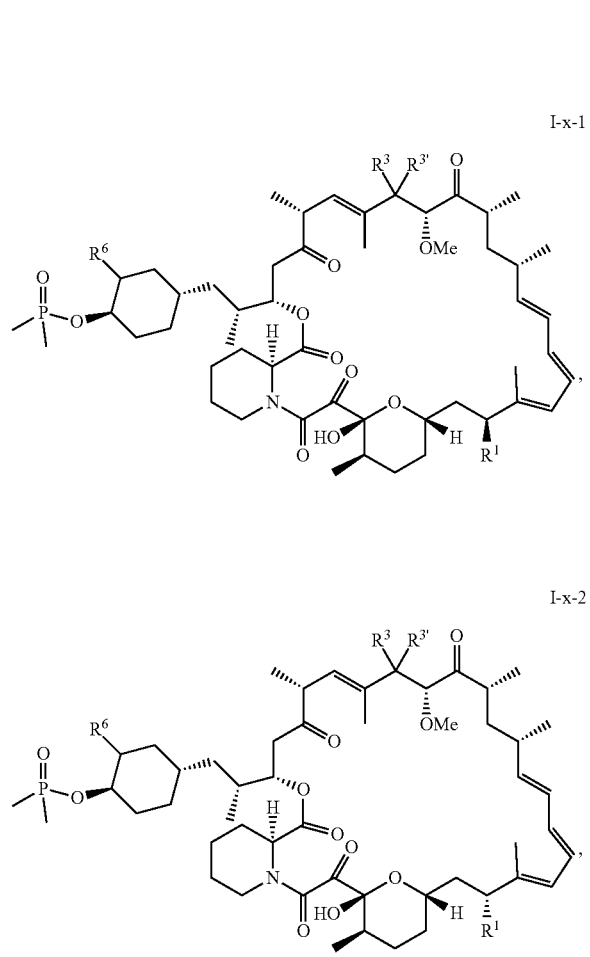

or a pharmaceutically acceptable salt thereof, wherein each of $R^1$, $R^3$, $R^{3'}$, and $R^6$ is as defined and described herein.

In certain embodiments, the present invention provides a compound of Formula I wherein $R^3$ is —OMe, $R^{3'}$ is hydrogen, and the stereochemistry is as shown below, thereby providing a compound of Formula I-y-1, I-y-2, or I-y-3:

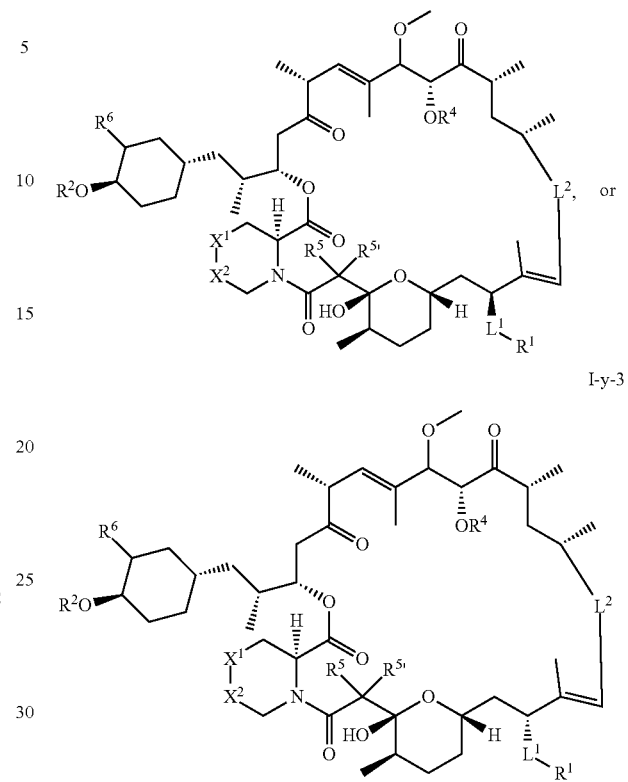

or a pharmaceutically acceptable salt thereof, wherein each of $R^1$, $R^2$, $R^4$, $R^5$, $R^{5'}$, $R^6$, $L^1$, $L^2$, $X^1$, and $X^2$ is as defined and described herein.

In certain embodiments, the present invention provides a compound of Formula I wherein $R^3$ is —OMe, $R^{3'}$ is hydrogen, $X^1$ is —CH$_2$—, $X^2$ is —CH$_2$—, $R^5$ and $R^{5'}$ are =O, $L^2$ is

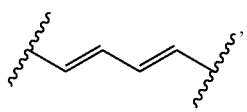 [SMILES: */C=C/C=C/*]

and the stereochemistry is as shown below, thereby providing a compound of Formula I-y-4, I-y-5, or I-y-6:

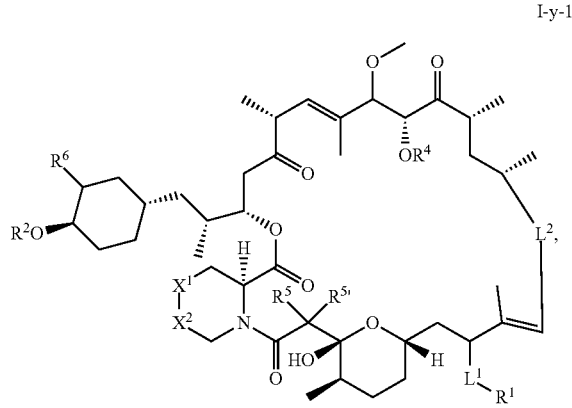
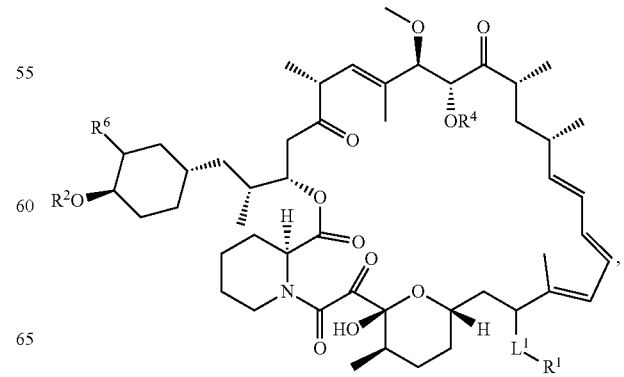

I-y-5

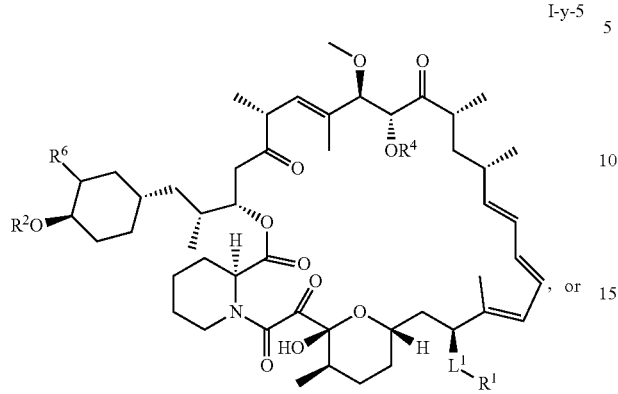

, or

I-z-2

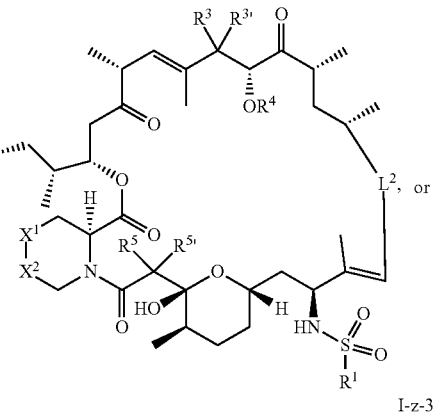

, or

I-y-6

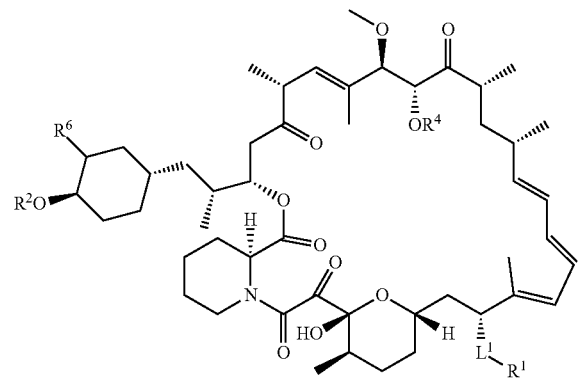

I-z-3 or a pharmaceutically acceptable salt thereof, wherein each of $R^1$, $R^2$, $R^3$, $R^{3'}$, $R^4$, $R^5$, $R^{5'}$, $R^6$, $L^1$, $L^2$, $X^1$, and $X^2$ is as defined and described herein.

or a pharmaceutically acceptable salt thereof, wherein each of R, $R^1$, $R^2$, $R^4$, $R^6$, $L^1$, and m is as defined and described herein.

In certain embodiments, the present invention provides a compound of Formula I wherein $L^1$ is —NH—SO$_2$—, $X^1$ is —CH$_2$—, $X^2$ is —CH$_2$—, $R^5$ and $R^{5'}$ are =O, $L^2$ is In certain embodiments, the present invention provides a compound of Formula I wherein $L^1$ is —NH—SO$_2$— and the stereochemistry is as shown below, thereby providing a compound of Formula I-z-1, I-z-2, or I-z-3:

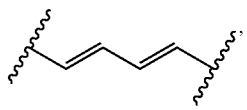 [SMILES: */C=C/C=C/*]

and the stereochemistry is as shown below, thereby providing a compound of Formula I-z-4, I-z-5, or I-z-6:

I-z-1

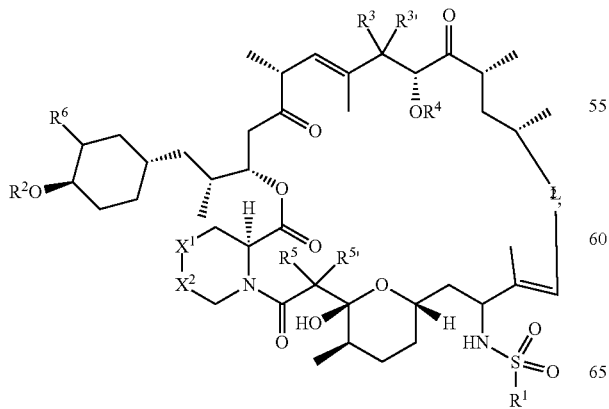

I-z-4

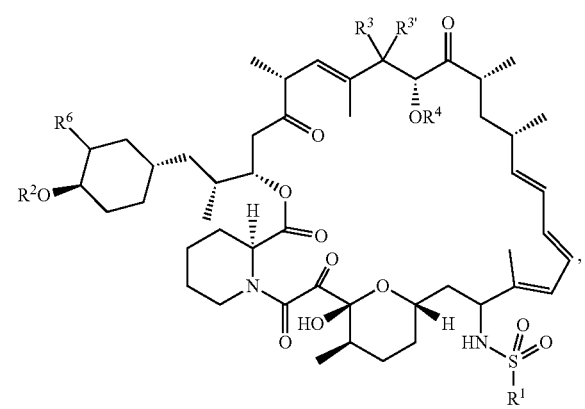

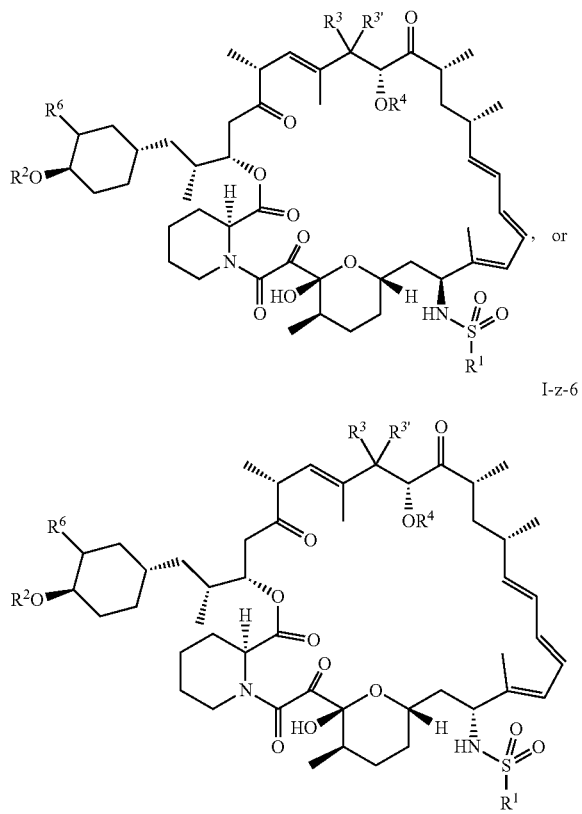

or a pharmaceutically acceptable salt thereof, wherein each of $R^1$, $R^2$, $R^3$, $R^{3'}$, $R^4$, and $R^6$ is as defined and described herein.

Rapamycin is marketed under the brand name Rapamune® (generic name, sirolimus) and is well known for its antiproliferative and immunosuppressive activity. Rapamycin is FDA approved for the prevention of transplant rejection and for coating stents to prevent restenosis. Aside from the documented benefits of rapamycin, it is well known that rapamycin is associated with a number of serious side effects. Such side effects include diabetes-like symptoms of decreased glucose tolerance and lowering of insulin sensitivity. In addition, it has been reported that rapamycin activates the Akt signaling pathway (including activation of Akt and ERK) thereby increasing a patient's risk of cancer.

As used herein the phrase "rapamycin alone" is intended to compare a compound of the present invention with rapamycin, or an analog thereof such as everolimus, as alternatives.

In some embodiments, a provided compound of Formula I is more efficacious than rapamycin alone.

In some embodiments, a provided compound of Formula I-a-1 is more efficacious than rapamycin alone.

In some embodiments, a provided compound of Formula I-a-2 is more efficacious than rapamycin alone.

In some embodiments, a provided compound of Formula I, when administered to a patient, results in fewer and/or lesser severity of side effects than when rapamycin is administered.

In some embodiments, a provided compound of Formula I-a-1, when administered to a patient, results in fewer and/or lesser severity of side effects than when rapamycin is administered.

In some embodiments, a provided compound of Formula I-a-2, when administered to a patient, results in fewer and/or lesser severity of side effects than when rapamycin is administered.

Exemplary compounds of the invention are set forth in Table 1, below.

TABLE 1

| Exemplary Compounds | |
|---|---|
| I-# | Structure |
| I-1 | 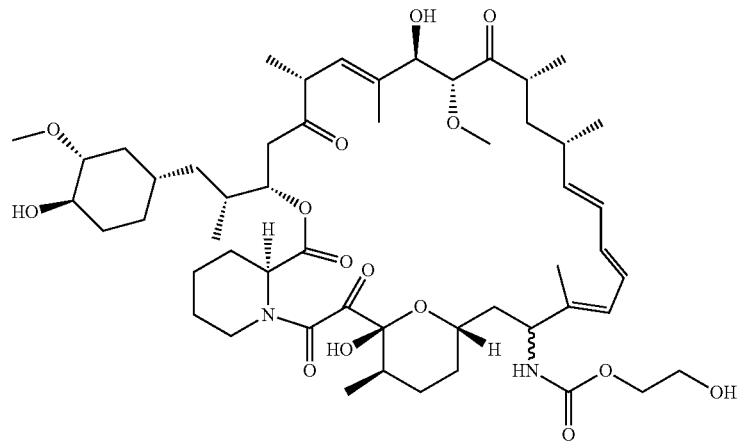 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(NC(=O)OCCO)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-2 | 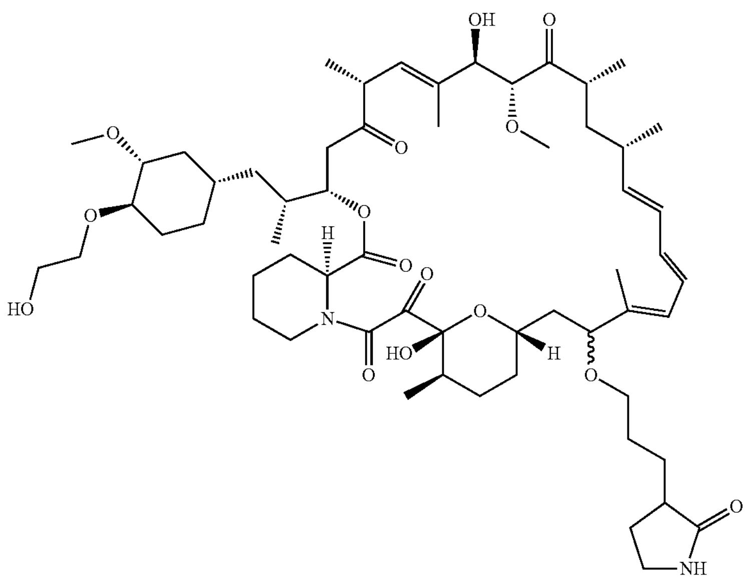 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCCC3CCNC3=O)C[C@@H]3CC[C@@H](C)[C@@](O)(O3)C(=O)C(=O)N3CCCC[C@H]3C(=O)O2)CC[C@H]1OCCO] |
| I-3 | 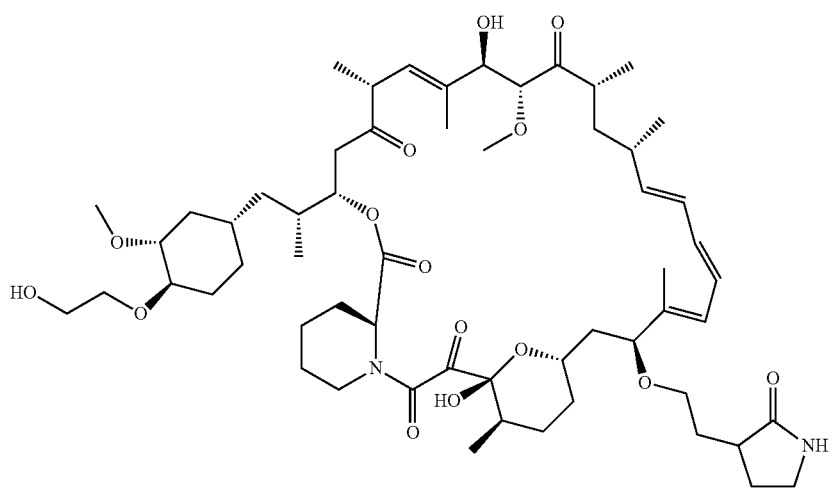 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCC3CCNC3=O)C[C@@H]3CC[C@@H](C)[C@@](O)(O3)C(=O)C(=O)N3CCCC[C@H]3C(=O)O2)CC[C@H]1OCCO] |

TABLE 1-continued
Exemplary Compounds
| I-# | Structure |
|---|---|
| I-4 | 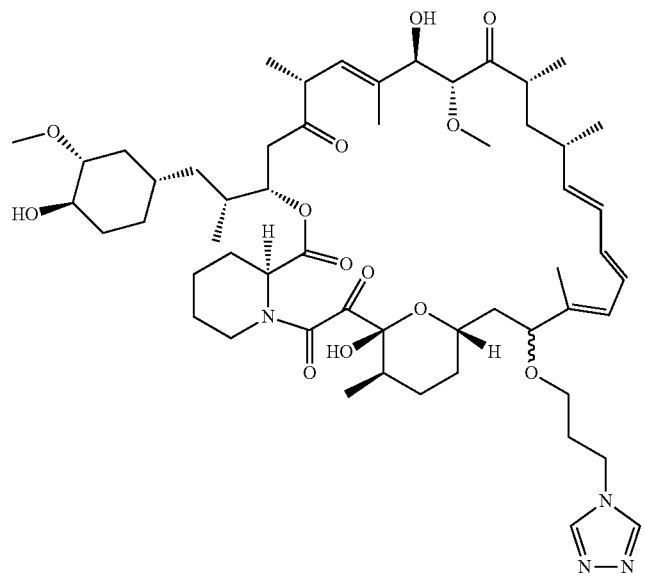 |
| I-5 | 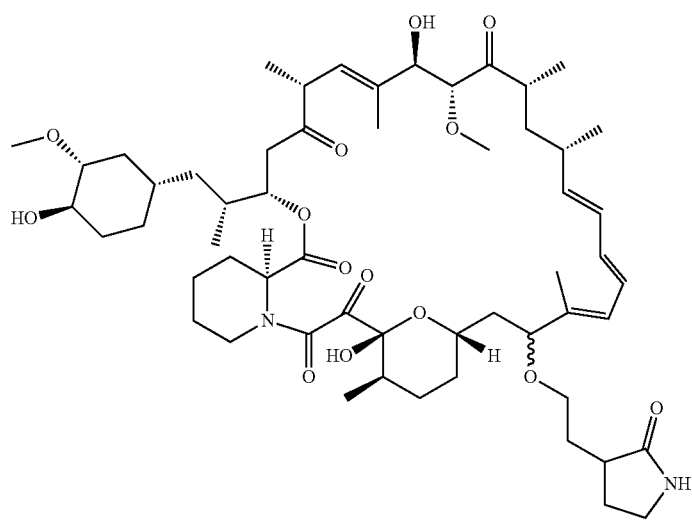 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCC3CCNC3=O)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-6 | 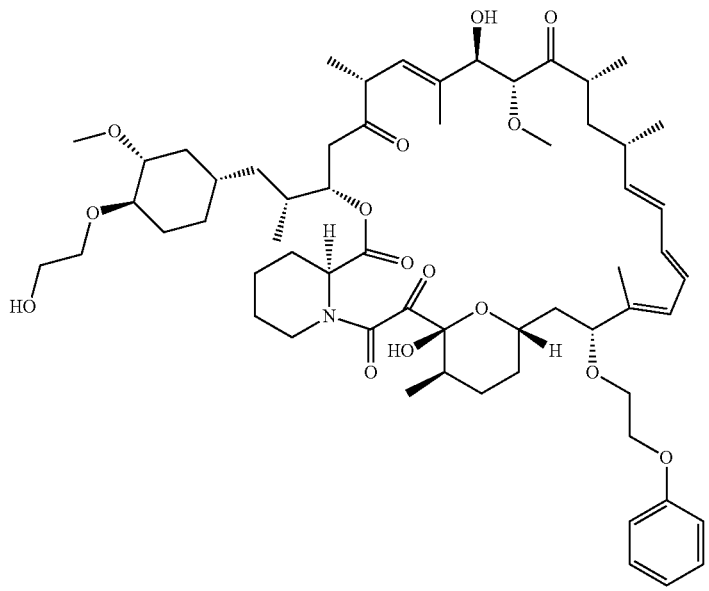 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCOc3ccccc3)C[C@@H]3CC[C@@H](C)[C@@](O)(O3)C(=O)C(=O)N3CCCC[C@H]3C(=O)O2)CC[C@H]1OCCO] |
| I-7 | 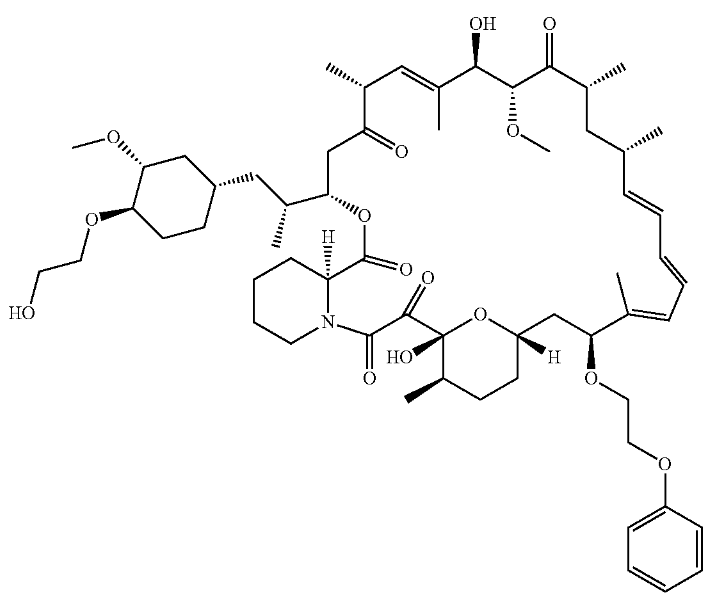 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOc3ccccc3)C[C@@H]3CC[C@@H](C)[C@@](O)(O3)C(=O)C(=O)N3CCCC[C@H]3C(=O)O2)CC[C@H]1OCCO] |

TABLE 1-continued
Exemplary Compounds
| I-# | Structure |
|---|---|
| I-8 | 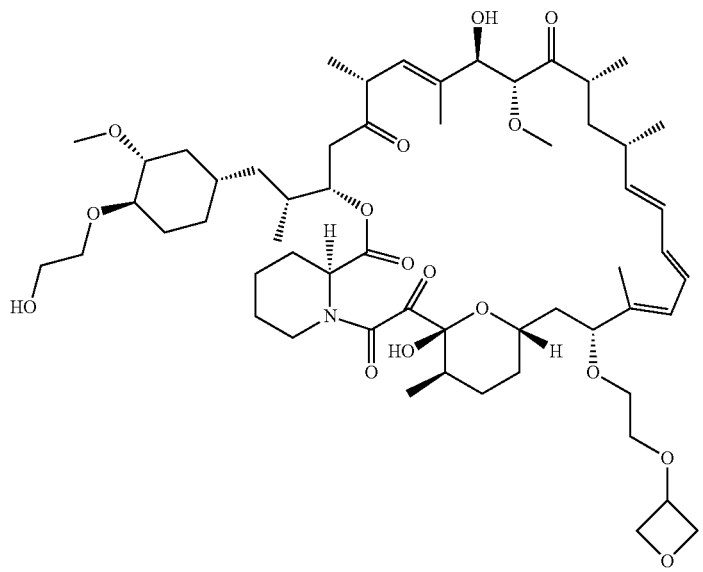 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCOC3COC3)C[C@@H]3CC[C@@H](C)[C@@](O)(O3)C(=O)C(=O)N3CCCC[C@H]3C(=O)O2)CC[C@H]1OCCO] |
| I-9 | 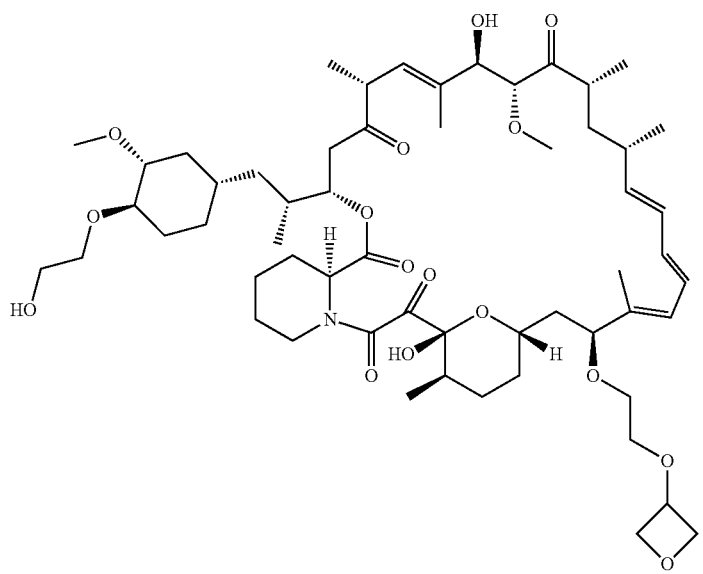 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOC3COC3)C[C@@H]3CC[C@@H](C)[C@@](O)(O3)C(=O)C(=O)N3CCCC[C@H]3C(=O)O2)CC[C@H]1OCCO] |

TABLE 1-continued
Exemplary Compounds
| I-# | Structure |
|---|---|
| I-10 | 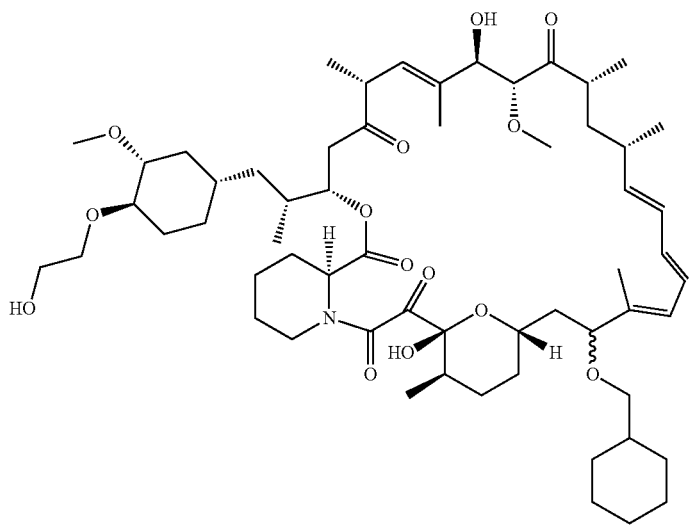 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCC3CCCCC3)C[C@@H]3CC[C@@H](C)[C@@](O)(O3)C(=O)C(=O)N3CCCC[C@H]3C(=O)O2)CC[C@H]1OCCO] |
| I-11 | 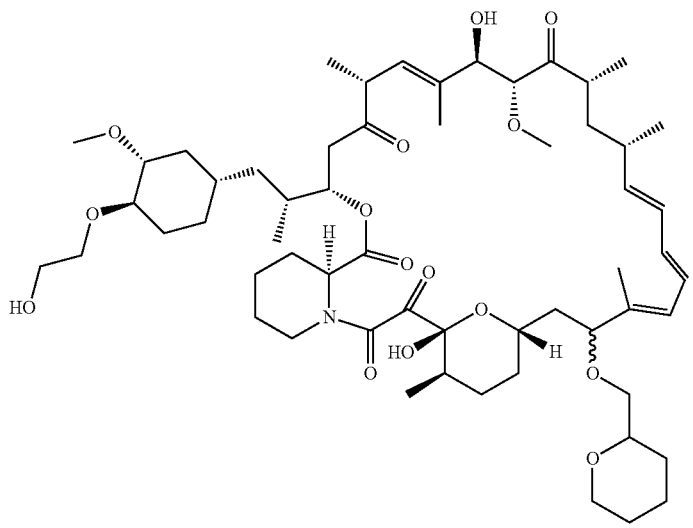 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCC3CCCCO3)C[C@@H]3CC[C@@H](C)[C@@](O)(O3)C(=O)C(=O)N3CCCC[C@H]3C(=O)O2)CC[C@H]1OCCO] |

TABLE 1-continued
Exemplary Compounds
| I-# | Structure |
|---|---|
| I-12 | 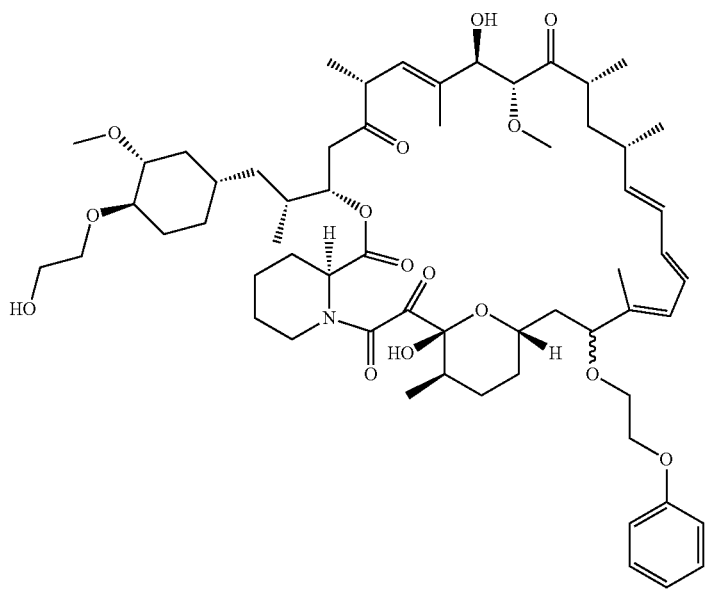 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOc3ccccc3)C[C@@H]3CC[C@@H](C)[C@@](O)(O3)C(=O)C(=O)N3CCCC[C@H]3C(=O)O2)CC[C@H]1OCCO] |
| I-13 | 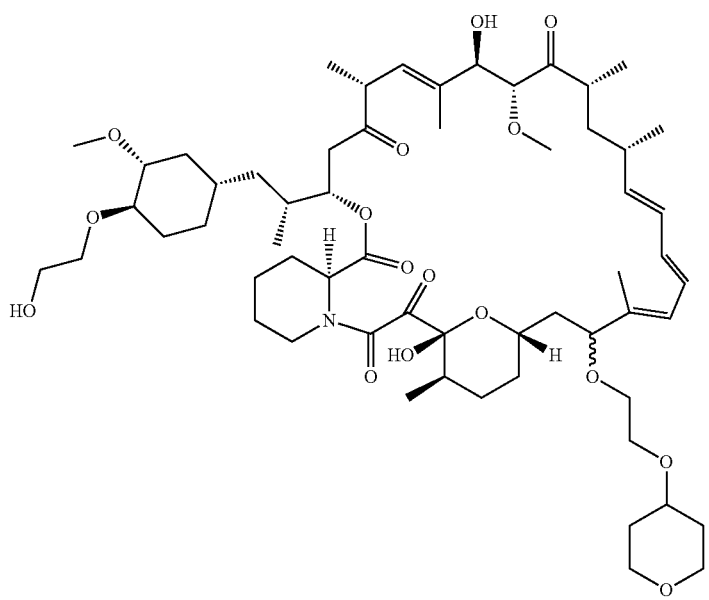 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOC3CCOCC3)C[C@@H]3CC[C@@H](C)[C@@](O)(O3)C(=O)C(=O)N3CCCC[C@H]3C(=O)O2)CC[C@H]1OCCO] |

TABLE 1-continued
Exemplary Compounds
| I-# | Structure |
|---|---|
| I-14 | 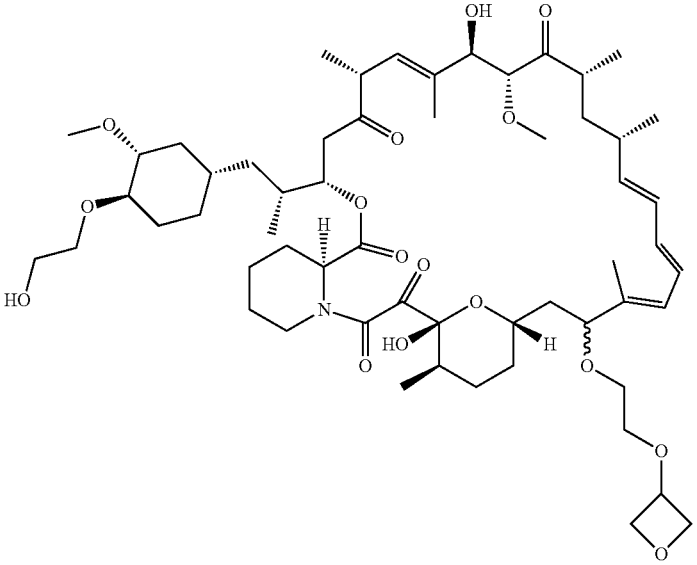 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOC3COC3)C[C@@H]3CC[C@@H](C)[C@@](O)(O3)C(=O)C(=O)N3CCCC[C@H]3C(=O)O2)CC[C@H]1OCCO] |
| I-15 | 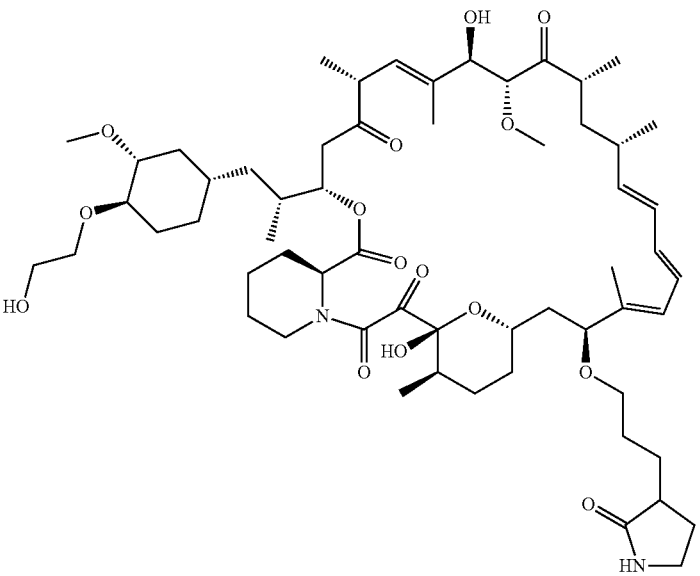 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCCC3CCNC3=O)C[C@@H]3CC[C@@H](C)[C@@](O)(O3)C(=O)C(=O)N3CCCC[C@H]3C(=O)O2)CC[C@H]1OCCO] |
| I-16 | 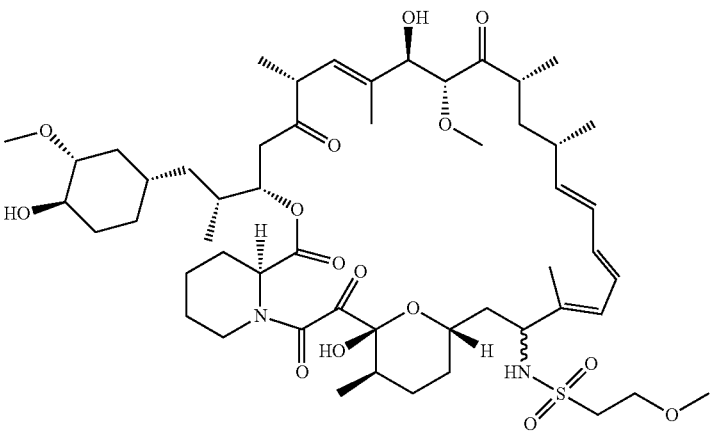 |

TABLE 1-continued
Exemplary Compounds
| I-# | Structure |
|---|---|
| I-17 | 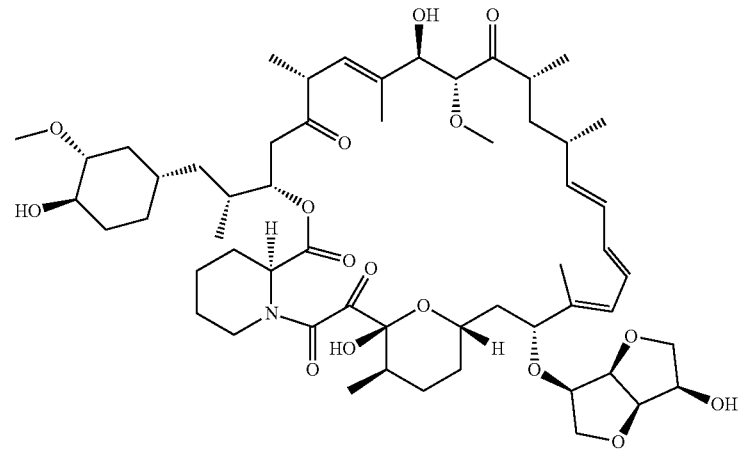 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](O[C@@H]3CO[C@H]4[C@@H]3OC[C@H]4O)C[C@@H]3CC[C@@H](C)[C@@](O)(O3)C(=O)C(=O)N3CCCC[C@H]3C(=O)O2)CC[C@H]1O] |
| I-18 | 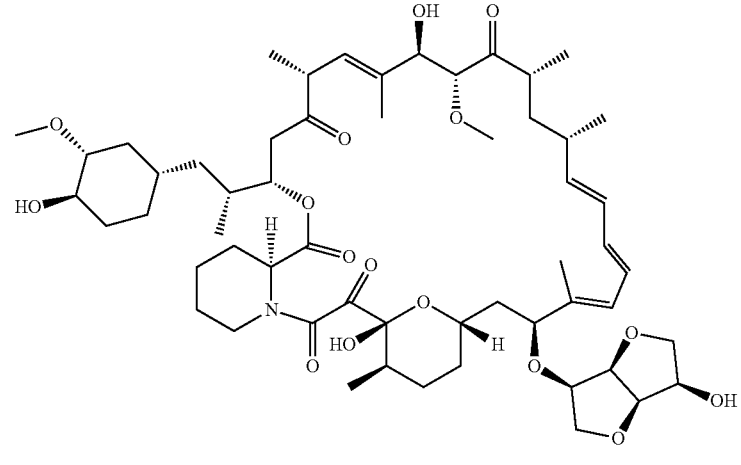 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](O[C@@H]3CO[C@H]4[C@@H]3OC[C@H]4O)C[C@@H]3CC[C@@H](C)[C@@](O)(O3)C(=O)C(=O)N3CCCC[C@H]3C(=O)O2)CC[C@H]1O] |
| I-19 | 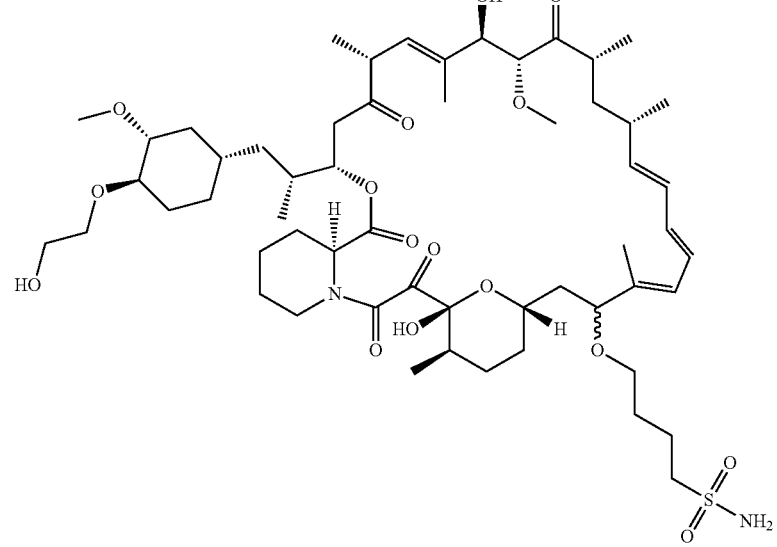 |

TABLE 1-continued
Exemplary Compounds
| I-# | Structure |
|-----|-----------|
| I-20 | 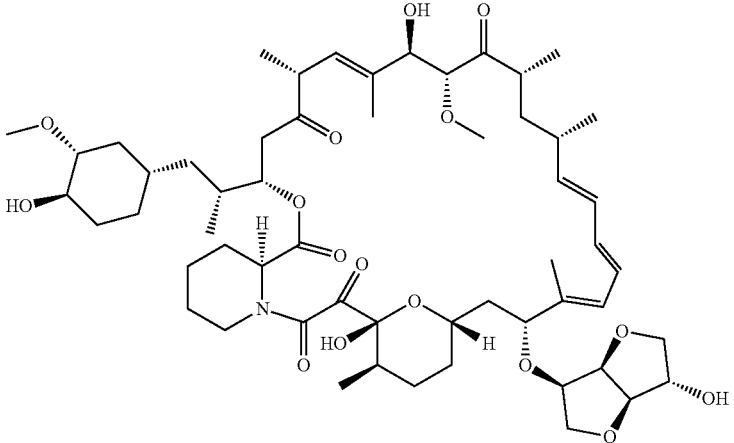 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](O[C@@H]3CO[C@H]4[C@@H]3OC[C@@H]4O)C[C@@H]3CC[C@@H](C)[C@@](O)(O3)C(=O)C(=O)N3CCCC[C@H]3C(=O)O2)CC[C@H]1O] |
| I-21 | 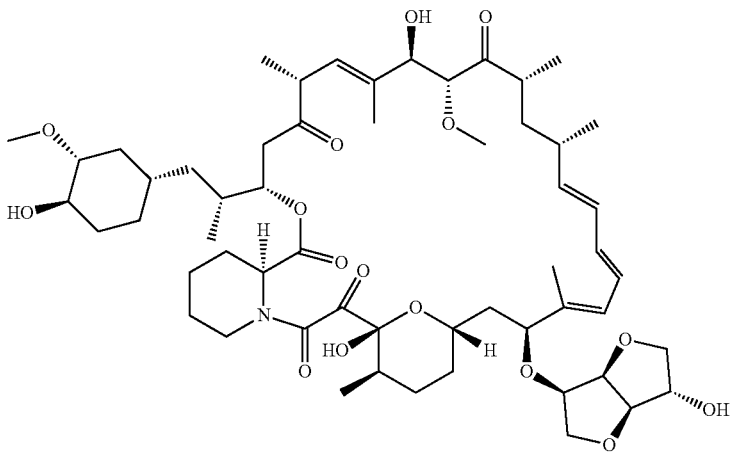 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](O[C@@H]3CO[C@H]4[C@@H]3OC[C@@H]4O)C[C@@H]3CC[C@@H](C)[C@@](O)(O3)C(=O)C(=O)N3CCCC[C@H]3C(=O)O2)CC[C@H]1O] |
| I-22 | 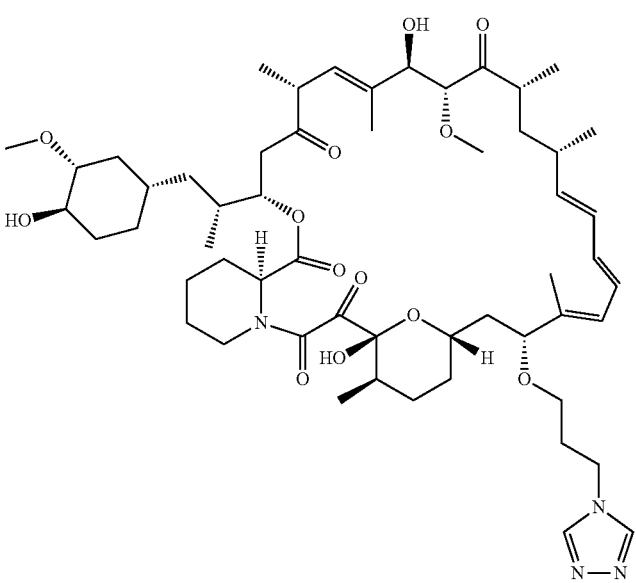 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCCn3cnnc3)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
| --- | --- |
| I-23 | 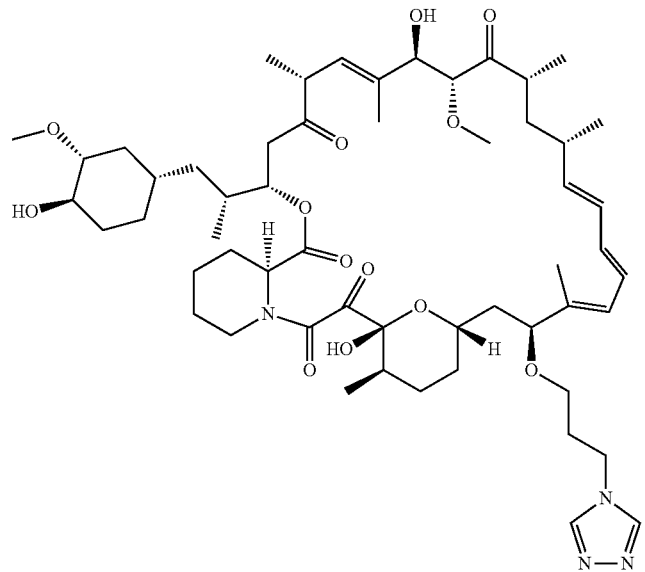 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCCn3cnnc3)C[C@@H]3CC[C@@H](C)[C@@](O)(O3)C(=O)C(=O)N3CCCC[C@H]3C(=O)O2)CC[C@H]1O] |
| I-24 | 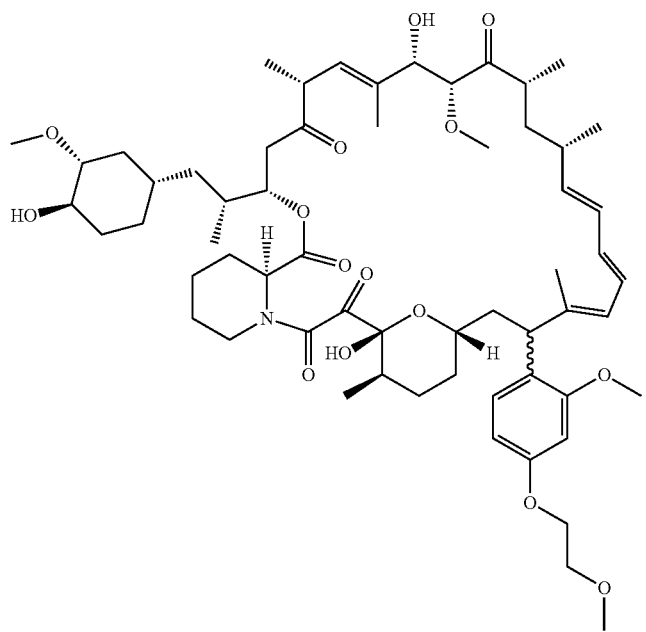 |

TABLE 1-continued
Exemplary Compounds
| I-# | Structure |
|---|---|
| I-25 | 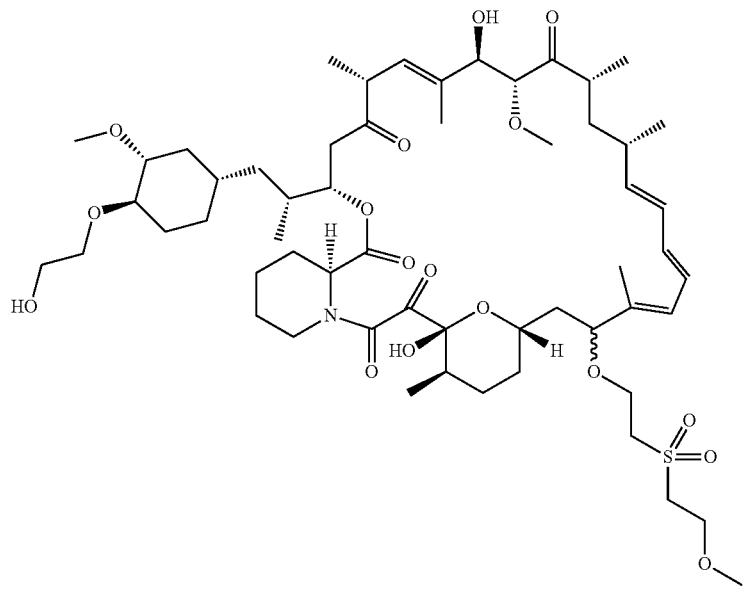 [SMILES: COCCS(=O)(=O)CCOC1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C] |
| I-26 | 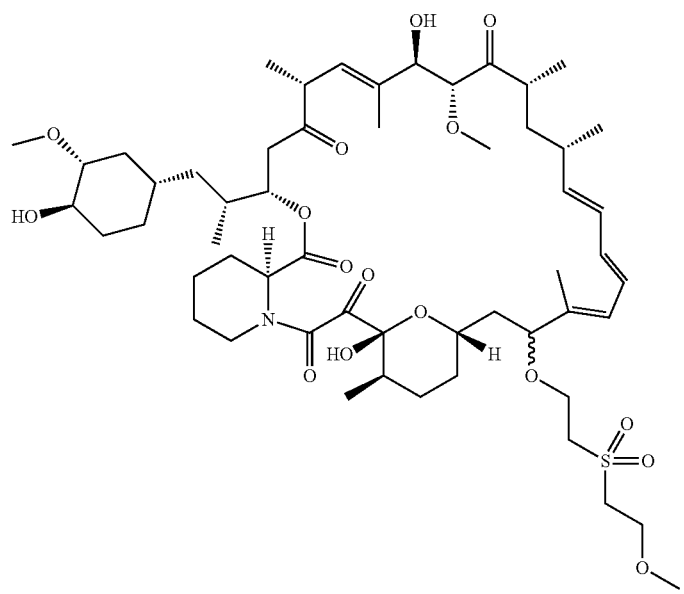 |

TABLE 1-continued
Exemplary Compounds
| I-# | Structure |
|---|---|
| I-27 | 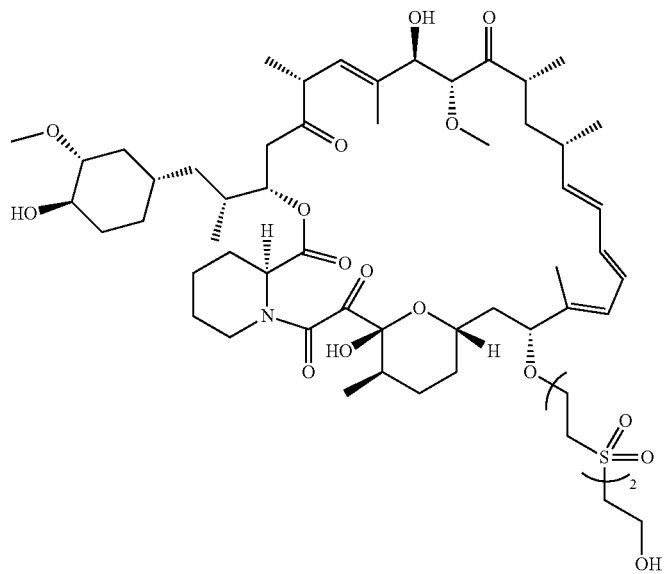 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCS(=O)(=O)CCO)C[C@@H]3CC[C@@H](C)[C@@](O)(O3)C(=O)C(=O)N3CCCC[C@H]3C(=O)O2)CC[C@H]1O] |
| I-28 | 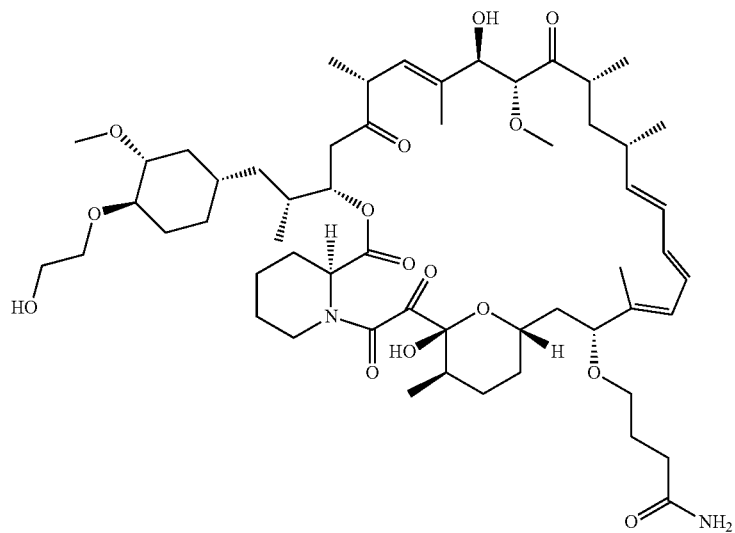 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCCC(N)=O)C[C@@H]3CC[C@@H](C)[C@@](O)(O3)C(=O)C(=O)N3CCCC[C@H]3C(=O)O2)CC[C@H]1OCCO] |

TABLE 1-continued

Exemplary Compounds

| I-# | Structure |
|---|---|
| I-29 | 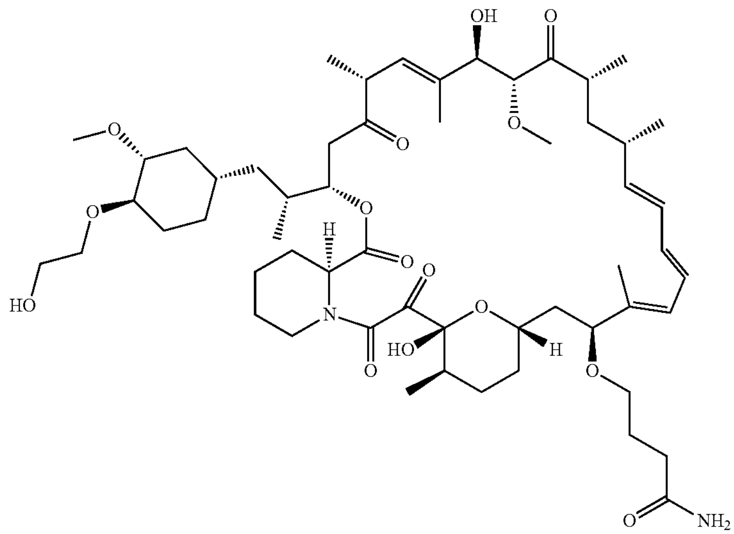 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCCC(N)=O)C[C@@H]3CC[C@@H](C)[C@@](O)(O3)C(=O)C(=O)N3CCCC[C@H]3C(=O)O2)CC[C@H]1OCCO] |
| I-30 | 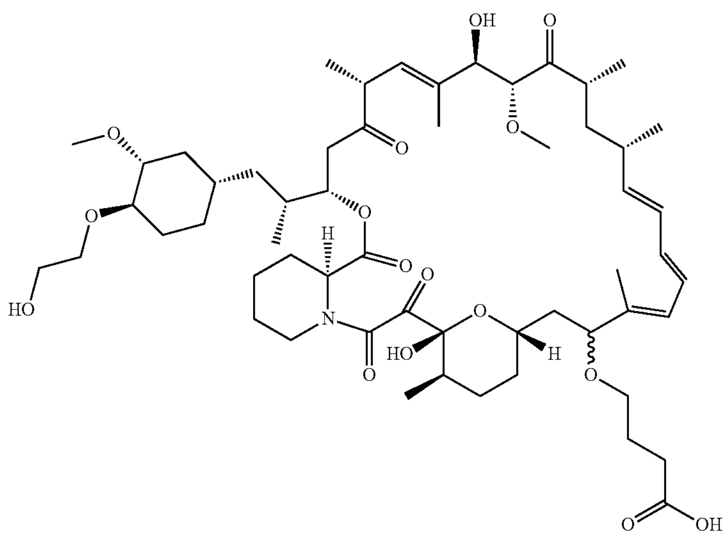 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCCC(=O)O)C[C@@H]3CC[C@@H](C)[C@@](O)(O3)C(=O)C(=O)N3CCCC[C@H]3C(=O)O2)CC[C@H]1OCCO] |
| I-31 | 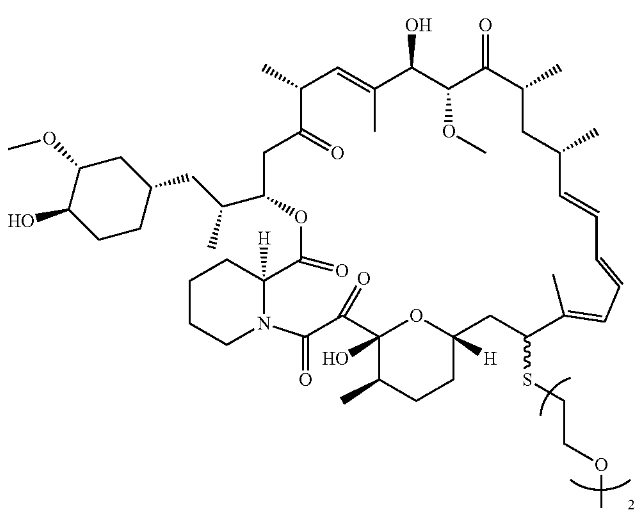 [SMILES: COCCSC1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C] |

TABLE 1-continued
Exemplary Compounds
| I-# | Structure |
|---|---|
| I-32 | 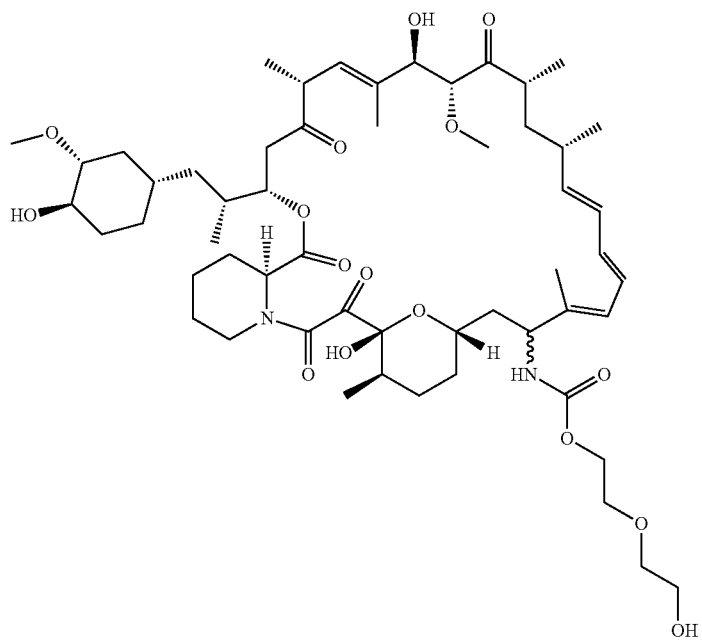 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(NC(=O)OCCOCCO)C[C@@H]3CC[C@@H](C)[C@@](O)(O3)C(=O)C(=O)N3CCCC[C@H]3C(=O)O2)CC[C@H]1O] |
| I-33 | 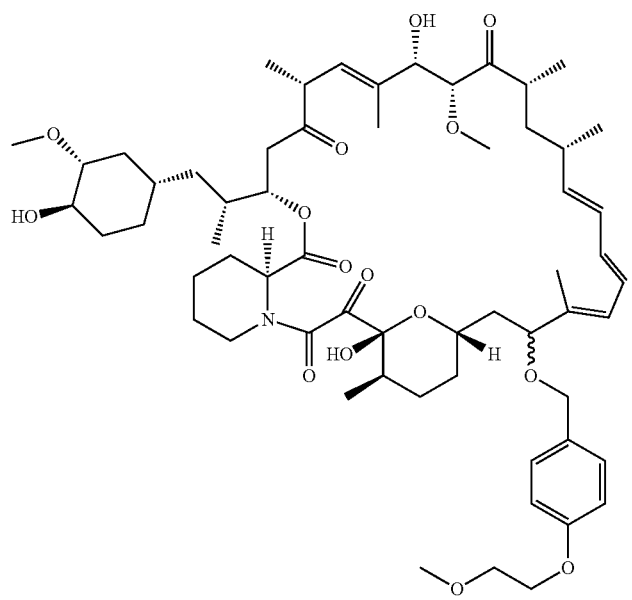 [SMILES: COCCOc1ccc(COC2C[C@@H]3CC[C@@H](C)[C@@](O)(O3)C(=O)C(=O)N3CCCC[C@H]3C(=O)O[C@H]([C@H](C)C[C@@H]3CC[C@@H](O)[C@H](OC)C3)CC(=O)[C@H](C)/C=C(\C)[C@H](O)[C@@H](OC)C(=O)[C@H](C)C[C@H](C)/C=C/C=C/C=C/2C)cc1] |

TABLE 1-continued
Exemplary Compounds
| I-# | Structure |
|---|---|
| I-34 | 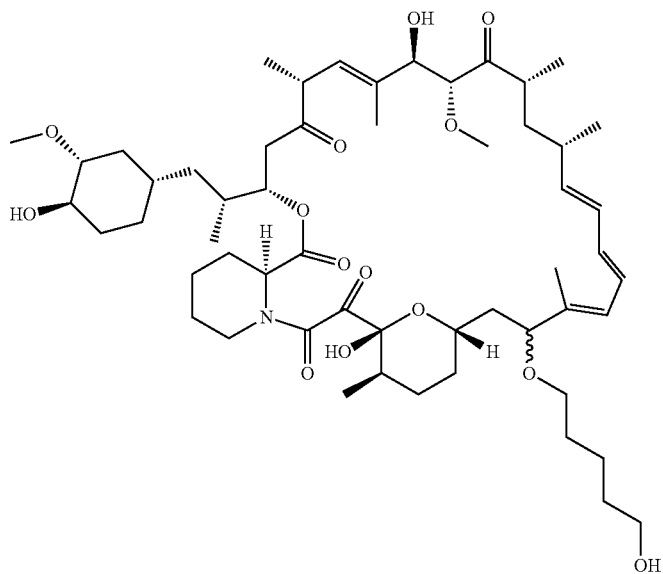 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCCCCO)C[C@@H]3CC[C@@H](C)[C@@](O)(O3)C(=O)C(=O)N3CCCC[C@H]3C(=O)O2)CC[C@H]1O] |
| I-35 | 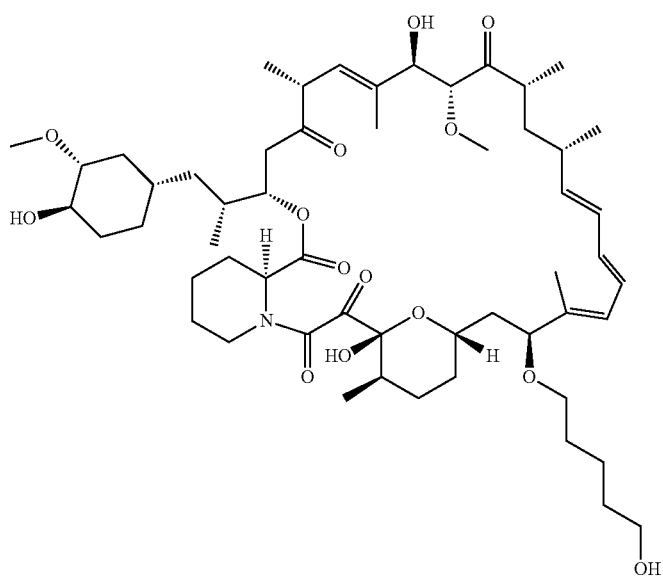 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCCCCO)C[C@@H]3CC[C@@H](C)[C@@](O)(O3)C(=O)C(=O)N3CCCC[C@H]3C(=O)O2)CC[C@H]1O] |

TABLE 1-continued

Exemplary Compounds

| I-# | Structure |
|---|---|
| I-36 | 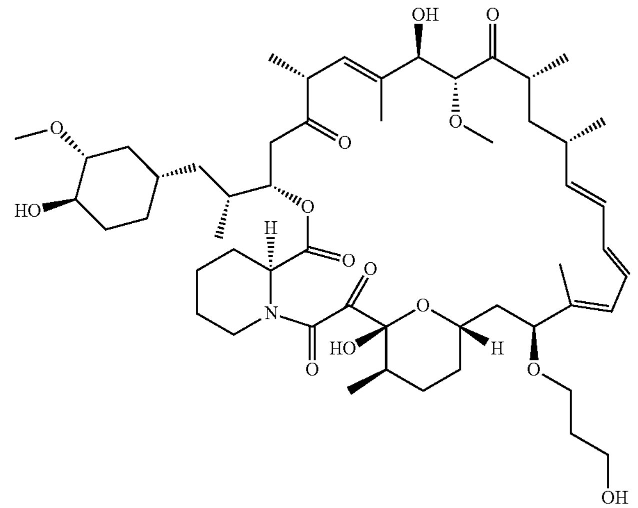 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCCO)C[C@@H]3CC[C@@H](C)[C@@](O)(O3)C(=O)C(=O)N3CCCC[C@H]3C(=O)O2)CC[C@H]1O] |
| I-37 | 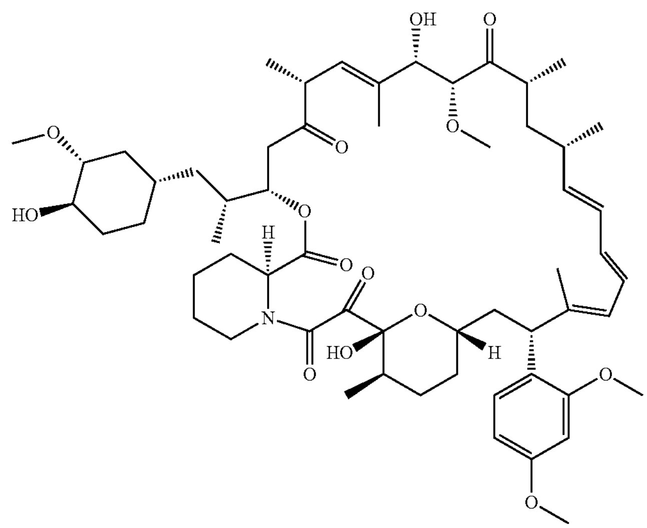 |
| I-38 | 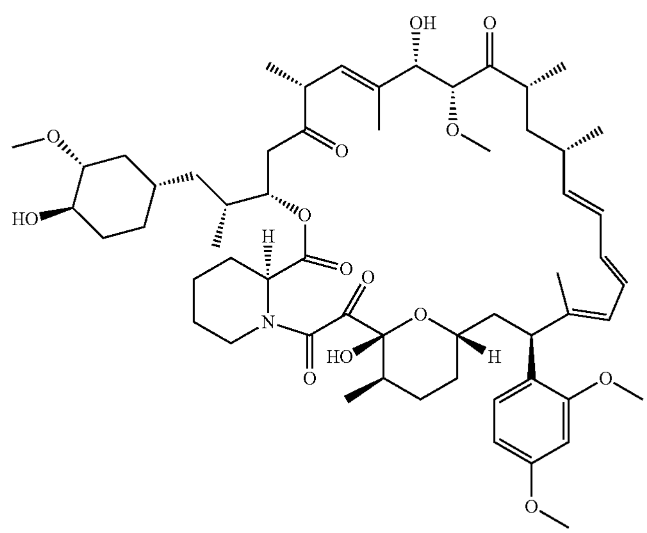 |

TABLE 1-continued
Exemplary Compounds
| I-# | Structure |
|---|---|
| I-39 | 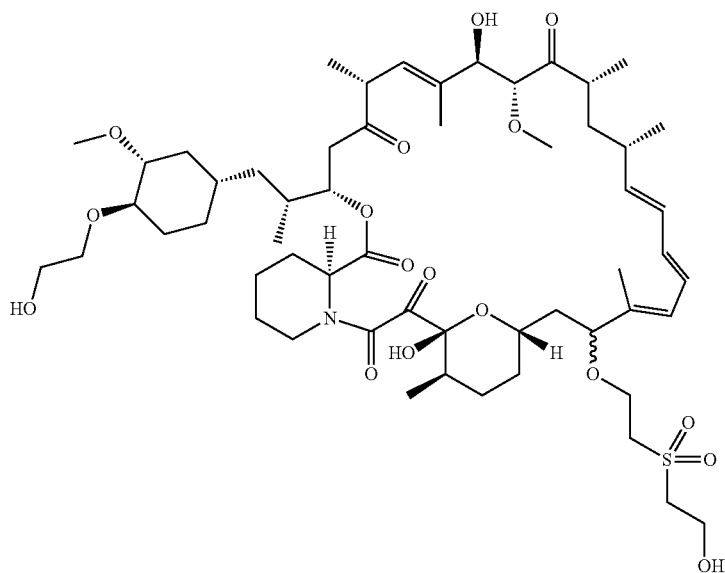 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCS(=O)(=O)CCO)C[C@@H]3CC[C@@H](C)[C@@](O)(O3)C(=O)C(=O)N3CCCC[C@H]3C(=O)O2)CC[C@H]1OCCO] |
| I-40 | 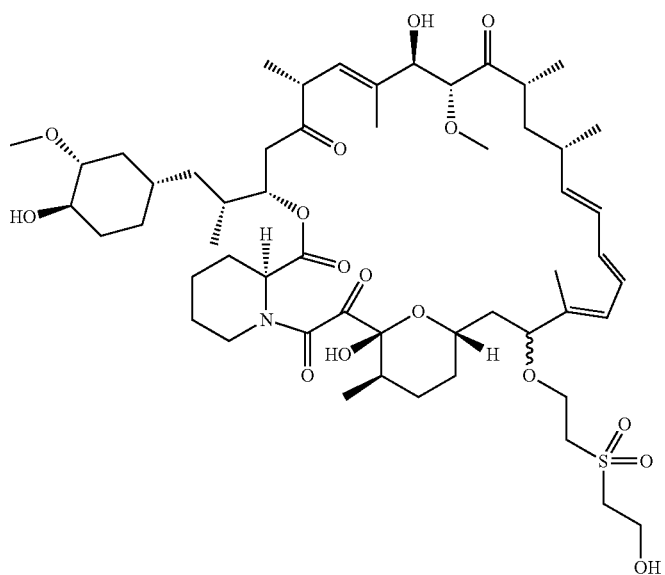 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCS(=O)(=O)CCO)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-41 | 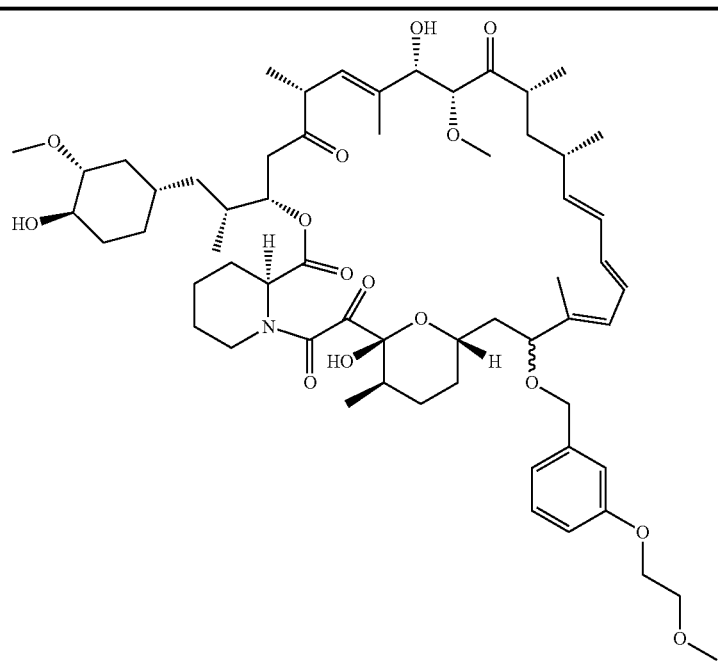 |
| I-42 | 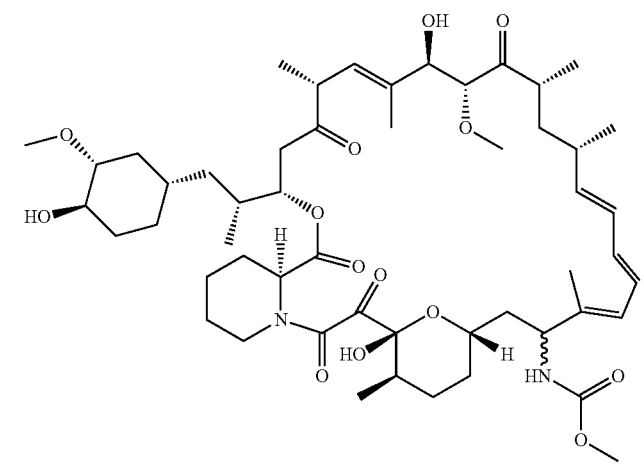 |
| I-43 | 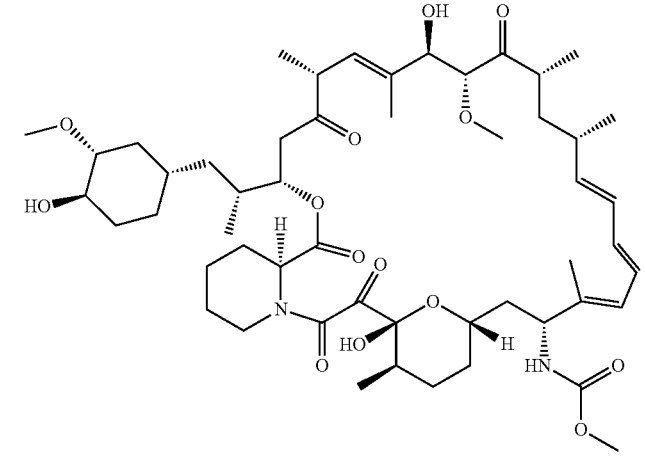 [SMILES: COC(=O)N[C@@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C] |

103                                      104
TABLE 1-continued
| Exemplary Compounds |
|---|
| I-# | Structure |
I-44
I-45
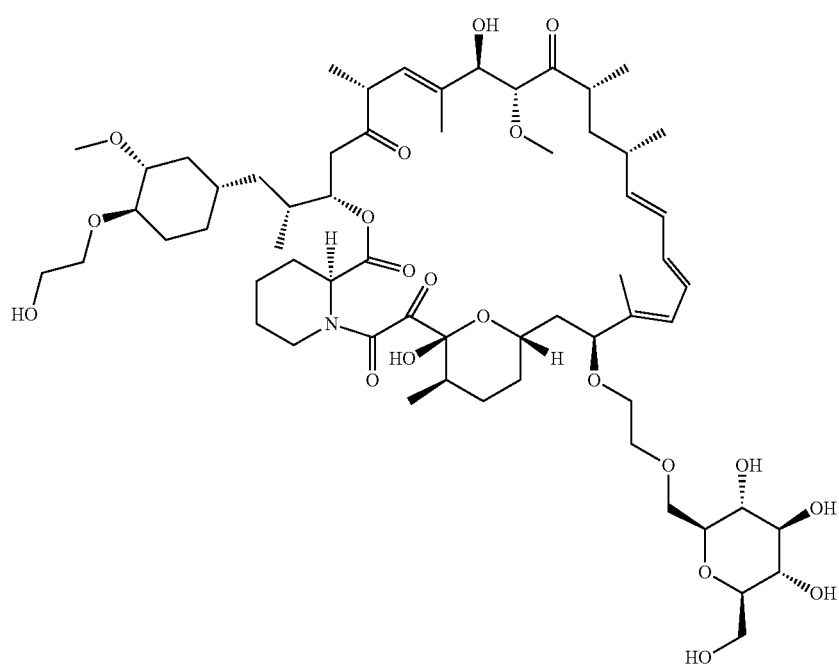 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOC[C@@H]3O[C@H](CO)[C@@H](O)[C@H](O)[C@H]3O)C[C@@H]3CC[C@@H](C)[C@@](O)(O3)C(=O)C(=O)N3CCCC[C@H]3C(=O)O2)CC[C@H]1OCCO]

TABLE 1-continued
Exemplary Compounds
| I-# | Structure |
|---|---|
| I-46 | 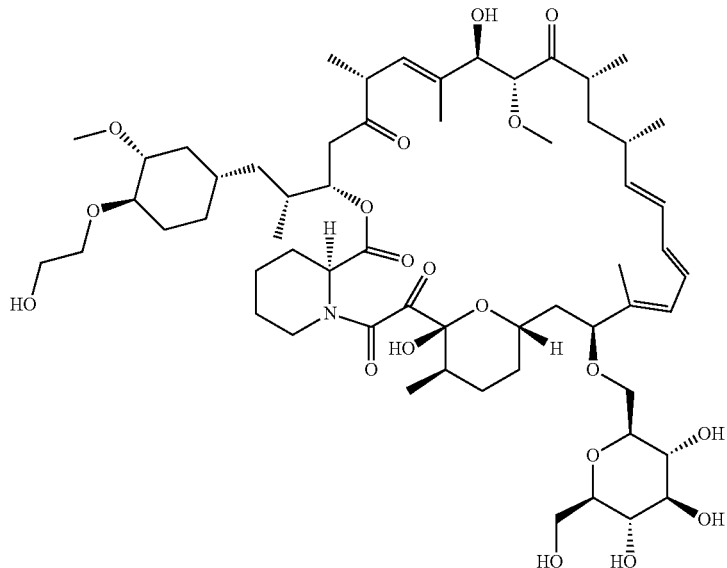 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC[C@@H]3O[C@H](CO)[C@@H](O)[C@H](O)[C@H]3O)C[C@@H]3CC[C@@H](C)[C@@](O)(O3)C(=O)C(=O)N3CCCC[C@H]3C(=O)O2)CC[C@H]1OCCO] |
| I-47 | 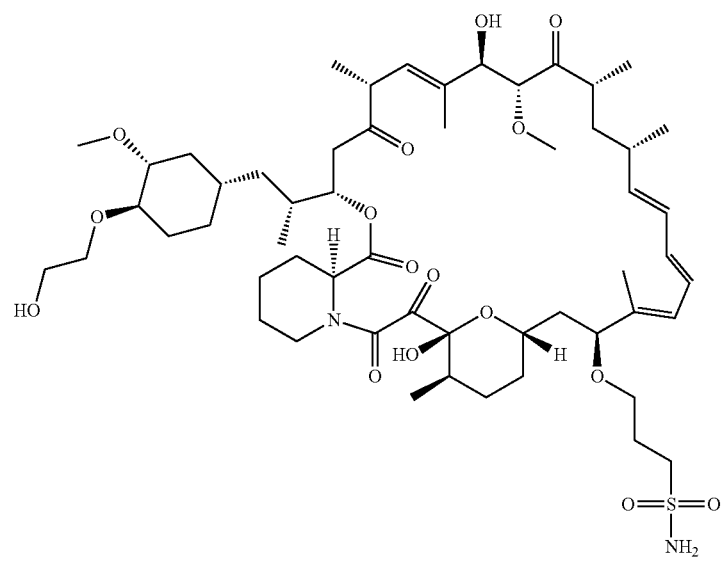 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCCS(N)(=O)=O)C[C@@H]3CC[C@@H](C)[C@@](O)(O3)C(=O)C(=O)N3CCCC[C@H]3C(=O)O2)CC[C@H]1OCCO] |

TABLE 1-continued
Exemplary Compounds
| I-# | Structure |
|---|---|
| I-48 | 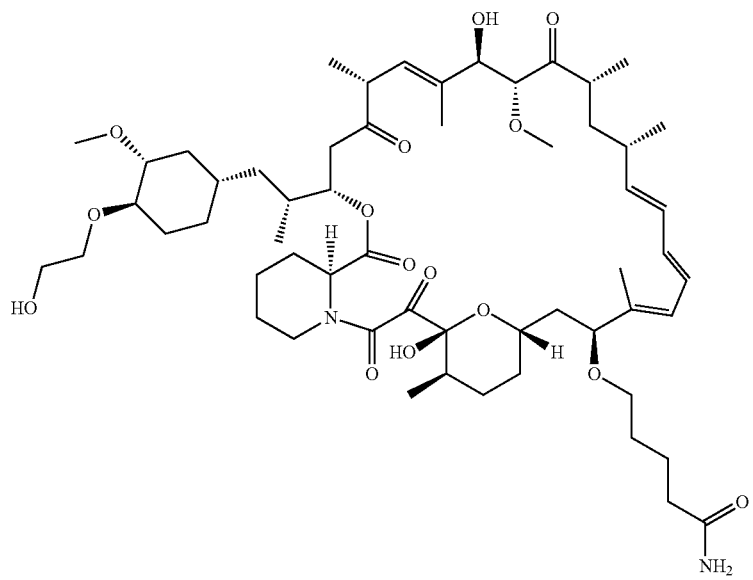 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCCCC(N)=O)C[C@@H]3CC[C@@H](C)[C@@](O)(O3)C(=O)C(=O)N3CCCC[C@H]3C(=O)O2)CC[C@H]1OCCO] |
| I-49 | 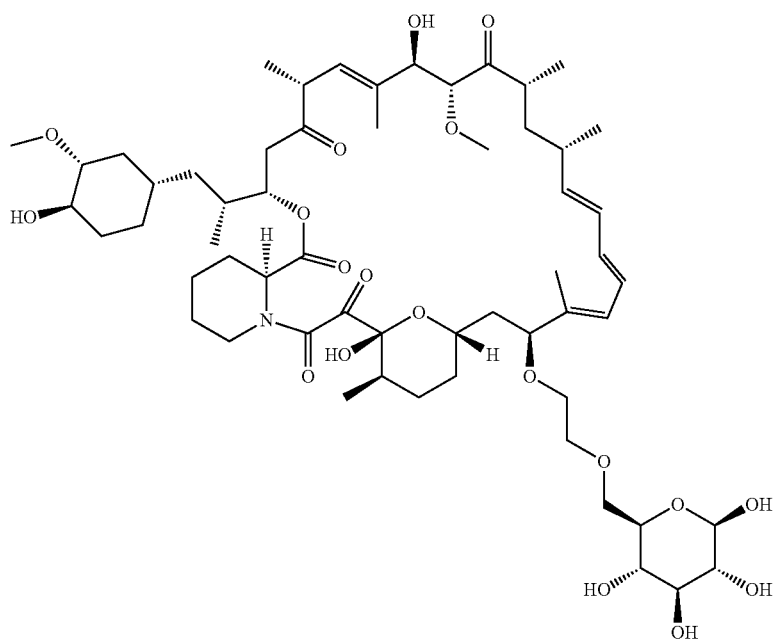 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOC[C@H]3O[C@@H](O)[C@H](O)[C@@H](O)[C@@H]3O)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-50 | 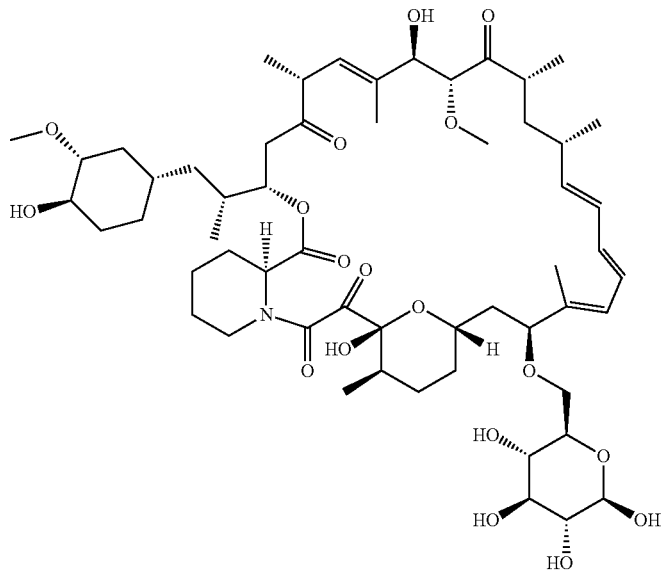 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC[C@H]3O[C@@H](O)[C@H](O)[C@@H](O)[C@@H]3O)C[C@@H]3CC[C@@H](C)[C@@](O)(O3)C(=O)C(=O)N3CCCC[C@H]3C(=O)O2)CC[C@H]1O] |
| I-51 | 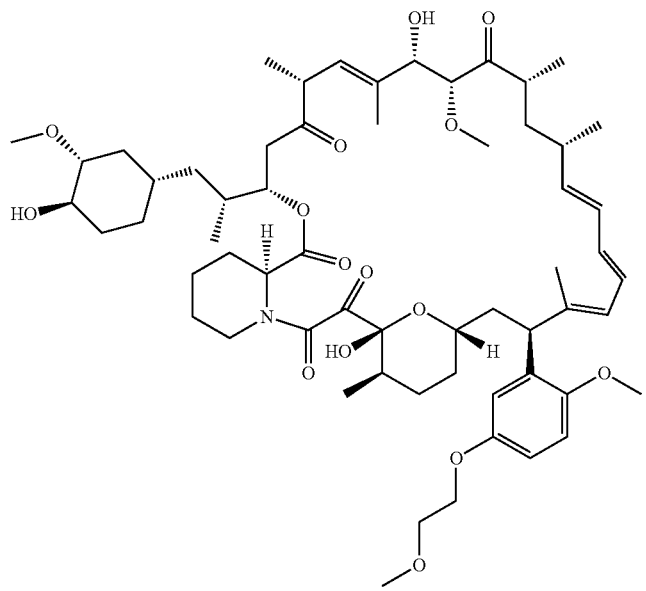 |

TABLE 1-continued
Exemplary Compounds
| I-# | Structure |
|---|---|
| I-52 | 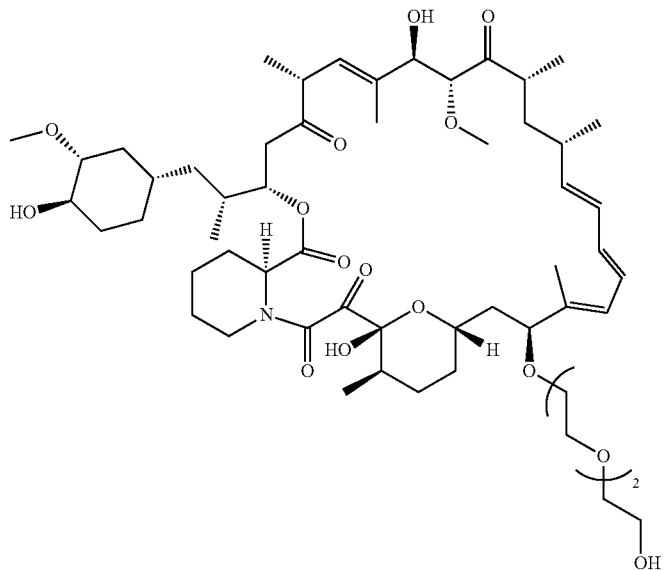 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOCCO)C[C@@H]3CC[C@@H](C)[C@@](O)(O3)C(=O)C(=O)N3CCCC[C@H]3C(=O)O2)CC[C@H]1O] |
| I-53 | 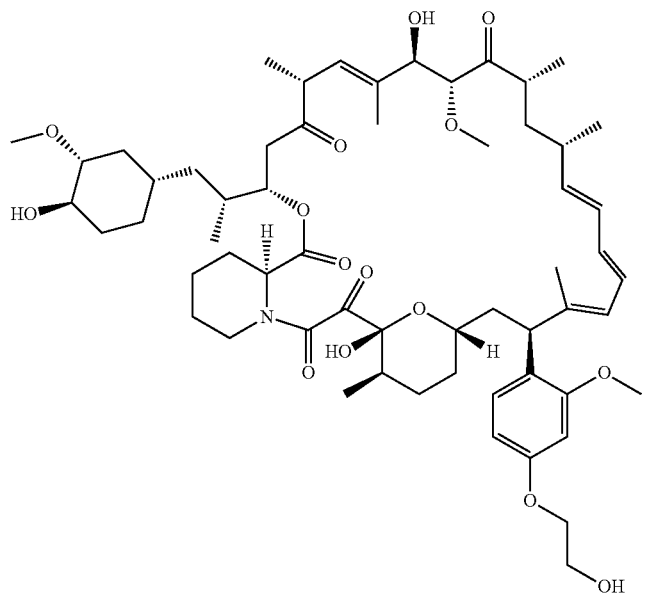 |

TABLE 1-continued
Exemplary Compounds
| I-# | Structure |
|---|---|
| I-54 | 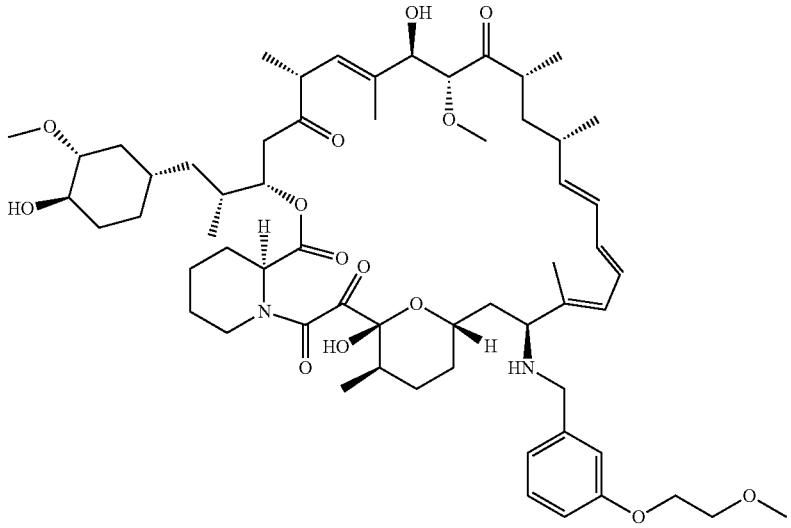 |
| I-55 | 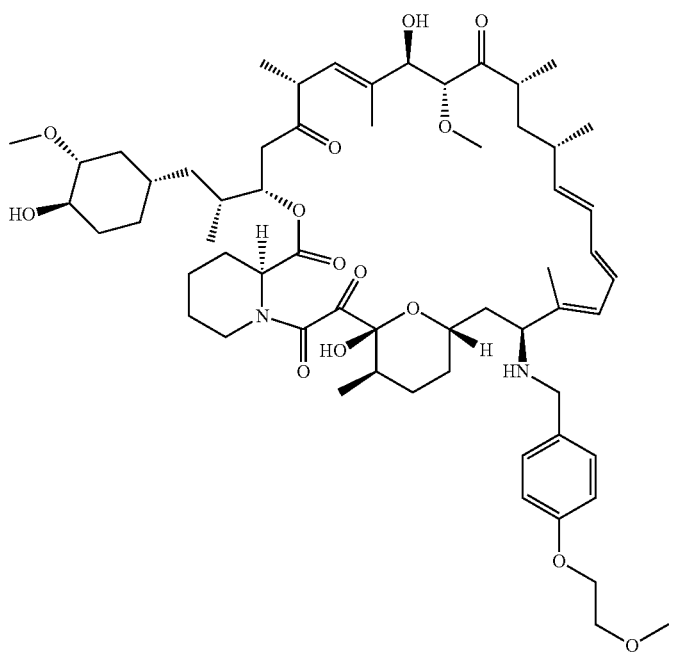 |

TABLE 1-continued

Exemplary Compounds

| I-# | Structure |
|---|---|
| I-56 | 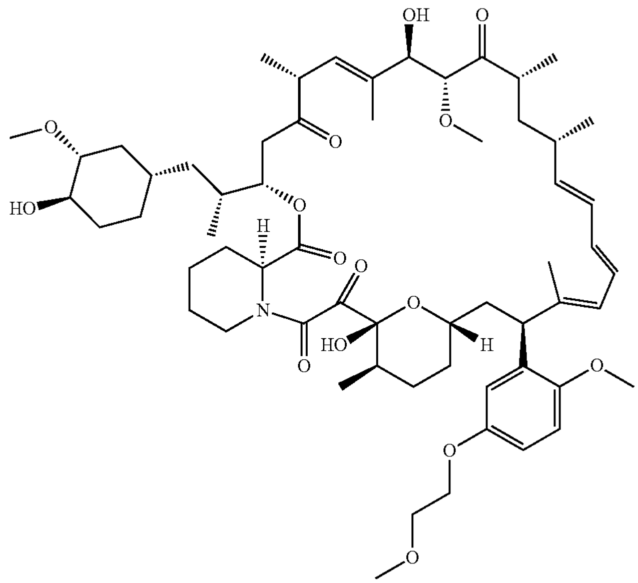 |
| I-57 | 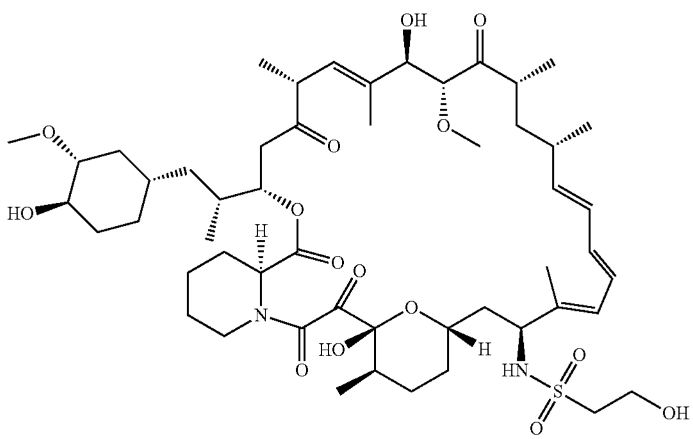 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](NS(=O)(=O)CCO)C[C@@H]3CC[C@@H](C)[C@@](O)(O3)C(=O)C(=O)N3CCCC[C@H]3C(=O)O2)CC[C@H]1O] |
| I-58 | 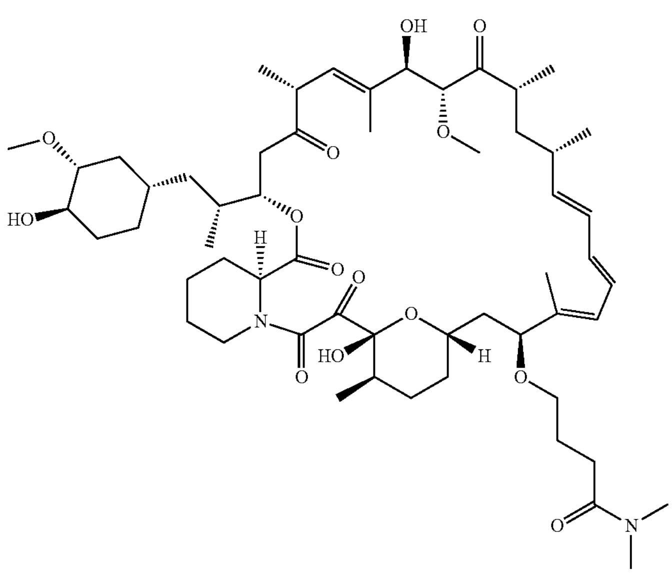 |

TABLE 1-continued
Exemplary Compounds
| I-# | Structure |
|---|---|
| I-59 | 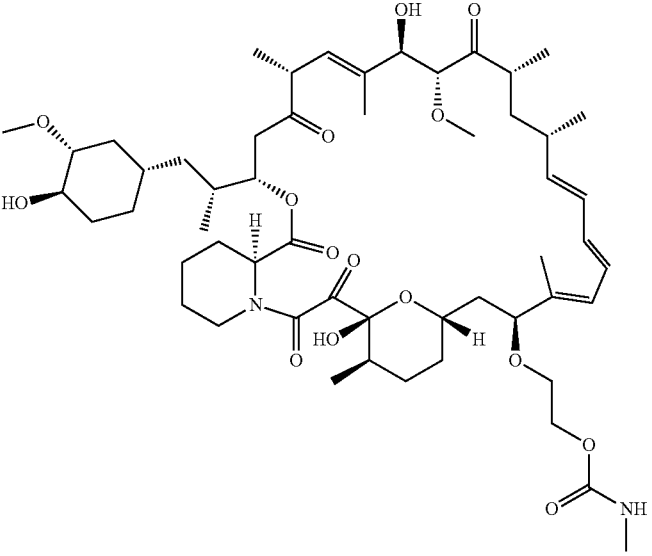 |
| I-60 | 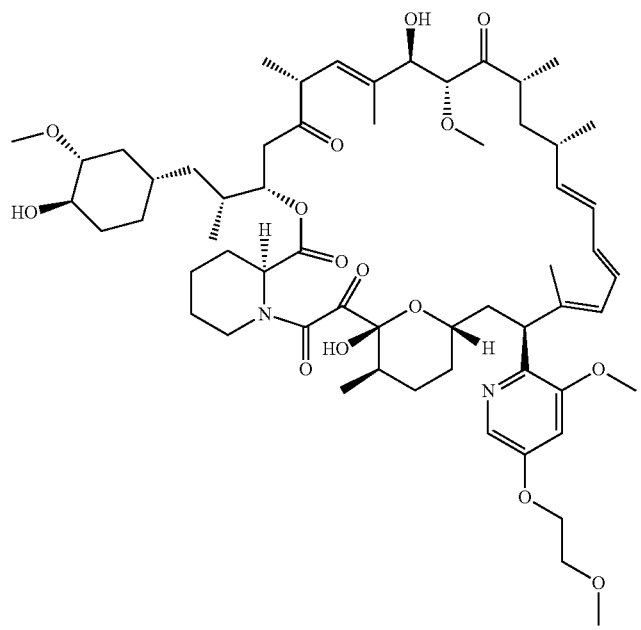 |

TABLE 1-continued
Exemplary Compounds
| I-# | Structure |
|---|---|
| I-61 | 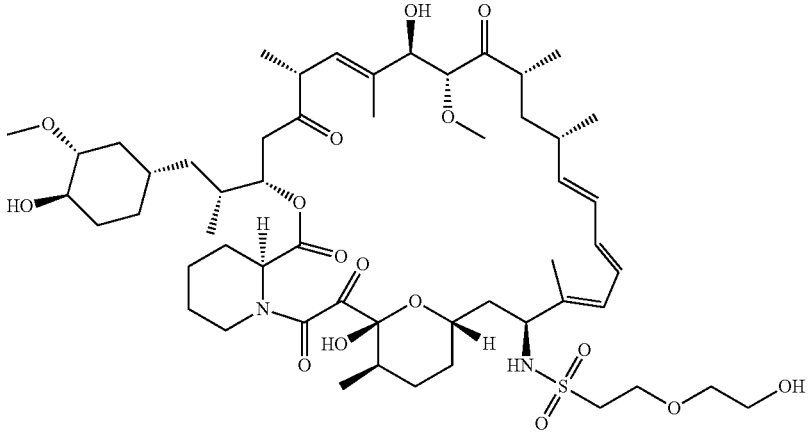 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](NS(=O)(=O)CCOCCO)C[C@@H]3CC[C@@H](C)[C@@](O)(O3)C(=O)C(=O)N3CCCC[C@H]3C(=O)O2)CC[C@H]1O] |
| I-62 | 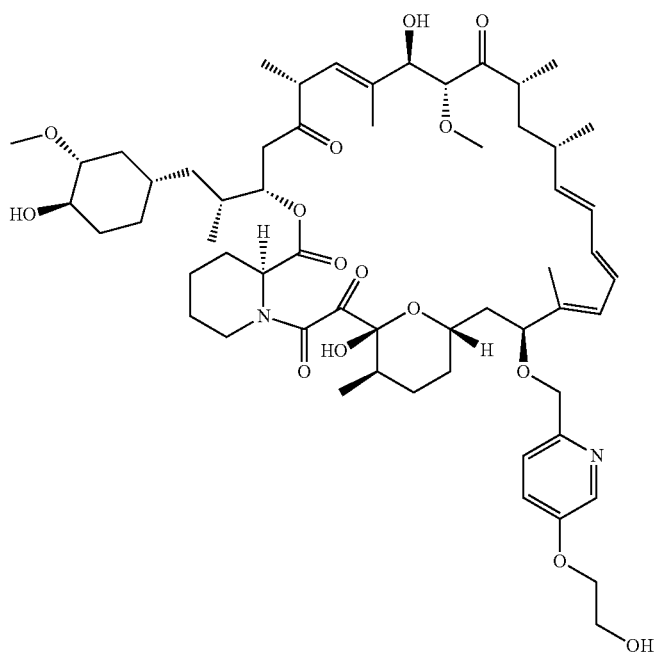 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCc3ccc(OCCO)cn3)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-63 | 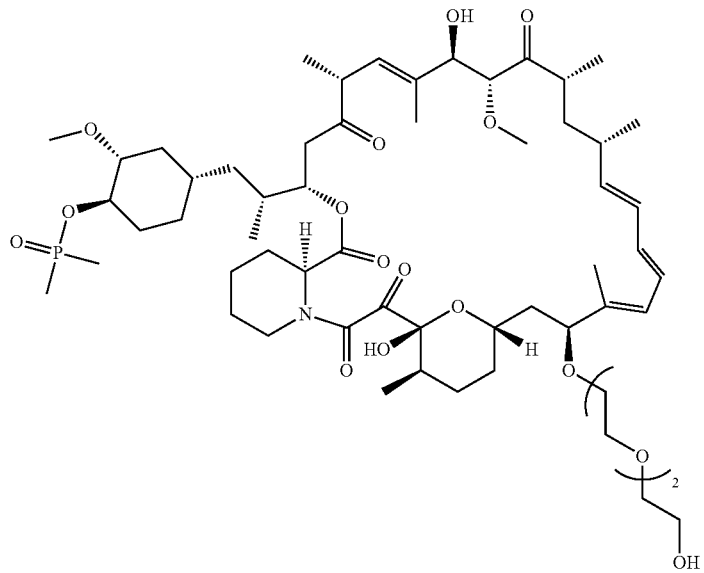 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOCCO)C[C@@H]3CC[C@@H](C)[C@@](O)(O3)C(=O)C(=O)N3CCCC[C@H]3C(=O)O2)CC[C@H]1OP(C)(C)=O] |
| I-64 | 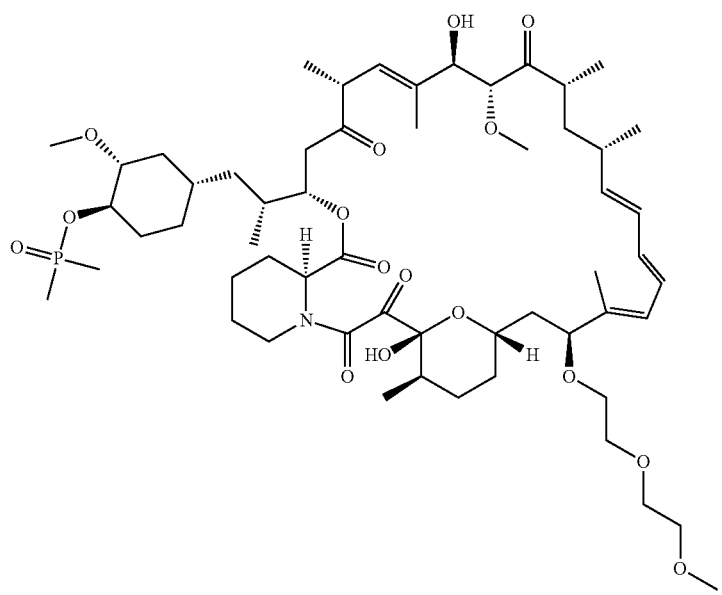 [SMILES: COCCOCCO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OP(C)(C)=O)[C@H](OC)C2)CC(=O)[C@H](C)/C=C(\C)[C@@H](O)[C@@H](OC)C(=O)[C@H](C)C[C@H](C)/C=C/C=C/C=C/1C] |

TABLE 1-continued
Exemplary Compounds
| I-# | Structure |
|---|---|
| I-65 | 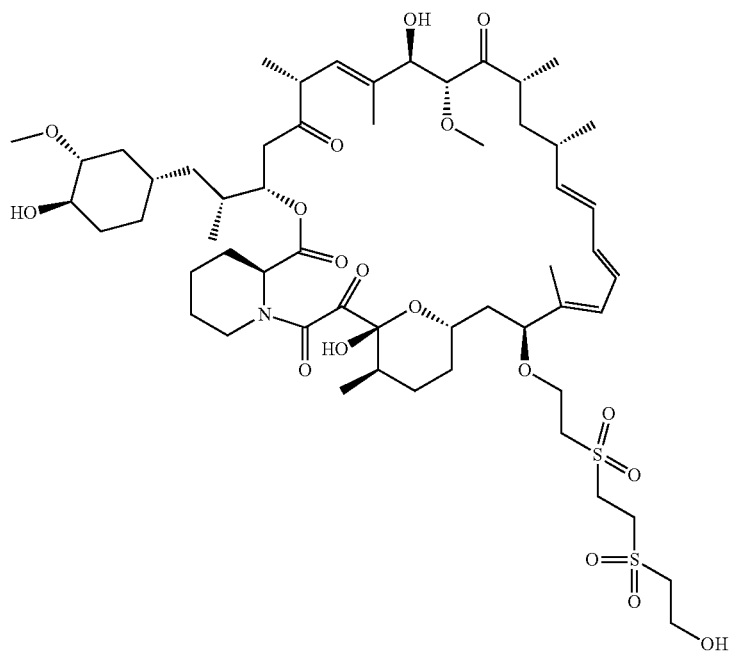 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCS(=O)(=O)CCS(=O)(=O)CCO)C[C@@H]3CC[C@@H](C)[C@@](O)(O3)C(=O)C(=O)N3CCCC[C@H]3C(=O)O2)CC[C@H]1O] |
| I-66 | 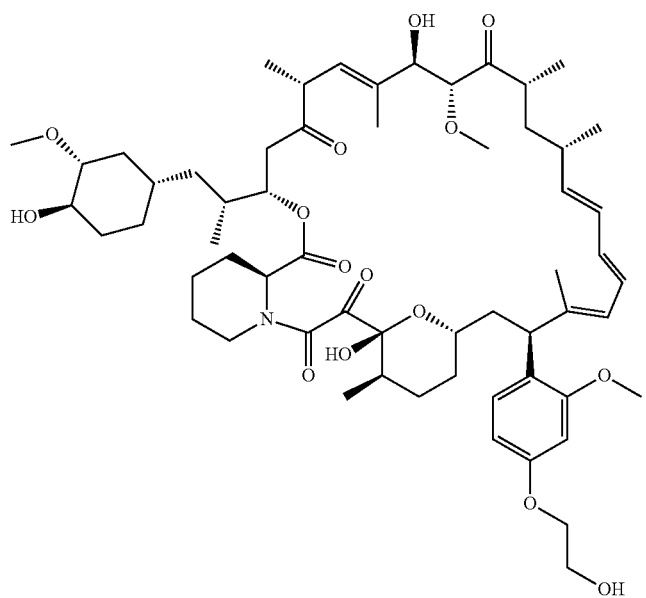 |

TABLE 1-continued
Exemplary Compounds
| I-# | Structure |
|---|---|
| I-67 | 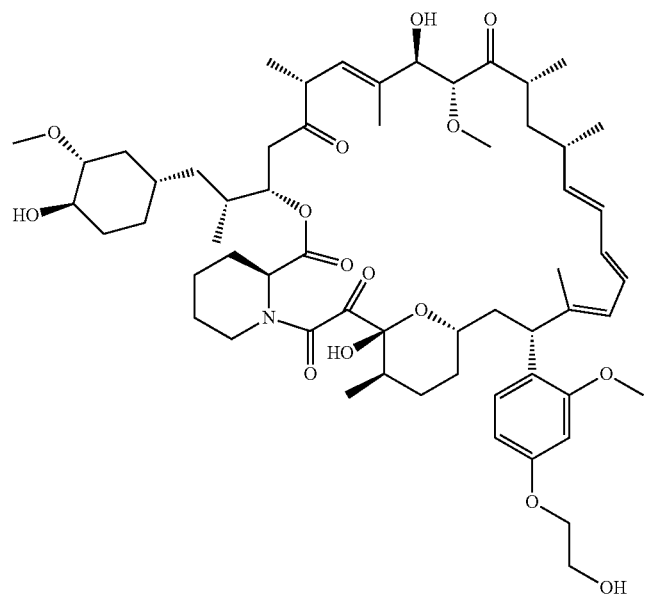 |
| I-68 | 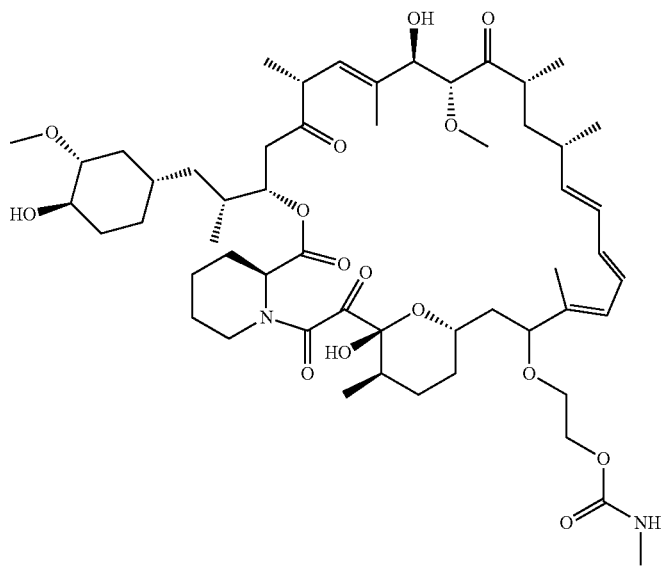 |

TABLE 1-continued

Exemplary Compounds

| I-# | Structure |
|---|---|
| I-69 | 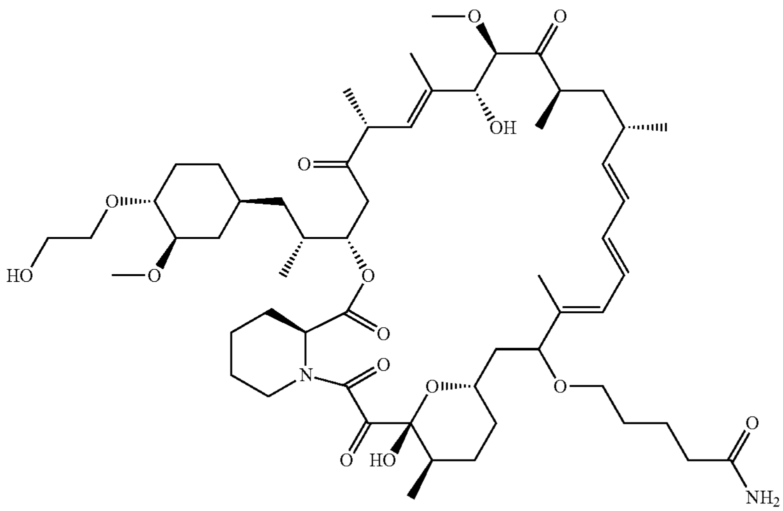 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCCCC(N)=O)C[C@@H]3CC[C@@H](C)[C@@](O)(O3)C(=O)C(=O)N3CCCC[C@H]3C(=O)O2)CC[C@H]1OCCO] |
| I-70 | 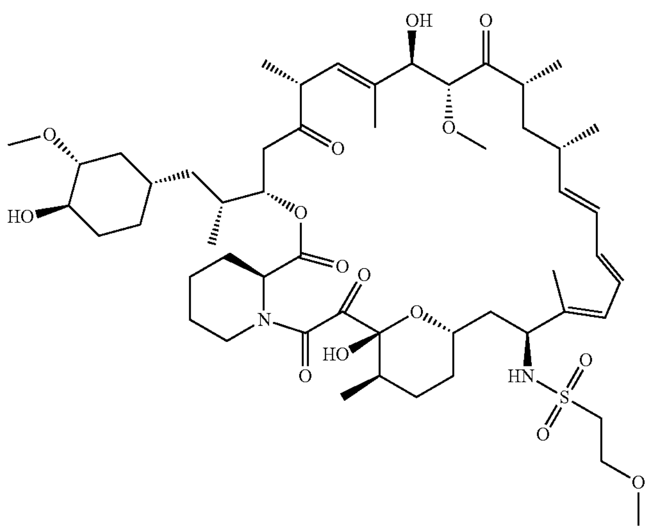 |
| I-71 | 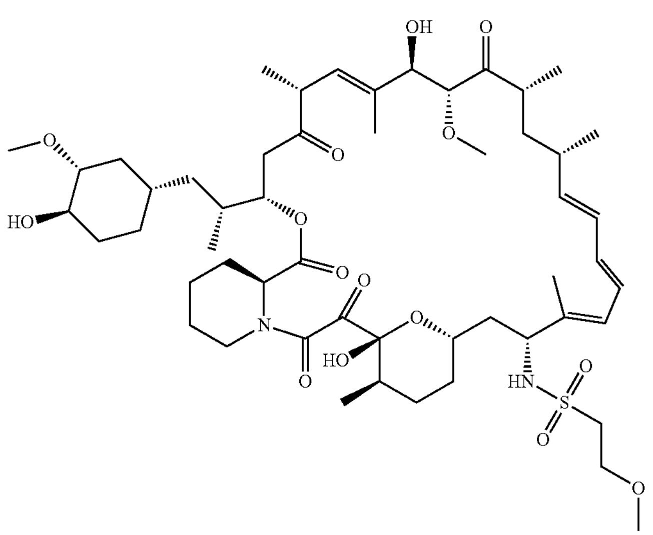 |

US 11,819,476 B2
129                                                              130
TABLE 1-continued
Exemplary Compounds
I-#                                    Structure
I-72
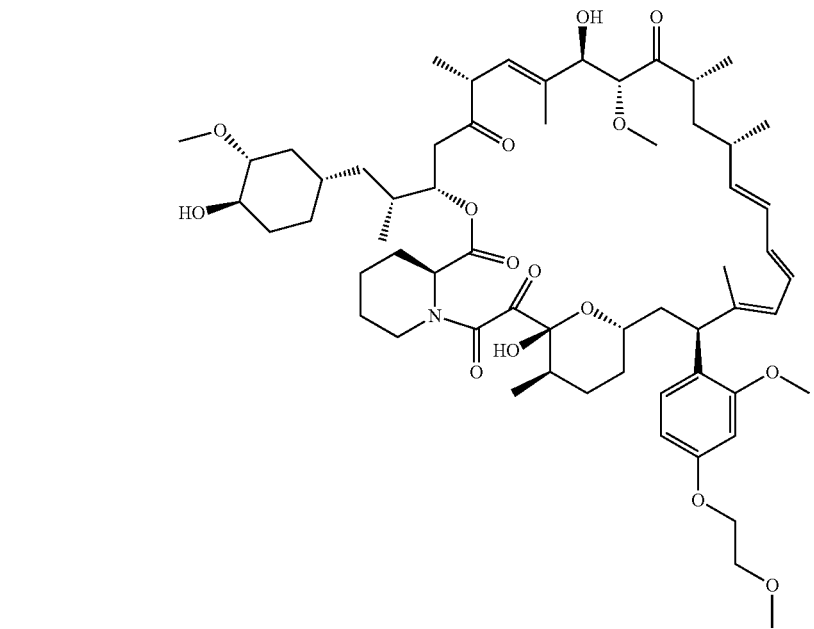
I-73
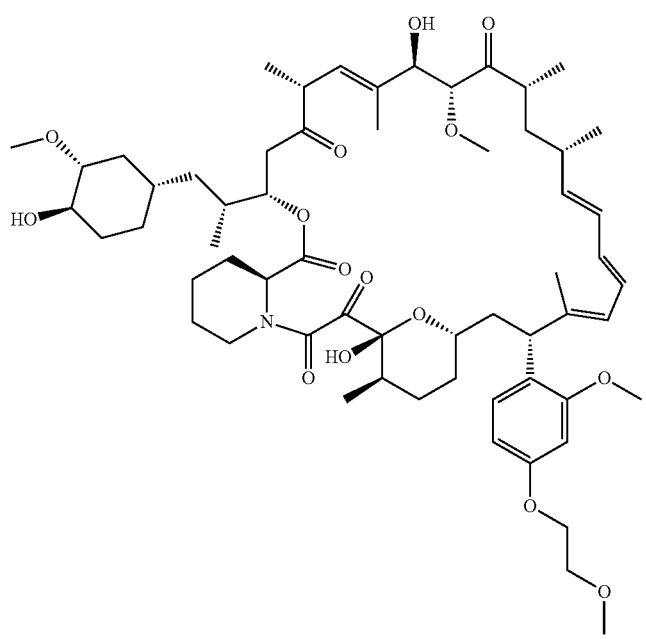

TABLE 1-continued
Exemplary Compounds
| I-# | Structure |
|---|---|
| I-74 | 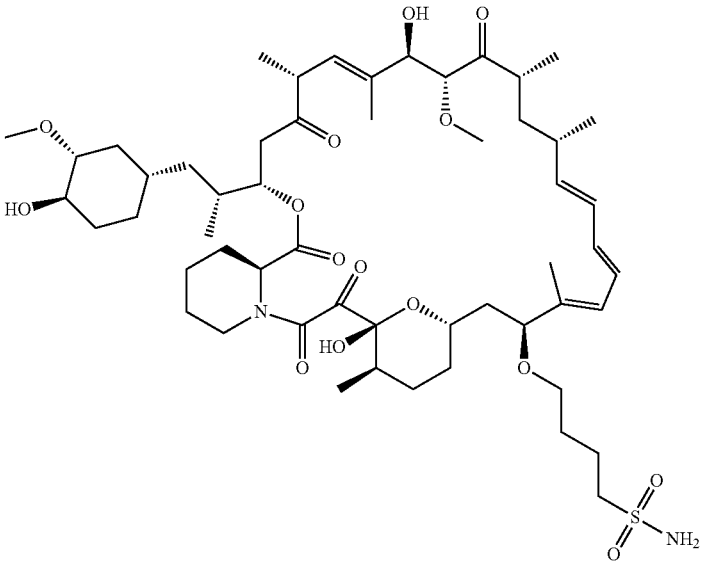 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCCCS(N)(=O)=O)C[C@@H]3CC[C@@H](C)[C@@](O)(O3)C(=O)C(=O)N3CCCC[C@H]3C(=O)O2)CC[C@H]1O] |
| I-75 | 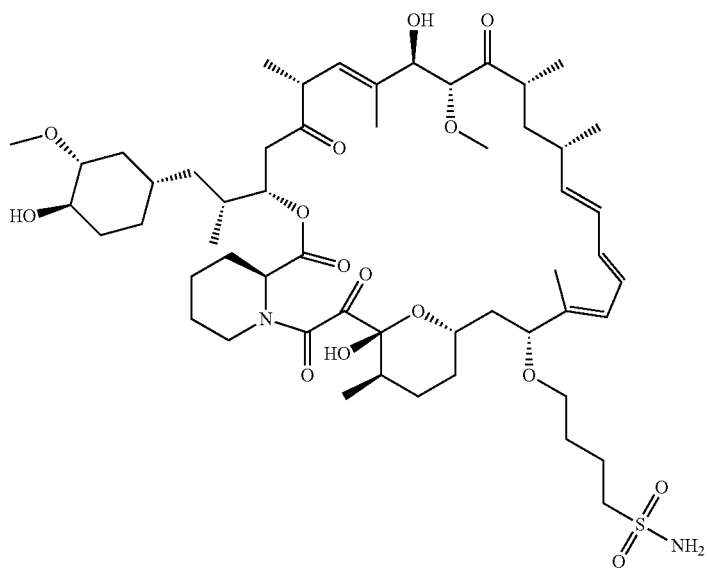 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCCCS(N)(=O)=O)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-76 | 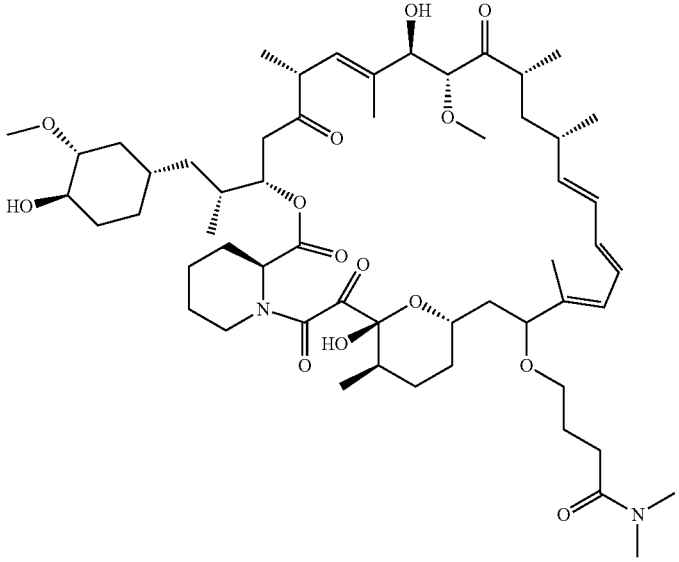 |
| I-77 | 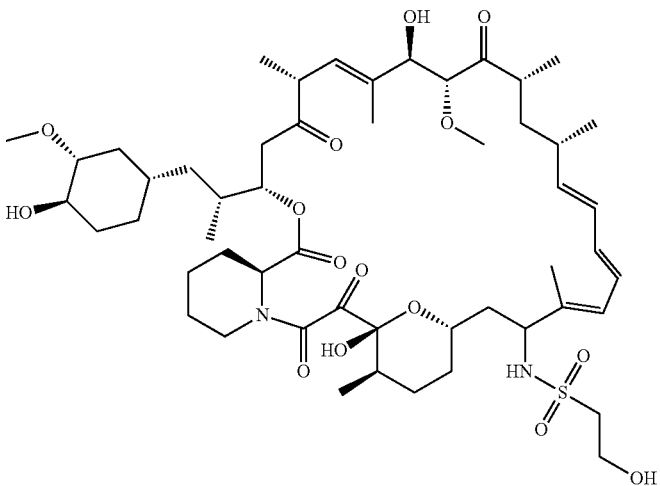 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(NS(=O)(=O)CCO)C[C@@H]3CC[C@@H](C)[C@@](O)(O3)C(=O)C(=O)N3CCCC[C@H]3C(=O)O2)CC[C@H]1O] |
| I-78 | 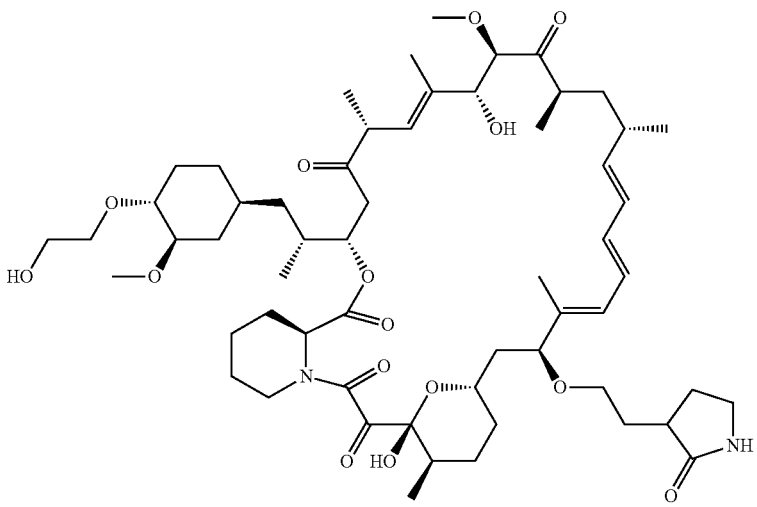 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCC3CCNC3=O)C[C@@H]3CC[C@@H](C)[C@@](O)(O3)C(=O)C(=O)N3CCCC[C@H]3C(=O)O2)CC[C@H]1OCCO] |

TABLE 1-continued
Exemplary Compounds
| I-# | Structure |
|---|---|
| I-79 | 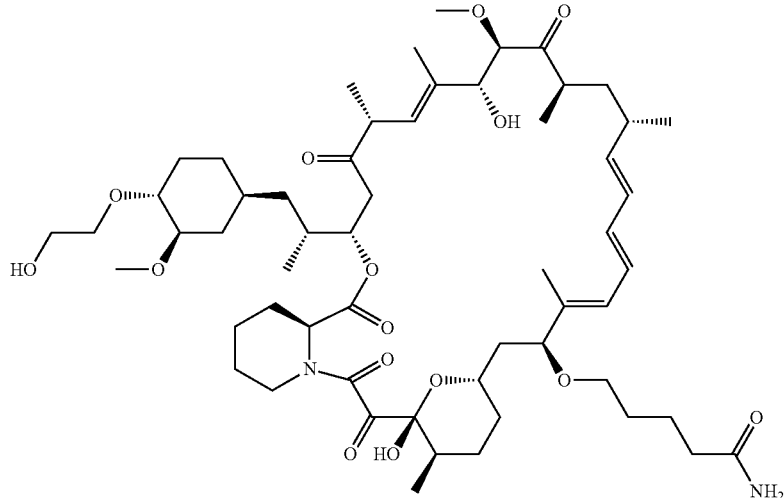 |
| I-80 | 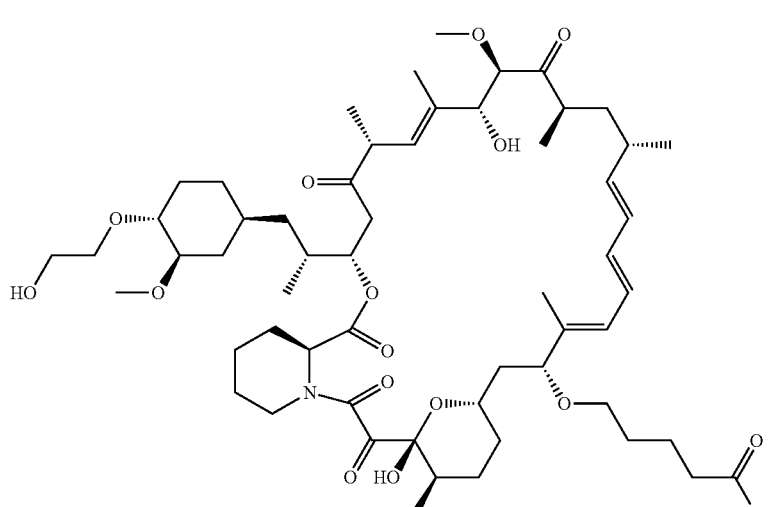 |
| I-81 | 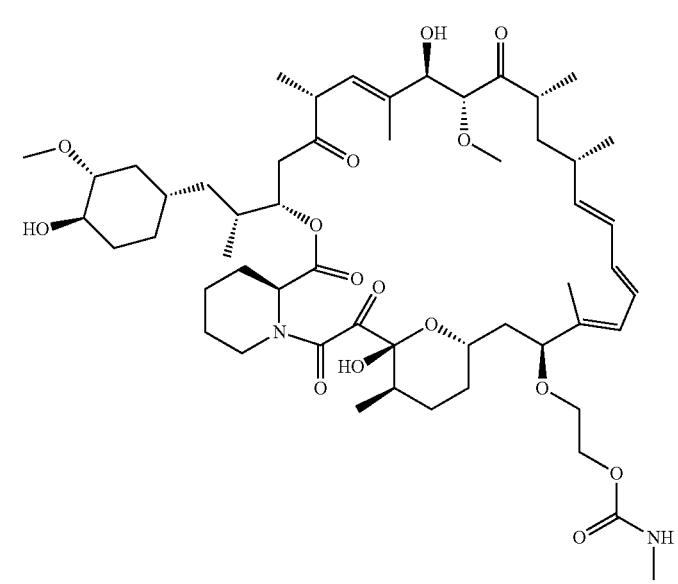 |

TABLE 1-continued
Exemplary Compounds
| I-# | Structure |
|---|---|
| I-82 | 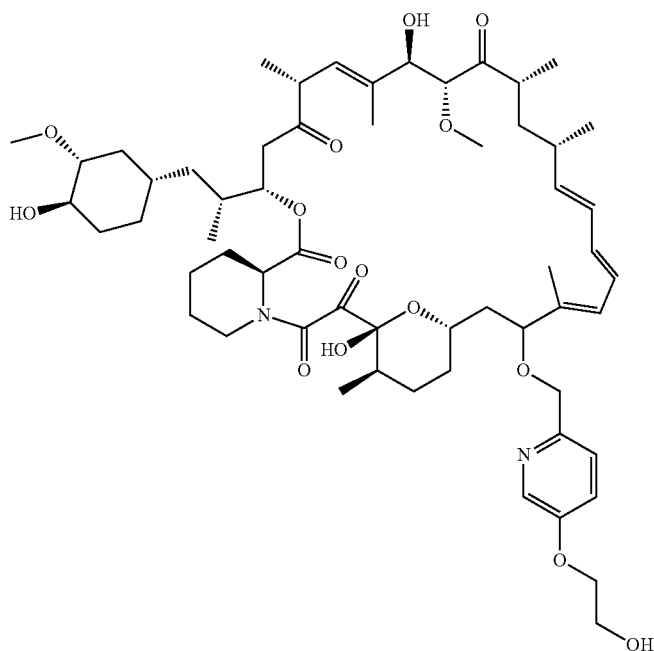 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCc3ccc(OCCO)cn3)C[C@@H]3CC[C@@H](C)[C@@](O)(O3)C(=O)C(=O)N3CCCC[C@H]3C(=O)O2)CC[C@H]1O] |
| I-83 | 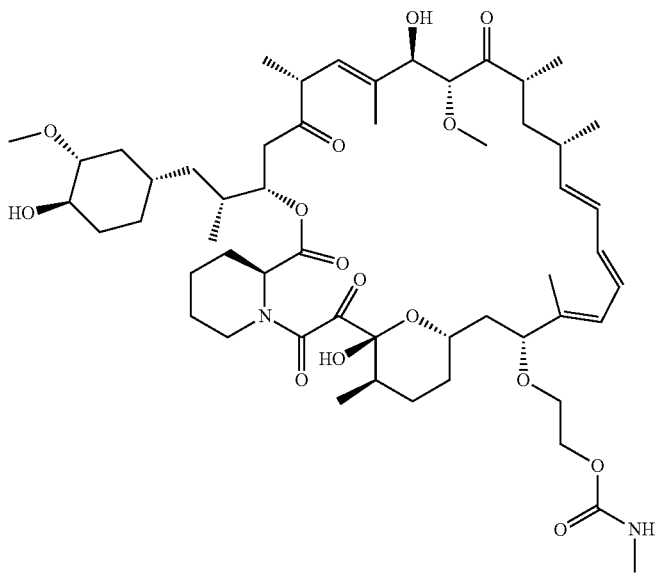 |

TABLE 1-continued
Exemplary Compounds
| I-# | Structure |
|---|---|
| I-84 | 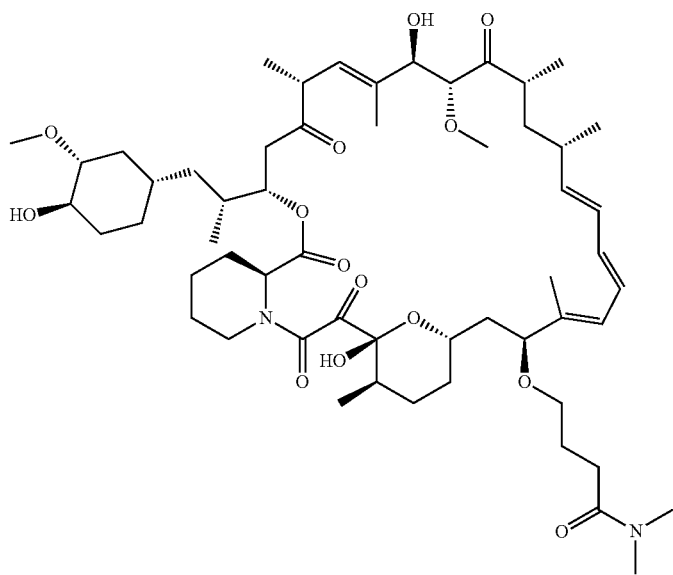 |
| I-85 | 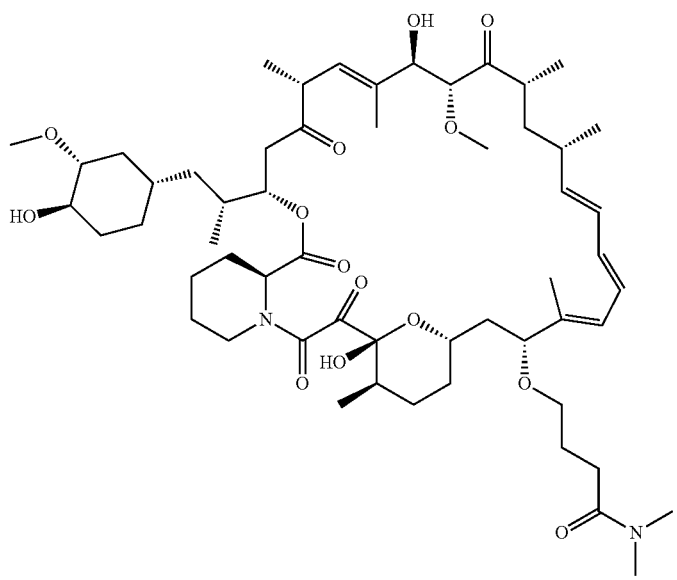 |

TABLE 1-continued
Exemplary Compounds
| I-# | Structure |
|---|---|
| I-86 | 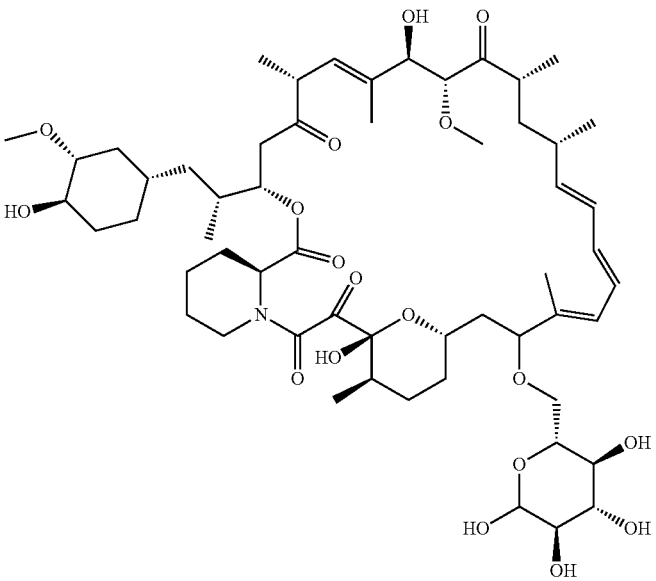 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC[C@H]3OC(O)[C@H](O)[C@@H](O)[C@@H]3O)C[C@@H]3CC[C@@H](C)[C@@](O)(O3)C(=O)C(=O)N3CCCC[C@H]3C(=O)O2)CC[C@H]1O] |
| I-87 | 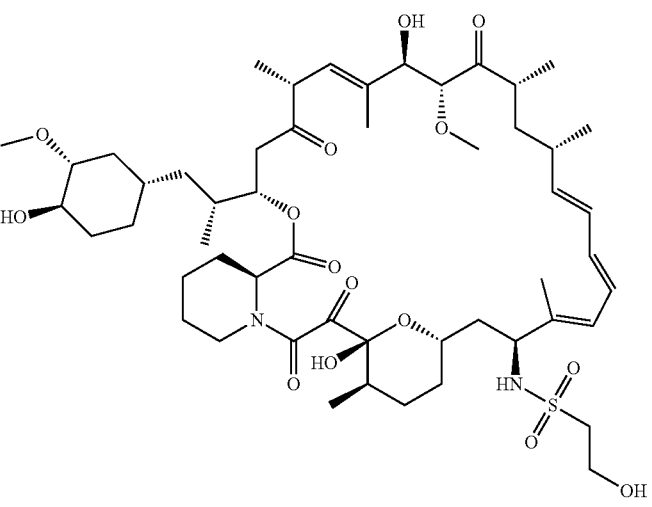 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](NS(=O)(=O)CCO)C[C@@H]3CC[C@@H](C)[C@@](O)(O3)C(=O)C(=O)N3CCCC[C@H]3C(=O)O2)CC[C@H]1O] |
| I-88 | 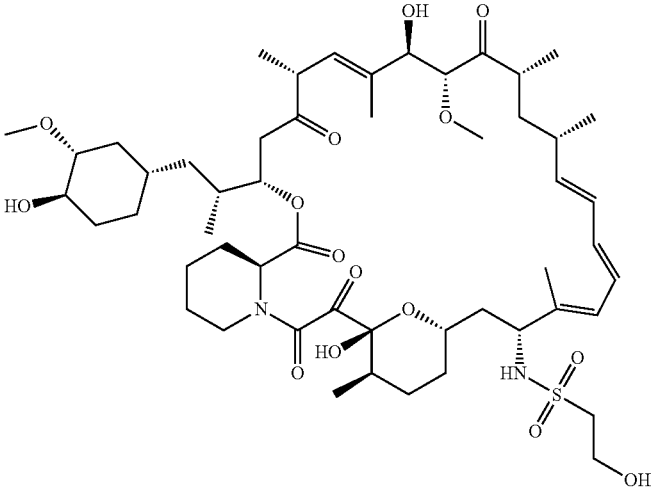 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](NS(=O)(=O)CCO)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-89 | 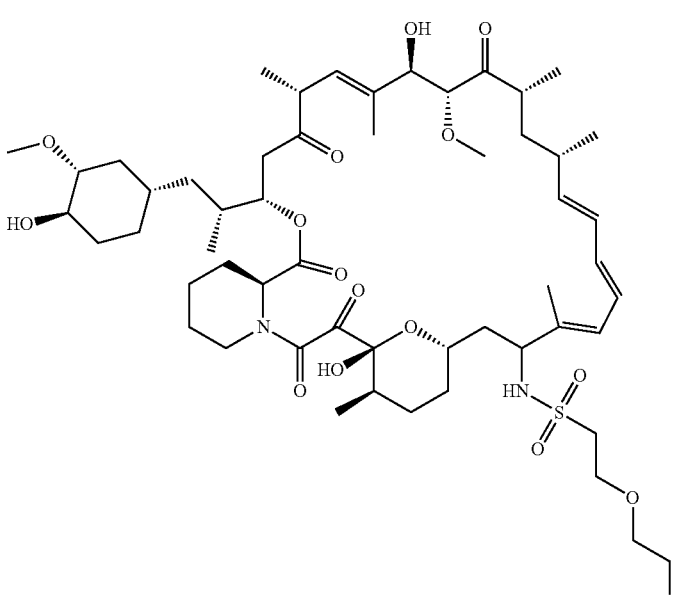 |
| I-90 | 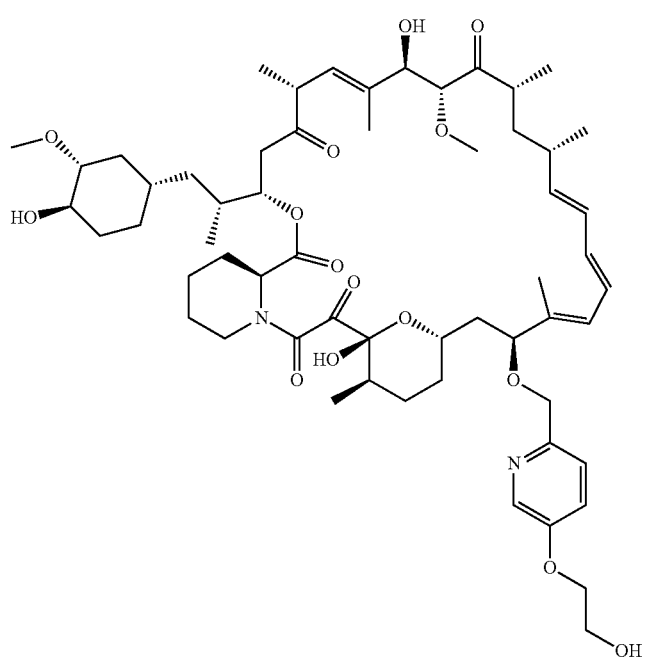 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCc3ccc(OCCO)cn3)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-91 | 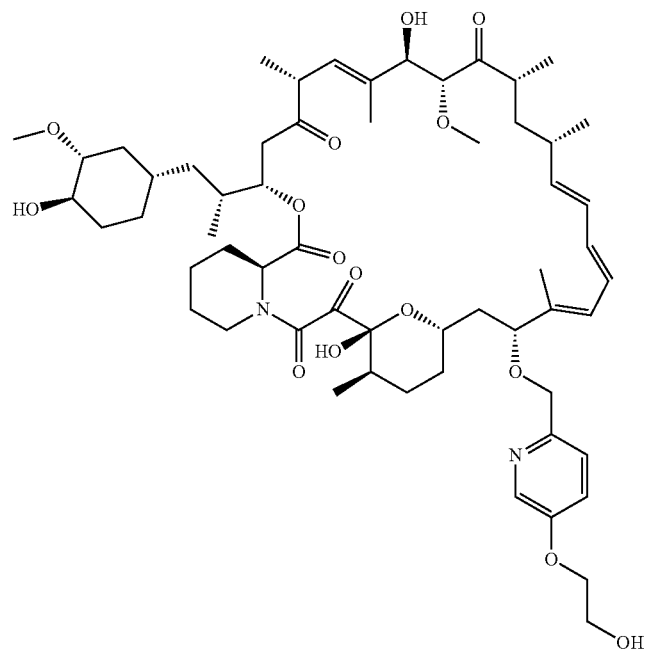 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCc3ccc(OCCO)cn3)C[C@@H]3CC[C@@H](C)[C@@](O)(O3)C(=O)C(=O)N3CCCC[C@H]3C(=O)O2)CC[C@H]1O] |
| I-92 | 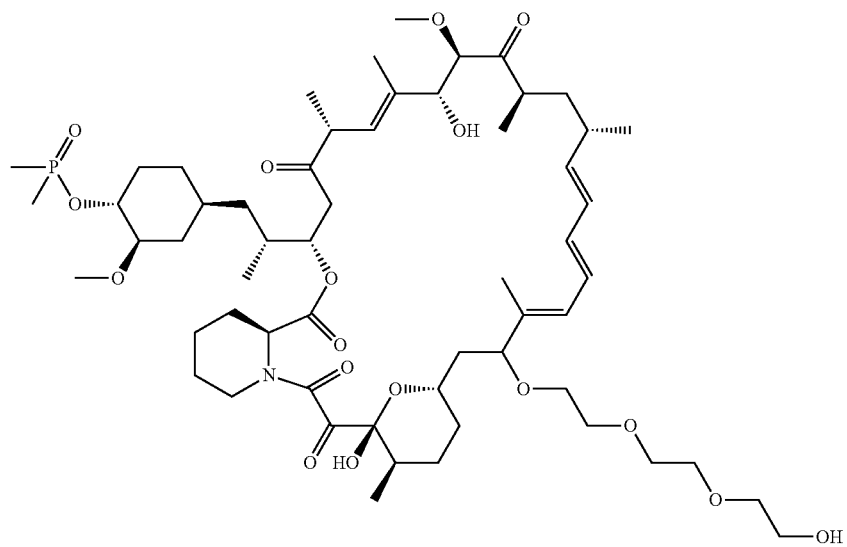 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOCCOCCO)C[C@@H]3CC[C@@H](C)[C@@](O)(O3)C(=O)C(=O)N3CCCC[C@H]3C(=O)O2)CC[C@H]1OP(C)(C)=O] |

TABLE 1-continued
Exemplary Compounds
| I-# | Structure |
|---|---|
| I-93 | 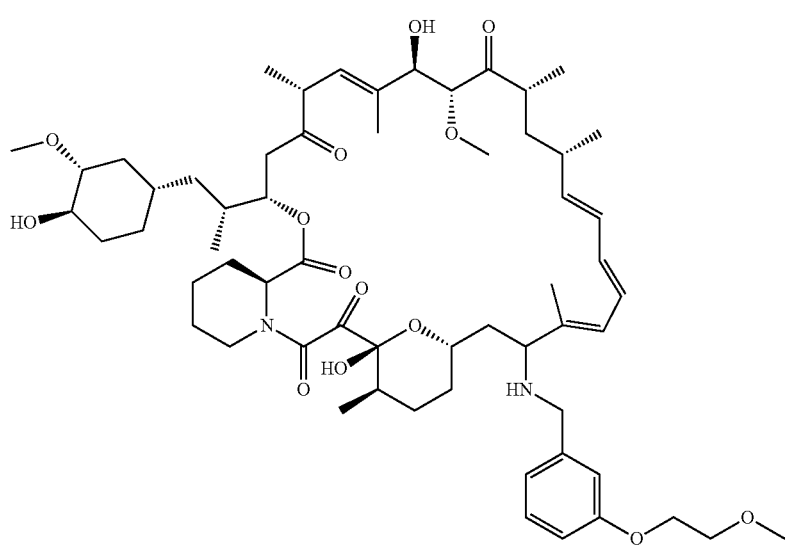 |
| I-94 | 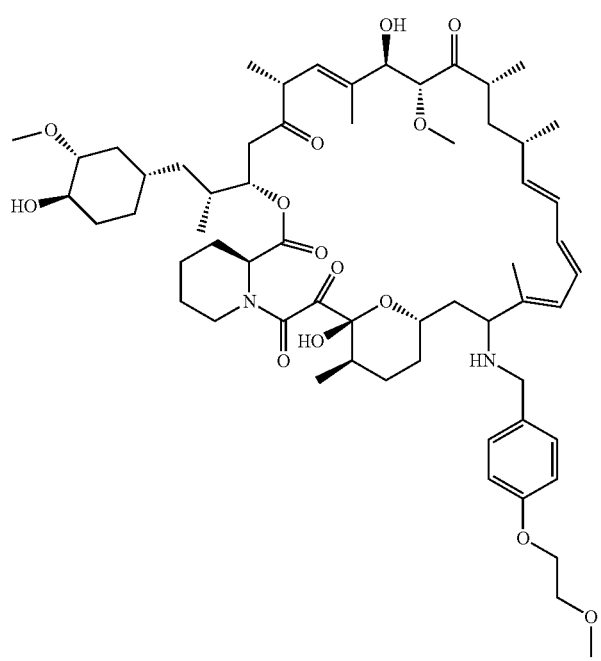 |

TABLE 1-continued
Exemplary Compounds
| I-# | Structure |
|---|---|
| I-95 | 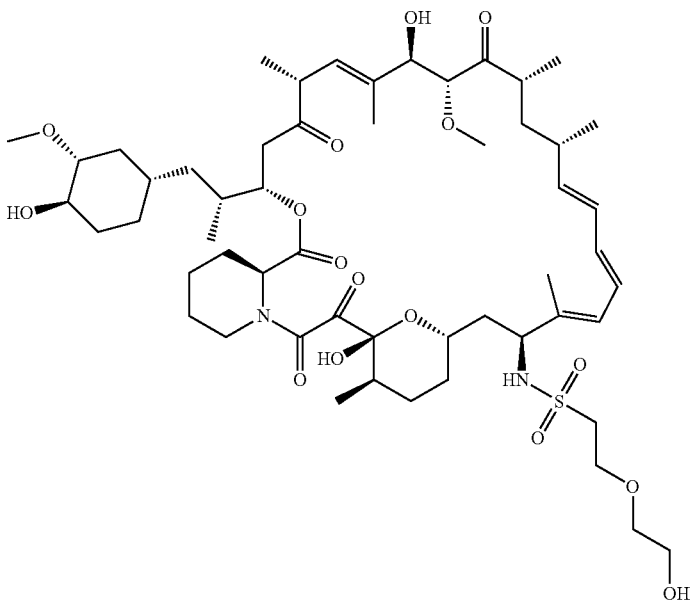 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](NS(=O)(=O)CCOCCO)C[C@@H]3CC[C@@H](C)[C@@](O)(O3)C(=O)C(=O)N3CCCC[C@H]3C(=O)O2)CC[C@H]1O] |
| I-96 | 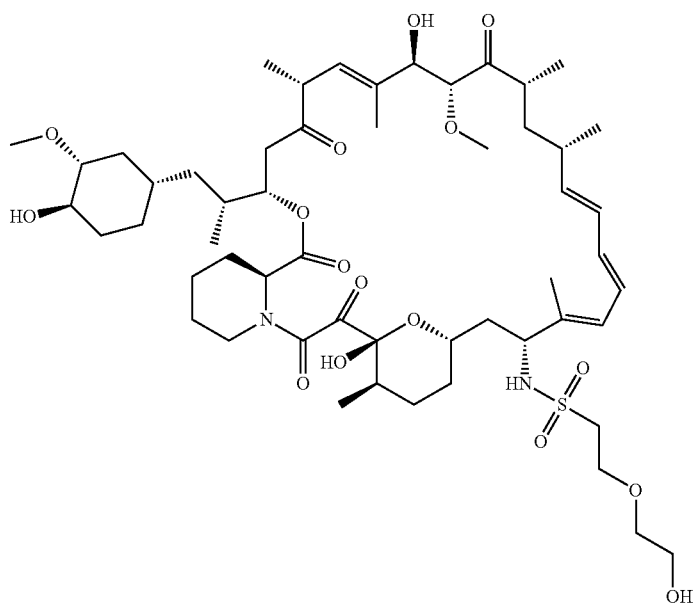 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](NS(=O)(=O)CCOCCO)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-97 | 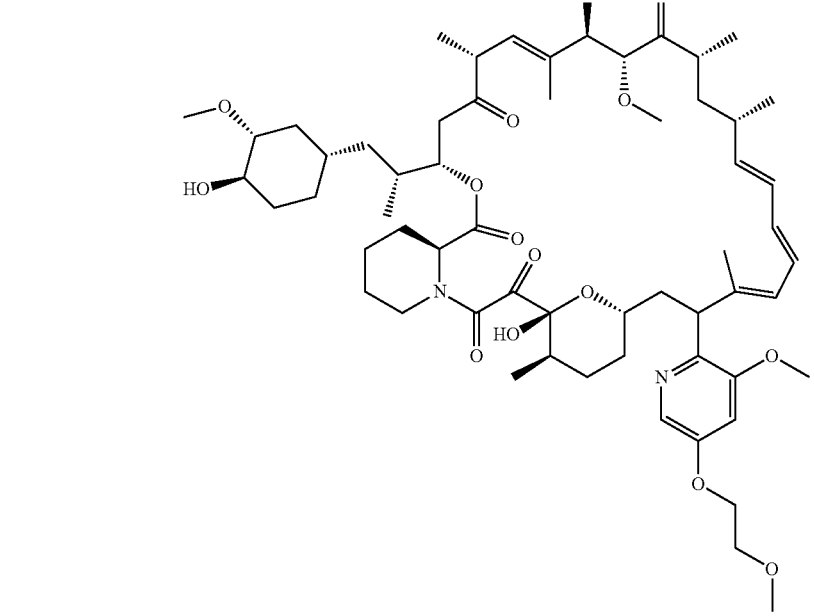 |
| I-98 | 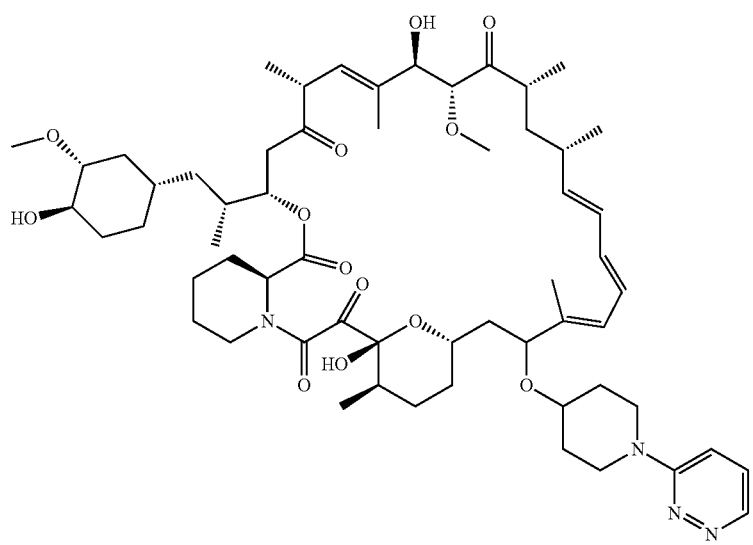 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC3CCN(c4cccnn4)CC3)C[C@@H]3CC[C@@H](C)[C@@](O)(O3)C(=O)C(=O)N3CCCC[C@H]3C(=O)O2)CC[C@H]1O] |

US 11,819,476 B2
153                                                                 154
TABLE 1-continued
| Exemplary Compounds |
|---|
| I-# | Structure |
I-99
I-100
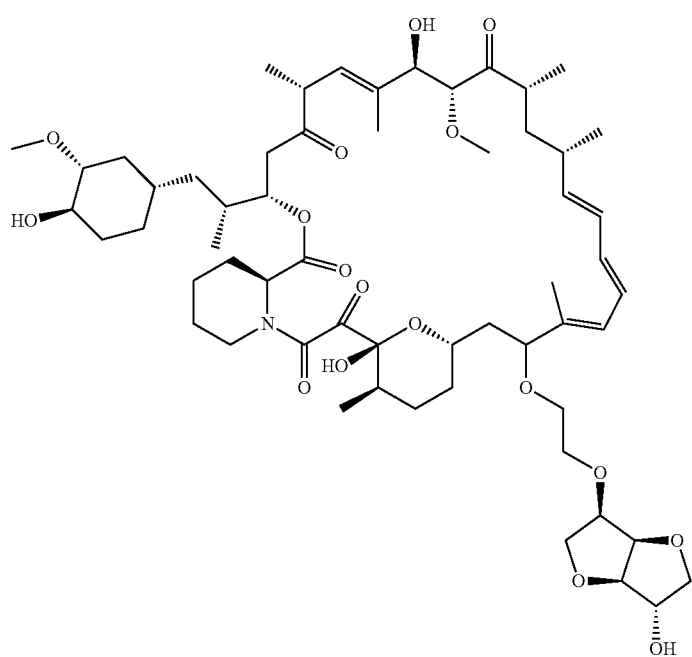 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCO[C@@H]3CO[C@H]4[C@@H]3OC[C@@H]4O)C[C@@H]3CC[C@@H](C)[C@@](O)(O3)C(=O)C(=O)N3CCCC[C@H]3C(=O)O2)CC[C@H]1O]

TABLE 1-continued
Exemplary Compounds
| I-# | Structure |
|---|---|
| I-101 | 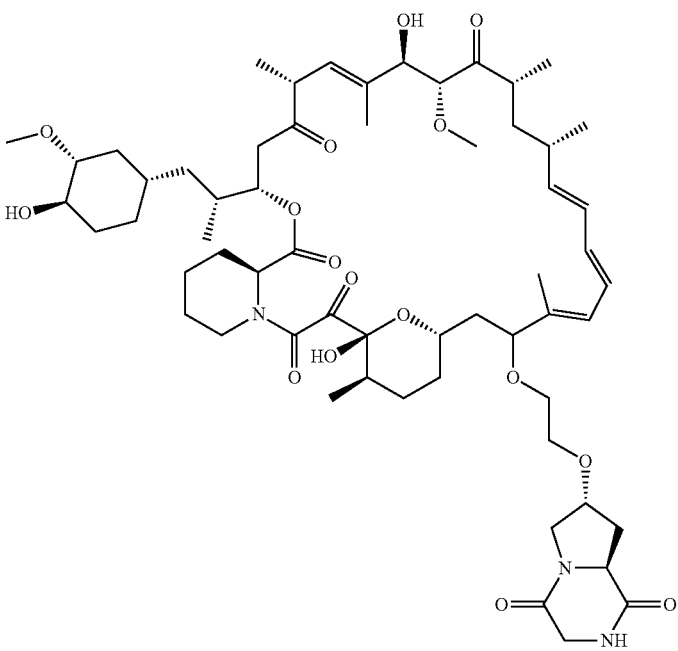 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCO[C@@H]3C[C@H]4C(=O)NCC(=O)N4C3)C[C@@H]3CC[C@@H](C)[C@@](O)(O3)C(=O)C(=O)N3CCCC[C@H]3C(=O)O2)CC[C@H]1O] |
| I-102 | 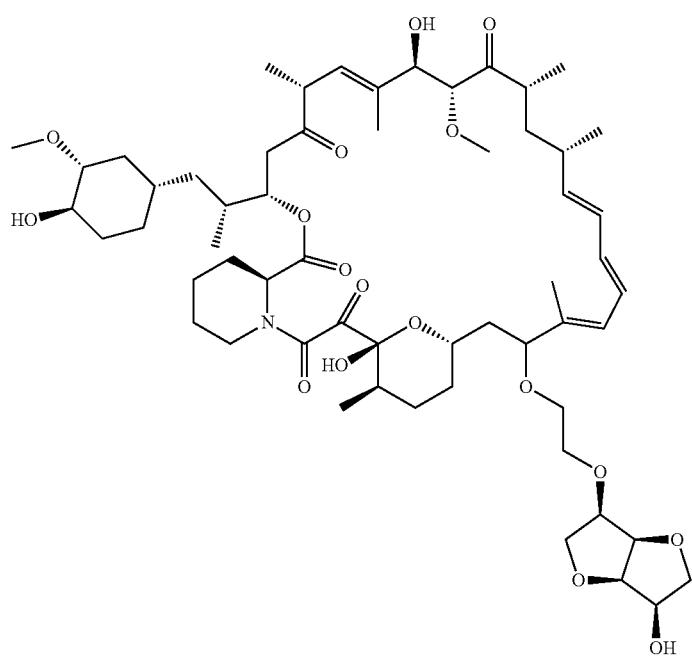 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCO[C@@H]3CO[C@H]4[C@@H]3OC[C@H]4O)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-103 | 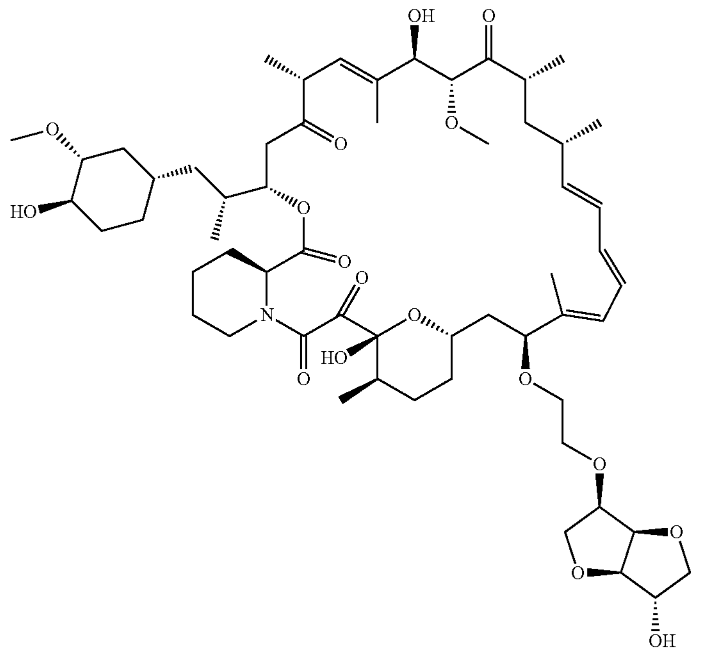 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCO[C@@H]3CO[C@H]4[C@@H]3OC[C@@H]4O)C[C@@H]3CC[C@@H](C)[C@@](O)(O3)C(=O)C(=O)N3CCCC[C@H]3C(=O)O2)CC[C@H]1O] |
| I-104 | 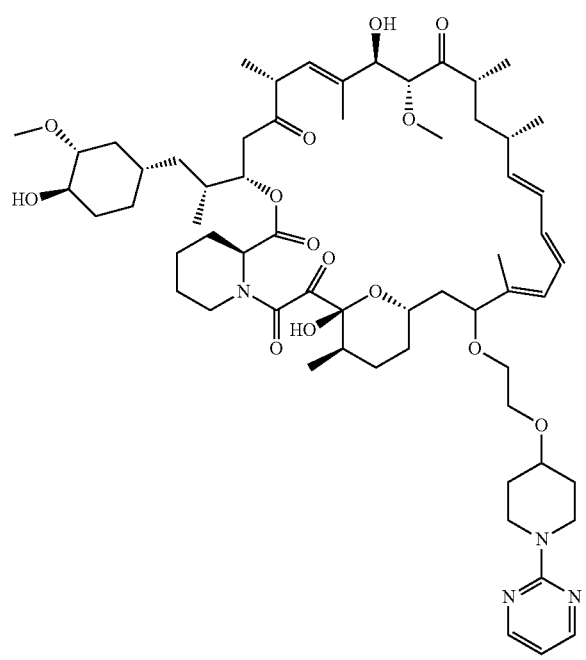 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOC3CCN(c4ncccn4)CC3)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-105 | 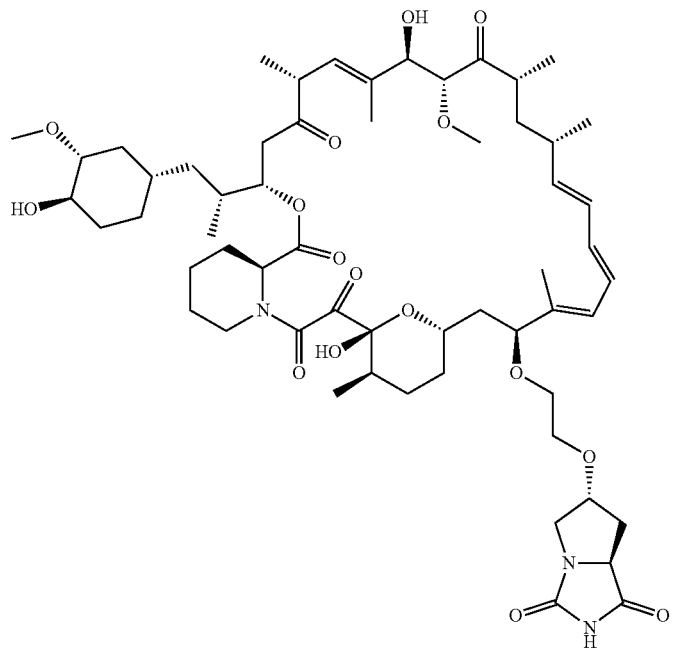 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCO[C@@H]3C[C@H]4C(=O)NC(=O)N4C3)C[C@@H]3CC[C@@H](C)[C@@](O)(O3)C(=O)C(=O)N3CCCC[C@H]3C(=O)O2)CC[C@H]1O] |
| I-106 | 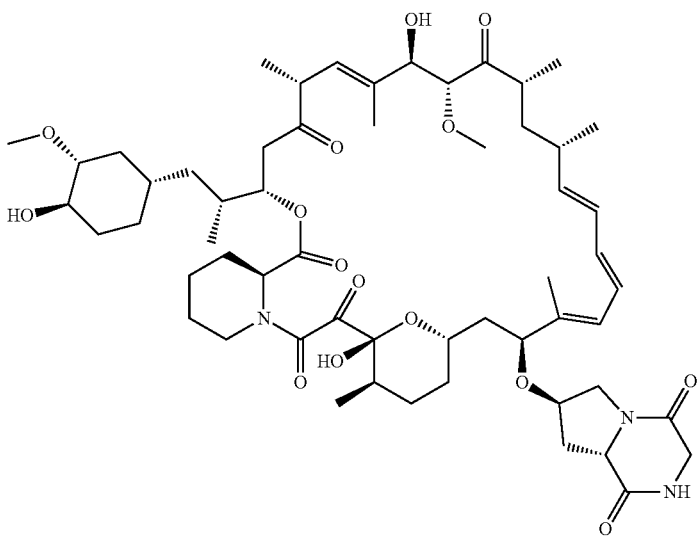 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](O[C@@H]3C[C@H]4C(=O)NCC(=O)N4C3)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-107 | 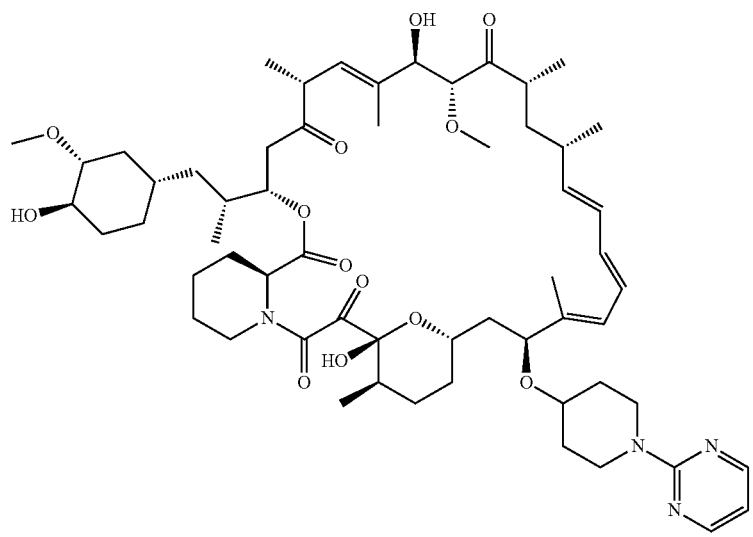 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC3CCN(c4ncccn4)CC3)C[C@@H]3CC[C@@H](C)[C@@](O)(O3)C(=O)C(=O)N3CCCC[C@H]3C(=O)O2)CC[C@H]1O] |
| I-108 | 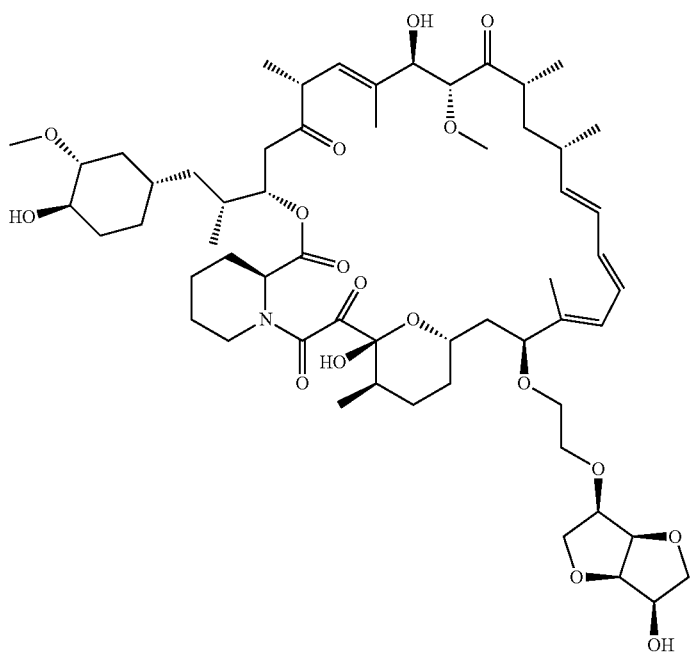 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCO[C@@H]3CO[C@H]4[C@@H]3OC[C@H]4O)C[C@@H]3CC[C@@H](C)[C@@](O)(O3)C(=O)C(=O)N3CCCC[C@H]3C(=O)O2)CC[C@H]1O] |

TABLE 1-continued

Exemplary Compounds

| I-# | Structure |
|---|---|
| I-109 | 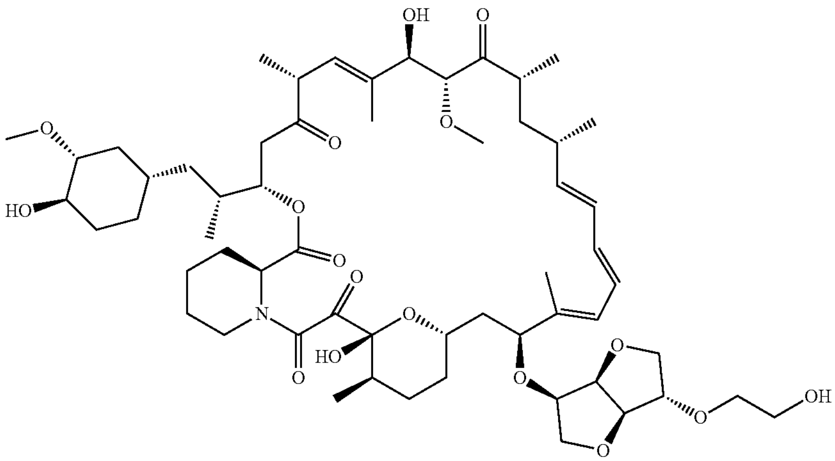 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](O[C@@H]3CO[C@H]4[C@@H]3OC[C@@H]4OCCO)C[C@@H]3CC[C@@H](C)[C@@](O)(O3)C(=O)C(=O)N3CCCC[C@H]3C(=O)O2)CC[C@H]1O] |
| I-110 | 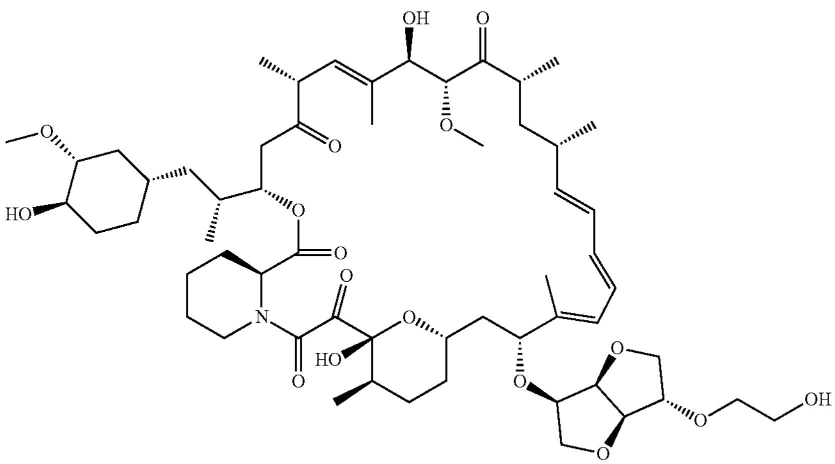 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](O[C@@H]3CO[C@H]4[C@@H]3OC[C@@H]4OCCO)C[C@@H]3CC[C@@H](C)[C@@](O)(O3)C(=O)C(=O)N3CCCC[C@H]3C(=O)O2)CC[C@H]1O] |
| I-111 | 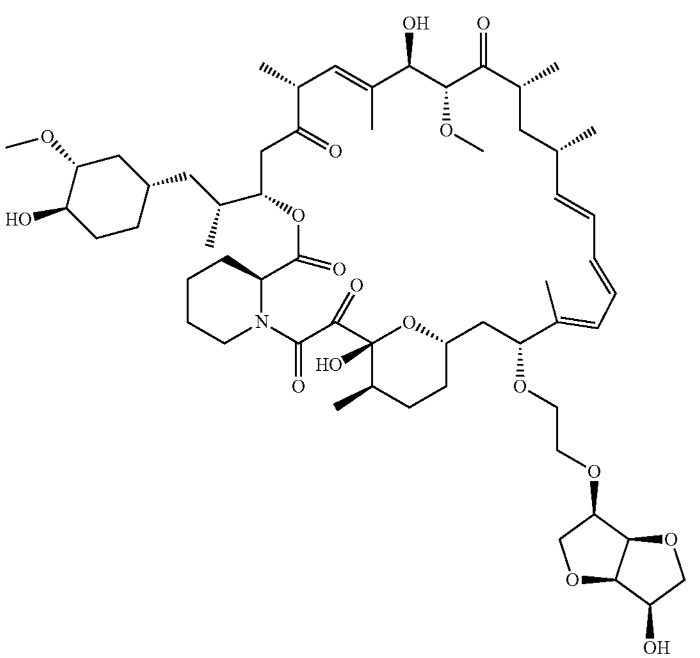 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCO[C@@H]3CO[C@H]4[C@@H]3OC[C@H]4O)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
| I-112 | 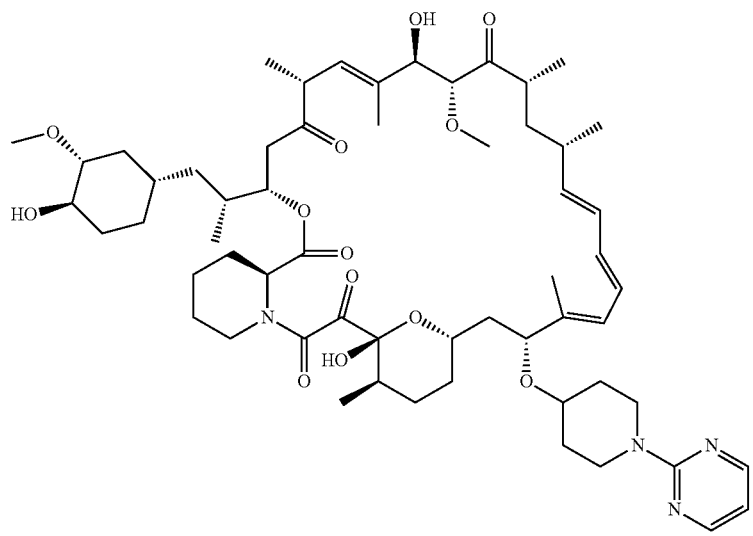 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OC3CCN(c4ncccn4)CC3)C[C@@H]3CC[C@@H](C)[C@@](O)(O3)C(=O)C(=O)N3CCCC[C@H]3C(=O)O2)CC[C@H]1O] |
| I-113 | 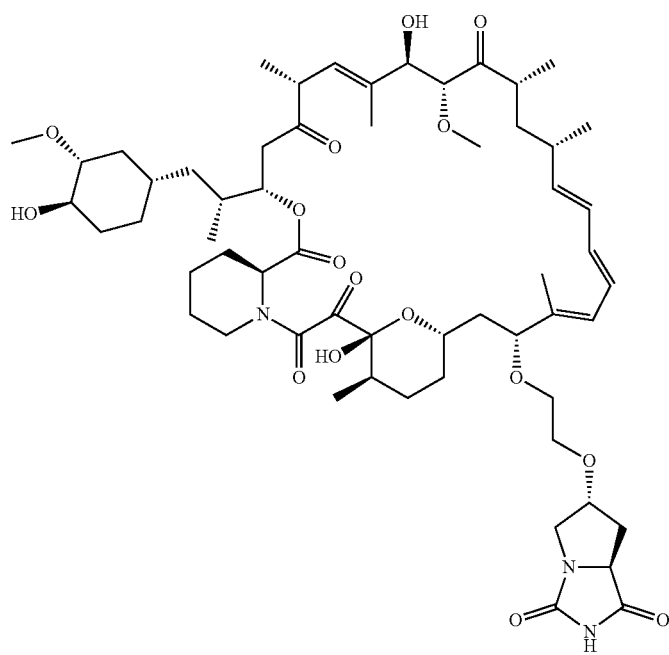 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCO[C@@H]3C[C@H]4C(=O)NC(=O)N4C3)C[C@@H]3CC[C@@H](C)[C@@](O)(O3)C(=O)C(=O)N3CCCC[C@H]3C(=O)O2)CC[C@H]1O] |

TABLE 1-continued
Exemplary Compounds
| I-# | Structure |
|---|---|
I-114
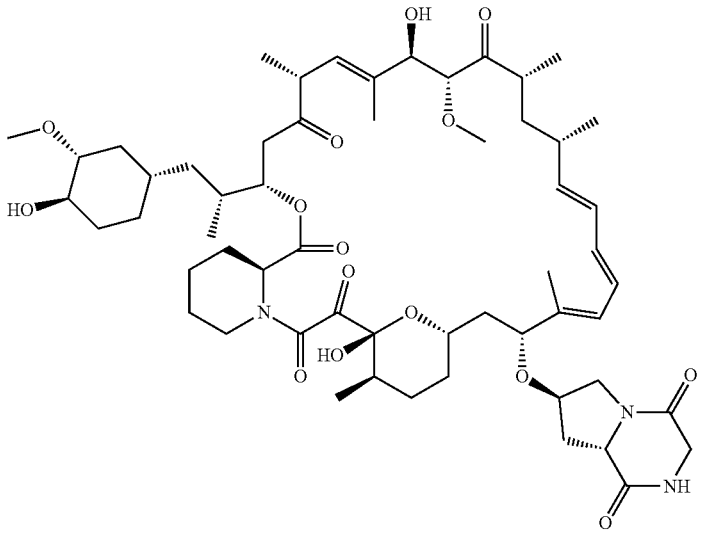 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](O[C@@H]3C[C@H]4C(=O)NCC(=O)N4C3)C[C@@H]3CC[C@@H](C)[C@@](O)(O3)C(=O)C(=O)N3CCCC[C@H]3C(=O)O2)CC[C@H]1O]
I-115
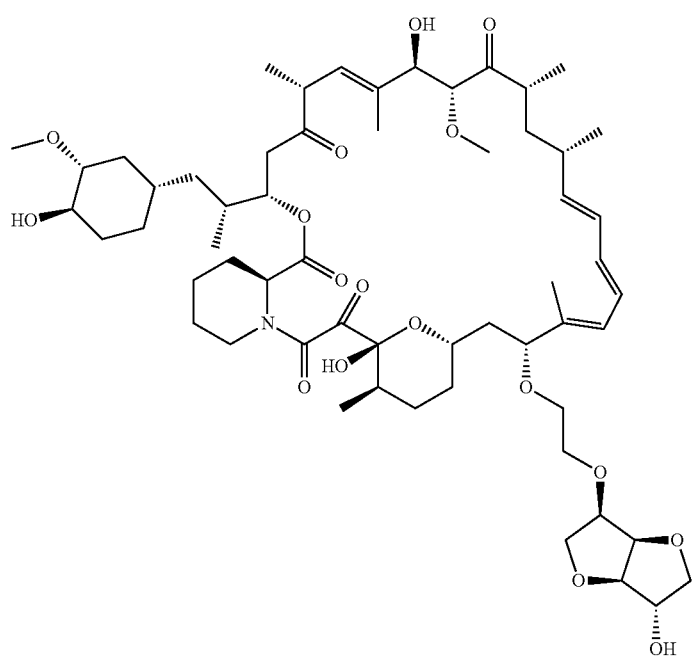 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCO[C@@H]3CO[C@H]4[C@@H]3OC[C@@H]4O)C[C@@H]3CC[C@@H](C)[C@@](O)(O3)C(=O)C(=O)N3CCCC[C@H]3C(=O)O2)CC[C@H]1O]

TABLE 1-continued
Exemplary Compounds
| I-# | Structure |
|---|---|
| I-116 | 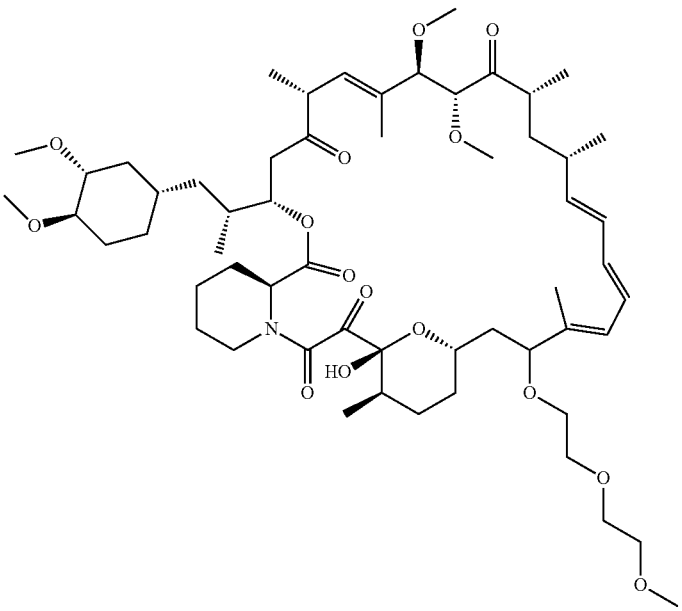 |
| I-117 | 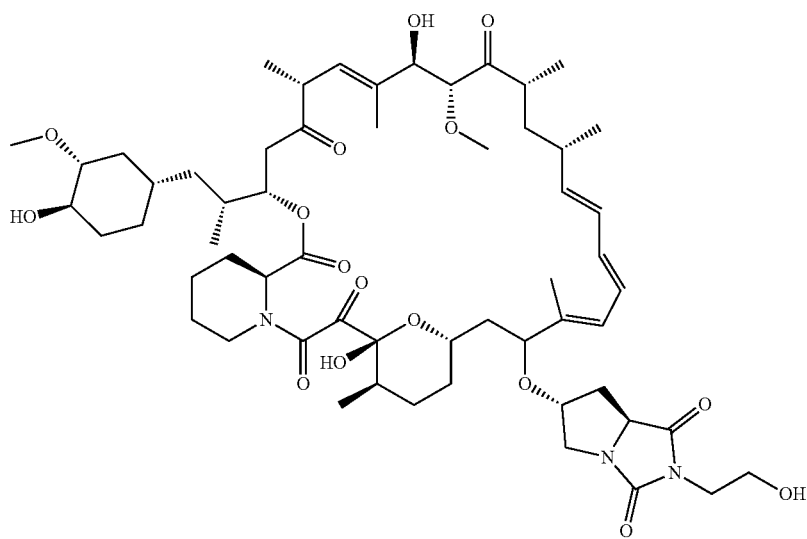 |

TABLE 1-continued
Exemplary Compounds
| I-# | Structure |
|---|---|
| I-118 | 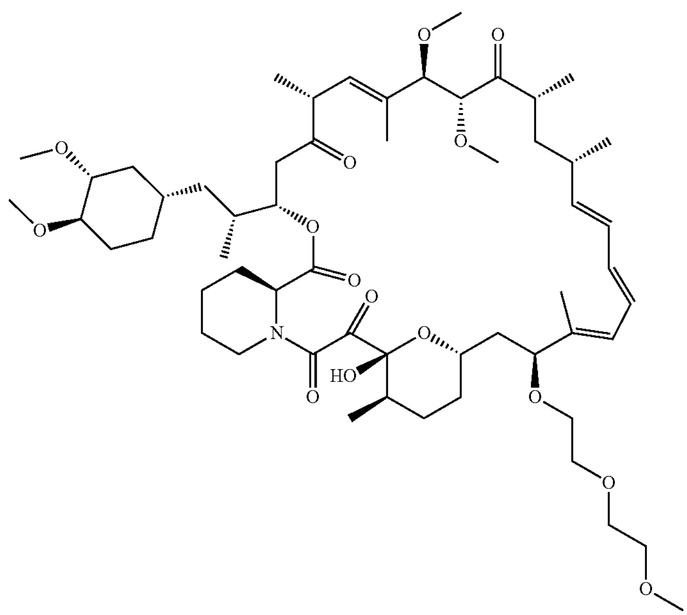 |
| I-119 | 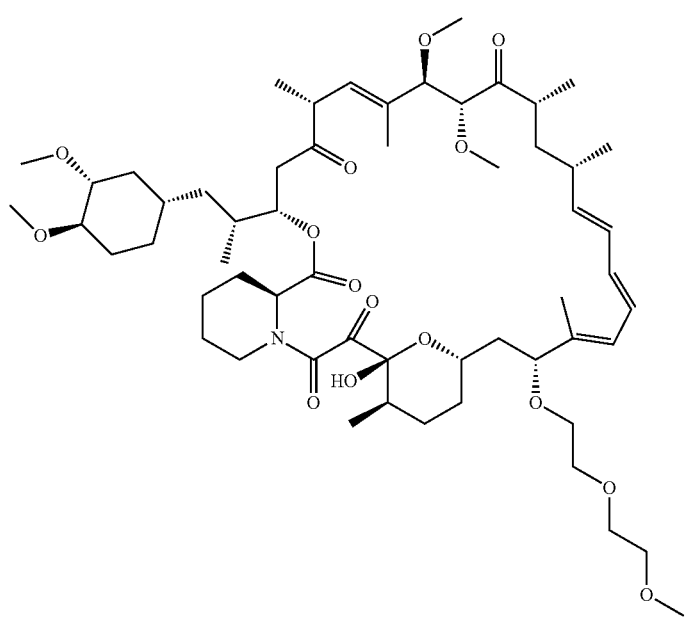 |

TABLE 1-continued
Exemplary Compounds
| I-# | Structure |
|---|---|
| I-120 | 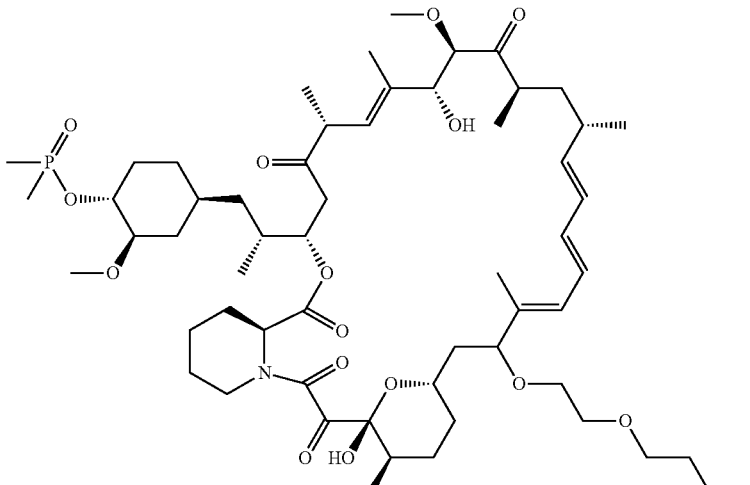 |
| I-121 | 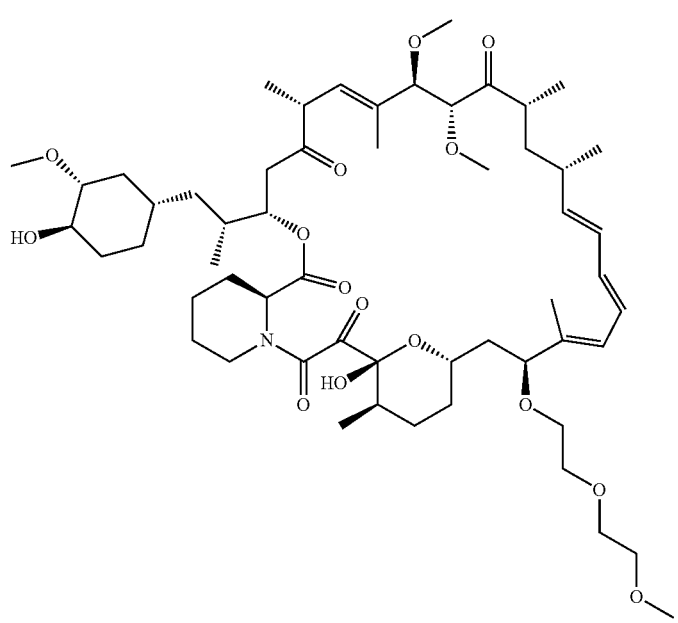 |

TABLE 1-continued
Exemplary Compounds
| I-# | Structure |
|---|---|
| I-122 | 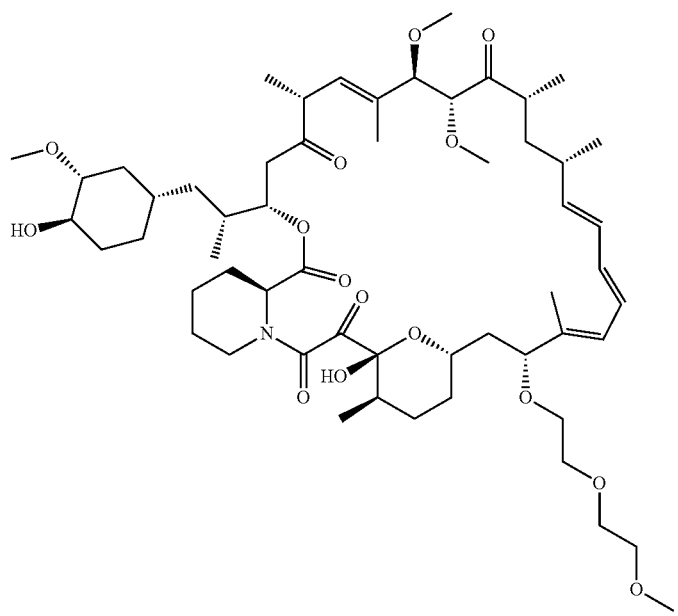 |
| I-123 | 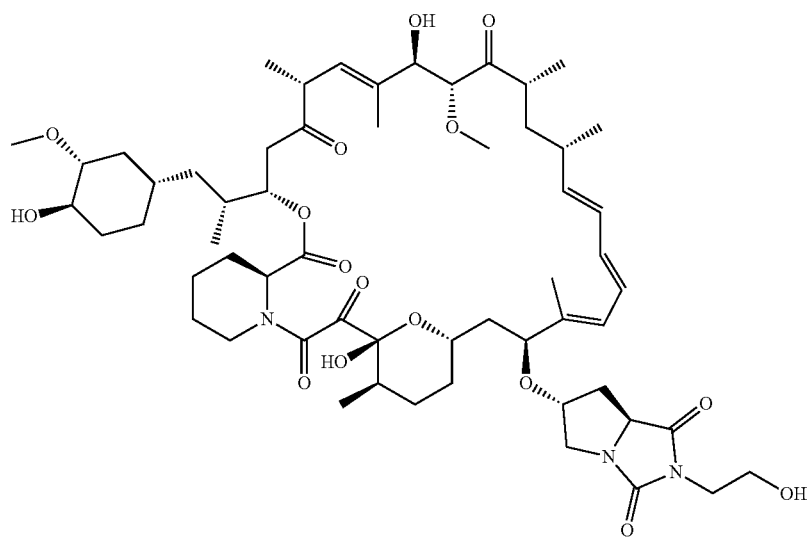 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](O[C@@H]3C[C@H]4C(=O)N(CCO)C(=O)N4C3)C[C@@H]3CC[C@@H](C)[C@@](O)(O3)C(=O)C(=O)N3CCCC[C@H]3C(=O)O2)CC[C@H]1O] |

TABLE 1-continued

Exemplary Compounds

| I-# | Structure |
|---|---|
| I-124 | 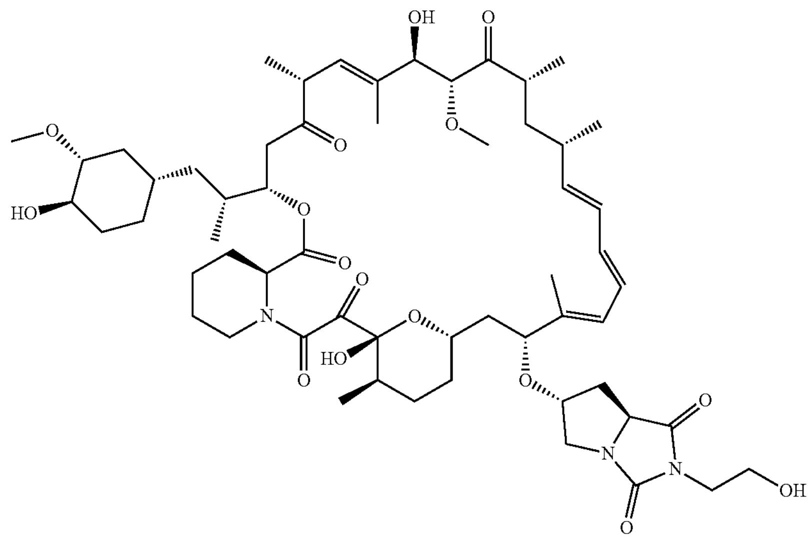 |
| I-125 | 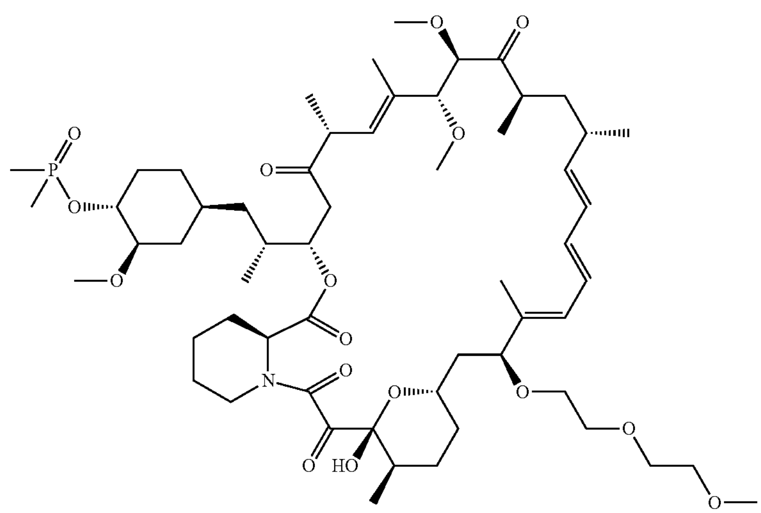 |
| I-126 | 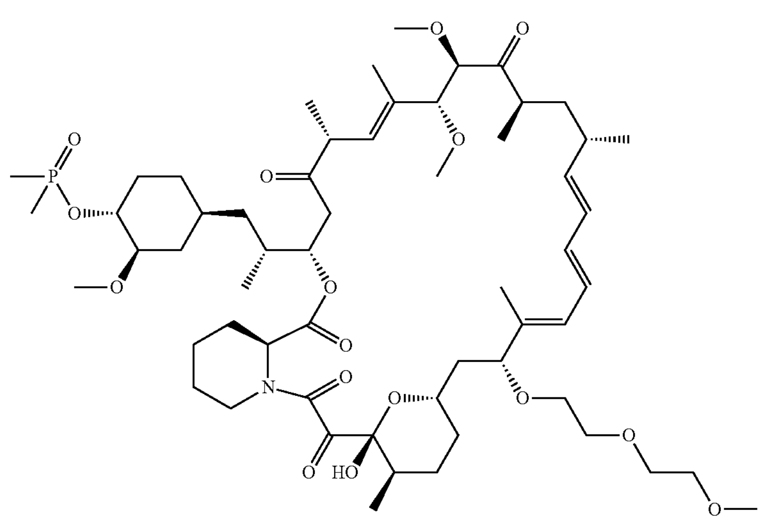 |

TABLE 1-continued
Exemplary Compounds
| I-# | Structure |
|---|---|
I-127
I-128
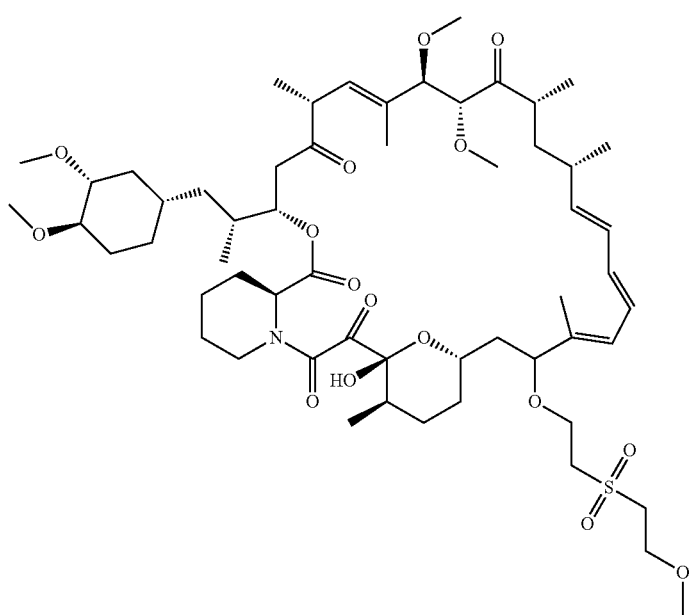

TABLE 1-continued
Exemplary Compounds
| I-# | Structure |
|---|---|
| I-129 | 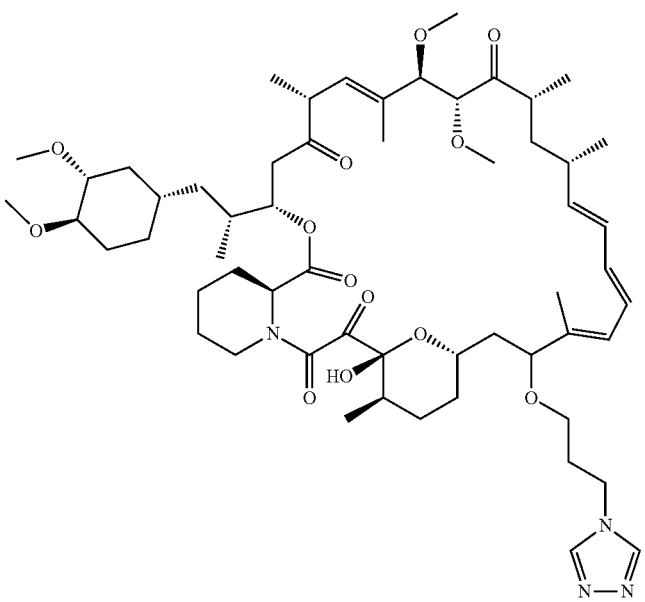 [SMILES: CO[C@@H]1/C(C)=C/[C@@H](C)C(=O)C[C@@H]([C@H](C)C[C@@H]2CC[C@@H](OC)[C@H](OC)C2)OC(=O)[C@@H]2CCCCN2C(=O)C(=O)[C@]2(O)O[C@@H](CC[C@H]2C)CC(OCCCn2cnnc2)/C(C)=C/C=C/C=C/[C@@H](C)C[C@@H](C)C(=O)[C@@H]1OC] |
| I-130 | 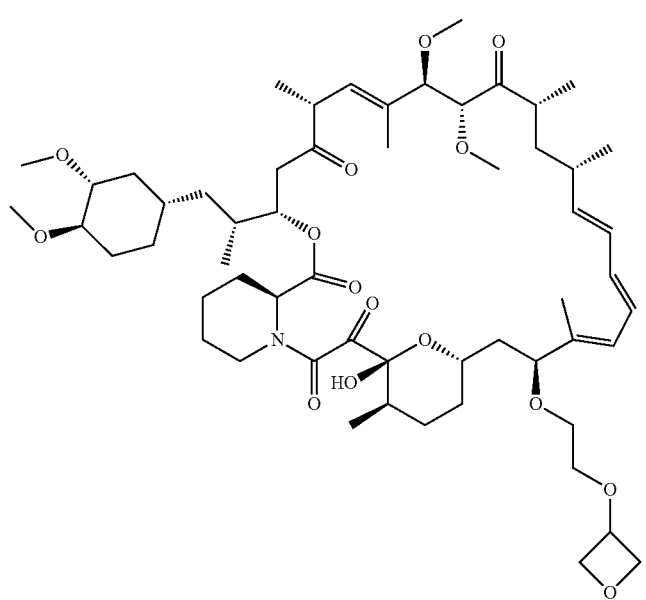 [SMILES: CO[C@@H]1/C(C)=C/[C@@H](C)C(=O)C[C@@H]([C@H](C)C[C@@H]2CC[C@@H](OC)[C@H](OC)C2)OC(=O)[C@@H]2CCCCN2C(=O)C(=O)[C@]2(O)O[C@@H](CC[C@H]2C)C[C@H](OCCOC2COC2)/C(C)=C/C=C/C=C/[C@@H](C)C[C@@H](C)C(=O)[C@@H]1OC] |

TABLE 1-continued
Exemplary Compounds
| I-# | Structure |
|---|---|
| I-131 | 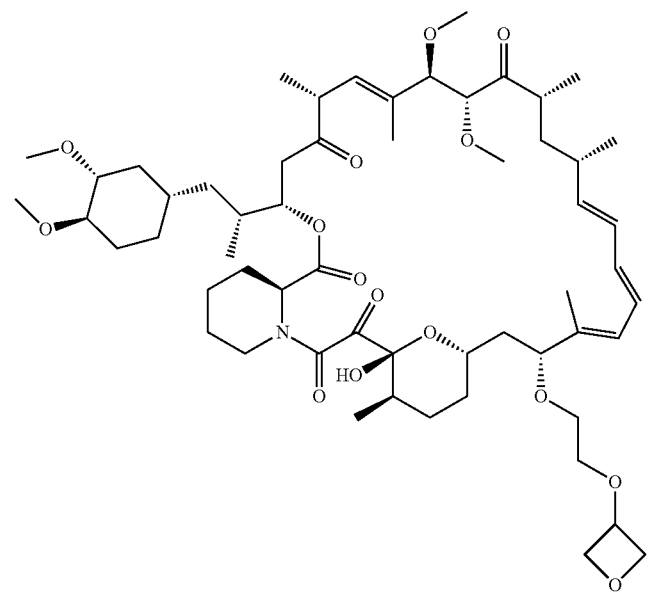 [SMILES: CO[C@@H]1/C(C)=C/[C@@H](C)C(=O)C[C@@H]([C@H](C)C[C@@H]2CC[C@@H](OC)[C@H](OC)C2)OC(=O)[C@@H]2CCCCN2C(=O)C(=O)[C@]2(O)O[C@@H](CC[C@H]2C)C[C@@H](OCCOC2COC2)/C(C)=C/C=C/C=C/[C@@H](C)C[C@@H](C)C(=O)[C@@H]1OC] |
| I-132 | 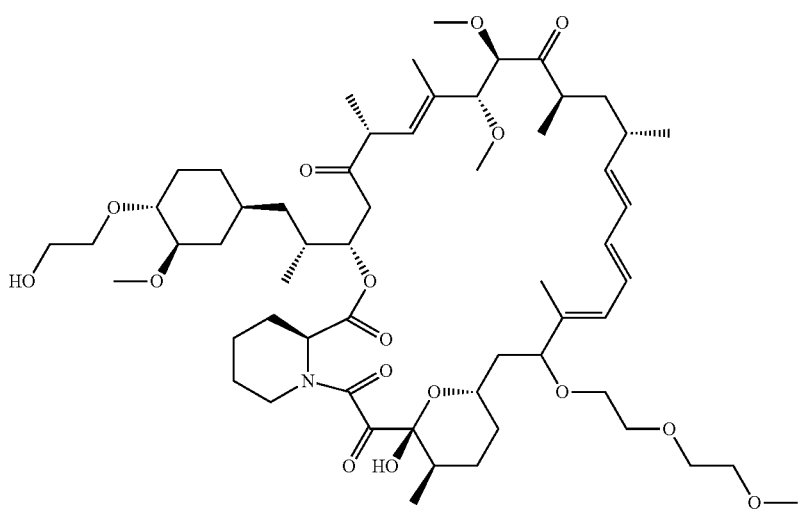 [SMILES: COCCOCCOC1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](OC)[C@@H](OC)C(=O)[C@H](C)C[C@H](C)/C=C/C=C/C=C/1C] |

TABLE 1-continued
Exemplary Compounds
| I-# | Structure |
|---|---|
| I-133 | 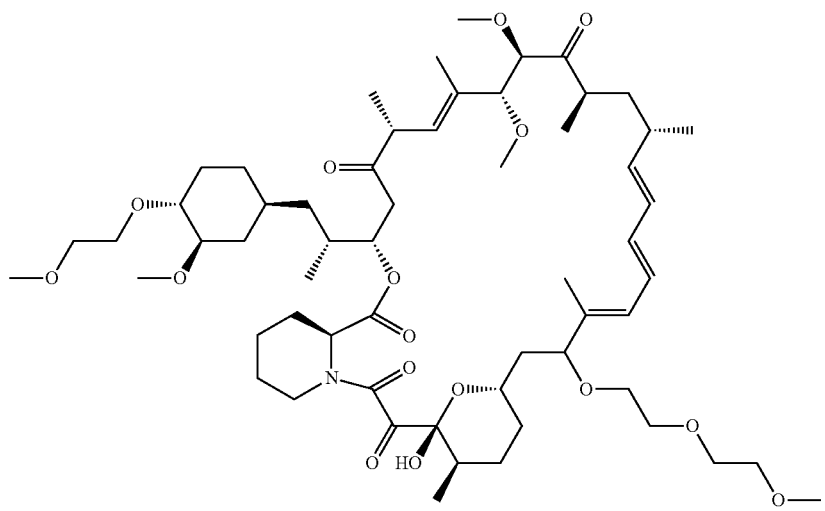 |
| I-134 | 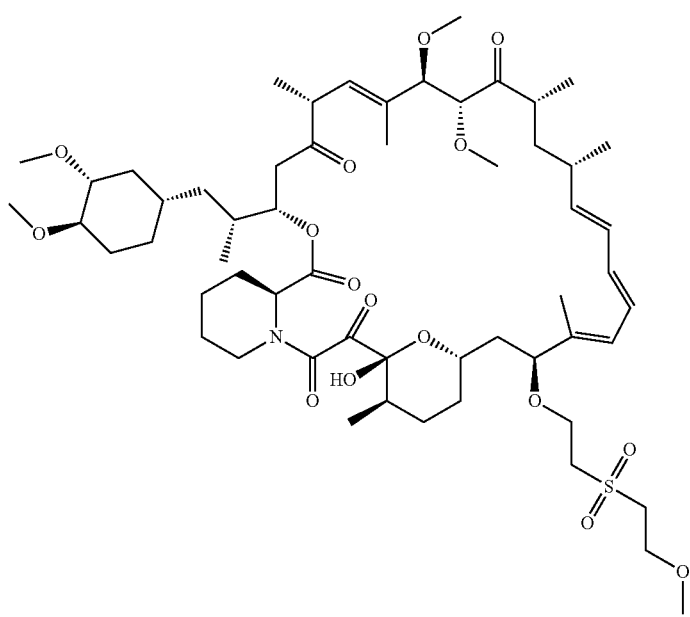 |

TABLE 1-continued
Exemplary Compounds
| I-# | Structure |
|---|---|
| I-135 | 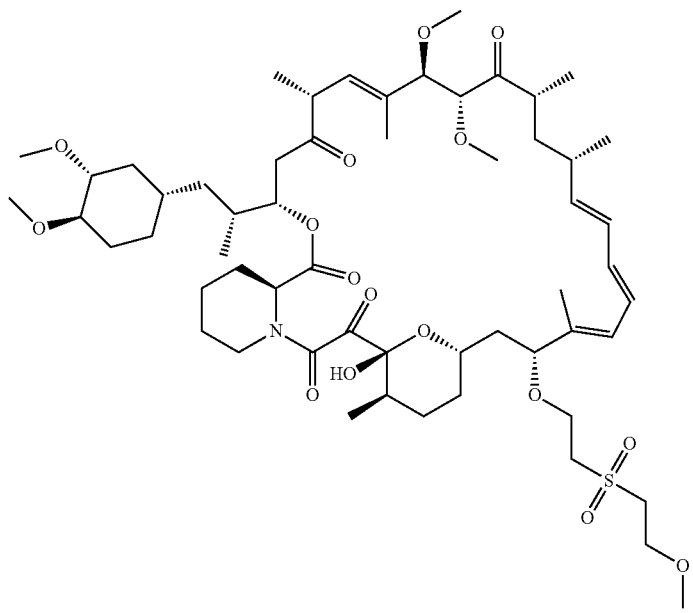 |
| I-136 | 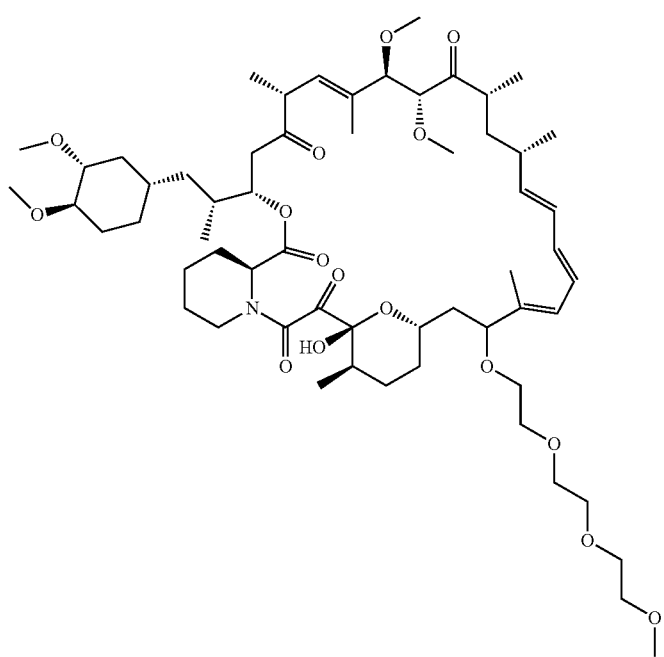 |

TABLE 1-continued
Exemplary Compounds
| I-# | Structure |
|---|---|
| I-137 | 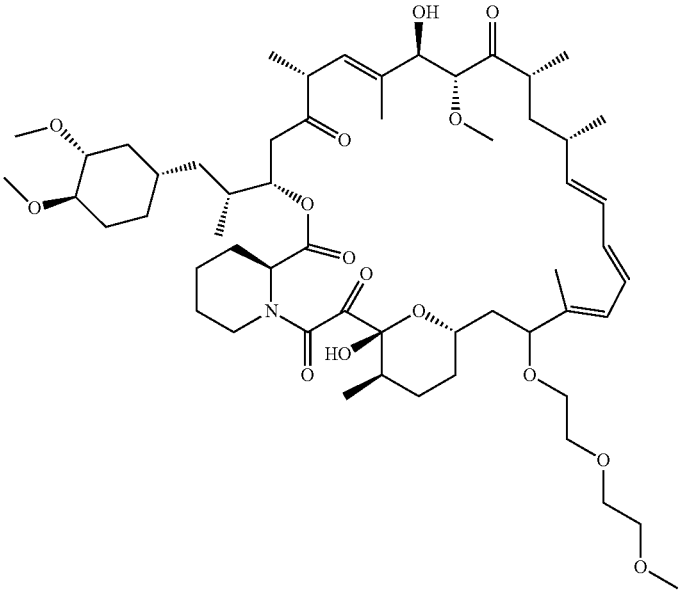 |
| I-138 | 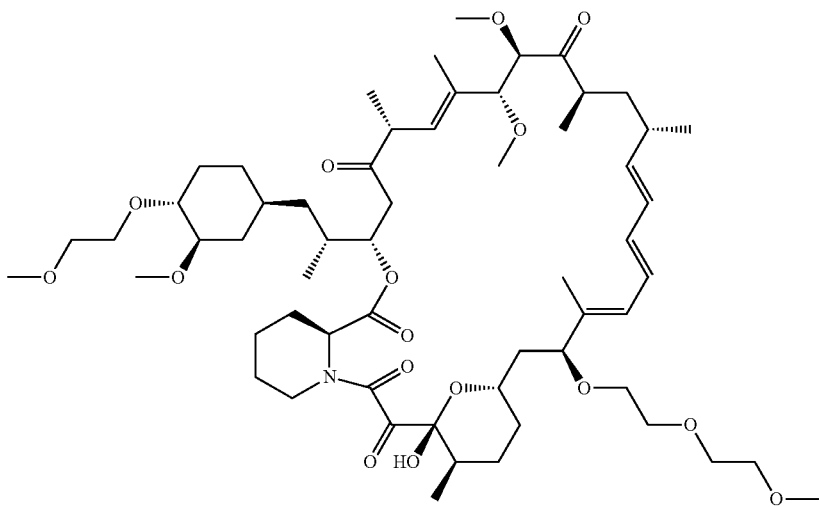 |

TABLE 1-continued
Exemplary Compounds
| I-# | Structure |
|---|---|
| I-139 | 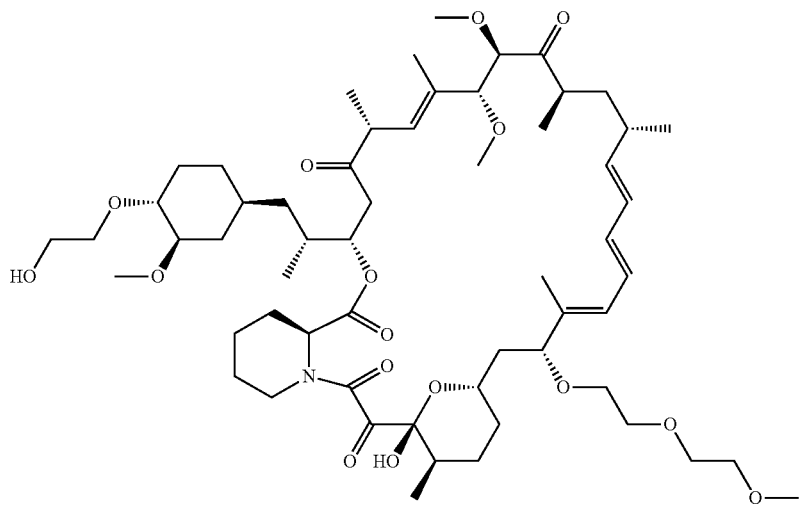 |
| I-140 | 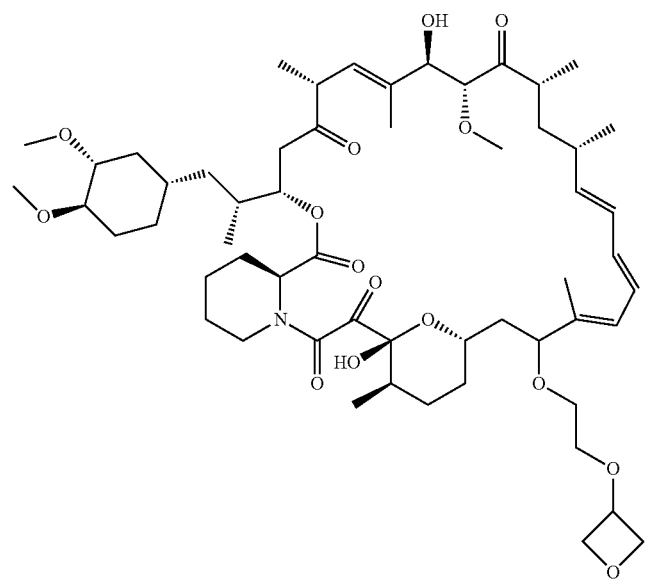 [SMILES: CO[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOC3COC3)C[C@@H]3CC[C@@H](C)[C@@](O)(O3)C(=O)C(=O)N3CCCC[C@H]3C(=O)O2)C[C@H]1OC] |

TABLE 1-continued
Exemplary Compounds
| I-# | Structure |
|---|---|
| I-141 | 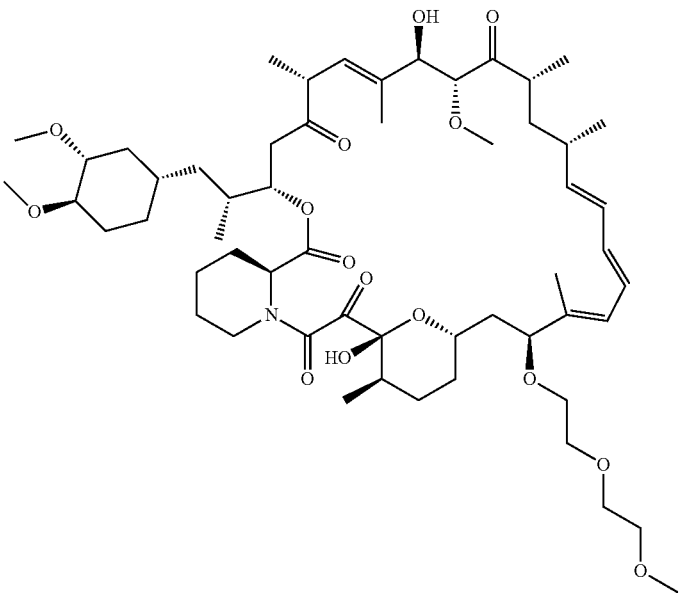 |
| I-142 | 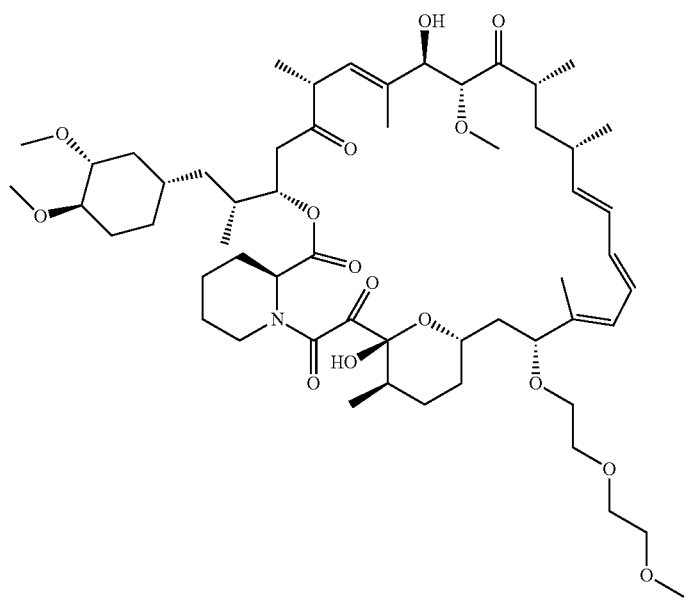 |

TABLE 1-continued
Exemplary Compounds
| I-# | Structure |
|---|---|
| I-143 | 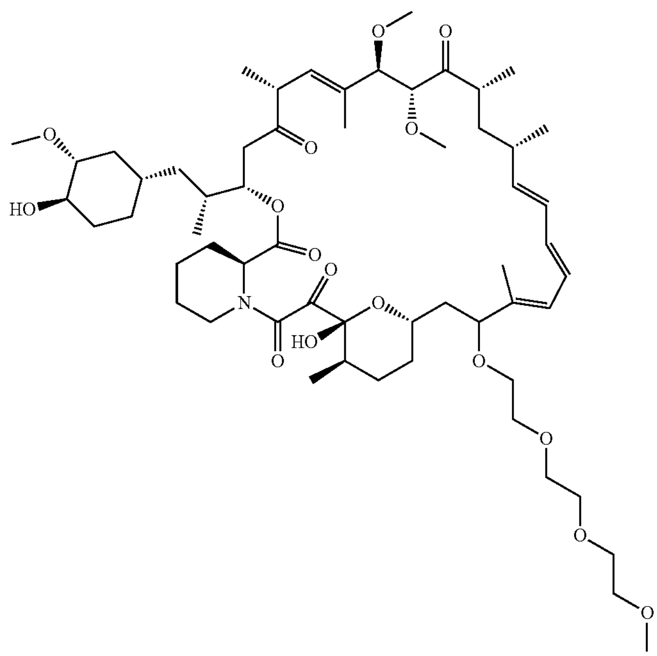 |
| I-144 | 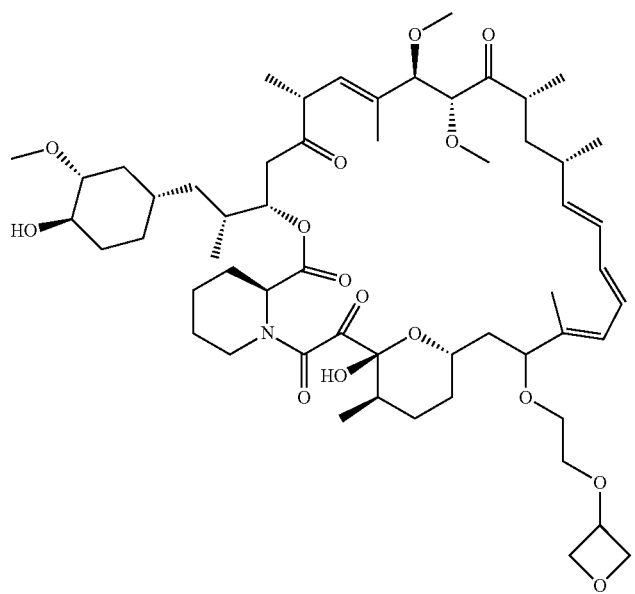 [SMILES: CO[C@@H]1/C(C)=C/[C@@H](C)C(=O)C[C@@H]([C@H](C)C[C@@H]2CC[C@@H](O)[C@H](OC)C2)OC(=O)[C@@H]2CCCCN2C(=O)C(=O)[C@]2(O)O[C@@H](CC[C@H]2C)CC(OCCOC2COC2)/C(C)=C/C=C/C=C/[C@@H](C)C[C@@H](C)C(=O)[C@@H]1OC] |

TABLE 1-continued
Exemplary Compounds
| I-# | Structure |
|---|---|
| I-145 | 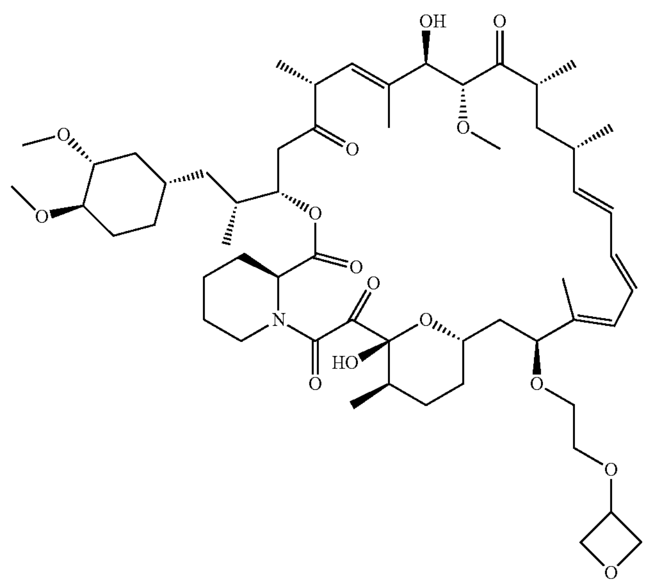 [SMILES: CO[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOC3COC3)C[C@@H]3CC[C@@H](C)[C@@](O)(O3)C(=O)C(=O)N3CCCC[C@H]3C(=O)O2)C[C@H]1OC] |
| I-146 | 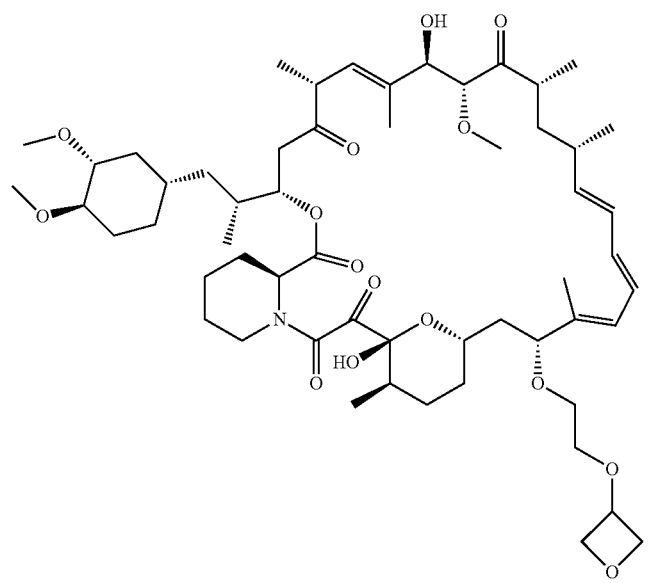 |

TABLE 1-continued
Exemplary Compounds
| I-# | Structure |
|---|---|
| I-147 | 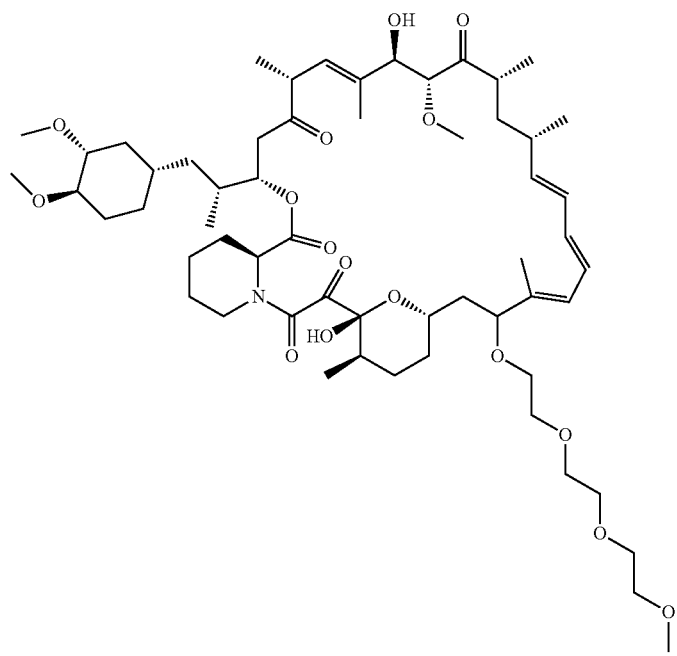 |
| I-148 | 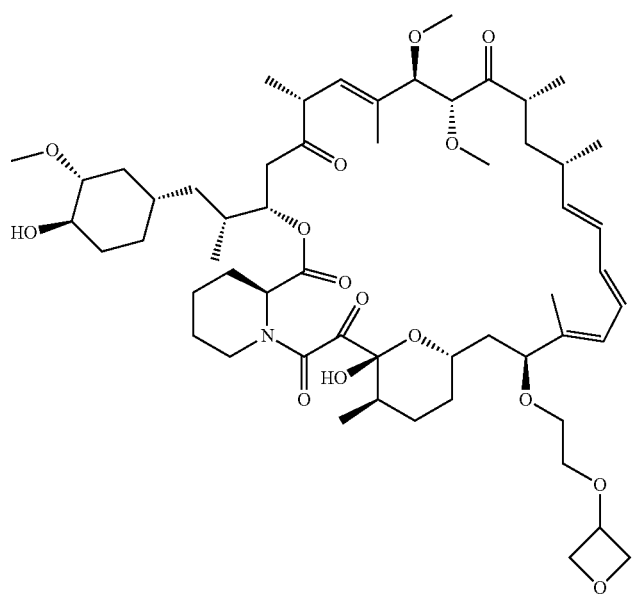 [SMILES: CO[C@@H]1/C(C)=C/[C@@H](C)C(=O)C[C@@H]([C@H](C)C[C@@H]2CC[C@@H](O)[C@H](OC)C2)OC(=O)[C@@H]2CCCCN2C(=O)C(=O)[C@]2(O)O[C@@H](CC[C@H]2C)C[C@H](OCCOC2COC2)/C(C)=C/C=C/C=C/[C@@H](C)C[C@@H](C)C(=O)[C@@H]1OC] |

TABLE 1-continued
Exemplary Compounds
| I-# | Structure |
|---|---|
| I-149 | 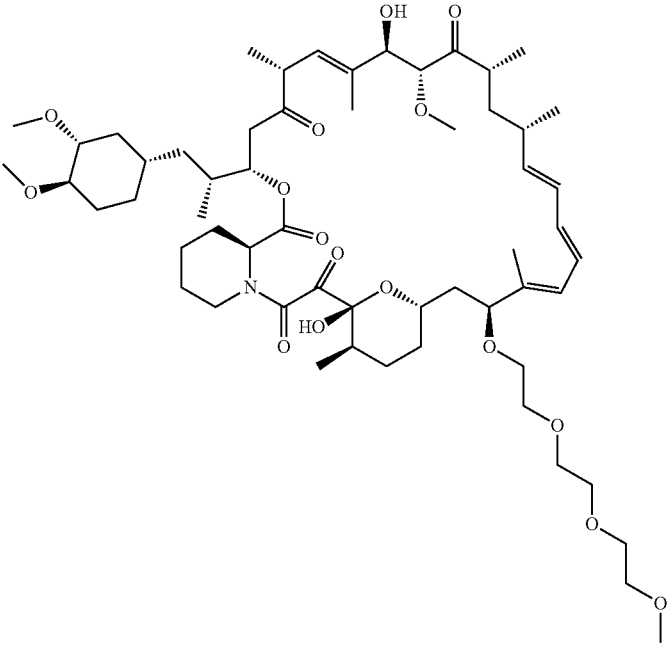 |
| I-150 | 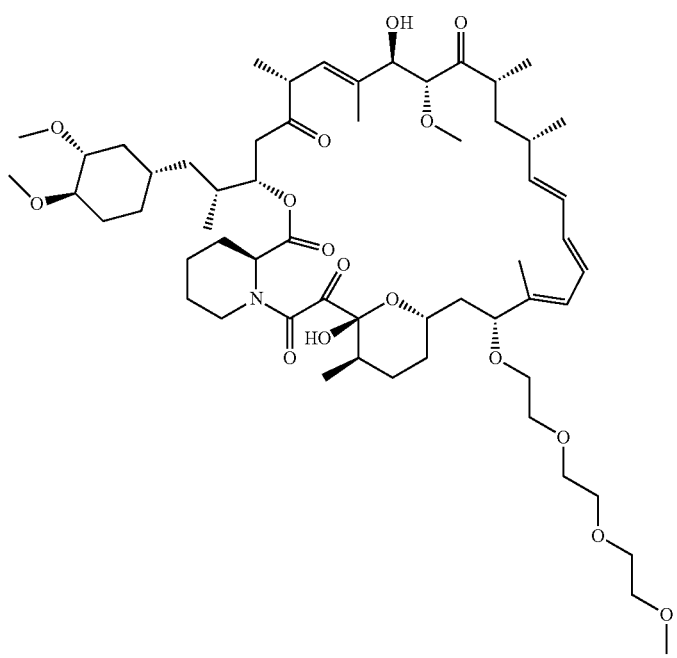 |

TABLE 1-continued
Exemplary Compounds
| I-# | Structure |
|---|---|
| I-151 | 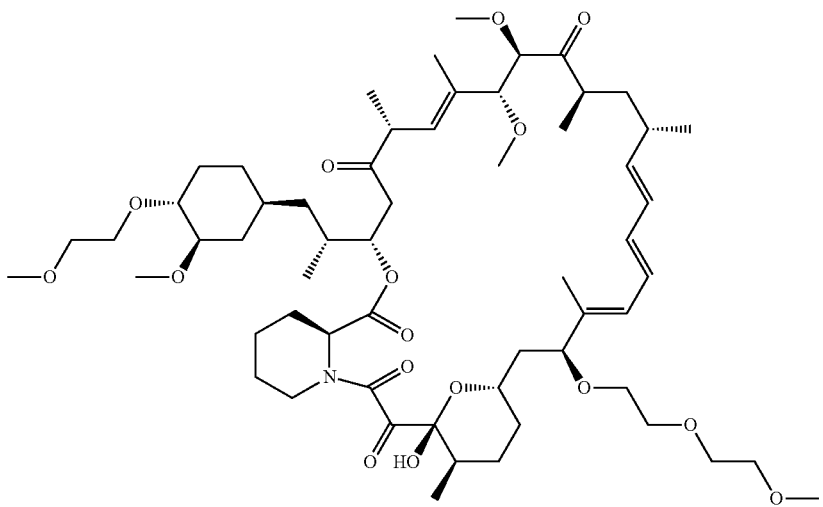 |
| I-152 | 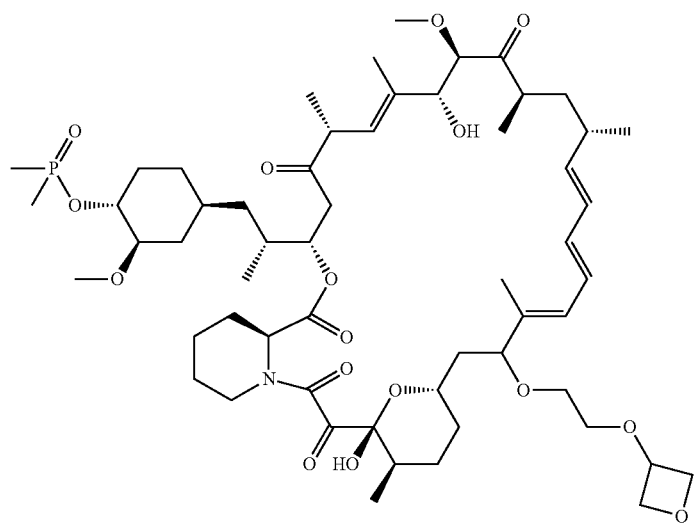 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOC3COC3)C[C@@H]3CC[C@@H](C)[C@@](O)(O3)C(=O)C(=O)N3CCCC[C@H]3C(=O)O2)CC[C@H]1OP(C)(C)=O] |

TABLE 1-continued
Exemplary Compounds
| I-# | Structure |
|---|---|
| I-153 | 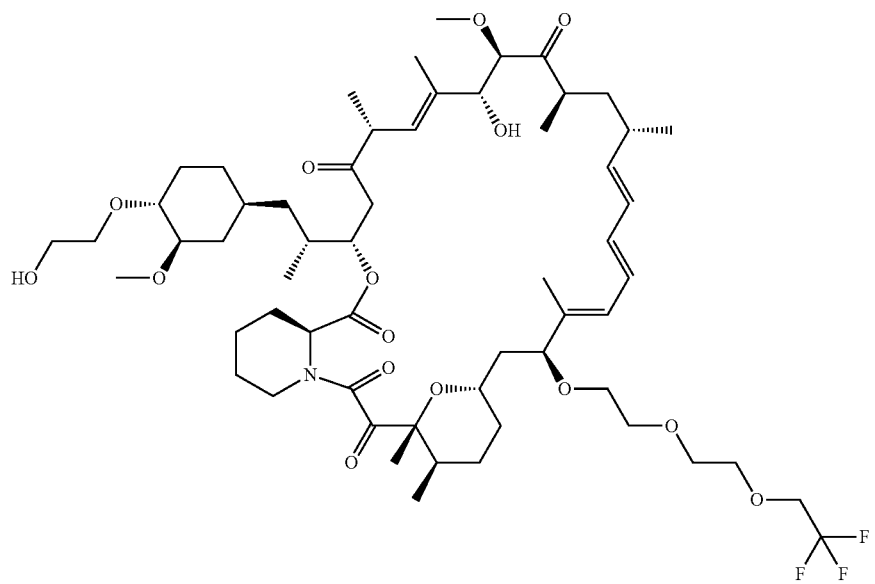 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOCCOCC(F)(F)F)C[C@@H]3CC[C@@H](C)[C@@](C)(O3)C(=O)C(=O)N3CCCC[C@H]3C(=O)O2)CC[C@H]1OCCO] |
| I-154 | 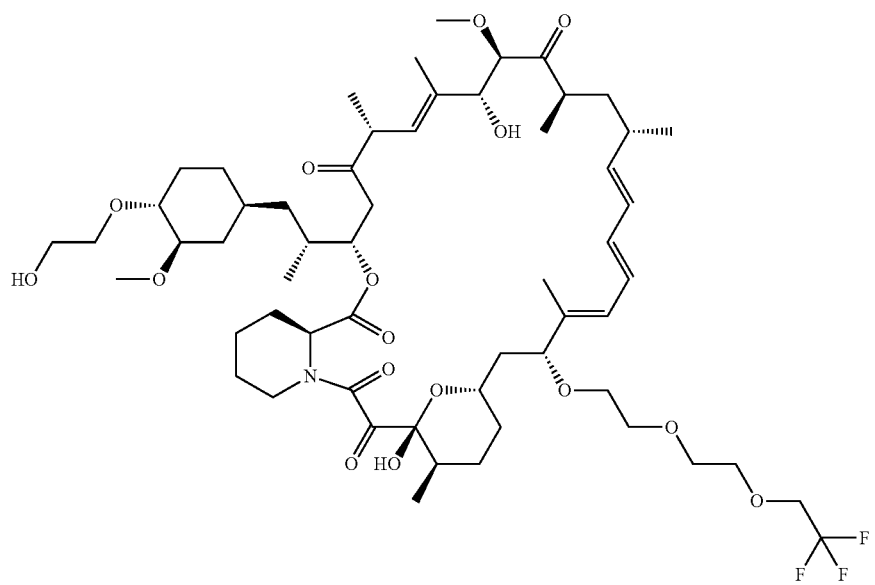 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCOCCOCC(F)(F)F)C[C@@H]3CC[C@@H](C)[C@@](O)(O3)C(=O)C(=O)N3CCCC[C@H]3C(=O)O2)CC[C@H]1OCCO] |

TABLE 1-continued
Exemplary Compounds
| I-# | Structure |
|---|---|
| I-155 | 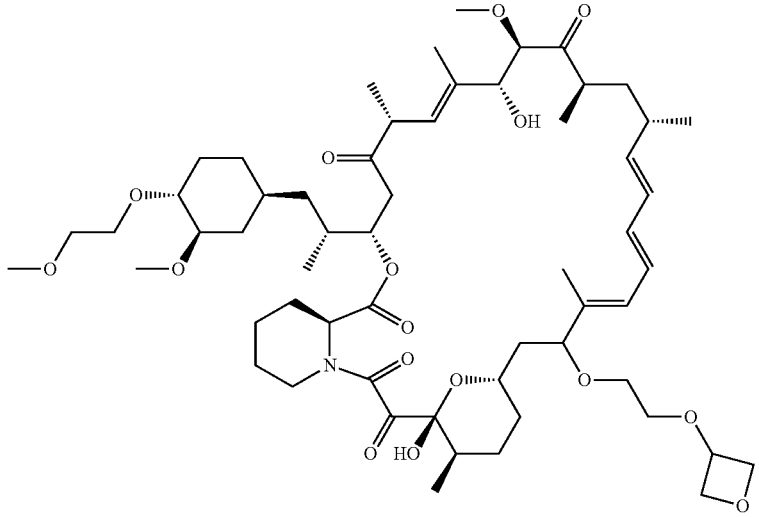 [SMILES: COCCO[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOC3COC3)C[C@@H]3CC[C@@H](C)[C@@](O)(O3)C(=O)C(=O)N3CCCC[C@H]3C(=O)O2)C[C@H]1OC] |
| I-156 | 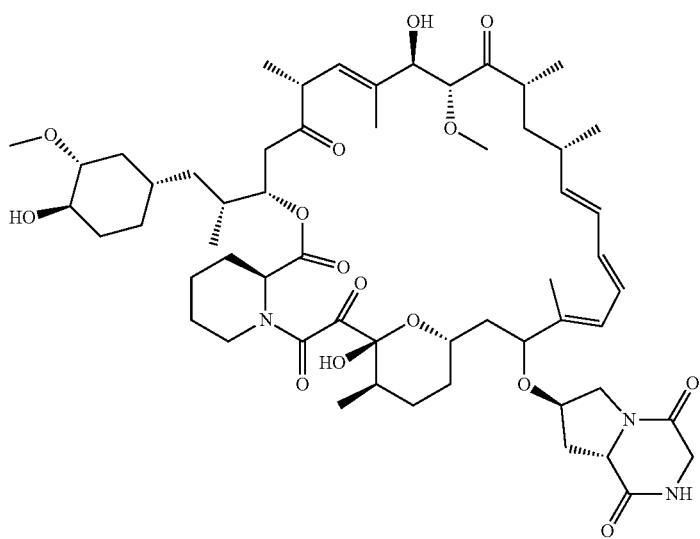 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(O[C@@H]3C[C@H]4C(=O)NCC(=O)N4C3)C[C@@H]3CC[C@@H](C)[C@@](O)(O3)C(=O)C(=O)N3CCCC[C@H]3C(=O)O2)CC[C@H]1O] |

TABLE 1-continued

Exemplary Compounds

| I-# | Structure |
|---|---|
| I-157 | 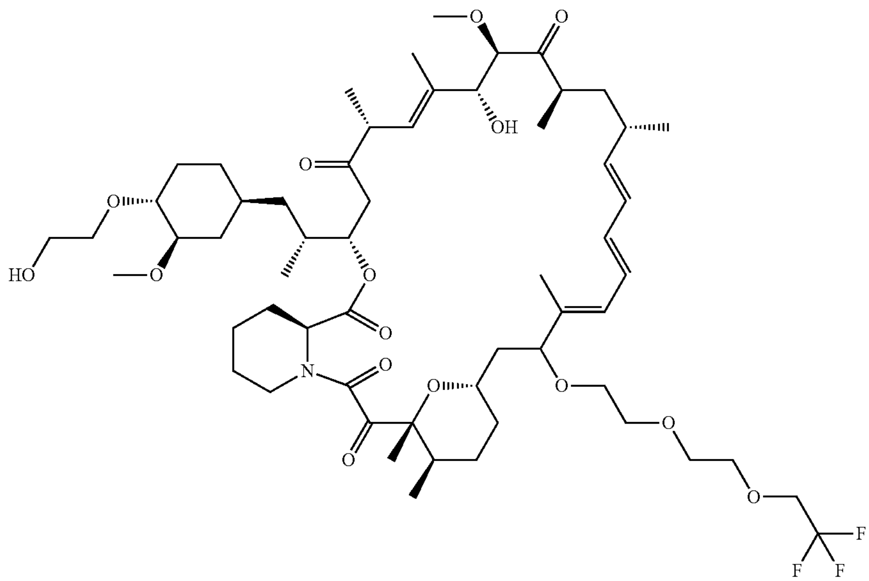 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOCCOCC(F)(F)F)C[C@@H]3CC[C@@H](C)[C@@](C)(O3)C(=O)C(=O)N3CCCC[C@H]3C(=O)O2)CC[C@H]1OCCO] |

In some embodiments, the present invention provides a compound set forth in Table 1, above, or a pharmaceutically acceptable salt thereof. It will be appreciated that the present invention also provides a compound set forth in Table 1, above, as a racemic mixture at the C7 position, or a pharmaceutically acceptable salt thereof. Further, it will be appreciated that compounds set forth in Table 1, above, as racemic mixtures at the C7 hydroxyl position may be separated into diastereomers by various methods, e.g., chiral chromatography.

TABLE 2

| # | Structure |
|---|---|
| 1 | 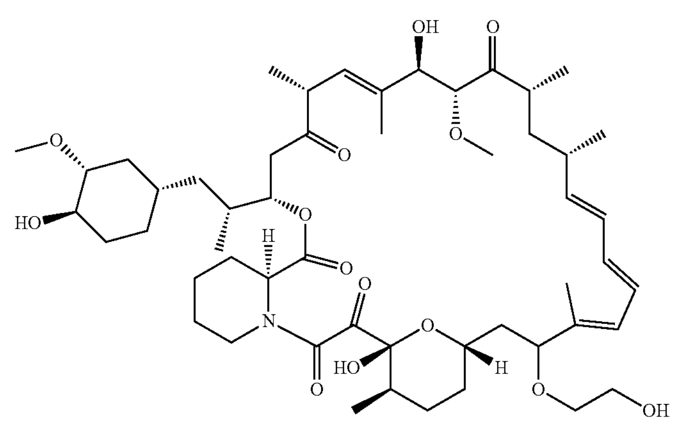 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCO)C[C@@H]3CC[C@@H](C)[C@@](O)(O3)C(=O)C(=O)N3CCCC[C@H]3C(=O)O2)CC[C@H]1O] |

TABLE 2-continued
| # | Structure |
|---|---|
| 2 | 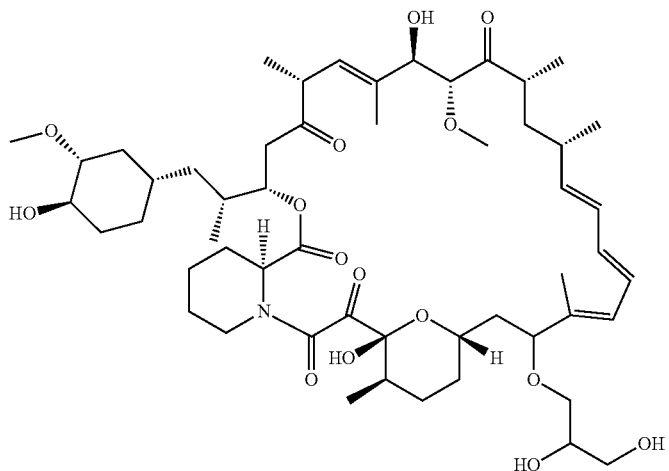 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCC(O)CO)C[C@@H]3CC[C@@H](C)[C@@](O)(O3)C(=O)C(=O)N3CCCC[C@H]3C(=O)O2)CC[C@H]1O] |
| 3 | 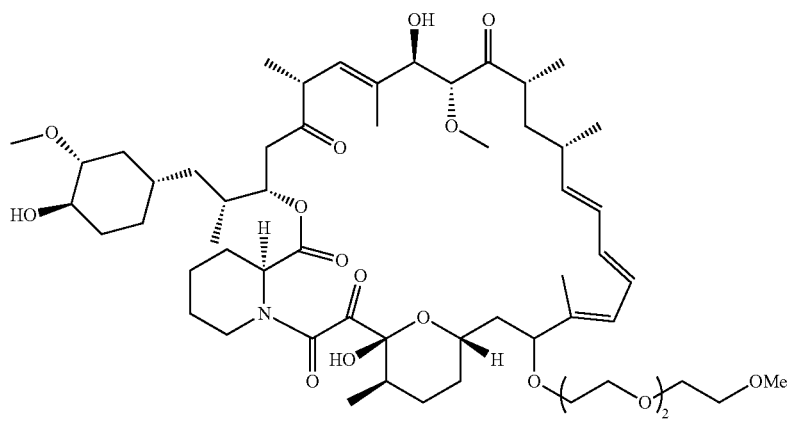 |
| 4 | 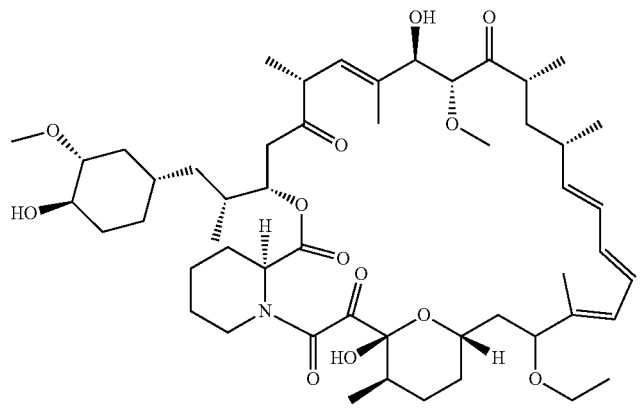 [SMILES: CCOC1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C] |

TABLE 2-continued
| # | Structure |
|---|---|
| 5 | 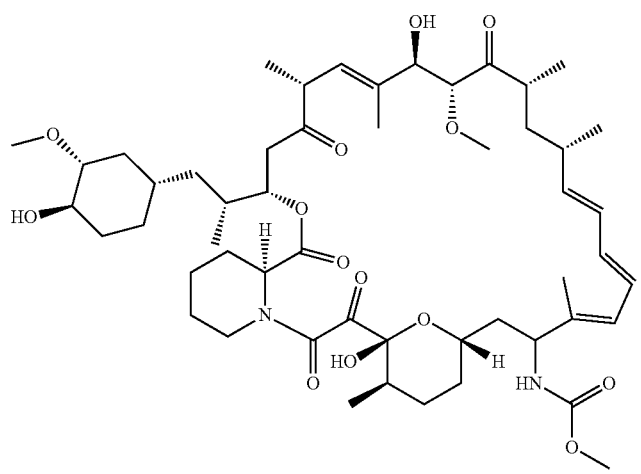 [SMILES: COC(=O)NC1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C] |
| 6 | 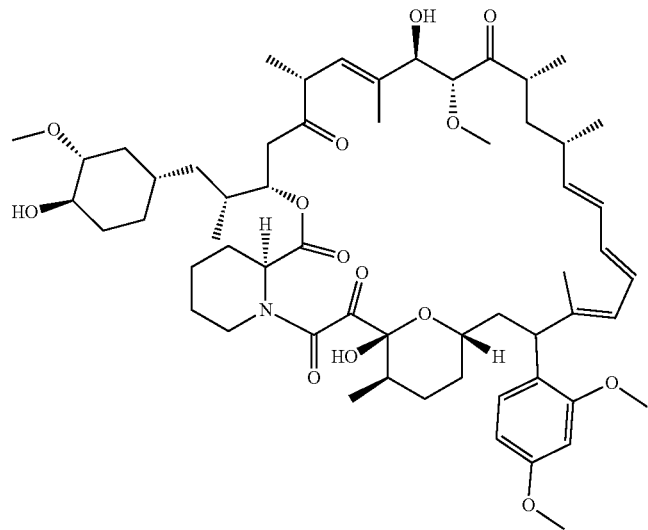 |
| 7 | 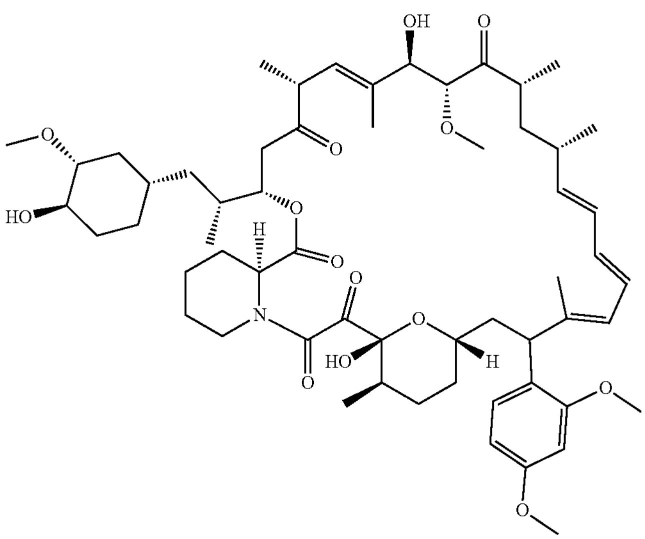 |

TABLE 2-continued
| # | Structure |
|---|-----------|
| 8 | 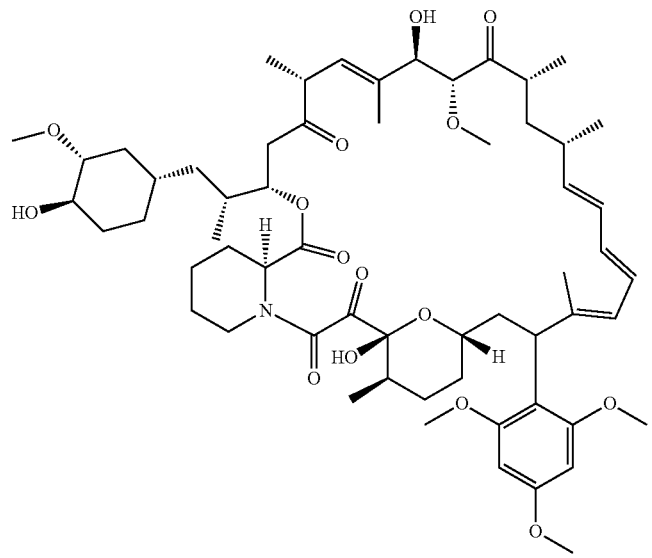 |
| 9 | 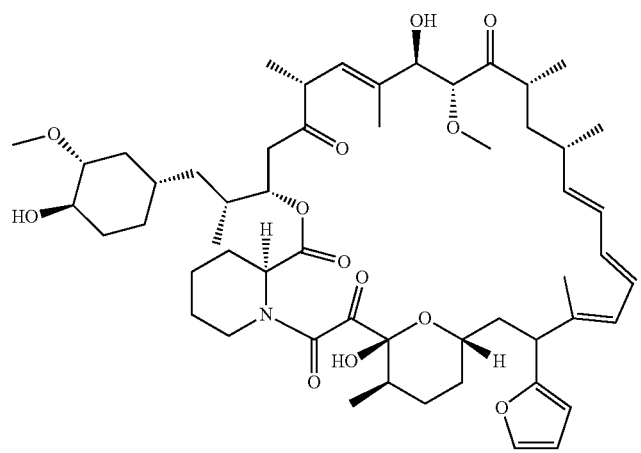 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(c3ccco3)C[C@@H]3CC[C@@H](C)[C@@](O)(O3)C(=O)C(=O)N3CCCC[C@H]3C(=O)O2)CC[C@H]1O] |
| 10 | 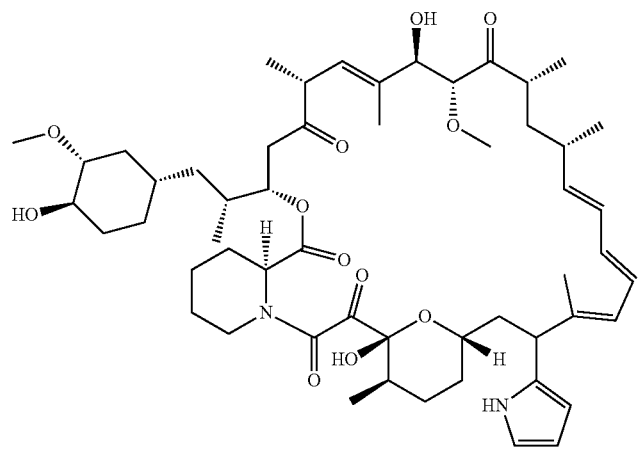 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(c3ccc[nH]3)C[C@@H]3CC[C@@H](C)[C@@](O)(O3)C(=O)C(=O)N3CCCC[C@H]3C(=O)O2)CC[C@H]1O] |

TABLE 2-continued

| # | Structure |
|---|---|
| 11 | 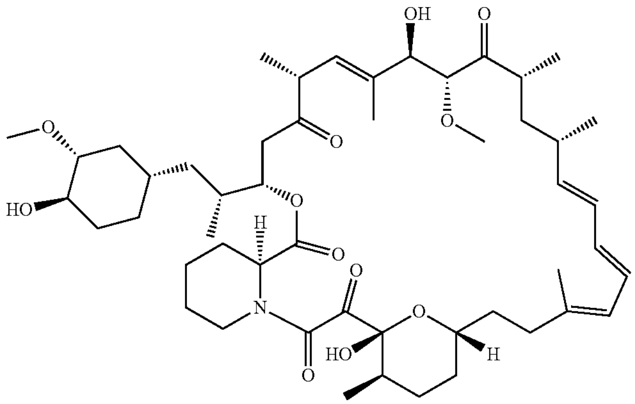 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)CC[C@@H]3CC[C@@H](C)[C@@](O)(O3)C(=O)C(=O)N3CCCC[C@H]3C(=O)O2)CC[C@H]1O] |
| 12 | 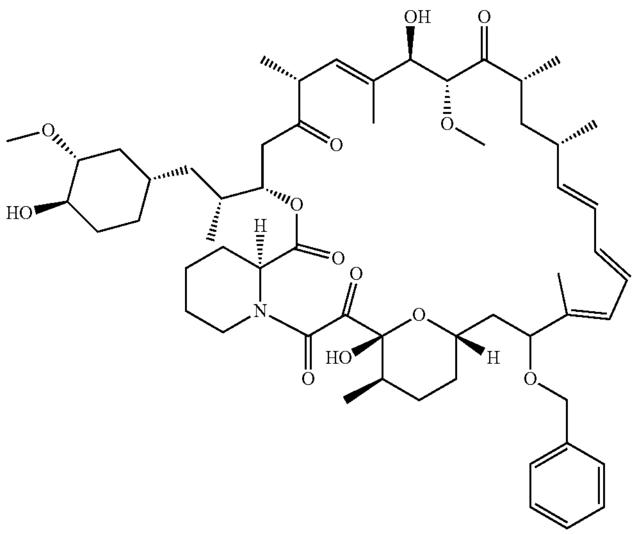 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCc3ccccc3)C[C@@H]3CC[C@@H](C)[C@@](O)(O3)C(=O)C(=O)N3CCCC[C@H]3C(=O)O2)CC[C@H]1O] |
| 13 | 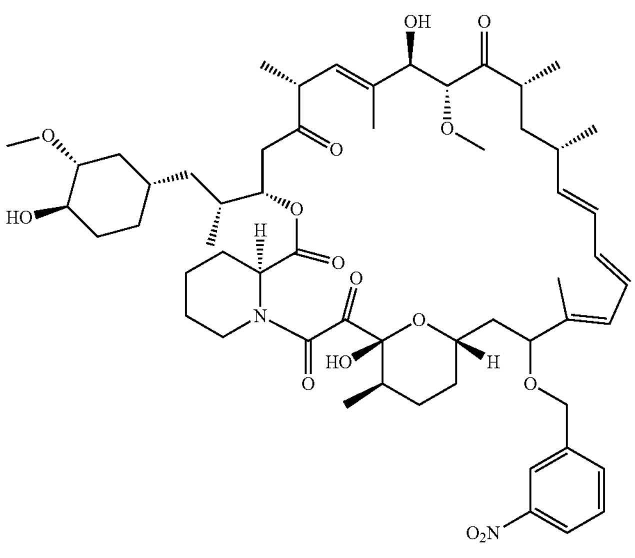 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCc3cccc([N+](=O)[O-])c3)C[C@@H]3CC[C@@H](C)[C@@](O)(O3)C(=O)C(=O)N3CCCC[C@H]3C(=O)O2)CC[C@H]1O] |

TABLE 2-continued
| # | Structure |
|---|---|
| 14 | 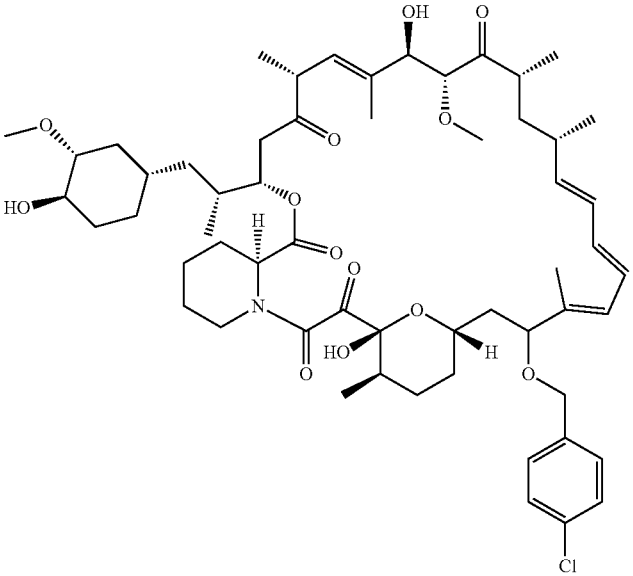 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCc3ccc(Cl)cc3)C[C@@H]3CC[C@@H](C)[C@@](O)(O3)C(=O)C(=O)N3CCCC[C@H]3C(=O)O2)CC[C@H]1O] |
| 15 | 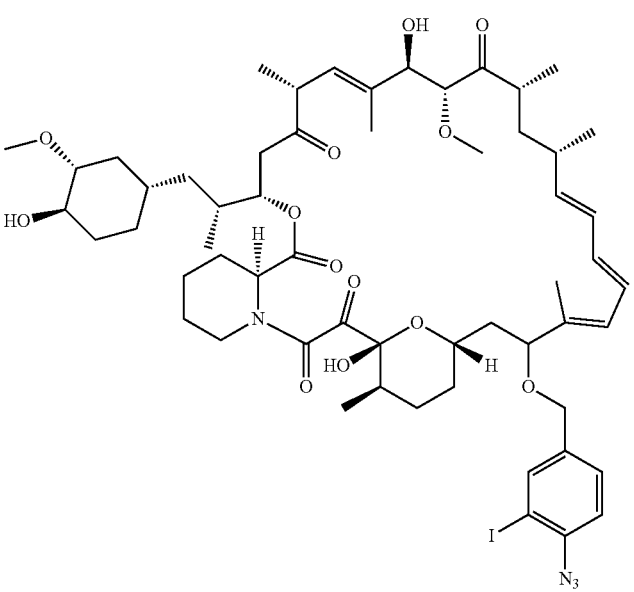 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCc3ccc(N=[N+]=[N-])c(I)c3)C[C@@H]3CC[C@@H](C)[C@@](O)(O3)C(=O)C(=O)N3CCCC[C@H]3C(=O)O2)CC[C@H]1O] |
| 16 | 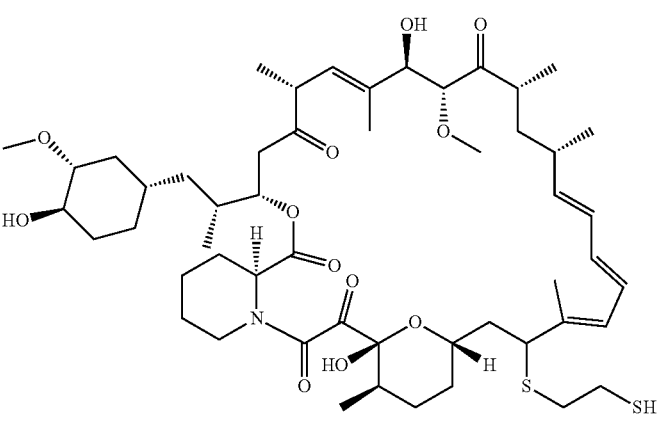 |

TABLE 2-continued

| # | Structure |
|---|---|
| 17 | (chemical structure with OH, O, OMe, HO, Bu₃Su, N₃ substituents on a macrocyclic rapamycin-like scaffold) |

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit mTORC1, in abiological sample or in a patient. In certain embodiments, the amount of compound in compositions of this invention is such that is effective to measurably inhibit mTORC1, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of mTORC1 and are therefore useful for treating one or more disorders associated with activity of mTORC1. Thus, in certain embodiments, the present invention provides a method for treating an mTORC1-mediated disorder comprising the step of administering to a patient in need thereof a compound of the present invention, or pharmaceutically acceptable composition thereof.

As used herein, the terms "mTORC1-mediated" disorders, diseases, and/or conditions as used herein means any disease or other deleterious condition in which mTORC1, is known to play a role. Accordingly, another embodiment of the present invention relates to treating or lessening the severity of one or more diseases in which mTORC1 is known to play a role. In certain embodiments, an mTORC1-mediated disorder, disease, and/or condition is selected from those described by Matt Kaeberlin, Scientifica, vol. 2013, Article ID 849186.

The methods described herein include methods for the treatment of cancer in a subject. As used in this context, to "treat" means to ameliorate or improve at least one symptom or clinical parameter of the cancer. For example, a treatment can result in a reduction in tumor size or growth rate. A treatment need not cure the cancer or cause remission 100% of the time, in all subjects.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancer cells.

Cancers that can be treated or diagnoses using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In some embodiments, the cancers that are treated by the methods described herein are cancers that have increased levels of mTORC1 or an increased expression or activity of a mTORC1 relative to normal tissues or to other cancers of the same tissues; methods known in the art and described herein can be used to identify those cancers. In some embodiments, the methods include obtaining a sample comprising cells of the cancer, determining the mTORC1 activity in the sample, and administering a treatment as described herein (e.g., a provided inhibitor of mTORC1). In some embodiments, the cancer is one that is shown herein to have increased levels of mTORC1 activity.

In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by inhibiting mTORC1 activity. Cellular proliferative disorders described herein include, e.g., cancer, obesity, and proliferation-dependent diseases. Such disorders may be diagnosed using methods known in the art.

Cancer

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Fibrotic Diseases

Idiopathic Pulmonary Fibrosis (IPF). The PI3K pathway is activated in fibrotic foci, the cardinal lesions in IPF. mTOR kinase inhibitor GSK2126458 reduces PI3K pathway signaling and functional responses in IPF-derived lung fibroblasts and mTOR inhibition reduces collagen expression in models of IPF patients. In the bleomycin model of pulmonary fibrosis, rapamycin treatment is antifibrotic, and rapamycin also decreases expression of α-smooth muscle actin and fibronectin by fibroblasts in vitro.

In some embodiments, the method of inhibiting mTORC1 activity is used to treat idiopathic pulmonary fibrosis (IPF) (see Mercer, P. F. et al., Thorax., 71(8): 701-11 (2016); Patel, A. S., et al., PLoS One, 7(7): e41394 (2012)) Accordingly, in some embodiments, the present invention provides a method of treating idiopathic pulmonary fibrosis (IPF), in a patient in need thereof, comprising the step of administering to said patient a provided compound or pharmaceutically acceptable salt thereof.

Kidney Fibrosis. mTORC1 is activated in myofibroblasts, a major pathogenic cell type in kidney fibrosis. Inhibition of mTOR with rapamycin in a murine model of kidney fibrosis (UUO), attenuated expression of markers of fibrosis and tubulointerstitial damage.

In some embodiments, the method of inhibiting mTORC1 activity is used to treat kidney fibrosis (see Jiang, L., et al., J Am Soc Nephrol, 24(7): 1114-26 (2013); Wu, M. J. et al., Kidney International, 69(11): 2029-36 (2006); Chen, G. et al., PLoS One, 7(3): e33626 (2012); Liu, C. F. et al., Clin Invest Med, 37(34): E142-53 (2014)). Accordingly, in some embodiments, the present invention provides a method of treating kidney fibrosis, in a patient in need thereof, comprising the step of administering to said patient a provided compound or pharmaceutically acceptable salt thereof.

In some embodiments, the method of inhibiting mTORC1 activity is used to treat scleroderma (see Mitra, A., et al., J Invest Dermatol. 135(11): 2873-6 (2015)). Accordingly, in some embodiments, the present invention provides a method of treating scleroderma, in a patient in need thereof, comprising the step of administering to said patient a provided compound or pharmaceutically acceptable salt thereof.

In some embodiments, the method of inhibiting mTORC1 activity is used to treat hypertrophic scarring and keloid disease (see Syed, F., et al., Am J Pathol. 181(5): 1642-58 (2012)). Accordingly, in some embodiments, the present invention provides a method of treating hypertrophic scarring and keloid disease, in a patient in need thereof, comprising the step of administering to said patient a provided compound or pharmaceutically acceptable salt thereof.

In some embodiments, the method of inhibiting mTORC1 activity is used to treat cardiac fibrosis (see Yano, T., et al., J Mol Cell Cardiol. 91: 6-9 (2016)). Accordingly, in some embodiments, the present invention provides a method of treating cardiac fibrosis, in a patient in need thereof, comprising the step of administering to said patient a provided compound or pharmaceutically acceptable salt thereof.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Other Disorders

Other disorders include lysosomal storage diseases, including, but not limited to, Pompe disease, Gaucher disease, mucopolysaccharidosis, multiple sulfatase deficiency; neurodegenerative diseases such as Parkinson's disease, Alzheimer's disease, Huntington's disease, alpha1-antitrypsin deficiency, and spinal bulbar muscular atrophy.

In some embodiments, the method of inhibiting mTORC1 activity is used to treat asthma (see Hua, W., et al., Respirology, 20(7): 1055-65 (2015)). Accordingly, in some embodiments, the present invention provides a method of treating asthma, in a patient in need thereof, comprising the step of administering to said patient a provided compound or pharmaceutically acceptable salt thereof.

In some embodiments, the method of inhibiting mTORC1 activity is used to treat a lysosomal storage disease (see Sardiello, M., Annals of the New York Academy of Sciences, 1371(1): 3-14 (2016); Awad, O., et al., Hum Mol Genet. 24(20): 5775-88 (2015); Spampanato, C., et al., EMBO Mol Med., 5(5): 691-706 (2013); Medina, D. L., et al., Dev Cell., 21(3): 421-30 (2011)). Accordingly, in some embodiments, the present invention provides a method of treating a lysosomal storage disease, in a patient in need thereof, comprising the step of administering to said patient a provided compound or pharmaceutically acceptable salt thereof.

In some embodiments, the method of inhibiting mTORC1 activity is used to treat Parkinson's disease (see Decressac, M., et al., Proc Natl Acad Sci USA., 110(19):E1817-26 (2013)). Accordingly, in some embodiments, the present invention provides a method of treating Parkinson's disease, in a patient in need thereof, comprising the step of administering to said patient a provided compound or pharmaceutically acceptable salt thereof.

In some embodiments, the method of inhibiting mTORC1 activity is used to treat Alzheimer's disease (see Polito, V. A., et al., EMBO Mol Med. 6(9):1142-60 (2014)). Accordingly, in some embodiments, the present invention provides a method of treating Alzheimer's disease, in a patient in need thereof, comprising the step of administering to said patient a provided compound or pharmaceutically acceptable salt thereof.

In some embodiments, the method of inhibiting mTORC1 activity is used to treat Huntington's disease (see Tsunemi, T., et al., Sci Transl Med., 4(142): 142ra97 (2012)). Accordingly, in some embodiments, the present invention provides a method of treating Huntington's disease, in a patient in need thereof, comprising the step of administering to said patient a provided compound or pharmaceutically acceptable salt thereof.

In some embodiments, the method of inhibiting mTORC1 activity is used to treat alpha-1-anti-trypsin deficiency (see Pastore, N. et al., EMBO Mol Med., 5(3): 397-412 (2013)). Accordingly, in some embodiments, the present invention provides a method of treating alpha1-anti-trypsin deficiency, in a patient in need thereof, comprising the step of administering to said patient a provided compound or pharmaceutically acceptable salt thereof.

In some embodiments, the method of inhibiting mTORC1 activity is used to treat spinal bulbar muscular atrophy (see Cortes, C. J., et al., Nat Neurosci., 17(9): 1180-9 (2014)). Accordingly, in some embodiments, the present invention provides a method of treating spinal bulbar muscular atrophy, in a patient in need thereof, comprising the step of administering to said patient a provided compound or pharmaceutically acceptable salt thereof.

In some embodiment, the method of inhibiting mTORC1 activity is used to treat Fragile X syndrome (FXS), amyotrophic lateral sclerosis (ALS), epilepsy, focal cortical dysplasia (FCD), hemimegalencephaly (HME), familial focal epilepsy with variable foci (FFEV), temporal lobe epilepsy (TLE), seizures, neurodegenerative diseases, Down syndrome, Rett syndrome (RTS), or diseases associated with activation or hyperactivation of mTOR signaling in the brain.

In some embodiments, the present invention provides a method of treating Fragile X syndrome (FXS) in a patient in need thereof, comprising administering a compound of the present invention, or a pharmaceutically salt thereof.

In some embodiments, the present invention provides a method of treating amyotrophic lateral sclerosis (ALS) in a patient in need thereof, comprising administering a compound of the present invention, or a pharmaceutically salt thereof.

In some embodiments, the present invention provides a method of treating epilepsy in a patient in need thereof, comprising administering a compound of the present invention, or a pharmaceutically salt thereof.

In some embodiments, the present invention provides a method of treating focal cortical dysplasia (FCD) in a patient in need thereof, comprising administering a compound of the present invention, or a pharmaceutically salt thereof.

In some embodiments, the present invention provides a method of treating hemimegalencephaly (HME) in a patient in need thereof, comprising administering a compound of the present invention, or a pharmaceutically salt thereof.

In some embodiments, the present invention provides a method of treating familial focal epilepsy with variable foci (FFEV) in a patient in need thereof, comprising administering a compound of the present invention, or a pharmaceutically salt thereof.

In some embodiments, the present invention provides a method of treating temporal lobe epilepsy (TLE) in a patient in need thereof, comprising administering a compound of the present invention, or a pharmaceutically salt thereof.

In some embodiments, the present invention provides a method of treating seizures in a patient in need thereof, comprising administering a compound of the present invention, or a pharmaceutically salt thereof.

In some embodiments, the present invention provides a method of treating neurodegenerative diseases in a patient in need thereof, comprising administering a compound of the present invention, or a pharmaceutically salt thereof.

In some embodiments, the present invention provides a method of treating Down syndrome in a patient in need thereof, comprising administering a compound of the present invention, or a pharmaceutically salt thereof.

In some embodiments, the present invention provides a method of treating Rett syndrome (RTS) in a patient in need thereof, comprising administering a compound of the present invention, or a pharmaceutically salt thereof.

In some embodiments, the present invention provides a method of treating diseases associated with activation or hyperactivation of mTOR signaling in the brain in a patient in need thereof, comprising administering a compound of the present invention, or a pharmaceutically salt thereof.

In some embodiments, a compound of the present invention binds to FKBP12 to form a complex. In some embodiments, the complex between a compound of the present invention and FKBP12 interacts with the FK506-rapamycin binding domain of mTOR.

In some embodiments, a compound of the present invention binds FKBP12 and interferes with protein-protein interaction between FRAP and FKBP12. In some embodiments, the $R^1$ group of a compound of the present invention interacts with both FRAP and FKBP12.

The present invention provides compounds that are inhibitors of mTORC1 activity and were shown to selectively inhibit mTORC1 over mTORC2 as measured by pS6K inhibition (a measure of mTORC1 activity) and pAKT activation (a measure of mTORC2 activity). In some embodiments, a provided compound inhibits mTORC1 selectively over mTORC2. In some embodiments, a provided compound does not measurably inhibit mTORC2. In some embodiments, a provided compound has a pAKT activation $IC_{50}$ of >10 µM. In some embodiments, a provided compound inhibits mTORC1 with >10-fold selectivity over mTORC2. In some embodiments, a provided compound inhibits mTORC1 with >20-fold selectivity over mTORC2. In some embodiments, a provided compound inhibits mTORC1 with >50-fold selectivity over mTORC2. In some embodiments, a provided compound inhibits mTORC1 with >100-fold selectivity over mTORC2. In some embodiments, a provided compound inhibits mTORC1 with >150-fold selectivity over mTORC2. In some embodiments, a provided compound inhibits mTORC1 with >200-fold selectivity over mTORC2. In some embodiments, a provided compound inhibits mTORC1 with >500-fold selectivity over mTORC2. In some embodiments, a provided compound inhibits mTORC1 with >1,000-fold selectivity over mTORC2.

In some embodiments, a provided compound inhibits mTORC1 selectively over mTORC2 after chronic treatment or exposure. In some embodiments, a provided compound inhibits mTORC1 selectively over mTORC2 after about 24 hours of treatment or exposure. In some embodiments, a provided compound inhibits mTORC1 selectively over mTORC2 after about 36 hours of treatment or exposure. In some embodiments, a provided compound inhibits mTORC1 selectively over mTORC2 after about 48 hours of treatment or exposure. In some embodiments, a provided compound inhibits mTORC1 selectively over mTORC2 after about 72 hours of treatment or exposure. In some embodiments, a provided compound inhibits mTORC1 selectively over mTORC2 after about 96 hours of treatment or exposure. In some embodiments, a provided compound inhibits mTORC1 selectively over mTORC2 after about 120 hours of treatment or exposure. In some embodiments, a provided compound inhibits mTORC1 selectively over mTORC2 after about 144 hours of treatment or exposure. In some embodiments, a provided compound inhibits mTORC1 selectively over mTORC2 after about one week of treatment or exposure. In some embodiments, a provided compound inhibits mTORC1 selectively over mTORC2 after more than about one week of treatment or exposure.

In some embodiments, a provided compound is less immunosuppressive than existing rapalogs. In some embodiments, a provided compound is less immunosuppressive than rapamycin. In some embodiments, a provided compound is less immunosuppressive than everolimus. In some embodiments, a provided compound is less immunosuppressive than temsirolimus. In some embodiments, a provided compound is less immunosuppressive than ridaforolimus. In some embodiments, a provided compound is less immunosuppressive than umirolimus.

In some embodiments, a provided compound suppresses interferon gamma (IFN-γ) production less than rapalogs. In some embodiments, a provided compound suppresses IFN-γ production less than rapamycin. In some embodiments, a provided compound suppresses IFN-γ production less than everolimus. In some embodiments, a provided compound suppresses IFN-γ production less than temsirolimus. In some embodiments, a provided compound suppresses IFN-γ production less than ridaforolimus. In some embodiments, a provided compound suppresses IFN-γ production less than umirolimus.

In some embodiments, a provided compound decreases the expression of fibrosis biomarkers in tissue that has been damaged. In some embodiments, a provided compound decreases the expression of collagen I (COL1A2) in tissue that has been damaged. In some embodiments, a provided compound decreases the expression of collagen III (COL3A1) in tissue that has been damaged. In some embodiments, a provided compound decreases the expression of fibronectin (FN1) in tissue that has been damaged.

In some embodiments, a provided compound decreases the propensity of immune cells from infiltrating damaged tissue. In some embodiments, a provided compound decreases the propensity of macrophage cells from infiltrating damaged tissue.

In some embodiments, a provided compound induces less glucose tolerance than rapalogs. In some embodiments, a provided compound induces less glucose tolerance than rapamycin. In some embodiments, a provided compound induces less glucose tolerance than everolimus. In some embodiments, a provided compound induces less glucose tolerance than temsirolimus. In some embodiments, a provided compound induces less glucose tolerance than ridaforolimus. In some embodiments, a provided compound induces less glucose tolerance than umirolimus. In some embodiments, a provided compound does not induce glucose tolerance significantly more than a placebo or vehicle alone.

Accordingly, in some embodiments, the present invention provides a method of treating a disorder associate with mTORC1 comprising administering to patient a compound that inhibits mTORC1 wherein said compound does not inhibit mTORC2. Such compounds may be employed for indications where rapamycin and rapalogs demonstrated a benefit either in animal models or in a human disease setting. Such indications include:

Treatment of Metabolic Disease (Obesity and Insulin Resistance in Type 2 Diabetes). Inhibition of mTORC1 pathway leads to extension of life span in yeast, fly and mouse, and caloric restriction improves longevity and insulin sensitivity. The underlying mechanism has been proposed to function by regulation of mTORC1 activation. Rapamycin-induced insulin resistance has been shown to be mediated by inhibition of mTORC2 and selective mTORC1 inhibitor is predicted to improve insulin sensitivity and glucose homeostasis.

In some embodiments, the method of inhibiting mTORC1 activity is used to treat metabolic disease (obesity and insulin resistance in type 2 diabetes) (see Yu, Z., et al., J Gerontol A Biol Sci Med Sci, 70(4), 410-20 (2015); Fok, W. C., et al., Aging Cell 13 (2): 311-9 (2014); Shum, M., et al., Diabetologia, 59(3):592-603 (2016); Lamming, D. W., et al., Science 335(6076): 1638-43 (2012)). Accordingly, in some embodiments, the present invention provides a method of treating metabolic disease (obesity and insulin resistance in type 2 diabetes), in a patient in need thereof, comprising the step of administering to said patient a provided compound or pharmaceutically acceptable salt thereof.

Neurofibromatosis. Neurofibromatosis type 1 (NF1) is caused by mutations in the NF1 gene. Its protein product, neurofibromin, functions as a tumor suppressor and ultimately produces constitutive upregulation of mTOR. mTOR inhibitors have been shown to reduce tumor size and induce anti-proliferative effect in NF1-associated plexiform neurofibroma.

In some embodiments, the method of inhibiting mTORC1 activity is used to treat neurofibromatosis (see Franz, D. N., et al., Curr Neurol Neurosci Rep., 12(3): 294-301 (2012); Varin, J., et al., Oncotarget., 7: 35753-67 (2016)). Accordingly, in some embodiments, the present invention provides a method of treating neurofibromatosis, in a patient in need thereof, comprising the step of administering to said patient a provided compound or pharmaceutically acceptable salt thereof.

Cardiomyopathy and skeletal muscle dystrophy, Emery-Dreifuss muscular dystrophy model (LMNA$^{-/-}$). Mutations in LMNA result in several human diseases including limb-girdle muscular dystrophy (LGMD1B), Emery-Dreifuss muscular dystrophy (EDMD2/3), dilated cardiomyopathy (DCM) and conduction-system disease (CMD1A), lipodystrophy, Charcot-Marie-Tooth disease, and Hutchinson-Gilford progeria syndrome (HGPS). Lmna$^{-/-}$ mice have elevated mTORC1 activity and short-term treatment with rapamycin in Lmna$^{-/-}$ mice results in reduced mTORC1 signaling, improved cardiac and skeletal muscle function and enhanced survival by 50%.

In some embodiments, the method of inhibiting mTORC1 activity is used to treat cardiomyopathy and skeletal muscle dystrophy (see Ramos, F., et al., Sci Transl Med., 4(144): 144ra103 (2012); Bonne, G. & Quijano-Roy, S., Handb Clin Neurol., 113: 1367-76 (2013)). Accordingly, in some embodiments, the present invention provides a method of treating cardiomyopathy and skeletal muscle dystrophy, in a patient in need thereof, comprising the step of administering to said patient a provided compound or pharmaceutically acceptable salt thereof.

Leigh syndrome. Ndufs4 knockout (KO) mice are used as a model of Leigh syndrome and exhibit hyperactivation of mTORC1 and metabolic defects. Treatment of Ndufs4 KO mice with rapamycin extended lifespan, improve metabolic and neurological defect associated with this disease.

In some embodiments, the method of inhibiting mTORC1 activity is used to treat Leigh syndrome (see Johnson, S. C., et al., Science, 342(6165): 1524-8 (2013)). Accordingly, in some embodiments, the present invention provides a method of treating Leigh syndrome, in a patient in need thereof, comprising the step of administering to said patient a provided compound or pharmaceutically acceptable salt thereof.

Oncology. Inhibition of mTOR with rapalogs has been shown to have antitumor activity in murine cancer models and in cancer patients. Examples of sensitive cancer types include, but are not limited to, hepatocellular carcinoma, breast cancers, mantle cell lymphomas, lung carcinoma, tuberous sclerosis and lymphangioleiomyomatosis.

In some embodiments, the method of inhibiting mTORC1 activity is used to treat cancer and oncologic disorders (see Ilagan, E. & manning, B. D., Trends Cancer, 2(5): 241-51 (2016)). Accordingly, in some embodiments, the present invention provides a method of treating cancer and oncologic disorders, in a patient in need thereof, comprising the step of administering to said patient a provided compound or pharmaceutically acceptable salt thereof.

Non-alcoholic steatohepatitis (NASH). The present invention provides inhibitors that induce autophagy to clear degraded cytoplasmic proteins, and NASH disease is characterized by lipid deposits, inflammation and fibrosis in the liver. The inhibition of mTORC1 pathway induce autophagy and down regulate SREBP-1 to decrease lipid biosynthesis to reduce lipid storage.

In some embodiments, the method of inhibiting mTORC1 activity is used to treat non-alcoholic steatohepatitis (NASH) (see Puri, P. & Chandra, A., J Clin Exp Hepatol, 4(1): 51-9 (2014)). Accordingly, in some embodiments, the present invention provides a method of treating non-alcoholic steatohepatitis (NASH), in a patient in need thereof, comprising the step of administering to said patient a provided compound or pharmaceutically acceptable salt thereof.

Tuberous sclerosis (TSC) and lymphangioleiomyomatosis (LAM). Failure in the regulation of mTOR is critical to the pathogenesis of the inherited disorder tuberous sclerosis complex (TSC) and the related lung disease, lymphangioleiomyomatosis (LAM). Both diseases are caused by mutations of TSC1 or TSC2 leading to inappropriate activity of signaling downstream of mTORC1. TSC patients develop nonmalignant tumors in many organs, including the brain, while LAM patients, mostly women, accumulate abnormal, muscle-like cells in certain organs or tissues, especially the lungs, lymph nodes, and kidneys. The rapalogs, everolimus and sirolimus, are currently approved for the treatment of both TSC and LAM, respectively, by the U.S. FDA.

In some embodiments, the method of inhibiting mTORC1 activity is used to treat tuberous sclerosis and lymphangioleiomyomatosis (see Wander, S. A., et al., J. Clin. Invest., 121(4): 1231-41 (2011); Taveira-DaSilva, A. M. & Moss, J., J. Clin Epidemiol., 7: 249-57 (2015)). Accordingly, in some embodiments, the present invention provides a method of treating tuberous sclerosis and lymphangioleiomyomatosis, in a patient in need thereof, comprising the step of administering to said patient a provided compound or pharmaceutically acceptable salt thereof.

Senescence and diseases of aging. Rapamycin suppresses the mammalian TORC1 complex, which regulates translation, and extends lifespan in diverse species, including mice. Rapamycin was shown to inhibit the pro-inflammatory phenotype of senescent cells. As senescent cells accumulate with age, the senescence-associated secretory phenotype (SASP) can disrupt tissues and contribute to age-related pathologies, including cancer. Inhibition of mTOR suppressed the secretion of inflammatory cytokines by senescent cells. Rapamycin reduced cytokine levels including IL6 and suppressed translation of the membrane-bound cytokine IL1A. Reduced IL1A diminishes NF-κB transcriptional activity, which controls the SASP. Thus, mTORC1 inhibitors might ameliorate age-related pathologies, including late-life cancer, by suppressing senescence-associated inflammation.

In some embodiments, the method of inhibiting mTORC1 activity is used to treat senescence and diseases of aging (see Laberge, R. M., et al., Nature Cell Biology, 17(8): 1049-61 (2015); Nacarelli, T., et al., Free Radic Biol Med., 95: 133-54 (2016)). Accordingly, in some embodiments, the present invention provides a method of treating senescence and diseases of aging, in a patient in need thereof, comprising the step of administering to said patient a provided compound or pharmaceutically acceptable salt thereof.

Diabetic nephropathy and kidney-related complications of type 1 diabetes and type 2 diabetes. Diabetic nephropathy is a kidney complication of type-1 and type-2 diabetes, affecting up to nearly 40% of people with diabetes. High levels of glucose force the kidneys work excessively to filter blood, resulting in kidney damage. Studies suggest that the mTOR pathway is highly activated in patients with diabetic neuropathy and may play a role in the pathological changes and renal dysfunction due to chronic high glucose. Further, mTOR inhibition may attenuate hyperinsulinemia.

In some embodiments, the method of inhibiting mTORC1 activity is used to treat diabetic nephropathy or kidney-related complications of type 1 diabetes and type 2 diabetes (see Mori, H., et al., Biochem. Res. Commun. 384(4): 471-5 (2009)). Accordingly, in some embodiments, the present invention provides a method of treating diabetic nephropathy or kidney-related complications of type 1 diabetes and type 2 diabetes in a patient in need thereof, comprising the step of administering to said patient a provided compound or pharmaceutically acceptable salt thereof.

Polycystic kidney disease. Polycystic kidney disease (PKD) is characterized by the development and accumulation of destructive kidney cysts that eventually result in kidney failure. PKD may be autosomal dominant (ADPKD) or recessive (ARPKD). Dysfunctional mTOR signaling pathway has been observed in ADPKD and ARPKD. Thus, normalization of the mTORC1 pathway may ameliorate the development of cysts and progression of the disease.

In some embodiments, the method of inhibiting mTORC1 activity is used to treat PKD (see Torres, V. E., et al., Clin. J. Am. Soc. Nephrol. 5(7): 1312-29 (2010)). Accordingly, in some embodiments, the present invention provides a method of treating PKD in a patient in need thereof, comprising the step of administering to said patient a provided compound or pharmaceutically acceptable salt thereof. In some embodiments, PKD is autosomal dominate. In some embodiments, PKD is autosomal recessive.

Focal Segmental Glomerulosclerosis (FSGS) and other diseases associated with sclerosis of the kidney. FSGS is the most common primary glomerular disorder causing end-stage renal disease (ESRD) in the United States. As the disease progresses there is a mismatch of podocyte cells in Bowman's capsule and the surface area of the glomerular basement membrane they cover. Studies have shown that podocyte size control is regulated by mTOR and that mTOR activation contributes to disease progression. Further, constitutive mTORC1 activation has been shown to cause FSGS-like lesions in mouse knockdown experiments. Thus, mTORC1 inhibition might ameliorate (FSGS) or other diseases associated with sclerosis of the kidney by normalizing or increasing autophagic activity.

In some embodiments, the method of inhibiting mTORC1 activity is used to treat FSGS or other diseases associated with sclerosis of the kidney (see Zschiedrich, S. et al., J. Am. Soc. Nephrol. 28(7): 2144-57 (2017)). Accordingly, in some embodiments, the present invention provides a method of treating FSGS or other diseases associated with sclerosis of the kidney in a patient in need thereof, comprising the step of administering to said patient a provided compound or pharmaceutically acceptable salt thereof.

Age-Related Macular Degeneration. Age-related macular degeneration (AMD) is a leading cause of blindness characterized by the death of photoreceptors in the macula. Possible mechanisms of AMD progression include oxidative stress leading to deposits of proteins and dysfunctional organelles, leading to retinal pigment epithelium hypertrophy, dedifferentiation, and eventual atrophy. mTOR is implicated in the dedifferentiation of the retinal pigment epithelium. Thus, mTORC1 inhibition may ameliorate AMD by blocking hypertrophy and dedifferentiation.

In some embodiments, the method of inhibiting mTORC1 activity is used to treat age-related macular degeneration (see Kolosova, N. G., et al., Am. J. Path. 181(2): 472-7 (2012) and Zhen, C. & Vollrath, D., Aging 3(4): 346-47 (2011)). Accordingly, in some embodiments, the present invention provides a method of treating age-related macular degeneration in a patient in need thereof, comprising the step of administering to said patient a provided compound or pharmaceutically acceptable salt thereof.

Diabetic Macular Edema. Diabetic macular edema (DME) is a leading cause of blindness in persons with diabetes, affecting approximately 35% of people with diabetes. Studies suggest that the pathogenesis of DME is an inflammatory disease involving various cytokines and chemokines. Chronic inflammatory and oxidative stress may contribute to the progression of DME. Thus, inhibition of mTORC1 may ameliorate DME symptoms and progression by decreasing the inflammatory response.

In some embodiments, the method of inhibiting mTORC1 activity is used to treat DME (see Okamoto, T., et al., PLOS ONE, (11)(1): e0146517, https://doi.org/10.1371/journal.pone.0146517 (2016)). Accordingly, in some embodiments, the present invention provides a method of treating DME in a patient in need thereof, comprising the step of administering to said patient a provided compound or pharmaceutically acceptable salt thereof.

Diabetic retinopathy. Diabetic retinopathy (DR) is a common eye disease accounting for ~5% of blindness in adults and is associated with chronic hyperglycemia and defects of insulin signaling pathways. DR patients suffer persistent injury to retinal blood vessels and neurons by inflammation, reactive oxygen species and endoplasmic reticulum stress caused by chronic hyperglycemia. Significantly, rapamycin has been shown to block the action of insulin-induced hypoxia-inducible factor-1 (HIF-1) and retinal cell senescence, and induces autophagy, and could be beneficial in promoting apoptosis of nascent blood vessels and preventing angiogenesis. Thus, inhibition of mTORC1 may ameliorate DR symptoms and progression by decreasing inflammation and inhibiting pathogenic signaling pathways.

In some embodiments, the method of inhibiting mTORC1 activity is used to treat DR (see Di Rosa, M., et al., Curr. Neuropharmacol. 14(8): 810-25 (2016)). Accordingly, in some embodiments, the present invention provides a method of treating DR in a patient in need thereof, comprising the step of administering to said patient a provided compound or pharmaceutically acceptable salt thereof.

Glaucoma. Glaucoma is a common optic neuropathy associated with aging and elevated intraocular pressure, and is the leading cause of irreversible blindness. Studies suggest that mTOR dependent dysregulation of autophagocytosis may be a factor in the progression of the disease. Thus, inhibition of mTORC1 may slow the progression or ameliorate glaucoma by normalizing or increasing autophagy.

In some embodiments, the method of inhibiting mTORC1 activity is used to treat glaucoma (see Porter, K., et al., Biochim. Biophys. Acta. 1852(3): 379-85 (2014)). Accordingly, in some embodiments, the present invention provides a method of treating glaucoma in a patient in need thereof, comprising the step of administering to said patient a provided compound or pharmaceutically acceptable salt thereof.

Restoring immune function. mTORC1 inhibition has been shown to reduce the expression of programmed death-1

(PD-1) receptor in CD4$^+$ and CD8$^+$ T lymphocytes, promoting T-cell signaling. Thus, mTORC1 inhibition may restore immune function by improving the adaptive immune response.

In some embodiments, the method of inhibiting mTORC1 activity is used to restore immune function (see Mannick, J. B., et al., Sci. Trans. Med. 6(268): ppra179 (2014)). Accordingly, in some embodiments, the present invention provides a method of restoring immune function in a patient in need thereof, comprising the step of administering to said patient a provided compound or pharmaceutically acceptable salt thereof.

Treatment of respiratory and/or urinary tract infections. mTORC1 inhibition may reduce infections by upregulation of antiviral gene expression and response. Thus, mTORC1 inhibition may enhance the ability of a patient's immune system to defend against respiratory and/or urinary tract infections.

In some embodiments, the method of inhibiting mTORC1 activity is used to treat respiratory and/or urinary tract infections. (see Mannick, J. B., et al., Sci. Trans. Med. 10(449): eaaq1564 (2018)). Accordingly, in some embodiments, the present invention provides a method of restoring immune function in a patient in need thereof, comprising the step of administering to said patient a provided compound or pharmaceutically acceptable salt thereof.

Heart failure. mTORC1 activity is essential for cardiac hypertrophy in response to stress but can lead to cardiac derangements as a result of cardiac remodeling following infarction. Inhibition of mTORC1 reduces cardiac remodeling and heart failure in response to pressure overload. Thus, inhibition of mTORC1 may decrease heart failure in patients who have suffered damage to the myocardium.

In some embodiments, the method of inhibiting mTORC1 activity is used to treat heart failure (see Sciarretta, S. et al., Circ. Res. 122(3): 489-505 (2018)). Accordingly, in some embodiments, the present invention provides a method of treating heart failure in a patient in need thereof, comprising the step of administering to said patient a provided compound or pharmaceutically acceptable salt thereof.

Osteoarthritis. Osteoarthritis (OA) is a chronic degenerative disease resulting in loss of cartilage and joint inflammation. mTOR may play a significant role in collagen homeostasis and turnover and remodeling of cartilage. Thus, inhibition of mTORC1 may slow the progression or ameliorate osteoarthritis symptoms by normalizing cartilage turnover.

In some embodiments, the method of inhibiting mTORC1 activity is used to treat osteoarthritis (see Pal, B., et al., Drugs R&D, 15(1): 27-36 (2017))). Accordingly, in some embodiments, the present invention provides a method of treating osteoarthritis in a patient in need thereof, comprising the step of administering to said patient a provided compound or pharmaceutically acceptable salt thereof.

Pulmonary arterial hypertension. Pulmonary arterial hypertension (PAH) is a progressive, fatal disease associated with increases pulmonary vascular resistance. Pulmonary arterial smooth muscle cell proliferation and migration are implicated in the progressing of arterial wall thickening, exacerbating vasoconstriction. Thus, inhibition of mTORC1 may alleviate PAH by reducing vascular remodeling.

In some embodiments, the method of inhibiting mTORC1 activity is used to treat PAH (see Ma, X., et al., Interact. Cardiovasc. Thorac. Surg. 25(2): 206-11 (2017)). Accordingly, in some embodiments, the present invention provides a method of treating PAH is a patient in need thereof, comprising the step of administering to said patient a provided compound or pharmaceutically acceptable salt thereof.

Chronic Obstructive Pulmonary Disease. Reduced autophagy results in the accumulation of proteins and other cellular materials that accelerate cellular senescence in patients with chronic obstructive pulmonary disease (COPD). Thus, inhibition of mTORC1 may slow the progression or ameliorate COPD symptoms by normalizing or increasing autophagy.

In some embodiments, the method of inhibiting mTORC1 activity is used to treat COPD (see Fujii, S., et al., Oncoimmunology 1(5): 630-41 (2012)). Accordingly, in some embodiments, the present invention provides a method of treating COPD in a patient in need thereof, comprising the step of administering to said patient a provided compound or pharmaceutically acceptable salt thereof.

Additional therapeutic indications where mTORC inhibition may be beneficial are: cardiovascular disease (acute coronary syndrome), coronary occlusions with eluting stents, polycystic kidney disease, and kidney disease associated with cyst formation or cystogenesis), neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, autism, and vascular rheumatoid arthritis.

In some embodiments, the method of inhibiting mTORC1 activity is used to treat cardiovascular disease (acute coronary syndrome), coronary occlusions with eluting stents, polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma associated with TSC1/2 mutations, breast cancer, hepatocellular cancer, leukemia, glioma, adenoid cystic carcinoma, senescence, autism, and vascular rheumatoid arthritis.

Accordingly, in some embodiments, the present invention provides a method of treating cardiovascular disease (acute coronary syndrome), coronary occlusions with eluting stents, polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, autism, and vascular rheumatoid arthritis, in a patient in need thereof, comprising the step of administering to said patient a provided compound or pharmaceutically acceptable salt thereof.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

In other embodiments, the present invention provides a method for treating a disorder mediated by mTORC1 in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethyl-amino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g., in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g., under the trademark Carboplat™. Oxaliplatin can be administered, e.g., in the form as it is marketed, e.g., under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g., BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, P3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO 2008/118802), navitoclax (and analogs thereof, see U.S. Pat. No. 7,390,799), NH-1 (Shenayng Pharmaceutical University), obatoclax (and analogs thereof, see WO 2004/106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO 2008/039218 and WO 2011/090760, the entirety of which are incorporated herein by reference.

Further examples of SYK inhibitory compounds, and conditions treatable by such compounds in combination with compounds of this invention can be found in WO 2003/063794, WO 2005/007623, and WO 2006/078846, the entirety of which are incorporated herein by reference.

Further examples of PI3K inhibitory compounds, and conditions treatable by such compounds in combination with compounds of this invention can be found in WO 2004/019973, WO 2004/089925, WO 2007/016176, U.S. Pat. No. 8,138,347, WO 2002/088112, WO 2007/084786, WO 2007/129161, WO 2006/122806, WO 2005/113554, and WO 2007/044729 the entirety of which are incorporated herein by reference.

Further examples of JAK inhibitory compounds, and conditions treatable by such compounds in combination with compounds of this invention can be found in WO 2009/114512, WO 2008/109943, WO 2007/053452, WO 2000/142246, and WO 2007/070514, the entirety of which are incorporated herein by reference.

Further anti-angiogenic compounds include compounds having another mechanism for their activity, e.g., unrelated to protein or lipid kinase inhibition, e.g., thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are, e.g., inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art (see Hellman, Principles of Radiation Therapy, Cancer, in Principles and Practice of Oncology, Devita et al., Eds., 4$^{th}$ Edition, Vol. 1, pp. 248-275 (1993)).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocortisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g., Patents International (e.g., IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the additional therapeutic agent administered in combination with a compound of the present invention is another mTOR inhibitor. In some embodiments, the additional mTOR inhibitor inhibits mTOR by binding the catalytic active site of mTOR. Examples of such additional mTOR inhibitors include: dactolisib, 8-(6-methoxypyridin-3-yl)-3-methyl-1-(4-piperazin-1-yl-3-trifluoromethyl-phenyl)-1,3-dihydro-imidazo[4,5-c]quinolin-2-one (WO 2006/122806), vistusertib (AZD2014; WO 2009/153597); AZD8055 (WO 2009/153597; XL388 (U.S. Pat. App. Pub. 2010/0305093); sapanisertib (MLN0128; INK128; WO 2015/051043); DS3078; apitolisib (GDC0980; WO 2008/070740); omipalisib (GSK-2126458; WO 2008/14446); NVP-BGT226 (Chang, K. Y., et al., Clin. Cancer Res. 17(22): 7116-26 (2011)); voxtalisib (XL765; SAR245409; WO 2007/044813); PF04691502 (WO 2008/032162); gedatolisib (PF05212384; PKI-587; WO 2009/143313); SF1126 (WO 2004/089925); GSK1059615 (WO 2007/136940); BI-860585; OSI 027 (WO 2007/061737); VS 5584 (WO 2010/114484); CC-223 (WO 2010/062571); DCBCI-0901 (Lee, Y. E., et al., Mol. Canc. Thera. 12(11 Suppl): Abstract nr C270 (2013)):); LY3023414 (WO 2012/097039); P529 (WO 2007/133249); panulisib (P7170; WO 2012/007926); DS-7423 (Kashiyama, T., et al., PLoS One 9(2): e87220 (2014)); PWT33567 mesylate (VCD-597; WO 2010/110685); ME-344 (NV-128; Navarro, P., et al., Cell Rep. 15(12):2705-18 (2016)); ABTLO812 (WO 2010/106211); WYE-132; EXEL-3885 (Eur J Cancer Suppl. 6(12): Abst 322 (2008)); EXEL-4431 (Eur J Cancer Suppl. 6(12): Abst 322 (2008)); AR-mTOR-26 (101st Annu Meet Am Assoc Cancer Res (AACR) (April 17-21, Washington, D.C.) 2010, Abst 4484); NV-128 (A. B. Alvero et al., Mol Cancer Ther. 10(8): 1385-93 (2011)); salinomycin (VS-507; Gupta, P. B., et al., Cell 138(4): 645-59 (2009)); BN-107; BN-108; WAY-600; WYE-687; WYE-354 (Yu, K., et al., Cancer Res. 69(15): 6232-40 (2009)); Ku-063794 (Garcia-Martinez, J. M., et al., Biochem. J. 421(1): 29-42 (2009)); torkinib (PP242; Apsel, B., et al., Nat. Chem. Biol. 4(11): 691-99 (2008)); PP30; CZ415 (REF); INK1069; EXEL-2044; EXEL-7518; SB2158; SB2280; AR-mTOR-1 (Wallace, E. M., et al., Mol. Canc. Thera. 8(12 Suppl): Abst. B267 (2009)).

Reference to any particular additional mTOR inhibitor herein also comprises any pharmaceutically acceptable salts, stereoisomers, tautomers, solvates, hydrates and polymorphs thereof.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein (see also Luengo, J. I. et al., Chem. Biol., 2(7): 471-81 (1995); and Grinfeld, A. A. et al., Tet. Lett., 35(37): 6835-38 (1994)).

List of Abbreviations Used in the Experimental Section.
$Cs_2CO_3$: cesium carbonate
$CH_3CN$: acetonitrile
DCM: dichloromethane
DMAP: dimethyl aminopyridine
DMF: N,N-dimethylformamide
DMSO: dimethyl sulfoxide
EDCI: 1-ethyl-3-(3-dimethylaminopropyl)carbodiimide
ESI: electrospray ionization
EtOAc: ethyl acetate
$Et_2O$: diethyl ether
EtOH: ethanol
h: hours
HCl: hydrogen chloride
HF: hydrogen fluoride
HND-8: acidic ion exchange resin (e.g., Amberlyst)

H₂O: water
HPLC: high performance liquid chromatography
K₂CO₃: potassium carbonate
MeOH: methanol
min: minutes
MgSO₄: magnesium sulfate
mL: milliliters
mM: millimolar
mmol: millimoles
MS: mass spectrometry
N₂: nitrogen gas
NaHCO₃: sodium bicarbonate
NaOH: sodium hydroxide
Na₂SO₃: sodium sulfite
Na₂SO₄: sodium sulfate
NH₃: ammonia
NH₄Cl: ammonium chloride NMR: nuclear magnetic resonance
° C.: degrees Celsius
POCl₃: phosphorus oxychloride
prep-HPLC: preparative high performance liquid chromatography
PE: petroleum ether p-TsOH: para toluenesulfonic acid
rt: room temperature
TASF: tris(dimethylamino)sulfonium difluorotrimethylsilicate
TEA: triethylamine
TFA: trifluoroacetic acid
THF: tetrahydrofuran Example 1: Synthesis of 2-Hydroxyethyl N-[(21E, 23E,25E,26E,30R,31S,32R,33R,35S,37S,40S,41R, 42R,52R)-41,52-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-45,46, 47,48,49-pentaoxo-65,66-dioxa-54-azatricyclohexatriaconta-21,23,25(43),26(44)-tetraen-39-yl]carbamate (I-1)

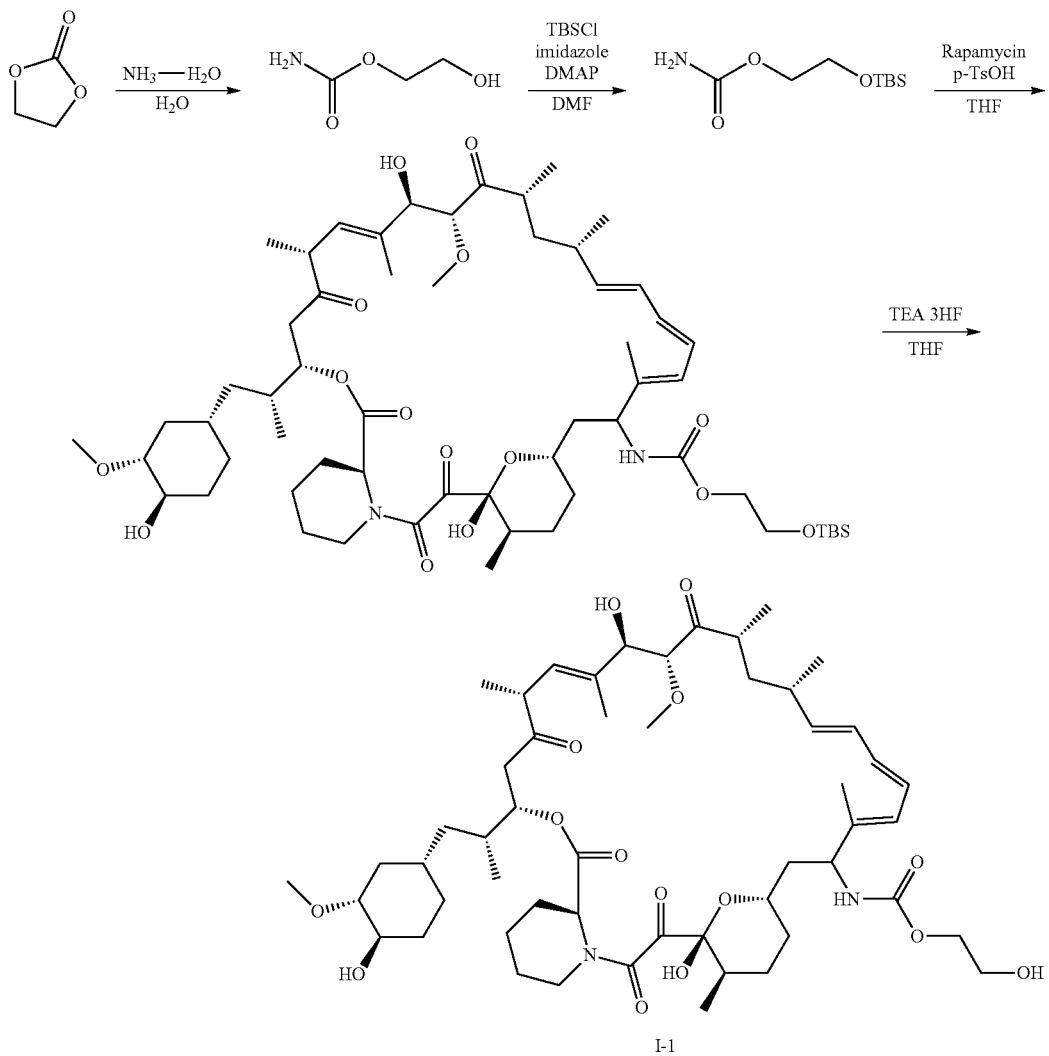

Step 1: 2-hydroxyethyl carbamate: 1,3-dioxolan-2-one (10 g, 113.56 mmol) was dissolved in H₂O (75 mL) and a solution of NH₃ in water (159 g, 1.14 mol, 3:1) was added at 0° C. The mixture was stirred for 20 h at 20° C. then concentrated in vacuo to provide 2-hydroxyethyl carbamate (11.5 g, 96% yield) as a colorless oil. ESI-MS (EI⁺, m/z):

128.0 [M+Na]$^+$; $^1$H NMR (400 MHz, DMSO-d6): δ 6.46 (s, 2H, NH), 4.71 (t, J=5.4 Hz, 1H, OH), 3.95-3.86 (m, 2H), 3.52 (dd, J=10.6, 5.3 Hz, 2H).

Step 2: 2-[tert-butyl (dimethyl)silyl]oxyethyl carbamate: To a solution of 2-hydroxyethyl carbamate (2 g, 19 mmol), imidazole (3.37 g, 49.5 mmol) and DMAP (465 mg, 3.8 mmol) in DMF (30 mL) was added tert-butyl-chloro-dimethyl-silane (3.73 g, 4.6 mL) in DMF (10 mL) dropwise under N$_2$ at 0° C. The reaction was stirred at room temperature for 24 h then diluted with EtOAc (10 mL) and water (100 mL). The resulting mixture was extracted with EtOAc (60 mL×2) and petroleum ether (30 mL) and the combined organic layers were washed with water (100 mL×3), brine (100 mL), dried over anhydrous Na$_2$SO$_4$, and concentrated. The residue was purified via silica gel chromatography (10%-20% EtOAc in PE) to provide 2-[tert-butyl (dimethyl) silyl]oxyethyl carbamate (2.69 g, 64% yield) as a white solid. $^1$H NMR (400 MHz, CDCl$_3$) δ 4.92 (s, 2H), 4.11 (dd, J=7.3, 2.5 Hz, 2H), 3.79 (t, J=4.8 Hz, 2H), 0.88 (s, 9H), 0.06 (s, 6H).

Step 3: 2-[tert-butyl(dimethyl)silyl]oxyethyl N-[(26E,28E,30E,31E,35R,36S,37R,38R,40S,42S,45S,46R,47R,57R)-46,57-dihydroxy-45-[(1R)-2-[(1S,3R,4R)-4-hydroxy-3-methoxy-cyclohexyl]-1-methyl-ethyl]-47-methoxy-35,36,37,38,48,49-hexamethyl-50,51,52,53,54-pentaoxo-70,71-dioxa-60-azatricyclohexatriaconta-26,28,30(48),31(49)-tetraen-44-yl]carbamate: To a solution of rapamycin (0.5 g, 0.55 mmol) in THF (10 mL) was added 4-methylbenzenesulfonic acid (0.47 g, 2.73 mmol) at 0° C. under N$_2$. The reaction mixture was stirred for 10 min at 0° C. 2-[tert-butyl (dimethyl)silyl]oxyethyl carbamate (2.4 g, 10.94 mmol) was added and stirring continued at 25° C. for 6 h. The mixture was poured into sat. NaHCO$_3$ (40 mL) and extracted with EtOAc (40 mL×2). The combined organic layers were washed with brine (40 mL), dried over Na$_2$SO$_4$, filtered and concentrated. The residue was purified via silica gel chromatography (5% to 65% EtOAc in petroleum ether) to provide crude 2-[tert-butyl(dimethyl)silyl]oxyethyl N-[(26E,28E,30E,31E,35R,36S,37R,38R,40S,42S,45S,46R,47R,57R)-46,57-dihydroxy-45-[(1R)-2-[(1S,3R,4R)-4-hydroxy-3-methoxy-cyclohexyl]-1-methyl-ethyl]-47-methoxy-35,36,37,38,48,49-hexamethyl-50,51,52,53,54-pentaoxo-70,71-dioxa-60-azatricyclohexatriaconta-26,28,30(48),31(49)-tetraen-44-yl]carbamate (0.22 g, 37% yield) as a light yellow oil. LC-MS (EI$^+$, m/z): 1123.6 [M+Na]$^+$, RT=2.17 at 254 nm.

Step 4: 2-hydroxyethyl N-[(21E,23E,25E,26E,30R,31S,32R,33R,35S,37S,40S,41R,42R,52R)-41,52-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-45,46,47,48,49-pentaoxo-65,66-dioxa-54-azatricyclohexatriaconta-21,23,25(43),26(44)-tetraen-39-yl]carbamate (I-1): To a solution of 2-[tert-butyl(dimethyl) silyl]oxyethyl N-[(26E,28E,30E,31E,35R,36S,37R,38R,40S,42S,45S,46R,47R,57R)-46,57-dihydroxy-45-[(1R)-2-[(1S,3R,4R)-4-hydroxy-3-methoxy-cyclohexyl]-1-methyl-ethyl]-47-methoxy-35,36,37,38,48,49-hexamethyl-50,51,52,53,54-pentaoxo-70,71-dioxa-60-azatricyclohexatriaconta-26,28,30(48),31(49)-tetraen-44-yl]carbamate (0.45 g, 0.41 mmol) in THF (5 mL) was added TEA.3HF (0.74 g, 4.1 mmol). The reaction mixture was stirred for 20 h at room temperature then poured into iced sat. NaHCO$_3$ (20 mL) and extracted with EtOAc (20 mL×2). The combined organic layers were washed with brine (30 mL), dried over anhydrous Na$_2$SO$_4$, filtered and concentrated. The residue was purified via reverse phase chromatography (60% CH$_3$CN in water) to provide I-1 (45 mg, 11% yield) as a white solid. ESI-MS (EI$^+$, m/z): 1009.5 [M+Na]$^+$; $^1$H NMR (400 MHz, CDCl$_3$) δ 6.25-5.91 (m, 4H), 5.30-5.00 (m, 5H), 4.30-3.73 (m, 9H), 3.57-3.42 (m, 2H), 3.33-3.25 (m, 8H), 3.00-2.83 (m, 2H), 2.66-2.48 (m, 4H), 2.19-1.92 (m, 5H), 1.79-1.56 (m, 20H), 1.34-1.14 (m, 4H), 1.14-0.78 (m, 18H), 0.52-0.49 (m, 1H).

Example 2: Synthesis of (23E,25E,27E,28E,34R,35S,36R,37R,39S,42S,44S,45S,46R,47R,57R)-46,57-dihydroxy-45-[(1R)-2-[(1S,3R,4R)-4-(2-hydroxy-ethoxy)-3-methoxy-cyclohexyl]-1-methyl-ethyl]-47-methoxy-34,35,36,37,48,49-hexamethyl-44-[2-(2-oxopyrrolidin-3-yl)ethoxy]-69,70-dioxa-59-azatricyclohexatriaconta-23,25,27(48),28(49)-tetraene-50,51,53,54,55-pentone (I-3)

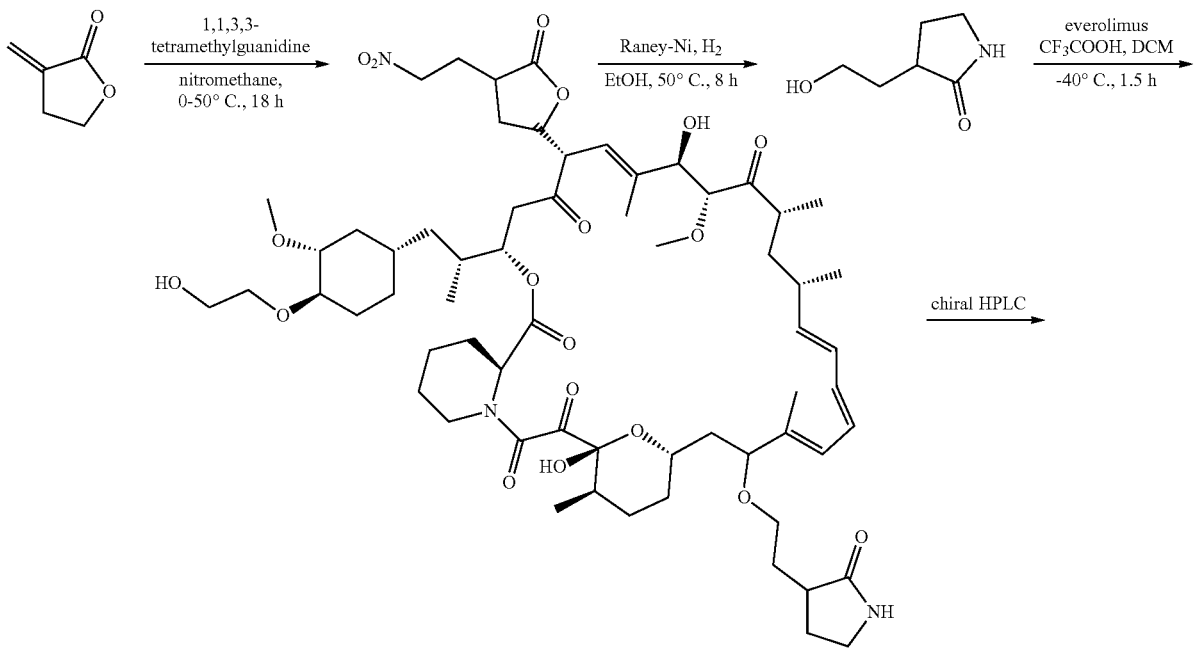

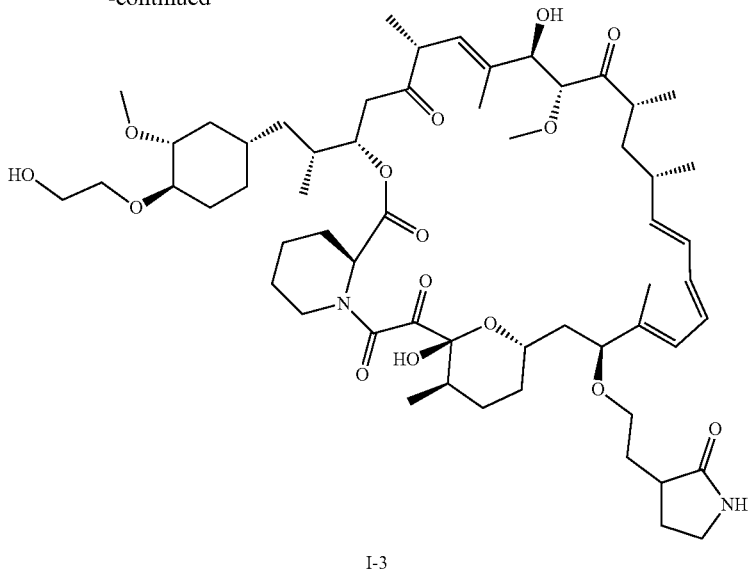

I-3

Step 1: Synthesis of 3-(2-nitroethyl) tetrahydrofuran-2-one: To a solution of 3-methylenetetrahydrofuran-2-one (15 g, 152.91 mmol) in nitromethane (57 mL) was added 1,1,3,3-tetramethylguanidine (1.76 g, 15.29 mmol) dropwise at 0° C. under nitrogen. The reaction mixture was stirred at 50° C. for 18 h, then cooled and quenched with 0.5M HCl aqueous solution to pH 4. The mixture was then extracted with EtOAc (100 mL×3) and the combined organic layers dried over MgSO$_4$, filtered and concentrated to provide 3-(2-nitroethyl) tetrahydrofuran-2-one (20 g, 82% yield) which was used without further purification. ESI-MS (EI$^+$, m/z): 160.1 [M+H]$^+$, 182.1 [M+Na]$^+$. $^1$H NMR (400 MHz, CDCl$_3$) δ 4.69-4.49 (m, 1H), 4.38-4.28 (m, 1H), 4.20-4.07 (m, 2H), 2.57-2.32 (m, 2H), 2.27-2.06 (m, 1H), 1.93 (td, J=20.4, 9.7 Hz, 2H).

Step 2: Synthesis of 3-(2-hydroxyethyl) pyrrolidin-2-one: To a solution of 3-(2-nitroethyl) tetrahydrofuran-2-one (10 g, 62.84 mmol) and in ethanol (80 mL) was added Raney-Ni (3.7 g) and the mixture stirred under hydrogen at 50° C. for 8 h. The reaction was then filtered, concentrated and purified via silica gel chromatography (MeOH:DCM=1:20 to 1:5) to provide 3-(2-hydroxyethyl) pyrrolidin-2-one (1.7 g, 21%) as a thick oil. ESI-MS (EI$^+$, m/z): 130.1 [M+H]$^+$. $^1$H NMR (400 MHz, DMSO-d$_6$) δ 7.56 (s, 1H), 4.54 (t, J=5.3 Hz, 1H), 3.55-3.38 (m, 2H), 3.21-3.04 (m, 2H), 2.32-2.10 (m, 2H), 1.88-1.75 (m, 1H), 1.63 (dq, J=12.2, 8.7 Hz, 1H), 1.38-1.24 (m, 1H).

Step 3: Synthesis of (23E,25E,27E,28E,34R,35S,36R,37R,39S,42S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-44-[2-(2-oxopyrrolidin-3-yl)ethoxy]-69,70-dioxa-59-azatricyclohexatriaconta-23,25,27(48),28(49)-tetraene-50,51,53,54,55-pentone: To a solution of everolimus (0.5 g, 0.52 mmol) in DCM (30 mL) was added TFA (1.60 mL) at −40° C. under N$_2$. This was stirred at the same temperature for 10 minutes then 3-(2-hydroxyethyl) pyrrolidin-2-one (0.27 g, 2.09 mmol) was added and the mixture stirred at −40° C. for 1.5 h. The reaction was quenched with sat.NaHCO$_3$ (aq.), diluted with DCM (60 mL) and the organic layer was washed with water (60 mL), brine (60 mL), dried over anhydrous Na$_2$SO$_4$, filtered and concentrated. The residue was purified via reverse phase chromatography (60% CH$_3$CN in H$_2$O) to provide (23E,25E,27E,28E,34R,35S,36R,37R,39S,42S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-44-[2-(2-oxopyrrolidin-3-yl)ethoxy]-69,70-dioxa-59-azatricyclohexatriaconta-23,25,27(48),28(49)-tetraene-50,51,53,54,55-pentone (80 mg, 14% yield) as a white solid. ESI-MS (EI$^+$, m/z): 1077.4 [M+Na]$^+$. $^1$H NMR (400 MHz, CDCl$_3$) δ 6.33-5.96 (m, 4H), 5.41-5.11 (m, 4H), 4.76 (d, J=20 Hz, 1H), 4.43-3.87 (m, 5H), 3.79-3.51 (m, 5H), 3.36-3.27 (m, 9H), 3.14-2.49 (m, 7H), 2.22-1.92 (m, 6H), 1.75-1.55 (m, 21H), 1.40-1.14 (m, 9H), 0.99-0.81 (m, 18H), 0.56 (q, J=12 Hz, 1H).

Step 4: Synthesis of (23E,25E,27E,28E,34R,35S,36R,37R,39S,42S,44S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-44-[2-(2-oxopyrrolidin-3-yl)ethoxy]-69,70-dioxa-59-azatricyclohexatriaconta-23,25,27(48),28(49)-tetraene-50,51,53,54,55-pentone (I-3): 146 mg of the racemic mixture was separated via chiral HPLC to provide I-3 (64 mg, 44% yield) as a white solid.

Chiral Separation Method:

| | |
|---|---|
| Column | CHIRALPAK IC |
| Column size | 2.5 cm I.D. × 25 cm L, 10 μm |
| Injection | 11 mL |
| Mobile phase | Hexane/EtOH = 70/30 (V/V) |
| Flow rate | 60 mL/min |
| Wave length | UV 254 nm |
| Temperature | 35° C. |

I-3: ESI-MS (EI+, m/z): 1077.4 [M+H]$^+$. $^1$H NMR (400 MHz, CDCl$_3$) δ 6.46-5.99 (m, 4H), 5.53-5.11 (m, 4H), 4.86-4.55 (m, 1H), 4.23 (d, J=14.5 Hz, 2H), 4.08-3.90 (m, 2H), 3.89-3.47 (m, 6H), 3.44-2.96 (m, 13H), 2.94-2.41 (m, 5H), 2.37-1.94 (m, 6H), 1.92-1.67 (m, 15H), 1.56-1.13 (m, 13H), 1.10-0.77 (m, 18H), 0.71-0.54 (m, 1H).

Example 3: Synthesis of (23E,25E,27E,28E,34R, 35S,36R,37R,39S,42S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-44-[2-(2-oxopyrrolidin-3-yl)ethoxy]-69,70-dioxa-59-azatricyclohexatriaconta-23,25,27(48),28(49)-tetraene-50,51,53,54,55-pentone (I-5)

matography (MeOH:DCM=1:20 to 1:5) to provide 3-(2-hydroxyethyl)pyrrolidin-2-one (1.7 g, 21% yield) as a thick oil. ESI-MS (EI$^+$, m/z): 130.1 [M+H]$^+$. H NMR (400 MHz, DMSO-d$_6$) δ 7.56 (s, 1H), 4.54 (t, J=5.3 Hz, 1H), 3.55-3.38 (m, 2H), 3.21-3.04 (m, 2H), 2.32-2.10 (m, 2H), 1.88-1.75 (m, 1H), 1.63 (dq, J=12.2, 8.7 Hz, 1H), 1.38-1.24 (m, 1H).

Step 3: Synthesis of (23E,25E,27E,28E,34R,35S,36R, 37R,39S,42S,45S,46R,47R,57R)-46,57-dihydroxy-45-[(1R)-2-[(1S,3R,4R)-4-(2-hydroxyethoxy)-3-methoxy-cy-

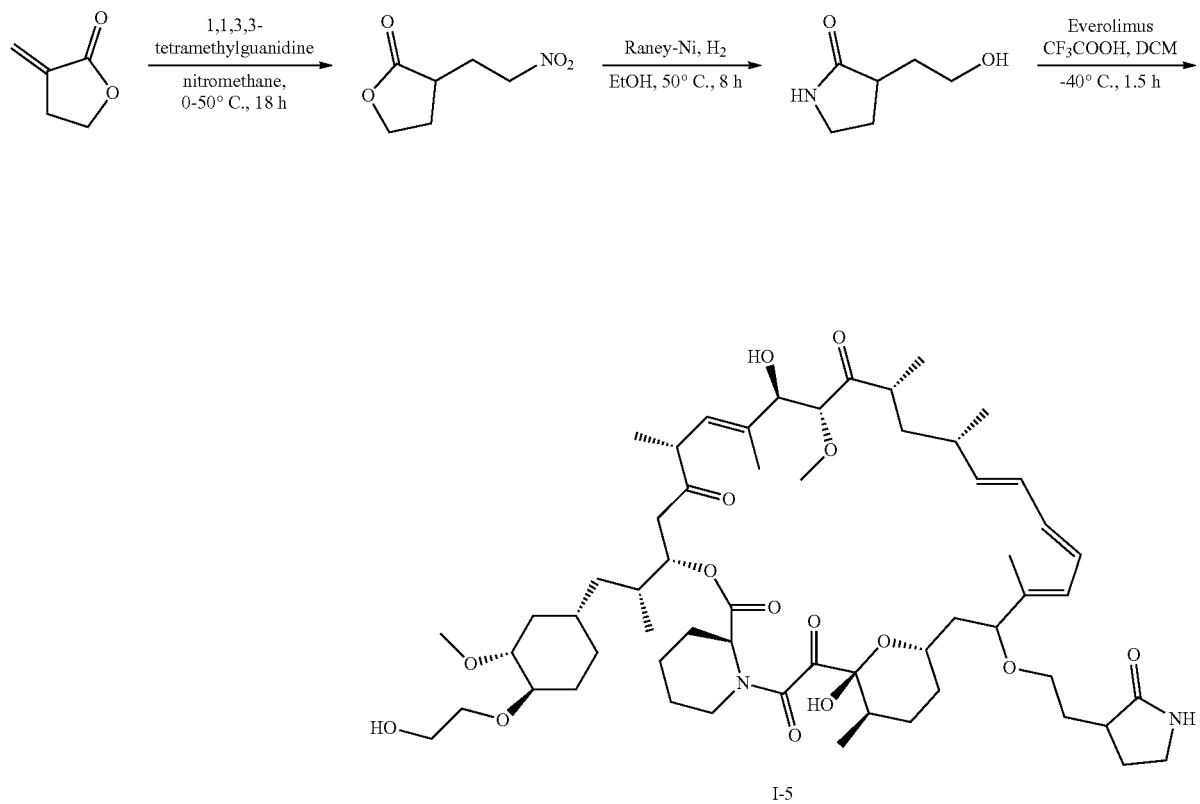

I-5

Step 1: Synthesis of 3-(2-nitroethyl)tetrahydrofuran-2-one: To a solution of 3-methylenetetrahydrofuran-2-one (15 g, 152.9 mmol) in nitromethane (65.33 g, 1.07 mol) was added 1,1,3,3-tetramethylguanidine (1.76 g, 15.29 mmol) dropwise at 0° C. under nitrogen. The reaction mixture was stirred at 50° C. for 18 h, then cooled, quenched with 0.5M HCl aqueous solution to pH 4 then extracted with EtOAc (100 mL×3). The organic layers were combined and dried over MgSO4, filtered and concentrated to obtain 3-(2-nitroethyl)tetrahydrofuran-2-one (20 g, 82% yield). This material was used in the next step without further purification. ESI-MS (EI$^+$, m/z): 160.1 [M+H]$^+$, 182.1 [M+Na]$^+$. $^1$H NMR (400 MHz, CDCl$_3$) δ 4.69-4.49 (m, 1H), 4.38-4.28 (m, 1H), 4.20-4.07 (m, 2H), 2.57-2.32 (m, 2H), 2.27-2.06 (m, 1H), 1.93 (td, J=20.4, 9.7 Hz, 2H).

Step 2: Synthesis of 3-(2-hydroxyethyl)pyrrolidin-2-one: A mixture of 3-(2-nitroethyl)tetrahydrofuran-2-one (10 g, 62.84 mmol) and Raney-Ni (3.7 g) in ethanol (80 mL) was stirred under hydrogen at 50° C. for 8 h then filtered and concentrated. The residue was purified via silica gel chroclohexyl]-1-methyl-ethyl]-47-methoxy-34,35,36,37,48,49-hexamethyl-44-[2-(2-oxopyrrolidin-3-yl)ethoxy]-69,70-dioxa-59-azatricyclohexatriaconta-23,25,27(48),28(49)-tetraene-50,51,53,54,55-pentone (I-5): To a solution of everolimus (0.5 g, 0.52 mmol) in DCM (30 mL) was added TFA (1.6 mL) at −40° C. under N$_2$. After stirring for 10 min. 3-(2-hydroxyethyl)pyrrolidin-2-one (0.27 g, 2.09 mmol) was added and the reaction stirred for 1.5 h then quenched with sat.NaHCO$_3$ (aq.), diluted with DCM (60 mL), and organic layer washed with water (60 mL), brine (60 mL), dried over anhydrous Na$_2$SO$_4$, filtered and concentrated. The residue was purified by reverse phase chromatography (C18, 60% CH$_3$CN in H$_2$O) to provide I-5 (80 mg, 14% yield) as a white solid. ESI-MS (EI$^+$, m/z): 1077.4 [M+Na]$^+$. $^1$H NMR (400 MHz, CDCl$_3$) δ 6.33-5.96 (m, 4H), 5.41-5.11 (m, 4H), 4.76 (d, J=20 Hz, 1H), 4.43-3.87 (m, 5H), 3.79-3.51 (m, 5H), 3.36-3.27 (m, 9H), 3.14-2.49 (m, 7H), 2.22-1.92 (m, 6H), 1.75-1.55 (m, 21H), 1.40-1.14 (m, 9H), 0.99-0.81 (m, 18H), 0.56 (q, J=12 Hz, 1H).

Example 4: Synthesis of (23E,25E,27E,28E,34R, 35S,36R,37R,39S,41S,44S,46R,47R,56R)-46,56-dihydroxy-44-[(1R)-2-[(1S,3R,4R)-4-(2-hydroxy-ethoxy)-3-methoxy-cyclohexyl]-1-methyl-ethyl]-47-methoxy-34,35,36,37,48,49-hexamethyl-43-[2-(oxetan-3-yloxy)ethoxy]-67,68-dioxa-57-azatricyclohexatriaconta-23,25,27(48),28(49)-tetraene-50,51,52,53,54-pentone (I-14), (23E,25E, 27E,28E,34R,35S,36R,37R,39S,41S,43R,44S,46R, 47R,56R)-46,56-dihydroxy-44-[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-43-[2-(oxetan-3-yloxy)ethoxy]-67,68-dioxa-57-azatricyclohexatriaconta-23,25,27(48),28(49)-tetraene-50,51,52,53,54-pentone (I-8) and (23E,25E,27E,28E,34R,35S,36R,37R,39S,41S,43S, 44S,46R,47R,56R)-46,56-dihydroxy-44-[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-43-[2-(oxetan-3-yloxy)ethoxy]-67,68-dioxa-57-azatricyclohexatriaconta-23,25,27(48),28(49)-tetraene-50,51,52,53,54-pentone (I-9)

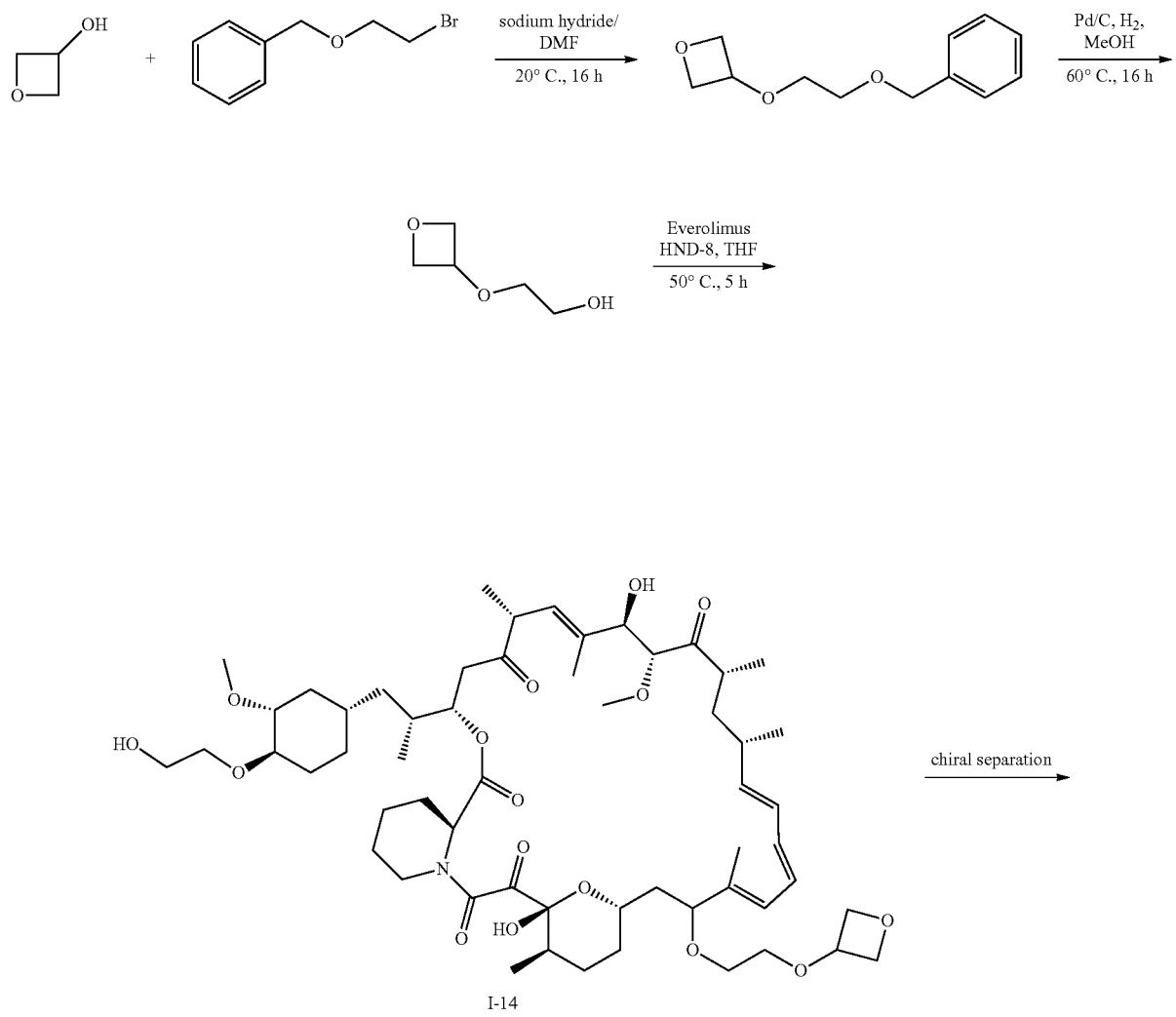

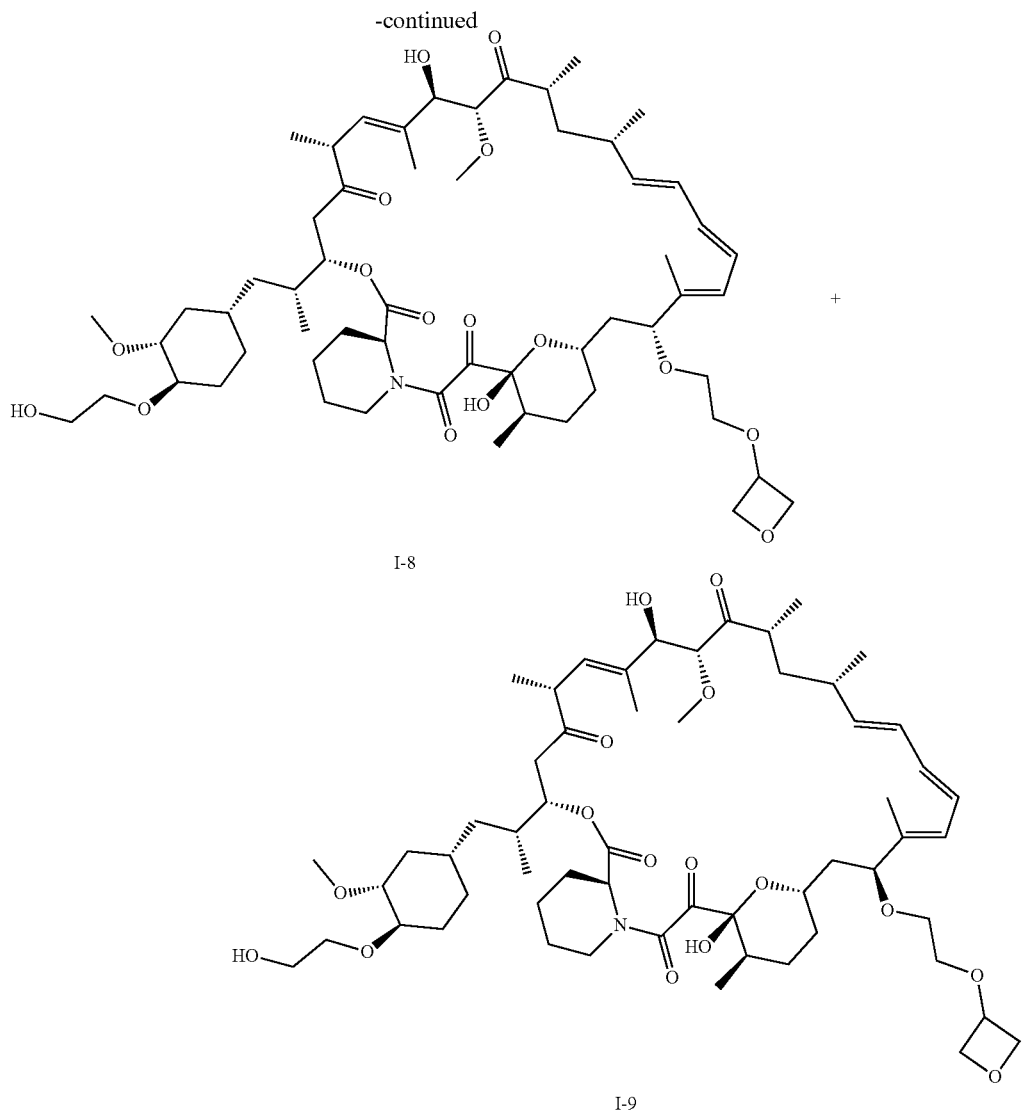

I-8

I-9

Step 1: Synthesis of 3-(2-(benzyloxy)ethoxy)oxetane: To a solution of oxetan-3-ol (1 g, 13.5 mmol) and 2-bromoethoxymethylbenzene (2.9 g, 13.5 mmol) in DMF (30 mL) was added sodium hydride (648 mg, 27 mmol) slowly in several portions. The resulting solution was stirred for 2 h at 0° C. then warmed to room temperature and stirred for 16 h. The reaction was quenched by the addition of 50 mL of $NH_4Cl$ (sat., aq.) and extracted with EtOAc (50 mL×2). The organic layers were combined and concentrated under vacuum. The residue was purified via silica gel chromatography (DCM:MeOH=9:1) to obtain 3-(2-benzyloxyethoxy)oxetane (404 mg, 14.4% yield) as a solid. ESI-MS ($EI^+$, m/z): 231.3 $[M+Na]^+$. $^1H$ NMR (400 MHz, $CDCl_3$) δ 7.33 (m, J=3.3 Hz, 4H), 7.28 (m, J=4.5, 3.6 Hz, 1H), 4.72 (dd, J=6.3, 5.7 Hz, 2H), 4.64-4.55 (m, 3H), 4.54 (s, 2H), 3.57 (dd, J=11.0, 5.1 Hz, 4H).

Step 2: Synthesis of 2-(oxetan-3-yloxy) ethanol: To a solution of 3-(2-benzyloxyethoxy) oxetane (0.4 g, 1.94 mmol) in MeOH (20 mL) was added Pd/C (0.206 g). The resulting mixture was heated to 60° C. under $H_2$ and stirred for 16 h. Upon cooling, the reaction was filtered and the solvent was removed under reduced pressure to obtain 2-(oxetan-3-yloxy) ethanol (200 mg, 87.3% yield) as a colorless oil. H NMR (400 MHz, $CDCl_3$) δ 4.76 (dd, J=6.8, 5.9 Hz, 2H), 4.64-4.59 (dd, 2H), 4.59-4.54 (m, 1H), 3.72 (dd, J=9.3, 5.2 Hz, 2H), 3.50-3.41 (m, 2H), 2.44 (t, J=5.8 Hz, 1H).

Step 3: Synthesis of (23E,25E,27E,28E,34R,35S,36R,37R,39S,41S,44S,46R,47R,56R)-46,56-dihydroxy-44-[(1R)-2-[(1S,3R4R)-4-(2-hydroxyethoxy)-3-methoxy-cyclohexyl]-1-methyl-ethyl]-47-methoxy-34,35,36,37,48,49-hexamethyl-43-[2-(oxetan-3-yloxy)ethoxy]-67,68-dioxa-57-azatricyclohexatriaconta-23,25,27(48),28(49)-tetraene-50,51,52,53,54-pentone (I-14): A mixture of everolimus (1 g, 1.04 mmol) and 2-(oxetan-3-yloxy)ethanol (2.47 g, 20.87 mmol) was dissolved in THF (8 mL) and heated to 50° C. HND-8 (0.2 g) (20 wt % yield) was added and the reaction stirred at 50° C. for 5 h. The mixture was filtered, washing with EtOAc (20 mL). The organic layer was washed with water (30 mL) and brine (30 mL), dried over anhydrous $Na_2SO_4$, filtered and concentrated. The residue was purified by reverse-phase chromatography (C18, $CH_3CN:H_2O$=50:50 to 70:30) to provide (23E,25E,27E,28E,34R,35S,36R,37R,39S,41S,44S,46R,47R,56R)-46,56-dihydroxy-44-

[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-43-[2-(oxetan-3-yloxy)ethoxy]-67,68-dioxa-57-azatricyclohexatriaconta-23,25,27(48),28(49)-tetraene-50,51,52,53,54-pentone (0.1 g, 9% yield) as a white solid. ESI-MS (EI+, m/z): 1066.4 [M+Na]+. $^1$H NMR (400 MHz, CDCl$_3$) δ 6.33-5.79 (m, 4H), 5.49-5.09 (m, 4H), 4.73 (d, J=20 Hz, 1H), 4.20-3.92 (m, 2H), 3.69-3.52 (m, 12H), 3.37-3.26 (m, 9H), 3.13-2.98 (m, 8H), 2.81-2.53 (m, 3H), 2.24-1.92 (m, 6H), 1.80-1.54 (m, 14H), 1.42-1.16 (m, 9H), 1.03-0.83 (m, 16H), 0.65 (q, J=11.6 Hz, 1H).

Step 4: Synthesis of (23E,25E,27E,28E,34R,35S,36R,37R,39S,41S,43R,44S,46R,47R,56R)-46,56-dihydroxy-44-[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-43-[2-(oxetan-3-yloxy)ethoxy]-67,68-dioxa-57-azatricyclohexatriaconta-23,25,27(48),28(49)-tetraene-50,51,52,53,54-pentone (I-8) and (23E,25E,27E,28E,34R,35S,36R,37R,39S,41S,43S,44S,46R,47R,56R)-46,56-dihydroxy-44-[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-43-[2-(oxetan-3-yloxy)ethoxy]-67,68-dioxa-57-azatricyclohexatriaconta-23,25,27(48),28(49)-tetraene-50,51,52,53,54-pentone (I-9): 140 mg of (23E,25E,27E,28E,34R,35S,36R,37R,39S,41S,44S,46R,47R,56R)-46,56-dihydroxy-44-[(1R)-2-[(1S,3R,4R)-4-(2-hydroxyethoxy)-3-methoxy-cyclohexyl]-1-methyl-ethyl]-47-methoxy-34,35,36,37,48,49-hexamethyl-43-[2-(oxetan-3-yloxy)ethoxy]-67,68-dioxa-57-azatricyclohexatriaconta-23,25,27(48),28(49)-tetraene-50,51,52,53,54-pentone was purified via prep chiral HPLC and the resulting epimers repurified via silica gel chromatography (hexane:DCM:EtOAc:MeOH=3:3:1:0.5) to provide I-8 (21 mg, 15% yield) and I-9 (22 mg, 15% yield), both as white solids.

Chiral Separation Method:

| Column | CHIRALPAK IC |
|---|---|
| Column size | 5.0 cm I.D. × 25 cm L |
| Solution concentration | 1.3 mg/ml |
| Injection | 10 ml |
| Mobile phase | Hexane/EtOH = 50/50 (v/v) |
| Flow rate | 60 mL/min |
| Wave length | UV 254 nm |
| Temperature | 35° C. |

I-8: ESI-MS (EI+, m/z): 1066.4 [M+Na]+. $^1$H NMR (400 MHz, CDCl$_3$) δ 6.41-5.85 (m, 4H), 5.63-5.06 (m, 5H), 4.20 (dd, J=44.7, 10.2 Hz, 3H), 3.99 (d, J=4.5 Hz, 1H), 3.88-2.95 (m, 24H), 2.91-1.91 (m, 10H), 1.90-1.69 (m, 15H), 1.54-1.18 (m, 8H), 1.00 (ddt, J=31.2, 24.0, 6.7 Hz, 18H), 0.81-0.62 (m, 1H).

I-9: ESI-MS (EI+, m/z): 1066.3 [M+Na]+. $^1$H NMR (400 MHz, CDCl$_3$) δ 6.25 (dtd, J=44.9, 14.9, 10.1 Hz, 3H), 5.90 (dd, J=29.4, 10.4 Hz, 1H), 5.58-5.44 (m, 1H), 5.41 (d, J=10.0 Hz, 1H), 5.27 (d, J=5.4 Hz, 1H), 5.15 (t, J=11.8 Hz, 1H), 4.80 (d, J=18.6 Hz, 1H), 4.17 (d, J=5.6 Hz, 1H), 3.91-3.64 (m, 12H), 3.59 (dd, J=15.9, 7.0 Hz, 3H), 3.48-3.27 (m, 12H), 3.14 (ddt, J=15.6, 10.1, 4.8 Hz, 4H), 2.91-2.64 (m, 2H), 2.57 (d, J=17.1 Hz, 1H), 2.39-2.19 (m, 2H), 2.01 (dd, J=43.7, 31.2 Hz, 6H), 1.83-1.67 (m, 8H), 1.50 (dd, J=23.1, 11.8 Hz, 5H), 1.36-1.17 (m, 9H), 1.14-0.80 (m, 18H), 0.71 (q, J=11.6 Hz, 1H).

Example 5: Synthesis of (26E,28E,30E,31E,36R,37S,38R,39R,42S,44S,47S,48R,49R,58R)-46-(cyclohexylmethoxy)-48,58-dihydroxy-47-[(1R)-2-[(1S,3R,4R)-4-(2-hydroxyethoxy)-3-methoxy-cyclohexyl]-1-methyl-ethyl]-49-methoxy-36,37,38,39,50,51-hexamethyl-68,69-dioxa-59-azatricyclohexatriaconta-26,28,30(50),31(51)-tetraene-52,53,54,55,56-pentone (I-10)

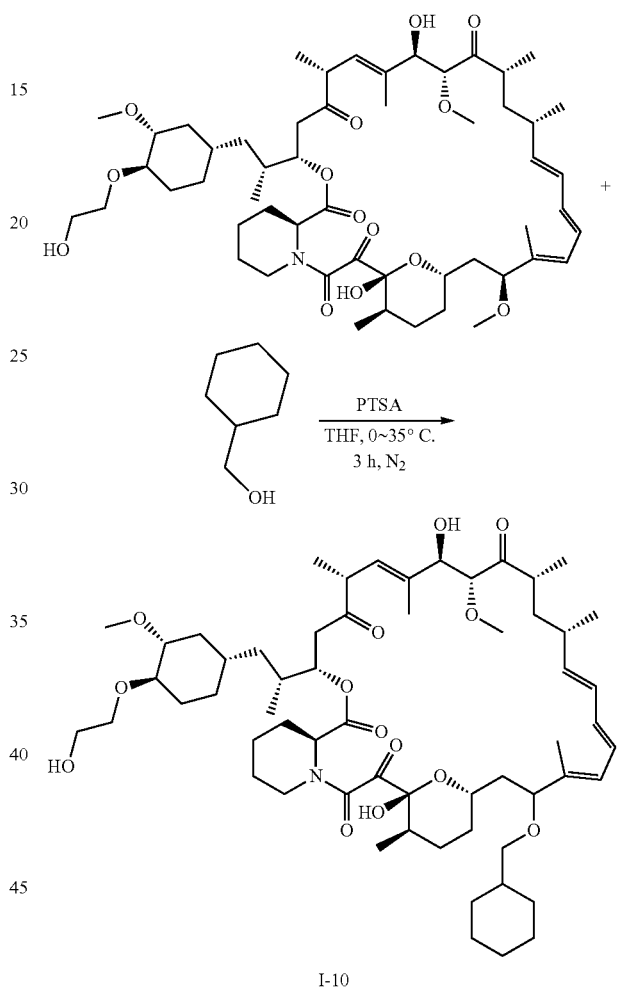

I-10

To a solution of everolimus (0.5 g, 0.52 mmol) and cyclohexylmethanol (0.89 g, 7.83 mmol) in THF (15 mL) at 0° C. under N$_2$ was added p-TsOH (0.46 g, 2.61 mmol). The mixture was warmed to 35° C. and stirred for 3 h then poured into ice cold sat.NaHCO$_3$ and extracted with EtOAc (35 mL×3). The combined organic layers were washed with water (50 mL), brine (50 mL), dried over anhydrous Na$_2$SO$_4$, filtered and concentrated. The resulting residue was purified via reverse phase chromatography (C18, 80 g, CH$_3$CN:H$_2$O=78:22) to provide I-10 (0.11 g, 20% yield) as a light white solid. ESI-MS (EI+, m/z): 1062.4 [M+Na]+. $^1$H NMR (500 MHz, CDCl$_3$) δ 6.47-5.78 (m, 4H), 5.63-5.07 (m, 4H), 4.75 (s, 1H), 4.34-3.99 (m, 2H), 3.83-3.53 (m, 6H), 3.50-3.25 (m, 9H), 3.24-3.02 (m, 4H), 2.86-2.45 (m, 3H), 2.44-2.23 (m, 2H), 2.21-1.92 (m, 4H), 1.85-1.64 (m, 16H), 1.56-1.37 (m, 7H), 1.31-0.81 (m, 29H), 0.76-0.60 (m, 1H).

Example 6: Synthesis of (25E,27E,29E,30E,35R, 36S,37R,38R,40S,43S,46S,47R,48R,57R)-47,57-dihydroxy-46-[(1R)-2-[(1S,3R,4R)-4-(2-hydroxy-ethoxy)-3-methoxy-cyclohexyl]-1-methyl-ethyl]-48-methoxy-35,36,37,38,49,50-hexamethyl-45-(tetrahydropyran-2-ylmethoxy)-68,69-dioxa-58-azatricyclohexatriaconta-25,27,29(49),30(50)-tetraene-51,52,53,54,55-pentone (I-11)

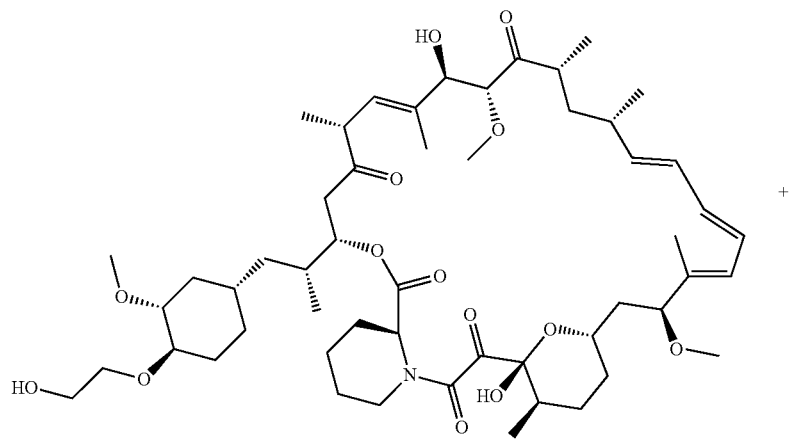

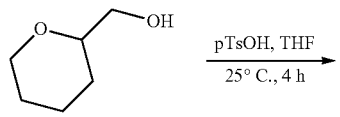

pTsOH, THF
25° C., 4 h

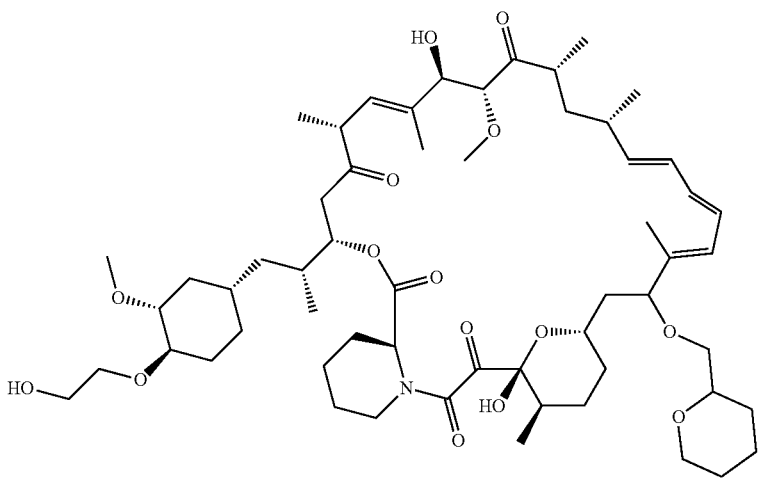

I-11

To a solution of everolimus (1 g, 1.04 mmol) in THF (5 mL) was added p-toluenesulfonic acid (0.9 g, 5.22 mmol) in toluene (10 mL) at 0° C. under $N_2$. The reaction was stirred for 10 min then tetrahydropyran-2-ylmethanol (3.64 g, 31.31 mmol) was added and the mixture stirred at 25° C. for 3 h. The reaction was diluted with EtOAc (30 mL), poured into sat. ice cold $NaHCO_3$ (aq. 40 mL) and extracted with EtOAc (30 mL). The combined organic layers were washed with water (30 mL×2), brine (50 mL), dried over anhydrous $Na_2SO_4$, filtered and concentrated. The residue was purified by reverse phase chromatography (C18, $CH_3CN:H_2O=60:40$) to obtain I-11 (106 mg, 9.7% yield) as a white solid. ESI-MS (EI$^+$, m/z): 1064.3 [M+Na]$^+$. $^1$H NMR (400 MHz, CDCl$_3$) δ 6.32-5.86 (m, 4H), 5.56-5.12 (m, 4H), 4.71 (d, J=20 Hz, 1H), 4.37-3.92 (m, 4H), 3.71-3.50 (m, 6H), 3.37-3.24 (m, 11H), 3.13-3.02 (m, 4H), 2.83-2.52 (m, 4H), 2.28-1.94 (m, 8H), 1.76-1.44 (m, 24H), 1.26-1.08 (m, 24H), 0.65 (q, J=12 Hz, 1H).

Example 7: Synthesis of (26E,28E,30E,31E,38R, 39S,40R,41R,43S,45S,48S,49R,50R,59R)-49,59-dihydroxy-48-[(1R)-2-[(1S,3R,4R)-4-(2-hydroxy-ethoxy)-3-methoxy-cyclohexyl]-1-methyl-ethyl]-50-methoxy-38,39,40,41,51,52-hexamethyl-47-(2-phenoxyethoxy)-69,70-dioxa-60-azatricyclohexatriaconta-26,28,30(51),31(52)-tetraene-53,54,55,56,57-pentone (I-12), (26E,28E, 30E,31E,38R,39S,40R,41R,43S,45S,47R,48S,49R, 50R,59R)-49,59-dihydroxy-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-47-(2-phenoxyethoxy)-69,70-dioxa-60-azatricyclohexatriaconta-26,28,30(51),31(52)-tetraene-53,54,55,56,57-pentone (I-6), and (26E, 28E,30E,31E,38R,39S,40R,41R,43S,45S,47S,48S, 49R,50R,59R)-49,59-dihydroxy-48-[(1R)-2-[(1S,3R, 4R)-4-(2-hydroxyethoxy)-3-methoxy-cyclohexyl]-1-methyl-ethyl]-50-methoxy-38,39,40,41,51,52-hexamethyl-47-(2-phenoxyethoxy)-69,70-dioxa-60-azatricyclohexatriaconta-26,28,30(51),31(52)-tetraene-53,54,55,56,57-pentone (I-7)

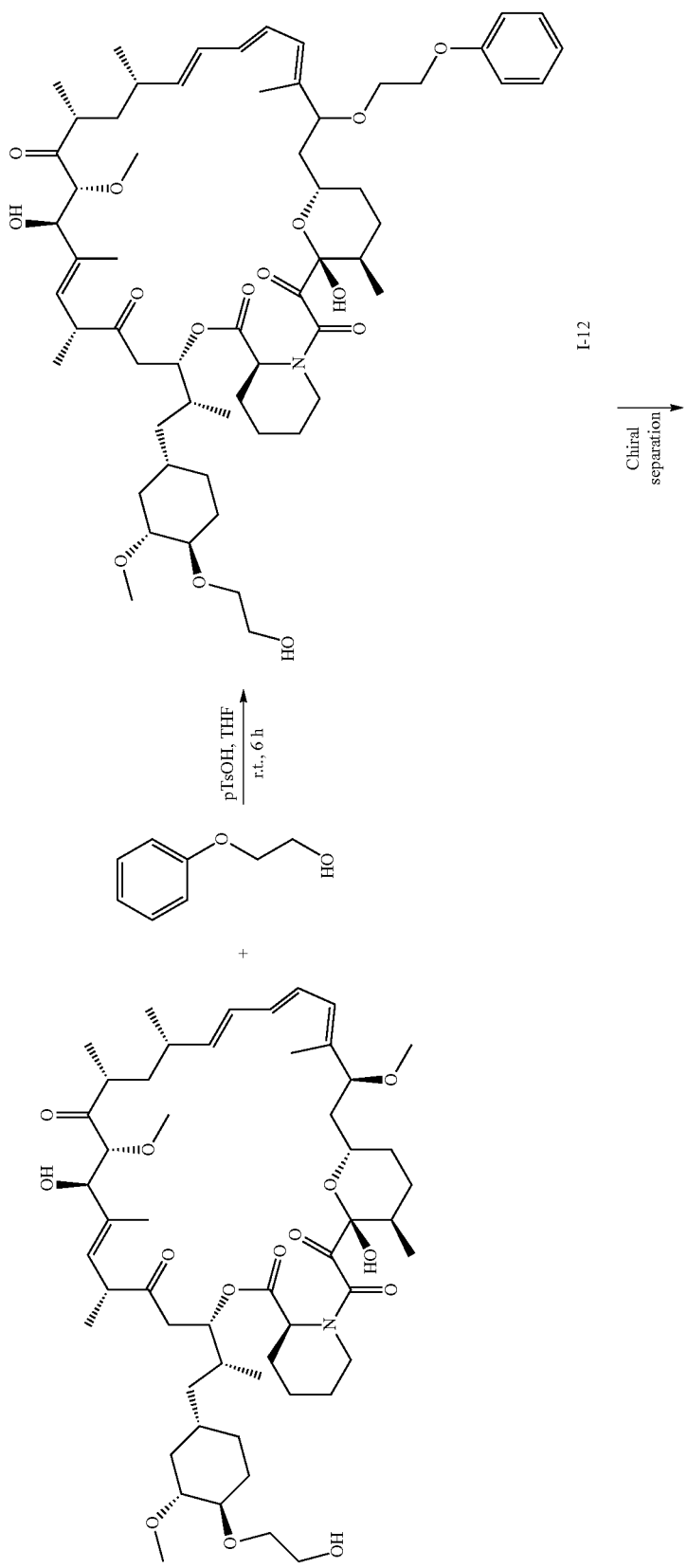

-continued
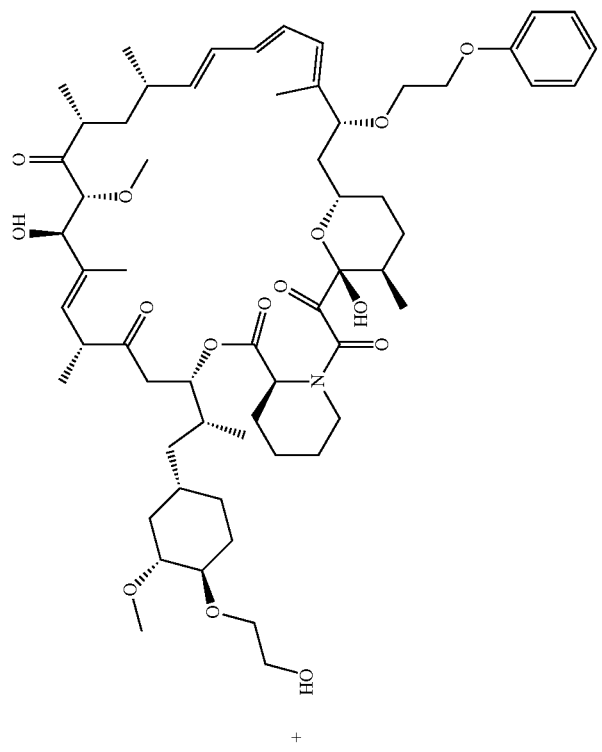
I-6
+
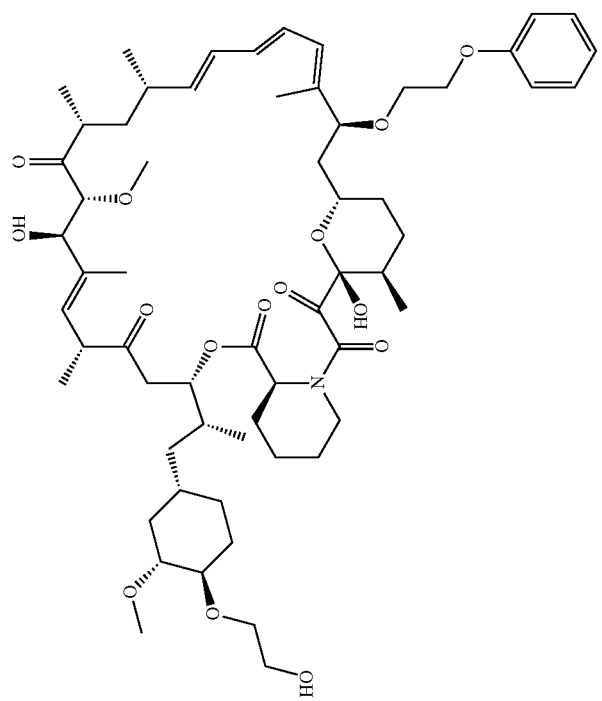
I-7

Step 1: Synthesis of (26E,28E,30E,31E,38R,39S,40R, 41R,43S,45S,48S,49R,50R,59R)-49,59-dihydroxy-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-47-(2-phenoxyethoxy)-69,70-dioxa-60-azatricyclohexatriaconta-26,28,30(51),31(52)-tetraene-53, 54,55,56,57-pentone (I-12): To a degassed solution of everolimus (0.5 g, 0.52 mmol) in THF (10 mL) was added 4-methylbenzenesulfonic acid (89.9 mg, 0.52 mmol) at 0° C. and 2-phenoxyethanol (1.44 g, 10.44 mmol) and this was stirred at 0° C. for 0.5 h under N$_2$, then at 23° C. for 4 h. The mixture was poured into sat.NaHCO$_3$ (40 mL) and extracted with EtOAc (30 mL). The organic layer was washed with water (30 mL×2), brine (40 mL), dried over anhydrous Na$_2$SO$_4$, filtered and concentrated under reduced pressure at room temperature. The residue was purified via silica gel chromatography (PE:EtOAc=50% to pure EtOAc) and then by reverse phase chromatography (C18, CH$_3$CN:H$_2$O=75: 25) to provide I-12 (100 mg, 18% yield) as a white solid. ESI-MS (EI$^+$, m/z): 1086.3 [M+Na]$^+$. $^1$H NMR (400 MHz, CDCl$_3$) δ 7.35-7.23 (m, 3H), 7.02-6.83 (m, 2H), 6.27 (m, J=35.4, 24.7, 15.0, 10.1 Hz, 3H), 5.96 (d, J=24.2, 11.2 Hz, 1H), 5.66-5.38 (m, 2H), 5.37-5.25 (m, 1H), 5.19 (dd, J=22.2, 9.5 Hz, 1H), 4.77 (d, J=20.9 Hz, 1H), 4.27 (s, 1H), 4.09 (ddd, J=25.7, 19.5, 4.9 Hz, 3H), 3.91-3.63 (m, 5H), 3.58 (s, 2H), 3.53-3.24 (m, 9H), 3.20 (s, 2H), 3.10 (d, J=6.9 Hz, 2H), 2.81-2.62 (m, 2H), 2.46 (dd, J=108.6, 8.4 Hz, 3H), 2.25-2.14 (m, 1H), 1.82 (d, J=10.7 Hz, 8H), 1.73 (d, J=20.8 Hz, 8H), 1.56-1.17 (m, 11H), 1.22-0.79 (m, 18H), 0.71 (d, J=11.6 Hz, 1H).

Step 2: Synthesis of (26E,28E,30E,31E,38R,39S,40R, 41R,43S,45S,47R,48S,49R,50R,59R)-49,59-dihydroxy-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-47-(2-phenoxyethoxy)-69,70-dioxa-60-azatricyclohexatriaconta-26,28,30(51),31(52)-tetraene-53, 54,55,56,57-pentone (I-6) and (26E,28E,30E,31E,38R,39S, 40R,41R,43S,45S,47S,48S,49R,50R,59R)-49,59-dihydroxy-48-[(1R)-2-[(1S,3R,4R)-4-(2-hydroxyethoxy)-3-methoxy-cyclohexyl]-1-methyl-ethyl]-50-methoxy-38,39, 40,41,51,52-hexamethyl-47-(2-phenoxyethoxy)-69,70-dioxa-60-azatricyclohexatriaconta-26,28,30(51),31(52)-tetraene-53,54,55,56,57-pentone (I-7): 94 mg of (26E,28E, 30E,31E,38R,39S,40R,41R,43S,45S,48S,49R,50R,59R)-49,59-dihydroxy-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-47-(2-phenoxyethoxy)-69,70-dioxa-60-azatricyclohexatriaconta-26,28,30(51),31(52)-tetraene-53,54,55,56,57-pentone was purified via prep chiral HPLC and the resulting epimers purified via silica gel chromatography (hexane:DCM:EtOAc:MeOH=3:3:1:0.6) to provide I-6 (12 mg, 13% yield) and I-7 (11 mg, 12% yield) both as white solids.

Chiral Separation Method:

| Column | CHIRALPAK IC |
|---|---|
| Column size | 2.5 cm I.D. × 25 cm L, 10 μm |
| Sample solution | 0.5 mg/ml in Mobile phase |
| Injection | 18 ml |
| Mobile phase | Hexane/EtOH = 60/40 (V/V) |
| Flow rate | 60 mL/min |
| Wave length | UV 254 nm |
| Temperature | 35° C. |

I-6: ESI-MS (EI$^+$, m/z): 1086.4 [M+Na]$^+$. $^1$H NMR (400 MHz, CDCl$_3$) δ 7.53 (d, J=8.6 Hz, 1H), 7.35 (s, 1H), 7.29 (dd, J=11.5, 5.9 Hz, 1H), 7.10 (ddd, J=18.1, 8.6, 2.4 Hz, 1H), 6.94 (dd, J=19.8, 7.6 Hz, 1H), 6.44-5.74 (m, 4H), 5.55-4.84 (m, 5H), 4.34-2.90 (m, 28H), 2.73-1.86 (m, 12H), 1.80-1.47 (m, 16H), 1.40-0.56 (m, 19H).

I-7: ESI-MS (EI$^+$, m/z): 1086.4 [M+Na]$^+$. $^1$H NMR (400 MHz, CDCl$_3$) δ 7.24 (d, J=33.9 Hz, 2H), 6.96-6.76 (m, 3H), 6.37-5.79 (m, 4H), 5.54-4.96 (m, 5H), 4.68 (s, 1H), 4.18-3.90 (m, 4H), 3.88-3.18 (m, 20H), 3.17-2.90 (m, 3H), 2.84-2.44 (m, 3H), 2.33-1.79 (m, 9H), 1.53 (ddd, J=70.2, 22.3, 10.6 Hz, 16H), 1.05-0.71 (m, 18H), 0.71-0.53 (m, 1H).

Example 8: Synthesis of (25E,27E,29E,30E,36R, 37S,38R,39R,42S,44S,47S,48R,49R,58R)-48,58-dihydroxy-47-[(1R)-2-[(1S,3R,4R)-4-(2-hydroxyethoxy)-3-methoxy-cyclohexyl]-1-methyl-ethyl]-49-methoxy-36,37,38,39,50,51-hexamethyl-46-(2-tetrahydropyran-4-yloxyethoxy)-69,70-dioxa-59-azatricyclohexatriaconta-25,27,29(50),30(51)-tetraene-52,53,54,55,56-pentone (I-13)

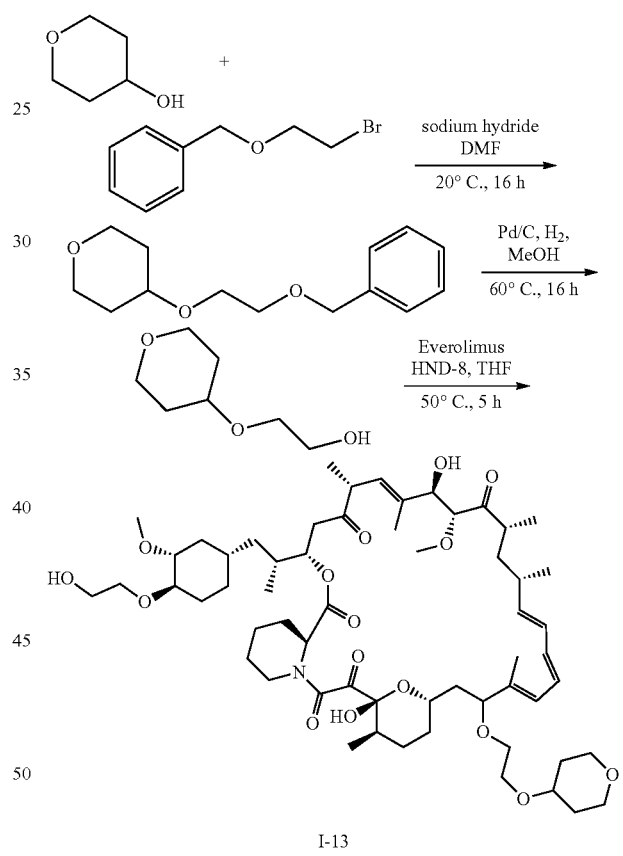

I-13

Step 1: Synthesis of 4-(2-benzyloxyethoxy)tetrahydropyran: To a solution of tetrahydropyran-4-ol (5 g, 48.96 mmol) and 2-bromoethoxymethylbenzene (21.06 g, 97.91 mmol) in DMF (20 mL) was added sodium hydride (2.94 g, 122.39 mmol) in several batches. The resulting solution was stirred for 2 h at 0° C. then warmed to room temperature and stirred for 16 h. The reaction was quenched by the addition of 50 mL of NH$_4$Cl (sat., aq.), extracted with EtOAc (50 mL×2) and the organic layers were combined and concentrated under vacuum. The residue was purified via silica gel chromatography (PE:EtOAc=8:1) to afford 4-(2-benzyloxyethoxy)tetrahydropyran (5 g, 43.2% yield) as a solid. ESI-MS (EI$^+$, m/z): 259.4 [M+Na]$^+$. $^1$H NMR (400 MHz, CDCl$_3$) δ 7.35 (d, J=4.3 Hz, 4H), 7.32-7.27 (m, 1H), 4.58 (s, 2H), 3.95 (dt, J=11.5, 4.2 Hz, 2H), 3.71-3.57 (m, 4H), 3.53 (td, J=8.9, 4.4 Hz, 1H), 3.48-3.37 (m, 2H), 1.96-1.85 (m, 2H), 1.61 (dtd, J=13.4, 9.5, 4.1 Hz, 2H).

Step 2: Synthesis of 2-(oxetan-3-yloxy) ethanol: To a solution of 4-(2-benzyloxyethoxy)tetrahydropyran (1 g, 4.23 mmol) in MeOH (10 mL) was added Pd/C (0.45 g). The resulting solution was stirred under H$_2$ for 16 h at 60° C. then cooled and filtered through a short celite plug. The filtrate was concentrated to obtain 2-tetrahydropyran-4-yloxyethanol (516 mg, 83.4% yield) as a colorless oil. $^1$H NMR (400 MHz, CDCl$_3$) δ 3.94 (t, J=4.3 Hz, 1H), 3.91 (t, J=4.3 Hz, 1H), 3.75-3.68 (m, 2H), 3.56 (dd, J=5.8, 3.5 Hz, 2H), 3.51 (td, J=9.0, 4.4 Hz, 1H), 3.45 (d, J=2.2 Hz, 1H), 3.42 (dd, J=4.5, 2.6 Hz, 1H), 2.31 (s, 1H), 1.96-1.85 (m, 2H), 1.58 (dtd, J=13.4, 9.5, 4.1 Hz, 2H).

Step 3: Synthesis of (25E,27E,29E,30E,36R,37S,38R,39R,42S,44S,47S,48R. 49R,58R)-48,58-dihydroxy-47-[(1R)-2-[(1S,3R,4R)-4-(2-hydroxyethoxy)-3-methoxy-cyclohexyl]-1-methyl-ethyl]-49-methoxy-36,37,38,39,50,51-hexamethyl-46-(2-tetrahydropyran-4-yloxyethoxy)-69,70-dioxa-59-azatricyclohexatriaconta-25,27,29(50),30(51)-tetraene-52,53,54,55,56-pentone (I-13): A mixture of everolimus (1 g, 1.04 mmol) and 2-tetrahydropyran-4-yloxyethanol (3.05 g, 20.87 mmol) was dissolved in THF (10 mL) under N$_2$ and heated to 50° C. HND-8 (0.2 g) and the reaction was stirred for 5 h, filtered and concentrated. The residue was purified by reverse phase chromatography (C18, CH$_3$CN:H$_2$O=65:35) to provide I-13 (0.2 g, 17.9% yield) as a light yellow solid. ESI-MS (EI$^+$, m/z): 1094.4 [M+Na]$^+$. $^1$H NMR (400 MHz, CDCl$_3$) δ 6.51-6.11 (m, 4H), 5.73-5.14 (m, 5H), 4.71-4.21 (m, 3H), 3.96-3.60 (m, 13H), 3.42-3.09 (m, 14H), 2.72-2.29 (m, 8H), 2.07-2.00 (m, 4H), 1.99-1.50 (m, 22H), 1.28-0.84 (m, 18H), 0.72-0.58 (m, 1H).

Example 9: Synthesis of (23E,25E,27E,28E,35R, 36S,37R,38R,40S,43S,45S,46S,47R,48R,58R)-47, 58-dihydroxy-46-[(1R)-2-[(1S,3R,4R)-4-(2-hydroxyethoxy)-3-methoxy-cyclohexyl]-1-methyl-ethyl]-48-methoxy-35,36,37,38,49,50-hexamethyl-45-[3-(2-oxopyrrolidin-3-yl)propoxy]-70,71-dioxa-60-azatricyclohexatriaconta-23,25,27(49),28(50)-tetraene-51,52,54,55,56-pentone (I-15)

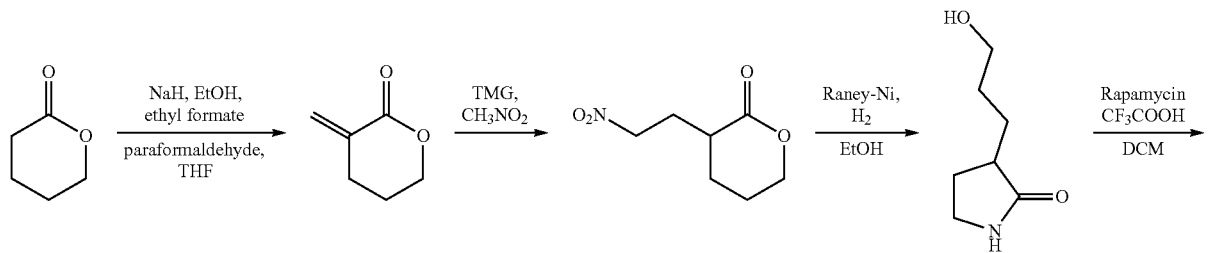

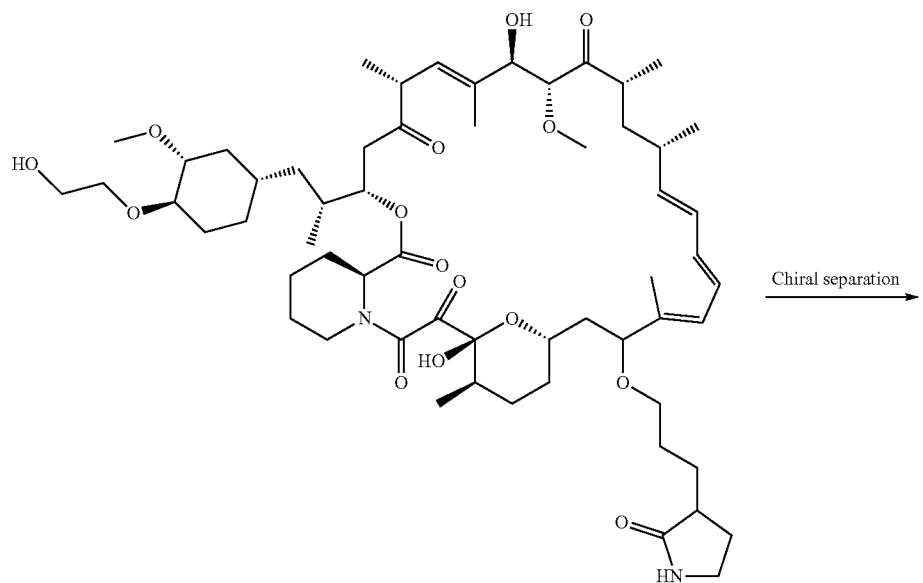

Chiral separation

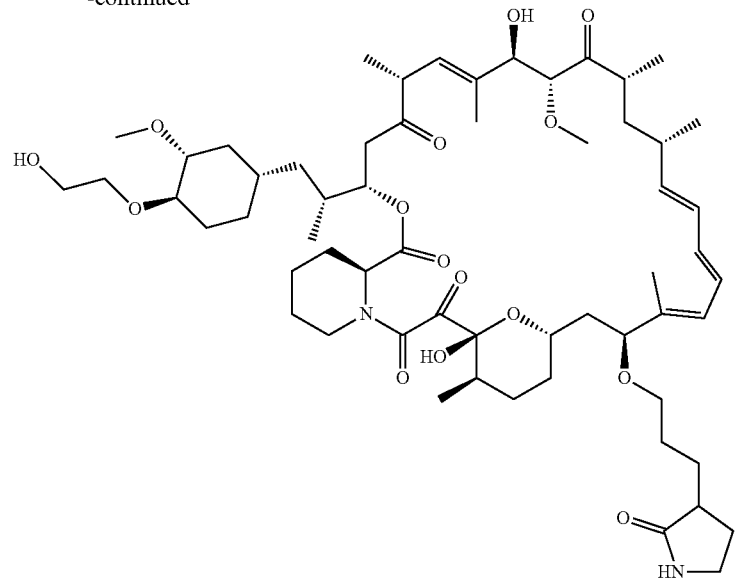

I-15

Step 1: 3-methylenetetrahydropyran-2-one: To a stirred suspension of sodium hydride (4.39 g, 109.87 mmol, 60% purity) in $Et_2O$ (100 mL) under $N_2$ was added absolute EtOH (0.64 mL, 11 mmol) dropwise. The mixture was warmed to reflux and ethyl formate (8.88 g, 119.86 mmol) and tetrahydropyran-2-one (10 g, 99.88 mmol) were added slowly over 40 minutes. The reaction was stirred at 40° C. for 1 hour then cooled to room temperature. The resulting solid was collected via filtration, washed with $Et_2O$ and dried under vacuum. The solid was then dissolved in THF (200 mL) under $N_2$ and paraformaldehyde (15 g, 499.42 mmol) added. The mixture was refluxed at 78° C. for 1 h then cooled to room temperature. $K_2CO_3$ sat. aqueous solution (30 mL) was added at 0° C. to quench the reaction. The THF was removed under reduced pressure and the resulting aqueous mixture extracted by $Et_2O$ (20 mL×3). The combined organic layers were washed with water (30 mL), brine (40 mL), dried over anhydrous $Na_2SO_4$, filtered and concentrated. The residue was purified via silica gel chromatography (PE:EtOAc=4% to 20%) to provide 3-methylenetetrahydropyran-2-one (2.3 g, 21% yield) as a colorless liquid. ESI-MS (EI$^+$, m/z): 113.2 [M+H]$^+$. $^1$HNMR (400 MHz, $CDCl_3$): δ 6.42 (s, 1H), 5.57 (s, 1H), 4.386 (t, J=4.4 Hz, 2H), 2.674 (t, J=7.8 Hz, 2H), 1.98-1.94 (m, 2H).

Step 2: 3-(2-nitroethyl) tetrahydropyran-2-one: To a solution of 3-methylenetetrahydropyran-2-one (3 g, 26.76 mmol) in nitromethane (14.3 mL) at 0° C. under nitrogen was added 1,1,3,3-tetramethylguanidine (0.31 g, 2.68 mmol) dropwise. The reaction mixture was stirred at 50° C. for 18 h then cooled to rt, quenched with 0.5M HCl aqueous solution to adjust the pH to 4. The mixture was extracted with EtOAc (150 mL×3) and the combined organic layers dried over $MgSO_4$, filtered and concentrated. The residue was purified via silica gel chromatography (acetone:PE=1:5) to provide 3-(2-nitroethyl) tetrahydropyran-2-one (1.5 g, 32% yield). ESI-MS (EI$^+$, m/z): 174.1 [M+H]$^+$.

Step 3: 3-(3-hydroxypropyl) pyrrolidin-2-one: To a solution of 3-(2-nitroethyl) tetrahydropyran-2-one (1.5 g, 8.66 mmol) in ethanol (20 mL) was added Raney-Ni (0.51 g) and the mixture stirred at 50° C. for 8 h under $H_2$. The reaction was filtered, concentrated and then purified via silica gel chromatography then reverse phase chromatography to provide 3-(3-hydroxypropyl) pyrrolidin-2-one (0.35 g, 28% yield). ESI-MS (EI$^+$, m/z): 144.2 [M+H]$^+$. $^1$H NMR (400 MHz, $CDCl_3$): δ 6.65 (s, 1H), 3.65 (t, J=6.0 Hz, 2H), 3.36-3.35 (m, 2H), 3.04 (s, 1H), 2.45-2.37 (m, 1H), 2.34-2.26 (m, 1H), 1.93-1.76 (m, 2H), 1.71-1.59 (m, 2H), 1.53-1.44 (m, 1H).

Step 4: Synthesis of (23E,25E,27E,28E,35R,36S,37R,38R,40S,43S,46S,47R,48R,58R)-47,58-dihydroxy-46-[(1R)-2-[(1S,3R,4R)-4-(2-hydroxyethoxy)-3-methoxy-cyclohexyl]-1-methyl-ethyl]-48-methoxy-35,36,37,38,49,50-hexamethyl-45-[3-(2-oxopyrrolidin-3-yl)propoxy]-70,71-dioxa-60-azatricyclohexatriaconta-23,25,27(49),28(50)-tetraene-51,52,54,55,56-pentone: To a solution of everolimus (0.4 g, 0.42 mmol) in DCM (10 mL) was added TFA (1.9 g, 16.7 mmol) at −40° C. under $N_2$. After stirring for 10 minutes 3-(3-hydroxypropyl) pyrrolidin-2-one (0.24 g, 1.67 mmol) was added. The mixture was stirred at −40° C. for 1.5 h then quenched with ice cold sat.$NaHCO_3$ (aq.) and diluted with DCM (60 mL). The organic layer was washed with water (60 mL), brine (60 mL), dried over anhydrous $Na_2SO_4$, filtered and concentrated. The residue was purified via reverse phase chromatography (60% $CH_3CN$ in $H_2O$) to provide (23E,25E,27E,28E,35R,36S,37R,38R,40S,43S,46S,47R,48R,58R)-47,58-dihydroxy-46-[(1R)-2-[(1S,3R,4R)-4-(2-hydroxyethoxy)-3-methoxy-cyclohexyl]-1-methyl-ethyl]-48-methoxy-35,36,37,38,49,50-hexamethyl-45-[3-(2-oxopyrrolidin-3-yl)propoxy]-70,71-dioxa-60-azatricyclohexatriaconta-23,25,27(49),28(50)-tetraene-51,52,54,55,56-pentone (66 mg, 15% yield) as white solid. ESI-MS (EI$^+$, m/z): 1092.3 [M+Na]$^+$. $^1$H NMR (400 MHz, $CDCl_3$): δ 6.32-6.12 (m, 4H), 5.58-5.10 (m, 5H), 4.61 (s, 1H), 4.33-3.91 (m, 3H), 3.84-3.49 (m, 6H), 3.48-3.25 (m, 11H), 3.24-2.94 (m, 4H), 2.86-2.40 (m, 2H), 2.39-1.89 (m, 4H), 1.88-1.63 (m, 11H), 1.37-1.12 (m, 13H), 1.11-0.80 (m, 25H), 0.79-0.55 (m, 3H).

Step 5: Synthesis of (23E,25E,27E,28E,35R,36S,37R, 38R,40S,43S,45S,46S,47R,48R,58R)-47,58-dihydroxy-46-[(1R)-2-[(1S,3R,4R)-4-(2-hydroxyethoxy)-3-methoxy-cyclohexyl]-1-methyl-ethyl]-48-methoxy-35,36,37,38,49,50-hexamethyl-45-[3-(2-oxopyrrolidin-3-yl)propoxy]-70,71-dioxa-60-azatricyclohexatriaconta-23,25,27(49),28(50)-tetraene-51,52,54,55,56-pentone (I-15): 90 mg of the racemic mixture was separated via chiral HPLC to provide I-15 (19 mg).

Chiral Separation Method:

| HPLC equipment | Shimadzu LC-20AT CP-HPLC-09 |
| --- | --- |
| Column | CHIRALPAK IC (IC00CD-NA012) |
| Column size | 0.46 cm I.D. × 15 cm L |
| Injection | 20.0 μL |
| Mobile phase | Hexane/EtOH = 60/40 (V/V) |
| Flow rate | 1.0 ml/min |
| Wave length | UV 254 nm |
| Temperature | 35° C. |

I-15: ESI-MS (EI+, m/z): 1092.3 [M+Na]+. H NMR (400 MHz, CDCl₃) δ 6.46-6.03 (m, 4H), 5.61-5.12 (m, 5H), 4.66-4.44 (m, 1H), 4.38-4.13 (m, 2H), 4.09-3.90 (m, 2H), 3.68 (qdd, J=21.0, 20.3, 9.2 Hz, 6H), 3.47-2.98 (m, 12H), 2.92-2.39 (m, 5H), 2.35-1.93 (m, 6H), 1.90-1.69 (m, 10H), 1.55-1.15 (m, 20H), 1.12-0.81 (m, 18H), 0.61 (q, J=23.9, 12.1 Hz, 1H).

Example 10: Synthesis of N-[(22E,24E,26E,27E, 31R,32S,33R,34R,36S,38S,41S,42R,43R,52R)-42, 52-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-46,47,48,49,50-pentaoxo-65,66-dioxa-54-azatricyclohexatriaconta-22,24,26(44),27(45)-tetraen-40-yl]-2-methoxy-ethanesulfonamide (I-16)

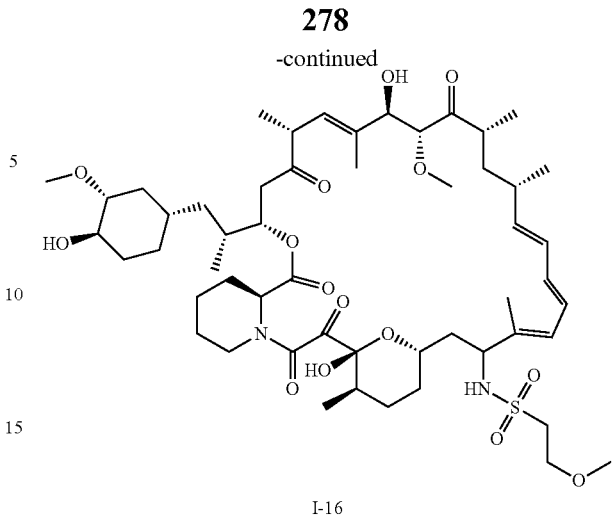

I-16

Step 1: Synthesis of sodium 2-methoxyethane-1-sulfonate: A solution of 1-bromo-2-methoxy-ethane (5 g, 35.97 mmol) and Na₂SO₃ (4.76 g, 37.77 mmol) in H₂O (50 mL) was stirred at 100° C. for 16 h. The solution was cooled to rt, concentrated and then triturated with Et₂O (20 mL) to provide 2-methoxyethylsulfonyloxysodium (9 g, 93% yield) as a white solid. ¹H NMR (500 MHz, DMSO-d6): δ 3.57-3.54 (m, 2H), 3.21 (s, 3H), 2.73-2.70 (m, 2H).

Step 2: Synthesis of 2-methoxyethane-1-sulfonyl chloride: A solution of 2-methoxyethylsulfonyloxysodium (1 g, 6.17 mmol) in POCl₃ (5 mL) was stirred at 110° C. for 3 h then at rt for 16 h. The solution was concentrated then diluted with ice water (30 mL) and extracted with EtOAc (50 mL). The organic layer was washed with brine (30 mL), dried over anhydrous Na₂SO₄, filtered and concentrated to give 2-methoxyethanesulfonyl chloride (0.4 g, 40% yield) as a yellow oil. ¹H NMR (500 MHz, CDCl₃): δ 4.06-3.92 (m, 4H), 3.43 (s, 3H).

Step 3: Synthesis of 2-methoxyethane-1-sulfonamide: A solution of 2-methoxyethanesulfonyl chloride (4.5 g, 28.37 mmol) in NH₃.H₂O (3 mL) was stirred at rt for 16 h. The solution was concentrated by lyophilization then dissolved in DCM (30 mL), filtered and concentrated. The residue was purified via reverse phase chromatography (5% CH₃CN in water) to provide 2-methoxyethanesulfonamide (1.8 g, 46% yield) as a brown oil. ¹H NMR (500 MHz, CDCl₃): δ 5.04 (s, 2H), 3.86 (t, J=6.0 Hz, 2H), 3.42 (s, 3H), 3.40-3.37 (m, 2H).

Step 4: Synthesis of N-[(22E,24E,26E,27E,31R,32S,33R, 34R,36S,38S,41S,42R,43R,52R)-42,52-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-46,47,48,49,50-pentaoxo-65,66-dioxa-54-azatricyclohexatriaconta-22,24,26(44),27(45)-tetraen-40-yl]-2-methoxy-ethanesulfonamide (I-16): To a solution of rapamycin (0.4 g, 0.44 mmol) in DCM (5 mL) was added TFA (0.25 g, 2.19 mmol) at −40° C. under argon. 2-methoxyethanesulfonamide (0.61 g, 4.38 mmol) was then added. The resulting mixture was stirred at −10° C. for 2 h then quenched with ice cold NaHCO₃ (20 mL) aqueous solution and extracted with DCM (50 mL×2). The combined organic layers were washed with brine (50 mL), dried over Na₂SO₄, filtered and concentrated. The residue was purified by reverse phase chromatography (80% CH₃CN in H₂O) to provide I-16 (0.16 g, 36% yield) as a white solid. ESI-MS (EI+, m/z): 1043.1 [M+Na]+. ¹H NMR (500 MHz, CDCl₃): δ 6.40-5.97 (m, 4H), 5.69-5.13 (m, 4H), 4.62-3.46 (m, 8H), 3.48-3.33 (m, 12H), 3.29-3.04 (m, 4H), 2.97-2.93 (m, 2H), 2.86-2.50 (m, 4H), 2.42-1.85 (m, 12H), 1.63-1.19 (m, 15H), 1.48-0.83 (m, 18H), 0.71-0.61 (m, 1H).

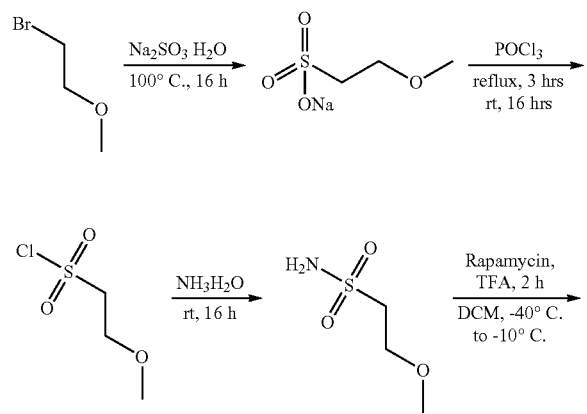

Example 11: Synthesis of (23E,25E,27E,28E,30R, 31S,32R,33R,35S,37S,39S,40S,45R,46R,55R)-39- [[(3R,3aR,6R,6aR)-3-hydroxy-2,3,3a,5,6,6a-hexahydrofuro[3,2-b]furan-6-yl]oxy]-45,55-dihydroxy-40- [(1R)-2-[(1S,3R,4R)-4-hydroxy-3-methoxy-cyclohexyl]-1-methyl-ethyl]-46-methoxy-30,31,32, 33,47,48-hexamethyl-68,69-dioxa-56-azatricyclohexatriaconta-23,25,27(47),28(48)-tetraene-49,50,51,52,53-pentone (I-18) and (23E, 25E,27E,28E,30R,31S,32R,33R,35S,37S,39R,40S, 45R,46R,55R)-39-[[(3R,3aR,6R,6aR)-3-hydroxy-2, 3,3a,5,6,6a-hexahydrofuro[3,2-b]furan-6-yl]oxy]-45, 55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone (I-17)

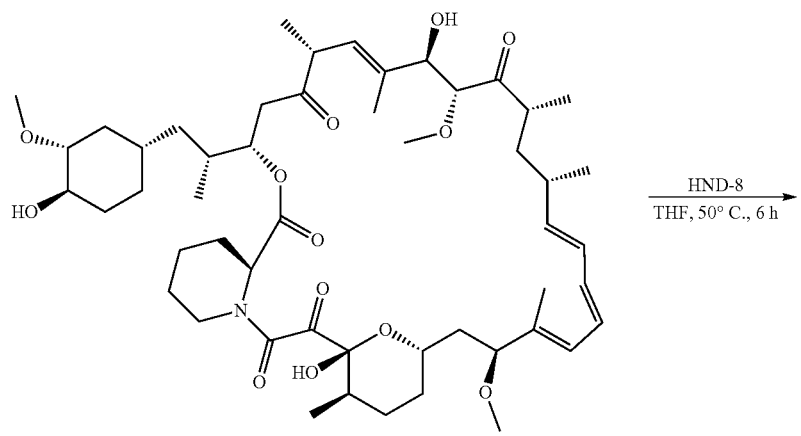

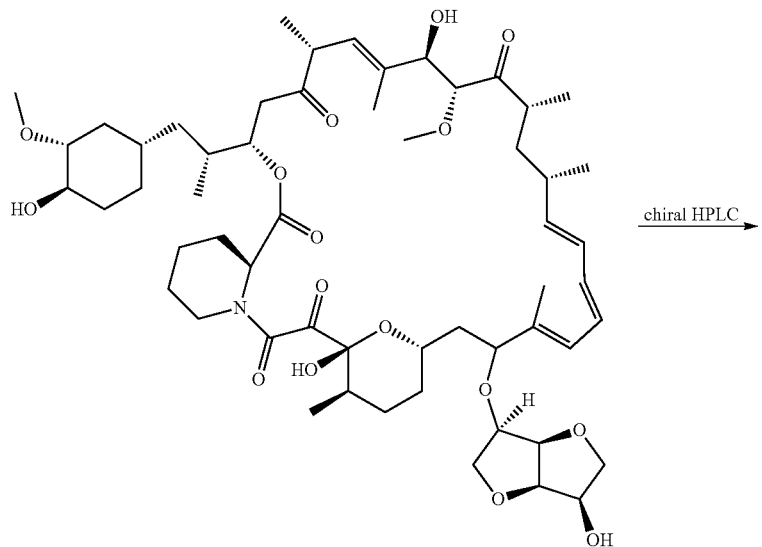

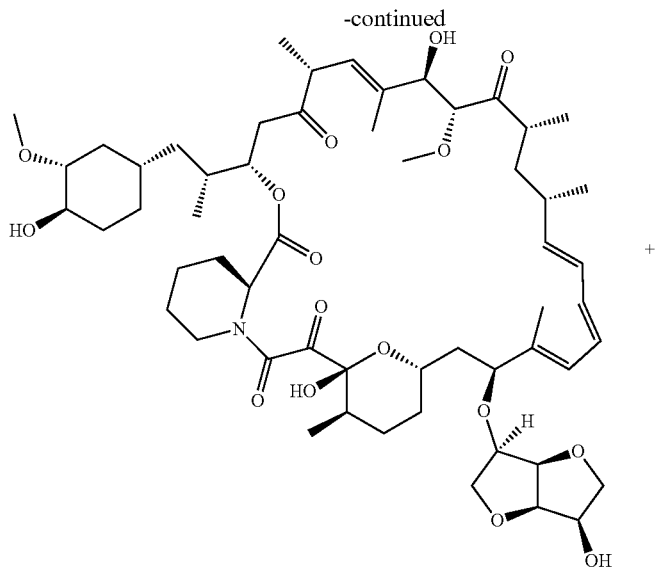

I-18

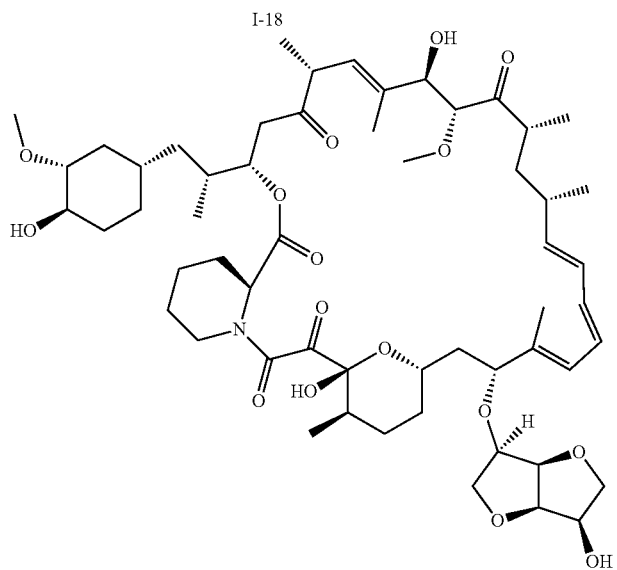

I-17

Step 1: Synthesis of (23E,25E,27E,28E,30R,31S,32R, 33R,35S,37S,40S,45R,46R,55R)-39-[[(3R,3aR,6R,6aR)-3-hydroxy-2,3,3a,5,6,6a-hexahydrofuro[3,2-b]furan-6-yl]oxy]-45,55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone: A solution of rapamycin (0.5 g, 0.55 mmol) and (3R,3aR,6R,6aR)-2,3,3a,5,6,6a-hexahydrofuro[3,2-b]furan-3,6-diol (1.20 g, 8.20 mmol) in THF (10 mL) was heated to 50° C. under an argon atmosphere. HND-8 (70 mg) was added and the mixture was stirred for 6 h at the same temperature. The reaction was cooled and filtered, the filtrate was concentrated and the residue was purified via reverse-phase chromatography (58% CH$_3$CN in water) to provide (23E,25E,27E,28E,30R,31S,32R,33R,35S,37S,40S,45R,46R,55R)-39-[[(3R,3aR,6R,6aR)-3-hydroxy-2,3,3a,5,6,6a-hexahydrofuro[3,2-b]furan-6-yl]oxy]-45,55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone (30 mg, 5% yield) as a yellow solid.

Step 2: Synthesis of (23E,25E,27E,28E,30R,31S,32R,33R,35S,37S,39S,40S,45R,46R,55R)-39-[[(3R,3aR,6R,6aR)-3-hydroxy-2,3,3a,5,6,6a-hexahydrofuro[3,2-b]furan-6-yl]oxy]-45,55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone (I-18) and (23E,25E,27E,28E,30R,31S,32R,33R,35S,37S,39R,40S,45R,46R,55R)-39-[[(3R,3aR,6R,6aR)-3-hydroxy-2,3,3a,5,6,6a-hexahydrofuro[3,2-b]furan-6-yl]oxy]-45,55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone (I-17): 300 mg of the racemic mixture was separated via chiral HPLC and then further purified by silica gel chromatography (PE:DCM:EtOAc:MeOH=3:3:1:1.2) to provide I-18 (39 mg) and I-17 (38 mg) as a white solid.

Chiral Separation Method:

| | |
|---|---|
| Column | CHIRALPAK IC |
| Column size | 5 cm I.D. × 25 cm L, 10 μm |
| Injection | 2 mg/mL in Mobile phase |
| Mobile phase | Hexane/EtOH = 40/60 (V/V) |
| Flow rate | 60 mL/min |
| Wave length | UV 254 nm |
| Temperature | 38° C. |

I-18: ESI-MS (EI+, m/z): 1050.2 [M+Na]$^+$. $^1$H NMR (400 MHz, CDCl$_3$) δ 6.33 (dq, J=29.2, 14.7 Hz, 2H), 6.20-6.08 (m, 1H), 5.97 (d, J=11.2 Hz, 1H), 5.61-5.03 (m, 4H), 4.88 (s, 1H), 4.49-4.38 (m, 1H), 4.33-4.04 (m, 3H), 3.99-3.76 (m, 5H), 3.72-3.53 (m, 4H), 3.50-3.25 (m, 10H), 2.97-2.53 (m, 6H), 2.18 (ddd, J=88.0, 52.8, 10.5 Hz, 8H), 1.82-1.65 (m, 10H), 1.50-1.18 (m, 10H), 1.15-0.80 (m, 18H), 0.73-0.60 (m, 1H).

I-17: ESI-MS (EI+, m/z): 1050.2 [M+Na]$^+$. $^1$H NMR (400 MHz, CDCl3) δ 6.57-5.91 (m, 4H), 5.81-5.01 (m, 4H), 4.61-3.50 (m, 12H), 3.49-3.11 (m, 13H), 3.01-2.48 (m, 5H), 2.42-1.85 (m, 3H), 1.45-0.60 (m, 44H).

Example 12: Synthesis of (23E,25E,27E,28E,30R, 31S,32R,33R,35S,37S,39S,40S,45R,46R,55R)-39-[[(3S,3aR,6R,6aR)-3-hydroxy-2,3,3a,5,6,6a-hexahydrofuro[3,2-b]furan-6-yl]oxy]-45,55-dihydroxy-40-[(1R)-2-[(1S,3R,4R)-4-hydroxy-3-methoxycyclohexyl]-1-methyl-ethyl]-46-methoxy-30,31,32, 33,47,48-hexamethyl-68,69-dioxa-56-azatricyclohexatriaconta-23,25,27(47),28(48)-tetraene-49,50,51,52,53-pentone (I-21) and (23E, 25E,27E,28E,30R,31S,32R,33R,35S,37S,39R,40S, 45R,46R,55R)-39-[[(3S,3aR,6R,6aR)-3-hydroxy-2, 3,3a,5,6,6a-hexahydrofuro[3,2-b]furan-6-yl]oxy]-45, 55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone (I-20)

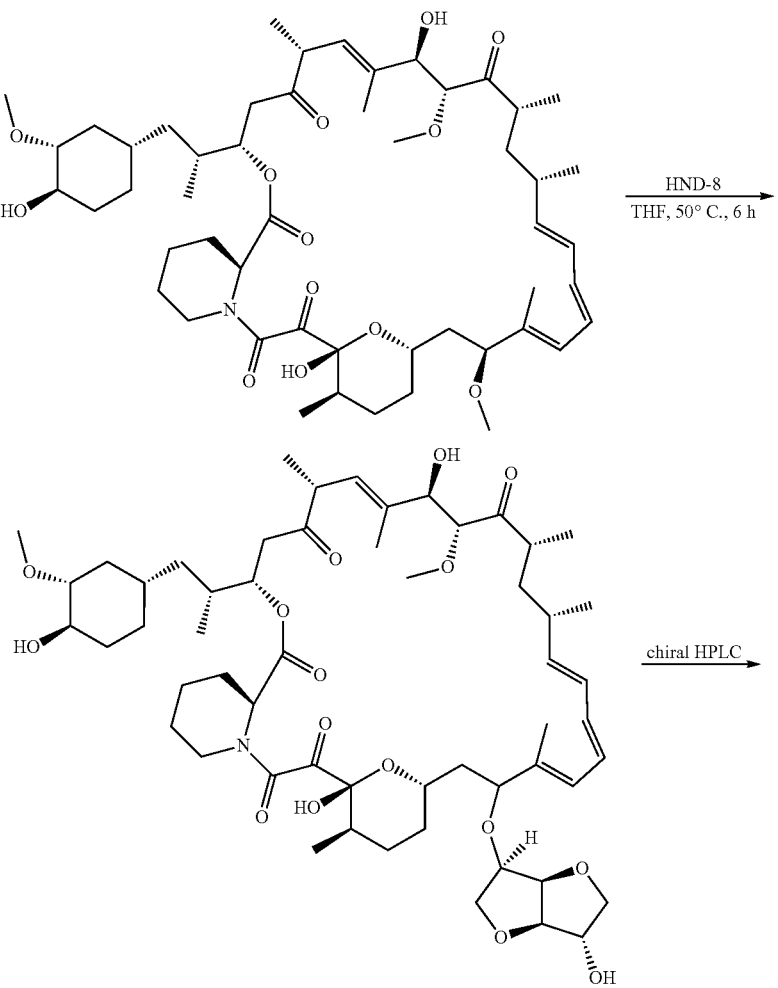

-continued

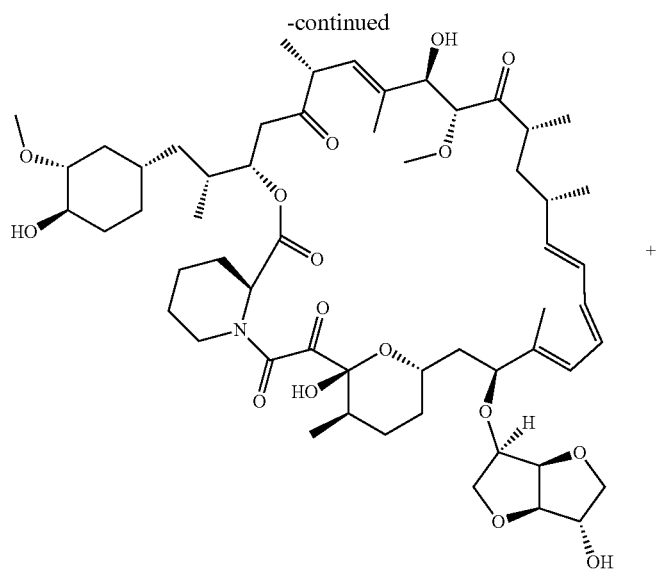

I-21

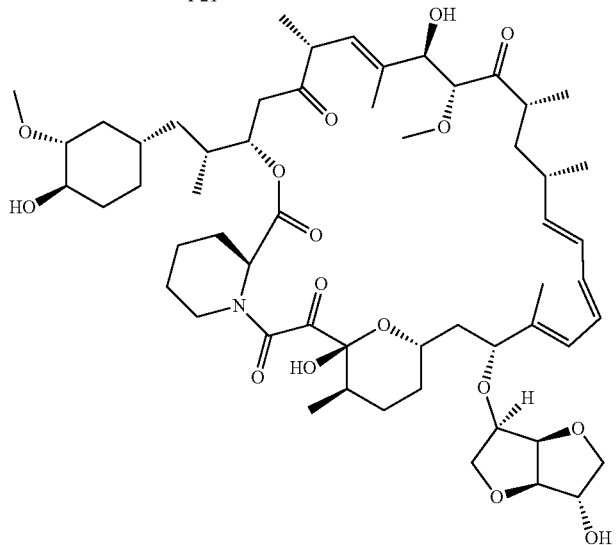

I-20

Step 1: Synthesis of (23E,25E,27E,28E,30R,31S,32R, 33R,35S,37S,40S,45R,46R,55R)-39-[[(3S,3aR,6R,6aR)-3-hydroxy-2,3,3a,5,6,6a-hexahydrofuro[3,2-b]furan-6-yl]oxy]-45,55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone: A solution of rapamycin (1 g, 1.09 mmol) and (3S,3aR,6R,6aR)-2,3,3a,5,6,6a-hexahydrofuro[3,2-b]furan-3,6-diol (2.4 g, 16.41 mmol) in THF (20 mL) was heated to 50° C. under an argon atmosphere. HND-8 (130 mg) was then added and the mixture was stirred for 6 h at the same temperature. The reaction was cooled to rt, filtered, the filtrate was concentrated and the residue was purified via reverse-phase chromatography (58% CH₃CN in water) to provide (23E,25E,27E,28E,30R,31S,32R,33R,35S,37S,40S,45R,46R,55R)-39-[[(3S,3aR,6R,6aR)-3-hydroxy-2,3,3a,5,6,6a-hexahydrofuro[3,2-b]furan-6-yl]oxy]-45,55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone (0.111 g, 10% yield) as a white solid. ESI-MS (EI+, m/z): 1050.1 [M+Na]⁺. ¹H NMR (400 MHz, CDCl₃) δ 6.40-6.06 (m, 3H), 5.93 (dd, J=29.4, 10.0 Hz, 1H), 5.59-5.08 (m, 4H), 5.00 (s, 1H), 4.60 (t, J=5.1 Hz, 1H), 4.47-4.13 (m, 4H), 3.84 (ddt, J=15.2, 9.5, 7.4 Hz, 5H), 3.68 (d, J=6.3 Hz, 1H), 3.62-3.27 (m, 11H), 2.99-2.86 (m, 2H), 2.79-2.50 (m, 4H), 2.38-1.91 (m, 6H), 1.86-1.69 (m, 13H), 1.53-1.19 (m, 10H), 1.18-0.80 (m, 18H), 0.67 (q, J=12.0, 24.0 Hz, 1H).

Step 2: Synthesis of (23E,25E,27E,28E,30R,31S,32R,33R,35S,37S,39S,40S,45R,46R,55R)-39-[[(3S,3aR,6R,6aR)-3-hydroxy-2,3,3a,5,6,6a-hexahydrofuro[3,2-b]furan-6-yl]oxy]-45,55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone (I-21) and (23E,25E,27E,28E,30R,31S,32R,33R,35S,37S,39R,40S,45R,46R,55R)-39-[[(3S, 3aR,6R,6aR)-3-hydroxy-2,3,3a,5,6,6a-hexahydrofuro[3,2-b]furan-6-yl]oxy]-45,55-dihydroxy-40-[(1R)-2-[(1S,3R,4R)-4-hydroxy-3-methoxy-cyclohexyl]-1-methyl-ethyl]-46-methoxy-30,31,32,33,47,48-hexamethyl-68,69-dioxa-56-azatricyclohexatriaconta-23,25,27(47),28(48)-tetraene-49,50,51,52,53-pentone (I-20): 400 mg of the racemic mixture was separated via chiral HPLC and then further purified by silica gel chromatography (PE:DCM:EtOAc:MeOH=3:3:1:0.9) to I-21 (110 mg) and I-20 (30 mg) as a white solid.

Chiral Separation Method:

| Column | CHIRALPAK IC |
|---|---|
| Column size | 5 cm I.D. × 25 cm L, 10 μm |
| Injection | 2.7 mg/mL in Mobile phase |
| Mobile phase | Hexane/EtOH = 50/50 (V/V) |
| Flow rate | 60 mL/min |
| Wave length | UV 254 nm |
| Temperature | 38° C. |

I-21: ESI-MS (EI+, m/z): 1050.1 [M+Na]$^+$. H NMR (500 MHz, CDCl$_3$) δ 6.40-6.24 (m, 2H), 6.23-6.08 (m, 1H), 5.93 (dd, J=36.7, 10.2 Hz, 1H), 5.54 (dd, J=15.1, 9.0 Hz, 1H), 5.41 (d, J=9.9 Hz, 1H), 5.29 (d, J=5.3 Hz, 1H), 5.16 (dt, J=15.9, 7.9 Hz, 1H), 4.99 (s, 1H), 4.60 (t, J=5.1 Hz, 1H), 4.32-4.12 (m, 3H), 3.98-3.74 (m, 6H), 3.67 (s, 1H), 3.62-3.52 (m, 2H), 3.48 (d, J=13.7 Hz, 2H), 3.42-3.28 (m, 8H), 2.98-2.90 (m, 1H), 2.79-2.57 (m, 4H), 2.33 (d, J=14.2 Hz, 2H), 2.10 (t, J=9.7 Hz, 1H), 1.99 (d, J=13.0 Hz, 3H), 1.87-1.66 (m, 10H), 1.63-1.18 (m, 13H), 1.17-0.82 (m, 18H), 0.71-0.62 (m, 1H).

I-20: ESI-MS (EI+, m/z): 1050.2 [M+Na]$^+$. H NMR (500 MHz, CDCl$_3$) δ 6.52-5.87 (m, 4H), 5.58-4.98 (m, 5H), 4.67-3.58 (m, 9H), 3.55-3.14 (m, 12H), 3.00-2.45 (m, 5H), 2.34-1.93 (m, 4H), 1.87-1.64 (m, 12H), 1.47-1.12 (m, 15H), 1.10-0.80 (m, 18H), 0.66 (d, J=12.3 Hz, 1H).

Example 13: Synthesis of (23E,25E,27E,28E,33R,34S,35R,36R,38S,40S,42S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[3-(1,2,4-triazol-4-yl)propoxy]-67,68-dioxa-58-azatricyclohexatriaconta-23,25,27(46),28(47)-tetraene-48,49,50,51,52-pentone (I-23) and (23E,25E,27E,28E,33R,34S,35R,36R,38S,40S,42R,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[3-(1,2,4-triazol-4-yl)propoxy]-67,68-dioxa-58-azatricyclohexatriaconta-23,25,27(46),28(47)-tetraene-48,49,50,51,52-pentone (I-22)

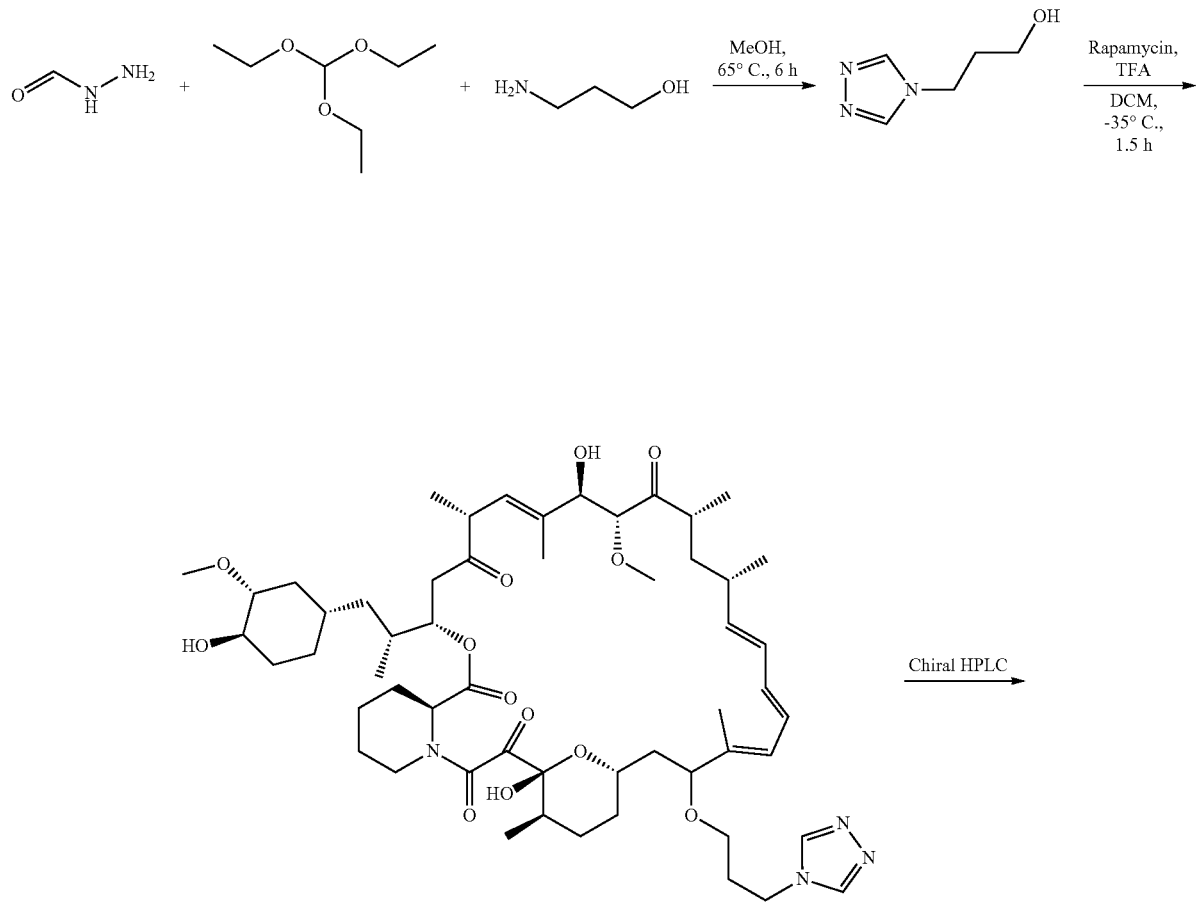

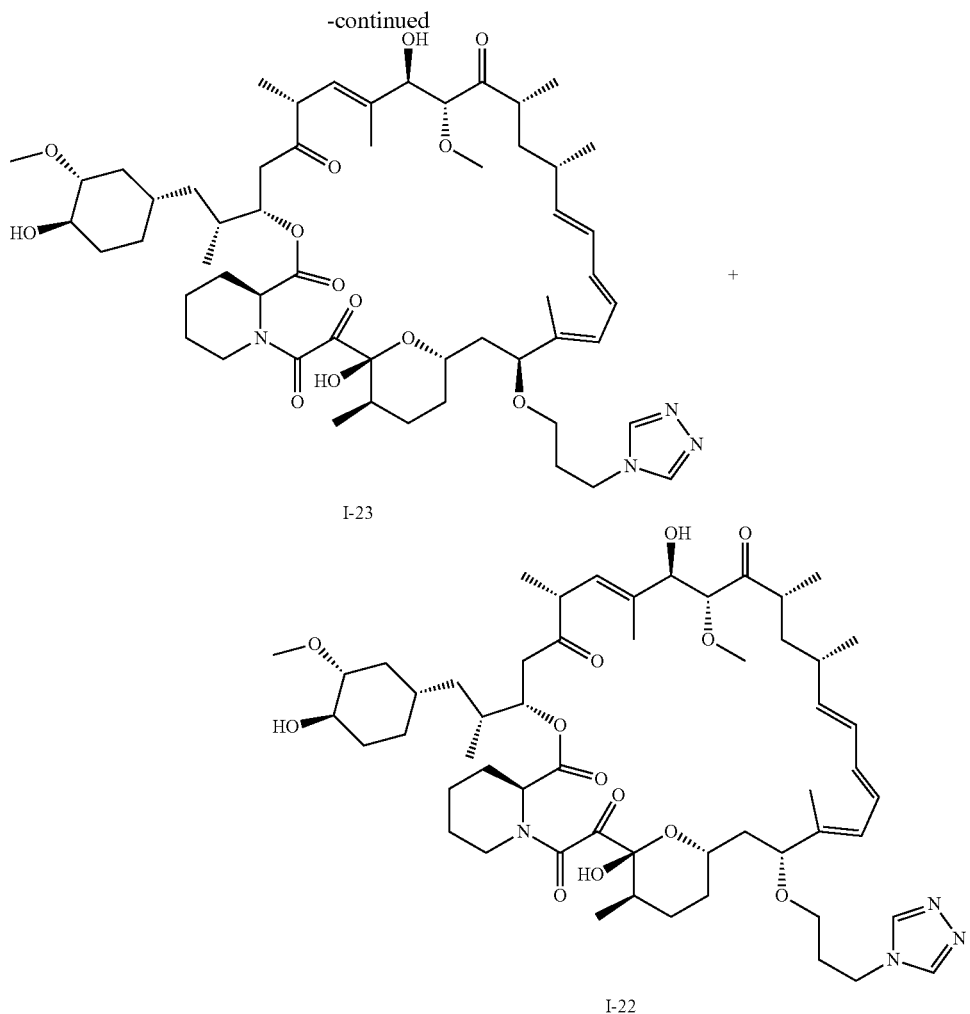

Step 1: Synthesis of 3-(1,2,4-triazol-4-yl) propan-1-ol: A solution of formohydrazide (10 g, 166.51 mmol) and diethoxymethoxyethane (29.61 g, 199.82 mmol) in methanol (200 mL) was heated at reflux for 2 h then 3-aminopropan-1-ol (12.51 g, 166.51 mmol) was added dropwise and the mixture was refluxed for a further 4 h. The solvent was subsequently removed under in vacuo to provide an oil which was purified by reverse-phase chromatography ($CH_3CN:H_2O=1:9$) giving 3-(1,2,4-triazol-4-yl) propan-1-ol (13.2 g, 62%) as a pink oil. ESI-MS (EI+, m/z): 128.2 [M+H]$^+$. $^1$H NMR (400 MHz, DMSO-$d_6$) δ 8.51 (s, 2H), 4.70 (t, J=5.0 Hz, 1H), 4.09 (t, J=7.1 Hz, 2H), 3.38-3.32 (m, 2H), 3.17 (d, J=5.3 Hz, 1H), 1.91-1.81 (m, 2H).

Step 2: Synthesis of (23E,25E,27E,28E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-42-[4-(3-hydroxypropyl)-1,2,4-triazol-1-ium-1-yl]-45-methoxy-33,34,35,36,46,47-hexamethyl-6869-dioxa-58-azatricyclohexatriaconta-23,25,27(46),28(47)-tetraene-48,49,50,51,52-pentone: To a solution of rapamycin (1.0 g, 1.09 mmol) in DCM (30 mL) and 3-(1,2,4-triazol-4-yl) propan-1-ol (692 mg, 5.45 mmol) at −30° C. under $N_2$ was added TFA (2.2 mL). The resulting solution was stirred for 1 h then diluted with by DCM (30 mL) and ice cold saturated aqueous $NaHCO_3$. The organic layer was dried over anhydrous $Na_2SO_4$, filtered and concentrated. The residue was purified via reverse phase chromatography ($CH_3CN:H_2O=4:6$) to provide (23E,25E,27E,28E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[3-(1,2,4-triazol-4-yl)propoxy]-67,68-dioxa-58-azatricyclohexatriaconta-23,25,27(46),28(47)-tetraene-48,49,50,51,52-pentone (65 mg) as a white solid. ESI-MS (EI+, m/z): 1009.1 [M+H]$^+$, 1031.0 [M+Na]$^+$. $^1$H NMR (500 MHz, $CDCl_3$) δ 8.26-7.98 (m, 2H), 6.47-5.82 (m, 4H), 5.54-5.04 (m, 4H), 4.36-3.98 (m, 3H), 3.92-3.53 (m, 2H), 3.50-3.12 (m, 12H), 3.00-2.43 (m, 6H), 2.41-1.64 (m, 19H), 1.53-1.17 (m, 13H), 1.13-0.80 (m, 18H), 0.74-0.60 (m, 1H).

Step 3: Synthesis of (23E,25E,27E,28E,33R,34S,35R,36R,38S,40S,42S,43S,44R45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[3-(1,2,4-triazol-4-yl)propoxy]-67,68-dioxa-58-azatricyclohexatriaconta-23,25,27(46),28(47)-tetraene-48,49,50,51,52-pentone (I-23) and (23E,25E,27E,28E,33R,34S,35R,36R,38S,40S,42R,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[3-(1,2,4-triazol-4-yl)propoxy]-67,68-dioxa-58-azatricyclohexatriaconta-23,25,27(46),28(47)-tetraene-48,49,50,51,52-pentone (I-22): 125 mg of the racemic mixture was separated via chiral HPLC and then further purified by silica gel chromatography (PE:DCM:EtOAc:MeOH=3:3:1:0.5) to provide I-23 (28 mg, 22% yield) as a white solid and I-22 (24 mg, 19% yield) as a white solid.

Chiral Separation Method:

| | |
|---|---|
| Column | CHIRALPAK IC |
| Column size | 5 cm I.D. × 25 cm L, 10 μm |
| Injection | 13 mg/mL in Mobile phase |
| Mobile phase | EtOH |
| Flow rate | 60 mL/min |
| Wave length | UV 214 nm |
| Temperature | 35° C. |

I-23: ESI-MS (EI+, m/z): 1009.4 [M+H]$^+$, 1031.0 [M+Na]$^+$. $^1$H NMR (500 MHz, CDCl$_3$) δ 8.30-8.08 (m, 2H), 6.44-5.82 (m, 4H), 5.61-5.04 (m, 4H), 5.01-4.69 (m, 1H), 4.15 (ddd, J=29.3, 23.0, 20.5 Hz, 4H), 3.95-3.48 (m, 3H), 3.47-3.12 (m, 11H), 3.06-2.46 (m, 5H), 2.38-1.70 (m, 18H), 1.57-1.17 (m, 13H), 1.15-0.79 (m, 18H), 0.65 (dt, J=26.2, 13.1 Hz, 1H).

I-22: ESI-MS (EI+, m/z): 1009.4 [M+H]$^+$, 1031.0 [M+Na]$^+$. $^1$H NMR (500 MHz, CDCl$_3$) δ 9.26 (s, 1H), 8.23-7.92 (m, 1H), 6.22 (dddd, J=55.2, 44.5, 20.3, 8.5 Hz, 4H), 5.35 (ddd, J=78.4, 45.8, 16.7 Hz, 5H), 4.34-3.55 (m, 5H), 3.53-3.10 (m, 12H), 3.05-2.84 (m, 4H), 2.79-2.47 (m, 3H), 2.23 (dd, J=22.9, 15.3 Hz, 4H), 2.10-1.71 (m, 15H), 1.49-1.14 (m, 11H), 1.09-0.76 (m, 18H), 0.63 (q, J=12.0, 24.0 Hz, 1H).

Example 14: Synthesis of (26E,28E,30E,31E,38R,39S,40R,41R,43S,45S,48S,49S,50R,59R)-49,59-dihydroxy-48-[(1R)-2-[(1S,3R,4R)-4-hydroxy-3-methoxy-cyclohexyl]-1-methyl-ethyl]-50-methoxy-46-[2-methoxy-4-(2-methoxyethoxy)phenyl]-38,39,40,41,51,52-hexamethyl-69,70-dioxa-60-azatricyclohexatriaconta-26,28,30(51),31(52)-tetraene-53,54,55,56,57-pentone (I-24)

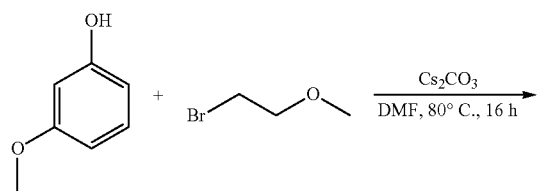

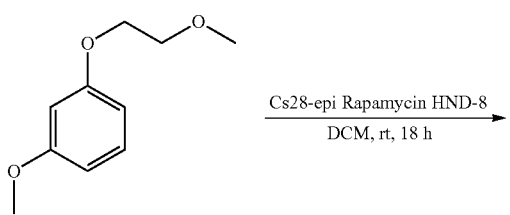

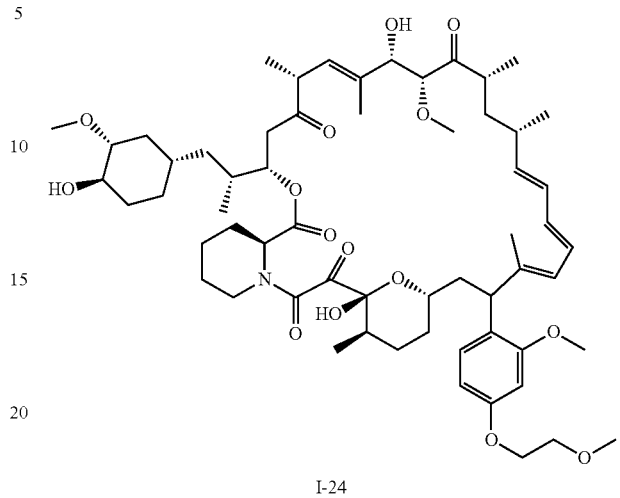

I-24

Step 1: Synthesis of 1-methoxy-3-(2-methoxyethoxy) benzene: A mixture of 3-methoxyphenol (1.00 g, 8.06 mmol), 1-bromo-2-methoxy-ethane (1.34 g, 9.67 mmol) and Cs$_2$CO$_3$ (5.25 g, 16.11 mmol) in DMF (5 mL) was stirred at 80° C. for 16 h. The reaction mixture was diluted with HCl (10 mL, 1N in water), and then extracted with EtOAc (40 mL×3). The combined organic layers were dried over anhydrous Na$_2$SO$_4$, filtered and concentrated. The residue was purified by silica gel chromatography (EtOAc:PE: 0-35%) to provide 1-methoxy-3-(2-methoxyethoxy) benzene (1 g, 68% yield) as a colorless oil. ESI-MS (EI$^+$, m/z):183.1 [M+H]$^+$.

Step 2: Synthesis of (26E,28E,30E,31E,38R,39S,40R,41R,43S,45S,48S,49S,50R,59R)-49,59-dihydroxy-48-[(1R)-2-[(1S,3R,4R)-4-hydroxy-3-methoxy-cyclohexyl]-1-methyl-ethyl]-50-methoxy-46-[2-methoxy-4-(2-methoxyethoxy)phenyl]-38,39,40,41,51,52-hexamethyl-69,70-dioxa-60-azatricyclohexatriaconta-26,28,30(51),31(52)-tetraene-53,54,55,56,57-pentone (I-24): To a solution of 28-epi rapamycin (0.2 g, 0.22 mmol) 1-methoxy-3-(2-methoxyethoxy) benzene 0.2 g, 1.09 mmol) in DCM (10 mL) was added HND-8 (60 mg) and the mixture stirred at 25° C. for 18 h. The reaction mixture was filtered and concentrated and the residue was purified by reverse phase chromatography to provide (26E,28E,30E,31E,38R,39S,40R,41R,43S,45S,48S,49S,50R,59R)-49,59-dihydroxy-48-[(1R)-2-[(1S,3R,4R)-4-hydroxy-3-methoxy-cyclohexyl]-1-methyl-ethyl]-50-methoxy-46-[2-methoxy-4-(2-methoxyethoxy)phenyl]-38,39,40,41,51,52-hexamethyl-69,70-dioxa-60-azatricyclohexatriaconta-26,28,30(51),31(52)-tetraene-53,54,55,56,57-pentone (0.1 g, 45% yield) as a white solid. ESI-MS (EI$^+$, m/z):1086.1 [M+Na]$^+$. $^1$H NMR (400 MHz, CDCl$_3$) δ 7.13-6.86 (m, 1H), 6.60-5.87 (m, 6H), 5.51-5.07 (m, 4H), 4.33-3.55 (m, 13H), 3.58-3.09 (m, 15H), 3.02-2.60 (m, 5H), 2.49-2.06 (m, 6H), 2.04-1.88 (m, 5H), 1.60-1.24 (m, 12H), 1.18-0.64 (m, 22H).

Example 15: Synthesis of (22E,24E,26E,27E,35R, 36S,37R,38R,40S,42S,45S,46R,47R,56R)-46,56-dihydroxy-45-[(1R)-2-[(1S,3R,4R)-4-(2-hydroxy-ethoxy)-3-methoxy-cyclohexyl]-1-methyl-ethyl]-47-methoxy-44-[2-(2-methoxyethylsulfonyl)ethoxy]-35, 36,37,38,48,49-hexamethyl-68,69-dioxa-57-azatricyclohexatriaconta-22,24,26(48),27(49)-tetraene-50,51,52,53,54-pentone (I-25)

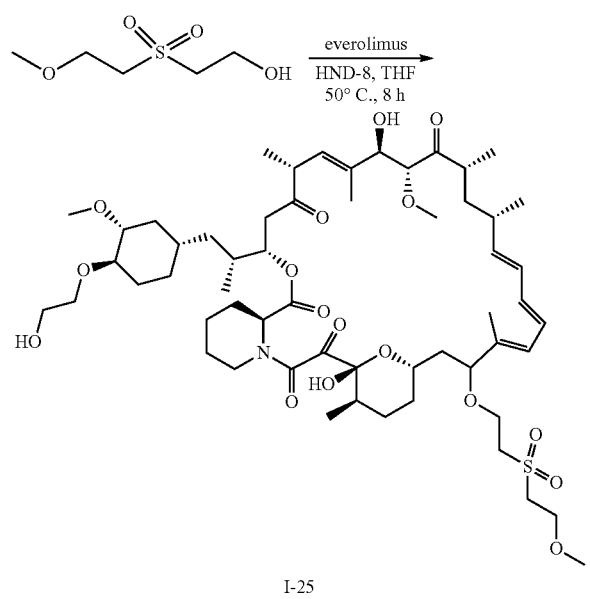

I-25

To a solution of everolimus (0.3 g, 0.31 mmol) and 2-(2-methoxyethylsulfonyl)ethanol (0.53 g, 3.13 mmol) in THF (20 mL) was added HND-8 (30 mg) at 50° C. The mixture was stirred at 50° C. for 8 hours then treated with aq.NaHCO₃ (20 mL) and extracted with EtOAc (2×20 mL). The combined organic layers were concentrated and the residue was purified via reverse-phase chromatography (CH₃CN:H₂O=6.8:3.2) to provide I-25 (22 mg, 6.4% yield) as a white solid. LC-MS (EI$^+$, m/z): 1117.1 [M+Na]*; $^1$H NMR (400 MHz, CDCl₃): δ 5.94-6.47 (m, 4H), 5.12-5.73 (m, 4H), 3.95-4.44 (m, 3H), 3.53-3.91 (m, 10H), 3.31-3.49 (m, 15H), 3.04-3.30 (m, 3H), 2.53-2.82 (m, 3H), 1.95-2.42 (m, 6H), 1.68-1.92 (m, 13H), 1.18-1.55 (m, 10H), 0.83-1.17 (m, 18H), 0.66-0.79 (m, 1H).

Example 16: Synthesis of (22E,24E,26E,27E,33R, 34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-42-[2-(2-methoxyethylsulfonyl)ethoxy]-33,34,35,36, 46,47-hexamethyl-66,67-dioxa-55-azatricyclohexatriaconta-22,24,26(46),27(47)-tetraene-48,49,50,51,52-pentone (I-26)

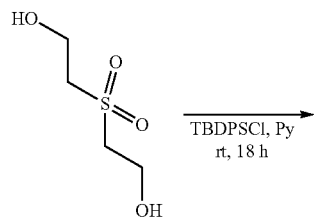

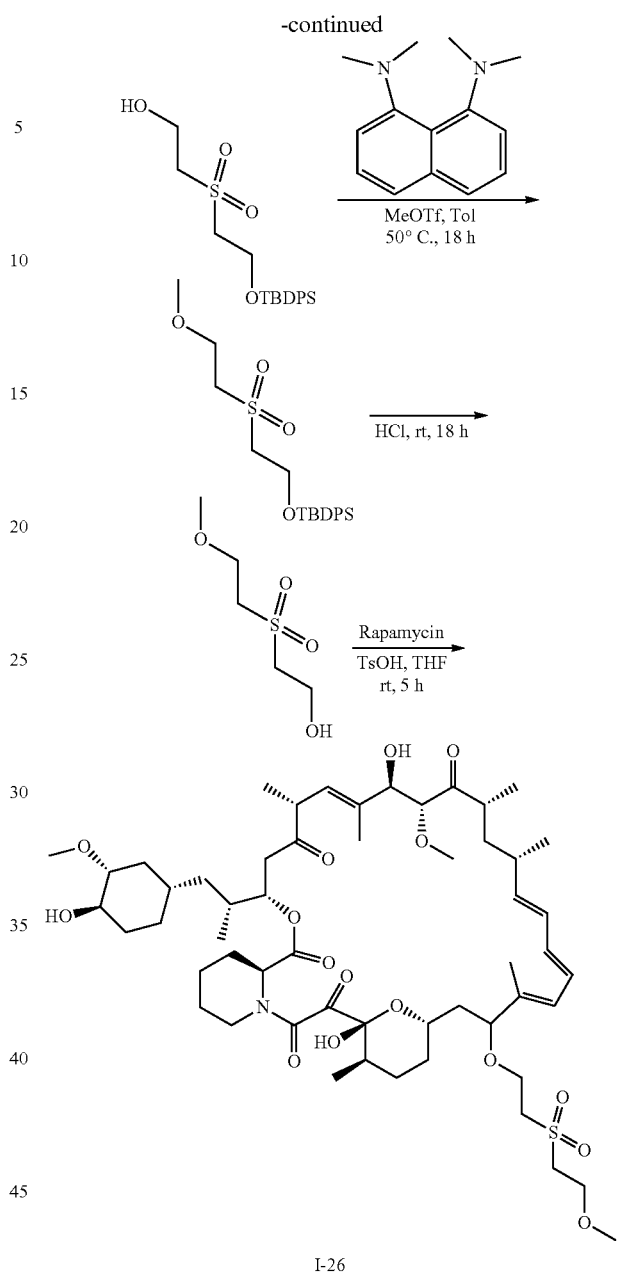

I-26

Step 1: 2-[2-[tert-butyl (diphenyl)silyl]oxyethylsulfonyl] ethanol: To a solution of 2-(2-hydroxyethylsulfonyl) ethanol (0.67 g, 4.37 mmol, 89.3 mL) in pyridine (5 mL) was added tert-butyl-chloro-diphenyl-silane (0.6 g, 2.18 mmol, 0.56 mL) at 0° C. The reaction mixture was stirred at 20° C. for 18 hours then extracted with EtOAc and water. The combined organic layers were concentrated and purified by silica gel chromatography (EtOAc:PE=1:1) providing 2-[2-[tert-butyl(diphenyl)silyl]oxyethylsulfonyl]ethanol (0.62 g, 72% yield) as a white solid. LC-MS (EI$^+$, m/z): 415.0 [M+Na]$^+$; $^1$H NMR (400 MHz, CDCl₃) δ 7.73-7.57 (m, 4H), 7.53-7.36 (m, 6H), 4.12 (ddd, J=14.2, 7.1, 3.7 Hz, 4H), 3.53-3.40 (m, 2H), 3.26 (t, J=5.4 Hz, 2H), 2.57 (t, J=6.2 Hz, 1H), 1.07 (s, 9H).

Step 2: tert-butyl-[2-(2-methoxyethylsulfonyl) ethoxy]-diphenyl-silane: To a solution of 2-[2-[tert-butyl(diphenyl) silyl]oxyethylsulfonyl]ethanol (1.42 g, 3.62 mmol) and N1,N1,N8,N8-tetramethylnaphthalene-1,8-diamine (5.43 g, 25.32 mmol) in toluene (40 mL) was added methyl trifluoromethanesulfonate (2.37 g, 14.47 mmol) at 0° C. The mixture was stirred for 50° C. for 18 hours then concentrated, diluted with water (30 mL) and extracted with EtOAc (2×30 mL). The combined organic layers were concentrated, then purified via silica gel chromatography (PE:EtOAc=3:1) to provide tert-butyl-[2-(2-methoxyethylsulfonyl) ethoxy]-diphenyl-silane (1.2 g, 82% yield) as a yellow solid. LC-MS (EI$^+$, m/z): 429.0 [M+Na]$^+$; $^1$H NMR (500 MHz, CDCl$_3$) δ 7.68 (dd, J=7.9, 1.3 Hz, 4H), 7.49-7.33 (m, 6H), 4.08 (t, J=5.7 Hz, 2H), 3.83 (t, J=5.6 Hz, 2H), 3.41 (t, J=5.6 Hz, 2H), 3.38 (s, 3H), 3.30 (t, J=5.6 Hz, 2H), 1.06 (s, 9H).

Step 3: 2-(2-methoxyethylsulfonyl) ethanol: To a solution of hydrogen chloride (3 M in MeOH, 10 mL) was added tert-butyl-[2-(2-methoxyethylsulfonyl)ethoxy]-diphenyl-silane (1.2 g, 2.95 mmol). The mixture was stirred at 25° C. for 18 h then concentrated, treated with aq.NaHCO$_3$ (20 mL) and extracted with EtOAc (3×20 mL). The combined organic layers were concentrated then purified via silica gel chromatography (DCM:MeOH=8:1) to provide 2-(2-methoxyethylsulfonyl) ethanol (0.24 g, 48% yield) as a yellow oil. $^1$H NMR (400 MHz, CDCl$_3$) δ 4.11 (dd, J=10.4, 5.5 Hz, 2H), 3.90-3.79 (m, 2H), 3.40 (s, 3H), 3.38-3.29 (m, 4H), 2.70 (t, J=5.9 Hz, 1H).

Step 4: (22E,24E,26E,27E,33R,34S,35R,36R38S,40S, 43S,44R45R54R)-44,54-dihydroxy-43-[(1R)-2-[(1S,3R, 4R)-4-hydroxy-3-methoxy-cyclohexyl]-1-methyl-ethyl]-45-methoxy-42-[2-(2-methoxyethylsulfonyl)ethoxy]-33,34,35, 36,46,47-hexamethyl-66,67-dioxa-55-azatricyclohexatriaconta-22,24,26(46),27(47)-tetraene-48, 49,50,51,52-pentone (I-26): To a solution of rapamycin (0.3 g, 0.33 mmol), 2-(2-methoxyethylsulfonyl)ethanol (0.55 g, 3.28 mmol) in THF (3 mL) was added 4-methylbenzenesulfonic acid (0.28 g, 1.64 mmol) at 0° C. The resulting mixture was stirred at 28° C. for 5 h then treated with aq.NaHCO$_3$ (20 mL) and extracted with EtOAc (2×20 mL). The combined organic layers were concentrated then purified via reverse-phase chromatography (CH$_3$CN:H$_2$O=7:3) to provide crude product which was then purified via silica gel column chromatography (PE in EtOAc=0~100%) to give I-26 (34 mg, 10% yield) as a yellow solid. LC-MS (EI$^+$, m/z): 1072.4 [M+Na]$^+$, RT=2.182 in 254 nm; $^1$H NMR (400 MHz, CDCl$_3$): δ 5.91-6.41 (m, 4H), 5.06-5.69 (m, 5H), 4.07-4.35 (m, 1H), 3.77-3.89 (m, 4H), 3.65-3.77 (m, 2H), 3.52-3.64 (m, 1H), 3.38-3.45 (m, 5H), 3.10-3.37 (m, 7H), 2.87-3.01 (m, 2H), 2.50-2.79 (m, 5H), 2.25-2.42 (m, 2H), 2.07-2.19 (m, 2H), 1.93-2.06 (m, 4H), 1.64-1.84 (m, 15H), 1.21-1.49 (m, 10H), 1.05-1.16 (m, 4H), 0.83-1.03 (m, 13H), 0.63-0.76 (m, 1H).

Example 17: Synthesis of (21E,23E,25E,26E,34R, 35S,36R,37R,39S,41S,43S,44S,45R,46R,55R)-45, 55-dihydroxy-43-[2-[2-(2-hydroxyethylsulfonyl) ethylsulfonyl]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26 (48)-tetraene-49,50,51,52,53-pentone (I-65) and (21E,23E,25E,26E,34R,35S,36R,37R,39S,41S,43R, 44S,45R,46R,55R)-45,55-dihydroxy-43-[2-[2-(2-hydroxyethylsulfonyl)ethylsulfonyl]ethoxy]-44-[(1R)-2-[(1S,3R,4R)-4-hydroxy-3-methoxy-cyclohexyl]-1-methyl-ethyl]-46-methoxy-34,35,36, 37,47,48-hexamethyl-70,71-dioxa-56-azatricyclohexatriaconta-21,23,25(47),26(48)-tetraene-49,50,51,52,53-pentone (I-27)

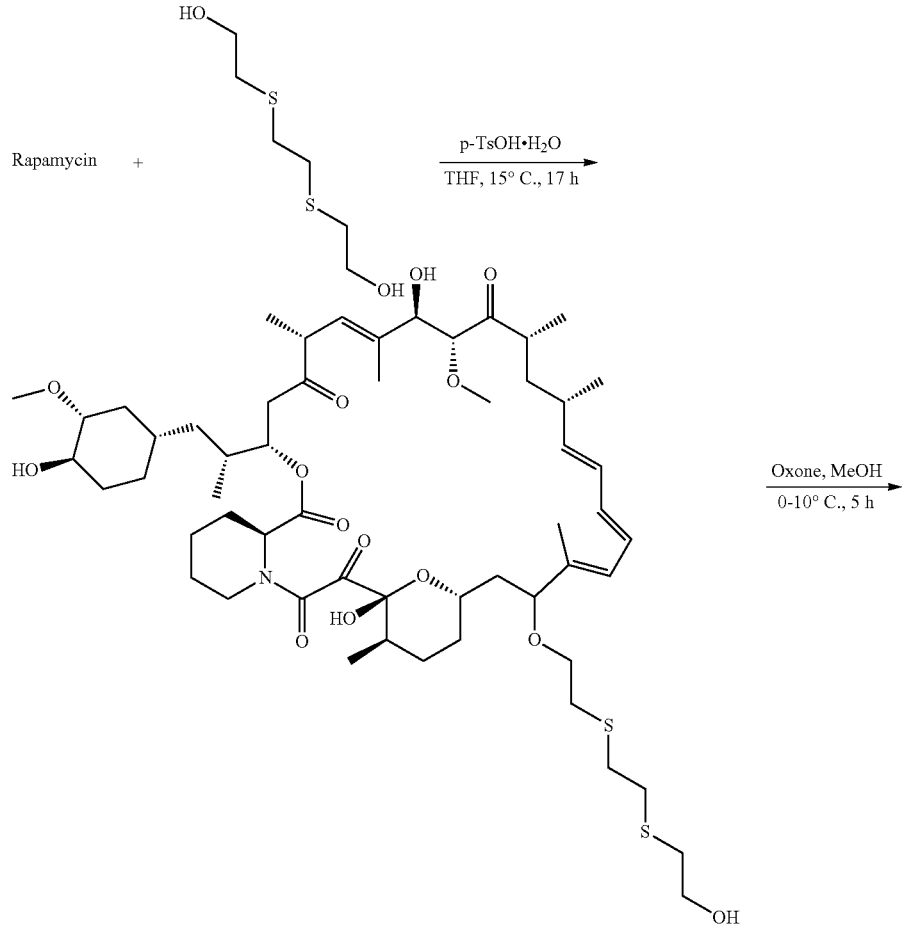

-continued
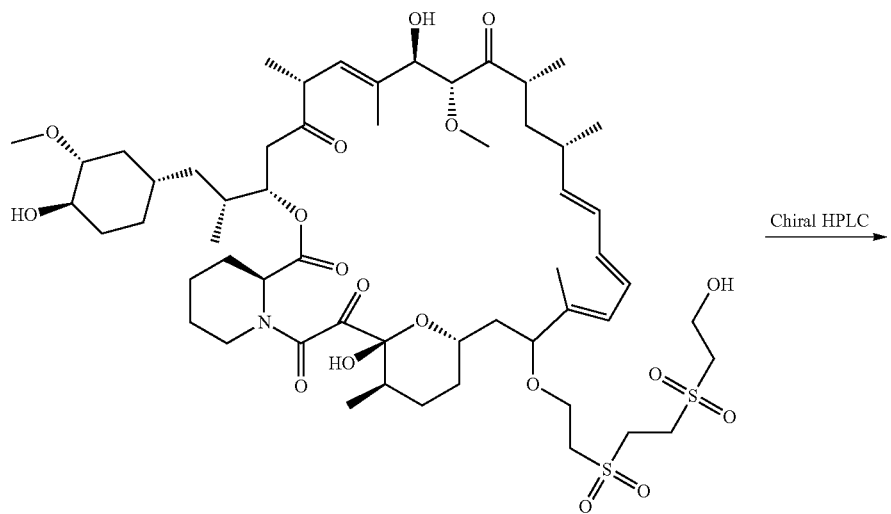
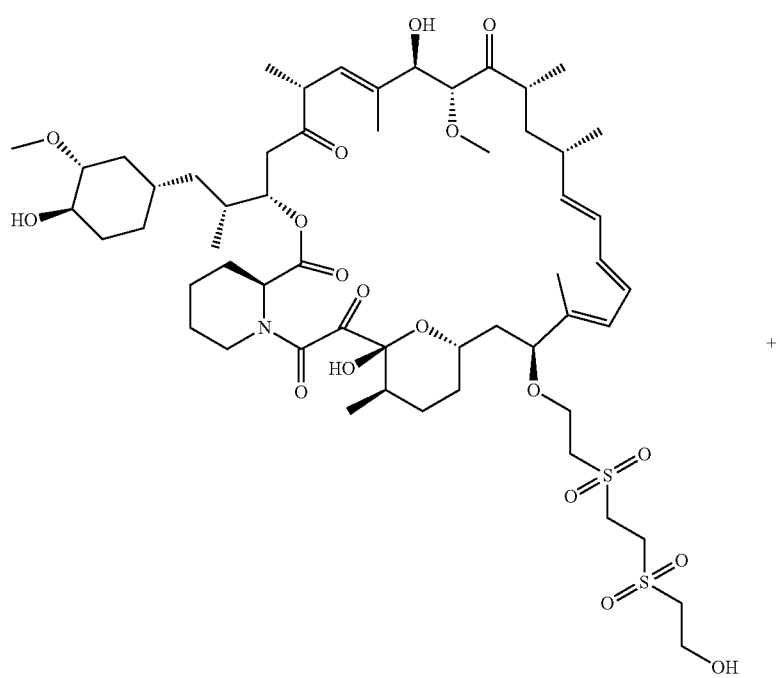
I-65

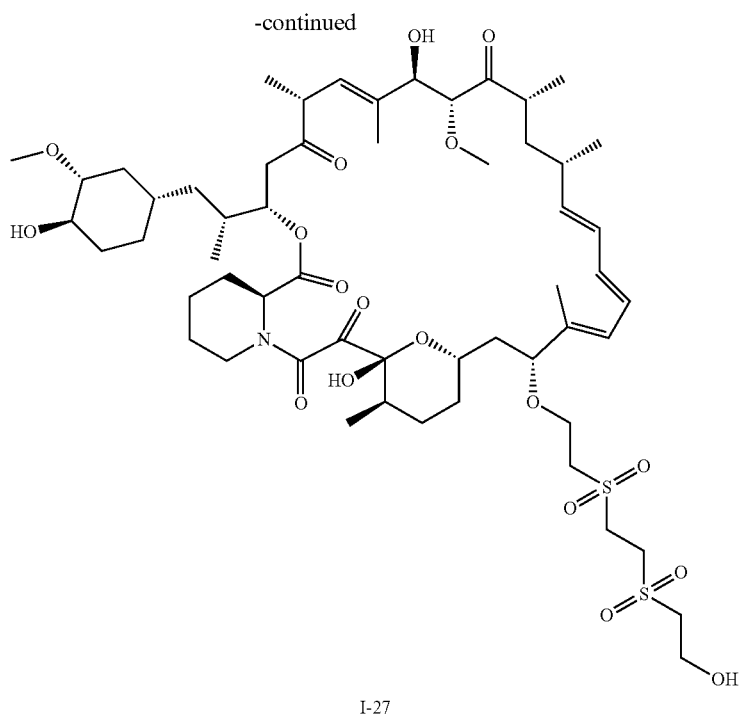

I-27

Step 1: Synthesis of (21E,23E,25E,26E,34R,35S,36R, 37R,39R,41S,44S,45R,46R,55S)-45,55-dihydroxy-43-[2-[2-(2-hydroxyethylsulfanyl)ethylsulfanyl]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone: To a solution of rapamycin (1 g, 1.09 mmol) and 2-[2-(2-hydroxyethylsulfanyl)ethylsulfanyl]ethanol (1.99 g, 10.94 mmol) in THF (20 mL) was added 4-methylbenzenesulfonic acid monohydrate (0.62 g, 3.28 mmol) at 15° C. The resulting mixture was stirred at 15° C. for 17 h then diluted with EtOAc (100 mL) and the pH adjusted to 9 using saturated aqueous NaHCO₃ solution (about 50 mL). The organic layer was concentrated in vacuo and the residue was purified via reverse-phase chromatography (CH₃CN:H₂O=6:4). The solvent was removed by lyophilization to provide (21E,23E, 25E,26E,34R,35S,36R,37R,39R,41S,44S,45R,46R,55S)-45,55-dihydroxy-43-[2-[2-(2-hydroxyethylsulfanyl) ethylsulfanyl]ethoxy]-44-[(1S)-2-[(1S,3R,4R)-4-hydroxy-3-methoxy-cyclohexyl]-1-methyl-ethyl]-46-methoxy-34,35, 36,37,47,48-hexamethyl-66,67-dioxa-56-azatricyclohexatriaconta-21,23,25(47),26(48)-tetraene-49, 50,51,52,53-pentone (0.15 g, 12) as a yellow solid. ESI-MS (EI⁺, m/z):1086.4 [M+Na]⁺. ¹H NMR (500 MHz, CDCl₃) δ 6.39-5.95 (m, 4H), 5.54-5.19 (m, 4H), 4.81-4.17 (m, 2H), 3.96-3.73 (m, 4H), 3.59-3.14 (m, 12H), 2.96-2.55 (m, 14H), 2.35-1.87 (m, 6H), 1.81-1.59 (m, 13H), 1.53-1.13 (m, 11H), 1.16-0.84 (m, 18H), 0.71-0.63 (m, 1H).

Step 2: Synthesis of (21E,23E,25E,26E,34R,35S,36R, 37R,39R,41S,44S,45R,46R,55S)-45,55-dihydroxy-43-[2-[2-(2-hydroxyethylsulfonyl)ethylsulfonyl]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26(48)-tetraene-49,50,51,52,53-pentone: To a solution of (21E, 23E,25E,26E,34R,35S,36R,37R,39R,41S,44S,45R,46R, 55S)-45,55-dihydroxy-43-[2-[2-(2-hydroxyethylsulfanyl) ethylsulfanyl]ethoxy]-44-[(1S)-2-[(1S,3R,4R)-4-hydroxy-3-methoxy-cyclohexyl]-1-methyl-ethyl]-46-methoxy-34,35, 36,37,47,48-hexamethyl-66,67-dioxa-56-azatricyclohexatriaconta-21,23,25(47),26(48)-tetraene-49, 50,51,52,53-pentone (0.17 g, 0.16 mmol) in methanol (8 mL) was added Oxone (0.4 g, 0.64 mmol) at 0° C. The resulting mixture was warmed to 10° C. then stirred for 5 h. The reaction mixture was filtered and the filtrate was purified by reverse phase chromatography (5-60% CH₃CN in water). The solvent was removed by lyophilization to provide (21E,23E,25E,26E,34R,35S,36R,37R,39R,41S,44S, 45R,46R,55S)-45,55-dihydroxy-43-[2-[2-(2-hydroxyethylsulfonyl)ethylsulfonyl]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26(48)-tetraene-49, 50,51,52,53-pentone (0.03 g, 17%) as a white solid. ESI-MS (EI⁺, m/z):1150.8 [M+Na]⁺. H NMR (500 MHz, CDCl₃) δ 6.40-5.90 (m, 4H), 5.57-5.08 (m, 5H), 4.14 (s, 4H), 3.68 (tdd, J=37.6, 33.2, 11.6 Hz, 11H), 3.48-3.13 (m, 20H), 2.95 (s, 2H), 2.68 (dd, J=36.4, 30.5 Hz, 5H), 2.37-1.70 (m, 12H), 1.31 (dd, J=78.6, 46.8 Hz, 7H), 1.13-0.81 (m, 18H), 0.67 (d, J=11.9 Hz, 1H).

Step 3: Synthesis of (21E,23E,25E,26E,34R,35S,36R, 37R,39S,41S,43S,44S,45R,46R,55R)-45,55-dihydroxy-43-[2-[2-(2-hydroxyethylsulfonyl)ethylsulfonyl]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26 (48)-tetraene-49,50,51,52,53-pentone (I-65) and (21E,23E, 25E,26E,34R,35S,36R,37R,39S,41S,43R,44S,45R,46R, 55R)-45,55-dihydroxy-43-[2-[2-(2-hydroxyethylsulfonyl) ethylsulfonyl]ethoxy]-44-[(1R)-2-[(1S,3R,4R)-4-hydroxy-3-methoxy-cyclohexyl]-1-methyl-ethyl]-46-methoxy-34,35, 36,37,47,48-hexamethyl-70,71-dioxa-56-azatricyclohexatriaconta-21,23,25(47),26(48)-tetraene-49, 50,51,52,53-pentone (I-27): 170 mg of (21E,23E,25E,26E, 34R,35S,36R,37R,39R,41S,44S,45R,46R,55S)-45,55-dihydroxy-43-[2-[2-(2-hydroxyethylsulfonyl)ethylsulfonyl]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26(48)-tetraene-49,50,51,52,53-pentone was separated via chiral HPLC to provide I-65 (43 mg) as a white solid and I-27 (39 mg) as a white solid.

Chiral Separation Method:

| | |
|---|---|
| Column | CHIRALPAK IC |
| Column size | 2.5 cm I.D. × 25 cm L, 5 μm |
| Injection | 0.7 mg/mL in Mobile phase |
| Injection | 15 ml |
| Mobile phase | EtOH |
| Flow rate | 15 mL/min |
| Wave length | UV 254 nm |
| Temperature | 35° C. |

I-65: ESI-MS (EI+, m/z):1150.3 [M+Na]$^+$. $^1$H NMR (500 MHz, CDCl$_3$) δ 6.32 (td, J=24.8, 14.8 Hz, 2H), 6.13 (dd, J=14.9, 9.9 Hz, 1H), 5.98 (dd, J=22.1, 10.3 Hz, 1H), 5.56-5.31 (m, 2H), 5.26 (d, J=5.4 Hz, 1H), 5.14 (d, J=4.1 Hz, 1H), 4.86 (s, 1H), 4.16 (dd, J=11.9, 5.5 Hz, 3H), 3.92-3.49 (m, 11H), 3.44-3.17 (m, 15H), 2.93 (dd, J=14.1, 5.5 Hz, 1H), 2.78-2.50 (m, 5H), 2.36-2.17 (m, 2H), 2.01 (ddd, J=21.5, 18.0, 9.0 Hz, 5H), 1.84-1.65 (m, 11H), 1.49-1.16 (m, 12H), 1.14-0.82 (m, 14H), 0.66 (dd, J=23.8, 12.0 Hz, 1H).

I-27: ESI-MS (EI$^+$, m/z):1150.3 [M+Na]$^+$. $^1$H NMR (500 MHz, CDCl$_3$) δ 6.70-5.90 (m, 4H), 5.65-5.06 (m, 5H), 4.27-4.04 (m, 4H), 3.98-3.51 (m, 9H), 3.47-3.09 (m, 20H), 2.99-2.48 (m, 7H), 2.39-1.94 (m, 5H), 1.49-1.15 (m, 16H), 1.13-0.80 (m, 18H), 0.75-0.65 (m, 1H).

Example 18: Synthesis of 4-[[(21E,23E,25E,26E, 33R,34S,35R,36R,38S,40S,42S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-21,23,25(46),26(47)-tetraen-42-yl]oxy]butanamide (I-29) and 4-[[(21E, 23E,25E,26E,33R,34S,35R,36R,38S,40S,42R,43S, 44R,45R,55R)-44,55-dihydroxy-43-[(1R)-2-[(1S,3R, 4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-21,23,25(46),26(47)-tetraen-42-yl]oxy]butanamide (I-28)

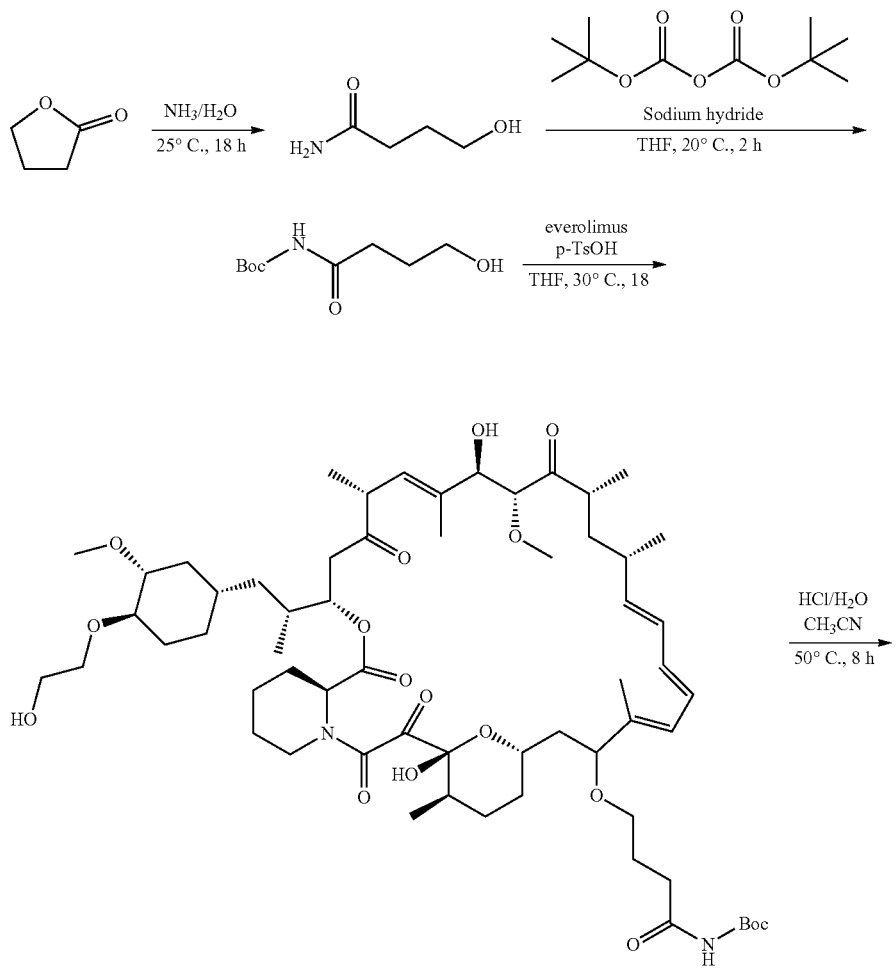

-continued
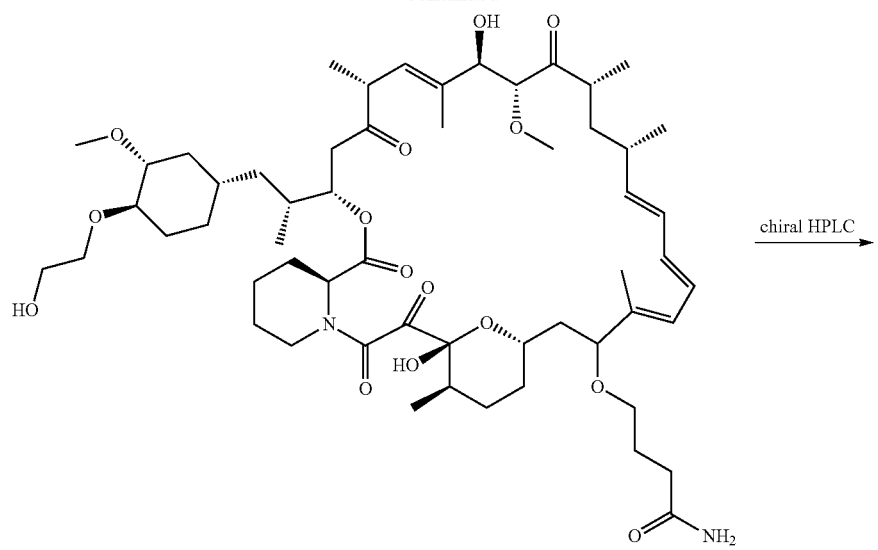
chiral HPLC →
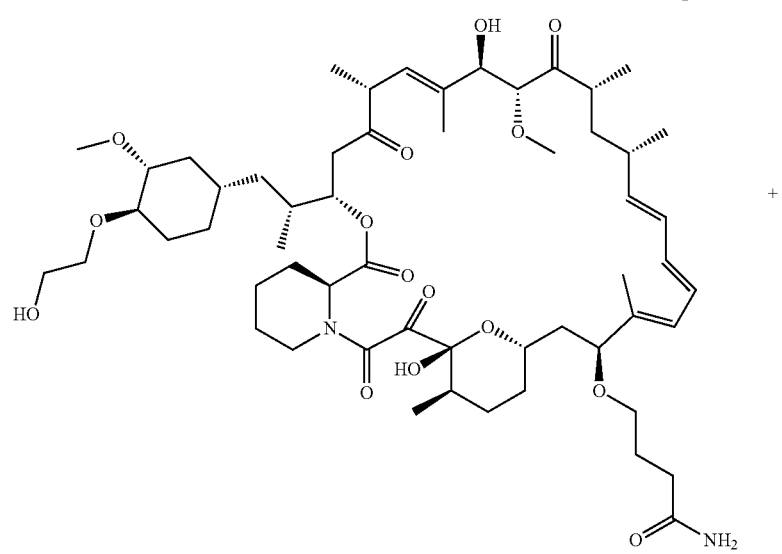
I-29
+
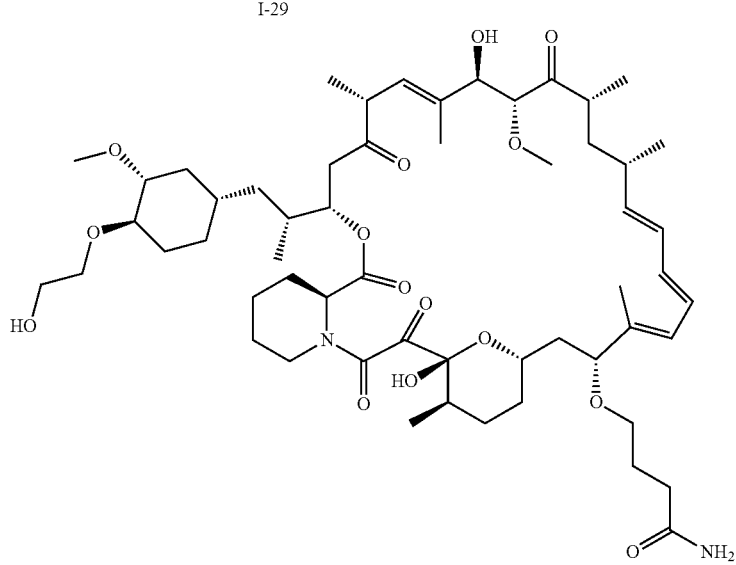
I-28

Step 1: Synthesis of 4-hydroxybutanamide: A solution of tetrahydrofuran-2-one (20 g, 232.32 mmol) in 25% aqueous ammonia (13 M, 53.61 mL) was stirred at 25° C. for 18 hr then concentrated in vacuo. The crude product was frozen to provide 4-hydroxybutanamide (23.1 g, 96% yield) as an off white solid. ESI-MS (EI$^+$, m/z): 104.2 [M+H]$^+$. $^1$H NMR (400 MHz, DMSO-d$_6$): δ 7.35 (s, 1H), 6.79 (s, 1H), 4.09 (s, 1H), 3.39 (t, J=6.4 Hz, 2H), 2.10 (t, J=7.6 Hz, 2H), 1.67-1.60 (m, 2H).

Step 2: Synthesis of tert-butyl N-(4-hydroxybutanoyl) carbamate: Sodium hydride (6.05 g, 252.13 mmol) was added in portions to a solution of 4-hydroxybutanamide (13 g, 126.07 mmol) in THF (250 mL) at 0° C. The mixture was then stirred at 20° C. for 30 min when di-tert-butyl dicarbonate (30.27 g, 138.67 mmol) was added. The resulting mixture was stirred at 20° C. for a further 2 h then poured into ice cold water (300 mL) and extracted with EtOAc (250 mL). The organic layer was washed with water (100 mL), brine (100 mL) and then dried by anhydrous Na$_2$SO$_4$, filtered and concentrated. The residue was purified by silica gel chromatography (PE:acetone=2:1) to provide tert-butyl N-(4-hydroxybutanoyl)carbamate (12.4 g, 48% yield). ESI-MS (EI$^+$, m/z): 226.0 [M+Na]$^+$. $^1$H NMR (400 MHz, CDCl$_3$) δ 5.58 (s, 2H), 4.13 (t, J=6.0 Hz, 2H), 2.36 (t, J=7.6 Hz, 2H), 2.01 (m, 2H), 1.71 (s, 1H), 1.49 (s, 1H).

Step 3: Synthesis of tert-butyl N-[4-[[(24E,26E,28E,29E,36R,37S,38R,39R,41S,43S,46S,47R,48R,59R)-47,59-dihydroxy-46-[(1R)-2-[(1S,3R,4R)-4-(2-hydroxyethoxy)-3-methoxy-cyclohexyl]-1-methyl-ethyl]-48-methoxy-36,37,38,39,49,50-hexamethyl-51,52,53,54,55-pentaoxo-73,74-dioxa-62-azatricyclohexatriaconta-24,26,28(49),29(50)-tetraen-45-yl]oxy]butanoyl]carbamate: A solution of everolimus (1 g, 1.04 mmol) and tert-butyl N-(4-hydroxybutanoyl) carbamate (2.12 g, 10.44 mmol) in THF (25 mL) was stirred at 20° C. for 10 min. p-TsOH (0.9 g, 5.22 mmol) was added and the reaction was stirred at 30° C. for 18 h under N. The mixture was poured into ice cold sat.NaHCO$_3$ (60 mL) aqueous solution, extracted with DCM (100 mL) and the organic layer was washed with water (50 mL) and brine (50 mL), dried over anhydrous Na$_2$SO$_4$, filtered and concentrated. The residue was purified via reverse phase chromatography (75% CH$_3$CN in water) to provide tert-butyl N-[4-[[(24E,26E,28E,29E,36R,37S,38R,39R,41S,43S,46S,47R,48R,59R)-47,59-dihydroxy-46-[(1R)-2-[(1S,3R,4R)-4-(2-hydroxyethoxy)-3-methoxy-cyclohexyl]-1-methyl-ethyl]-48-methoxy-36,37,38,39,49,50-hexamethyl-51,52,53,54,55-pentaoxo-73,74-dioxa-62-azatricyclohexatriaconta-24,26,28(49),29(50)-tetraen-45-yl]oxy]butanoyl]carbamate (0.4 g, 34% yield). ESI-MS (EI$^+$, m/z): 1151.2 [M+Na]$^+$.

Step 4: Synthesis of 4-[[(21E,23E,25E,26E,33R,34S,35R,36R,38S,40S,43S,44R45R55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-21,23,25(46),26(47)-tetraen-42-yl]oxy]butanamide: To a solution of tert-butyl N-[4-[[(24E,26E,28E,29E,36R,37S,38R,39R,41S,43S,46S,47R,48R,59R)-47,59-dihydroxy-46-[(1R)-2-[(1S,3R,4R)-4-(2-hydroxyethoxy)-3-methoxy-cyclohexyl]-1-methyl-ethyl]-48-methoxy-36,37,38,39,49,50-hexamethyl-51,52,53,54,55-pentaoxo-73,74-dioxa-62-azatricyclohexatriaconta-24,26,28(49),29(50)-tetraen-45-yl]oxy]butanoyl]carbamate (0.4 g, 0.36 mmol) in CH$_3$CN (6 mL) under N$_2$ was added HCl (0.5 N in water, 6 mL) at 20° C. The mixture was stirred at 50° C. for 18 h then quenched with NaHCO$_3$ aqueous solution (15 mL) and EtOAc (50 mL) and washed with water (50 mL). The organic layer was dried over Na$_2$SO$_4$, filtered and concentrated. The residue was purified via reverse-phase chromatography (55% CH$_3$CN in water) to provide 4-[[(21E,23E,25E,26E,33R,34S,35R,36R,38S,40S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-21,23,25(46),26(47)-tetraen-42-yl]oxy]butanamide (0.05 g, 0.05 mmol, 13% yield) as a light yellow solid. ESI-MS (EI$^+$, m/z): 1052.6 [M+Na]$^+$. $^1$H NMR (400 MHz, CDCl$_3$): δ 6.46-5.96 (m, 4H), 5.65-5.09 (m, 5H), 4.53-4.14 (m, 3H), 4.03-3.88 (m, 1H), 3.83-3.54 (m, 13H), 3.41-3.31 (m, 6H), 3.25-3.01 (m, 6H), 2.99-2.85 (m, 1H), 2.84-2.47 (m, 4H), 2.45-2.15 (m, 7H), 2.14-1.52 (m, 12H), 1.50-0.78 (m, 20H), 0.76-0.54 (m, 6H).

Step 5: Synthesis of 4-[[(21E,23E,25E,26E,33R,34S,35R,36R,38S,40S,42S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-21,23,25(46),26(47)-tetraen-42-yl]oxy]butanamide (I-29) and 4-[[(21E,23E,25E,26E,33R,34S,35R,36R,38S,40S,42R,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-21,23,25(46),26(47)-tetraen-42-yl]oxy]butanamide (I-28): 120 mg of the racemic mixture was separated via chiral HPLC and then further purified by silica gel chromatography (PE:DCM:EtOAc:MeOH=3:3:1:0.8) to provide I-29 (16 mg) as a white solid and I-28 (12 mg) as a light yellow solid.

Chiral Separation Method:

| | |
|---|---|
| Column | CHIRALPAK IC |
| Column size | 2.5 cm I.D. × 25 cm L, 10 μm |
| Sample solution | 0.9 mg/ml in Mobile phase |
| Injection | 15 ml |
| Mobile phase | Hexane/EtOH = 60/40 (V/V) |
| Flow rate | 25 ml/min |
| Wave length | UV 254 nm |
| Temperature | 35° C. |

I-29: ESI-MS (EI$^+$, m/z): 1029.1 [M+H]$^+$, 1051.0 [M+Na]$^+$. $^1$H NMR (500 MHz, CDCl$_3$) δ 6.42-5.95 (m, 4H), 5.45-5.09 (m, 5H), 4.37 (d, J=99.3 Hz, 2H), 3.96 (d, J=4.5 Hz, 1H), 3.69 (t, J=42.9 Hz, 9H), 3.26 (dd, J=125.9, 47.1 Hz, 17H), 2.69-2.50 (m, 2H), 2.45-2.14 (m, 5H), 2.02 (s, 3H), 1.92-1.69 (m, 10H), 1.34 (d, J=71.6 Hz, 11H), 1.11-0.79 (m, 18H), 0.70 (d, J=12.5 Hz, 1H).

I-28: ESI-MS (EI$^+$, m/z): 1029.0 [M+H]$^+$, 1051.0 [M+Na]$^+$. $^1$H NMR (400 MHz, CDCl$_3$) δ 6.47-5.74 (m, 4H), 5.62-5.01 (m, 5H), 4.62-4.15 (m, 3H), 3.78-3.52 (m, 11H), 3.50-3.02 (m, 21H), 2.85-2.49 (m, 4H), 2.42-1.96 (m, 11H), 1.43-0.51 (m, 29H).

Example 19: Synthesis of 4-[[(21E,23E,25E,26E,33R,34S,35R,36R,38S,40S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-56-azatricyclohexatriaconta-21,23,25(46),26(47)-tetraen-42-yl]oxy]butanoic acid (I-30)

Step 1: Synthesis of 2-trimethylsilylethyl 4-benzyloxybutanoate: A solution of 4-benzyloxybutanoic acid (5 g, 25.74 mmol), 2-trimethylsilylethanol (3.35 g, 28.32 mmol), EDCI (5.43 g, 28.32 mmol) and DMAP (0.315 g, 2.57 mmol) in DCM (70 mL) was stirred at 10° C. for 18 h. The mixture was washed with water (50 mL×2) and brine (50 mL), dried (Na$_2$SO$_4$), filtered and concentrated in vacuo. The residue was purified by silica gel chromatography (8% ethyl acetate in petroleum ether) to afford 2-trimethylsilylethyl 4-benzy-

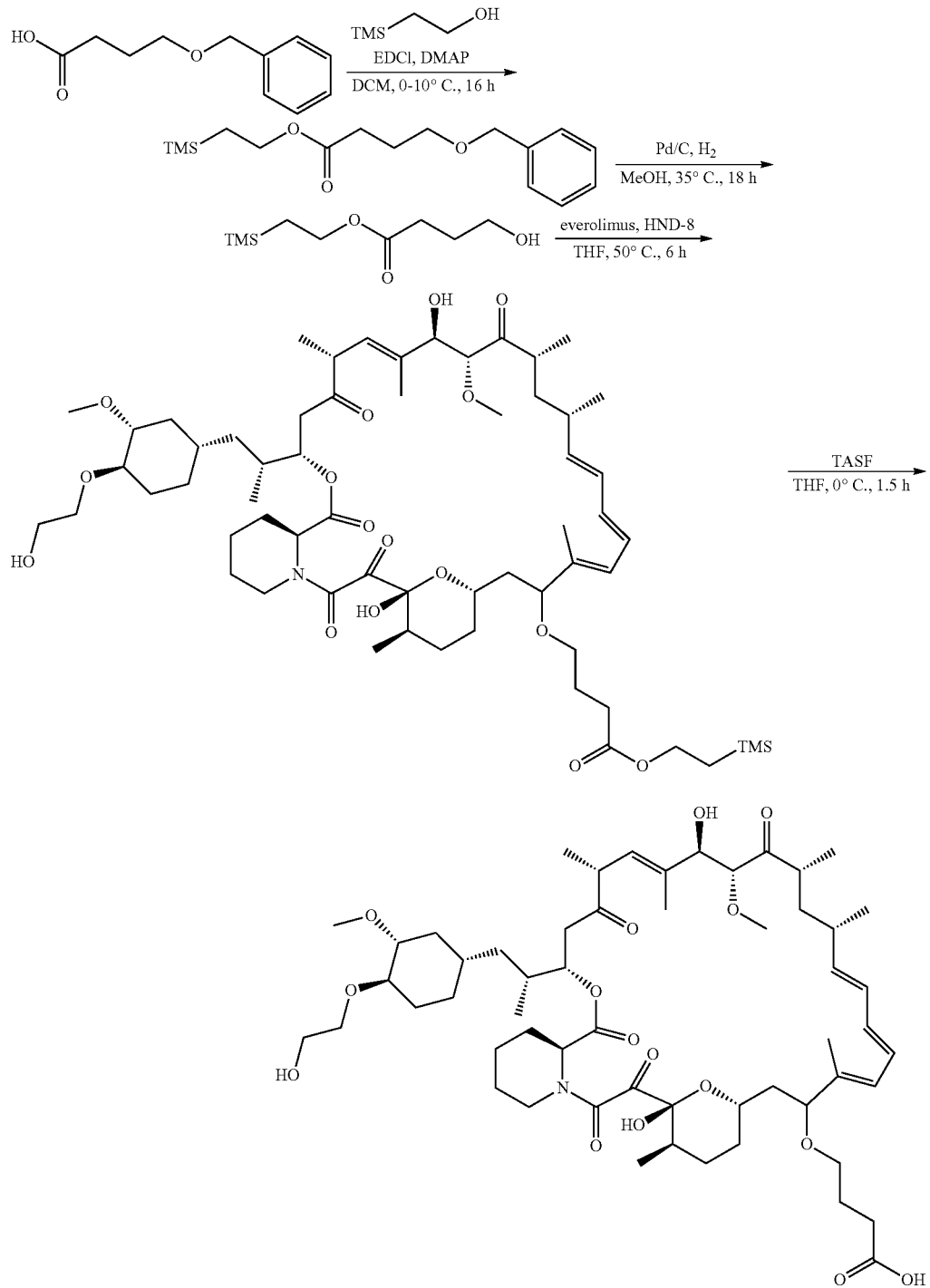

loxybutanoate (5.8 g, 76% yield) as a colorless oil. $^1$H NMR (400 MHz, CDCl$_3$) δ 7.40-7.16 (m, 5H), 4.46 (s, 2H), 4.21-3.99 (m, 2H), 3.47 (t, J=6.2 Hz, 2H), 2.37 (t, J=7.4 Hz, 2H), 1.97-1.81 (m, 2H), 1.03-0.82 (m, 2H), 0.01 (s, 9H).

Step 2: Synthesis of 2-trimethylsilylethyl 4-hydroxybutanoate: A mixture of 2-trimethylsilylethyl 4-benzyloxybutanoate (7.2 g, 24.45 mmol) and Pd/C (2.5 g) in CH$_3$OH (50 mL) was stirred at 35° C. for 18 h under H$_2$. The mixture was filtered then concentrated in vacuo to provide 2-trimethylsilylethyl 4-hydroxybutanoate (4.1 g, 82% yield) as colorless oil. ESI-MS (EI$^+$, m/z):227.1 [M+Na]$^+$. $^1$H NMR (500 MHz, CDCl$_3$) δ 4.13 (ddd, J=13.5, 8.7, 5.3 Hz, 2H), 3.68-3.58 (m, 2H), 2.38 (t, J=7.2 Hz, 2H), 2.15 (t, J=4.9 Hz, 1H), 1.84 (qd, J=6.7, 4.5 Hz, 2H), 0.99-0.91 (m, 2H), 0.01--0.02 (m, 9H).

Step 3: Synthesis of 2-trimethylsilylethyl 4-[[(24E,26E,28E,29E,38R,39S,40R,41R,43S,45S,48S,49R,50R,60R)-49,60-dihydroxy-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-53,54,55,56,57-pentaoxo-71,72-dioxa-61-azatricyclohexatriaconta-24,26,28(51),29(52)-tetraen-47-yl]oxy]butanoate: A solution of everolimus (0.5 g, 0.52 mmol), 2-trimethylsilylethyl 4-hydroxybutanoate (2.13 g, 10.44 mmol) in THF (15 mL) was heated to 50° C. under argon then HND-8 (50 mg, 0.52 mmol) was added. The mixture was stirred at 50° C. for 6 h then filtered and concentrated in vacuo. The residue was purified by reverse phase chromatography (CH$_3$CN: H$_2$O=82:18) to afford 2-trimethylsilylethyl 4-[[(24E,26E,28E,29E,38R,39S,40R,41R,43S,45S,48S,49R,50R,60R)-49,60-dihydroxy-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-53,54,55,56,57-pentaoxo-71,72-dioxa-61-azatricyclohexatriaconta-24,26,28(51),29(52)-tetraen-47-yl]oxy]butanoate (0.105 g, 18% yield) as alight yellow solid. ESI-MS (EI$^+$, m/z): 1152.3 [M+Na]$^+$.

Step 4: Synthesis of 4-[[(21E,23E,25E,26E,33R,34S,35R,36R,38S,40S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-56-azatricyclohexatriaconta-21,23,25(46),26(47)-tetraen-42-yl]oxy]butanoic acid (I-30): To a solution of 2-trimethylsilylethyl 4-[[(24E,26E,28E,29E,38R,39S,40R,41R,43S,45S,48S,49R,50R,60R)-49,60-dihydroxy-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-53,54,55,56,57-pentaoxo-71,72-dioxa-61-azatricyclohexatriaconta-24,26,28(51),29(52)-tetraen-47-yl]oxy]butanoate (0.097 g, 0.086 mmol) in THF (20 mL) was added TASF (22.4 mg, 0.086 mmol) at 0° C. The mixture was stirred at 0° C. for a further 1.5 h then quenched with NH$_4$Cl, poured into water and extracted with EtOAc (25 mL×3). The combined organic layers were washed with water (30 mL), brine (30 mL) then concentrated and purified via reverse phase chromatography (CH$_3$CN in H$_2$O from 0%100%) to provide I-30 (0.01 g, 11% yield) as white solid. ESI-MS (EI$^+$, m/z): 1052.0 [M+Na]$^+$. $^1$H NMR (400 MHz, CDCl$_3$) δ 6.79-6.65 (m, 1H), 6.46-5.86 (m, 5H), 5.39 (d, J=37.1 Hz, 2H), 4.36 (d, J=98.4 Hz, 3H), 3.68 (t, J=38.5 Hz, 10H), 3.45-3.03 (m, 15H), 2.88-2.17 (m, 8H), 2.02 (s, 8H), 1.83-1.39 (m, 10H), 1.35-1.11 (m, 6H), 1.08-0.72 (m, 19H).

Example 20: Synthesis of (22E,24E,26E,27E,33R,34S,35R,36R,38S,40S,43S,44S,45R,54R)-44,54-dihydroxy-43-[(1R)-2-[(1S,3R,4R)-4-hydroxy-3-methoxy-cyclohexyl]-1-methyl-ethyl]-45-methoxy-42-[2-(2-methoxyethoxy)ethylsulfanyl]-33,34,35,36,46,47-hexamethyl-64,65-dioxa-55-azatricyclohexatriaconta-22,24,26(46),27(47)-tetraene-48,49,50,51,52-pentone (I-31)

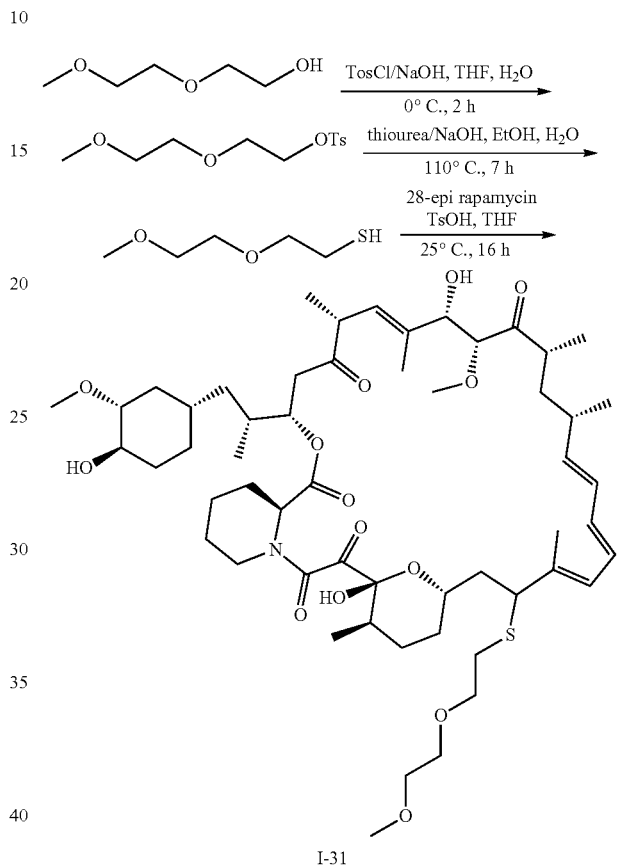

I-31

Step 1: Synthesis of 2-(2-methoxyethoxy) ethyl 4-methylbenzenesulfonate: To a solution of 2-(2-methoxyethoxy) ethanol (10 g, 83.23 mmol) in THF (100 mL) was added sodium hydroxide (5.99 g, 149.82 mmol) in H$_2$O (100 mL) at 0° C., and the mixture stirred for 0.5 h. 4-methylbenzenesulfonyl chloride (30.15 g, 158.14 mmol) in THF (160 mL) was then added and the mixture stirred for 1 h. The reaction was warmed to room temperature and stirred for another 1 h then was extracted with Et$_2$O (400 ml) and the organic layer was washed with 1 M NaOH aqueous solution (100 mL), water (100 mL×2) and dried over MgSO4, filtered and concentrated. The residue was purified by silica gel chromatography (EtOAc:PE=1:4) to provide 2-(2-methoxyethoxy) ethyl 4-methylbenzenesulfonate (17.6 g, 77% yield) as a solid. $^1$H NMR (500 MHz, CDCl$_3$) δ 7.80 (d, J=8.3 Hz, 2H), 7.34 (d, J=8.1 Hz, 2H), 4.19-4.15 (m, 2H), 3.71-3.67 (m, 2H), 3.58 (dd, J=5.6, 3.5 Hz, 2H), 3.48 (dd, J=5.6, 3.5 Hz, 2H), 3.35 (s, 3H), 2.45 (s, 3H).

Step 2: Synthesis of 2-(2-methoxyethoxy) ethanethiol: To a mixture of 2-(2-methoxyethoxy) ethyl 4-methylbenzenesulfonate (2 g, 4.59 mmol), EtOH (4 mL) and thiourea (0.37 g, 4.82 mmol) was added distilled H$_2$O (0.3 mL) and the reaction was refluxed for 3 h. A solution of sodium hydroxide (0.28 g, 6.89 mmol) in distilled H$_2$O (5 mL) was added, and the mixture was refluxed for 3.75 h. The reaction mixture was concentrated to 2 mL, diluted with distilled H₂O (4 mL), neutralized with con. HCl (37% in water), extracted with CH₂Cl2 (25 mL×2), dried over Na₂SO₄, filtered and concentrated to obtain 2-(2-methoxyethoxy) ethanethiol (0.11 g, 18% yield) as a clear liquid. $^1$H NMR (400 MHz, CDCl₃) δ3.62-3.54 (m, 4H), 3.51 (dd, J=5.7, 3.0 Hz, 2H), 3.35 (s, 3H), 2.66 (dt, J=8.2, 6.5 Hz, 2H), 1.54 (t, J=8.2 Hz, 1H).

Step 3: Synthesis of (22E,24E,26E,27E,33R,34S,35R, 36R,38S,40S,43S,44S,45R,54R)-44,54-dihydroxy-43-[(1R)-2-[(1S,3R,4R)-4-hydroxy-3-methoxy-cyclohexyl]-1-methyl-ethyl]-45-methoxy-42-[2-(2-methoxyethoxy) ethylsulfanyl]-33,34,35,36,46,47-hexamethyl-64,65-dioxa-55-azatricyclohexatriaconta-22,24,26(46),27(47)-tetraene-48,49,50,51,52-pentone (I-31): A solution of 2-(2-methoxyethoxy) ethanethiol (0.745 g, 5.47 mmol), 28-epi-rapamycin (0.5 g, 0.547 mmol) and 4-methylbenzenesulfonic acid (0.52 g, 2.73 mmol) in THF (10 mL) was stirred at 25° C. for 16 h then poured into ice cold NaHCO₃ aqueous solution (50 mL) and extracted with EtOAc (50 mL×2). The combined organic layers were dried over Na₂SO₄, filtered and concentrated. The residue was purified by reverse phase chromatography (70% CH₃CN in water) to provide I-31 (0.12 g, 21% yield) as a white solid. ESI-MS (EI+, m/z): 1039.9 [M+Na]⁺. $^1$H NMR (400 MHz, CDCl₃) δ 6.48-5.88 (m, 4H), 5.76-5.01 (m, 11H), 4.82-4.64 (m, 1H), 4.38 (dd, J=64.1, 49.6 Hz, 3H), 4.05-3.81 (m, 5H), 3.71-3.49 (m, 15H), 3.49-3.28 (m, 23H), 3.18-2.81 (m, 7H), 2.84-2.47 (m, 11H), 2.46-2.18 (m, 7H), 2.06 (dd, J=58.1, 22.9 Hz, 9H), 1.75 (ddd, J=10.7, 8.6, 6.8 Hz, 29H), 1.49-1.20 (m, 14H), 1.12-0.99 (m, 13H), 0.98-0.84 (m, 18H), 0.75-0.61 (m, 2H).

Example 21: Synthesis of 2-(2-hydroxyethoxy)ethyl N-[(21E,23E,25E,26E,32R,33S,34R,35R,37S,39S, 42S,43R,44R,54R)-43,54-dihydroxy-42-[(1R)-2-[(1S,3R,4R)-4-hydroxy-3-methoxy-cyclohexyl]-1-methyl-ethyl]-44-methoxy-32,33,34,35,45,46-hexamethyl-47,48,49,50,51-pentaoxo-67,68-dioxa-56-azatricyclohexatriaconta-21,23,25(45),26(46)-tetraen-41-yl]carbamate (I-32)

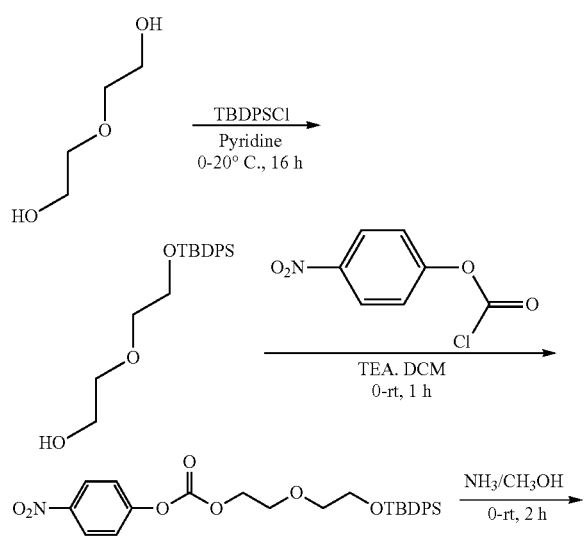

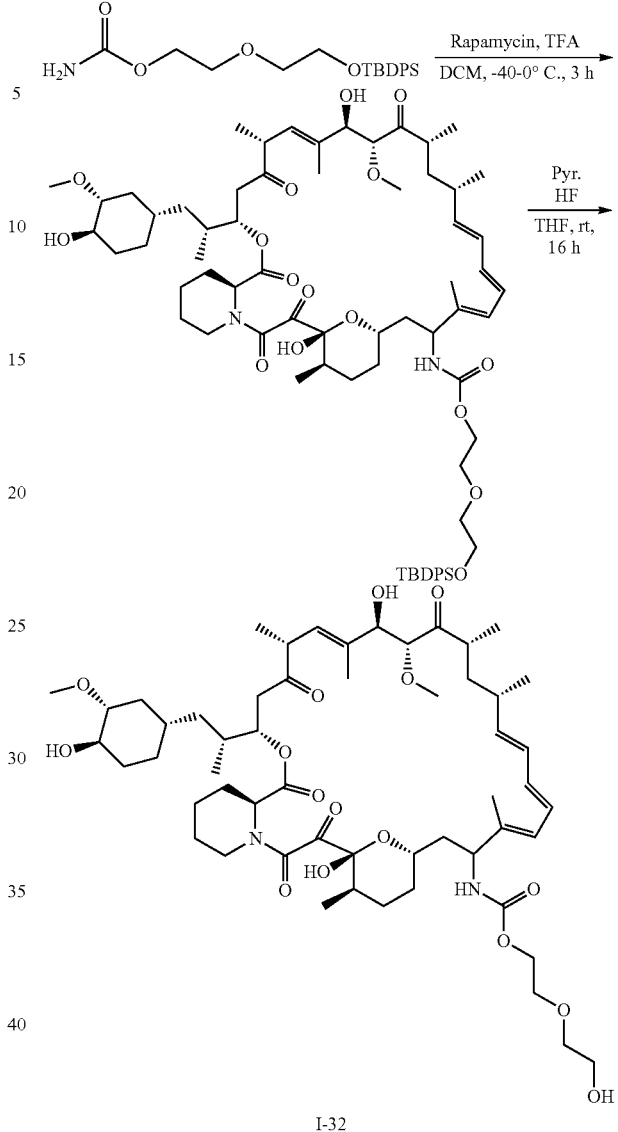

I-32

Step 1: Synthesis of 2-(2-(tert-butyldiphenylsilyloxy) ethoxy) ethanol: To a solution of 2-(2-hydroxyethoxy) ethanol (8.83 g, 83.23 mmol) in pyridine (6.73 mL, 83.23 mmol) was added tert-butyl-chloro-diphenyl-silane (3.56 mL, 13.87 mmol) at 0° C. The reaction mixture was stirred at 20° C. overnight then poured into water (300 mL) and extracted with EtOAc (200 mL×3). The combined organic layers were concentrated and purified via silica gel chromatography (EtOAc:PE=2:3) to provide 2-(2-(tert-butyldiphenylsilyloxy) ethoxy) ethanol (3.77 g, 79%) as a thick oil. $^1$H NMR (400 MHz, CDCl₃): δ 7.70-7.67 (m, 4H), 7.43-7.26 (m, 6H), 3.83-3.69 (m, 4H), 3.63-3.57 (m, 4H), 1.07-1.04 (m, 9H).

Step 2: Synthesis of 2-(2-(tert-butyldiphenylsilyloxy) ethoxy) ethyl 4-nitrophenyl carbonate: To a solution of 2-[2-[tert-butyl(diphenyl)silyl]oxyethoxy]ethanol (1 g, 2.9 mmol) and N,N-diethylethanamine (1.01 mL, 7.26 mmol) in DCM (15 mL) at 0° C. under N₂ was added (4-nitrophenyl) carbonochloridate (1.35 g, 6.68 mmol), the resulting mixture was allowed to warm to rt and stirred for 1 h. The reaction mixture was used in the following step without further purification. ESI-MS (EI+, m/z): 531.9 [M+H]⁺.

Step 3: Synthesis of 2-(2-(tert-butyldiphenylsilyloxy) ethoxy) ethyl carbamate: A solution of 2-[2-[tert-butyl(diphenyl) silyl]oxyethoxy]ethyl (4-nitrophenyl) carbonate (7.4 g, 14.52 mmol) in ammonia (7 M, 62.23 mL) was stirred at 0° C. for 10 min, then 25° C. for 2 h. The reaction mixture was quenched with water (100 mL) then concentrated in vacuo. The residue was extracted with DCM (50 mL×3) and the combined organic layers washed with brine (50 mL×3), dried over anhydrous $Na_2SO_4$, filtered and concentrated in vacuo. The residue was purified by silica gel chromatography eluting with 25% EtOAc in PE to provide 2-[2-[tert-butyl (diphenyl)silyl]oxyethoxy]ethyl carbamate (5.5 g, 98% yield) as a yellow oil. ESI-MS (EI+, m/z): 410.0 [M+Na]$^+$. $^1$H NMR (400 MHz, CDCl$_3$) δ 7.75-7.62 (m, 4H), 7.47-7.32 (m, 6H), 4.76 (s, 2H), 4.26-4.17 (m, 2H), 3.81 (t, J=5.2 Hz, 2H), 3.72-3.65 (m, 2H), 3.60 (t, J=5.2 Hz, 2H), 1.05 (s, 9H).

Step 4: Synthesis of 2-[2-[tert-butyl(diphenyl)silyl]oxyethoxy]ethyl N-[(34E,36E,38E,39E,47R,48S,49R,50R,52S,54S,57S,58R,59R,69R)-58,69-dihydroxy-57-[(1R)-2-[(1S,3R,4R)-4-hydroxy-3-methoxy-cyclohexyl]-1-methyl-ethyl]-59-methoxy-47,48,49,50,60,61-hexamethyl-62,63,64,65,66-pentaoxo-82,83-dioxa-72-azatricyclohexatriaconta-34,36,38(60),39(61)-tetraen-56-yl]carbamate: To a solution of rapamycin (1 g, 1.09 mmol) in DCM (60 mL) was added TFA (3.11 g, 27.26 mmol) slowly dropwise at −50° C. under N$_2$. The mixture was stirred for 20 min then a solution of 2-[2-[tert-butyl (diphenyl)silyl]oxyethoxy]ethyl carbamate (8.48 g, 21.88 mmol) in 20 mL DCM was added to the reaction mixture dropwise at −40° C. The reaction was allowed to warm to 0° C. and stirred 3 h. Saturated NaHCO$_3$ (aq) was added to adjust the pH to 7 and the mixture was extracted with DCM (60 mL×1). The organic layer was washed with brine (40 mL×2), dried over anhydrous sodium sulfate, filtered and the concentrated in vacuo. The residue was purified by silica gel chromatography eluting with 80% EtOAc in PE, then by reverse phase chromatography eluting with 80% CH$_3$CN in water to provide 2-[2-[tert-butyl(diphenyl)silyl]oxyethoxy]ethyl N-[(34E,36E,38E,39E,47R,48S,49R,50R,52S,54S,57S,58R,59R,69R)-58,69-dihydroxy-57-[(1R)-2-[(1S,3R,4R)-4-hydroxy-3-methoxy-cyclohexyl]-1-methyl-ethyl]-59-methoxy-47,48,49,50,60,61-hexamethyl-62,63,64,65,66-pentaoxo-82,83-dioxa-72-azatricyclohexatriaconta-34,36,38(60),39(61)-tetraen-56-yl]carbamate (0.37 g, 27% yield) as a white solid. ESI-MS (EI+, m/z): 1293.2 [M+Na]$^+$.

Step 5: Synthesis of 2-(2-hydroxyethoxy)ethyl N-[(21E,23E,25E,26E,32R,33S,34R,35R,37S,39S,42S,43R,44R,54R)-43,54-dihydroxy-42-[(1R)-2-[(1S,3R,4R)-4-hydroxy-3-methoxy-cyclohexyl]-1-methyl-ethyl]-44-methoxy-32,33,34,35,45,46-hexamethyl-47,48,49,50,51-pentaoxo-67,68-dioxa-56-azatricyclohexatriaconta-21,23,25(45),26(46)-tetraen-41-yl]carbamate (I-32): To a solution of 2-[2-[tert-butyl(diphenyl)silyl]oxyethoxy]ethyl N-[(34E,36E,38E,39E,47R,48S,49R,50R,52S,54S,57S,58R,59R,69R)-58,69-dihydroxy-57-[(1R)-2-[(1S,3R,4R)-4-hydroxy-3-methoxy-cyclohexyl]-1-methyl-ethyl]-59-methoxy-47,48,49,50,60,61-hexamethyl-62,63,64,65,66-pentaoxo-82,83-dioxa-72-azatricyclohexatriaconta-34,36,38(60),39(61)-tetraen-56-yl]carbamate (0.63 g, 0.5 mmol) in THF (100 mL) was added HF.pyridine (5.62 g, 39.7 mmol). The reaction was then stirred at rt for 16 h. Saturated aqueous NaHCO$_3$ solution (100 mL) was added to adjust the pH to 7 and this was extracted with DCM (50 mL×2). The combined organic layers were washed with brine (50 mL×2), dried over anhydrous Na$_2$SO$_4$, filtered and was concentrated in vacuo. The residue was purified via reverse phase chromatography eluting with 50% CH$_3$CN in water to obtain I-32 (0.15 g, 29% yield) as a white solid. ESI-MS (EI+, m/z): 1054.1 [M+Na]$^+$. $^1$H NMR (400 MHz, CDCl3) δ 6.38-5.99 (m, 4H), 5.55-5.50 (m, 5H), 4.49-4.21 (m, 4H), 4.05-4.02 (m, 1H), 3.89-3.49 (m, 8H), 3.42-3.41 (m, 8H), 2.97-2.90 (m, 2H), 2.77-2.46 (m, 4H), 2.31-2.22 (m, 2H), 2.10-1.90 (m, 4H), 1.79-1.61 (m, 26H), 1.54-1.17 (m, 9H), 1.15-0.86 (m, 18H), 0.68-0.61 (m, 1H).

Example 22: Synthesis of (26E,28E,30E,31E,38R,39S,40R,41R,43S,45S,48S,49S,50R,59R)-49,59-dihydroxy-48-[(1R)-2-[(1S,3R,4R)-4-hydroxy-3-methoxy-cyclohexyl]-1-methyl-ethyl]-50-methoxy-47-[[3-(2-methoxyethoxy)phenyl]methoxy]-38,39,40,41,51,52-hexamethyl-69,70-dioxa-60-azatricyclohexatriaconta-26,28,30(51),31(52)-tetraene-53,54,55,56,57-pentone (I-33)

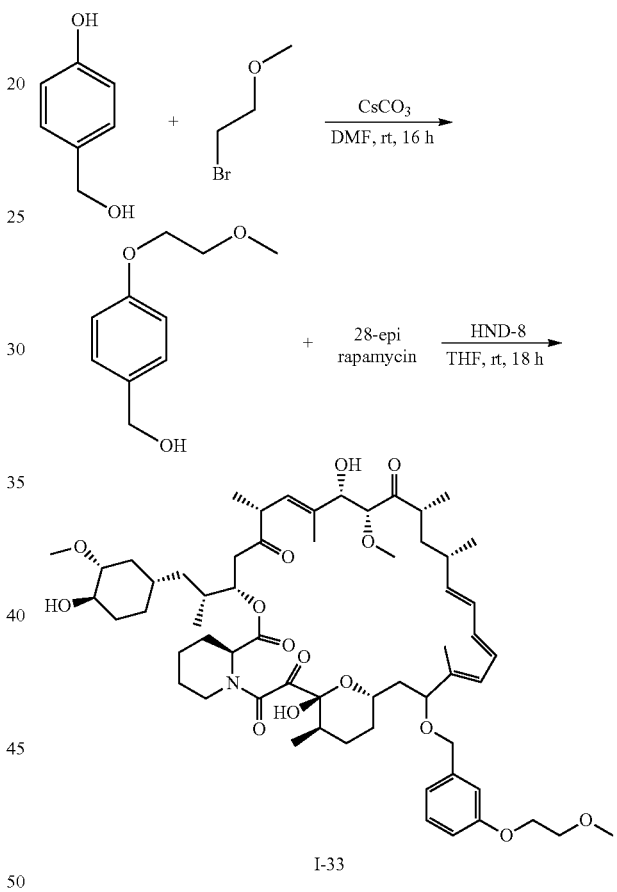

I-33

Step 1: Synthesis of (4-(2-methoxyethoxy) phenyl) methanol: A solution of 3-methoxyphenol (0.2 g, 1.61 mmol), 1-bromo-2-methoxy-ethane (0.27 g, 1.93 mmol) and Cs$_2$CO$_3$ (1.05 g, 3.22 mmol) in DMF (10 mL) was stirred at 25° C. for 16 h then diluted with HCl (10 mL, 1N in water) and extracted with EtOAc (20 mL×3). The combined organic layers were dried over anhydrous Na$_2$SO$_4$, filtered and concentrated. The residue was purified by reverse phase chromatography to obtain 1-methoxy-3-(2-methoxyethoxy) benzene (0.18 g, 61% yield) as a colorless oil. ESI-MS (EI+, m/z): 183.1 [M+H]$^+$.

Step 2: Synthesis of (26E,28E,30E,31E,38R,39S,40R,41R,43S,45S,48S,49S,50R,59R)-49,59-dihydroxy-48-[(1R)-2-[(1S,3R,4R)-4-hydroxy-3-methoxy-cyclohexyl]-1-methyl-ethyl]-50-methoxy-47-[[3-(2-methoxyethoxy)phenyl]methoxy]-38,39,40,41,51,52-hexamethyl-69,70-dioxa-60-azatricyclohexatriaconta-26,28,30(51),31(52)- tetraene-53,54,55,56,57-pentone (I-33): To a solution of 28-epi rapamycin (0.2 g, 0.22 mmol) and [3-(2-methoxyethoxy) phenyl]methanol (0.08 g, 0.44 mmol) in THF (5 mL) was added HND-8 (20 mg) at 25° C. The mixture was stirred at 25° C. for 18 h then filtered and the filtrate was treated with aq.NaHCO$_3$ (10 mL) and extracted with DCM (10 mL×2). The combined organic layers were concentrated and the residue purified by reverse phase chromatography (CH$_3$CN in water: 0-70%) to provide I-33 (52 mg, 22% yield) as a white solid. ESI-MS (EI+, m/z): 1087 [M+Na]$^+$. $^1$H NMR (400 MHz, DMSO-d$_6$) δ 7.19 (dt, J=17.1, 8.6 Hz, 2H), 6.99-6.81 (m, 2H), 6.62-6.40 (m, 2H), 6.26-6.12 (m, 2H), 5.63-5.29 (m, 2H), 5.10-4.96 (m, 2H), 4.93 (d, J=7.9 Hz, 1H), 4.63 (d, J=4.3 Hz, 1H), 4.25 (t, J=13.2 Hz, 1H), 4.15-3.98 (m, 4H), 3.83 (dt, J=39.7, 18.3 Hz, 2H), 3.78-3.58 (m, 2H), 3.29 (dd, J=10.2, 3.4 Hz, 8H), 3.18 (d, J=8.9 Hz, 6H), 3.03 (d, J=11.7 Hz, 2H), 2.87-2.66 (m, 4H), 2.35 (dd, J=25.4, 17.2 Hz, 3H), 2.12 (s, 2H), 2.04-1.88 (m, 4H), 1.68 (dd, J=14.6, 10.0 Hz, 9H), 1.61-1.48 (m, 7H), 1.24 (s, 5H), 1.13 (d, J=12.7 Hz, 2H), 1.04-1.00 (m, 3H), 0.85 (dd, J=8.8.6 Hz, 6H), 0.75 (dd, J=11.5, 5.3 Hz, 4H), 0.56 (d, J=11.6 Hz, 1H).

Example 23: Synthesis of (21E,23E,25E,26E,33R, 34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-42-(5-hydroxypentoxy)-45-methoxy-33,34,35,36,46,47-hexamethyl-65,66-dioxa-55-azatricyclohexatriaconta-21,23,25(46),26(47)-tetraene-48,49,50,51,52-pentone (I-34) and (21E, 23E,25E,26E,33R,34S,35R,36R,38S,40S,42S,43S, 44R,45R,54R)-44,54-dihydroxy-43-[(1R)-2-[(1S,3R, 4R)-4-hydroxy-3-methoxy-cyclohexyl]-1-methyl-ethyl]-42-(5-hydroxypentoxy)-45-methoxy-33,34,35, 36,46,47-hexamethyl-65,66-dioxa-55-azatricyclohexatriaconta-21,23,25(46),26(47)-tetraene-48,49,50,51,52-pentone (I-35)

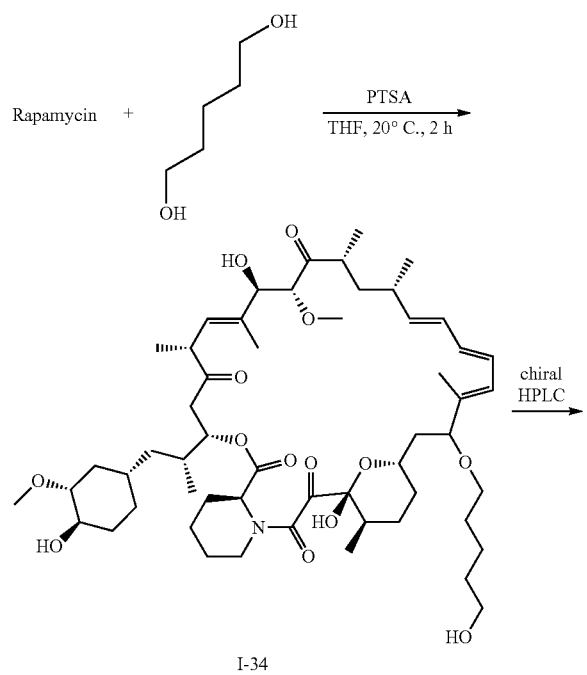

I-34

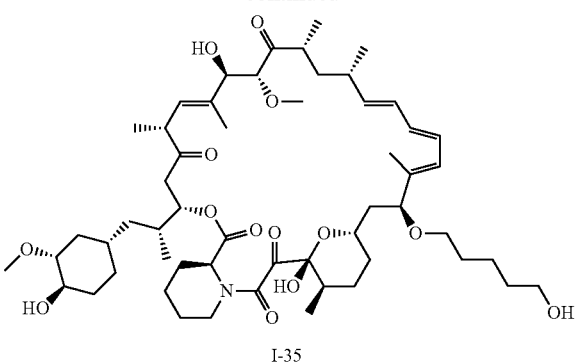

I-35

Step 1: Synthesis of (21E,23E,25E,26E,33R,34S,35R, 36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-42-(5-hydroxypentoxy)-45-methoxy-33,34, 35,36,46,47-hexamethyl-65,66-dioxa-55-azatricyclohexatriaconta-21,23,25(46),26(47)-tetraene-48, 49,50,51,52-pentone (I-34): To a solution of rapamycin (0.5 g, 0.55 mol) in THF (10 mL) was added 4-methylbenzenesulfonic acid hydrate (0.52 g, 2.73 mmol) and pentane-1,5-diol (3 mL). The resulting solution was stirred at rt for 2 h, then poured into cold aq. NaHCO$_3$ and extracted with EtOAc. The organic layer was concentrated then purified by reverse-phase chromatography (C18, CH$_3$CN:H$_2$O from 10% to 72%) to provide I-34 (0.15 g, 28% yield) as a white solid. ESI-MS (EI$^+$, m/z):1008.0 [M+Na]$^+$; $^1$HNMR (500 MHz, CDCl3) δ 6.42-5.82 (m, 4H), 5.58-5.37 (m, 2H), 5.32-5.02 (m, 2H), 4.78 (t, J=25.9 Hz, 1H), 4.31-4.08 (m, 1H), 4.00-3.53 (m, 5H), 3.53-3.05 (m, 12H), 2.99-2.80 (m, 2H), 2.77-2.51 (m, 3H), 2.48-2.23 (m, 2H), 2.15-1.89 (m, 4H), 1.89-1.16 (m, 32H), 1.15-0.78 (m, 18H), 0.65 (dt, J=24.1, 12.0 Hz, 1H).

Step 2: (21E,23E,25E,26E,33R,34S,35R,36R,38S,40S, 42S,43S,44R,45R,54R)-44,54-dihydroxy-43-[(1R)-2-[(1S, 3R,4R)-4-hydroxy-3-methoxy-cyclohexyl]-1-methyl-ethyl]-42-(5-hydroxypentoxy)-45-methoxy-33,34,35,36,46, 47-hexamethyl-65,66-dioxa-55-azatricyclohexatriaconta-21,23,25(46),26(47)-tetraene-48,49,50,51,52-pentone (I-35): 190 mg of the racemic mixture separated via chiral HPLC and then further purified by silica gel chromatography (hexane:DCM:EtOAc:MeOH=3:3:1:0 to 3:3:1:1.3) to provide I-35 (8.6 mg, 4.5% yield) as a white solid.

Chiral Separation Method:

| Column | CHIRALPAK IC |
|---|---|
| Column size | 5.0 cm I.D. × 25 cm L, 10 µm |
| Sample solution | 10 mg/ml in Mobile phase |
| Injection | 5 ml |
| Mobile phase | Hexane/EtOH = 60/40 (V/V) |
| Flow rate | 60 ml/min |
| Wave length | UV 254 nm |
| Temperature | 35° C. |

I-35: ESI-MS (EI+, m/z): 1008.0 [M+Na]$^+$. $^1$H NMR (500 MHz, CDCl$_3$) δ 6.42-5.82 (m, 4H), 5.57-5.02 (m, 5H), 4.79 (s, 1H), 4.17 (s, 1H), 3.93-3.53 (m, 6H), 3.48-3.27 (m, 11H), 3.10 (d, J=9.5 Hz, 1H), 2.99-2.52 (m, 5H), 2.37-1.91 (m, 7H), 1.90-1.64 (m, 12H), 1.50-1.16 (m, 15H), 1.16-0.80 (m, 18H), 0.72-0.60 (m, 1H).

Example 24: Synthesis of (21E,23E,25E,26E,31R, 32S,33R,34R,36S,38S,40S,41S,42S,43R,52R)-42, 52-dihydroxy-41-[(1R)-2-[(1S,3R,4R)-4-hydroxy-3-methoxy-cyclohexyl]-1-methyl-ethyl]-40-(3-hydroxypropoxy)-43-methoxy-31,32,33,34,44,45-hexamethyl-63,64-dioxa-53-azatricyclohexatriaconta-21,23,25(44),26(45)-tetraene-46,47,48,49,50-pentone (I-36)

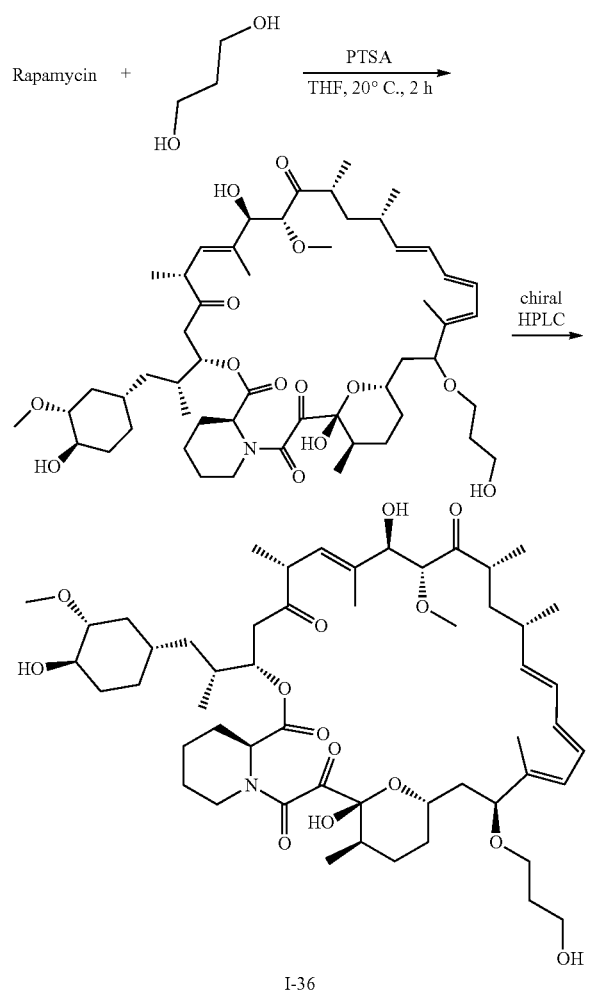

I-36

Step 1: Synthesis of (21E,23E,25E,26E,31R,32S,33R, 34R,35S,38S,40S,42R,43R,52R)-42,52-dihydroxy-40-[(1R)-2-[(1S,2R,3R)-3-hydroxy-2-methoxy-cyclohexyl]-1-methyl-ethyl]-39-(3-hydroxypropoxy)-43-methoxy-31,32, 33,34,44,45-hexamethyl-63,64-dioxa-53-azatricyclohexatriaconta-21,23,25(44),26(45)-tetraene-46, 47,48,49,50-pentone: To a solution of rapamycin (0.5 g, 0.55 mmol), propane-1,3-diol (13.13 g, 172.48 mmol) in THF (37.5 mL) was added p-TsOH (0.47 g, 2.74 mmol) and the resulting mixture stirred at 20° C. for 2 h then poured into ice cold NaHCO$_3$ aqueous solution (100 mL) and extracted with EtOAc (100 mL×3). The combined organic layers were washed with water, brine, then concentrated and the residue purified via reverse phase chromatography (CH$_3$CN/water=7:3) to afford (21E,23E,25E,26E,31R,32S,33R,34R, 35S,38S,40S,42R,43R,52R)-42,52-dihydroxy-40-[(1R)-2-[(1S,2R,3R)-3-hydroxy-2-methoxy-cyclohexyl]-1-methyl-ethyl]-39-(3-hydroxypropoxy)-43-methoxy-31,32,33,34,44,45-hexamethyl-63,64-dioxa-53-azatricyclohexatriaconta-21,23,25(44),26(45)-tetraene-46,47,48,49,50-pentone (0.15 g, 29% yield) as a white solid. ESI-MS (EI+, m/z): 980.3 [M+Na]$^+$. $^1$H NMR (500 MHz, CDCl$_3$) δ 6.58-5.84 (m, 4H), 5.72-4.83 (m, 4H), 4.65-4.06 (m, 2H), 4.03-3.63 (m, 5H), 3.62-3.05 (m, 12H), 3.03-2.40 (m, 6H), 2.42-1.91 (m, 7H), 1.89-1.56 (m, 17H), 1.53-1.27 (m, 6H), 1.25-0.76 (m, 19H), 0.62 (m, 1H).

Step 2: Synthesis of (21E,23E,25E,26E,31R,32S,33R, 34R,36S,38S,40S,41S,42S,43R,52R)-42,52-dihydroxy-41-[(1R)-2-[(1S,3R,4R)-4-hydroxy-3-methoxy-cyclohexyl]-1-methyl-ethyl]-40-(3-hydroxypropoxy)-43-methoxy-31,32, 33,34,44,45-hexamethyl-63,64-dioxa-53-azatricyclohexatriaconta-21,23,25(44),26(45)-tetraene-46, 47,48,49,50-pentone: 500 mg of the racemic mixture was separated via chiral HPLC and then further purified by silica gel chromatography (hexane:DCM:EtOAc:MeOH=3:3:1:0 to 3:3:1:0.8) to obtain I-36 (50 mg, 10% yield) as a white solid.

Chiral Separation Method:

| Column: | CHIRALPAK IC |
|---|---|
| Column size: | 5.0 cm I.D. × 25 cm L, 10 μm |
| Sample solution: | 10 mg/ml in Mobile phase |
| Injection: | 5 ml |
| Mobile phase: | Hexane/EtOH = 60/40 (V/V) |
| Flow rate: | 60 ml/min |
| Wave length: | UV 254 nm |
| Temperature: | 35° C. |

I-36: ESI-MS (EI+, m/z): 980.2 [M+Na]$^+$. $^1$H NMR (500 MHz, CDCl$_3$) δ 6.42-5.87 (m, 4H), 5.35 (ddt, J=108.4, 52.7, 28.7 Hz, 5H), 4.88 (s, 1H), 4.28-4.13 (m, 1H), 3.93-3.63 (m, 5H), 3.62-3.07 (m, 15H), 3.01-2.49 (m, 6H), 2.44-1.92 (m, 9H), 1.88-1.69 (m, 8H), 1.53-1.18 (m, 10H), 1.16-0.80 (m, 18H), 0.64 (q, J=12.0, 24.0 Hz, 1H).

Example 25: Synthesis of (26E,28E,30E,31E,36R, 37S,38R,39R,41S,43S,44R,46S,47R,48R,57R)-44-(2,4-dimethoxyphenyl)-47,57-dihydroxy-46-[(1R)-2-[(1S,3R,4R)-4-hydroxy-3-methoxy-cyclohexyl]-1-methyl-ethyl]-48-methoxy-36,37,38,39,49,50-hexamethyl-67,68-dioxa-58-azatricyclohexatriaconta-26,28,30(49),31(50)-tetraene-51,52,53,54,55-pentone (I-37) and (26E, 28E,30E,31E,36R,37S,38R,39R,41S,43S,44S,46S, 47R,48R,57R)-44-(2,4-dimethoxyphenyl)-47,57-dihydroxy-46-[(1R)-2-[(1S,3R,4R)-4-hydroxy-3-methoxy-cyclohexyl]-1-methyl-ethyl]-48-methoxy-36,37,38,39,49,50-hexamethyl-67,68-dioxa-58-azatricyclohexatriaconta-26,28,30(49),31(50)-tetraene-51,52,53,54,55-pentone (I-38)

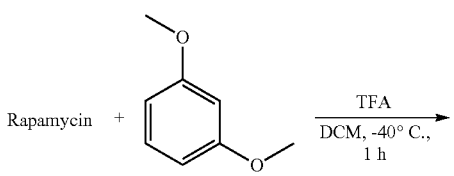

5.55-5.11 (m, 4H), 4.36-4.12 (m, 2H), 3.95-3.66 (m, 8H), 3.61-3.05 (m, 11H), 2.97-2.53 (m, 4H), 2.48-2.07 (m, 4H), 2.02-1.42 (m, 20H), 1.39-1.18 (m, 6H), 1.12-0.80 (m, 18H), 0.65 (q, J=12.0, 24.0 Hz, 1H).

Example 26: Synthesis of (21E,23E,25E,26E,34R, 35S,36R,37R,39S,41S,44S,45R,46R,55R)-45,55-dihydroxy-44-[(1R)-2-[(1S,3R,4R)-4-(2-hydroxy-ethoxy)-3-methoxy-cyclohexyl]-1-methyl-ethyl]-43-12-(2-hydroxyethylsulfonyl)ethoxyl-46-methoxy-34, 35,36,37,47,48-hexamethyl-68,69-dioxa-56-azatricyclohexatriaconta-21,23,25(47),26(48)-tetraene-49,50,51,52,53-pentone (I-39)

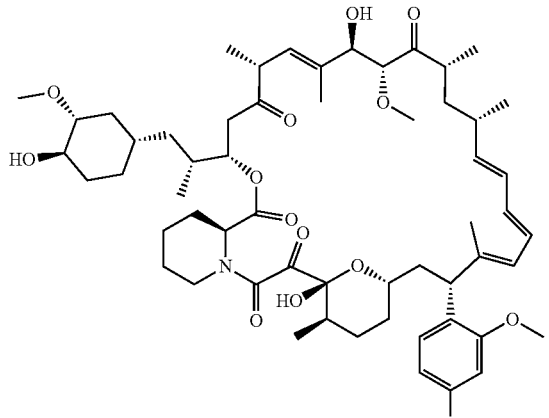

I-37

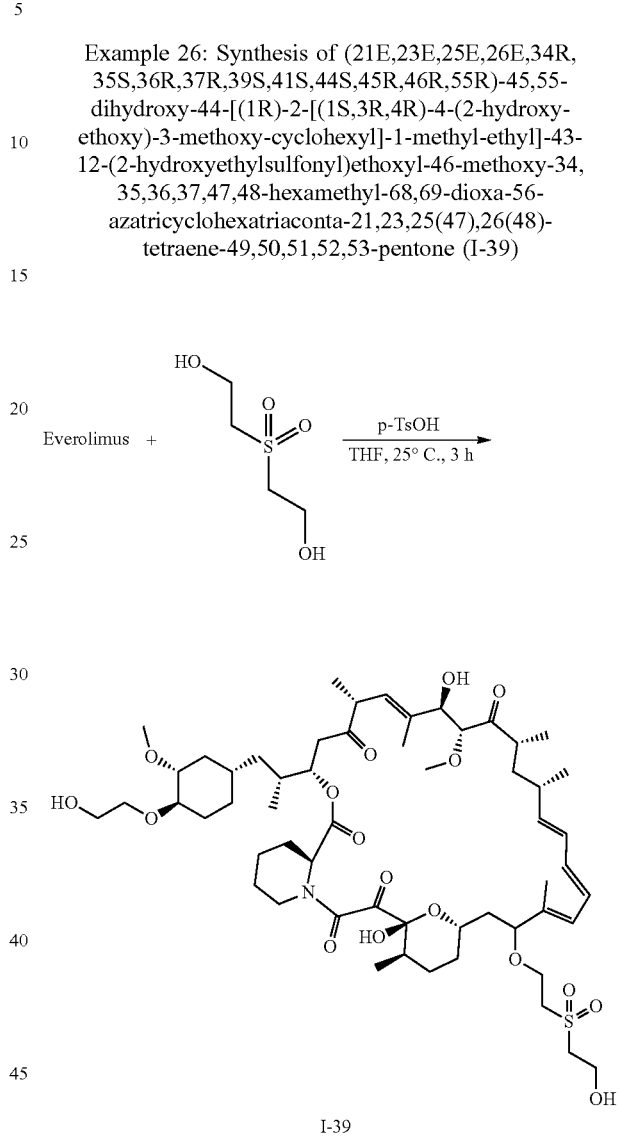

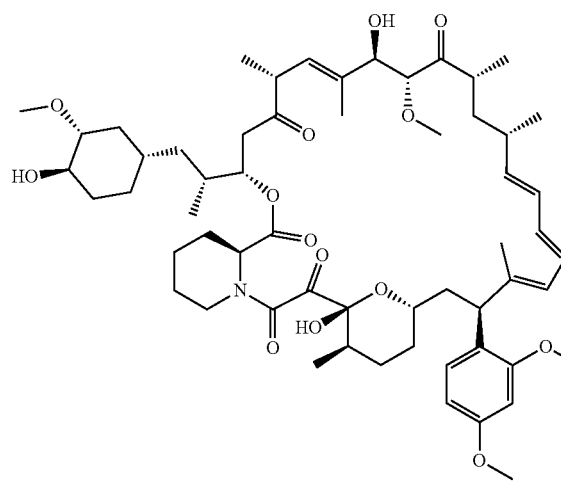

I-38

I-39

To a solution of rapamycin (0.2 g, 0.22 mmol) in DCM (10 mL) was added TFA (0.24 mL) at −40° C. under N2. The reaction was stirred for 10 min, then 1,3-dimethoxybenzene (0.15 g, 1.09 mmol) was added and the resulting solution was stirred at −40° C. for 1 h then poured into a mixture of EtOAc (30 mL) and ice cold NaHCO₃ aqueous solution (50 mL). The organic layer was washed with water (30 mL) and brine (30 mL), dried over Na₂SO₄, filtered and concentrated. The residue was purified via reverse-phase chromatography (70% CH₃CN in water) to provide I-37 (0.05 g, 22.4% yield) and I-38 (0.1 g, 45% yield) as white solids.

I-37: ESI-MS (EI⁺, m/z): 1042.0[M+Na]⁺. ¹H NMR (400 MHz, CDCl₃) δ7.03 (t, J=8.5 Hz, 1H), 6.50-6.17 (m, 5H), 5.83-5.67 (m, 1H), 5.58-5.47 (m, 1H), 5.42-5.15 (m, 3H), 4.12 (d, J=1.4 Hz, 1H), 4.02 (dd, J=10.7, 4.6 Hz, 1H), 3.92-3.56 (m, 13H), 3.49-3.23 (m, 12H), 3.00-2.76 (m, 2H), 2.66 (dd, J=15.8, 7.0 Hz, 2H), 2.29 (ddd, J=42.8, 14.5, 7.7 Hz, 2H), 2.15-1.88 (m, 9H), 1.71-1.23 (m, 13H), 1.23-0.79 (m, 18H), 0.66 (q, J=12.0, 24.0 Hz, 1H).

I-38: ESI-MS (EI⁺, m/z): 1042.1 [M+Na]⁺. ¹H NMR (400 MHz, CDCl₃) δ56.99-6.87 (m, 1H), 6.52-5.96 (m, 6H),

To a solution of 2-(2-hydroxyethylsulfonyl)ethanol (0.4 g, 2.61 mmol) and everolimus (0.25 g, 0.26 mmol) in THF (15 mL) added 4-methylbenzenesulfonic acid (0.22 g, 1.3 mmol) at 0° C. and the resulting mixture stirred at 25° C. for 3 h under N₂. The reaction was then poured into ice cold NaHCO₃ aqueous solution and extracted with DCM (20 mL×3). The combined organic layers were washed with water (30 mL) and brine (30 mL), then dried, concentrated and purified via reverse phase chromatography (CH₃CN/H₂O=62:38) to afford I-39 (40 mg, 14% yield) as a white solid. ESI-MS (EI⁺, m/z): 1102.0 [M+Na]⁺. ¹H NMR (400 MHz, CDCl₃) δ 6.46-5.91 (m, 4H), 5.62-5.06 (m, 4H), 4.97 (d, J=14.1 Hz, 1H), 4.18 (dd, J=28.5, 23.3 Hz, 4H), 3.98-3.52 (m, 9H), 3.50-2.98 (m, 17H), 2.90 (s, 1H), 2.65 (ddd, J=22.8, 16.7, 8.6 Hz, 3H), 2.44-1.90 (m, 6H), 1.88-1.67 (m, 11H), 1.53-1.15 (m, 10H), 1.15-0.63 (m, 19H).

Example 27: Synthesis of (21E,23E,25E,26E,32R, 33S,34R,35R,37S,39S,42S,43R,44R,53R)-43,53-dihydroxy-41-[2-(2-hydroxyethylsulfonyl)ethoxy]-42-[(1R)-2-[(1S,3R,4R)-4-hydroxy-3-methoxy-cyclohexyl]-1-methyl-ethyl]-44-methoxy-32,33,34,35,45,46-hexamethyl-66,67-dioxa-54-azatricyclohexatriaconta-21,23,25(45),26(46)-tetraene-47,48,49,50,51-pentone (I-40)

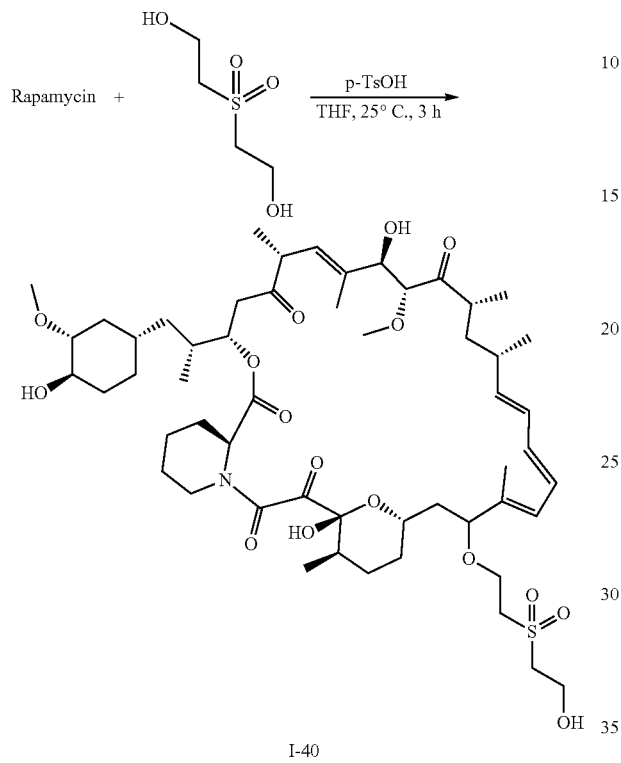

I-40

To a solution of rapamycin (0.2 g, 0.22 mmol) and 4-methylbenzenesulfonic acid (0.21 g, 1.09 mmol) in THF (10 mL) was added 2-(2-hydroxyethylsulfonyl) ethanol (0.34 g, 2.19 mmol). The resulting solution was stirred at 25° C. for 3 h then poured into ice cold NaHCO$_3$ aqueous solution (50 mL), extracted with EtOAc (50 mL×2), dried over Na$_2$SO$_4$, filtered and concentrated. The residue was then purified by reverse-phase chromatography (CH$_3$CN/H$_2$O=65:35) to provide I-40 (40 mg, 17.6% yield) as a white solid. ESI-MS (EI$^+$, m/z): 1058.1 [M+Na]$^+$. $^1$H NMR (400 MHz, CDCl$_3$) δ 6.55-5.91 (m, 4H), 5.63-5.11 (m, 4H), 4.95 (s, 1H), 4.17 (dd, J=27.0, 21.4 Hz, 4H), 3.98-3.51 (m, 5H), 3.48-3.13 (m, 14H), 3.03-2.52 (m, 6H), 2.38-1.90 (m, 7H), 1.90-1.67 (m, 11H), 1.54-1.17 (m, 10H), 1.14-0.79 (m, 18H), 0.71-0.63 (m, 1H).

Example 28: Synthesis of (26E,28E,30E,31E,38R, 39S,40R,41R,43S,45S,48S,49S,50R,59R)-49,59-dihydroxy-48-[(1R)-2-[(1S,3R,4R)-4-hydroxy-3-methoxy-cyclohexyl]-1-methyl-ethyl]-50-methoxy-47-[[3-(2-methoxyethoxy)phenyl]methoxy]-38,39,40,41,51,52-hexamethyl-69,70-dioxa-60-azatricyclohexatriaconta-26,28,30(51),31(52)-tetraene-53,54,55,56,57-pentone (I-41)

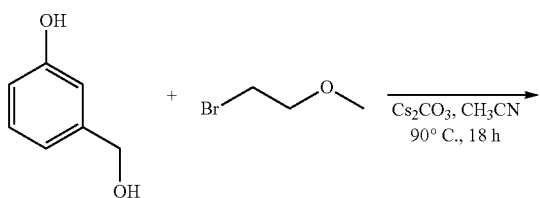

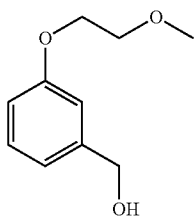

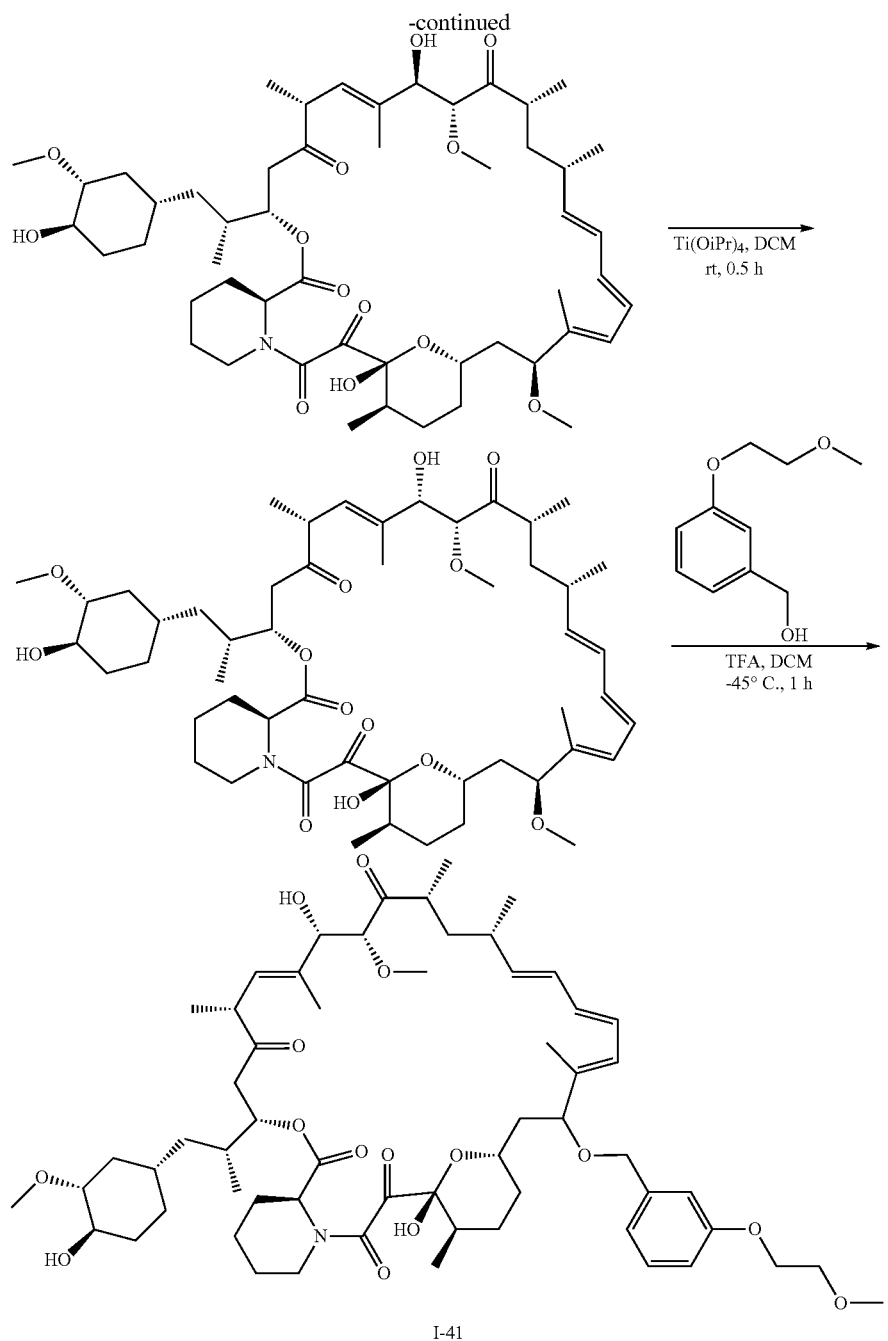

I-41

Step 1: [3-(2-methoxyethoxy)phenyl]methanol: A mixture of 3-(hydroxymethyl)phenol (2 g, 16.11 mmol, 1.72 mL), 1-bromo-2-methoxy-ethane (2.69 g, 19.33 mmol, 1.82 mL) and $Cs_2CO_3$ (7.87 g, 24.17 mmol) in $CH_3CN$ (10 mL) was stirred at 90° C. for 18 h. The reaction mixture was then concentrated and purified via silica gel chromatography (DCM:MeOH=10:1) to provide [3-(2-methoxyethoxy)phenyl]methanol (2.02 g, 69% yield) as a yellow oil. LC-MS ($EI^+$, m/z): 183.1 $[M+H]^+$; $^1H$ NMR (400 MHz, $CDCl_3$) δ7.26 (dd, J=8.9, 6.8 Hz, 1H), 6.93 (d, J=7.5 Hz, 2H), 6.94-6.81 (m, 1H), 4.65 (d, J=3.1 Hz, 2H), 4.12 (dd, J=5.4, 4.0 Hz, 2H), 3.81-3.70 (m, 2H), 3.45 (s, 3H), 1.90 (s, 1H).

Step 2: (22E,24E,26E,27E,29R,30S,31R,32R,34S,36S, 38S,39S,40S,41R,50R)-40,50-dihydroxy-39-[(1R)-2-[(1S, 3R,4R)-4-hydroxy-3-methoxy-cyclohexyl]-1-methyl-ethyl]-38,41-dimethoxy-29,30,31,32,42,43-hexamethyl-60, 61-dioxa-51-azatricyclohexatriaconta-22,24,26(42),27(43)-tetraene-44,45,46,47,48-pentone. To a solution of rapamycin (2 g, 2.19 mmol) in DCM (140 mL) was added $Ti(OiPr)_4$ (1.87 g, 6.56 mmol, 1.94 mL) dropwise at room temperature. The reaction mixture turned pale yellow. After 30 minutes, the solution was poured into a separatory funnel containing a heterogeneous mixture of 1N HCl and EtOAc. The organic layer was sequentially washed with saturated aqueous $NaHCO_3$, $H_2O$, brine, dried over $Na_2SO_4$, filtered and concentrated under vacuum. The resulting residue was purified via silica gel chromatography (DCM:MeOH=15:1) to give the crude product (22E,24E,26E,27E,29R,30S,31R, 32R,34S,36S,38S,39S,40S,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (1.82 g, 91% yield) as a yellow solid. LC-MS (EI+, m/z): 937.1 [M+Na]+.

Step 3: (26E,28E,30E,31E,38R,39S,40R,41R,43S,45S,48S,49S,50R,59R)-49,59-dihydroxy-48-[(1R)-2-[(1S,3R,4R)-4-hydroxy-3-methoxy-cyclohexyl]-1-methyl-ethyl]-50-methoxy-47-[[3-(2-methoxyethoxy)phenyl]methoxy]-38,39,40,41,51,52-hexamethyl-69,70-dioxa-60-azatricyclohexatriaconta-26,28,30(51),31(52)-tetraene-53,54,55,56,57-pentone: To a solution of (22E,24E,26E,27E,29R,30S,31R,32R,34S,36S,38S,39S,40S,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (0.3 g, 0.33 mmol) in DCM (10 mL) was added 2,2,2-trifluoroacetic acid (0.75 g, 6.56 mmol, 0.5 mL) at −45° C. and the mixture stirred for 10 minutes. [3-(2-methoxyethoxy) phenyl]methanol (0.12 g, 0.66 mmol) in DCM (2 mL) was added and the mixture stirred at −45° C. for 1 h. The reaction was treated with aq.NaHCO$_3$ (50 mL) and extracted with DCM (2×30 mL). The combined organic layers were concentrated and the residue purified via silica gel chromatography (DCM:MeOH=10:1) to provide crude product which was further purified by reverse-phase chromatography (CH$_3$CN:H$_2$O=7.5:2.5) to provide I-41 (31 mg, 9% yield) as a white solid. LC-MS (EI+, m/z): 1087.0 [M+Na]+. $^1$H NMR (400 MHz, CDCl$_3$) δ 7.22-7.27 (m, 1H), 6.81-7.07 (m, 3H), 5.93-6.45 (m, 4H), 5.12-5.68 (m, 4H), 4.08-4.66 (m, 5H), 3.57-4.02 (m, 5H), 3.33-3.50 (m, 13H), 3.06-3.32 (m, 2H), 2.83-3.01 (m, 2H), 2.50-2.78 (m, 3H), 1.88-2.41 (m, 4H), 1.66-1.82 (m, 10H), 1.18-1.47 (m, 10H), 0.79-1.16 (m, 22H), 0.61-0.75 (m, 1H).

Example 29: Synthesis of methyl N-[(22E,24E,26E,27E,29R,30S,31R,32R,34S,36S,39S,40R,41R,51R)-40,51-dihydroxy-39-[(1R)-2-[(1S,3R,4R)-4-hydroxy-3-methoxy-cyclohexyl]-1-methyl-ethyl]-41-methoxy-29,30,31,32,42,43-hexamethyl-44,45,46,47,48-pentaoxo-63,64-dioxa-53-azatricyclohexatriaconta-22,24,26(42),27(43)-tetraen-38-yl]carbamate (I-42), methyl N-[(22E,24E,26E,27E,29R,30S,31R,32R,34S,36S,38R,39S,40R,41R,51R)-40,51-dihydroxy-39-[(1R)-2-[(1S,3R,4R)-4-hydroxy-3-methoxy-cyclohexyl]-1-methyl-ethyl]-41-methoxy-29,30,31,32,42,43-hexamethyl-44,45,46,47,48-pentaoxo-63,64-dioxa-53-azatricyclohexatriaconta-22,24,26(42),27(43)-tetraen-38-yl]carbamate (I-43), and methyl N-[(22E,24E,26E,27E,29R,30S,31R,32R,34S,36S,38S,39S,40R,41R,51R)-40,51-dihydroxy-39-[(1R)-2-[(1S,3R,4R)-4-hydroxy-3-methoxy-cyclohexyl]-1-methyl-ethyl]-41-methoxy-29,30,31,32,42,43-hexamethyl-44,45,46,47,48-pentaoxo-63,64-dioxa-53-azatricyclohexatriaconta-22,24,26(42),27(43)-tetraen-38-yl]carbamate (I-44)

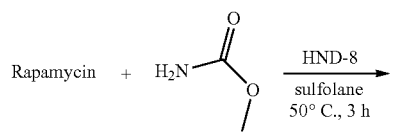

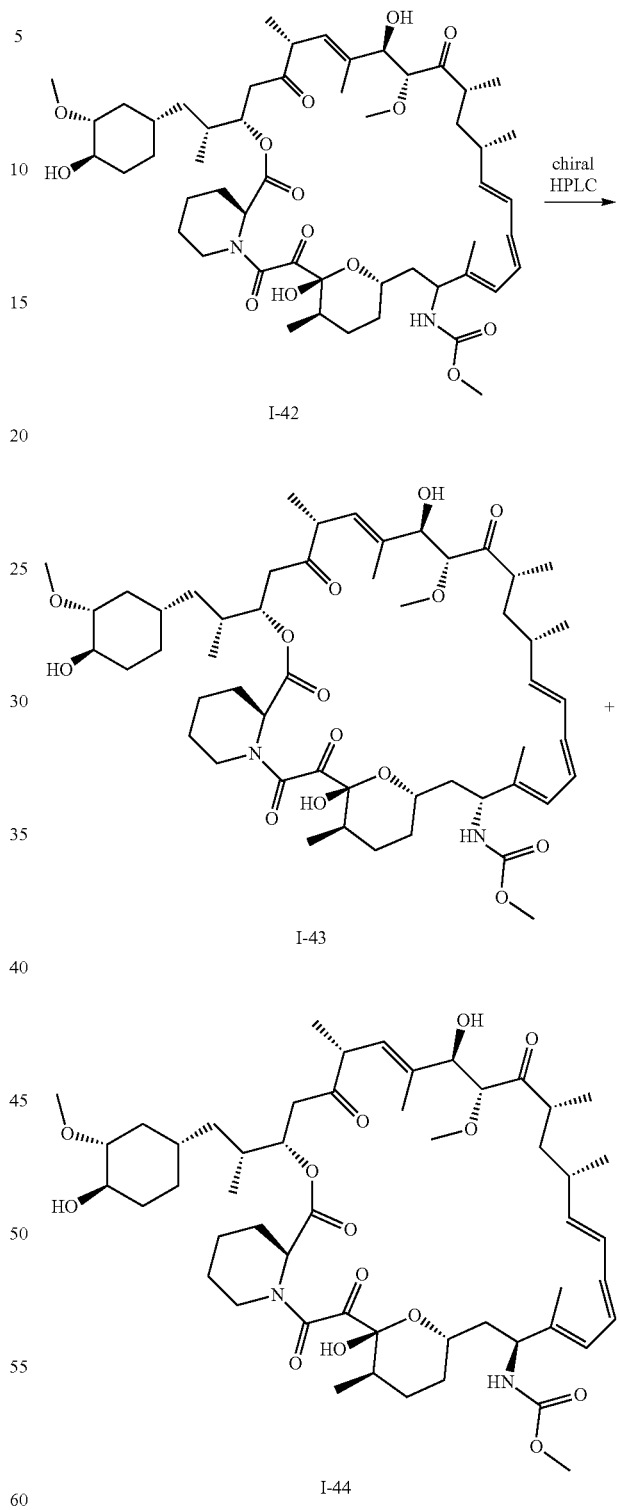

Step 1: Synthesis of methyl N-[(22E,24E,26E,27E,29R,30S,31R,32R,34S,36S,39S,40R,41R,51R)-40,51-dihydroxy-39-[(1R)-2-[(1S,3R,4R)-4-hydroxy-3-methoxy-cyclohexyl]-1-methyl-ethyl]-41-methoxy-29,30,31,32,42,43-hexamethyl-44,45,46,47,48-pentaoxo-63,64-dioxa-53-azatricyclohexatriaconta-22,24,26(42),27(43)-tetraen-38- yl]carbamate (I-42): Rapamycin (0.5 g, 0.55 mmol) and methyl carbamate (0.62 g, 8.2 mmol) were dissolved in sulfolane (10 mL) under an argon atmosphere. The mixture was heated to 50° C. and HND-8 (0.1 g) was added. The mixture was stirred for a further 3 h at 50° C. then diluted with EtOAc (20 mL) and poured into water (40 mL). The organic layer was washed with water (50 mL×5), brine (30 mL) then dried over anhydrous $Na_2SO_4$, filtered and concentrated. The resulting residue was purified via reverse-phase chromatography (65% $CH_3CN$ in water) to obtain I-42 (0.24 g, 45% yield) as a white solid. ESI-MS (EI$^+$, m/z): 979.5 [M+Na]$^+$; $^1$H NMR (400 MHz, CDCl$_3$): δ 6.29-5.95 (m, 4H), 5.33-5.05 (m, 4H), 4.81-4.73 (m, 1H), 4.30-4.18 (m, 2H), 3.70-3.58 (m, 4H), 3.33-3.25 (m, 8H), 2.99-2.85 (m, 2H), 2.66-2.60 (m, 2H), 2.44-1.92 (m, 7H), 1.73-1.48 (m, 20H), 1.42-1.15 (m, 8H), 0.99-0.82 (m, 16H), 0.60-0.54 (m, 1H).

Step 2: Synthesis of methyl N-[(22E,24E,26E,27E,29R,30S,31R,32R,34S,36S,38S,39S,40R,41R,51R)-40,51-dihydroxy-39-[(1R)-2-[(1S,3R,4R)-4-hydroxy-3-methoxy-cyclohexyl]-1-methyl-ethyl]-41-methoxy-29,30,31,32,42,43-hexamethyl-44,45,46,47,48-pentaoxo-63,64-dioxa-53-azatricyclohexatriaconta-22,24,26(42),27(43)-tetraen-38-yl]carbamate (I-43) and Methyl N-[(22E,24E,26E,27E,29R,30S,31R,32R,34S,36S,38R,39S,40R,41R,51R)-40,51-dihydroxy-39-[(1R)-2-[(1S,3R,4R)-4-hydroxy-3-methoxy-cyclohexyl]-1-methyl-ethyl]-41-methoxy-29,30,31,32,42,43-hexamethyl-44,45,46,47,48-pentaoxo-63,64-dioxa-53-azatricyclohexatriaconta-22,24,26(42),27(43)-tetraen-38-yl]carbamate (I-44): 0.2 g of methyl N-[(22E,24E,26E,27E,29R,30S,31R,32R,34S,36S,39S,40R,41R,51R)-40,51-dihydroxy-39-[(1R)-2-[(1S,3R,4R)-4-hydroxy-3-methoxy-cyclohexyl]-1-methyl-ethyl]-41-methoxy-29,30,31,32,42,43-hexamethyl-44,45,46,47,48-pentaoxo-63,64-dioxa-53-azatricyclohexatriaconta-22,24,26(42),27(43)-tetraen-38-yl]carbamate was separated via chiral HPLC and then purified by silica gel chromatography (hexane:DCM: EtOAc:MeOH from 3:3:1:0 to 3:3:1:0.5) which provided I-43 (37 mg, 18% yield) and I-44 (53 mg, 26% yield) as a white solid.

Chiral Separation Method:

| Column: | CHIRALPAK IC |
|---|---|
| Column size: | 5.0 cm I.D. × 25 cm L, 10 μm |
| Sample solution: | 2 mg/ml in Mobile phase |
| Injection: | 10 ml |
| Mobile phase: | Hexane/EtOH = 60/40 (V/V) |
| Flow rate: | 60 ml/min |
| Wave length: | UV 254 nm |
| Temperature: | 35° C. |

I-43: ESI-MS (EI$^+$, m/z): 979.0 [M+Na]$^+$; $^1$H NMR (500 MHz, CDCl3) δ 6.42-5.90 (m, 4H), 5.61-4.89 (m, 5H), 4.76 (d, J=8.6 Hz, 1H), 4.55-4.10 (m, 3H), 3.91-3.16 (m, 16H), 2.97-2.53 (m, 5H), 2.39-1.69 (m, 16H), 1.52-1.17 (m, 11H), 1.16-0.78 (m, 18H), 0.66 (q, J=15.0, 25.0 Hz, 1H).

I-44: ESI-MS (EI$^+$, m/z): 979.0 [M+Na]$^+$; $^1$H NMR (500 MHz, CDCl$_3$) δ 6.41-5.97 (m, 4H), 5.37 (dd, J=16.7, 9.8 Hz, 2H), 5.18 (dd, J=55.6, 4.4 Hz, 2H), 4.87 (d, J=9.4 Hz, 1H), 4.50-4.16 (m, 3H), 3.98 (dd, J=21.3, 7.1 Hz, 2H), 3.65 (s, 4H), 3.42-3.21 (m, 9H), 3.06-2.87 (m, 2H), 2.76-2.64 (m, 2H), 2.58-2.42 (m, 2H), 2.25 (dd, J=27.6, 10.2 Hz, 2H), 2.19-1.94 (m, 7H), 1.67-1.13 (m, 19H), 1.11-0.78 (m, 18H), 0.63 (q, J=15.0, 25.0 Hz, 1H).

Example 30: Synthesis of (25E,27E,29E,30E,37R,38S,39R,40R,42S,44S,45S,47S,48R,49R,58R)-48,58-dihydroxy-45-[4-(2-hydroxyethoxy)-2-methoxy-phenyl]-47-[(1R)-2-[(1S,3R,4R)-4-hydroxy-3-methoxy-cyclohexyl]-1-methyl-ethyl]-49-methoxy-37,38,39,40,50,51-hexamethyl-69,70-dioxa-59-azatricyclohexatriaconta-25,27,29(50),30(51)-tetraene-52,53,54,55,56-pentone (I-66) and (25E,27E,29E,30E,37R,38S,39R,40R,42S,44S,45R,47S,48R,49R,58R)-48,58-dihydroxy-45-[4-(2-hydroxyethoxy)-2-methoxy-phenyl]-47-[(1R)-2-[(1S,3R,4R)-4-hydroxy-3-methoxy-cyclohexyl]-1-methyl-ethyl]-49-methoxy-37,38,39,40,50,51-hexamethyl-69,70-dioxa-59-azatricyclohexatriaconta-25,27,29(50),30(51)-tetraene-52,53,54,55,56-pentone (I-67)

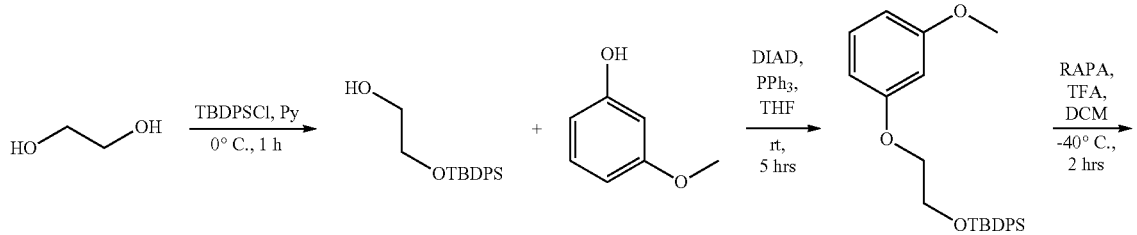

-continued
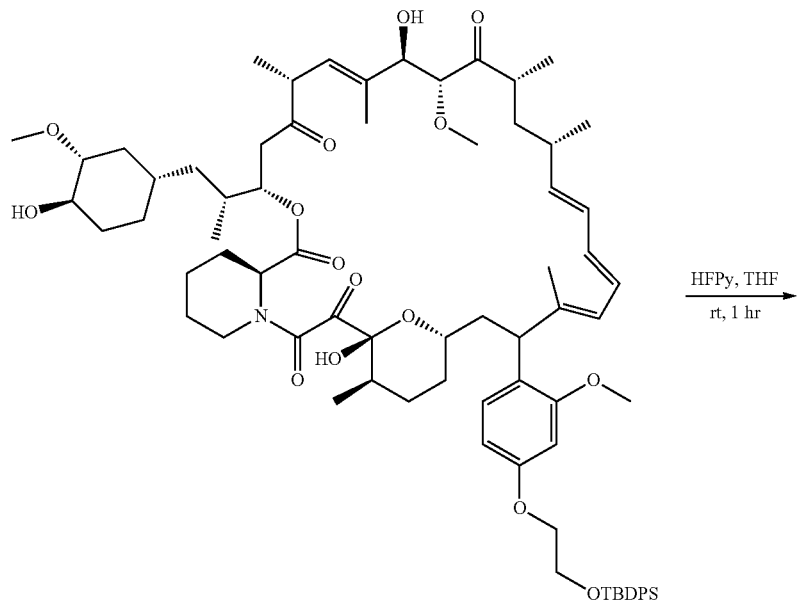
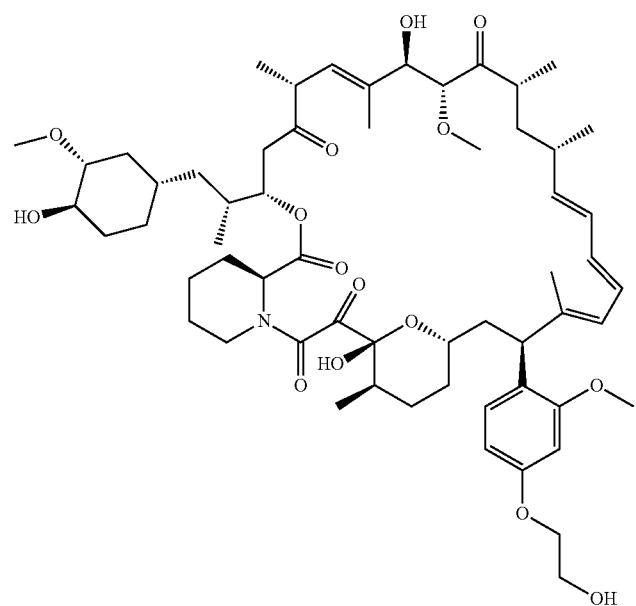
I-66

-continued

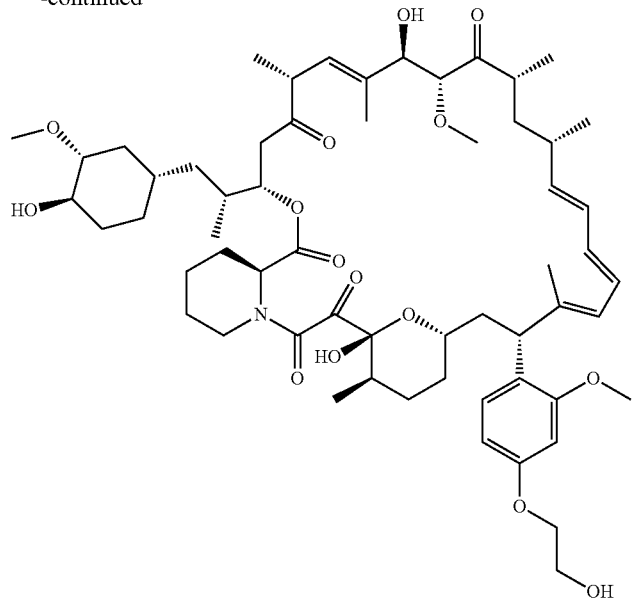

I-67

Step 1: 2-[tert-butyl (diphenyl) silyl] oxyethanol. To a solution of ethylene glycol (54.16 g, 872.65 mmol) in pyridine (47.13 g, 595.84 mmol) was added tert-butyl-chloro-diphenyl-silane (30 g, 109.15 mmol) at 0° C., the resulting solution was stirred at rt for 1 h then poured into 2 M HCl aqueous (600 mL) and extracted with EtOAc (500 mL×2). The organic layer was washed with water (500 mL), brine (500 mL), dried over $Na_2SO_4$, filtered, concentrated and the resulting material was purified via silica gel chromatography (EtOAc:PE=1:8) to provide the titled compound (23.42 g, 69% yield) as a colorless liquid. ESI-MS (EI+, m/z): 323.0 [M+Na]$^+$. $^1$H NMR (400 MHz, $CDCl_3$) δ 7.74-7.63 (m, 4H), 7.47-7.34 (m, 6H), 3.77 (dd, J=5.6, 3.7 Hz, 2H), 3.70-3.63 (m, 2H), 1.07 (s, 9H).

Step 2: tert-butyl-[2-(3-methoxyphenoxy) ethoxy]-diphenyl-silane: To a solution of 3-methoxyphenol (3 g, 24.17 mmol) and 2-[tert-butyl(diphenyl)silyl]oxyethanol (14.52 g, 48.33 mmol) in THF (50 mL) was added DIAD (6.35 g, 31.42 mmol) and $PPh_3$ (8.24 g, 31.42 mmol) at 25° C. The resulting mixture was stirred at room temperature for 5 h. The mixture was then poured into ice-cold saturated $NaHCO_3$ (60 mL) and extracted with EtOAc (100 mL). The organic layer was washed with water (50 mL) and brine (50 mL) then dried over anhydrous $Na_2SO_4$, filtered and concentrated to obtain crude material. This was purified via silica gel chromatography (PE:acetone=9:1) to provide the titled compound (5.0 g, 51% yield) as a colorless liquid. ESI-MS (EI+, m/z): 407.0 [M+H]$^+$, 429.0 [M+Na]$^+$.

Step 3: (38E,40E,42E,43E,52R,53S,54R,55R,57S,59S,62S,63R,64R,73R)-60-[4-[2-[tert-butyl(diphenyl)silyl]oxyethoxy]-2-methoxy-phenyl]-63,73-dihydroxy-62-[(1R)-2-[(1S,3R,4R)-4-hydroxy-3-methoxy-cyclohexyl]-1-methyl-ethyl]-64-methoxy-52,53,54,55,65,66-hexamethyl-84,85-dioxa-75-azatricyclohexatriaconta-38,40,42(65),43(66)-tetraene-67,68,69,70,71-pentone. To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (1 g, 1.09 mmol) in DCM (5 mL) was added 2,2,2-trifluoroacetic acid (1.25 g, 10.94 mmol) at −40° C. The mixture was stirred at −40° C. for 10 minutes. Tert-butyl-[2-(3-methoxyphenoxy) ethoxy]-diphenyl-silane (1.33 g, 3.28 mmol) in DCM (0.5 mL) was added and the mixture was stirred at −40° C. for 2 h. The mixture was treated with aqueous $NaHCO_3$ (40 mL) and extracted with EtOAc (30 mL×2). The combined organic layers were concentrated and the residue was purified via reverse-phase chromatography (80% $CH_3CN$ in water) to provide the titled compound (0.7 g, 50% yield) as a white solid. ESI-MS (EI+, m/z): 1311.9 [M+Na]$^+$.

Step 4: (25E,27E,29E,30E,37R,38S,39R,40R,42S,44S,47S,48R,49R,58R)-48,58-dihydroxy-45-[4-(2-hydroxy-ethoxy)-2-methoxy-phenyl]-47-[(1R)-2-[(1S,3R,4R)-4-hydroxy-3-methoxy-cyclohexyl]-1-methyl-ethyl]-49-methoxy-37,38,39,40,50,51-hexamethyl-69,70-dioxa-59-azatricyclohexatriaconta-25,27,29(50),30(51)-tetraene-52,53,54,55,56-pentone. To a solution of (38E,40E,42E,43E,52R,53S,54R,55R,57S,59S,62S,63R,64R,73R)-60-[4-[2-[tert-butyl(diphenyl)silyl]oxyethoxy]-2-methoxy-phenyl]-63,73-dihydroxy-62-[(1R)-2-[(1S,3R,4R)-4-hydroxy-3-methoxy-cyclohexyl]-1-methyl-ethyl]-64-methoxy-52,53,54,55,65,66-hexamethyl-84,85-dioxa-75-azatricyclohexatriaconta-38,40,42(65),43(66)-tetraene-67,68, 69, 70, 71-pentone (700 mg, 0.54 mmol) in THF (5 mL) was added HF.Py (1.10 g, 11.11 mmol). The mixture was stirred at 30° C. for 1 h then treated with aqueous $NaHCO_3$ (40 mL) and extracted with EtOAc (30 mL×2). The combined organic layers were concentrated and the residue purified via reverse-phase chromatography (80% $CH_3CN$ in water) to provide the titled compounds (I-66: 82.1 mg, 14%) and (I-67: 92.6 mg, 16%) as white solids.

I-66: ESI-MS (EI+, m/z): 1072.1 [M+Na]$^+$. $^1$H NMR (400 MHz, $CDCl_3$) δ 6.92 (d, J=8.3 Hz, 1H), 6.52-6.02 (m, 6H), 5.47-5.12 (m, 4H), 4.38-4.16 (m, 2H), 4.06 (d, J=4.8 Hz, 2H), 3.96 (s, 3H), 3.77 (d, J=21.6 Hz, 4H), 3.44-3.31 (m, 9H), 3.28-3.05 (m, 2H), 2.77 (dd, J=68.2, 57.9 Hz, 4H), 2.49-1.92 (m, 8H), 1.90-1.59 (m, 11H), 1.48-1.19 (m, 8H), 1.15-0.79 (m, 22H), 0.65 (d, J=12.0 Hz, 1H).

I-67: ESI-MS (EI+, m/z): 1072.1 [M+Na]$^+$. $^1$H NMR (400 MHz, $CDCl_3$) δ 7.12-6.85 (m, 1H), 6.51-5.97 (m, 6H), 5.59-5.05 (m, 4H), 4.35-3.47 (m, 13H), 3.35 (dt, J=54.4, 26.5 Hz, 10H), 3.06-2.21 (m, 8H), 2.15-1.66 (m, 12H), 1.52-1.18 (m, 12H), 1.15-0.80 (m, 20H), 0.66 (d, J=11.6 Hz, 1H).

Example 31: Synthesis of 2-[[(22E,24E,26E,27E,31R,32S,33R,34R,36S,38S,41S,42R,43R,53R)-42,53-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-46,47,48,49,50-pentaoxo-65,66-dioxa-55-azatricyclohexatriaconta-22,24,26(44),27(45)-tetraen-40-yl]oxy]ethyl N-methylcarbamate (I-68), 2-[[(22E,24E,26E,27E,31R,32S,33R,34R,36S,38S,40S,41S,42R,43R,53R)-42,53-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-46,47,48,49,50-pentaoxo-65,66-dioxa-55-azatricyclohexatriaconta-22,24,26(44),27(45)-tetraen-40-yl]oxy]ethyl N-methylcarbamate (I-81) and 2-[[(22E,24E,26E,27E,31R,32S,33R,34R,36S,38S,40R,41S,42R,43R,53R)-42,53-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-46,47,48,49,50-pentaoxo-65,66-dioxa-55-azatricyclohexatriaconta-22,24,26(44),27(45)-tetraen-40-yl]oxy]ethyl N-methylcarbamate (I-83)

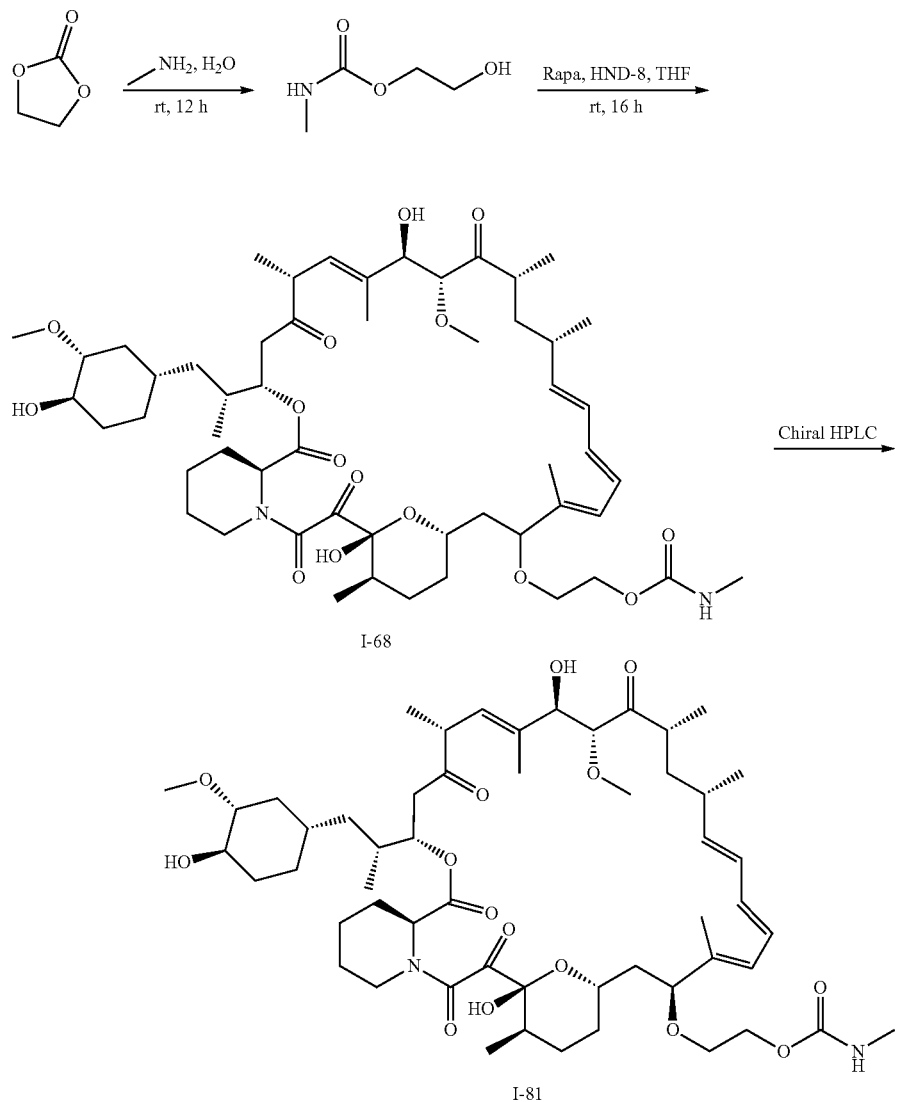

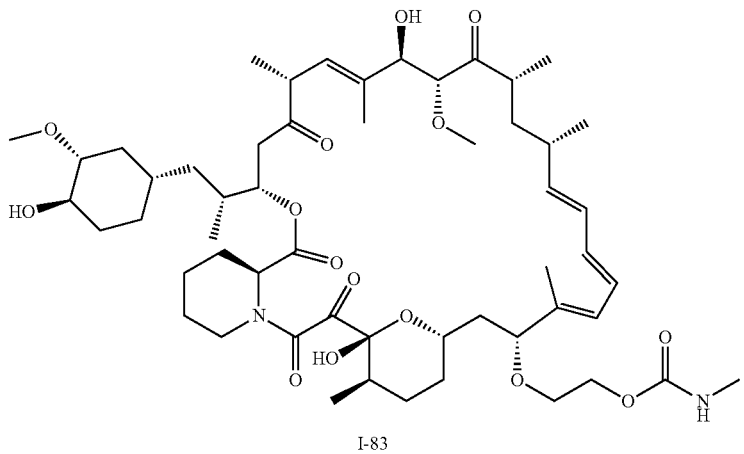

I-83

Step 1: 2-hydroxyethyl N-methylcarbamate. To a solution of 1,3-dioxolan-2-one (17 g, 193.05 mmol) and 1,3-dioxolan-2-one (17 g, 193.05 mmol) in $H_2O$ (100 mL) was added methylamine (22 g, 212.35 mmol) and the resulting solution was stirred at 25° C. for 12 h. The reaction mixture was extracted with EtOAc (200 mL×2) then water layer was freeze dried to give the titled compound (18 g, 78% yield) as a colorless oil. ESI-MS (EI+, m/z): 120.1 $[M+H]^+$.

Step 2: 2-[[(22E,24E,26E,27E,31R,32S,33R,34R,36S, 38S,41S,42R,43R,53R)-42,53-dihydroxy-41-[(1R)-2-[(1S, 3R,4R)-4-hydroxy-3-methoxy-cyclohexyl]-1-methyl-ethyl]-43-methoxy-31,32,33,34,44,45-hexamethyl-46,47, 48,49,50-pentaoxo-65,66-dioxa-55-azatricyclohexatriaconta-22,24,26(44),27(45)-tetraen-40-yl]oxy]ethyl N-methylcarbamate (I-68). Rapamycin (1 g, 1.09 mmol) was dissolved in THF (20 mL), then HND-8 (80 mg, 1.09 mmol) and 2-hydroxyethyl N-methylcarbamate (2.61 g, 21.88 mmol) was added at 0° C. The mixture was stirred at 25° C. for 16 h then extracted with EtOAc (30 mL), washed with water (20 mL), brine (20 mL), dried over anhydrous $Na_2SO_4$, filtered and concentrated. The resulting residue was purified via reverse-phase chromatography (50% to 70% $CH_3CN$ in $H_2O$) to provide the titled compound (178 mg, 16% yield) as a white solid. ESI-MS (EI+, m/z): 1023. $[M+Na]^+$. 1H NMR (400 MHz, CDCl3) δ 6.14 (dddd, J=56.2, 40.8, 20.7, 10.8 Hz, 4H), 5.56-5.05 (m, 4H), 5.02-4.35 (m, 2H), 4.11 (ddd, J=45.3, 40.1, 19.5 Hz, 4H), 3.70 (ddd, J=78.1, 46.8, 35.4 Hz, 3H), 3.33 (ddd, J=48.5, 24.9, 20.0 Hz, 11H), 2.96-2.52 (m, 8H), 2.37-2.23 (m, 2H), 1.99 (d, J=41.7 Hz, 8H), 1.81-1.58 (m, 16H), 1.25 (d, J=24.1 Hz, 6H), 1.04-0.85 (m, 15H), 0.64 (d, J=11.9 Hz, 1H).

Step 3: 2-[[(22E,24E,26E,27E,31R,32S,33R,34R,36S, 38S,40S,41S,42R,43R,53R)-42,53-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-46,47, 48,49,50-pentaoxo-65,66-dioxa-55-azatricyclohexatriaconta-22,24,26(44),27(45)-tetraen-40-yl]oxy]ethyl N-methylcarbamate (I-81) and 2-[[(22E,24E, 26E,27E,31R,32S,33R,34R,36S,38S,40R,41S,42R,43R, 53R)-42,53-dihydroxy-41-[(1R)-2-[(1S,3R,4R)-4-hydroxy-3-methoxy-cyclohexyl]-1-methyl-ethyl]-43-methoxy-31,32, 33,34,44,45-hexamethyl-46,47,48,49,50-pentaoxo-65,66-dioxa-55-azatricyclohexatriaconta-22,24,26(44),27(45)-tetraen-40-yl]oxy]ethyl N-methylcarbamate (I-83). 173 mg of the racemate was separated via chiral HPLC and then purified by silica gel chromatography (hexane:DCM: EtOAc:MeOH=3:3:1:0.4) to provide the titled compounds (I-81:18.9 mg, 11% yield) and (I-83:21.7 mg, 13% yield) as white solids.

Chiral Separation Method:

| Column: | CHIRALPAK IC |
|---|---|
| Column size: | 5.0 cm I.D. × 25 cm L, 10 μm |
| Sample solution: | 0.8 mg/ml in Mobile phase |
| Injection: | 16 ml |
| Mobile phase: | Hexane/EtOH = 50/50(V/V) |
| Flow rate: | 60 ml/min |
| Wave length: | UV 254 nm |
| Temperature: | 35° C. |

I-81: ESI-MS (EI+, m/z): 1023.2 $[M+Na]^+$. 1H NMR (500 MHz, CDCl3) δ 6.42-6.06 (m, 3H), 5.92 (dd, J=31.9, 10.7 Hz, 1H), 5.58-5.05 (m, 4H), 4.72 (d, J=33.2 Hz, 1H), 4.28-4.03 (m, 3H), 3.76 (ddd, J=31.6, 25.3, 21.3 Hz, 3H), 3.60-3.24 (m, 13H), 2.98-2.54 (m, 8H), 2.38-1.87 (m, 7H), 1.84-1.65 (m, 11H), 1.53-1.18 (m, 11H), 1.16-0.82 (m, 18H), 0.71-0.54 (m, 1H).

I-83: ESI-MS (EI+, m/z): 1023.0 $[M+Na]^+$. 1H NMR (400 MHz, CDCl3) δ 6.52-5.84 (m, 4H), 5.61-5.08 (m, 4H), 5.05-4.82 (m, 1H), 4.59-4.02 (m, 4H), 3.95-3.59 (m, 4H), 3.51-3.16 (m, 9H), 2.92 (dd, J=13.5, 6.4 Hz, 2H), 2.84-2.53 (m, 5H), 2.51-2.16 (m, 5H), 2.14-1.92 (m, 4H), 1.65 (dt, J=28.0, 15.6 Hz, 13H), 1.52-1.22 (m, 10H), 1.16-0.80 (m, 18H), 0.71-0.55 (m, 1H).

Example 32: Synthesis of 5-[[(21E,23E,25E,26E, 34R,35S,36R,37R,39S,41S,44S,45R,46R,56R)-45, 56-dihydroxy-44-[(1R)-2-[(1S,3R,4R)-4-(2-hydroxy-ethoxy)-3-methoxy-cyclohexyl]-1-methyl-ethyl]-46-methoxy-34,35,36,37,47,48-hexamethyl-49,50,51, 52,53-pentaoxo-68,69-dioxa-58-azatricyclohexatriaconta-21,23,25(47),26(48)-tetraen-43-yl]oxy]pentanamide (I-69), 5-[[(21E,23E, 25E,26E,34R,35S,36R,37R,39S,41S,43S,44S,45R, 46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-21,23,25(47),26(48)-tetraen-43-yl]oxy]pentanamide (I-79) and 5-[[(21E, 23E,25E,26E,34R,35S,36R,37R,39S,41S,43R,44S, 45R,46R,56R)-45,56-dihydroxy-44-[(1R)-2-[(1S,3R, 4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-21,23,25(47),26(48)-tetraen-43-yl]oxy]pentanamide (I-80)

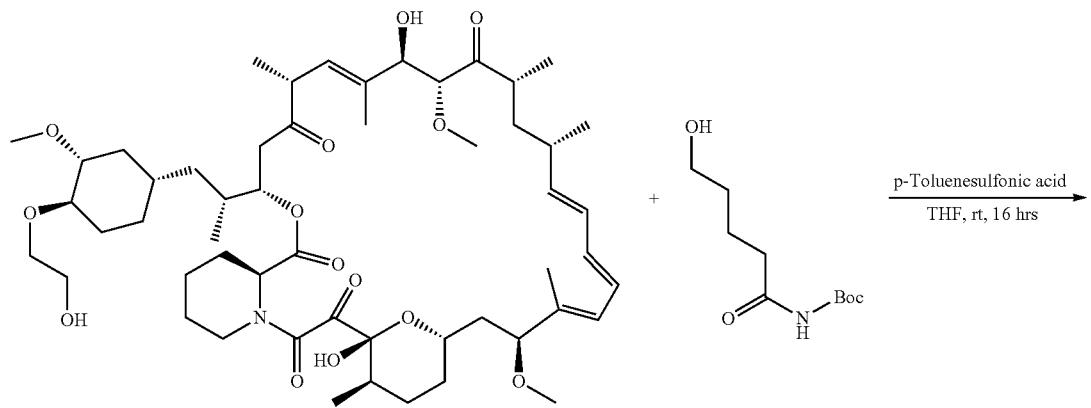

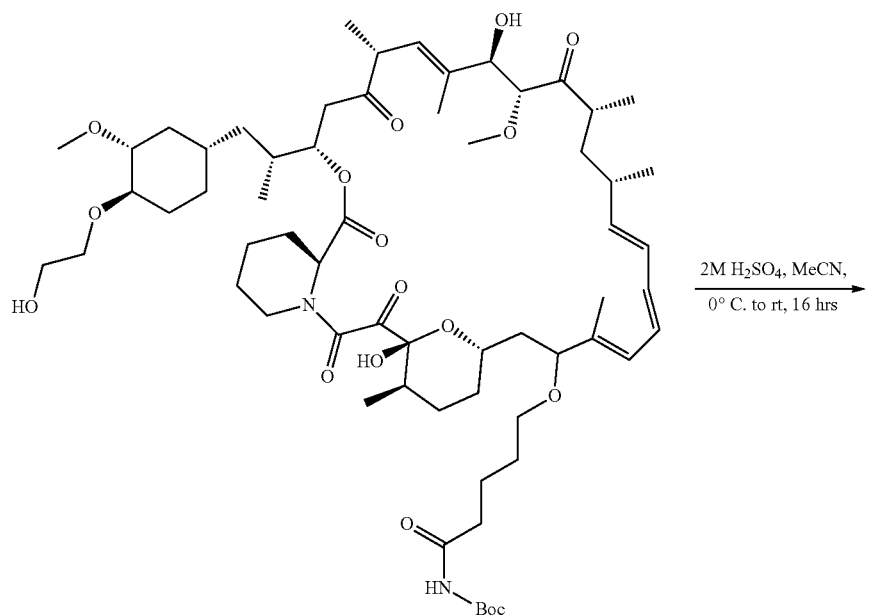

-continued
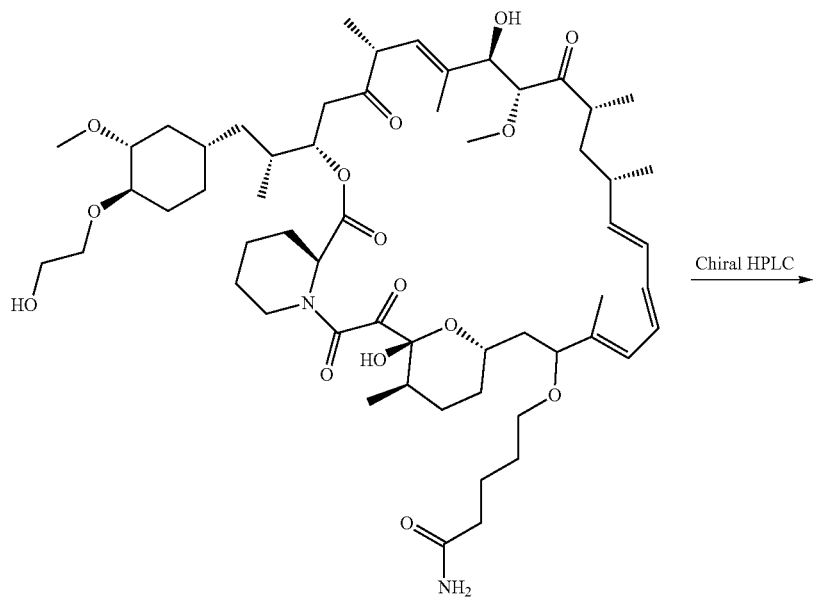
I-69
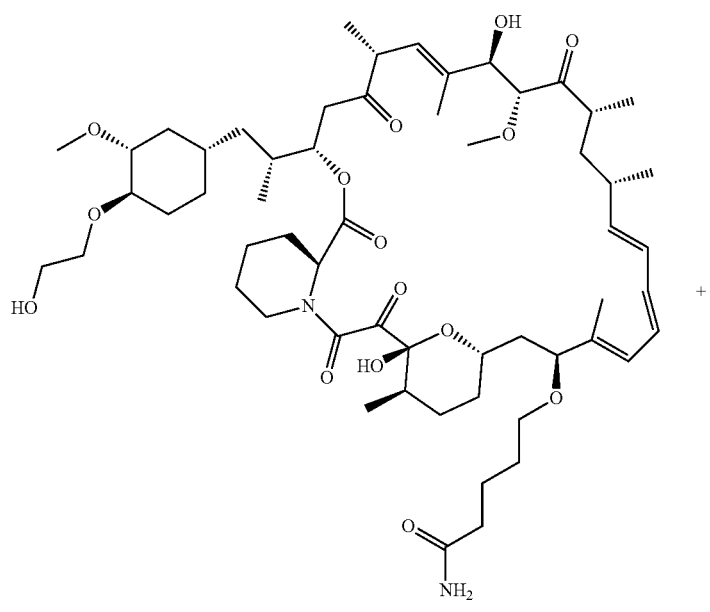
I-79

-continued

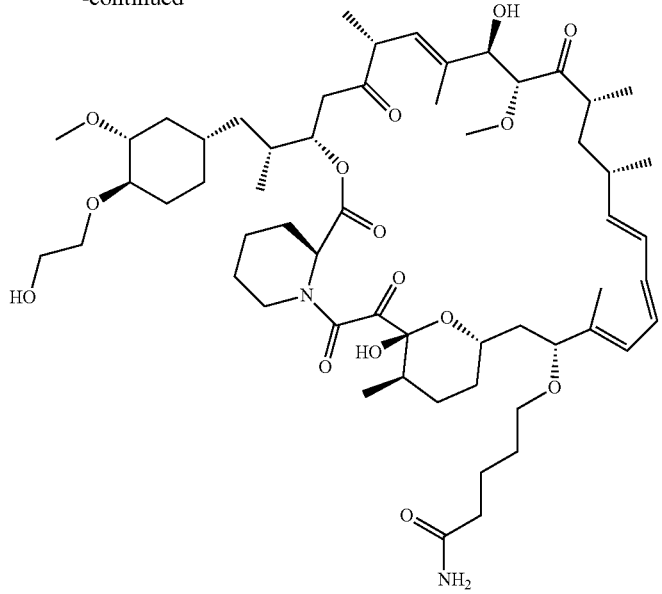

I-80

Step 1: Tert-butyl N-[5-[[(24E,26E,28E,29E,37R,38S, 39R,40R,42S,44S,47S,48R,49R,60R)-48,60-dihydroxy-47-[(1R)-2-[(1S,3R,4R)-4-(2-hydroxyethoxy)-3-methoxy-cyclohexyl]-1-methyl-ethyl]-49-methoxy-37,38,39,40,50,51-hexamethyl-52,53,54,55,56-pentaoxo-74,75-dioxa-63-azatricyclohexatriaconta-24,26,28(50),29(51)-tetraen-46-yl]oxy]pentanoyl]carbamate. To a solution of (22E,24E, 26E,27E,31R,32S,33R,34R,36S,38S,40S,41S,42R,43R, 52R)-42,52-dihydroxy-41-[(1R)-2-[(1S,3R,4R)-4-(2-hydroxyethoxy)-3-methoxy-cyclohexyl]-1-methyl-ethyl]-40,43-dimethoxy-31,32,33,34,44,45-hexamethyl-62,63-dioxa-53-azatricyclohexatriaconta-22,24,26(44),27(45)-tetraene-46,47,48,49,50-pentone (3 g, 3.13 mmol) in THF (20 mL) under $N_2$ was added p-TsOH (5 g, 29.04 mmol) and tert-butyl N-(5-hydroxypentanoyl)carbamate (6.8 g, 31.3 mmol) at 0° C. The resulting mixture was stirred at 0° C. for 0.5 h under $N_2$, then warmed to 30° C. for 16 hr. The reaction was quenched with ice cold $NaHCO_3$ (40 mL), extracted with EtOAc (100 mL×2), washed with brine (80 mL), dried over $Na_2SO_4$, filtered and concentrated. The residue was purified via reverse phase column chromatography (60% $CH_3CN$ in water) to provide the titled compound (370 mg, 10% yield) as a yellow solid. ESI-MS (EI+, m/z): 1165.1 $[M+Na]^+$.

Step 2: 5-[[(21E,23E,25E,26E,34R,35S,36R,37R,39S, 41S,44S,45R,46R,56R)-45,56-dihydroxy-44-[(1R)-2-[(1S, 3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-21,23,25(47),26(48)-tetraen-43-yl]oxy]pentanamide (I-69). To a stirred solution of tert-butyl N-[5-[[(24E,26E,28E,29E,37R,38S,39R,40R,42S,44S,47S, 48R,49R,60R)-48,60-dihydroxy-47-[(1R)-2-[(1S,3R,4R)-4-(2-hydroxyethoxy)-3-methoxy-cyclohexyl]-1-methyl-ethyl]-49-methoxy-37,38,39,40,50,51-hexamethyl-52,53, 54,55,56-pentaoxo-74,75-dioxa-63-azatricyclohexatriaconta-24,26,28(50),29(51)-tetraen-46-yl]oxy]pentanoyl]carbamate (440 mg, 0.38 mmol) in $CH_3CN$ (8 mL) at 0° C. was added $H_2SO_4$ (8 mL, 2M in water). The solution was stirred at rt for 16 h at rt then quenched with ice cold $NaHCO_3$ (40 mL), extracted with EtOAc (100 mL×2), washed with brine (80 mL). dried over $Na_2SO_4$, filtered and concentrated. The residue was purified via reverse phase column chromatography (60% $CH_3CN$ in water) to provide the titled compound (I-69: 70 mg, 17% yield) as a white solid. ESI-MS (EI+, m/z): 1065.1 $[M+Na]^+$. $^1H$ NMR (500 MHz, $CDCl_3$): δ 6.39-6 (m, 4H), 5.41-5.12 (m, 4H), 4.34-4.24 (m, 2H), 3.95-3.91 (m, 1H), 3.79-3.48 (m, 8H), 3.50-2.92 (m, 15H), 2.72-1.93 (m, 11H), 1.73-1.37 (m, 13H), 1.41-0.80 (m, 31H), 0.79-0.67 (m, 1H).

Step 3: 5-[[(21E,23E,25E,26E,34R,35S,36R,37R,39S, 41S,43S,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-21,23,25(47),26(48)-tetraen-43-yl]oxy]pentanamide (I-79) and 5-[[(21E,23E,25E,26E,34R, 35S,36R,37R,39S,41S,43R,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35, 36,37,47,48-hexamethyl-49,50,51,52,53-pentaoxo-68,69-dioxa-58-azatricyclohexatriaconta-21,23,25(47),26(48)-tetraen-43-yl]oxy]pentanamide (I-80). 129 mg of the mixture was separated via chiral HPLC to provide the titled compounds (I-79: 28 mg, 22% yield) and (I-80: 20 mg, 16% yield) as a white solids.

Chiral Separation Method:

| | |
|---|---|
| Column: | CHIRALPAK IC |
| Column size: | 5.0 cm I.D. × 25 cm L, 10 μm |
| Sample solution: | 1.2 mg/ml in Mobile phase |
| Injection: | 10 ml |
| Mobile phase: | Hexane/EtOH = 60/40(V/V) |
| Flow rate: | 60 ml/min |
| Wave length: | UV 254 nm |
| Temperature: | 35° C. |

I-79: ESI-MS (EI+, m/z): 1043.2 $[M+H]^+$, 1065.2$[M+Na]^+$. $^1H$ NMR (500 MHz, $CDCl_3$) δ 6.46-5.96 (m, 4H), 5.46-5.08 (m, 5H), 4.72 (s, 1H), 4.26 (s, 1H), 3.73 (ddd, J=62.4, 34.2, 13.2 Hz, 8H), 3.26 (dd, J=125.6, 53.7 Hz, 10H), 2.75-2.47 (m, 2H), 2.36-1.94 (m, 9H), 1.75 (d, J=13.1 Hz, 12H), 1.50-1.20 (m, 19H), 1.17-0.80 (m, 18H), 0.72-0.63 (m, 1H).

I-80: ESI-MS (EI⁺, m/z): 1065.2[M+Na]⁺. $^1$H NMR (500 MHz, CDCl$_3$) δ 6.41-5.93 (m, 4H), 5.43-5.15 (m, 5H), 4.07 (s, 1H), 3.87-2.99 (m, 23H), 2.96-2.48 (m, 4H), 2.40-1.73 (m, 14H), 1.47-1.19 (m, 20H), 1.16-0.79 (m, 18H), 0.72-0.62 (m, 1H).

Example 33: Synthesis of N-[(22E,24E,26E,27E,31R,32S,33R,34R,36S,38S,40S,41S,42R,43R,52R)-42,52-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-46,47,48,49,50-pentaoxo-65,66-dioxa-54-azatricyclohexatriaconta-22,24,26(44),27(45)-tetraen-40-yl]-2-methoxy-ethanesulfonamide (I-70) and N-[(22E,24E,26E,27E,31R,32S,33R,34R,36S,38S,40R,41S,42R,43R,52R)-42,52-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-46,47,48,49,50-pentaoxo-65,66-dioxa-54-azatricyclohexatriaconta-22,24,26(44),27(45)-tetraen-40-yl]-2-methoxy-ethanesulfonamide (I-71)

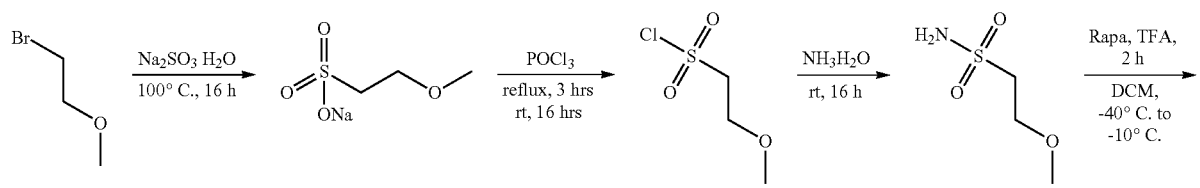

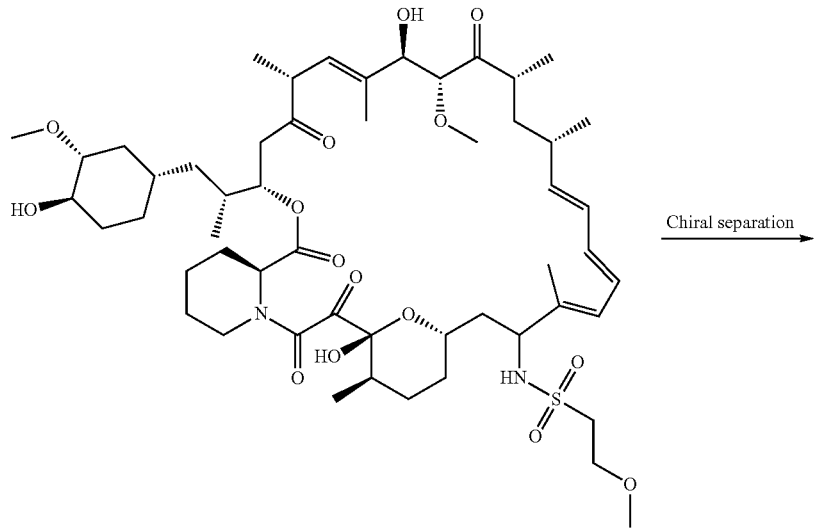

-continued

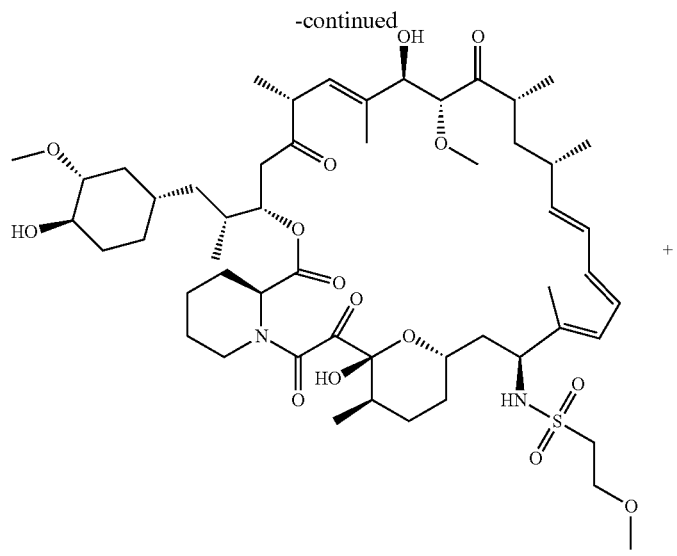

I-70

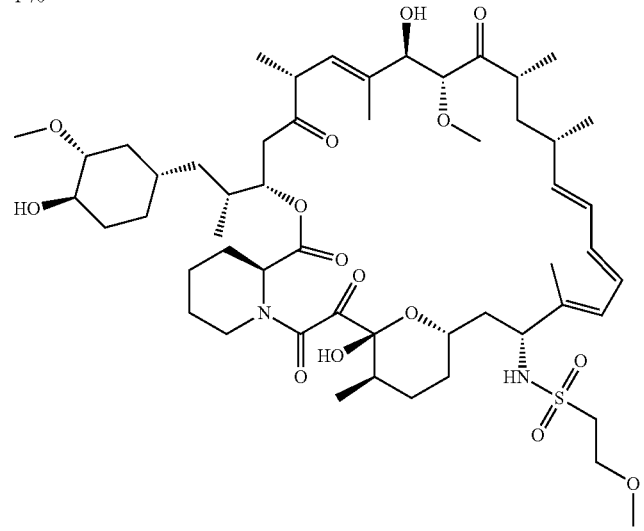

I-71

Step 1: Sodium 2-methoxyethane-1-sulfonate. A solution of 1-bromo-2-methoxy-ethane (5 g, 35.97 mmol) and $Na_2SO_3$ (4.76 g, 37.77 mmol) in $H_2O$ (50 mL) was stirred at 100° C. for 16 h. The solution was then cooled to rt, concentrated and triturated with $Et_2O$ (20 mL) to provide 2-methoxyethylsulfonyloxysodium (9 g, 93% yield) as a white solid. $^1H$ NMR (500 MHz, DMSO-$d_6$) δ 3.55 (t, J=10.8 Hz, 2H), 3.21 (s, 3H), 2.72 (d, J=10.8 Hz, 2H).

Step 2: 2-methoxyethane-1-sulfonyl chloride. A solution of 2-methoxyethylsulfonyloxysodium (1 g, 6.17 mmol) in $POCl_3$ (5 mL) was stirred at 110° C. for 3 h, then at rt for 16 h. The solution was concentrated and ice water (30 mL) was added. This was extracted with EtOAc (50 mL), washed with brine (30 mL), dried over anhydrous $Na_2SO_4$, filtered and concentrated to provide 2-methoxyethanesulfonyl chloride (0.4 g, 40% yield) as a yellow oil. $^1H$ NMR (500 MHz, $CDCl_3$): δ 4.06-3.92 (m, 4H), 3.43 (s, 3H).

Step 3: 2-methoxyethane-1-sulfonamide. A solution of 2-methoxyethanesulfonyl chloride (4.5 g, 28.37 mmol,) in $NH_3.H_2O$ (3 mL) was stirred at rt for 16 h. The solution was concentrated by lyophilization. The resulting material was dissolved in DCM (30 mL), filtered and concentrated, then purified via reverse phase chromatography (5% $CH_3CN$ in water) to provide 2-methoxyethanesulfonamide (1.8 g, 45.6% yield) as a brown oil. $^1H$ NMR (500 MHz, $CDCl_3$): δ 5.04 (s, 2H), 3.86 (t, J=6.0 Hz, 2H), 3.42 (s, 3H), 3.40-3.37 (m, 2H).

Step 4: N-[(22E,24E,26E,27E,31R,32S,33R,34R,36S, 38S,41S,42R,43R,52R)-42,52-dihydroxy-41-[(1R)-2-[(1S, 3R,4R)-4-hydroxy-3-methoxy-cyclohexyl]-1-methyl-ethyl]-43-methoxy-31,32,33,34,44,45-hexamethyl-46,47, 48,49,50-pentaoxo-65,66-dioxa-54-azatricyclohexatriaconta-22,24,26(44),27(45)-tetraen-40-yl]-2-methoxy-ethanesulfonamide. To a solution of rapamycin (400 mg, 0.44 mmol) in DCM (5 mL) was added TFA (250 mg, 2.19 mmol) at −40° C. under argon, after 5 min 2-methoxyethanesulfonamide (609 mg, 4.38 mmol) was added. The resulting mixture was stirred at −10° C. for 2 h under $N_2$ then quenched with ice cold $NaHCO_3$ (20 mL) aqueous solution, extracted with DCM (50 mL×2), washed with brine (50 mL), dried over $Na_2SO_4$, filtered and concentrated. The residue was purified by reverse phase column chromatography (80% CH₃CN in water) to provide the titled compound (160 mg, 36% yield) as a white solid. ESI-MS (EI⁺, m/z): 1043.1 [M+Na]⁺. ¹H NMR (500 MHz, CDCl₃): δ 6.40-5.97 (m, 4H), 5.69-5.13 (m, 4H), 4.62-3.46 (m, 8H), 3.48-3.33 (m, 12H), 3.29-3.04 (m, 4H), 2.97-2.93 (m, 2H), 2.86-2.50 (m, 4H), 2.42-1.85 (m, 12H), 1.63-1.19 (m, 15H), 1.48-0.83 (m, 18H), 0.71-0.61 (m, 1H).

Step 5: N-[(22E,24E,26E,27E,31R,32S,33R,34R,36S, 38S,40S,41S,42R,43R,52R)-42,52-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-46,47, 48,49,50-pentaoxo-65,66-dioxa-54-azatricyclohexatriaconta-22,24,26(44),27(45)-tetraen-40-yl]-2-methoxy-ethanesulfonamide (I-71) and N-[(22E,24E, 26E,27E,31R,32S,33R,34R,36S,38S,40R,41S,42R,43R, 52R)-42,52-dihydroxy-41-[(1R)-2-[(1S,3R,4R)-4-hydroxy-3-methoxy-cyclohexyl]-1-methyl-ethyl]-43-methoxy-31,32, 33,34,44,45-hexamethyl-46,47,48,49,50-pentaoxo-65,66-dioxa-54-azatricyclohexatriaconta-22,24,26(44),27(45)-tetraen-40-yl]-2-methoxy-ethanesulfonamide (I-72): 300 mg of the mixture was separated via chiral HPLC and then purified by silica gel chromatography (hexane:DCM: EtOAc:MeOH=3:3:1:0.35) to provide the titled compounds (I-71:33 mg, 11% yield) and (I-72: 78 mg, 26% yield) as white solids.

Chiral Separation Method:

| | |
|---|---|
| Column: | CHIRALPAK IC |
| Column size: | 5.0 cm I.D. × 25 cm L, 10 μm |
| Mobile phase: | Hexane/EtOH = 50/50(V/V) |
| Flow rate: | 20 ml/min |
| Wave length: | UV 254 nm |
| Temperature: | 35° C. |

I-71: ESI-MS (EI⁺, m/z): 1043.1 [M+Na]⁺. ¹H NMR (500 MHz, CDCl₃) δ 6.37-5.82 (m, 4H), 5.60-5.01 (m, 5H), 4.44 (d, J=8.6 Hz, 1H), 4.24-3.89 (m, 3H), 3.82-3.47 (m, 5H), 3.47-2.95 (m, 15H), 2.92-2.51 (m, 5H), 2.30-1.61 (m, 15H), 1.52-1.14 (m, 12H), 1.11-0.75 (m, 18H), 0.60 (dd, J=23.7, 11.9 Hz, 1H).

I-72: ESI-MS (EI⁺, m/z): 1043.1 [M+Na]⁺. ¹H NMR (500 MHz, CDCl₃) δ 6.47-5.95 (m, 4H), 5.60-5.09 (m, 5H), 4.50-3.97 (m, 4H), 3.88-3.61 (m, 4H), 3.50-3.10 (m, 17H), 3.08-2.51 (m, 8H), 2.40-1.73 (m, 10H), 1.33 (tdd, J=22.8, 15.8, 11.1 Hz, 13H), 1.16-0.81 (m, 18H), 0.66 (dd, J=23.7, 11.9 Hz, 1H).

Example 34: Synthesis of (26E,28E,30E,31E,38R, 39S,40R,41R,43S,45S,46S,48S,49R,50R,59R)-49, 59-dihydroxy-48-[(1R)-2-[(1S,3R,4R)-4-hydroxy-3-methoxy-cyclohexyl]-1-methyl-ethyl]-50-methoxy-46-[2-methoxy-4-(2-methoxyethoxy)phenyl]-38,39, 40,41,51,52-hexamethyl-69,70-dioxa-60-azatricyclohexatriaconta-26,28,30(51),31(52)-tetraene-53,54,55,56,57-pentone (I-72) and (26E, 28E,30E,31E,38R,39S,40R,41R,43S,45S,46R,48S, 49R,50R,59R)-49,59-dihydroxy-48-[(1R)-2-[(1S,3R, 4R)-4-hydroxy-3-methoxy-cyclohexyl]-1-methyl-ethyl]-50-methoxy-46-[2-methoxy-4-(2-methoxyethoxy)phenyl]-38,39,40,41,51,52-hexamethyl-69,70-dioxa-60-azatricyclohexatriaconta-26,28,30(51),31(52)-tetraene-53,54,55,56,57-pentone (I-73)

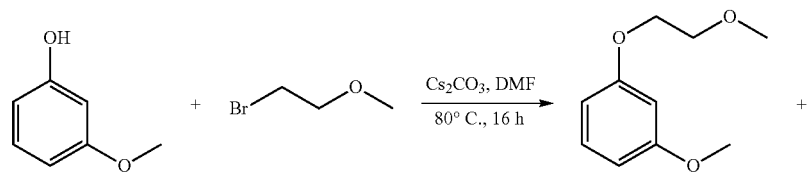

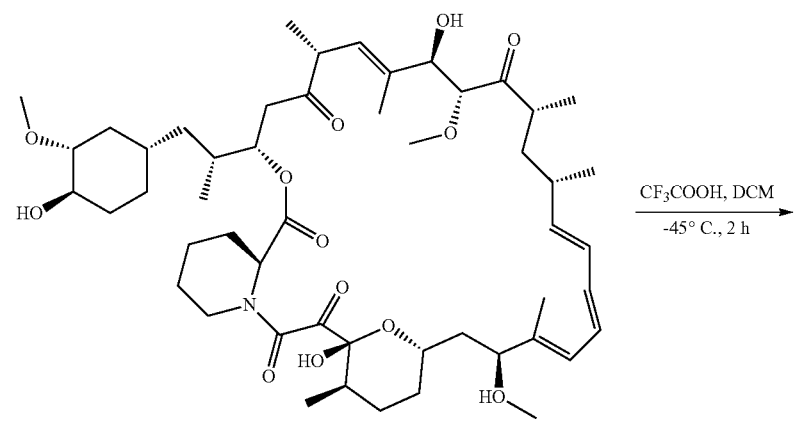

-continued
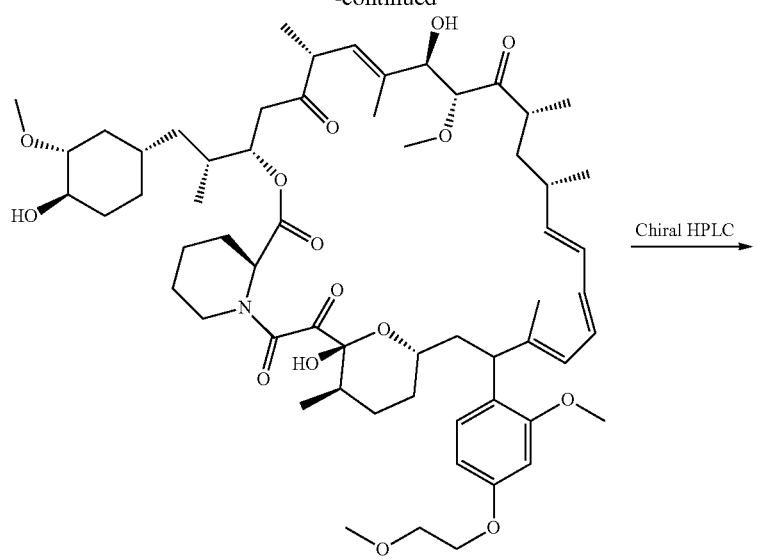
Chiral HPLC →
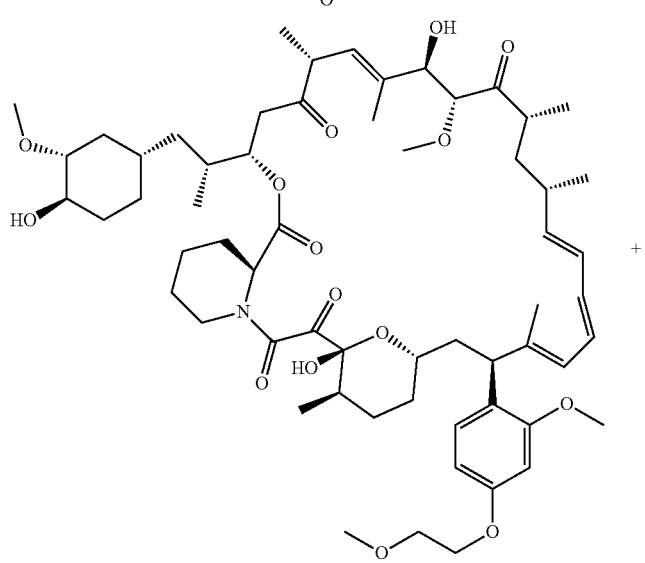
I-72
+
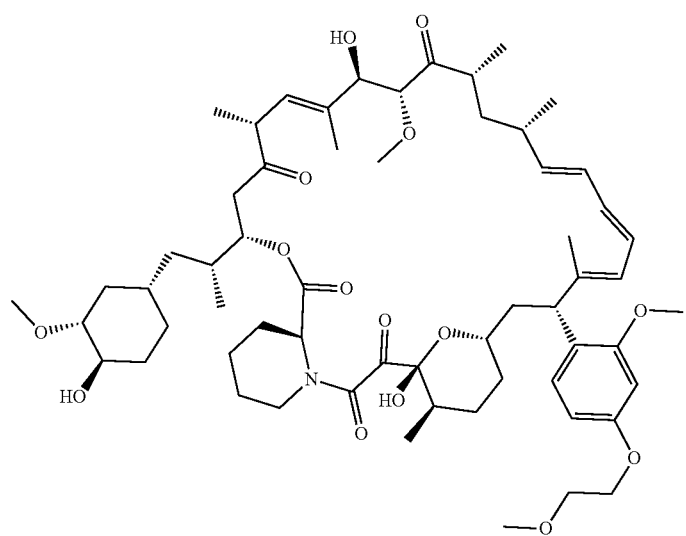
I-73

Step 1: 1-methoxy-3-(2-methoxyethoxy) benzene. To a solution of 3-methoxyphenol (1 g, 8.06 mmol), 1-bromo-2-methoxy-ethane (1.34 g, 9.67 mmol) in DMF (5 mL) was added $Cs_2CO_3$ (5.25 g, 16.11 mmol) and the resulting mixture was stirred at 80° C. for 16 h. The reaction mixture was then diluted with HCl (1M) and extracted with EtOAc (20 mL×3). The combined organic layers were dried over $Na_2SO_4$, filtered and concentrated. The residue was purified via silica gel chromatography with a gradient of EtOAc:PE (0-35%) to provide 1-methoxy-3-(2-methoxyethoxy) benzene (1 g, 68% yield) as a colorless oil. ESI-MS (EI+, m/z): 183.1 [M+H]$^+$. 1H NMR (400 MHz, CDCl3) δ 7.14 (t, J=4.3 Hz, 1H), 6.55-6.43 (m, 3H), 4.11-4.03 (m, 2H), 3.77-3.67 (m, 5H), 3.42 (s, 3H).

Step 2: (26E,28E,30E,31E,38R,39S,40R,41R,43S,45S, 48S,49R,50R,59R)-49,59-dihydroxy-48-[(1R)-2-[(1S,3R, 4R)-4-hydroxy-3-methoxy-cyclohexyl]-1-methyl-ethyl]-50-methoxy-46-[2-methoxy-4-(2-methoxyethoxy)phenyl]-38, 39,40,41,51,52-hexamethyl-69,70-dioxa-60-azatricyclohexatriaconta-26,28,30(51),31(52)-tetraene-53, 54,55,56,57-pentone. To a solution of (22E,24E,26E,27E, 29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32, 42,43-hexamethyl-60,61-dioxa-51-azatricyclohexatriaconta-22,24,26(42),27(43)-tetraene-44, 45,46,47,48-pentone (300 mg, 0.328 mmol) and 1-methoxy-3-(2-methoxyethoxy)benzene (300 mg, 1.64 mmol) in DCM (6 mL) was added 2,2,2-trifluoroacetic acid (187 mg, 1.64 mmol) at −45° C. The mixture was stirred at −45° C. for 2 h then poured into ice cold $NaHCO_3$ (aq) and extracted with EtOAc (20 mL), washed with water (20 mL), brine (20 mL×2), dried over anhydrous $Na_2SO_4$, filtered and concentrated. The residue was then purified via reverse phase chromatography to provide the titled compound (150 mg, 43% yield) as a white solid. ESI-MS (EI+, m/z): 1086.1 [M+Na]$^+$. 1H NMR (400 MHz, CDCl3) δ 7.09-6.82 (m, 1H), 6.47-6.42 (m, 1H), 6.35-6.20 (m, 1H), 6.19-5.97 (m, 2H), 5.52-5.10 (m, 4H), 4.38-3.89 (m, 5H), 3.80-3.60 (m, 6H), 3.59-3 (m, 14H), 2.95-2.76 (m, 2H), 2.74-2.54 (m, 2H), 2.50-2.19 (m, 3H), 2.18-1.60 (m, 19H), 1.53-1.13 (m, 12H), 1.12-0.99 (m, 6H), 0.98-0.80 (m, 11H), 0.73-0.61 (m, 1H).

Step 3: (26E,28E,30E,31E,38R,39S,40R,41R,43S,45S, 46S,48S,49R,50R,59R)-49,59-dihydroxy-48-[(1R)-2-[(1S, 3R,4R)-4-hydroxy-3-methoxy-cyclohexyl]-1-methyl-ethyl]-50-methoxy-46-[2-methoxy-4-(2-methoxyethoxy) phenyl]-38,39,40,41,51,52-hexamethyl-69,70-dioxa-60-azatricyclohexatriaconta-26,28,30(51),31(52)-tetraene-53, 54,55,56,57-pentone (I-72) and (26E,28E,30E,31E,38R, 39S,40R,41R,43S,45S,46R,48S,49R,50R,59R)-49,59-dihydroxy-48-[(1R)-2-[(1S,3R,4R)-4-hydroxy-3-methoxy-cyclohexyl]-1-methyl-ethyl]-50-methoxy-46-[2-methoxy-4-(2-methoxyethoxy)phenyl]-38,39,40,41,51,52-hexamethyl-69,70-dioxa-60-azatricyclohexatriaconta-26,28,30(51),31 (52)-tetraene-53,54,55,56,57-pentone (I-73). 268 mg of the mixture was separated via chiral HPLC and then purified by silica gel chromatography (hexane:DCM:EtOAc:MeOH from 3:3:1:0 to 3:3:1:1) to provide the titled compounds (I-72: 57.5 mg, 22% yield) and (I-73:44.3 mg, 17% yield) as white solids.

Chiral Separation Method:

| Column: | CHIRALPAK IC |
|---|---|
| Column size: | 5.0 cm I.D. × 25 cm L, 10 μm |
| Mobile phase | Hexane/EtOH = 50/50(V/V) |
| Flow rate: | 20 ml/min |
| Wave length: | UV 254 nm |
| Temperature: | 35° C. |

I-72: ESI-MS (EI$^+$, m/z): 1086.1 [M+Na]$^+$. $^1$H NMR (500 MHz, CDCl$_3$) δ 7.13-6.82 (m, 1H), 6.55-6.02 (m, 6H), 5.46-5.08 (m, 4H), 4.52-4.01 (m, 5H), 3.98-3.61 (m, 8H), 3.58-3.19 (m, 13H), 3.02-2.51 (m, 5H), 2.49-1.92 (m, 7H), 1.89-1.48 (m, 11H), 1.48-1.21 (m, 10H), 1.09-0.82 (m, 18H), 0.71-0.59 (m, 1H).

I-73: ESI-MS (EI$^+$, m/z): 1086.1 [M+Na]$^+$. $^1$H NMR (500 MHz, CDCl$_3$) δ 7.12-6.84 (m, 1H), 6.56-5.94 (m, 6H), 5.52-5.12 (m, 4H), 4.38-4.01 (m, 4H), 3.98-3.62 (m, 8H), 3.60-3.20 (m, 14H), 2.97-2.57 (m, 5H), 2.51-1.70 (m, 12H), 1.55-1.18 (m, 16H), 1.14-0.78 (m, 18H), 0.73-0.62 (m, 1H).

Example 35: Synthesis of 4-[[(21E,23E,25E,26E, 34R,35S,36R,37R,39S,41S,43S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-57-azatricyclohexatriaconta-21,23,25(47),26(48)-tetraen-43-yl]oxy]butane-1-sulfonamide (I-74) and 4-[[(21E,23E,25E,26E, 34R,35S,36R,37R,39S,41S, 43R,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36, 37,47,48-hexamethyl-49,50,51,52,53-pentaoxo-68, 69-dioxa-57-azatricyclohexatriaconta-21,23,25(47), 26(48)-tetraen-43-yl]oxy]butane-1-sulfonamide (I-75)

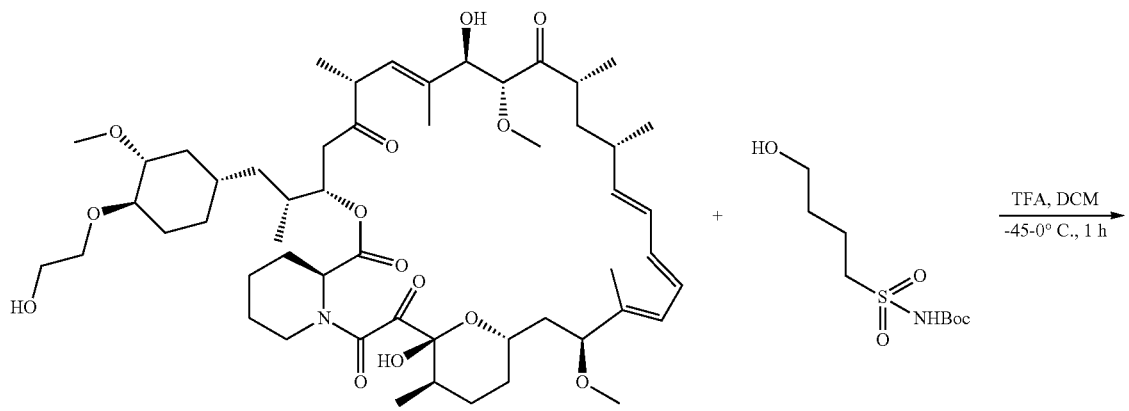

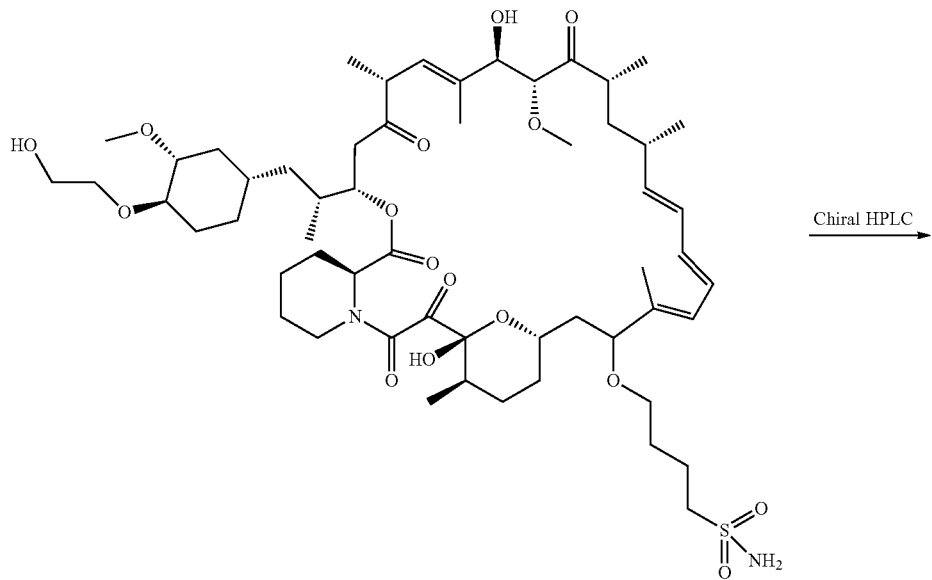
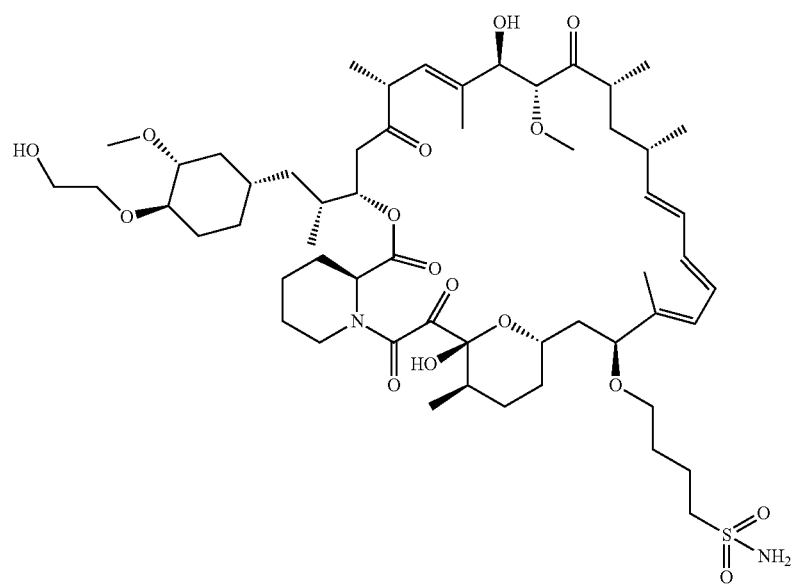
I-74

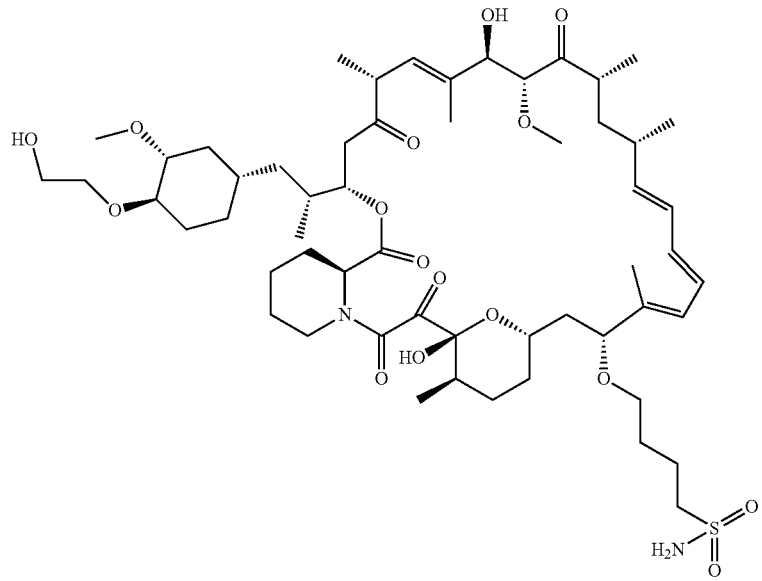

I-75

Step 1: 4-[[(21E,23E,25E,26E,34R,35S,36R,37R,39S, 41S,44S,45R,46R,55R)-45,55-dihydroxy-44-[(1R)-2-[(1S, 3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-57-azatricyclohexatriaconta-21,23,25(47),26(48)-tetraen-43-yl]oxy]butane-1-sulfonamide. To a solution of (22E,24E, 26E,27E,31R,32S,33R,34R,36S,38S,40S,41S,42R,43R, 52R)-42,52-dihydroxy-41-[(1R)-2-[(1S,3R,4R)-4-(2-hydroxyethoxy)-3-methoxy-cyclohexyl]-1-methyl-ethyl]-40,43-dimethoxy-31,32,33,34,44,45-hexamethyl-62,63-dioxa-53-azatricyclohexatriaconta-22,24,26(44),27(45)-tetraene-46,47,48,49,50-pentone (1 g, 1.04 mmol) in DCM (60 mL) was added 2,2,2-trifluoroacetic acid (2 mL, 26.1 mmol) dropwise at −45° C. under $N_2$. When the addition was complete, the mixture was stirred for a further 10-20 min then tert-butyl N-(4-hydroxybutylsulfonyl)carbamate (2.64 g, 10.44 mmol) (suspended in 80 mL DCM) was added to the reaction mixture dropwise at −45° C. The resulting mixture warmed to 0° C., stirred for 1 h then quenched by adding saturated aqueous $NaHCO_3$ and extracted with DCM (100 mL) at 0° C. The organic layer was washed with brine (80 mL×3), dried over anhydrous sodium sulfate, filtered and the filtrate was concentrated under vacuum. The residue was purified via reverse phase chromatography chromatography (eluting with 63% $CH_3CN$ in water) to give the titled compound (0.27 g, 24% yield) as a white solid. ESI-MS (EI+, m/z): 1101.1 [M+Na]$^+$. $^1$H NMR (400 MHz, CDCl$_3$) δ 6.40-6.05 (m, 4H), 5.49-5.17 (m, 4H),4.66 (s, 1H), 4.24-3.98 (m, 2H), 3.97-3.52 (m, 7H), 3.43-3.33 (m, 10H), 3.23-2.99 (m, 3H), 2.94-2.05 (m, 10H), 2.05-2 (m, 4H), 1.81-1.62 (m, 21H), 1.57-1.14 (m, 11H), 1.07-0.83 (m, 18H), 0.72-0.60 (m, 1H).

Step 2: 4-[[(21E,23E,25E,26E,34R,35S,36R,37R,39S, 41S,43S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-57-azatricyclohexatriaconta-21,23,25(47),26(48)-tetraen-43-yl]oxy]butane-1-sulfonamide (I-74) and 4-[[(21E,23E,25E, 26E,34R,35S,36R,37R,39S,41S,43R,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52, 53-pentaoxo-68,69-dioxa-57-azatricyclohexatriaconta-21, 23,25(47),26(48)-tetraen-43-yl]oxy]butane-1-sulfonamide (I-75). 245 mg of the mixture was separated via chiral HPLC and then purified by silica gel chromatography (hexane: DCM:EtOAc:MeOH from 3:3:1:0 to 3:3:1:1) to obtain the titled compounds (I-74: 91 mg, 37% yield) and (I-75: 25.3 mg, 10% yield) as white solids.

Chiral Separation Method:

| Column: | CHIRALPAK IC |
|---|---|
| Column size: | 5.0 cm I.D. × 25 cm L, 10 μm |
| Sample solution: | 12 mg/Ml in mobile phase: |
| Mobile phase: | Hexane/EtOH = 70/30(V/V) |
| Flow rate: | 60 ml/min |
| Wave length: | UV 254 nm |
| Temperature: | 38° C. |

I-74: ESI-MS (EI$^+$, m/z): 1101.2 [M+Na]$^+$. $^1$H NMR (500 MHz, CDCl$_3$) δ 6.48-6.02 (m, 4H), 5.60-5.11 (m, 4H), 4.31-4.13 (m, 2H), 4.07-3.83 (m, 2H), 3.82-3.65 (m, 4H), 3.63-3.51 (m, 2H), 3.45-2.99 (m, 12H), 2.95-2.43 (m, 5H), 2.38-1.95 (m, 9H), 1.90-1.58 (m, 16H), 1.52-1.17 (m, 11H), 1.13-0.82 (m, 18H), 0.70-0.57 (m, 1H).

I-75: ESI-MS (EI$^+$, m/z): 1101.2 [M+Na]$^+$. $^1$H NMR (500 MHz, CDCl$_3$) δ 6.45-6.01 (m, 4H), 5.50-5.14 (m, 4H), 4.24-3.82 (m, 4H), 3.88-3.49 (m, 2H), 3.49-3.17 (m, 11H), 3.04-2.42 (m, 7H), 2.35-1.57 (m, 26H), 1.52-1.19 (m, 13H), 1.15-0.80 (m, 18H), 0.66-0.43 (m, 1H).

Example 36: Synthesis of 4-[[(23E,25E,27E,28E, 33R,34S,35R,36R,38S,40S,43S,44R,45R,55R)-44, 55-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-48,49,50,51,52-pentaoxo-67,68-dioxa-56-azatricyclohexatriaconta-23,25,27(46),28(47)-tetraen-42-yl]oxy]-N,N-dimethyl-butanamide (I-76), 4-[[(23E,25E,27E,28E, 33R,34S,35R,36R,38S,40S,42S,43S,44R,45R,55R)-44,55-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-48,49,50, 51,52-pentaoxo-67,68-dioxa-56-azatricyclohexatriaconta-23,25,27(46),28(47)-tetraen-42-yl]oxy]-N,N-dimethyl-butanamide (I-84) and 4-[[(23E,25E,27E,28E,33R,34S,35R,36R,38S, 40S,42R,43S,44R,45R,55R)-44,55-dihydroxy-43-[(1R)-2-[(1S,3R,4R)-4-hydroxy-3-methoxy-cyclohexyl]-1-methyl-ethyl]-45-methoxy-33,34,35,36,46, 47-hexamethyl-48,49,50,51,52-pentaoxo-67,68-dioxa-56-azatricyclohexatriaconta-23,25,27(46),28 (47)-tetraen-42-yl]oxy]-N,N-dimethyl-butanamide (I-85)

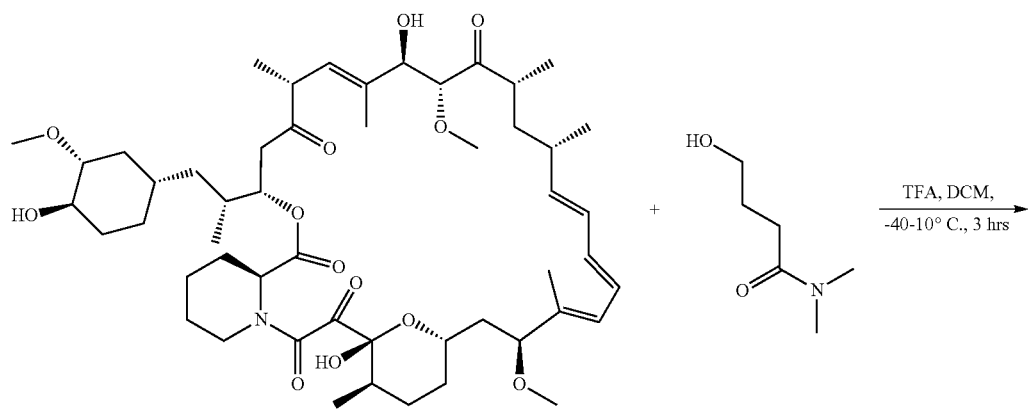

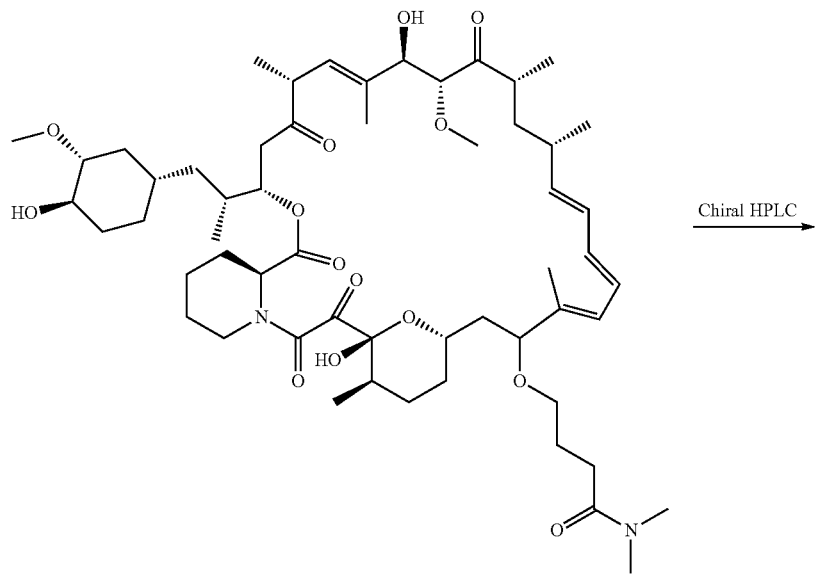

I-76

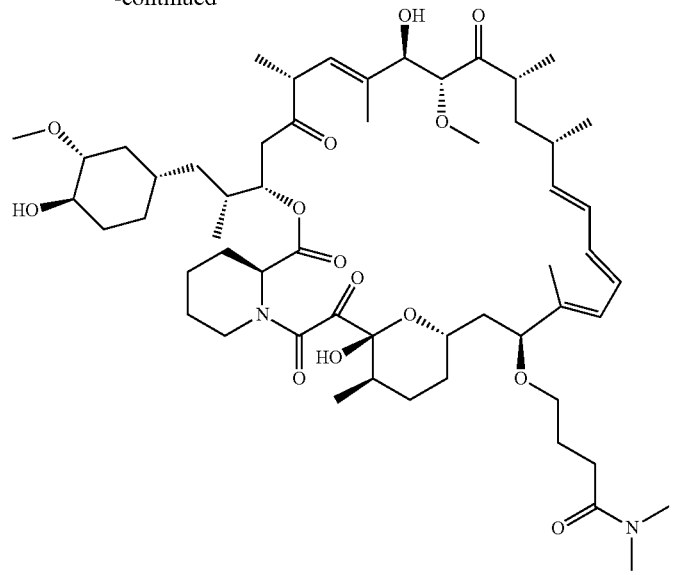

I-84

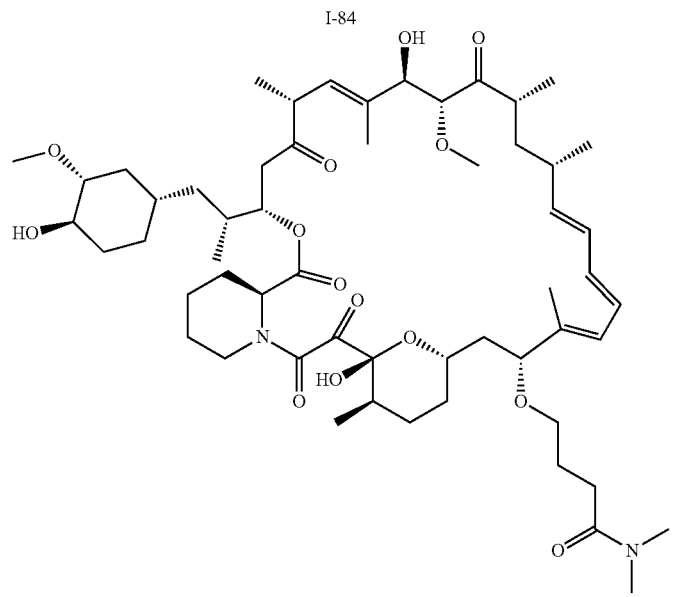

I-85

Step 1: 4-[[(23E,25E,27E,28E,33R,34S,35R,36R,38S, 40S,43S,44R,45R,55R)-44,55-dihydroxy-43-[(1R)-2-[(1S, 3R,4R)-4-hydroxy-3-methoxy-cyclohexyl]-1-methyl-ethyl]-45-methoxy-33,34,35,36,46,47-hexamethyl-48,49, 50,51,52-pentaoxo-67,68-dioxa-56-azatricyclohexatriaconta-23,25,27(46),28(47)-tetraen-42-yl]oxy]-N,N-dimethyl-butanamide (I-76). To a stirred solution of (22E,24E,26E,27E,29R,30S,31R,32R,34S,36S, 38S,39S,40R,41R,50R)-40,50-dihydroxy-39-[(1R)-2-[(1S, 3R,4R)-4-hydroxy-3-methoxy-cyclohexyl]-1-methyl-ethyl]-38,41-dimethoxy-29,30,31,32,42,43-hexamethyl-60, 61-dioxa-51-azatricyclohexatriaconta-22,24,26(42),27(43)-tetraene-44,45,46,47,48-pentone (600 mg, 0.66 mmol) in DCM (10 mL) was added TFA (740 mg, 6.49 mmol) at −40° C. The solution was stirred at −40° C. for 10 min under argon, then 4-hydroxy-N, N-dimethyl-butanamide (430 mg, 3.28 mmol) was added. The reaction mixture was stirred at −10° C. for 3 h then quenched with ice cold NaHCO$_3$ (60 mL) aqueous solution, extracted with DCM (100 mL×2), washed with brine (60 mL), filtered and concentrated. The residue was purified via reverse phase column chromatography (62% CH$_3$CN in water) to provide 4-[[(23E,25E,27E, 28E,33R,34S,35R,36R,38S,40S,43S,44R,45R,55R)-44,55-dihydroxy-43-[(1R)-2-[(1S,3R,4R)-4-hydroxy-3-methoxy-cyclohexyl]-1-methyl-ethyl]-45-methoxy-33,34,35,36,46, 47-hexamethyl-48,49,50,51,52-pentaoxo-67,68-dioxa-56-azatricyclohexatriaconta-23,25,27(46),28(47)-tetraen-42-yl]oxy]-N,N-dimethyl-butanamide (120 mg, 18% yield) as a white solid. ESI-MS (EI+, m/z): 1035.1 [M+Na]$^+$. $^1$H NMR (500 MHz, CDCl$_3$): δ 6.39-5.93 (m, 4H), 5.63-5.39 (m, 2H), 5.27-5.11 (m, 2H), 4.30-4.18 (m, 2H), 4.01-3.54 (m, 3H), 3.47-3.12 (m, 12H), 3.03-2.89 (m, 7H), 2.87-2.30 (m, 9H), 2.17-1.81 (m, 6H), 1.73-1.55 (m, 12H), 1.53-1.11 (m, 11H), 1.10-0.81 (m, 17H), 0.72-0.60 (m, 1H).

Step 2: 4-[[(23E,25E,27E,28E,33R,34S,35R,36R,38S,40S,42S,43S,44R,45R,55R)-44,55-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-48,49,50,51,52-pentaoxo-67,68-dioxa-56-azatricyclohexatriaconta-23,25,27(46),28(47)-tetraen-42-yl]oxy]-N,N-dimethyl-butanamide (I-84) and 4-[[(23E,25E,27E,28E,33R,34S,35R,36R,38S,40S,42R,43S,44R,45R,55R)-44,55-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-48,49,50,51,52-pentaoxo-67,68-dioxa-56-azatricyclohexatriaconta-23,25,27(46),28(47)-tetraen-42-yl]oxy]-N,N-dimethyl-butanamide (I-85). 235 mg of I-76 was separated via chiral HPLC and then purified by silica gel chromatography (PE:DCM:EtOAc:MeOH from 3:3:1:0 to 3:3:1:0.3) to obtain the titled compounds (I-84: 72 mg, 30.6% yield) and (I-85: 40 mg, 17% yield) as white solids.

Chiral Separation Method:

| | |
|---|---|
| Column: | CHIRALPAK IC |
| Column size: | 5.0 cm I.D. × 25 cm L, 10 μm |
| Sample solution: | 2.9 mg/mL in mobile phase: |
| Injection: | 18 mL |
| Mobile phase: | Hexane/EtOH = 40/60(V/V) |
| Flow rate: | 60 ml/min |
| Wave length: | UV 214 nm |
| Temperature: | 38° C. |

I-84: ESI-MS (EI$^+$, m/z): 1035.2 [M+Na]$^+$. $^1$H NMR (500 MHz, CDCl$_3$) δ 6.41-6.05 (m, 3H), 5.91 (dd, J=36.6, 10.9 Hz, 1H), 5.57-5.09 (m, 4H), 4.75 (s, 1H), 4.18 (d, J=5.7 Hz, 1H), 3.88 (s, 1H), 3.79-3.64 (m, 2H), 3.56 (d, J=13.2 Hz, 1H), 3.47-3.24 (m, 11H), 3.23-3.14 (m, 1H), 3.02-2.90 (m, 7H), 2.76-2.52 (m, 4H), 2.46-2.26 (m, 4H), 2.14-1.66 (m, 14H), 1.51-1.19 (m, 14H), 1.15-0.83 (m, 18H), 0.66 (dt, J=19.9, 9.8 Hz, 1H).

I-85: ESI-MS (EI$^+$, m/z): 1035.2 [M+Na]$^+$. $^1$H NMR (500 MHz, CDCl$_3$) δ 6.44-5.97 (m, 4H), 5.61 (dd, J=15.0, 8.1 Hz, 1H), 5.50-5.09 (m, 4H), 4.33-4.12 (m, 2H), 3.98 (d, J=4.0 Hz, 1H), 3.91-3.57 (m, 2H), 3.53-3.17 (m, 11H), 3.08-2.80 (m, 8H), 2.65-2.37 (m, 8H), 2.10 (ddd, J=45.6, 22.4, 8.0 Hz, 4H), 1.90-1.65 (m, 11H), 1.48-1.22 (m, 13H), 1.19-0.83 (m, 18H), 0.78-0.56 (m, 1H).

Example 37: Synthesis of N-[(21E,23E,25E,26E,30R,31S,32R,33R,35S,37S,40S,41R,42R,51R)-41,51-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-45,46,47,48,49-pentaoxo-65,66-dioxa-53-azatricyclohexatriaconta-21,23,25(43),26(44)-tetraen-39-yl]-2-hydroxy-ethanesulfonamide (I-77), N-[(21E,23E,25E,26E,30R,31S,32R,33R,35S,37S,39S,40S,41R,42R,51R)-41,51-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-45,46,47,48,49-pentaoxo-65,66-dioxa-53-azatricyclohexatriaconta-21,23,25(43),26(44)-tetraen-39-yl]-2-hydroxy-ethanesulfonamide (I-87) and N-[(21E,23E,25E,26E,30R,31S,32R,33R,35S,37S,39R,40S,41R,42R,51R)-41,51-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-45,46,47,48,49-pentaoxo-65,66-dioxa-53-azatricyclohexatriaconta-21,23,25(43),26(44)-tetraen-39-yl]-2-hydroxy-ethanesulfonamide (I-88)

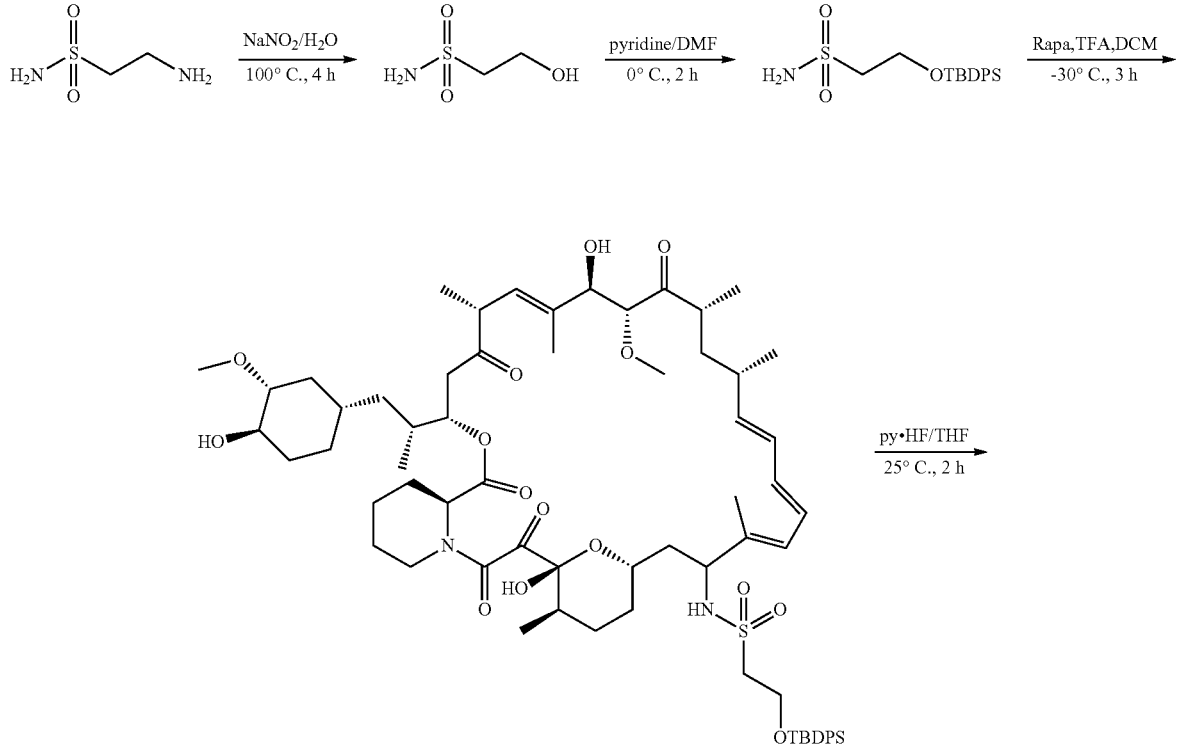

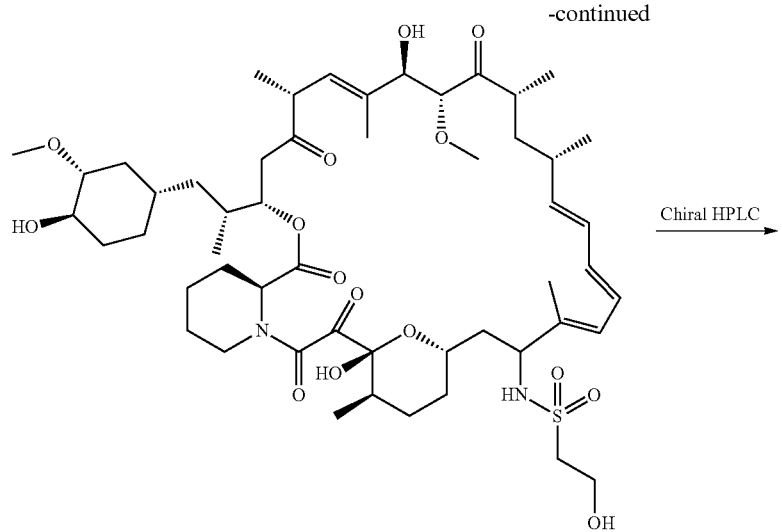
I-77
→ Chiral HPLC
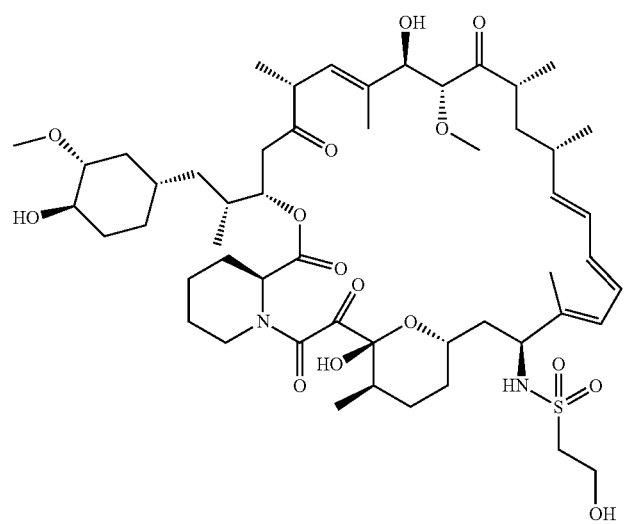
I-87
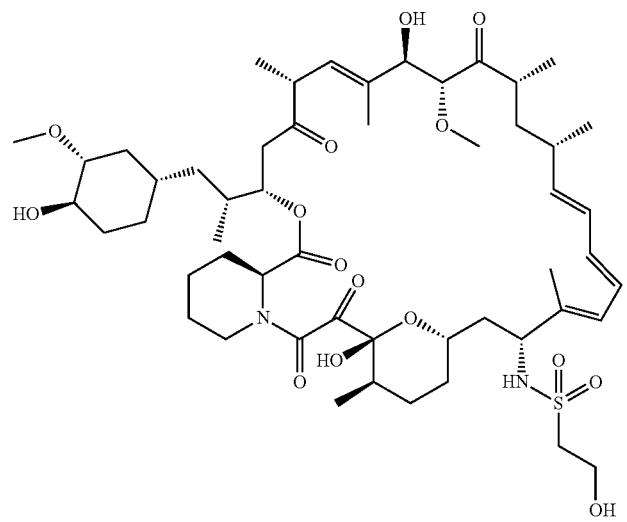
I-88

Step 1: 2-hydroxyethanesulfonamide. A mixture of 2-aminoethanesulfonamide (5 g, 31.13 mmol) and sodium nitrite (2.26 g, 32.69 mmol) in $H_2O$ (37.5 mL) was refluxed until gas evolution was no longer observed. The clear yellow solution was then cooled and concentrated in vacuo to provide 2-hydroxyethanesulfonamide (3.5 g, 90% yield) as thick oil. $^1$H NMR (500 MHz, MeOD-$d_4$) δ 5 (s, 3H), 4.13 (t, J=6.3 Hz, 2H), 3.46 (t, 2H).

Step 2: 2-[tert-butyl (diphenyl) silyl] oxyethanesulfonamide. To a solution of 2-hydroxyethanesulfonamide (1 g, 7.99 mmol) in pyridine (1.26 g, 15.98 mmol) was added tert-butyl-chloro-diphenyl-silane (2.31 g, 8.39 mmol) at 0° C. The resulting solution was stirred at rt for 2 h then poured into water (80 mL) and extracted with EtOAc (40 mL×2). The organic layer was washed with water (100 mL), brine (100 mL), dried over $Na_2SO_4$, filtered and concentrated. The residue was purified via silica gel chromatography (EtOAc: PE=1:2) to provide 2-[tert-butyl(diphenyl)silyl]oxyethanesulfonamide (1.2 g, 41.3% yield) as a white solid. $^1$HNMR (500 MHz, DMSO-$d_6$) δ 7.68-7.61 (m, 4H), 7.52-7.42 (m, 6H), 6.84 (s, 2H), 4 (t, J=10.0 Hz, 2H), 3.30 (t, J=10.0 Hz, 2H), 1 (s, 9H).

Step 3: 2-[tert-butyl(diphenyl)silyl]oxy-N-[(34E,36E,38E,39E,45R,46S,47R,48R,50S,52S,55S,56R,57R,66R)-56,66-dihydroxy-55-[(1R)-2-[(1S,3R,4R)-4-hydroxy-3-methoxy-cyclohexyl]-1-methyl-ethyl]-57-methoxy-45,46,47,48,58,59-hexamethyl-60,61,62,63,64-pentaoxo-80,81-dioxa-69-azatricyclohexatriaconta-34,36,38(58),39(59)-tetraen-54-yl]ethanesulfonamide. A mixture of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (200 mg, 218.78 umol), 2-[tert-butyl (diphenyl)silyl]oxyethanesulfonamide (398 mg, 1.09 mmol) and trifluoroacetic acid (748 mg, 6.56 mmol) in DCM (6 mL) was stirred at −30° C. for 3 h, then poured into ice cold $NaHCO_3$ aqueous solution (50 mL), extracted with EtOAc (50 mL×2), dried over $Na_2SO_4$, filtered and concentrated. The residue was purified via reverse phase chromatography (85% $CH_3CN$ in water) to provide the titled compound (146 mg, 54% yield) as a white solid. ESI-MS (EI$^+$, m/z): 1268.2 [M+Na]$^+$.

Step 4: N-[(21E,23E,25E,26E,30R,31S,32R,33R,35S,37S,40S,41R,42R,51R)-41,51-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-45,46,47,48,49-pentaoxo-65,66-dioxa-53-azatricyclohexatriaconta-21,23,25(43),26(44)-tetraen-39-yl]-2-hydroxy-ethanesulfonamide (I-77). A mixture of 2-[tert-butyl(diphenyl)silyl]oxy-N-[(34E,36E,38E,39E,45R,46S,47R,48R,50S,52S,55S,56R,57R,66R)-56,66-dihydroxy-55-[(1R)-2-[(1S,3R,4R)-4-hydroxy-3-methoxy-cyclohexyl]-1-methyl-ethyl]-57-methoxy-45,46,47,48,58,59-hexamethyl-60,61,62,63,64-pentaoxo-80,81-dioxa-69-azatricyclohexatriaconta-34,36,38(58),39(59)-tetraen-54-yl]ethanesulfonamide (256 mg, 205.51 umol) and Py.HF (331 mg, 2.06 mmol) in THF (6 mL) was stirred at rt for 2 h. The reaction mixture was concentrated then purified via reverse phase chromatography (70% $CH_3CN$ in water) to provide the titled compound (126 mg, 61% yield) as a white solid. ESI-MS (EI$^+$, m/z): 1029.1 [M+Na]$^+$. $^1$H NMR (500 MHz, CDCl$_3$) δ 6.41-6.19 (m, 2H), 6.17-5.86 (m, 2H), 5.64-5.05 (m, 4H), 4.06 (ddd, 4H), 3.88-3.52 (m, 2H), 3.52-3.29 (m, 8H), 3.30-3.02 (m, 3H), 3.01-2.88 (m, 1H), 2.88-2.60 (m, 4H), 2.36-1.88 (m, 7H), 1.88-1.46 (m, 26H), 1.37 (ddd, Hz, 5H), 1.29-1.16 (m, 4H), 1.13 (dt, 3H), 1.05 (dd, 4H), 0.98 (dd, 4H), 0.95-0.85 (m, 4H), 0.66 (d, 1H).

Step 5: N-[(21E,23E,25E,26E,30R,31S,32R,33R,35S,37S,39S,40S,41R,42R,51R)-41,51-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-45,46,47,48,49-pentaoxo-65,66-dioxa-53-azatricyclohexatriaconta-21,23,25(43),26(44)-tetraen-39-yl]-2-hydroxy-ethanesulfonamide (I-87) and N-[(21E,23E,25E,26E,30R,31S,32R,33R,35S,37S,39R,40S,41R,42R,51R)-41,51-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-45,46,47,48,49-pentaoxo-65,66-dioxa-53-azatricyclohexatriaconta-21,23,25(43),26(44)-tetraen-39-yl]-2-hydroxy-ethanesulfonamide (I-88). 125 mg of the mixture was separated via chiral HPLC and then purified by silica gel chromatography (PE:DCM:EtOAc: MeOH from 3:3:1:0 to 3:3:1:0.5) to obtain the titled compounds (I-87: 39 mg, 31% yield) and (I-88: 42 mg, 34% yield) as white solids.

Chiral Separation Method:

| | |
|---|---|
| Column: | CHIRALPAK IC |
| Column size: | 5.0 cm I.D. × 25 cm L, 10 μm |
| Sample solution: | 2.5 mg/mL in mobile phase: |
| Injection: | 5 mL |
| Mobile phase: | Hexane/EtOH = 50/50(V/V) |
| Flow rate: | 60 ml/min |
| Wave length: | UV 254 nm |
| Temperature: | 35° C. |

I-87: ESI-MS (EI$^+$, m/z): 1029.4 [M+Na]$^+$. $^1$H NMR (500 MHz, CDCl$_3$) δ 6.42-6.23 (m, 2H), 6.13 (dd, J=15.1, 10.2 Hz, 1H), 6 (d, J=10.4 Hz, 1H), 5.65-5.06 (m, 5H), 4.62 (s, 1H), 4.16 (t, J=15.6 Hz, 2H), 3.99 (t, J=5.3 Hz, 2H), 3.78 (t, J=11.6 Hz, 1H), 3.70-3.54 (m, 2H), 3.52-3.29 (m, 9H), 3.12 (dtd, J=19.9, 14.4, 5.4 Hz, 2H), 2.99-2.49 (m, 6H), 2.40-1.81 (m, 11H), 1.68-1.51 (m, 10H), 1.45-1.13 (m, 12H), 1.09-0.83 (m, 14H), 0.67 (dd, J=23.6, 11.8 Hz, 1H).

I-88: ESI-MS (EI$^+$, m/z): 1029.4 [M+Na]$^+$. $^1$H NMR (500 MHz, CDCl$_3$) δ 6.45-5.85 (m, 4H), 5.56-5.08 (m, 4H), 4.41-3.95 (m, 5H), 3.82 (dd, J=34.9, 5.5 Hz, 1H), 3.60 (d, J=13.5 Hz, 1H), 3.46-3.15 (m, 10H), 3.05-2.85 (m, 2H), 2.80-2.57 (m, 5H), 2.36-1.67 (m, 16H), 1.55-1.17 (m, 15H), 1.16-0.85 (m, 18H), 0.67 (dd, J=23.8, 11.9 Hz, 1H).

Example 38: Synthesis of (23E,25E,27E,28E,34R, 35S,36R,37R,39S,42S,44S,45S,46R,47R,57R)-46, 57-dihydroxy-45-[(1R)-2-[(1S,3R,4R)-4-(2-hydroxy-ethoxy)-3-methoxy-cyclohexyl]-1-methyl-ethyl]-47-methoxy-34,35,36,37,48,49-hexamethyl-44-[2-(2-oxopyrrolidin-3-yl)ethoxy]-69,70-dioxa-59-azatricyclohexatriaconta-23,25,27(48),28(49)-tetraene-50,51,53,54,55-pentone (I-78)
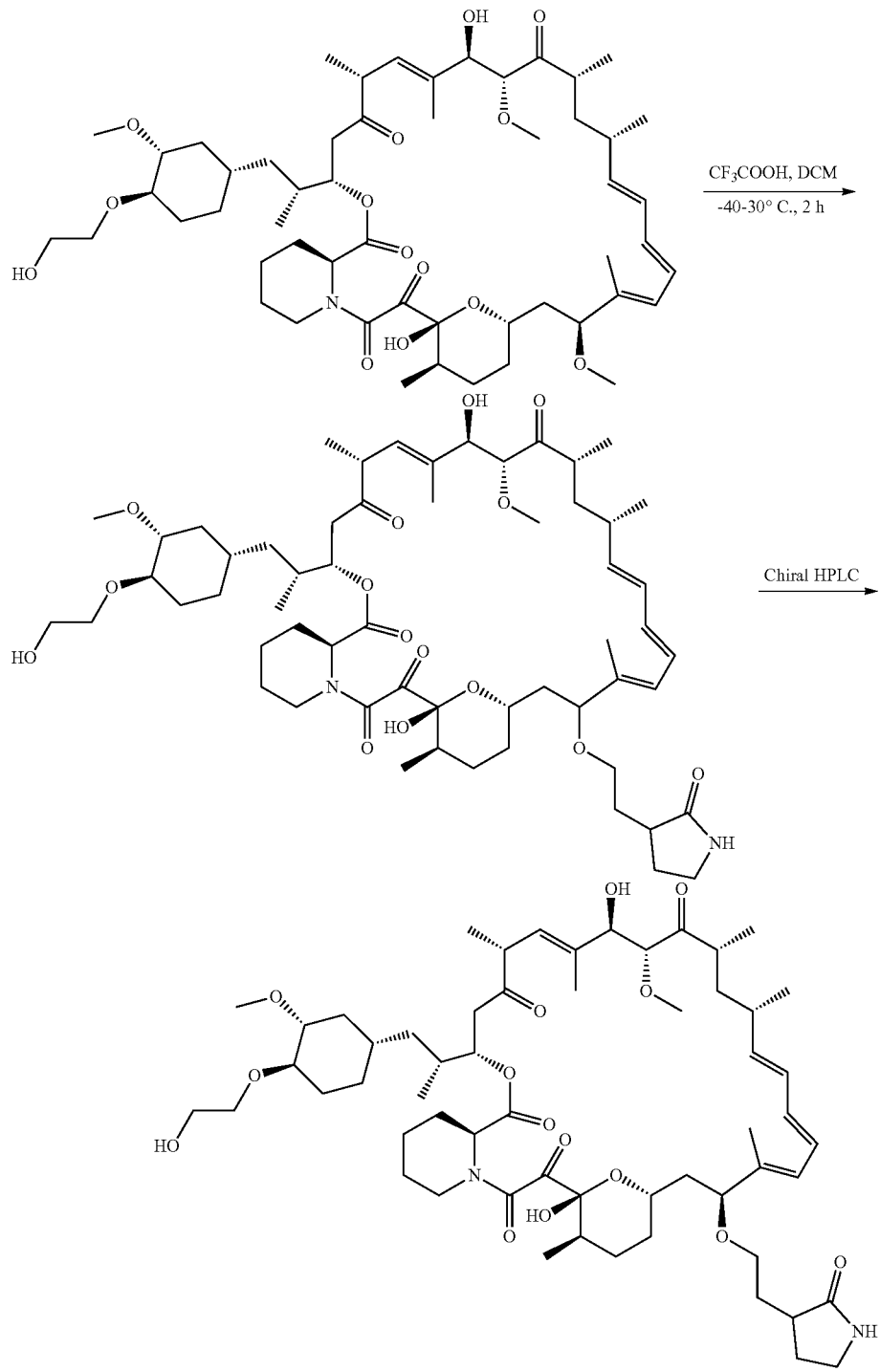
I-78

Step 1: (23E,25E,27E,28E,34R,35S,36R,37R,39S,42S, 45S,46R,47R,57R)-46,57-dihydroxy-45-[(1R)-2-[(1S,3R, 4R)-4-(2-hydroxyethoxy)-3-methoxy-cyclohexyl]-1-methyl-ethyl]-47-methoxy-34,35,36,37,48,49-hexamethyl-44-[2-(2-oxopyrrolidin-3-yl)ethoxy]-69,70-dioxa-59-azatricyclohexatriaconta-23,25,27(48),28(49)-tetraene-50, 51,53,54,55-pentone. To a solution of (22E,24E,26E,27E, 31R,32S,33R,34R,36S,38S,40S,41S,42R,43R,52R)-42,52-dihydroxy-41-[(1R)-2-[(1S,3R,4R)-4-(2-hydroxyethoxy)-3-methoxy-cyclohexyl]-1-methyl-ethyl]-40,43-dimethoxy-31, 32,33,34,44,45-hexamethyl-62,63-dioxa-53-azatricyclohexatriaconta-22,24,26(44),27(45)-tetraene-46, 47,48,49,50-pentone (0.5 g, 0.52 mmol) in DCM (50 mL) was added CF$_3$COOH (1.78 g, 15.65 mmol) at −50° C. under N$_2$. and th After stirring for 10 minutes, 3-(2-hydroxyethyl) pyrrolidin-2-one (1.68 g, 13.05 mmol) (dissolved in DCM) was added and the mixture was stirred at −40° C. for 1 h. The reaction was quenched by adding saturated aqueous NaHCO$_3$ at −30° C., then extracted with DCM (100 mL). The organic layer was washed with water (60 mL×2), brine (60 mL×2), dried over anhydrous Na$_2$SO$_4$, filtered and concentrated. The residue was purified via reverse phase chromatography (60% CH$_3$CN in water) to provide the titled compound (0.07 g, 13% yield) as a white solid.

Step 2: (23E,25E,27E,28E,34R,35S,36R,37R,39S,42S, 44S,45S,46R,47R,57R)-46,57-dihydroxy-45-[(1R)-2-[(1S, 3R,4R)-4-(2-hydroxyethoxy)-3-methoxy-cyclohexyl]-1-methyl-ethyl]-47-methoxy-34,35,36,37,48,49-hexamethyl-44-[2-(2-oxopyrrolidin-3-yl)ethoxy]-69,70-dioxa-59-azatricyclohexatriaconta-23,25,27(48),28(49)-tetraene-50, 51,53,54,55-pentone (I-78). 3 g of the mixture was separated via chiral HPLC and then purified by silica gel chromatography (PE:DCM:EtOAc:MeOH from 3:3:1:0 to 3:3:1:0.5) to provide the titled compound (I-78: 1 g, 28% yield) as a white solid.

Chiral Separation Method:

| Column: | CHIRALPAK IC |
| --- | --- |
| Column size: | 5.0 cm I.D. × 25 cm L, 10 μm |
| Sample solution: | 8.2 mg/mL in mobile phase: |
| Injection: | 25 mL |
| Mobile phase: | Hexane/EtOH = 60/40(V/V) |
| Flow rate: | 60 ml/min |
| Wave length: | UV 254 nm |
| Temperature: | 35° C. |

I-78: ESI-MS (EI$^+$, m/z): 1077.2 [M+Na]$^+$. $^1$H NMR (500 MHz, CDCl$_3$) δ 6.43-6.01 (m, 4H), 5.52-5.13 (m, 4H), 4.29-4.15 (m, 2H), 3.98 (dt, J=25.2, 16.5 Hz, 1H), 3.86-3.52 (m, 5H), 3.47-3.14 (m, 12H), 3.13-2.40 (m, 6H), 2.38-1.95 (m, 5H), 1.90-1.71 (m, 13H), 1.60-1.15 (m, 15H), 1.14-0.78 (m, 22H), 0.73-0.53 (m, 1H).

Example 39: Synthesis of (24E,26E,28E,29E,36R, 37S,38R,39R,41S,43S,46S,47R,48R,57R)-47,57-dihydroxy-45-[[5-(2-hydroxyethoxy)-2-pyridyl] methoxy]-46-[(1R)-2-[(1S,3R,4R)-4-hydroxy-3-methoxy-cyclohexyl]-1-methyl-ethyl]-48-methoxy-36,37,38,39,49,50-hexamethyl-69,70-dioxa-59-azatricyclohexatriaconta-24,26,28(49),29(50)-tetraene-51,52,53,54,55-pentone (I-82), (24E,26E, 28E,29E,36R,37S,38R,39R,41S,43S,45S,46S,47R, 48R,57R)-47,57-dihydroxy-45-[[5-(2-hydroxyethoxy)-2-pyridyl]methoxy]-46-[(1R)-2-[(1S,3R,4R)-4-hydroxy-3-methoxy-cyclohexyl]-1-methyl-ethyl]-48-methoxy-36,37,38,39,49,50-hexamethyl-69,70-dioxa-59-azatricyclohexatriaconta-24,26,28(49),29(50)-tetraene-51,52,53,54,55-pentone (I-90) and (24E, 26E,28E,29E,36R,37S,38R,39R,41S,43S,45R,46S, 47R,48R,57R)-47,57-dihydroxy-45-[[5-(2-hydroxyethoxy)-2-pyridyl]methoxy]-46-[(1R)-2-[(1S,3R,4R)-4-hydroxy-3-methoxy-cyclohexyl]-1-methyl-ethyl]-48-methoxy-36,37,38,39,49,50-hexamethyl-69,70-dioxa-59-azatricyclohexatriaconta-24,26,28(49),29(50)-tetraene-51,52,53,54,55-pentone (I-91)

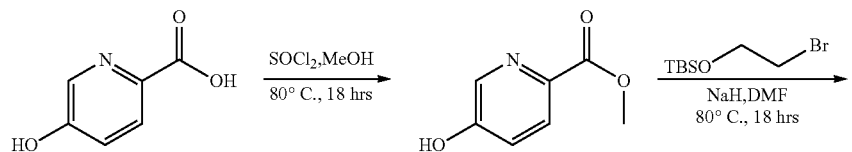

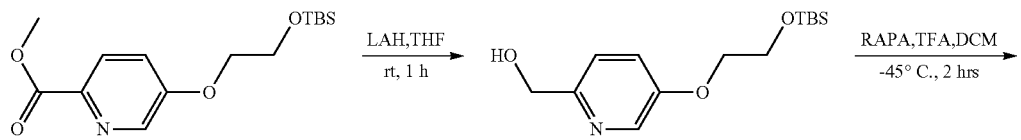

-continued
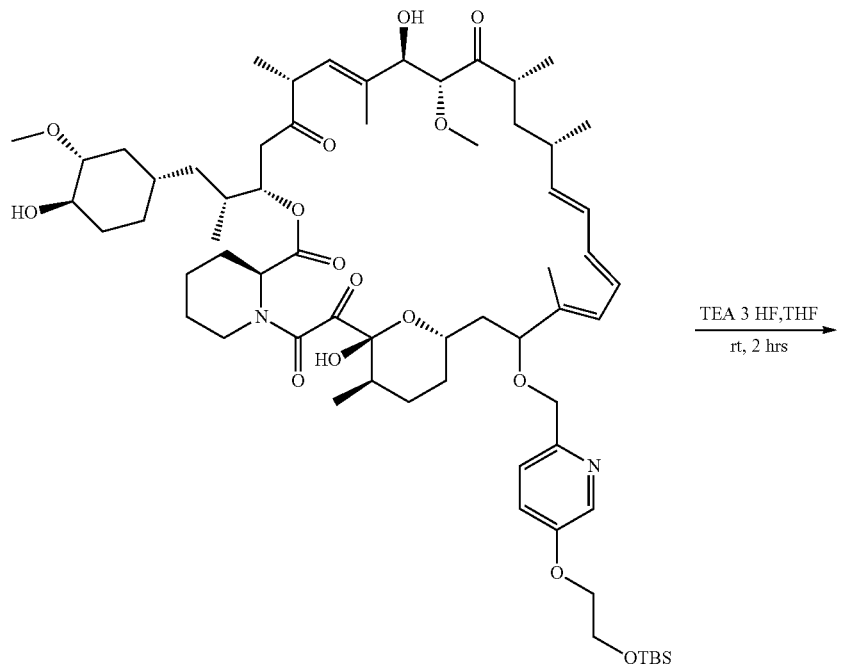
TEA 3 HF,THF
rt, 2 hrs
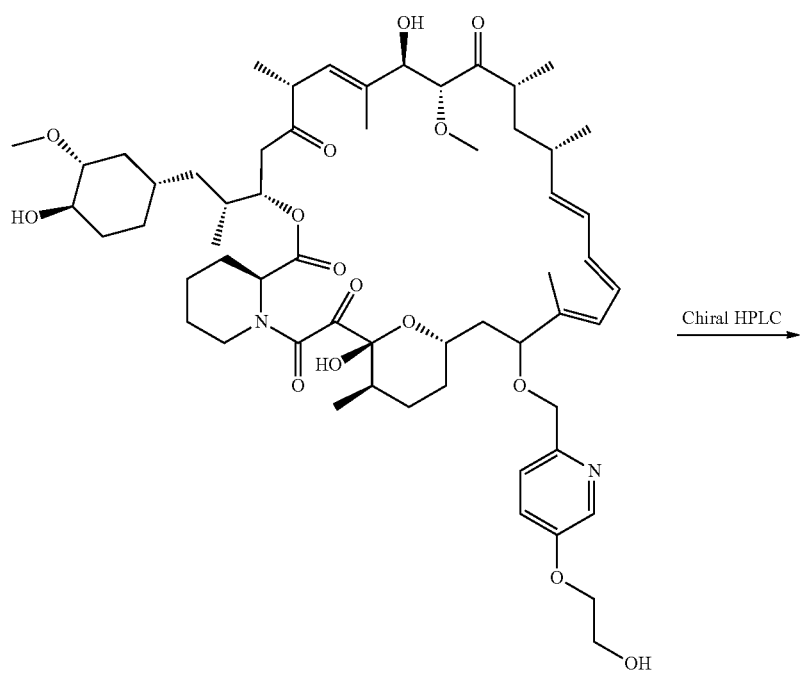
I-82
Chiral HPLC

-continued

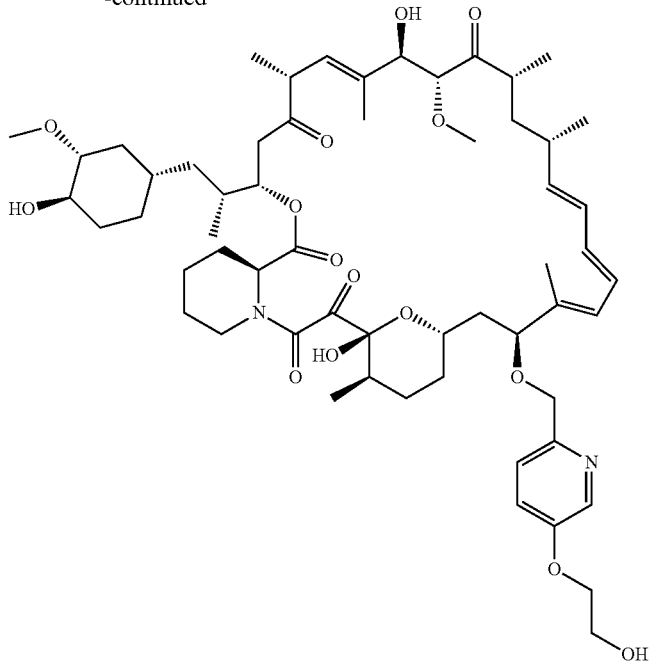

I-90

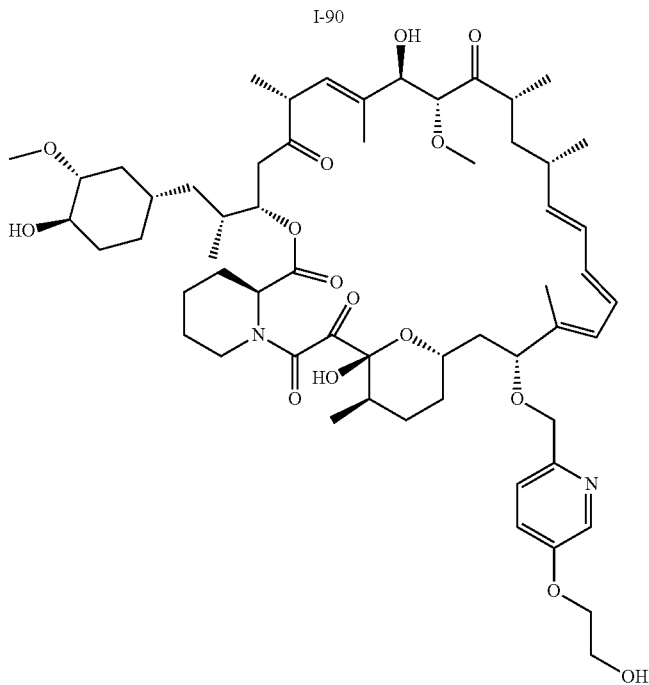

I-91

Step 1: methyl 5-hydroxypyridine-2-carboxylate. To a solution of 5-hydroxypyridine-2-carboxylic acid (10 g, 71.89 mmol) in MeOH (80 mL) was added SOCl$_2$ (17.11 g, 143.77 mmol) dropwise at 0° C. The mixture was stirred at 80° C. for 18 h then concentrated and purified via silica gel chromatography (DCM:MeOH=10:1) to provide methyl 5-hydroxypyridine-2-carboxylate (9.3 g, 85% yield) as a yellow oil. ESI-MS (EI$^+$, m/z): 154.1 [M+H]$^+$.

Step 2: methyl 5-[2-[tert-butyl (dimethyl)silyl]oxyethoxy]pyridine-2-carboxylate. To a solution of methyl 5-hydroxypyridine-2-carboxylate (8 g, 52.24 mmol) in DMF (50 mL) was added NaH (3.13 g, 78.36 mmol, 60% purity) at 0° C. The mixture was stirred at room temperature for 30 minutes. 2-bromoethoxy-tert-butyl-dimethyl-silane (18.75 g, 78.36 mmol) was added and the reaction stirred at 80° C. for 18 h. The reaction mixture was treated with H$_2$O (100 mL), extracted with EtOAc (60 mL×2) and the combined organic layers concentrated. The residue was purified by silica gel chromatography (PE:EtOAc=2:1) to provide methyl 5-[2-[tert-butyl (dimethyl)silyl]oxyethoxy]pyridine-2-carboxylate (6.1 g, 38% yield) as a white solid. ESI-MS (EI$^+$, m/z): 312.2 [M+H]$^+$. $^1$H NMR (400 MHz, CDCl$_3$) δ

8.30 (d, J=2.8 Hz, 1H), 8.01 (d, J=8.7 Hz, 1H), 7.20 (dd, J=8.7, 2.8 Hz, 1H), 4.07 (t, J=4.9 Hz, 2H), 3.97-3.84 (m, 5H), 0.80 (s, 9H), –0 (s, 6H).

Step 3: [5-[2-[tert-butyl (dimethyl)silyl]oxyethoxy]-2-pyridyl]methanol. To a solution of methyl 5-[2-[tert-butyl (dimethyl)silyl]oxyethoxy]pyridine-2-carboxylate (6.1 g, 19.59 mmol) in THF (10 mL) was added LAH (1 M, 29.38 mL) at 0° C. The reaction was stirred at 25° C. for 1 h then treated with $Na_2SO_4.10H_2O$ (20 g) and stirred at room temperature for 1 h. The mixture was filtered, washed with EtOAc (30 mL) and concentrated. The residue was purified by silica gel chromatography (PE:EtOAc=1:2) to provide [5-[2-[tert-butyl(dimethyl)silyl]oxyethoxy]-2-pyridyl] methanol (1.86 g, 34% yield) as a yellow oil. ESI-MS (EI$^+$, m/z): 284.0 [M+H]$^+$.

Step 4: (29E,31E,33E,34E,41R,42S,43R,44R,46S,48S, 51S,52R,53R,62R)-50-[[5-[2-[tert-butyl(dimethyl)silyl] oxyethoxy]-2-pyridyl]methoxy]-52,62-dihydroxy-51-[(1R)-2-[(1S,3R,4R)-4-hydroxy-3-methoxy-cyclohexyl]-1-methyl-ethyl]-53-methoxy-41,42,43,44,54,55-hexamethyl-74,75-dioxa-65-azatricyclohexatriaconta-29,31,33(54),34 (55)-tetraene-56,57,58,59,60-pentone. To a solution of (22E, 24E,26E,27E,29R,30S,31R,32R,34S,36S,38S,39S,40R, 41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44, 45,46,47,48-pentone (2 g, 2.19 mmol) in DCM (20 mL) was added 2,2,2-trifluoroacetic acid (2.49 g, 21.88 mmol) at –45° C. The mixture was stirred at –45° C. for 10 minutes. [5-[2-[tert-butyl(dimethyl)silyl]oxyethoxy]-2-pyridyl] methanol (1.86 g, 6.56 mmol) in DCM (0.5 mL) was added and the mixture was stirred at –45° C. for 2 h. The reaction was treated with aqueous $NaHCO_3$ (60 mL), extracted with EtOAc (50 mL×2) and the combined organic layers were concentrated. The residue was purified by reverse-phase chromatography (95% $CH_3CN$ in water) to provide the title compound (350 mg, 14% yield) as a yellow solid. ESI-MS (EI$^+$, m/z): 1188.9 [M+Na]$^+$.

Step 5: (24E,26E,28E,29E,36R,37S,38R,39R,41S,43S, 46S,47R,48R,57R)-47,57-dihydroxy-45-[[5-(2-hydroxyethoxy)-2-pyridyl]methoxy]-46-[(1R)-2-[(1S,3R,4R)-4-hydroxy-3-methoxy-cyclohexyl]-1-methyl-ethyl]-48-methoxy-36,37,38,39,49,50-hexamethyl-69,70-dioxa-59-azatricyclohexatriaconta-24,26,28(49),29(50)-tetraene-51, 52,53,54,55-pentone (I-82). To a solution of (29E,31E,33E, 34E,41R,42S,43R,44R,46S,48S,51S,52R,53R,62R)-50-[[5-[2-[tert-butyl(dimethyl)silyl]oxyethoxy]-2-pyridyl] methoxy]-52,62-dihydroxy-51-[(1R)-2-[(1S,3R,4R)-4-hydroxy-3-methoxy-cyclohexyl]-1-methyl-ethyl]-53-methoxy-41,42,43,44,54,55-hexamethyl-74,75-dioxa-65-azatricyclohexatriaconta-29,31,33(54),34(55)-tetraene-56, 57,58,59,60-pentone (350 mg, 0.3 mmol) in THF (5 mL) was added TEA-3HF (484 mg, 3 mmol). The mixture was stirred at 22° C. for 2 h then treated with aqueous $NaHCO_3$ (30 mL), extracted with EtOAc (20 mL×2) and the combined organic layers concentrated. The residue was purified by reverse phase chromatography (65% $CH_3CN$ in water) to provide the titled compound (200 mg, 63% yield) as a white solid. ESI-MS (EI$^+$, m/z): 1073.2 [M+Na]$^+$. $^1$H NMR (400 MHz, CDCl$_3$) δ 8.25 (s, 1H), 7.42-7.32 (m, 1H), 7.21 (m, 1H), 6.50-5.85 (m, 4H), 5.78-5.32 (m, 4H), 5.20 (d, J=6.3 Hz, 2H), 4.51 (dd, J=23.2, 12.1 Hz, 1H), 4.21 (ddd, J=25.9, 10.9, 6.8 Hz, 5H), 4 (s, 4H), 3.45-3.19 (m, 11H), 2.88 (d, J=34.9 Hz, 2H), 2.65 (s, 4H), 2.30 (s, 3H), 2.09 (s, 2H), 1.99 (d, J=14.2 Hz, 2H), 1.83-1.66 (m, 10H), 1.31 (d, J=63.1 Hz, 8H), 0.99 (qdd, J=31.4, 24.4, 12.2 Hz, 20H), 0.66 (d, J=11.9 Hz, 1H).

Step 6: (24E,26E,28E,29E,36R,37S,38R,39R,41S,43S, 45S,46S,47R,48R,57R)-47,57-dihydroxy-45-[[5-(2-hydroxyethoxy)-2-pyridyl]methoxy]-46-[(1R)-2-[(1S,3R,4R)-4-hydroxy-3-methoxy-cyclohexyl]-1-methyl-ethyl]-48-methoxy-36,37,38,39,49,50-hexamethyl-69,70-dioxa-59-azatricyclohexatriaconta-24,26,28(49),29(50)-tetraene-51, 52,53,54,55-pentone (I-90) and (24E,26E,28E,29E,36R, 37S,38R,39R,41S,43S,45R,46S,47R,48R,57R)-47,57-dihydroxy-45-[[5-(2-hydroxyethoxy)-2-pyridyl]methoxy]-46-[(1R)-2-[(1S,3R,4R)-4-hydroxy-3-methoxy-cyclohexyl]-1-methyl-ethyl]-48-methoxy-36,37,38,39,49, 50-hexamethyl-69,70-dioxa-59-azatricyclohexatriaconta-24,26,28(49),29(50)-tetraene-51,52,53,54,55-pentone (I-91). 200 mg of the mixture was separated via chiral HPLC and then purified by silica gel chromatography (PE:DCM: EtOAc:MeOH from 3:3:1:0 to 3:3:1:0.5) to provide the titled compounds (I-90: 20 mg, 10% yield) and (I-90: 42 mg, 21% yield) as white solids.

Chiral Separation Method:

| Column: | CHIRALPAK IC |
|---|---|
| Column size: | 5.0 cm I.D. × 25 cm L, 10 μm |
| Sample solution: | 2 mg/mL in mobile phase: |
| Injection: | 18 mL |
| Mobile phase: | Hexane/EtOH = 50/50(V/V) |
| Flow rate: | 60 ml/min |
| Wave length: | UV 254 nm |
| Temperature: | 38° C. |

I-90: ESI-MS (EI$^+$, m/z): 1051.1[M+H]$^+$. 1074.1 [M+Na]$^+$. $^1$H NMR (500 MHz, CDCl$_3$) δ 8.24 (dd, J=6.7, 2.9 Hz, 1H), 7.34 (d, J=8.6 Hz, 1H), 7.25-7.20 (m, 1H), 6.26 (dddd, J=34.3, 25.3, 14.9, 10.5 Hz, 3H), 5.94 (dd, J=33.9, 10.3 Hz, 1H), 5.36 (dddd, J=51.1, 16.3, 12.7, 7.4 Hz, 5H), 4.90 (s, 1H), 4.48 (dd, J=12.7, 5.3 Hz, 1H), 4.32-4.07 (m, 4H), 4.02-3.83 (m, 4H), 3.70 (dd, J=25.5, 6.2 Hz, 1H), 3.53 (d, J=12.5 Hz, 1H), 3.47-3.27 (m, 10H), 2.99-2.53 (m, 5H), 2.36-1.91 (m, 9H), 1.82-1.67 (m, 9H), 1.57-1.18 (m, 10H), 1.15-0.79 (m, 18H), 0.66 (dd, J=23.7, 11.9 Hz, 1H).

I-91: ESI-MS (EI$^+$, m/z): 1051.1[M+H]$^+$. 1074.1 [M+Na]$^+$. $^1$H NMR (500 MHz, CDCl$_3$) δ 8.31-8.24 (m, 1H), 7.33-7.22 (m, 4H), 6.50-5.88 (m, 4H), 5.77-5.07 (m, 5H), 4.65-3.81 (m, 8H), 3.44-3.19 (m, 10H), 3-2.43 (m, 5H), 2.39-1.94 (m, 9H), 1.90-1.73 (m, 9H), 1.55-1.21 (m, 12H), 1.17-0.79 (m, 18H), 0.74-0.56 (m, 1H).

Example 40: Synthesis of (21E,23E,25E,26E,29R, 30S,31R,32R,34S,36S,39S,44R,45R,55R)-44,55-dihydroxy-39-[(1R)-2-[(1S,3R,4R)-4-hydroxy-3-methoxy-cyclohexyl]-1-methyl-ethyl]-45-methoxy-29,30,31,32,47,48-hexamethyl-38-[[(2R,3S,4S,5R)-3,4,5,6-tetrahydroxytetrahydropyran-2-yl]methoxy]-69,70-dioxa-56-azatricyclohexatriaconta-21,23,25 (47),26(48)-tetraene-49,50,51,52,53-pentone (I-86)

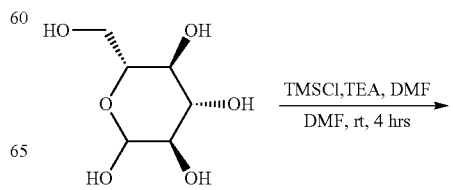

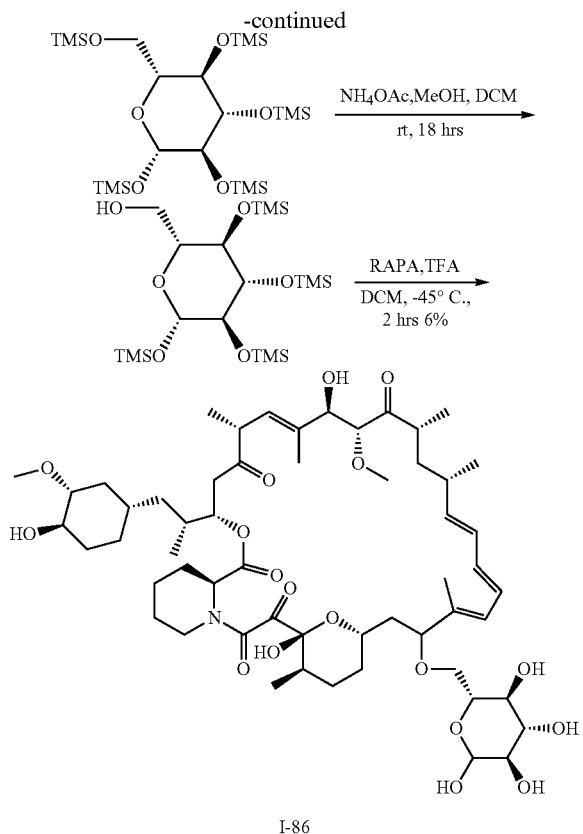

I-86

Step 1: trimethyl-[[(2R,3R,4S,5R,6S)-3,4,5,6-tetrakis(trimethylsilyloxy) tetrahydropyran-2-yl]methoxy]silane. To a solution of (2R,3R,4S,5S,6R)-6-(hydroxymethyl)tetrahydropyran-2,3,4,5-tetrol (4 g, 22.2 mmol) and N,N-diethylethanamine (12.36 g, 122.12 mmol) in DMF (80 mL) was added TMSCl (13.19 g, 122.12 mmol) at 0° C. The mixture was stirred at 20° C. for 4 h then treated with hexane (150 mL) and washed with H₂O (100 mL×3). The organic layer was concentrated to provide trimethyl-[[(2R,3R,4S,5R,6S)-3,4,5,6-tetrakis(trimethylsilyloxy)tetrahydropyran-2-yl]methoxy]silane (11.5 g, 96% yield) as a yellow oil. ¹H NMR (400 MHz, CDCl₃) δ 4.31 (d, J=7.3 Hz, 1H), 3.67-3.58 (m, 1H), 3.50-3.41 (m, 1H), 3.33-3.20 (m, 2H), 3.13-3.02 (m, 2H), 0.08--0.07 (m, 45H).

Step 2: [(2R,3R,4S,5R,6S)-3,4,5,6-tetrakis(trimethylsilyloxy)tetrahydropyran-2-yl]methanol. To a solution of trimethyl-[[(2R,3R,4S,5R,6S)-3,4,5,6-tetrakis(trimethylsilyloxy)tetrahydropyran-2-yl]methoxy]silane (5 g, 9.24 mmol) in MeOH (20 mL) and DCM (20 mL) was added ammonium acetate (1.42 g, 18.48 mmol). The mixture was stirred at 20° C. for 18 h. The reaction was concentrated, treated with n-hexane (100 mL) and washed with H₂O (50 mL×2). The organic layers were concentrated and the residue purified via silica gel column chromatography (PE:EtOAc=15:1) to provide [(2R,3R,4S,5R,6S)-3,4,5,6-tetrakis(trimethylsilyloxy)tetrahydropyran-2-yl]methanol (2.7 g, 62% yield) as a yellow oil. ESI-MS (EI⁺, m/z): 491.0 [M+Na]⁺. H NMR (400 MHz, CDCl₃) δ 4.86 (d, J=3.0 Hz, 1H), 3.70-3.48 (m, 4H), 3.35-3.26 (m, 1H), 3.19 (dd, J=9.1, 3.0 Hz, 1H), 1.59 (dd, J=7.1, 5.3 Hz, 1H), 0.08--0.08 (m, 36H).

Step 3: (21E,23E,25E,26E,29R,30S,31R,32R,34S,36S,39S,44R,45R,55R)-44,55-dihydroxy-39-[(1R)-2-[(1S,3R,4R)-4-hydroxy-3-methoxy-cyclohexyl]-1-methyl-ethyl]-45-methoxy-29,30,31,32,47,48-hexamethyl-38-[[(2R,3S,4S,5R)-3,4,5,6-tetrahydroxytetrahydropyran-2-yl]methoxy]-69,70-dioxa-56-azatricyclohexatriaconta-21,23,25(47),26(48)-tetraene-49,50,51,52,53-pentone (I-86). To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (0.5 g, 0.55 mmol) in DCM (8 mL) was added 2,2,2-trifluoroacetic acid (0.62 g, 5.47 mmol) at −45° C. The mixture was stirred at −45° C. for 10 minutes. [(2R,3R,4S,5R,6S)-3,4,5,6-tetrakis(trimethylsilyloxy)tetrahydropyran-2-yl]methanol (769 mg, 1.64 mmol) in DCM (0.5 mL) was added and the mixture was stirred at −45° C. for 2 h. The reaction was treated with aqueous NaHCO₃ (30 mL), extracted with EtOAc (20 mL×2) and the combined organic layers were concentrated. The residue was purified via reverse phase chromatography (60% CH₃CN in water) to provide the titled compound (35 mg, 6% yield) as a white solid. ESI-MS (EI⁺, m/z): 1084.5 [M+Na]⁺. ¹H NMR (400 MHz, CDCl₃) δ 6.50-5.92 (m, 4H), 5.70-5 (m, 4H), 4.69-4.11 (m, 3H), 4.07-3.73 (m, 3H), 3.40 (ddd, J=31.4, 19.8, 7.0 Hz, 16H), 2.71 (dd, J=90.1, 59.0 Hz, 3H), 2.40-1.90 (m, 9H), 1.85-1.54 (m, 13H), 1.52-1.22 (m, 8H), 1.21-0.77 (m, 22H), 0.73-0.56 (m, 1H).

Example 41: Synthesis of N-[(21E,23E,25E,26E,32R,33S,34R,35R,37S,39S,42S,43R,44R,53R)-43,53-dihydroxy-42-[(1R)-2-[(1S,3R,4R)-4-hydroxy-3-methoxy-cyclohexyl]-1-methyl-ethyl]-44-methoxy-32,33,34,35,45,46-hexamethyl-47,48,49,50,51-pentaoxo-67,68-dioxa-55-azatricyclohexatriaconta-21,23,25(45),26(46)-tetraen-41-yl]-2-(2-hydroxyethoxy)ethanesulfonamide (I-89), N-[(21E,23E,25E,26E,32R,33S,34R,35R,37S,39S,41S,42S,43R,44R,53R)-43,53-dihydroxy-42-[(1R)-2-[(1S,3R,4R)-4-hydroxy-3-methoxy-cyclohexyl]-1-methyl-ethyl]-44-methoxy-32,33,34,35,45,46-hexamethyl-47,48,49,50,51-pentaoxo-67,68-dioxa-55-azatricyclohexatriaconta-21,23,25(45),26(46)-tetraen-41-yl]-2-(2-hydroxyethoxy)ethanesulfonamide (I-95) and N-[(21E,23E,25E,26E,32R,33S,34R,35R,37S,39S,41R,42S,43R,44R,53R)-43,53-dihydroxy-42-[(1R)-2-[(1S,3R,4R)-4-hydroxy-3-methoxy-cyclohexyl]-1-methyl-ethyl]-44-methoxy-32,33,34,35,45,46-hexamethyl-47,48,49,50,51-pentaoxo-67,68-dioxa-55-azatricyclohexatriaconta-21,23,25(45),26(46)-tetraen-41-yl]-2-(2-hydroxyethoxy)ethanesulfonamide (I-96)

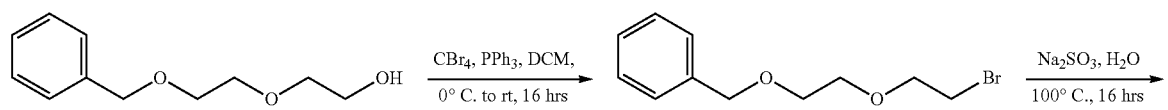

-continued
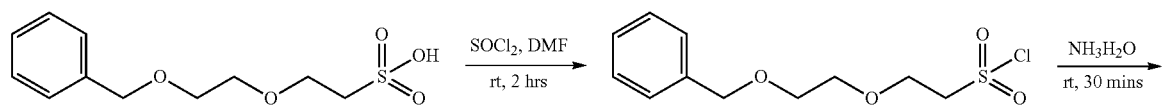
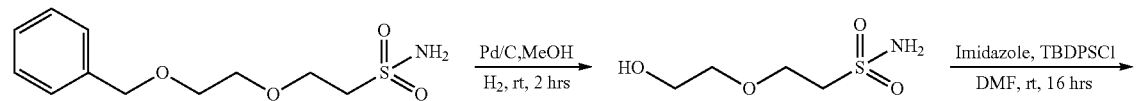
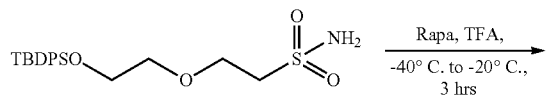
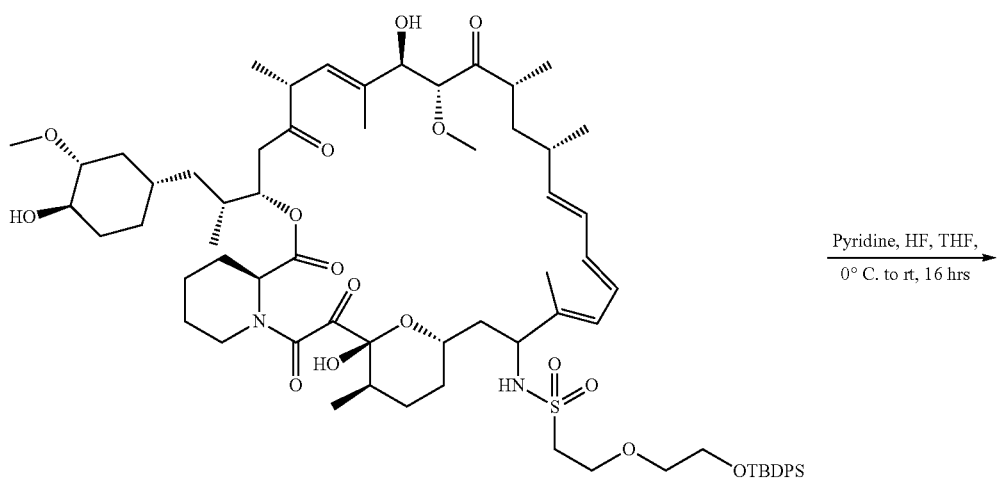
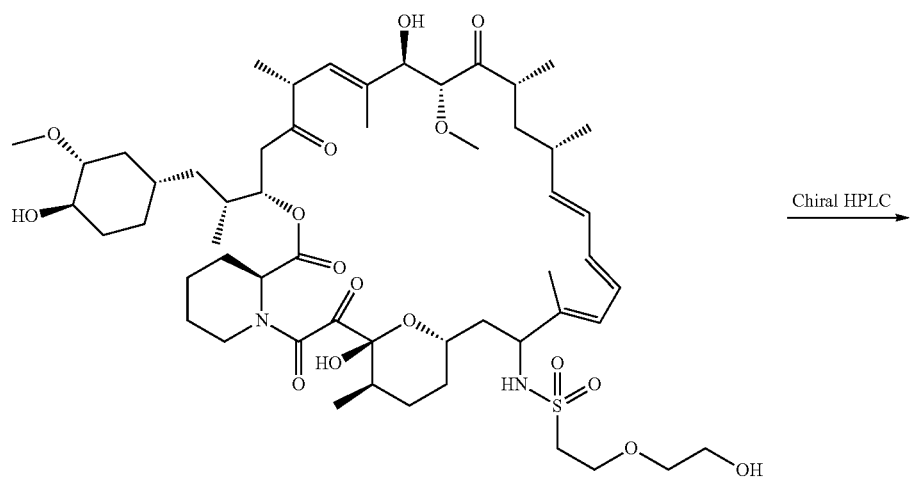
I-89

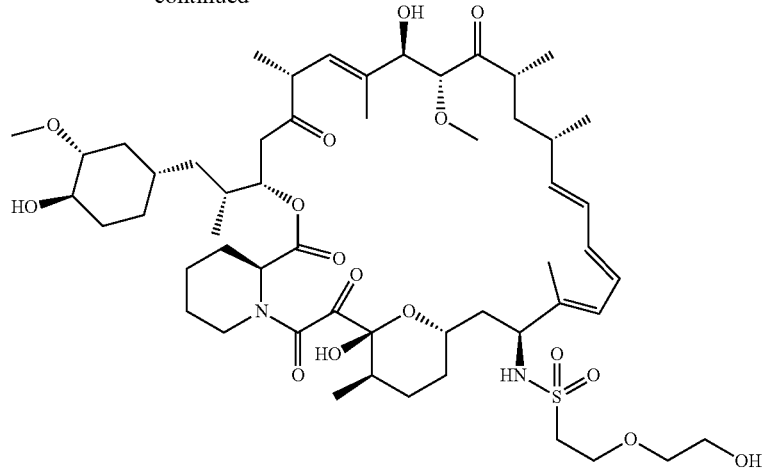

I-95

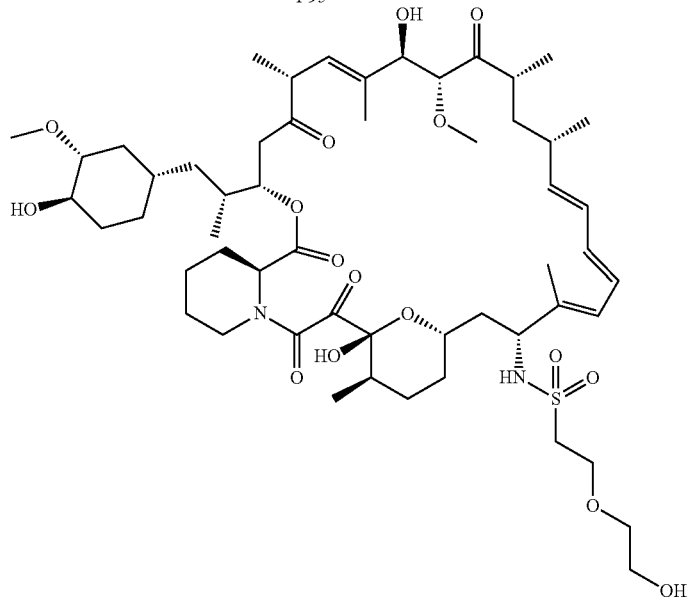

I-96

Step 1: ((2-(2-bromoethoxy) ethoxy) methyl) benzene. A solution of CBr$_4$ (1.69 g, 5.1 mmol) in DCM (5 mL) was added to a solution of 2-(2-benzyloxyethoxy)ethanol (1 g, 5.1 mmol) in DCM (5 mL) at 0° C. dropwise. Then the solution of PPh$_3$ (1.34 g, 5.1 mmol) was added to the reaction mixture at 0° C. and stirred at rt for 16 h. The reaction was concentrated and the residue was purified via silica gel chromatography (23% EtOAc in PE) to provide 2-(2-bromoethoxy) ethoxymethylbenzene (950 mg, 72% yield) as a clear oil. ESI-MS (EI+, m/z): 282.9 [M+Na]$^+$. $^1$H NMR (500 MHz, CDCl$_3$): δ 7.35-7.26 (m, 5H), 4.58 (s, 2H), 3.82 (t, J=6.0 Hz, 2H), 3.71-3.63 (m, 4H), 3.48 (t, J=6.5 Hz, 2H).

Step 2: 2-(2-benzyloxyethoxy) ethylsulfonyloxysodium. A solution of 2-(2-bromoethoxy) ethoxymethylbenzene (8.5 g, 32.8 mmol) and Na$_2$SO$_3$ (4.34 g, 34.44 mmol) in H$_2$O (80 mL) was stirred at 100° C. for 16 h then cooled and concentrated. The residue was purified via reverse phase column chromatography (100% water) to provide 2-(2-benzyloxyethoxy)ethylsulfonyloxysodium (7.4 g, 80% yield) as a white solid. $^1$H NMR (500 MHz, DMSO-d$_6$): δ 7.36-7.26 (m, 5H), 4.48 (s, 2H), 3.65-3.62 (m, 2H), 3.53 (s, 4H), 2.73-2.69 (m, 2H).

Step 3: 2-(2-benzyloxyethoxy) ethanesulfonyl chloride. A solution of 2-(2-benzyloxyethoxy)ethanesulfonic acid (3 g, 11.52 mmol) in SOCl$_2$(25 mL) and DMF (1 mL) was stirred at rt for 2 h. The solution was concentrated, poured into ice water and extracted with EtOAc (100 mL). The organic layer was washed with brine (60 mL), dried over Na$_2$SO$_4$, filtered and concentrated to provide 2-(2-benzyloxyethoxy)ethanesulfonyl chloride (2 g, 62% yield) as a yellow oil. ESI-MS (EI+, m/z): 300.9 [M+Na]$^+$.

Step 4: 2-(2-benzyloxyethoxy) ethanesulfonamide. A solution of 2-(2-benzyloxyethoxy)ethanesulfonyl chloride (2.0 g, 7.17 mmol) in ammonium hydroxide (50 mL) was stirred at rt for 1 h. The mixture was concentrated and the resulting residue purified via reverse phase column chromatography (26% CH$_3$CN in water) to provide 2-(2-benzyloxyethoxy) ethanesulfonamide (1.4 g, 75% yield) as a clear oil.

¹H NMR (400 MHz, CDCl₃): δ 7.37-7.27 (m, 5H), 5.14 (s, 2H), 4.54 (s, 2H), 3.96 (t, J=5.2 Hz, 2H), 3.70-3.62 (m, 4H), 3.32 (t, J=5.2 Hz, 2H).

Step 5: 2-(2-hydroxyethoxy) ethanesulfonamide. A solution of 2-(2-benzyloxyethoxy) ethanesulfonamide (4.9 g, 18.90 mmol) and Pd/C (2.45 g) in MeOH (200 mL) was stirred at rt for 3 h under a H₂ atmosphere. The reaction was then filtered and concentrated to provide 2-(2-hydroxyethoxy)ethanesulfonamide (3 g, 94% yield) as a clear oil. ¹H NMR (400 MHz, DMSO-d₆): δ 6.75 (s, 2H), 4.69 (t, J=4.8 Hz, 1H), 3.77 (t, J=6.8 Hz, 2H), 3.52-3.48 (m, 2H), 3.46-3.43 (m, 2H), 3.24 (t, J=6.8 Hz, 2H).

Step 6: 2-[2-[tert-butyl (diphenyl) silyl]oxyethoxy]ethanesulfonamide. To a stirred solution of 2-(2-hydroxyethoxy) ethanesulfonamide (3.3 g, 19.5 mmol) in DMF (20 mL) was added TBDPSCl (2.72 g, 23.4 mmol) and imidazole (2.66 g, 39 mmol) at 0° C. The reaction mixture was stirred at rt for 2 h then poured into water (50 mL) and extracted with EtOAc (100 mL×2). The combined organic layers were washed with water (50 mL×3), brine (100 mL), dried over Na₂SO₄, filtered and concentrated. The residue was purified via silica gel chromatography (50% EtOAc in PE) to provide 2-[2-[tert-butyl (diphenyl) silyl]oxyethoxy]ethanesulfonamide (6.75 g, 85% yield) as a white solid. ESI-MS (EI+, m/z): 430.0 [M+Na]⁺. ¹H NMR (500 MHz, CDCl₃): δ 7.67-7.65 (m, 4H), 7.44-7.38 (m, 6H), 4.83 (s, 2H), 3.95 (t, J=5.0 Hz, 2H), 3.82 (t, J=4.0 Hz, 2H), 3.60 (t, J=4.5 Hz, 2H), 3.31 (t, J=5.5 Hz, 2H), 1.05 (s, 9H).

Step 7: 2-[2-[tert-butyl(diphenyl)silyl]oxyethoxy]-N-[(34E,36E,38E,39E,47R,48S,49R,50R,52S,54S,57S,58R, 59R,68R)-58,68-dihydroxy-57-[(1R)-2-[(1S,3R,4R)-4-hydroxy-3-methoxy-cyclohexyl]-1-methyl-ethyl]-59-methoxy-47,48,49,50,60,61-hexamethyl-62,63,64,65,66-pentaoxo-82,83-dioxa-71-azatricyclohexatriaconta-34,36, 38(60),39(61)-tetraen-56-yl]ethanesulfonamide. To a stirred solution of (22E,24E,26E,27E,29R,30S,31R,32R,34S,36S, 39S,40R,41R,50R)-40,50-dihydroxy-39-[(1R)-2-[(1S,3R, 4R)-4-hydroxy-3-methoxy-cyclohexyl]-1-methyl-ethyl]-38, 41-dimethoxy-29,30,31,32,42,43-hexamethyl-60,61-dioxa-51-azatricyclohexatriaconta-22,24,26(42),27(43)-tetraene-44,45,46,47,48-pentone (1 g, 1.09 mmol) in DCM (10 mL) was added 2,2,2-trifluoroacetic acid (999 mg, 8.75 mmol) under argon, followed after 5 min, by 2-[tert-butyl(diphenyl) silyl]oxyethyl-(2-sulfamoylethyl)oxonium (1.34 g, 3.28 mmol). The resulting mixture was stirred at −20° C. for 3 h under argon, then quenched by ice cold aqueous NaHCO₃ (50 mL) and extracted with DCM (80 mL×2). The combined organic layers were washed with brine (50 mL), dried over Na₂SO₄, filtered and concentrated. The residue was purified via reverse phase column chromatography (80% CH₃CN in water) to provide the titled compound (0.38 g, 27% yield) as a white solid. ESI-MS (EI+, m/z): 1313.1 [M+Na]⁺. ¹H NMR (500 MHz, CDCl₃): δ 7.67-7.66 (m, 4H), 7.44-7.37 (m, 6H), 6.36-5.95 (m, 4H), 5.61-5.05 (m, 4H), 4.64-3.47 (m, 12H), 3.41-3.22 (m, 14H), 2.97-2.55 (m, 8H), 2.34-1.96 (m, 8H), 1.83-1.67 (m, 12H), 1.06-0.81 (m, 31H), 0.74-0.61 (m, 1H).

Step 8: N-[(21E,23E,25E,26E,32R,33S,34R,35R,37S, 39S,42S,43R,44R,53R)-43,53-dihydroxy-42-[(1R)-2-[(1S, 3R,4R)-4-hydroxy-3-methoxy-cyclohexyl]-1-methyl-ethyl]-44-methoxy-32,33,34,35,45,46-hexamethyl-47,48, 49,50,51-pentaoxo-67,68-dioxa-55-azatricyclohexatriaconta-21,23,25(45),26(46)-tetraen-4l-yl]-2-(2-hydroxyethoxy)ethanesulfonamide (I-89). To a solution of 2-[2-[tert-butyl(diphenyl)silyl]oxyethoxy]-N-[(34E,36E,38E,39E,47R,48S,49R,50R,52S,54S,57S,58R, 59R,68R)-58,68-dihydroxy-57-[(1R)-2-[(1S,3R,4R)-4-hydroxy-3-methoxy-cyclohexyl]-1-methyl-ethyl]-59-methoxy-47,48,49,50,60,61-hexamethyl-62,63,64,65,66-pentaoxo-82,83-dioxa-71-azatricyclohexatriaconta-34,36, 38(60),39(61)-tetraen-56-yl]ethanesulfonamide (373 mg, 0.28 mmol) in THF (4 mL) was added pyridine hydrofluoride (287 mg, 2.89 mmol) at 0° C. The solution was stirred at 0° C. for 3 h then warmed to rt overnight. Then reaction was quenched with ice cold aqueous NaHCO₃ (40 mL) and extracted with EtOAc (100 mL×2). The combined organic layers were washed with brine (80 mL), dried over Na₂SO₄, filtered and concentrated. The residue was purified via reverse phase column chromatography (60% CH₃CN in water) to provide the titled compound (180 mg, 59% yield) as a white solid. ESI-MS (EI+, m/z): 1073.1 [M+Na]⁺. ¹H NMR (500 MHz, CDCl₃): δ 6.38-5.97 (m, 4H), 5.61-5.14 (m, 4H), 4.24-3.01 (m, 23H), 2.95-2.52 (m, 7H), 2.29-1.87 (m, 7H), 1.85-1.52 (m, 16H), 1.49-1.31 (m, 5H), 1.28-0.83 (m, 19H), 0.70-0.63 (m, 1H).

Step 9: N-[(21E,23E,25E,26E,32R,33S,34R,35R,37S, 39S,41S,42S,43R,44R,53R)-43,53-dihydroxy-42-[(1R)-2-[(1S,3R,4R)-4-hydroxy-3-methoxy-cyclohexyl]-1-methyl-ethyl]-44-methoxy-32,33,34,35,45,46-hexamethyl-47,48, 49,50,51-pentaoxo-67,68-dioxa-55-azatricyclohexatriaconta-21,23,25(45),26(46)-tetraen-41-yl]-2-(2-hydroxyethoxy)ethanesulfonamide (I-95) and N-[(21E,23E,25E,26E,32R,33S,34R,35R,37S,39S,41R, 42S,43R,44R,53R)-43,53-dihydroxy-42-[(1R)-2-[(1S,3R, 4R)-4-hydroxy-3-methoxy-cyclohexyl]-1-methyl-ethyl]-44-methoxy-32,33,34,35,45,46-hexamethyl-47,48,49,50,51-pentaoxo-67,68-dioxa-55-azatricyclohexatriaconta-21,23, 25(45),26(46)-tetraen-41-yl]-2-(2-hydroxyethoxy) ethanesulfonamide (I-96). 280 mg of the mixture was separated via chiral HPLC and then purified by silica gel chromatography (PE:DCM:EtOAc:MeOH=3:3:1:0.6) to provide the titled compound (I-95: 69.3 mg, 25% yield) and (I-96: 53.2 mg, 19% yield) as white solids.

Chiral Separation Method:

| Column: | CHIRALPAK IC |
|---|---|
| Column size: | 5.0 cm I.D. × 25 cm L, 10 μm |
| Sample solution: | 2.6 mg/ml in Mobile phase |
| Injection: | 20 ml |
| Mobile phase: | Hexane/EtOH = 50/50(V/V) |
| Flow rate: | 60 ml/min |
| Wave length: | UV 254 nm |
| Temperature: | 35° C. |

I-95: ESI-MS (EI+, m/z): 1073.1 [M+Na]⁺. ¹H NMR (400 MHz, CDCl₃) δ 6.46-6.07 (m, 3H), 5.98 (d, J=9.3 Hz, 1H), 5.66-5.07 (m, 5H), 4.28-4.01 (m, 2H), 3.93-3.54 (m, 10H), 3.52-3.30 (m, 9H), 3.27-2.58 (m, 8H), 2.42-1.70 (m, 18H), 1.57-1.22 (m, 11H), 1.20-0.81 (m, 18H), 0.67 (dd, J=23.7, 11.9 Hz, 1H).

I-96: ESI-MS (EI+, m/z): 1073.1 [M+Na]⁺. ¹H NMR (400 MHz, CDCl₃) δ 6.42-6.12 (m, 4H), 5.56-5.14 (m, 5H), 4.61 (d, J=16.8 Hz, 1H), 4.18 (d, J=46.2 Hz, 3H), 3.97-3.56 (m, 9H), 3.51-3.19 (m, 11H), 3.17-2.48 (m, 8H), 2.43-1.73 (m, 11H), 1.50-1.18 (m, 15H), 1.16-0.83 (m, 18H), 0.69-0.65 (m, 1H).

Example 42: Synthesis of (23E,25E,27E,28E,36R, 37S,38R,39R,41S,43S,46S,47R,48R,57R)-46-[(1R)-2-[(1S,3R,4R)-4-dimethylphosphoryloxy-3-methoxy-cyclohexyl]-1-methyl-ethyl]-47,57-dihydroxy-45-[2-[2-(2-hydroxyethoxy)ethoxy]ethoxy]-48-methoxy-36,37,38,39,49,50-hexamethyl-68,69-dioxa-58-azatricyclohexatriaconta-23,25,27(49),28(50)-tetraene-51,52,53,54,55-pentone (I-92)
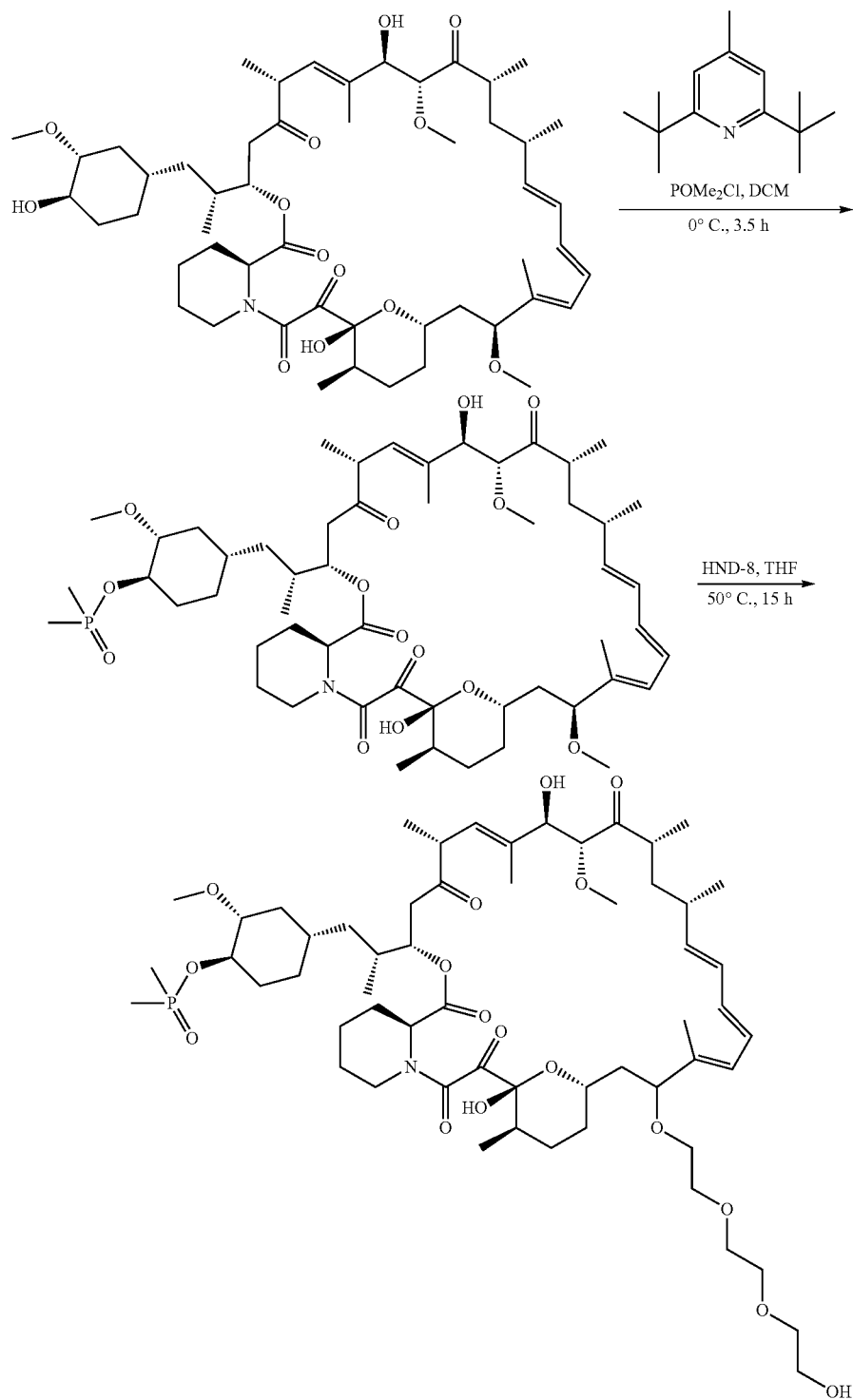
I-92

Step 1: (24E,26E,28E,29E,31R,32S,33R,34R,36S,38S, 40S,41S,42R,43R,52R)-41-[(1R)-2-[(1S,3R,4R)-4-dimethylphosphoryloxy-3-methoxy-cyclohexyl]-1-methyl-ethyl]-42,52-dihydroxy-40,43-dimethoxy-31,32,33,34,44,45-hexamethyl-62,63-dioxa-53-azatricyclohexatriaconta-24, 26,28(44),29(45)-tetraene-46,47,48,49,50-pentone. To a solution of (22E,24E,26E,27E,29R,30S,31R,32R,34S,36S, 38S,39S,40R,41R,50R)-40,50-dihydroxy-39-[(1R)-2-[(1S, 3R,4R)-4-hydroxy-3-methoxy-cyclohexyl]-1-methylethyl]-38,41-dimethoxy-29,30,31,32,42,43-hexamethyl-60, 61-dioxa-51-azatricyclohexatriaconta-22,24,26(42),27(43)-tetraene-44,45,46,47,48-pentone (0.5 g, 0.547 mmol) in DCM (9 mL) was added 2,6-di-tert-butyl-4-methyl-pyridine (0.84 g, 4.09 mmol) at 0° C. under $N_2$, followed immediately by the addition of a solution of [chloro(methyl)phosphoryl] methane (0.308 g, 2.73 mmol) in DCM (1 mL). The mixture was stirred at 0° C. for 3.5 h then diluted with 20 ml EtOAc and poured into a mixture of EtOAc (100 mL) and ice cold aqueous saturated aqueous $NaHCO_3$ solution (100 mL). The organic layer was washed with ice cold 1N HCl aqueous solution (100 mL), washed with Saturated aqueous $NaHCO_3$ aqueous solution (100 mL) and brine (100 mL) then dried over $Na_2SO_4$, filtered and concentrated. The residue was purified via silica gel chromatography (MeOH:DCM:EtOAc:PE=1:10:3:3) to provide the titled compound (0.5 g, 92% yield) as a white solid. ESI-MS (EI+, m/z): 1012.1 [M+Na]+. $^1$H NMR (500 MHz, $CDCl_3$) δ 6.48-5.82 (m, 4H), 5.58-5.05 (m, 4H), 4.79 (d, J=15.3 Hz, 1H), 4.26-4.13 (m, 1H), 3.95-3.54 (m, 4H), 3.50-3.28 (m, 9H), 3.27-3.10 (m, 4H), 3.08-2.54 (m, 5H), 2.40-1.78 (m, 12H), 1.71-1.45 (m, 13H), 1.43-1.20 (m, 8H), 1.15-0.81 (m, 18H), 0.80-0.63 (m, 1H).

Step 2: (23E,25E,27E,28E,36R,37S,38R,39R,41S,43S, 46S,47R,48R,57R)-46-[(1R)-2-[(1S,3R,4R)-4-dimethylphosphoryloxy-3-methoxy-cyclohexyl]-1-methyl-ethyl]-47,57-dihydroxy-45-[2-[2-(2-hydroxyethoxy)ethoxy] ethoxy]-48-methoxy-36,37,38,39,49,50-hexamethyl-68,69-dioxa-58-azatricyclohexatriaconta-23,25,27(49),28(50)-tetraene-51,52,53,54,55-pentone (I-92). To a solution of (24E,26E,28E,29E,31R,32S,33R,34R,36S,38S,40S,41S, 42R,43R,52R)-41-[(1R)-2-[(1S,3R,4R)-4-dimethylphosphoryloxy-3-methoxy-cyclohexyl]-1-methyl-ethyl]-42,52-dihydroxy-40,43-dimethoxy-31,32,33,34,44,45-hexamethyl-62,63-dioxa-53-azatricyclohexatriaconta-24, 26,28(44),29(45)-tetraene-46,47,48,49,50-pentone (0.2 g, 0.202 mmol) and 2-[2-(2-hydroxyethoxy)ethoxy]ethanol (0.6 g, 4.04 mmol) in THF (10 mL) was added HND-8 (35 mg, 0.202 mmol) at 50° C. under $N_2$ and the resulting solution was stirred at this temperature for 18 h. The reaction was filtered and concentrated then the residue purified via reverse phase chromatography (68% $CH_3CN$ in water) to provide the titled compound (I-92: 50 mg, 22% yield) as a light yellow solid. ESI-MS (EI+, m/z): 1130.1 [M+Na]+. $^1$H NMR (500 MHz, $CDCl_3$) δ 6.46-5.86 (m, 4H), 5.65-5.03 (m, 4H), 4.19-3.89 (m, 4H), 3.84-3.19 (m, 27H), 3.11-2.49 (m, 6H), 2.44-1.87 (m, 10H), 1.85-1.30 (m, 20H), 1.25-0.82 (m, 18H), 0.78-0.58 (m, 1H).

Example 43: Synthesis of (26E,28E,30E,31E,38R, 39S,40R,41R,43S,45S,48S,49R,50R,59R)-49,59-dihydroxy-48-[(1R)-2-[(1S,3R,4R)-4-hydroxy-3-methoxy-cyclohexyl]-1-methyl-ethyl]-50-methoxy-47-[[3-(2-methoxyethoxy)phenyl]methylamino]-38, 39,40,41,51,52-hexamethyl-70,71-dioxa-61-azatricyclohexatriaconta-26,28,30(51),31(52)-tetraene-53,54,55,56,57-pentone (I-93)

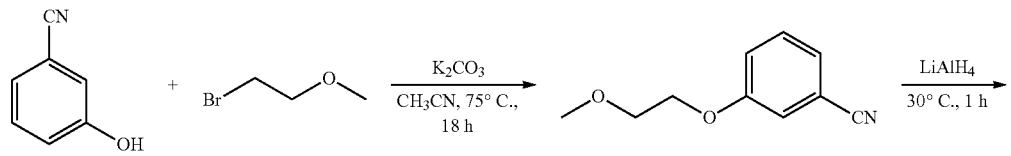

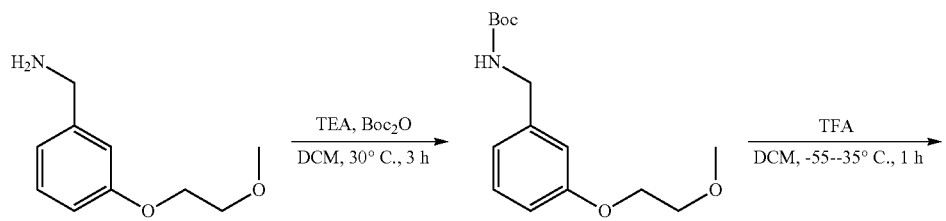

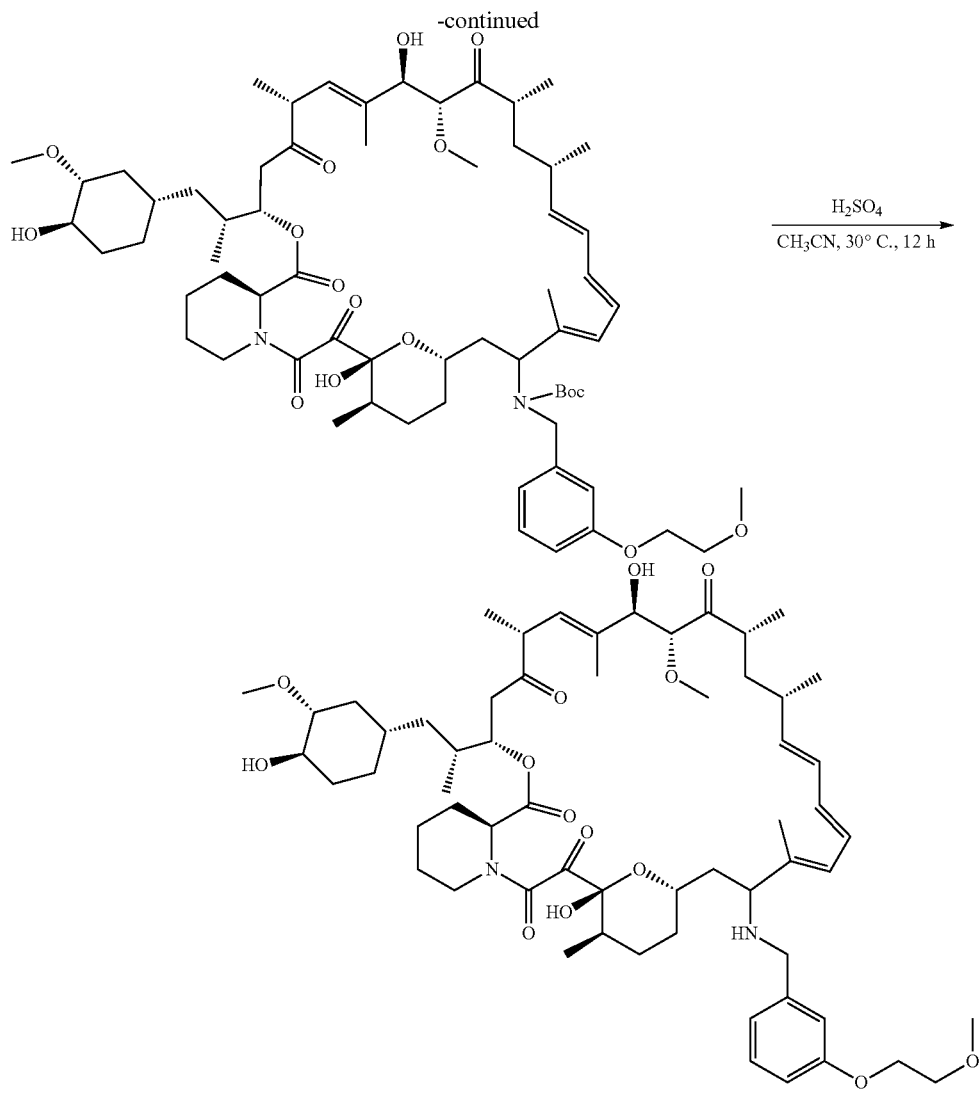

I-93

Step 1: 3-(2-methoxyethoxy) benzonitrile. A mixture of 3-hydroxybenzonitrile (20 g, 167.9 mmol), 1-bromo-2-methoxy ethane (25.67 g, 184.69 mmol) and $K_2CO_3$ (46.34 g, 335.79 mmol) in $CH_3CN$ (200 mL) was stirred at 75° C. for 18 h. The reaction was filtered, concentrated and the residue purified via silica gel chromatography (EtOAc: PE=1:15) to provide 3-(2-methoxyethoxy) benzonitrile (28.3 g, 84% yield) as a light yellow oil. ESI-MS (EI+, m/z): 178.0 [M+H]+.

Step 2: (3-(2-methoxyethoxy) phenyl) methanamine. Lithium Aluminum Hydride (1 M, 191.65 mL) was added to 3-(2-methoxyethoxy)benzonitrile (28.3 g, 159.71 mmol) at 0° C. and the mixture was stirred at 30° C. for 1 h. $Na_2SO_4 \cdot 10H_2O$ (50 g) was then added and the reaction stirred at rt for 1h. The mixture was filtered, washed with EtOAc (200 ml) and concentrated under vacuum. The residue was purified via silica gel chromatography (DCM: $CH_3OH$=15:1) to provide [3-(2-methoxyethoxy) phenyl] methanamine (9.9 g, 34% yield) as a yellow oil. ESI-MS (EI+, m/z): 182.2 [M+H]+.

Step 3: tert-butyl 3-(2-methoxyethoxy) benzylcarbamate. To a solution of [3-(2-methoxyethoxy) phenyl]methanamine (9.9 g, 54.63 mmol) in DCM (40 mL) were added triethylamine (8.29 g, 81.94 mmol) and $(Boc)_2O$ (14.31 g, 65.55 mmol) at rt. The reaction mixture was stirred for 3 h at 30° C. The reaction mixture was quenched by adding water and extracted with DCM. The organic layer was washed with water (40 mL×2) and brine (40 mL×2), dried over anhydrous sodium sulfate, filtered and the filtrate was concentrated in vacuo. The residue was purified via silica gel chromatography (DCM:$CH_3OH$=15:1) to provide tert-butyl N-[[3-(2-methoxyethoxy) phenyl]methyl]carbamate (7.5 g, 26.66 mmol, 49% yield) as a light-yellow solid. ESI-MS (EI+, m/z): 304.0 [M+Na]+.

Step 4: tert-butyl N-[(29E,31E,33E,34E,41R,42S,43R, 44R,46S,48S,51S,52R,53R,63R)-52,63-dihydroxy-51-[(1R)-2-[(1S,3R,4R)-4-hydroxy-3-methoxy-cyclohexyl]-1-methyl-ethyl]-53-methoxy-41,42,43,44,54,55-hexamethyl-56,57,58,59,60-pentaoxo-76,77-dioxa-65-azatricyclohexatriaconta-29,31,33(54),34(55)-tetraen-50-yl]-N-[[3-(2-methoxyethoxy)phenyl]methyl]carbamate. A solution of (22E,24E,26E,27E,29R,30S,31R,32R,34S,36S, 38S,39S,40R,41R,50R)-40,50-dihydroxy-39-[(1R)-2-[(1S, 3R,4R)-4-hydroxy-3-methoxy-cyclohexyl]-1-methyl-ethyl]-38,41-dimethoxy-29,30,31,32,42,43-hexamethyl-60, 61-dioxa-51-azatricyclohexatriaconta-22,24,26(42),27(43)- tetraene-44,45,46,47,48-pentone (3 g, 3.28 mmol) in DCM (180 mL) was added TFA (4.49 g, 39.38 mmol) at −50° C. The mixture was stirred at the same temperature for 10 minutes. Then tert-butyl N-[[3-(2-methoxyethoxy)phenyl]methyl]carbamate (18.47 g, 65.63 mmol) in DCM (10 mL) (divided into two batches) was added slowly over 0.5 h and the mixture was stirred at −40° C. for another 0.5 h. The mixture was quenched by adding saturated aqueous NaHCO$_3$ at −30° C. Then the mixture was warmed to rt and extracted with DCM (150 mL). The organic layer was washed with water (150 mL×2) and brine (150 mL×2), dried over anhydrous sodium sulfate, filtered and the filtrate was concentrated under vacuum. The residue was purified by reverse phase chromatography (eluting with 80% CH$_3$CN in water) to provide the titled compound (0.15 g, 4% yield) as a white solid. ESI-MS (EI+, m/z): 1185.2 [M+Na]$^+$.

Step 5: (26E,28E,30E,31E,38R,39S,40R,41R,43S,45S,48S,49R,50R,59R)-49,59-dihydroxy-48-[(1R)-2-[(1S,3R,4R)-4-hydroxy-3-methoxy-cyclohexyl]-1-methyl-ethyl]-50-methoxy-47-[[3-(2-methoxyethoxy)phenyl]methylamino]-38,39,40,41,51,52-hexamethyl-70,71-dioxa-61-azatricyclohexatriaconta-26,28,30(51),31(52)-tetraene-53,54,55,56,57-pentone (I-93). The solution of tert-butyl N-[(29E,31E,33E,34E,41R,42S,43R,44R,46S,48S,51S,52R,53R,63R)-52,63-dihydroxy-51-[(1R)-2-[(1S,3R,4R)-4-hydroxy-3-methoxy-cyclohexyl]-1-methyl-ethyl]-53-methoxy-41,42,43,44,54,55-hexamethyl-56,57,58,59,60-pentaoxo-76,77-dioxa-65-azatricyclohexatriaconta-29,31,33(54),34(55)-tetraen-50-yl]-N-[[3-(2-methoxyethoxy)phenyl]methyl]carbamate (0.2 g, 0.17 mmol) in H$_2$SO$_4$ (0.17 mmol, 3 mL, 2M) and CH$_3$CN (9 mL) was stirred at 30° C. for 12 h then saturated aqueous NaHCO$_3$ was added to adjust the pH to 8 at 0° C. The mixture was extracted with EtOAc (30 mL) and the organic layer was washed with water (20 mL×2) and brine (20 mL×2), dried over anhydrous sodium sulfate, filtered and the filtrate was concentrated under vacuum. The residue was purified via silica gel chromatography (eluting with 0-100% EtOAc in PE, then by 0-20% MeOH in DCM), then re-purified via reverse phase chromatography eluting with 46% CH$_3$CN in water (containing 0.01% HCOOH) to provide the titled compound (0.015 g, 8% yield) as a white solid. ESI-MS (EI+, m/z): 1063.1 [M+H]$^+$. $^1$H NMR (400 MHz, CDCl3) δ 7.04-6.80 (m, 4H), 6.42-6.08 (m, 4H), 5.58-5.14 (m, 5H), 4.33-3.95 (m, 5H), 3.92-3.51 (m, 4H), 3.45-3.34 (m, 18H), 3.09-2.891 (m, 3H), 2.84-2.46 (m, 4H), 2.13-1.50 (m, 41H), 1.50-1.19 (m, 23H), 1.15-0.78 (m, 26H), 1.75-0.61 (m, 1H).

Example 44: Synthesis of (26E,28E,30E,31E,38R,39S,40R,41R,43S,45S,48S,49R,50R,59R)-49,59-dihydroxy-48-[(1R)-2-[(1S,3R,4R)-4-hydroxy-3-methoxy-cyclohexyl]-1-methyl-ethyl]-50-methoxy-47-[[4-(2-methoxyethoxy)phenyl]methylamino]-38,39,40,41,51,52-hexamethyl-70,71-dioxa-61-azatricyclohexatriaconta-26,28,30(51),31(52)-tetraene-53,54,55,56,57-pentone (I-94)

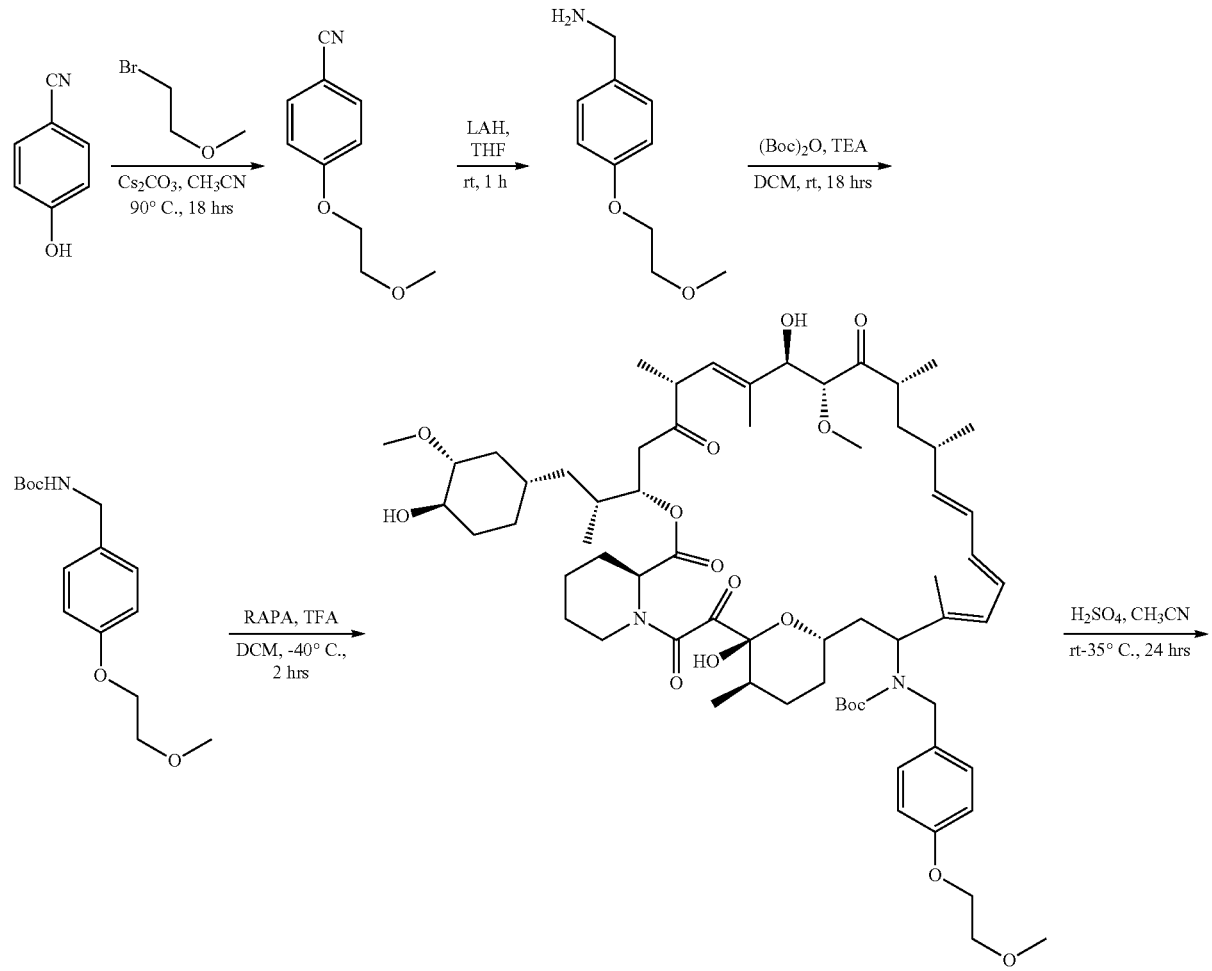

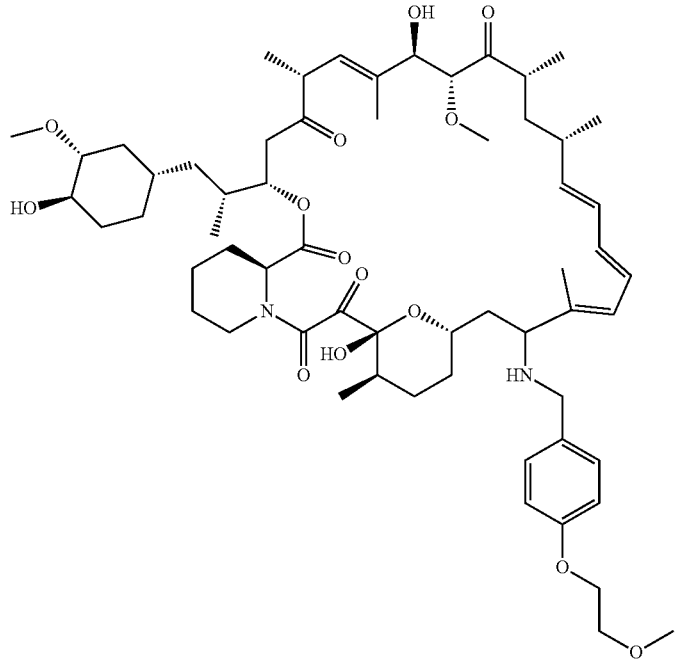

I-94

Step 1: 4-(2-methoxyethoxy) benzonitrile. The mixture of 4-hydroxybenzonitrile (5 g, 41.97 mmol), 1-bromo-2-methoxy-ethane (7 g, 50.37 mmol) and $Cs_2CO_3$ (20.51 g, 62.96 mmol) in $CH_3CN$ (50 mL) was stirred at 90° C. for 18 h. The mixture was treated with water (80 mL), extracted with EtOAc (50 mL×2). The combined organic layers were concentrated. The residue was purified via silica gel column chromatography (PE:EtOAc=7:1) to give 4-(2-methoxyethoxy) benzonitrile (7.2 g, 97% yield) as a white solid. ESI-MS (EI+, m/z): 178.0 [M+H]+. 1H NMR (400 MHz, $CDCl_3$) δ 7.58 (dd, J=9.2, 2.1 Hz, 2H), 6.98 (d, J=8.8 Hz, 2H), 4.22-4.02 (m, 2H), 3.89-3.67 (m, 2H), 3.45 (s, 3H).

Step 2: [4-(2-methoxyethoxy) phenyl]methanamine. LAH (1 M, 75.62 mL) was added to 4-(2-methoxyethoxy) benzonitrile (6.7 g, 37.81 mmol) at 0° C. The reaction was then stirred at 30° C. for 1 h. $Na_2SO_4.10H_2$ (5 g) was added and the reaction was stirred at room temperature for 1 h. The mixture was filtered, washed with EtOAc (50 mL) and the filtrate was concentrated. The residue was purified via silica gel column chromatography (DCM:MeOH=8:1) to provide [4-(2-methoxyethoxy) phenyl]methanamine (5 g, 73% yield) as a yellow oil. 1H NMR (400 MHz, DMSO-$d_6$) δ 7.22 (d, J=8.6 Hz, 2H), 6.85 (t, J=5.7 Hz, 2H), 4.12-3.97 (m, 2H), 3.64 (t, J=4.6 Hz, 4H), 3.30 (s, 3H).

Step 3: tert-butyl N-[[4-(2-methoxyethoxy) phenyl]methyl]carbamate. To a solution of [4-(2-methoxyethoxy) phenyl]methanamine (4.3 g, 23.73 mmol) and TEA (2.88 g, 28.47 mmol) in DCM (30 mL) was added tert-butoxycarbonyl tert-butyl carbonate (5.70 g, 26.10 mmol). The mixture was stirred at 22° C. for 18 h then concentrated and purified via silica gel column chromatography (PE:EtOAc=4:1) to provide tert-butyl N-[[4-(2-methoxyethoxy) phenyl]methyl]carbamate (2.3 g, 34.5% yield) as a yellow oil. ESI-MS (EI+, m/z): 304.1 [M+Na]+.

Step 4: tert-butyl N-[(29E,31E,33E,34E,41R,42S,43R,44R,46S,48S,51S,52R,53R,63R)-52,63-dihydroxy-51-[(1R)-2-[(1S,3R,4R)-4-hydroxy-3-methoxy-cyclohexyl]-1-methyl-ethyl]-53-methoxy-41,42,43,44,54,55-hexamethyl-56,57,58,59,60-pentaoxo-76,77-dioxa-65-azatricyclohexatriaconta-29,31,33(54),34(55)-tetraen-50-yl]-N-[[4-(2-methoxyethoxy)phenyl]methyl]carbamate. To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (0.5 g, 0.547 mmol) in DCM (10 mL) was added 2,2,2-trifluoroacetic acid (0.62 g, 5.47 mmol) at −40° C. The mixture was stirred at −40° C. for 10 minutes. Tert-butyl N-[[4-(2-methoxyethoxy) phenyl]methyl]carbamate (1.54 g, 5.47 mmol) in DCM (2 mL) was added and the mixture was stirred at −40° C. for 2 h. The mixture was treated with aqueous $NaHCO_3$ (40 mL), extracted with EtOAc (30 mL×2) and the combined organic layers were concentrated. The residue was purified via reverse phase chromatography (90% $CH_3CN$ in water) to provide the titled compound (0.1 g, 16% yield) as a white solid. LC-MS (EI+, m/z): 1186.2 [M+Na]+.

Step 5: (26E,28E,30E,31E,38R,39S,40R,41R,43S,45S,48S,49R,50R,59R)-49,59-dihydroxy-48-[(1R)-2-[(1S,3R,4R)-4-hydroxy-3-methoxy-cyclohexyl]-1-methyl-ethyl]-50-methoxy-47-[[4-(2-methoxyethoxy)phenyl]methylamino]-

38,39,40,41,51,52-hexamethyl-70,71-dioxa-61-azatricyclohexatriaconta-26,28,30(51),31(52)-tetraene-53,54,55,56,57-pentone (I-94). To a solution of tert-butyl N-[(29E,31E,33E,34E,41R,42S,43R,44R,46S,48S,51S,52R,53R,63R)-52,63-dihydroxy-51-[(1R)-2-[(1S,3R,4R)-4-hydroxy-3-methoxy-cyclohexyl]-1-methyl-ethyl]-53-methoxy-41,42,43,44,54,55-hexamethyl-56,57,58,59,60-pentaoxo-76,77-dioxa-65-azatricyclohexatriaconta-29,31,33(54),34(55)-tetraen-50-yl]-N-[[4-(2-methoxyethoxy)phenyl]methyl]carbamate (60 mg, 0.05 mmol) in CH$_3$CN (2 mL) was added H$_2$SO$_4$ (2 M, 600 uL) at 20° C. The reaction was stirred at 20° C. for 18 h and then at 35° C. for 5 h. The mixture was treated with aqueous NaHCO$_3$ (20 mL), extracted with EtOAc (20 mL×2) and the combined organic layers were concentrated. The residue was purified via reverse phase chromatography (45% CH$_3$CN in water) to provide the titled compound (5 mg, 9% yield) as a yellow solid. LC-MS (EI+, m/z): 1063.2 [M+H]$^+$. $^1$H NMR (400 MHz, CDCl$_3$) δ 7.16-7.28 (m, 2H), 6.85-6.93 (m, 2H), 6.06-6.53 (m, 4H), 5.05-5.64 (m, 4H), 4.20-4.30 (m, 1H), 4.02-4.20 (m, 3H), 3.71-3.82 (m, 3H), 3.12-3.51 (m, 17H), 2.86-3.03 (m, 2H), 2.46-2.85 (m, 4H), 1.93-2.16 (m, 8H), 1.52-1.91 (m, 15H), 1.10-1.43 (m, 8H), 0.83-1.11 (m, 16H), 0.62-0.77 (m, 1H).

Example 45: Synthesis of (25E,27E,29E,30E,37R,38S,39R,40R,42S,44S,47S,48R,49R,58R)-48,58-dihydroxy-47-[(1R)-2-[(1S,3R,4R)-4-hydroxy-3-methoxy-cyclohexyl]-1-methyl-ethyl]-49-methoxy-45-[3-methoxy-5-(2-methoxyethoxy)-2-pyridyl]-37,38,39,40,50,51-hexamethyl-69,70-dioxa-60-azatricyclohexatriaconta-25,27,29(50),30(51)-tetraene-52,53,54,55,56-pentone (I-97)

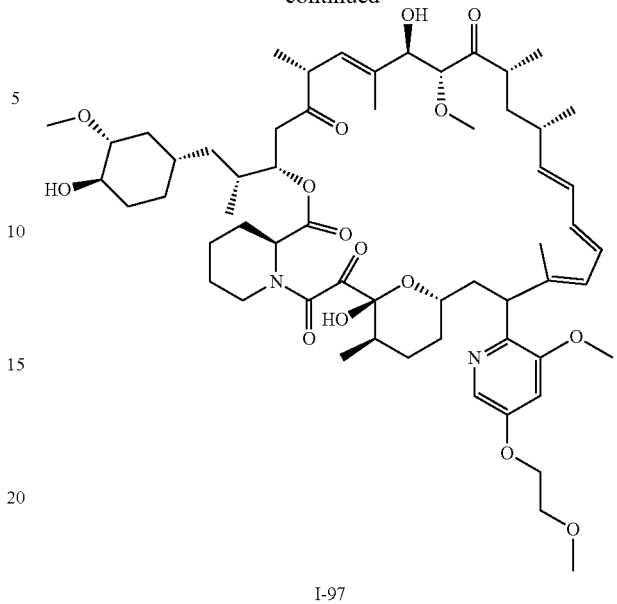

I-97

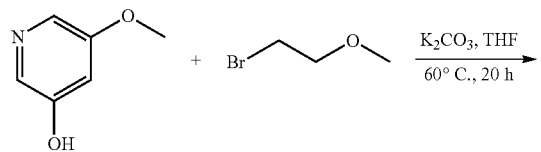

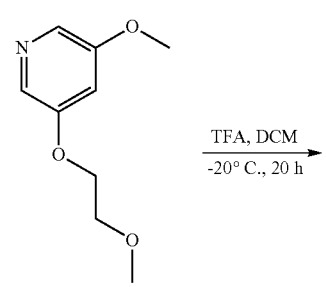

Step 1: 3-methoxy-5-(2-methoxyethoxy) pyridine. To a solution of 5-methoxypyridin-3-ol (1 g, 7.99 mmol, 4.39 mL), 1-bromo-2-methoxy-ethane (1.67 g, 11.99 mmol) in THF (20 mL) was added potassium carbonate (2.21 g, 15.98 mmol) and the mixture was stirred at 60° C. for 16 h. The reaction was washed with water (20 ml), and extracted with EtOAc (20 mL×3). The combined organic layers were dried over Na$_2$SO$_4$, filtered and concentrated. The residue was purified via silica gel chromatography with a gradient of EtOAc:PE from 0-80% to provide 3-methoxy-5-(2-methoxyethoxy) pyridine (300 mg, 21% yield) as a light brown oil. ESI-MS (EI$^+$, m/z): 184.1 [M+H]$^+$. $^1$H NMR (400 MHz, CDCl$_3$) δ 8.03-7.90 (m, 2H), 6.80 (t, J=2.3 Hz, 1H), 4.16 (dd, J=5.3, 3.9 Hz, 2H), 3.84 (s, 3H), 3.79-3.74 (m, 2H), 3.46 (s, 3H).

Step 2: (25E,27E,29E,30E,37R,38S,39R,40R,42S,44S,47S,48R,49R,58R)-48,58-dihydroxy-47-[(1R)-2-[(1S,3R,4R)-4-hydroxy-3-methoxy-cyclohexyl]-1-methyl-ethyl]-49-methoxy-45-[3-methoxy-5-(2-methoxyethoxy)-2-pyridyl]-37,38,39,40,50,51-hexamethyl-69,70-dioxa-60-azatricyclohexatriaconta-25,27,29(50),30(51)-tetraene-52,53,54,55,56-pentone (I-97). To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (0.5 g, 0.547 mmol) in DCM (15 mL) at −20° C. was added 2,2,2-trifluoroacetic acid (0.62 g, 5.47 mmol) and 3-methoxy-5-(2-methoxyethoxy) pyridine (1 g, 5.47 mmol). The reaction was stirred at −20° C. for a further 2 h. The mixture was poured into ice cold saturated NaHCO$_3$ solution and extracted with EtOAc (10 mL). The organic layer was washed with water (10 mL), brine (10 mL), dried over anhydrous Na$_2$SO$_4$, filtered and concentrated. The residue was purified via silica gel chromatography (20% MeOH in DCM) to provide the titled compound (I-97: 52 mg, 9% yield) as a white solid. ESI-MS (EI$^+$, m/z): 1065.1 [M+H]$^+$. $^1$HNMR (400 MHz, CDCl$_3$) δ 8.43-7.87 (m, 2H), 7.78-7.50 (m, 1H), 6.52-6.01 (m, 4H), 5.72-4.95 (m, 5H), 4.60-3.71 (m, 12H), 3.63-3.15 (m, 21H), 3.05-2.48 (m, 5H), 2.43-1.81 (m, 10H), 1.64-1.20 (m, 9H), 1.12-0.53 (m, 19H).

Example 46: Synthesis of (28E,30E,32E,33E,36R, 37S,38R,39R,42S,44S,47S,48R,49R,58R)-48,58-dihydroxy-47-[(1R)-2-[(1S,3R,4R)-4-hydroxy-3-methoxy-cyclohexyl]-1-methyl-ethyl]-49-methoxy-36,37,38,39,50,51-hexamethyl-46-[(1-pyridazin-3-yl-4-piperidyl)oxy]-71,72-dioxa-62-azatricyclohexatriaconta-28,30,32(50),33(51)-tetraene-52,53,54,55,56-pentone (I-98)

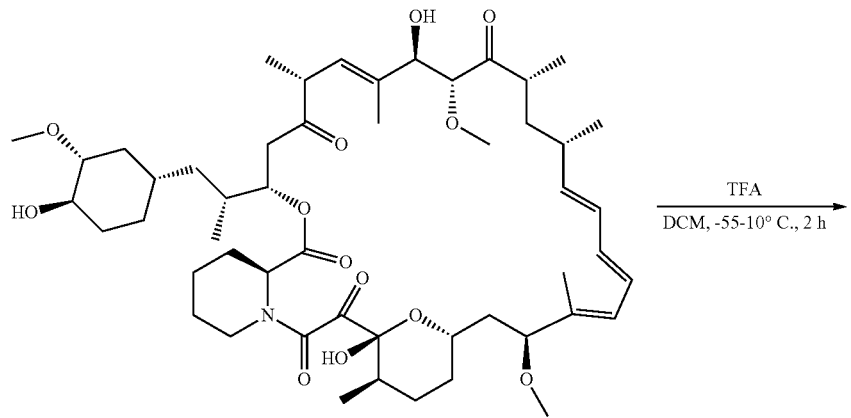

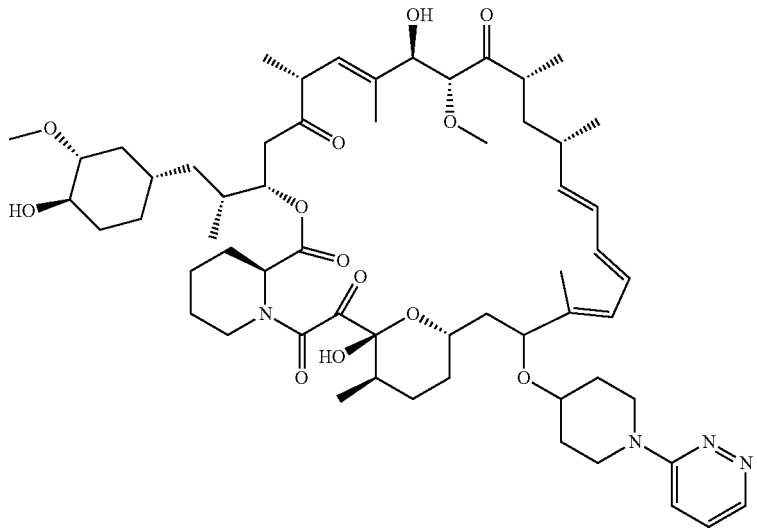

I-98

To a solution of (22E,24E,26E,27E,29R,30S,31R,32R, 34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (1 g, 1.09 mmol) in DCM (80 mL) was added TFA (2.49 g, 21.88 mmol) at −50° C. The mixture was stirred at the same temperature for 10 minutes. Then 1-pyridazin-3-ylpiperidin-4-ol (2.35 g, 13.13 mmol) in DCM (20 mL) was added and the mixture was stirred for 2 h while slowly arming to 10° C. The reaction was quenched by adding saturated aqueous NaHCO$_3$ at 0° C. then extracted with DCM (50 mL). The organic layer was washed with water (50 mL×2) and brine (50 mL×2), dried over anhydrous sodium sulfate, filtered and concentrated. The residue was purified via silica gel chromatography (eluting with 30% DCM in MeOH) then repurified via reverse phase chromatography (eluting with 35% CH$_3$CN in water) to provide the titled compound (73 mg, 6% yield) as a yellow solid. ESI-MS (EI+, m/z): 1061.1[M+H]$^+$. $^1$HNMR (400 MHz, CDCl3) δ 9.13-9.02 (m, 1H), 8.24-8.06 (m, 1H), 7.87-7.52 (m, 1H), 6.47-6.07 (m, 4H), 5.66-5.09 (m, 5H), 4.31-3.69 (m, 6H), 3.60-3.15 (m, 12H), 2.98-2.54 (m, 5H), 2.51-1.97 (m, 20H), 1.86-1.58 (m, 19H), 1.55-1.20 (m, 9H), 1.17-0.79 (m, 20H), 0.71-0.57 (m, 1H).

Example 47: Synthesis of (24E,26E,28E,29E,35R, 36S,37R,38R,40S,42S,45S,46R,47R,56R)-45-[(1R)-2-[(1S,3R,4R)-4-dimethylphosphoryloxy-3-methoxy-cyclohexyl]-1-methyl-ethyl]-46,56-dihydroxy-47-methoxy-44-[2-(2-methoxyethoxy)ethoxy]-35,36,37,38,48,49-hexamethyl-66,67-dioxa-57-azatricyclohexatriaconta-24,26,28(48),29(49)-tetraene-50,51,52,53,54-pentone (I-99)
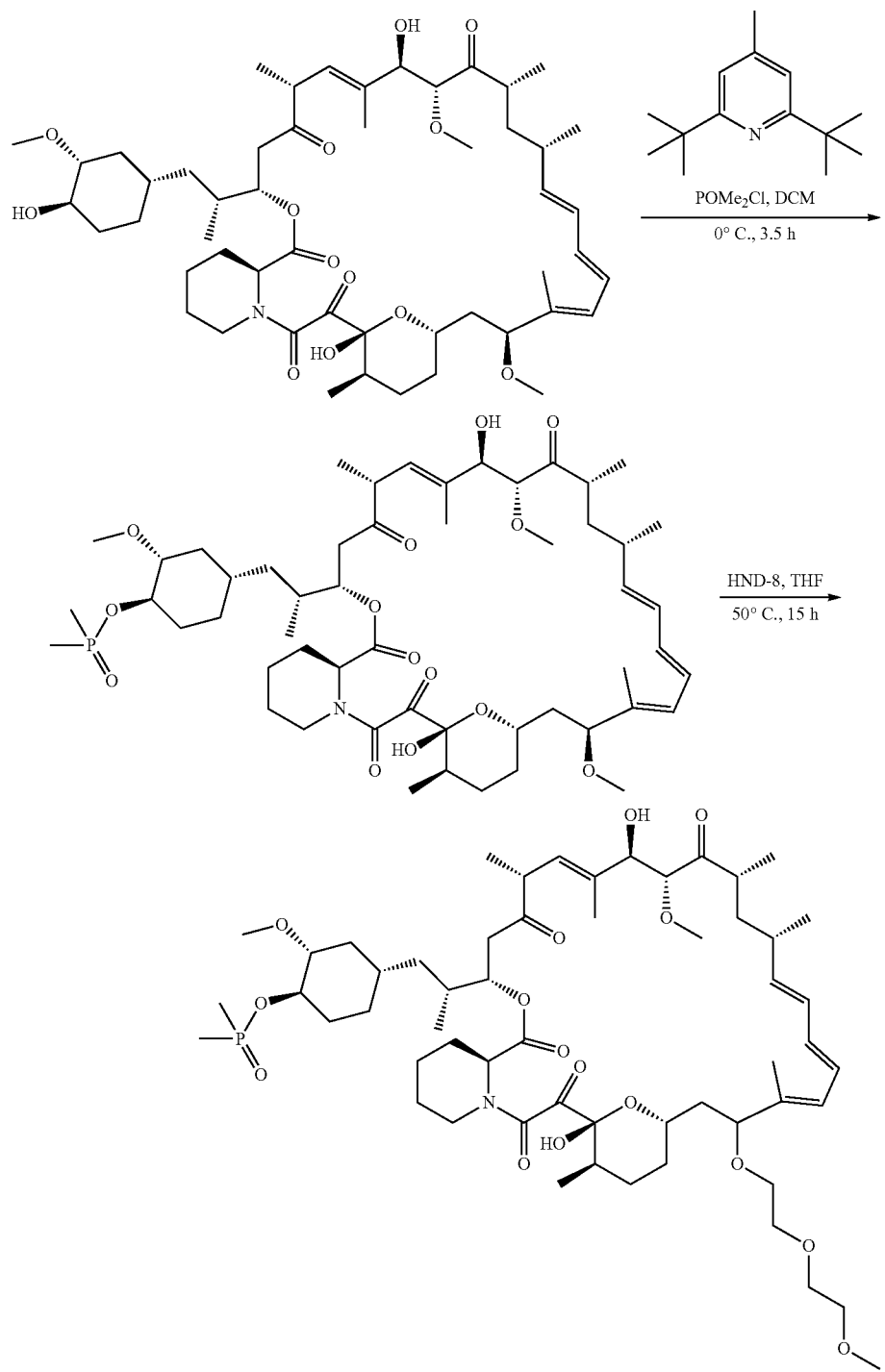
I-99

Step 1: (24E,26E,28E,29E,31R,32S,33R,34R,36S,38S, 40S,41S,42R,43R,52R)-41-[(1R)-2-[(1S,3R,4R)-4-dimethylphosphoryloxy-3-methoxy-cyclohexyl]-1-methyl-ethyl]-42,52-dihydroxy-40,43-dimethoxy-31,32,33,34,44,45-hexamethyl-62,63-dioxa-53-azatricyclohexatriaconta-24,26,28(44),29(45)-tetraene-46,47,48,49,50-pentone. To a solution of (22E,24E,26E,27E,29R,30S,31R,32R,34S,36S, 38S,39S,40R,41R,50R)-40,50-dihydroxy-39-[(1R)-2-[(1S, 3R,4R)-4-hydroxy-3-methoxy-cyclohexyl]-1-methyl-ethyl]-38,41-dimethoxy-29,30,31,32,42,43-hexamethyl-60, 61-dioxa-51-azatricyclohexatriaconta-22,24,26(42),27(43)-tetraene-44,45,46,47,48-pentone (0.5 g, 0.547 mmol) and 2,6-ditert-butyl-4-methyl-pyridine (0.84 g, 4.09 mmol) in DCM (9 mL) at 0° C. under N₂ was added a solution of [chloro(methyl)phosphoryl]methane (0.308 g, 2.73 mmol) in DCM (1 mL). The reaction was stirred at 0° C. for 3.5 h then diluted with EtOAc (20 ml) and poured into ice cold mixture of aqueous saturated NaHCO₃ (100 mL) and EtOAc (100 mL). The organic layer was washed with ice cold 1N HCl aqueous solution (100 mL), aqueous saturated NaHCO₃ solution (100 mL) and brine (100 mL) then dried over Na₂SO₄, filtered and concentrated. The residue was purified via silica gel chromatography (MeOH:DCM:EtOAc:PE=1: 10:3:3) to provide the titled compound (0.5 g, 92% yield) as a white solid. ESI-MS (EI⁺, m/z): 1012.1 [M+Na]⁺. ¹H NMR (500 MHz, CDCl₃) δ 6.48-5.82 (m, 4H), 5.58-5.05 (m, 4H), 4.79 (d, J=15.3 Hz, 1H), 4.26-4.13 (m, 1H), 3.95-3.54 (m, 4H), 3.50-3.28 (m, 9H), 3.27-3.10 (m, 4H), 3.08-2.54 (m, 5H), 2.40-1.78 (m, 12H), 1.71-1.45 (m, 13H), 1.43-1.20 (m, 8H), 1.15-0.81 (m, 18H), 0.80-0.63 (m, 1H).

Step 2: (24E,26E,28E,29E,35R,36S,37R,38R,40S,42S, 45S,46R,47R,56R)-45-[(1R)-2-[(1S,3R,4R)-4-dimethylphosphoryloxy-3-methoxy-cyclohexyl]-1-methyl-ethyl]-46,56-dihydroxy-47-methoxy-44-[2-(2-methoxyethoxy)ethoxy]-35,36,37,38,48,49-hexamethyl-66,67-dioxa-57-azatricyclohexatriaconta-24,26,28(48),29(49)-tetraene-50, 51,52,53,54-pentone (I-99). To a solution of (24E,26E,28E, 29E,31R,32S,33R,34R,36S,38S,40S,41S,42R,43R,52R)-41-[(1R)-2-[(1S,3R,4R)-4-dimethylphosphoryloxy-3-methoxy-cyclohexyl]-1-methyl-ethyl]-42,52-dihydroxy-40, 43-dimethoxy-31,32,33,34,44,45-hexamethyl-62,63-dioxa-53-azatricyclohexatriaconta-24,26,28(44),29(45)-tetraene-46,47,48,49,50-pentone (0.4 g, 0.404 mmol) and 2-(2-methoxyethoxy)ethanol (0.97 g, 8.08 mmol) in THF (20 mL) at 50° C. under N₂ was added HND-8 (60 mg). The reaction was stirred at this temperature for 18 h then filtered, concentrated and purified via reverse phase chromatography (75% CH₃CN in water) to provide the titled compound (90 mg, 21% yield) as a yellow solid. ESI-MS (EI⁺, m/z): 1100.1 [M+Na]⁺. ¹H NMR (500 MHz, CDCl₃) δ 6.45-5.84 (m, 4H), 5.63-5.08 (m, 4H), 4.34-3.99 (m, 3H), 3.92-3.14 (m, 22H), 3.10-2.43 (m, 5H), 2.42-1.72 (m, 15H), 1.57-1.23 (m, 17H), 1.22-0.61 (m, 22H).

Example 48: Synthesis of (23E,25E,27E,28E,32R, 33S,34R,35R,37S,39S,42S,47R,48R,57R)-41-[2-[[(3S,3aR,6R,6aR)-3-hydroxy-2,3,3a,5,6,6a-hexahydrofuro[3,2-b]furan-6-yl]oxy]ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-100), (23E,25E, 27E,28E,32R,33S,34R,35R,37S,39S,41S,42S,47R, 48R,57R)-41-[2-[[(3S,3aR,6R,6aR)-3-hydroxy-2,3, 3a,5,6,6a-hexahydrofuro[3,2-b]furan-6-yl]oxy]ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28 (50)-tetraene-51,52,53,54,55-pentone (I-103) and (23E,25E,27E,28E,32R,33S,34R,35R,37S,39S,41R, 42S,47R,48R,57R)-41-[2-[[(3S,3aR,6R,6aR)-3-hydroxy-2,3,3a,5,6,6a-hexahydrofuro[3,2-b]furan-6-yl]oxy]ethoxy]-47,57-dihydroxy-42-[(1R)-2-[(1S,3R, 4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27 (49),28(50)-tetraene-51,52,53,54,55-pentone (I-115)

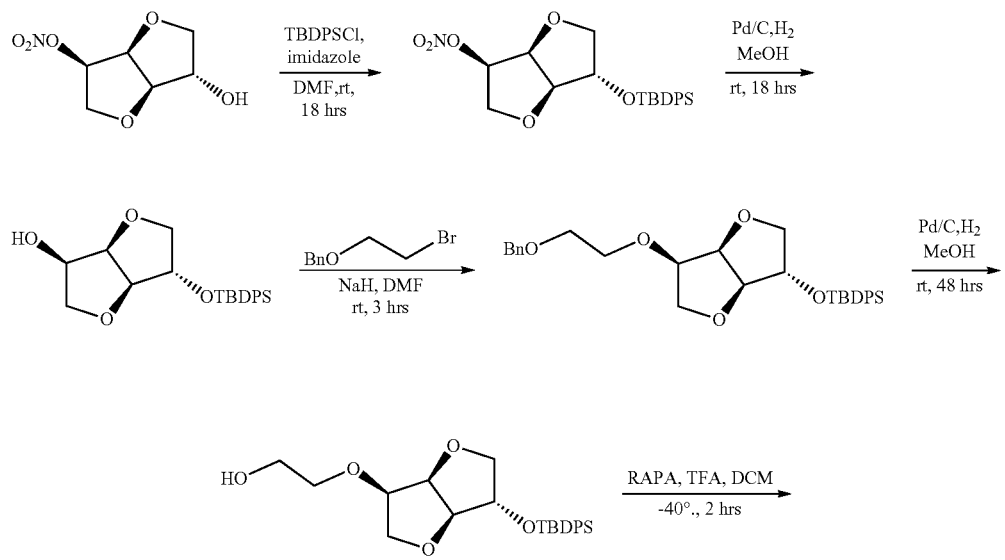

-continued
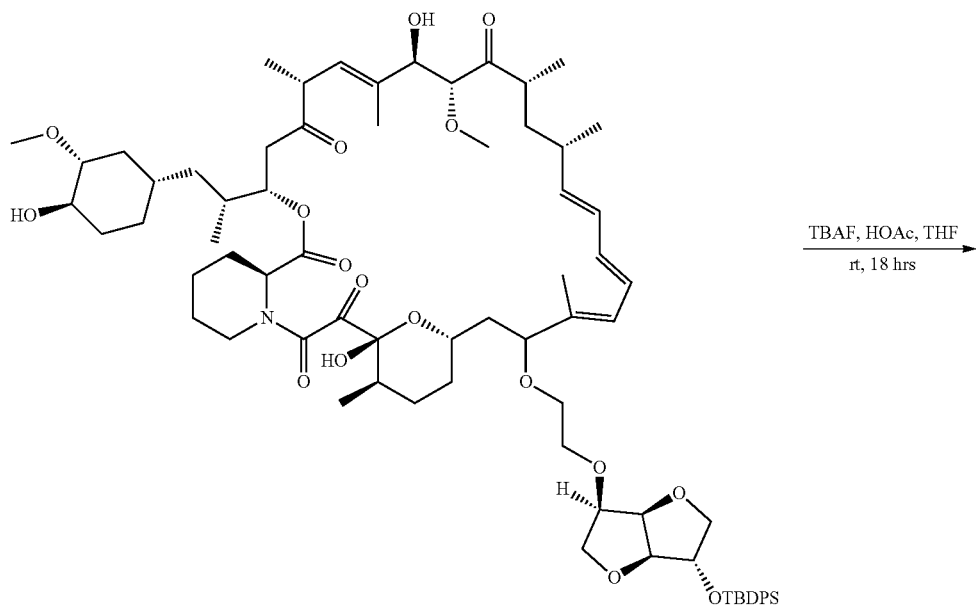
TBAF, HOAc, THF
rt, 18 hrs
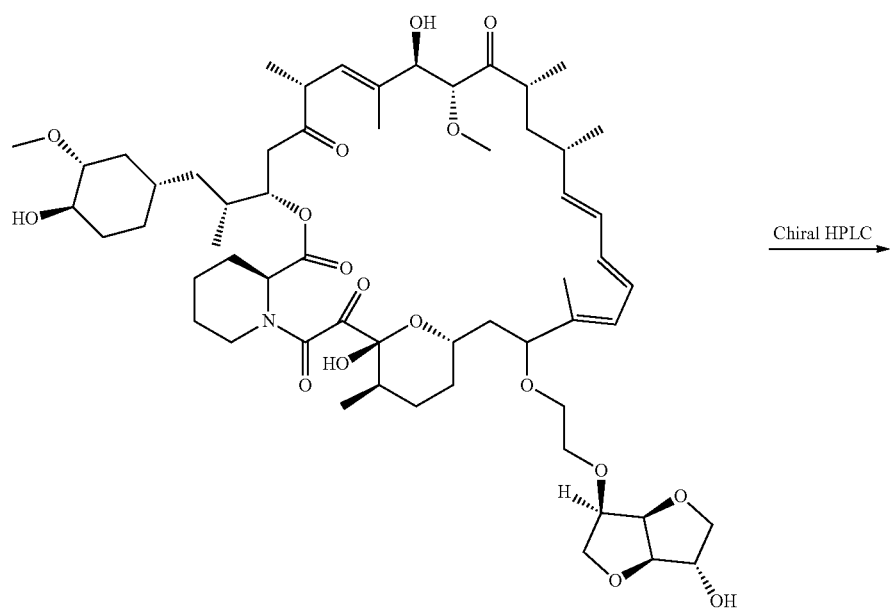
I-100
Chiral HPLC

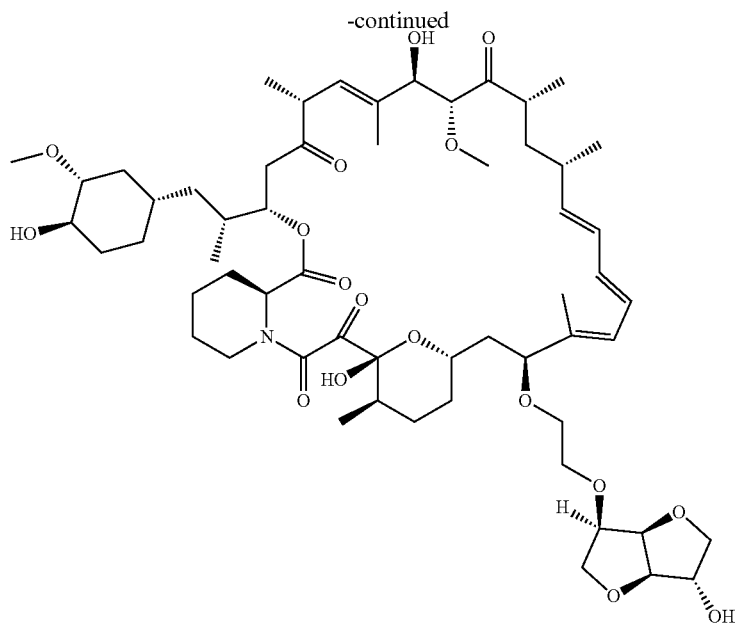

I-103

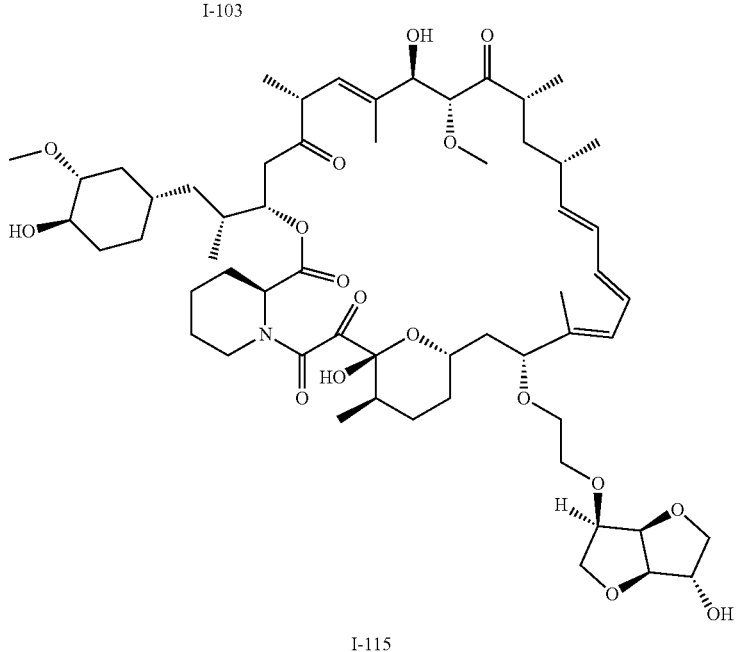

I-115

Step 1: [(3R,3aS,6S,6aS)-6-[tert-butyl(diphenyl)silyl]oxy-2,3,3a,5,6,6a-hexahydrofuro[3,2-b]furan-3-yl]nitrate. To a solution of [(3S,3aR,6R,6aS)-3-hydroxy-2,3,3a,5,6,6a-hexahydrofuro[3,2-b]furan-6-yl]nitrate (10 g, 52.32 mmol) and imidazole (5.34 g, 78.48 mmol) in DMF (50 mL) at 0° C. was added tert-butyl-chloro-diphenyl-silane (14.38 g, 52.32 mmol). The mixture was stirred at 20° C. for 18 h. The reaction was treated with H$_2$O (300 mL) and extracted with EtOAc (200 mL×2). The combined organic layers were concentrated. The residue was washed with MeOH (30 mL) to give [(3R,3aS,6S,6aS)-6-[tert-butyl(diphenyl)silyl]oxy-2,3,3a,5,6,6a-hexahydrofuro[3,2-b]furan-3-yl] nitrate (17.4 g, 77% yield) as a white solid. ESI-MS (EI$^+$, m/z): 451.9 [M+Na]$^+$. $^1$H NMR (400 MHz, CDCl$_3$) δ 7.71-7.57 (m, 4H), 7.49-7.32 (m, 6H), 5.30 (td, J=5.5, 3.5 Hz, 1H), 5.03 (t, J=5.0 Hz, 1H), 4.38 (d, J=4.6 Hz, 1H), 4.33 (d, J=2.6 Hz, 1H), 3.89-3.78 (m, 3H), 3.69 (dd, J=9.8, 3.0 Hz, 1H), 1.06 (s, 9H).

Step 2: (3R,3aR,6S,6aS)-6-[tert-butyl(diphenyl)silyl]oxy-2,3,3a,5,6,6a-hexahydrofuro[3,2-b]furan-3-ol. A mixture of [(3R,3aS,6S,6aS)-6-[tert-butyl(diphenyl)silyl]oxy-2,3,3a,5,6,6a-hexahydrofuro[3,2-b]furan-3-yl] nitrate (17.4 g, 40.51 mmol) and Pd/C (2 g) in MeOH (150 mL) was stirred at 20° C. under H$_2$ for 18 h. The reaction was filtered and washed with MeOH (30 mL). The filtrate was concentrated to provide (3R,3aR,6S,6aS)-6-[tert-butyl(diphenyl)silyl]oxy-2,3,3a,5,6,6a-hexahydrofuro[3,2-b]furan-3-ol (15 g, 96% yield) as a colorless oil. ESI-MS (EI$^+$, m/z): 407.0 [M+Na]$^+$.

Step 3: [(3R,3aR,6S,6aS)-3-(2-benzyloxyethoxy)-2,3,3a,5,6,6a-hexahydrofuro[3,2-b]furan-6-yl]oxy-tert-butyl-diphenyl-silane. To a solution of (3R,3aR,6S,6aS)-6-[tert-butyl(diphenyl)silyl]oxy-2,3,3a,5,6,6a-hexahydrofuro[3,2-b]furan-3-ol (2 g, 5.20 mmol) in DMF (10 mL) was added NaH (0.31 g, 7.8 mmol, 60% purity). The mixture was stirred at 20° C. for 30 minutes. 2-bromoethoxymethylbenzene (1.34 g, 6.24 mmol) was added and the mixture was stirred at 20° C. for a further 3 h. The reaction was then treated with H$_2$O (100 mL) and extracted with EtOAc (80 mL×2). The combined organic layers were concentrated. The residue was purified by reverse-phase chromatography (95% CH$_3$CN in water) to provide [(3R,3aR,6S,6aS)-3-(2-benzyloxyethoxy)-2,3,3a,5,6,6a-hexahydrofuro[3,2-b]furan-6-yl]oxy-tert-butyl-diphenyl-silane (0.8 g, 30% yield) as a colorless oil. ESI-MS (EI$^+$, m/z): 519.2 [M+H]$^+$.

Step 4: 2-[[(3R,3aR,6S,6aS)-6-[tert-butyl(diphenyl)silyl]oxy-2,3,3a,5,6,6a-hexahydrofuro[3,2-b]furan-3-yl]oxy]ethanol. A mixture of [(3R,3aR,6S,6aS)-3-(2-benzyloxyethoxy)-2,3,3a,5,6,6a-hexahydrofuro[3,2-b]furan-6-yl]oxy-tert-butyl-diphenyl-silane (800 mg, 1.54 mmol) and Pd/C (100 mg) in MeOH (15 mL) was stirred at 20° C. under H$_2$ for 48 h. The reaction was filtered and washed with MeOH (10 mL). The filtrate was concentrated and the residue purified via silica gel chromatography (PE:EtOAc=1:2) to provide 2-[[(3R,3aR,6S,6aS)-6-[tert-butyl(diphenyl)silyl]oxy-2,3,3a,5,6,6a-hexahydrofuro[3,2-b]furan-3-yl]oxy]ethanol (430 mg, 65% yield) as a colorless oil. ESI-MS (EI$^+$, m/z): 451.0 [M+H]$^+$. $^1$H NMR (400 MHz, CDCl$_3$) δ 7.63 (ddd, J=7.9, 5.0, 1.5 Hz, 4H), 7.47-7.33 (m, 6H), 4.75 (t, J=4.2 Hz, 1H), 4.44 (d, J=3.9 Hz, 1H), 4.32-4.26 (m, 1H), 4.09-4 (m, 1H), 3.92-3.83 (m, 2H), 3.79-3.67 (m, 5H), 3.47 (t, J=8.4 Hz, 1H), 2.84 (s, 1H), 1.07 (d, J=6.3 Hz, 9H).

Step 5: (36E,38E,40E,41E,47R,48S,49R,50R,52S,54S,57S,62R,63R,72R)-56-[2-[[(3R,3aR,6S,6aS)-6-[tert-butyl(diphenyl)silyl]oxy-2,3,3a,5,6,6a-hexahydrofuro[3,2-b]furan-3-yl]oxy]ethoxy]-62,72-dihydroxy-57-[(1R)-2-[(1S,3R,4R)-4-hydroxy-3-methoxy-cyclohexyl]-1-methyl-ethyl]-63-methoxy-47,48,49,50,64,65-hexamethyl-85,86-dioxa-74-azatricyclohexatriaconta-36,38,40(64),41(65)-tetraene-66,67,68,69,70-pentone. To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (1 g, 1.09 mmol) in DCM (15 mL) was added 2,2,2-trifluoroacetic acid (1.25 g, 10.94 mmol) at −40° C. The mixture was stirred at −40° C. for 10 minutes. 2-[[(3R,3aR,6S,6aS)-6-[tert-butyl(diphenyl)silyl]oxy-2,3,3a,5,6,6a-hexahydrofuro[3,2-b]furan-3-yl]oxy]ethanol (2.34 g, 5.47 mmol) in DCM (2 mL) was added and the mixture was stirred at −40° C. for a further 2 h. The mixture was treated with aqueous NaHCO$_3$ (40 mL) and extracted with EtOAc (30 mL×2). The combined organic layers were concentrated and the residue was purified via reverse phase chromatography (95% CH$_3$CN in water) to provide the titled compound (0.4 g, 28% yield) as a white solid. ESI-MS (EI$^+$, m/z): 1334.2 [M+Na]$^+$.

Step 6: (23E,25E,27E,28E,32R,33S,34R,35R,37S,39S,42S,47R,48R,57R)-41-[2-[[(3S,3aR,6R,6aR)-3-hydroxy-2,3,3a,5,6,6a-hexahydrofuro[3,2-b]furan-6-yl]oxy]ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-100). To a solution of (36E,38E,40E,41E,47R,48S,49R,50R,52S,54S,57S,62R,63R,72R)-56-[2-[[(3R,3aR,6S,6aS)-6-[tert-butyl(diphenyl)silyl]oxy-2,3,3a,5,6,6a-hexahydrofuro[3,2-b]furan-3-yl]oxy]ethoxy]-62,72-dihydroxy-57-[(1R)-2-[(1S,3R,4R)-4-hydroxy-3-methoxy-cyclohexyl]-1-methyl-ethyl]-63-methoxy-47,48,49,50,64,65-hexamethyl-85,86-dioxa-74-azatricyclohexatriaconta-36,38,40(64),41(65)-tetraene-66,67,68,69,70-pentone (0.4 g, 0.3 mmol) in THF (5 mL) was added acetic acid (82.5 mg, 1.37 mmol) and TBAF (1 M, 458 uL) at 0° C. The mixture was stirred at 20° C. for 18 h. The mixture was treated with EtOAc (50 mL) then washed with NaHCO$_3$ (50 mL) and water (50 mL×5). The organic layer was concentrated and the residue was purified via reverse phase chromatography (50% CH$_3$CN in water) to provide the titled compound (0.12 g, 37% yield) as a white solid. ESI-MS (EI$^+$, m/z): 1094.0 [M+Na]$^+$. $^1$H NMR (400 MHz, CDCl$_3$) δ 5.87-6.42 (m, 4H), 5.09-5.59 (m, 4H), 4.39-4.82 (m, 3H), 4.05-4.40 (m, 4H), 3.83-4.05 (m, 4H), 3.47-3.83 (m, 6H), 3.25-3.47 (m, 10H), 2.84-3.01 (m, 2H), 2.53-2.82 (m, 4H), 2.24-2.42 (m, 2H), 1.87-2.18 (m, 5H), 1.68-1.85 (m, 10H), 1.55-1.65 (m, 3H), 1.12-1.55 (m, 11H), 0.83-1.17 (m, 16H), 0.59-0.74 (m, 1H).

Step 7: (23E,25E,27E,28E,32R,33S,34R,35R,37S,39S,41S,42S,47R,48R,57R)-41-[2-[[(3S,3aR,6R,6aR)-3-hydroxy-2,3,3a,5,6,6a-hexahydrofuro[3,2-b]furan-6-yl]oxy]ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-103) and (23E,25E,27E,28E,32R,33S,34R,35R,37S,39S,41R,42S,47R,48R,57R)-41-[2-[[(3S,3aR,6R,6aR)-3-hydroxy-2,3,3a,5,6,6a-hexahydrofuro[3,2-b]furan-6-yl]oxy]ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-115). 150 mg of the mixture was separated via chiral HPLC to provide the titled compounds (I-103:69 mg, 46% yield) and (I-115: 33 mg, 22% yield) as white solids.

Chiral Separation Method:

| Column: | CHIRALPAK IC |
| --- | --- |
| Column size: | 5.0 cm I.D. × 25 cm L, 10 μm |
| Sample solution: | 1.6 mg/ml in Mobile phase |
| Injection: | 5 ml |
| Mobile phase: | Hexane/EtOH = 40/60(V/V) |
| Flow rate: | 30 ml/min |
| Wave length: | UV 254 nm |
| Temperature: | 35° C. |

I-103: ESI-MS (EI$^+$, m/z): 1094.5 [M+Na]$^+$. $^1$H NMR (500 MHz, CDCl$_3$) δ 6.40-6.10 (m, 3H), 5.92 (dd, J=37.7, 10.9 Hz, 1H), 5.56-5.39 (m, 2H), 5.27 (d, J=5.4 Hz, 1H), 5.13 (t, J=11.7 Hz, 1H), 4.71 (dd, J=22.3, 17.9 Hz, 2H), 4.44 (d, J=4.0 Hz, 1H), 4.32 (s, 1H), 4.19 (d, J=5.3 Hz, 1H), 4.10 (dd, J=11.8, 7.2 Hz, 1H), 4-3.84 (m, 4H), 3.83-3.46 (m, 7H), 3.45-3.23 (m, 11H), 2.99-2.54 (m, 5H), 2.41-1.85 (m, 8H), 1.82-1.70 (m, 7H), 1.53-1.18 (m, 14H), 1.15-0.81 (m, 18H), 0.71-0.62 (m, 1H).

I-115: ESI-MS (EI$^+$, m/z): 1094.6 [M+Na]$^+$. $^1$HNMR (500 MHz, CDCl$_3$) δ 6.45-5.84 (m, 4H), 5.57-5.11 (m, 5H), 4.77-3.15 (m, 19H), 3.02-1.92 (m, 14H), 1.88-1.66 (m, 14H), 1.57-1.21 (m, 13H), 1.11-0.86 (m, 18H), 0.77-0.56 (m, 2H).

409

Example 49: Synthesis of (24E,26E,28E,29E,33R, 34S,35R,36R,38S,40S,45S,46R,47R,58R)-44-[2-[[(7R,8aS)-1,4-dioxo-2,3,6,7,8,8a-hexahydropyrrolo [1,2-a]pyrazin-7-yl]oxy]ethoxy]-46,58-dihydroxy-45-[(1R)-2-[(1S,3R,4R)-4-hydroxy-3-methoxy-cyclohexyl]-1-methyl-ethyl]-47-methoxy-33,34,35, 36,48,49-hexamethyl-72,73-dioxa-60-azatricyclohexatriaconta-24,26,28(48),29(49)-tetraene-50,52,53,55,56-pentone (I-101)

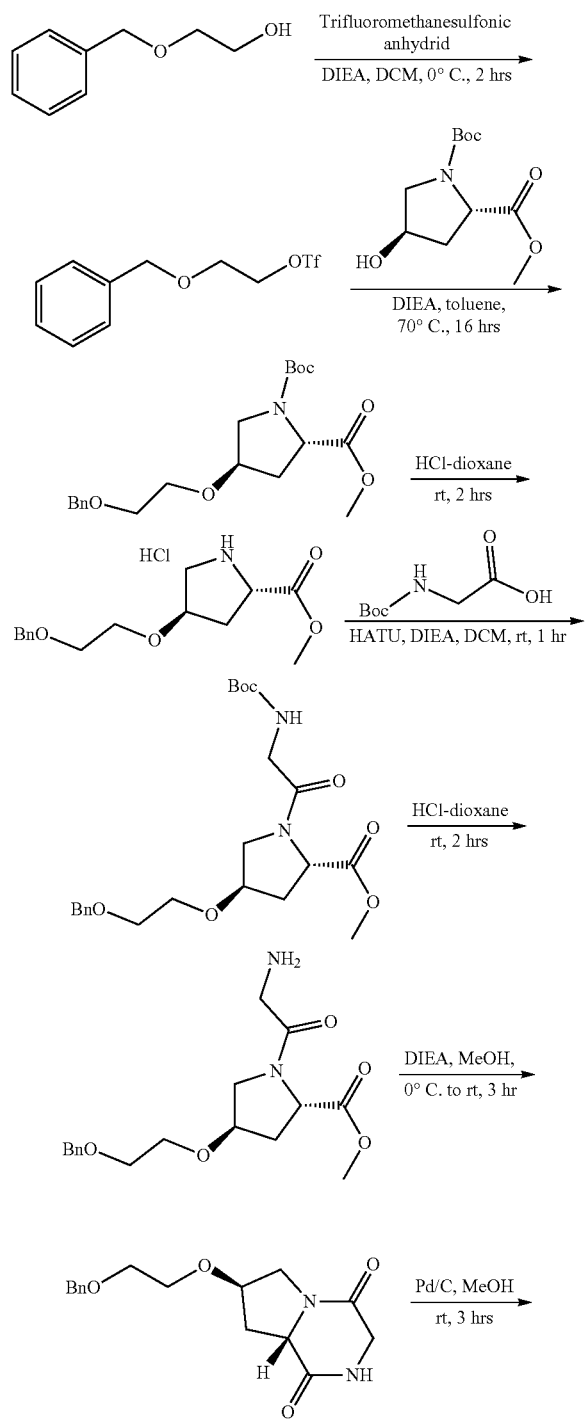

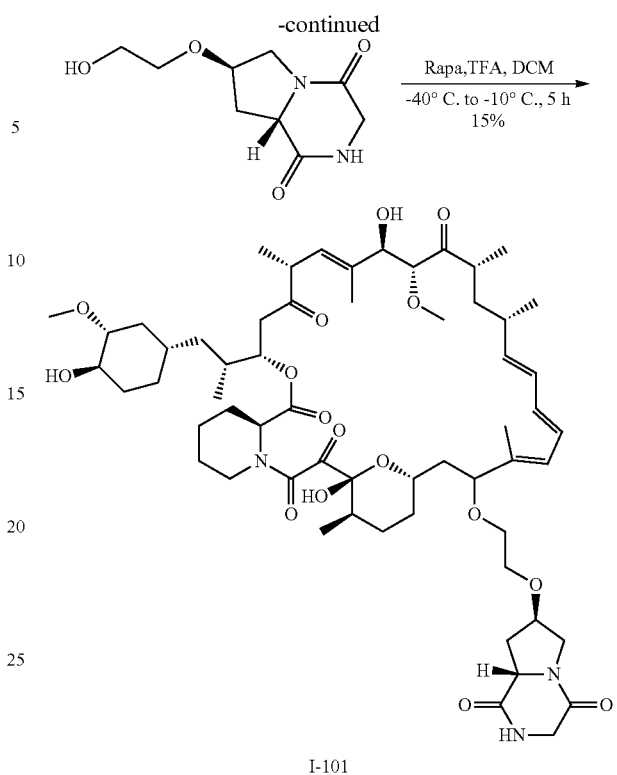

I-101

Step 1: 2-benzyloxyethyl trifluoromethanesulfonate. To a solution of 2-benzyloxyethanol (20 g, 131.41 mmol) and DIEA (25.48 g, 197.12 mmol) in DCM (200 mL) at 0° C. under $N_2$ was added $Tf_2O$ (40.78 g, 144.56 mmol) and the reaction was stirred at 0° C. for 2 h. The mixture was then diluted with DCM (150 mL), washed with saturated $NaHCO_3$ (150 mL), water (150 mL) and brine (150 mL). The organic layer was dried over $Na_2SO_4$, filtered and concentrated to provide 2-benzyloxyethyl trifluoromethanesulfonate (35 g, 94% yield) as a brown oil. This was used in the next step without further purification. $^1$H NMR (400 MHz, $CDCl_3$): δ 7.38-7.29 (m, 5H), 4.65 (t, J=4.0 Hz, 2H), 4.59 (s, 2H), 3.78 (t, J=4.4 Hz, 2H).

Step 2: O1-tert-butyl O2-methyl (2S,4R)-4-(2-benzyloxyethoxy) pyrrolidine-1,2-dicarboxylate. A solution of O1-tert-butyl O2-methyl (2S,4R)-4-hydroxypyrrolidine-1,2-dicarboxylate (15 g, 61.16 mmol), 2-benzyloxyethyl trifluoromethanesulfonate (34.77 g, 122.31 mmol) and N-ethyl-N-isopropyl-propan-2-amine (23.71 g, 183.47 mmol) in toluene (120 mL) was stirred at 70° C. for 16 h. The reaction mixture was then concentrated and purified via silica gel chromatography (30% EtOAc in PE) then reverse phase chromatography (60% $CH_3CN$ in water) to provide 1-(tert-butyl) 2-methyl (2S,4R)-4-(2-(benzyloxy) ethoxy) pyrrolidine-1,2-dicarboxylate (4.3 g, 28% yield) as a clear oil. ESI-MS (EI+, m/z): 402.0 [M+Na]$^+$.

Step 3: methyl (2S,4R)-1-(2-aminoacetyl)-4-(2-benzyloxyethoxy) pyrrolidine-2-carboxylate. To 1-(tert-butyl) 2-methyl (2S,4R)-4-(2-(benzyloxy)ethoxy)pyrrolidine-1,2-dicarboxylate (4.2 g, 9.62 mmol) was added hydrogen chloride in dioxane (4M, 33.6 g, 921.54 mmol) and the mixture was stirred for 2 h at rt. The reaction was concentrated to provide methyl (2S,4R)-1-(2-aminoacetyl)-4-(2-benzyloxyethoxy) pyrrolidine-2-carboxylate (3.2 g, 99% yield) which was used without further purification. ESI-MS (EI+, m/z): 280.0 [M+H]$^+$.

Step 4: methyl (2S,4R)-4-(2-benzyloxyethoxy)-1-[2-(tert-butoxycarbonylamino) acetyl]pyrrolidine-2-carboxylate. A solution of 2-(tert-butoxycarbonylamino)acetic acid (1.7 g, 9.7 mmol), methyl (2S,4R)-4-(2-benzyloxyethoxy)pyrrolidine-2-carboxylate (4.6 g, 14.56 mmol), N-ethyl-N-isopropyl-propan-2-amine (3.14 g, 24.26 mmol) and [dimethylamino(triazolo[4,5-b]pyridin-3-yloxy)methylene]-dimethyl ammonium hexafluorophosphate (4.06 g, 10.67 mmol) in DCM (20 mL) was stirred at rt for 2 h. The reaction mixture was then poured into water (50 mL) and extracted with DCM (50 mL×2). The combined organic layers were washed with H₂O (50 mL), brine (50 mL), dried over Na₂SO₄, filtered and concentrated. The residue was purified by reverse phase chromatography (50% CH₃CN in water) to provide methyl (2S,4R)-4-(2-benzyloxyethoxy)-1-[2-(tert-butoxycarbonylamino)acetyl]pyrrolidine-2-carboxylate (4.2 g, 99% yield) as a clear oil. ESI-MS (EI+, m/z): 437.0 [M+H]⁺.

Step 5: methyl (2S,4R)-1-(2-aminoacetyl)-4-(2-benzyloxyethoxy) pyrrolidine-2-carboxylate. A solution of methyl (2S,4R)-4-(2-benzyloxyethoxy)-1-[2-(tert-butoxycarbonylamino)acetyl]pyrrolidine-2-carboxylate (4.2 g, 9.62 mmol) in hydrogen chloride in dioxane (4M, 16 g, 438.83 mmol) was stirred for 2 h at rt. The mixture was concentrated to provide methyl (2S,4R)-1-(2-aminoacetyl)-4-(2-benzyloxyethoxy)pyrrolidine-2-carboxylate (3.2 g, 99% yield) which was used without further purification. ESI-MS (EI+, m/z): 337.0 [M+H]⁺.

Step 6: (7R,8aS)-7-(2-benzyloxyethoxy)-2,3,6,7,8,8a-hexahydropyrrolo[1,2-a]pyrazine-1,4-dione. To a stirred solution of methyl (2S,4R)-1-(2-aminoacetyl)-4-(2-benzyloxyethoxy) pyrrolidine-2-carboxylate (3.3 g, 9.81 mmol) in MeOH (5 mL) was added N-ethyl-N-isopropyl-propan-2-amine (1.22 g, 9.47 mmol) and the mixture stirred at rt for 3 h. The reaction was concentrated and purified via silica gel chromatography (15% MeOH in DCM) then reverse phase chromatography (30% CH₃CN in water) to provide (7R,8aS)-7-(2-benzyloxyethoxy)-2,3,6,7,8,8a-hexahydropyrrolo[1,2-a]pyrazine-1,4-dione (2.24 g, 75% yield) as a clear oil. ESI-MS (EI+, m/z): 305.0 [M+H]⁺.

Step 7: (7R,8aS)-7-(2-hydroxyethoxy)-2,3,6,7,8,8a-hexahydropyrrolo[1,2-a]pyrazine-1,4-dione. To a solution of (7R,8aS)-7-(2-benzyloxyethoxy)-2,3,6,7,8,8a-hexahydropyrrolo[1,2-a]pyrazine-1,4-dione (2.2 g, 7.23 mmol) in MeOH (50 mL) was added Pd/C (1.1 g) and the mixture was stirred at rt for 3 h under H₂. The reaction was filtered and concentrated to provide (7R,8aS)-7-(2-hydroxyethoxy)-2,3,6,7,8,8a-hexahydropyrrolo[1,2-a]pyrazine-1,4-dione (1.4 g, 90% yield) as a clear oil. ESI-MS (EI+, m/z): 215.1 [M+H]⁺.

Step 8: (24E,26E,28E,29E,33R,34S,35R,36R,38S,40S,45S,46R,47R,58R)-44-[2-[[(7R,8aS)-1,4-dioxo-2,3,6,7,8,8a-hexahydropyrrolo[1,2-a]pyrazin-7-yl]oxy]ethoxy]-46,58-dihydroxy-45-[(1R)-2-[[(1S,3R,4R)-4-hydroxy-3-methoxy-cyclohexyl]-1-methyl-ethyl]-47-methoxy-33,34,35,36,48,49-hexamethyl-72,73-dioxa-60-azatricyclohexatriaconta-24,26,28(48),29(49)-tetraene-50,52,53,55,56-pentone (I-101). To a stirred solution of (22E,24E,26E,27E,29R,30S,31R,32R,34S,36S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (600 mg, 0.66 mmol) in DCM (7 mL) was added TFA (748 mg, 6.56 mmol) at −40° C. under argon. After 10 mins, (7R,8aS)-7-(2-hydroxyethoxy)-2,3,6,7,8,8a-hexahydropyrrolo[1,2-a]pyrazine-1,4-dione (984 mg, 4.59 mmol) was added. The reaction mixture was stirred at −10° C. to rt for 5 h then quenched with ice cold aqueous NaHCO₃ (20 mL) then extracted with DCM (50 mL×2). He combined organic layers were washed with brine (50 mL), dried over Na₂SO₄, filtered and concentrated. The residue was purified via reverse phase chromatography (52% CH₃CN in water) to provide the titled compound (80 mg, 11% yield) as a white solid. ESI-MS (EI+, m/z): 1118.5 [M+Na]⁺. ¹H NMR (400 MHz, CDCl₃): δ 6.40-5.92 (m, 4H), 5.51-5.12 (m, 4H), 4.54-2.99 (m, 25H), 3.06-1.85 (m, 15H), 1.78-1.68 (m, 11H), 1.63-1.52 (m, 2H), 1.50-0.84 (m, 27H), 0.78-0.59 (m, 1H).

Example 50: Synthesis of (23E,25E,27E,28E,32R,33S,34R,35R,37S,39S,44S,45R,46R,57R)-43-[2-[[(6R,7aS)-1,3-dioxo-5,6,7,7a-tetrahydropyrrolo[1,2-c]imidazol-6-yl]oxy]ethoxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-71,72-dioxa-59-azatricyclohexatriaconta-23,25,27(47),28(48)-tetraene-49,50,51,53,54-pentone (I-101), (23E,25E,27E,28E,32R,33S,34R,35R,37S,39S,43S,44S,45R,46R,57R)-43-[2-[[(6R,7aS)-1,3-dioxo-5,6,7,7a-tetrahydropyrrolo[1,2-c]imidazol-6-yl]oxy]ethoxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-71,72-dioxa-59-azatricyclohexatriaconta-23,25,27(47),28(48)-tetraene-49,50,51,53,54-pentone (I-105) and (23E,25E,27E,28E,32R,33S,34R,35R,37S,39S,43R,44S,45R,46R,57R)-43-[2-[[(6R,7aS)-1,3-dioxo-5,6,7,7a-tetrahydropyrrolo[1,2-c]imidazol-6-yl]oxy]ethoxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-71,72-dioxa-59-azatricyclohexatriaconta-23,25,27(47),28(48)-tetraene-49,50,51,53,54-pentone (I-113)

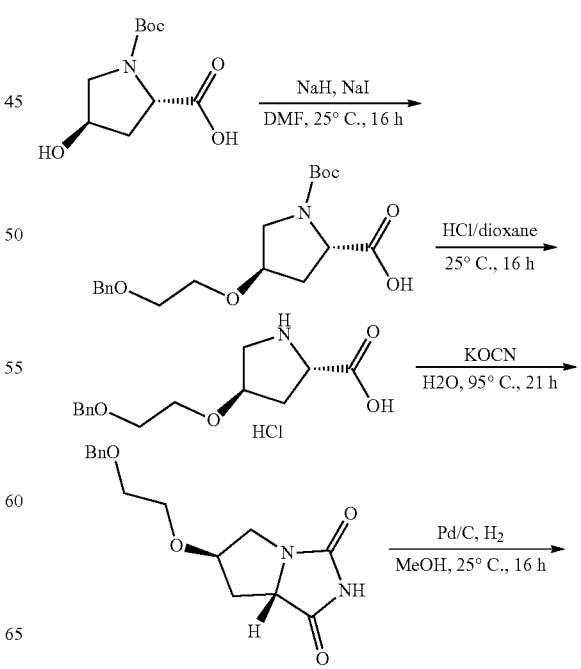

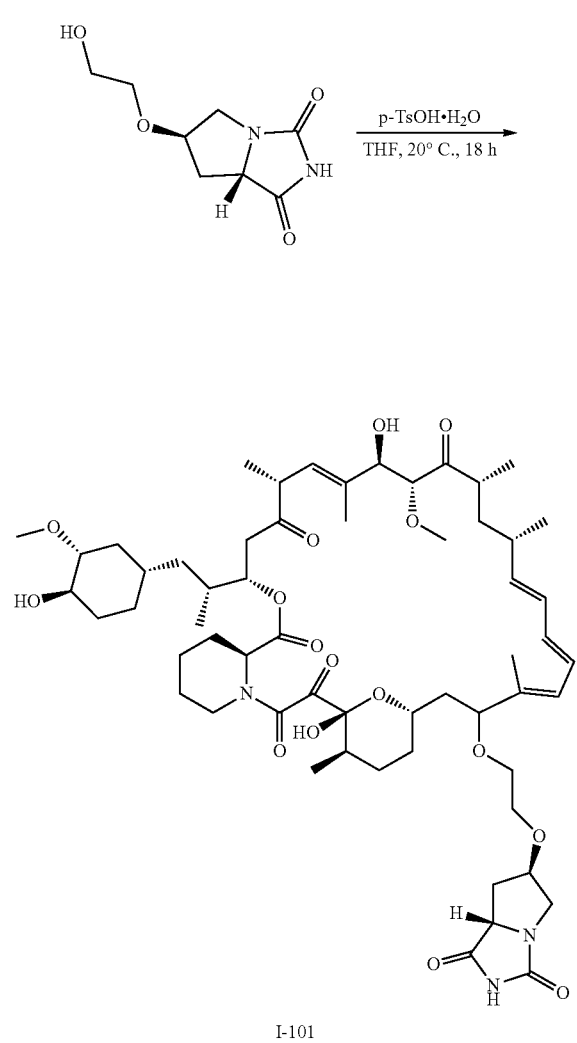

I-101

I-105

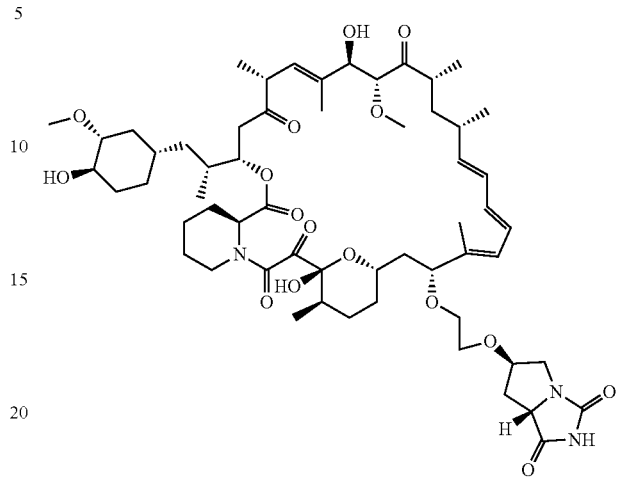

I-113

Step 1: (2S,4R)-4-(2-(benzyloxy) ethoxy)-1-(tert-butoxycarbonyl) pyrrolidine-2-carboxylic acid. To a solution of (2S,4R)-1-tert-butoxycarbonyl-4-hydroxy-pyrrolidine-2-carboxylic acid (20 g, 86.49 mmol) in DMF (200 mL) was added sodium hydride (9.69 g, 242.17 mmol, 60% purity) and NaI (1.43 g, 9.51 mmol) at 0° C. The mixture was stirred for 0.5 h at 0° C. then 2-bromoethoxymethylbenzene (21.39 g, 99.46 mmol, 15.73 mL) was added and stirring continued for an additional 16 h at rt. The reaction was quenched by adding water (50 mL) at 0° C. followed by 6 N HCl to adjust the pH=4. The mixture was extracted with EtOAc (100 mL×3) and the combined organic layers were washed with water (100 mL×3) and brine (100 mL×3), dried over anhydrous sodium sulfate, filtered and concentrated. The residue was purified via silica gel chromatography (eluting with 50% EtOAc in PE) to provide (2S,4R)-4-(2-benzyloxyethoxy)-1-tert-butoxycarbonyl-pyrrolidine-2-carboxylic acid (12.7 g, 34.75 mmol, 40% yield) as a yellow oil. ESI-MS (EI+, m/z): 388.1 [M+Na]$^+$. $^1$H NMR (400 MHz, CDCl$_3$): δ 7.36-7.26 (m, 5H), 4.56 (s, 2H), 4.42-4.46 (t, J=7.2 Hz, 0.5H), 4.37-4.33 (t, J=8.0 Hz, 0.5H), 4.15-4.11 (m, 1H), 3.64-3.53 (m, 6H), 2.46-2.40 (m, 0.5H), 2.32-2.29 (m, 1H), 2.14-2.07 (m, 0.5H), 1.47-1.41 (t, J=21.6 Hz, 9H).

Step 2: 2-(2-(tert-butyldiphenylsilyloxy) ethoxy) ethyl 4-nitrophenyl carbonate. To a solution of 2-[2-[tert-butyl(diphenyl)silyl]oxyethoxy]ethanol (1 g, 2.9 mmol) and TEA (0.73 g, 7.26 mmol) in DCM (15 mL) at 0° C. was added (4-nitrophenyl) carbonochloridate (1.35 g, 6.68 mmol). The mixture was warmed to rt and stirred for 1 h under N$_2$. The reaction solution was used without further purification in the next step. ESI-MS (EI$^+$, m/z): 266.1 [M+H]$^+$.

Step 3: (6R,7aS)-6-(2-(benzyloxy) ethoxy) tetrahydro-1H-pyrrolo[1,2-c]imidazole-1,3(2H)-dione. To a solution of (2S,4R)-4-(2-benzyloxyethoxy) pyrrolidine-2-carboxylic acid (11.5 g, 38.11 mmol) in water (120 mL) was added potassium cyanate (6.18 g, 76.22 mmol). The resulting solution was stirred at 95° C. for 16 h then cooled to room temperature. 1N HCl (120 mL) was added and the reaction stirred at 95° C. for 5 h. Upon cooling the reaction mixture was extracted with EtOAc (200 mL×3). The combined organic layers were washed with brine (200 mL×3), dried with anhydrous sodium sulfate, filtered and concentrated. The residue was purified via silica gel chromatography (eluting with 70% EtOAc in PE) to provide (6R,7aS)-6-(2-benzyloxyethoxy)-5,6,7,7a-tetrahydropyrrolo[1,2-c]imidazole-1,3-dione (5.4 g, 49% yield) as a colorless oil. ESI-MS (EI+, m/z): 291.1 [M+H]$^+$. $^1$H NMR (400 MHz, CDCl$_3$) δ 8.36 (s, 1H), 7.44-7.26 (m, 5H), 4.56 (s, 2H), 4.44-4.31 (m, 2H), 3.85 (dd, J=12.4, 5.4 Hz, 1H), 3.70-3.55 (m, 4H), 3.28 (d, J=12.5 Hz, 1H), 2.42 (dd, J=13.3, 6.6 Hz, 1H), 1.85-1.66 (m, 2H).

Step 4: (6R,7aS)-6-(2-hydroxyethoxy)tetrahydro-1H-pyrrolo[1,2-c]imidazole-1,3(2H)-dione
To a solution of (6R,7aS)-6-(2-benzyloxyethoxy)-5,6,7,7a-tetrahydropyrrolo[1,2-c]imidazole-1,3-dione (5.4 g, 18.60 mmol) in MeOH (60 mL) was added Pd/C (1.2 g, 10% purity) under N$_2$. The mixture was then stirred for 16h at 25° C. under H$_2$. The reaction mixture was filtered and the filtrate was concentrated to provide (6R,7aS)-6-(2-hydroxyethoxy)-5,6,7,7a-tetrahydropyrrolo[1,2-c]imidazole-1,3-dione (3.2 g, 15.98 mmol, 86% yield) as a white solid. ESI-MS (EI+, m/z): 201.1[M+H]$^+$. $^1$H NMR (400 MHz, CDCl$_3$): δ10.77 (s, 1H), 4.63-4.60 (t, J=4.8 Hz, 1H), 4.28-4.19 (m, 2H), 3.70-3.65 (m, 1H), 3.50-3.37 (m, 4H), 3.03 (d, J=12 Hz, 1H), 2.20-2.15 (m, 1H), 1.83-1.75 (m, 1H).

Step 5: (23E,25E,27E,28E,32R,33S,34R,35R,37S,39S,44S,45R,46R,57R)-43-[2-[[(6R,7aS)-1,3-dioxo-5,6,7,7a-tetrahydropyrrolo[1,2-c]imidazol-6-yl]oxy]ethoxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-71,72-dioxa-59-azatricyclohexatriaconta-23,25,27(47),28(48)-tetraene-49,50,51,53,54-pentone (I-101). To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (1 g, 1.09 mmol) and (6R,7aS)-6-(2-hydroxyethoxy)-5,6,7,7a-tetrahydropyrrolo[1,2-c]imidazole-1,3-dione (3.28 g, 16.41 mmol) in THF (100 mL) was added p-TsOH hydrate (1.04 g, 5.47 mmol) at 20° C. under N$_2$. The mixture was stirred at 20° C. for 18 h then diluted with EtOAc. Saturated aqueous NaHCO$_3$ was added to adjust the pH to 8 and the mixture was extracted with EtOAc (80 mL). The organic layer was washed with water (80 mL×2), brine (80 mL×2), dried over anhydrous sodium sulfate, filtered and concentrated. The residue was purified by reverse phase chromatography (60% CH$_3$CN in water) to provide the titled compound (0.125 g, 11% yield) as a white solid. ESI-MS (EI+, m/z): 1105.2 [M+Na]$^+$. $^1$H NMR (400 MHz, DMSO-d$_6$) δ 10.81 (s, 1H), 6.44-6.09 (m, 4H), 5.50-4.93 (m, 5H), 4.63-4.62 (m, 1H), 4.29-4.16 (m, 2H), 4.05-3.93 (m, 2H), 3.82-3.66 (m, 2H), 3.54-3.43 (m, 3H), 3.33-3.24 (m, 5H), 3.20-3.02 (m, 6H), 2.67-2.86 (m, 3H), 2.41-1.96 (m, 6H), 1.92-1.84 (m, 3H), 1.84-1.38 (m, 15H), 1.28-1.11 (m, 9H), 1.07-0.91 (m, 7H), 0.88-0.72 (m, 11H), 0.64-0.56 (m, 1H).

Step 6: (23E,25E,27E,28E,32R,33S,34R,35R,37S,39S,43S,44S,45R,46R,57R)-43-[2-[[(6R,7aS)-1,3-dioxo-5,6,7,7a-tetrahydropyrrolo[1,2-c]imidazol-6-yl]oxy]ethoxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-71,72-dioxa-59-azatricyclohexatriaconta-23,25,27(47),28(48)-tetraene-49,50,51,53,54-pentone (I-105) and (23E,25E,27E,28E,32R,33S,34R,35R,37S,39S,43R,44S,45R,46R,57R)-43-[2-[[(6R,7aS)-1,3-dioxo-5,6,7,7a-tetrahydropyrrolo[1,2-c]imidazol-6-yl]oxy]ethoxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-71,72-dioxa-59-azatricyclohexatriaconta-23,25,27(47),28(48)-tetraene-49,50,51,53,54-pentone (I-113). 150 mg of the mixture was separated via chiral HPLC and then purified by silica gel chromatography (hexane:DCM:EtOAc:MeOH from 3:3:1:0 to 3:3:1:0.6) to provide the titled compounds (I-105: 36 mg, 24% yield) and (I-113:20 mg, 13% yield) as white solids.

Chiral Separation Method:

| | |
|---|---|
| Column: | CHIRALPAK IC |
| Column size: | 5.0 cm I.D. × 25 cm L, 10 μm |
| Sample solution: | 1.5 mg/ml in Mobile phase |
| Injection: | 5 ml |
| Mobile phase: | Hexane/EtOH = 40/60(V/V) |
| Flow rate: | 20 ml/min |
| Wave length: | UV 254 nm |
| Temperature: | 35° C. |

I-105: ESI-MS (EI$^+$, m/z): 1104.5 [M+Na]$^+$. $^1$H NMR (500 MHz, CDCl$_3$) δ 640-6.11 (m, 3H), 5.93 (dd, J=33.4, 10.7 Hz, 1H), 5.55-5.06 (m, 4H), 4.77 (s, 1H), 4.53-4.07 (m, 4H), 3.97-3.67 (m, 4H), 3.63-3.22 (m, 16H), 2.98-2.51 (m, 5H), 2.47-2.18 (m, 3H), 2.14-1.86 (m, 5H), 1.81-1.69 (m, 8H), 1.53-1.17 (m, 14H), 1.15-0.81 (m, 18H), 0.71-0.62 (m, 1H).

I-113: ESI-MS (EI$^+$, m/z): 1104.4 [M+Na]$^+$. $^1$H NMR (400 MHz, CDCl$_3$) δ 6.43-5.95 (m, 4H), 5.56-5.07 (m, 4H), 4.58-3.99 (m, 6H), 3.93-3.73 (m, 2H), 3.66-3.17 (m, 16H), 3.04-2.63 (m, 5H), 2.59-2.26 (m, 4H), 2.21-1.97 (m, 4H), 1.89-1.65 (m, 12H), 1.55-1.19 (m, 11H), 1.15-0.81 (m, 18H), 0.77-0.55 (m, 1H).

Example 51: Synthesis of (23E,25E,27E,28E,32R, 33S,34R,35R,37S,39S,42S,47R,48R,57R)-41-[2-[[(3R,3aR,6R,6aR)-3-hydroxy-2,3,3a,5,6,6a-hexahydrofuro[3,2-b]furan-6-yl]oxy]ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-102), (23E,25E, 27E,28E,32R,33S,34R,35R,37S,39S,41S,42S,47R, 48R,57R)-41-[2-[[(3R,3aR,6R,6aR)-3-hydroxy-2,3, 3a,5,6,6a-hexahydrofuro[3,2-b]furan-6-yl]oxy] ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28 (50)-tetraene-51,52,53,54,55-pentone (I-108) and (23E,25E,27E,28E,32R,33S,34R,35R,37S,39S,41R, 42S,47R,48R,57R)-41-[2-[[(3R,3aR,6R,6aR)-3-hydroxy-2,3,3a,5,6,6a-hexahydrofuro[3,2-b]furan-6-yl] oxy]ethoxy]-47,57-dihydroxy-42-[(1R)-2-[(1S,3R, 4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27 (49),28(50)-tetraene-51,52,53,54,55-pentone (I-112)

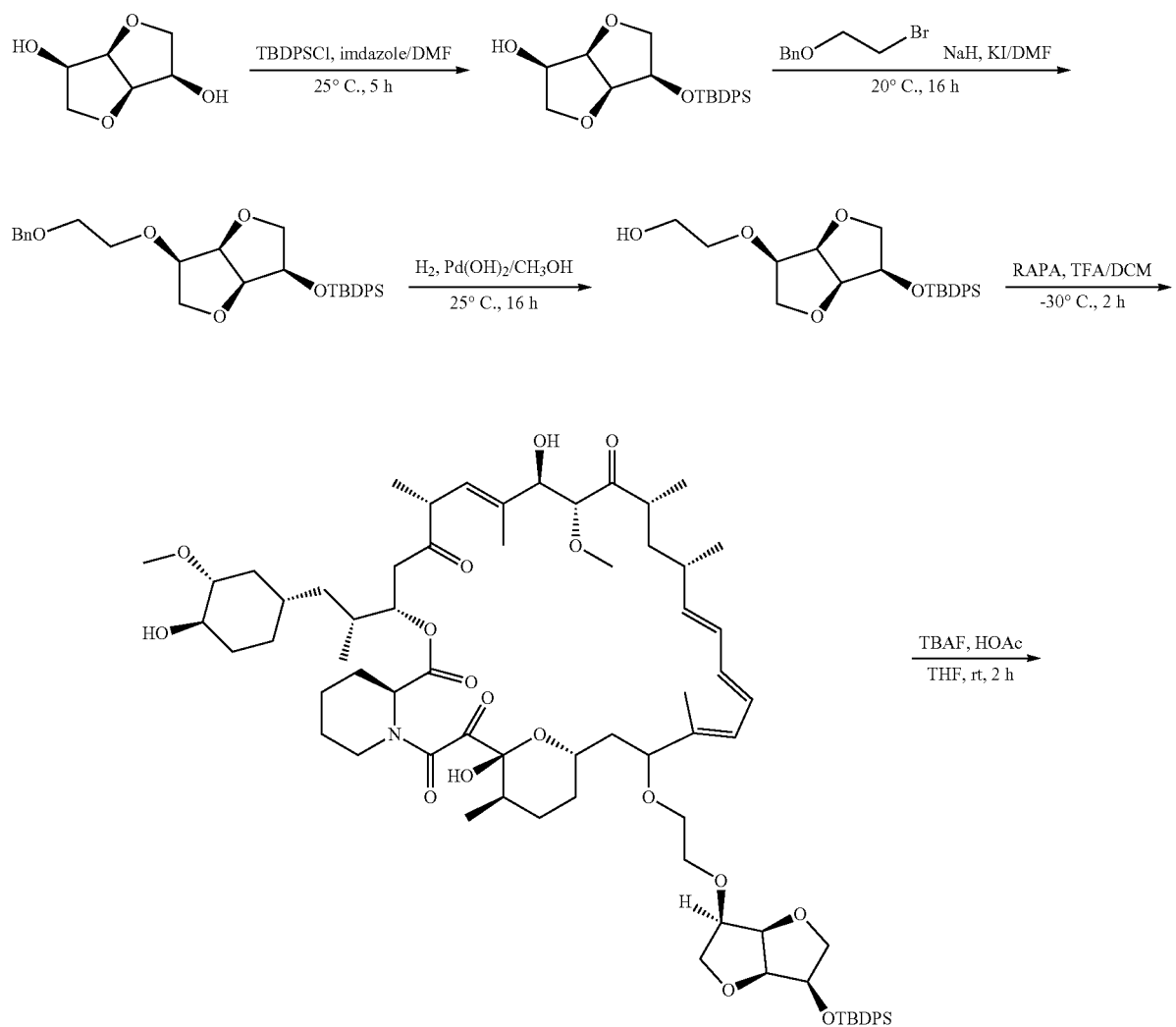

-continued
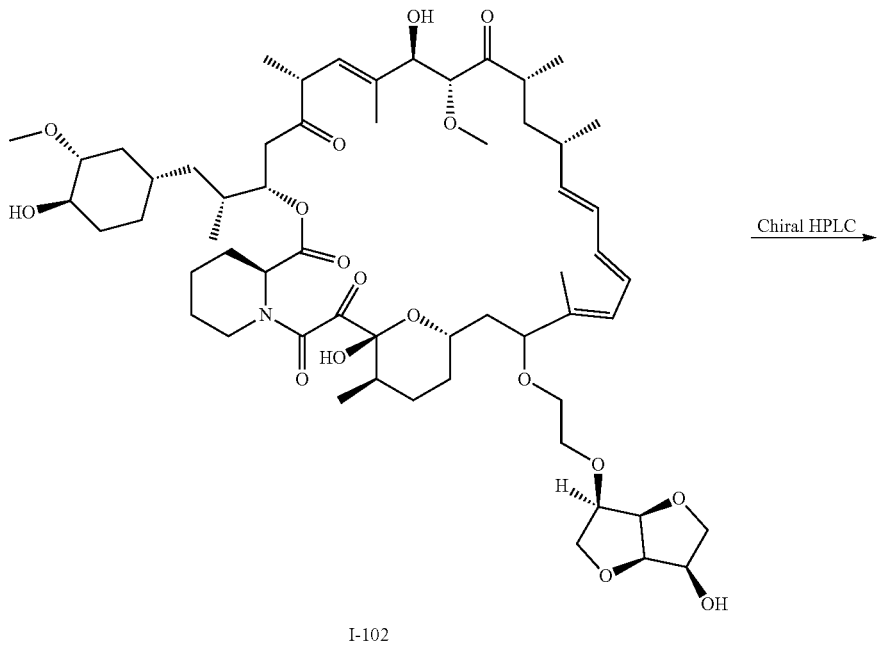
I-102
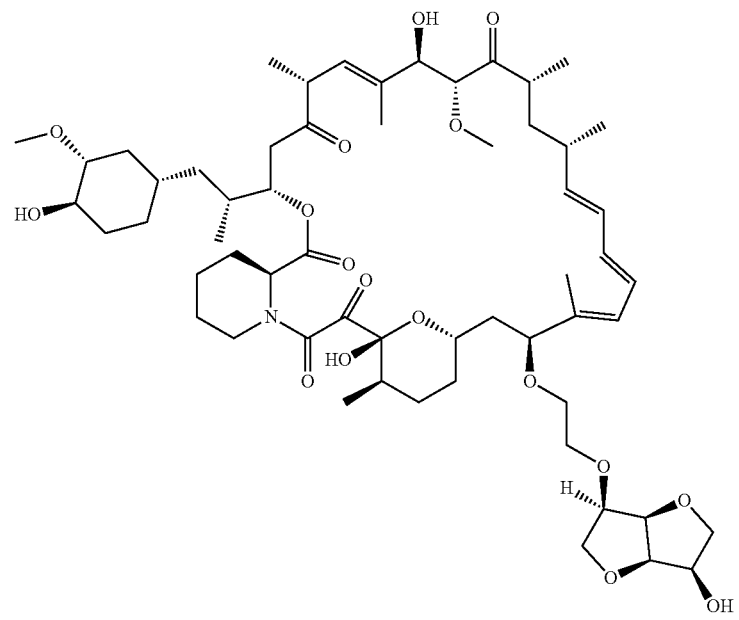
I-108

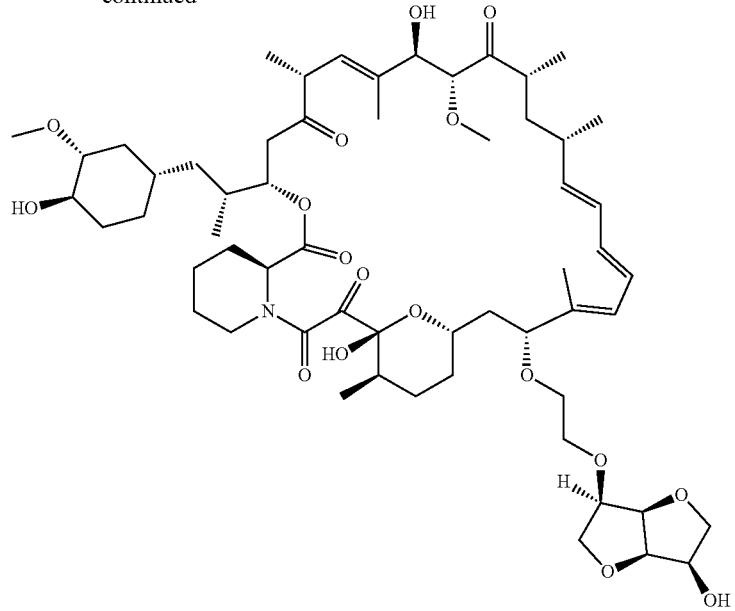

I-112

Step 1: (3R,3aR,6R,6aS)-6-[tert-butyl(diphenyl)silyl]oxy-2,3,3a,5,6,6a-hexahydrofuro[3,2-b]furan-3-ol. To a solution of (3R,3aR,6R,6aR)-2,3,3a,5,6,6a-hexahydrofuro[3,2-b]furan-3,6-diol (10 g, 68.43 mmol) in DMF (100 mL) was added imidazole (5.82 g, 85.53 mmol) and tert-butyl-chloro-diphenyl-silane (15.67 g, 57.02 mmol). The resulting solution was stirred at rt for 2 h then poured into a mixture of EtOAc and $H_2O$. The organic layer was concentrated and purified via silica gel chromatography (PE:EtOAc=2:1) to provide (3R,3aR,6R,6aS)-6-[tert-butyl(diphenyl)silyl]oxy-2,3,3a,5,6,6a-hexahydrofuro[3,2-b]furan-3-ol (11.2 g, 51% yield) as a thick oil. ESI-MS (EI+, m/z): 407.0 [M+Na]+. 1HNMR (400 MHz, $CDCl_3$) δ 7.80-7.62 (m, 4H), 7.48-7.33 (m, 6H), 4.38-4.32 (m, 1H), 4.26-4.18 (m, 3H), 4.01 (dd, J=9.4, 6.0 Hz, 1H), 3.79-3.71 (m, 2H), 3.68-3.61 (m, 1H), 2.93 (d, J=8.7 Hz, 1H), 1.07 (d, J=12.1 Hz, 9H).

Step 2: [(3R,3aR,6R,6aS)-3-(2-benzyloxyethoxy)-2,3,3a,5,6,6a-hexahydrofuro[3,2-b]furan-6-yl]oxy-tert-butyl-diphenyl-silane. (3R,3aR,6R,6aS)-6-[tert-butyl(diphenyl)silyl]oxy-2,3,3a,5,6,6a-hexahydrofuro[3,2-b]furan-3-ol (10 g, 26 mmol) was added to a mixture of sodium hydride (1.25 g, 52 mmol) and potassium iodide (4.32 g, 26 mmol) in DMF (100 mL) at 0° C. and stirred at this temperature for 1h. Then 2-bromoethoxymethylbenzene (6.71 g, 31.21 mmol) was added slowly. The reaction was stirred at rt for 16 h then diluted with EtOAc and washed with water (30 mL×2). The organic phase was dried over $Na_2SO_4$, concentrated and purified via reverse phase chromatography (60% $CH_3CN$ in water) to provide [(3R,3aR,6R,6aS)-3-(2-benzyloxyethoxy)-2,3,3a,5,6,6a-hexahydrofuro[3,2-b]furan-6-yl]oxy-tert-butyl-diphenyl-silane (3.8 g, 28% yield) as a colorless gum. ESI-MS (EI+, m/z): 541.0 [M+Na]+. 1H NMR (500 MHz, $CDCl_3$) δ 7.74 (d, J=6.5 Hz, 2H), 7.66 (d, J=8.0 Hz, 2H), 7.43 (d, J=8.8 Hz, 2H), 7.38 (t, J=7.1 Hz, 4H), 7.33 (d, J=4.4 Hz, 4H), 4.56 (d, J=6.2 Hz, 2H), 4.37 (t, J=4.5 Hz, 1H), 4.24-4.17 (m, 2H), 4.09 (dd, J=15.9, 7.9 Hz, 1H), 4.05 (dd, J=7.8, 3.0 Hz, 1H), 3.85-3.78 (m, 1H), 3.75 (dd, J=9.2, 7.4 Hz, 2H), 3.71-3.61 (m, 4H), 1.08 (s, 9H).

Step 3: 2-[[(3R,3aR,6R,6aS)-6-[tert-butyl(diphenyl)silyl]oxy-2,3,3a,5,6,6a-hexahydrofuro[3,2-b]furan-3-yl]oxy]ethanol. To a solution of [(3R,3aR,6R,6aS)-3-(2-benzyloxyethoxy)-2,3,3a,5,6,6a-hexahydrofuro[3,2-b]furan-6-yl]oxy-tert-butyl-diphenyl-silane (240 mg, 0.46 mmol) in $CH_3OH$ (10 mL) was added palladium hydroxide (130 mg) and the reaction mixture was stirred under hydrogen atmosphere at rt for 16 h. The reaction was filtered, concentrated and purified via silica gel chromatography (PE:EtOAc=4:1) to provide 2-[[(3R,3aR,6R,6aS)-6-[tert-butyl(diphenyl)silyl]oxy-2,3,3a,5,6,6a-hexahydrofuro[3,2-b]furan-3-yl]oxy]ethanol (130 mg, 66% yield) as a thick oil. ESI-MS (EI+, m/z): 451.1 [M+Na]+. H NMR (400 MHz, $CDCl_3$) δ 7.76-7.70 (m, 2H), 7.69-7.63 (m, 2H), 7.46-7.35 (m, 6H), 4.39 (q, J=4.6 Hz, 1H), 4.25-4.17 (m, 2H), 4.10 (dd, J=8.5, 7.1 Hz, 1H), 4.01 (ddd, J=8.4, 7.0, 5.0 Hz, 1H), 3.81-3.60 (m, 8H), 1.08 (s, 9H).

Step 4: (36E,38E,40E,41E,47R,48S,49R,50R,52S,54S,57S,62R,63R,72R)-56-[2-[[(3R,3aR,6R,6aS)-6-[tert-butyl(diphenyl)silyl]oxy-2,3,3a,5,6,6a-hexahydrofuro[3,2-b]furan-3-yl]oxy]ethoxy]-62,72-dihydroxy-57-[(1R)-2-[(1S,3R,4R)-4-hydroxy-3-methoxy-cyclohexyl]-1-methyl-ethyl]-63-methoxy-47,48,49,50,64,65-hexamethyl-85,86-dioxa-74-azatricyclohexatriaconta-36,38,40(64),41(65)-tetraene-66,67,68,69,70-pentone. To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (0.5 g, 0.547 mmol) and 2-[[(3R,3aR,6R,6aS)-6-[tert-butyl(diphenyl)silyl]oxy-2,3,3a,5,6,6a-hexahydrofuro[3,2-b]furan-3-yl]oxy]ethanol (4.69 g, 10.94 mmol) in DCM (10 mL) was added 2,2,2-trifluoroacetic acid (1.25 g, 10.94 mmol) at −40° C. under $N_2$. The mixture was stirred at −30° C. for 2 h then diluted with EtOAc and washed with $NaHCO_3$ twice. The organic layer was dried over $Na_2SO_4$, concentrated and purified via reverse phase chromatography (80% CH₃CN in water) to provide the titled compound (0.2 g, 28% yield) as white solid. ESI-MS (EI+, m/z): 1332.9 [M+Na]⁺.

Step 5: (23E,25E,27E,28E,32R,33S,34R,35R,37S,39S,42S,47R,48R,57R)-41-[2-[[(3R,3aR,6R,6aR)-3-hydroxy-2,3,3a,5,6,6a-hexahydrofuro[3,2-b]furan-6-yl]oxy]ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-102). To a solution of (36E,38E,40E,41E,47R,48S,49R,50R,52S,54S,57S,62R,63R,72R)-56-[2-[[(3R,3aR,6R,6aS)-6-[tert- butyl(diphenyl)silyl]oxy-2,3,3a,5,6,6a-hexahydrofuro[3,2-b]furan-3-yl]oxy]ethoxy]-62,72-dihydroxy-57-[(1R)-2-[(1S,3R,4R)-4-hydroxy-3-methoxy-cyclohexyl]-1-methyl-ethyl]-63-methoxy-47,48,49,50,64,65-hexamethyl-85,86-dioxa-74-azatricyclohexatriaconta-36,38,40(64),41(65)-tetraene-66,67,68,69,70-pentone (0.3 g, 0.23 mmol) in THF (3 mL) was added acetic acid (62 mg, 1.03 mmol) and TBAF (1 M, 343.32 uL) at 0° C. The mixture was stirred at 20° C. for 2 h then diluted with EtOAc (50 mL), washed with aqueous NaHCO₃ (40 mL) and brine (40 mL). The organic layer was concentrated then purified via reverse phase chromatography (55% CH₃CN in water) to provide the titled compound (50 mg, 20% yield) as a white solid. ESI-MS (EI⁺, m/z):1094.1 [M+Na]⁺. ¹H NMR (400 MHz, CDCl₃): δ 5.87-6.42 (m, 4H), 5.09-5.59 (m, 4H), 4.49-4.82 (m, 3H), 3.95-4.34 (m, 6H), 3.47-3.94 (m, 9H), 3.25-3.47 (m, 10H), 2.84-3.01 (m, 2H), 2.53-2.82 (m, 3H), 2.24-2.42 (m, 2H), 1.87-2.18 (m, 5H), 1.68-1.85 (m, 12H), 1.12-1.55 (m, 13H), 0.83-1.17 (m, 16H), 0.59-0.74 (m, 1H).

Step 6: (23E,25E,27E,28E,32R,33S,34R,35R,37S,39S,41S,42S,47R,48R,57R)-41-[2-[[(3R,3aR,6R,6aR)-3-hydroxy-2,3,3a,5,6,6a-hexahydrofuro[3,2-b]furan-6-yl]oxy]ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-108) and (23E,25E,27E,28E,32R,33S,34R,35R,37S,39S,41R,42S,47R,48R,57R)-41-[2-[[(3R,3aR,6R,6aR)-3-hydroxy-2,3,3a,5,6,6a-hexahydrofuro[3,2-b]furan-6-yl]oxy]ethoxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-112). 158 mg of the mixture was separated via chiral HPLC and then purified via silica gel chromatography (hexane:DCM:EtOAc:MeOH from 3:3:1:0 to 3:3:1:0.6) to provide the titled compound (I-108: 67.7 mg, 43% yield) and (I-112: 13.3 mg, 8% yield) as white solids.

Chiral Separation Method:

| Column: | CHIRALPAK IC |
|---|---|
| Column size: | 5.0 cm I.D. × 25 cm L, 10 μm |
| Sample solution: | 1.6 mg/ml in Mobile phase |
| Injection: | 5 ml |
| Mobile phase: | Hexane/EtOH = 40/60(V/V) |
| Flow rate: | 20 ml/min |
| Wave length: | UV 254 nm |
| Temperature: | 35° C. |

I-108: ESI-MS (EI⁺, m/z): 1094.4 [M+Na]⁺. ¹H NMR (500 MHz, CDCl₃) δ 6.42-6.09 (m, 3H), 5.92 (dd, J=38.1, 10.7 Hz, 1H), 5.47 (ddd, J=34.5, 19.7, 9.5 Hz, 2H), 5.27 (d, J=5.4 Hz, 1H), 5.14 (dt, J=27.7, 6.2 Hz, 1H), 4.77 (s, 1H), 4.53 (dt, J=15.8, 5.1 Hz, 2H), 4.32-4.16 (m, 2H), 4.15-4.02 (m, 2H), 3.96 (dd, J=9.4, 5.8 Hz, 1H), 3.89 (s, 1H), 3.82-3.67 (m, 5H), 3.65-3.47 (m, 3H), 3.46-3.26 (m, 11H), 3.03-2.87 (m, 2H), 2.81-2.50 (m, 4H), 2.34 (d, J=12.3 Hz, 2H), 2.14-1.87 (m, 5H), 1.82-1.55 (m, 13H), 1.54-1.17 (m, 10H), 1.16-0.83 (m, 18H), 0.72-0.57 (m, 1H).

I-112: ESI-MS (EI⁺, m/z): 1094.5 [M+Na]⁺. ¹H NMR (500 MHz, CDCl₃) δ 6.43-5.95 (m, 4H), 5.76-5.07 (m, 5H), 4.69 (s, 1H), 4.55 (ddt, J=33.5, 28.1, 9.7 Hz, 3H), 4.33-3.47 (m, 16H), 3.45-3.28 (m, 10H), 3.27-3.13 (m, 2H), 3.02-2.82 (m, 3H), 2.76-2.43 (m, 4H), 2.39-1.69 (m, 12H), 1.55-1.22 (m, 10H), 1.17-0.81 (m, 18H), 0.74-0.61 (m, 1H).

Example 52: Synthesis of (28E,30E,32E,33E,38R,39S,40R,41R,44S,46S,49S,50R,51R,60R)-50,60-dihydroxy-49-[(1R)-2-[(1S,3R,4R)-4-hydroxy-3-methoxy-cyclohexyl]-1-methyl-ethyl]-51-methoxy-38,39,40,41,52,53-hexamethyl-48-[2-[(1-pyrimidin-2-yl-4-piperidyl)oxy]ethoxy]-73,74-dioxa-64-azatricyclohexatriaconta-28,30,32(52),33(53)-tetraene-54,55,56,57,58-pentone (I-104)

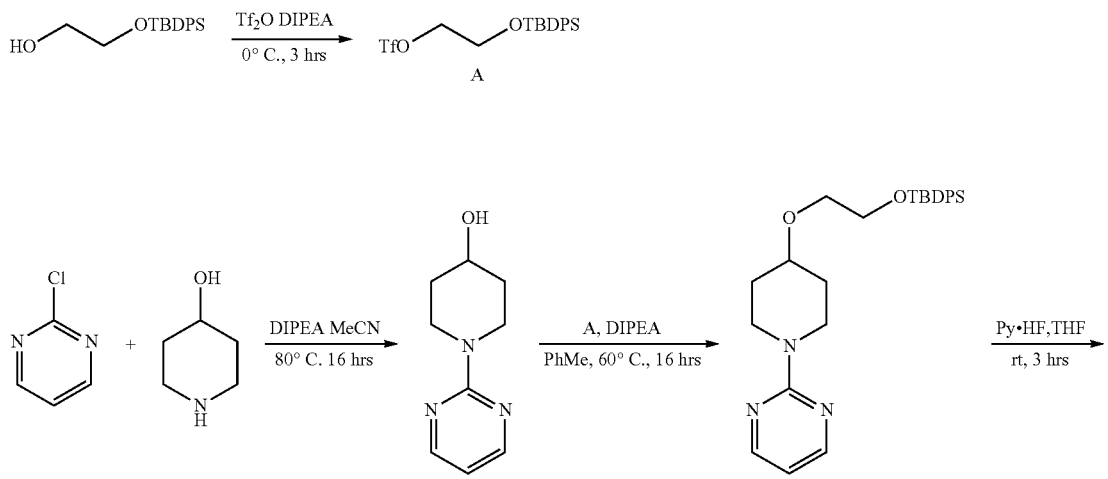

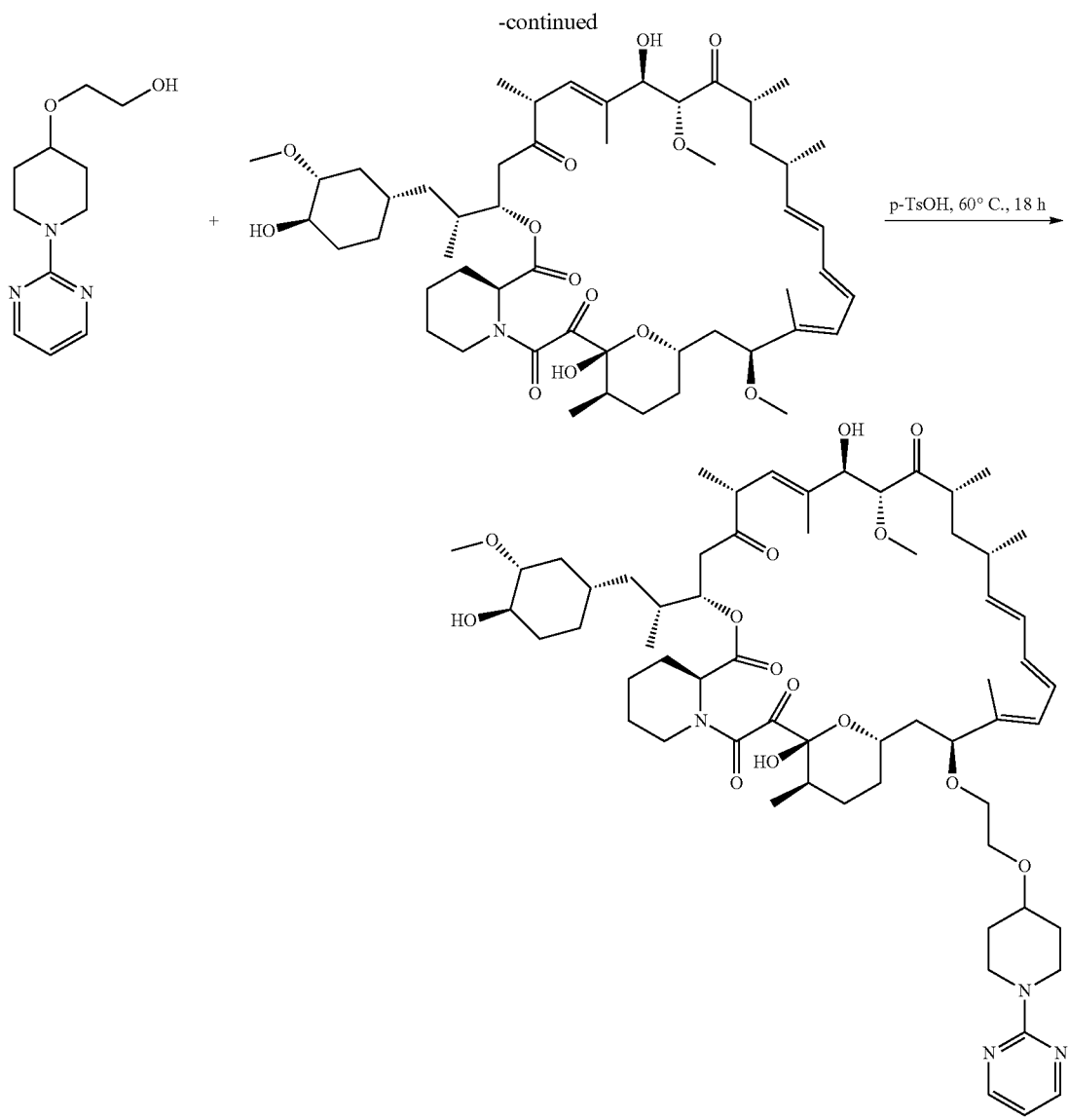

I-104

Step 1: 1-pyrimidin-2-ylpiperidin-4-ol. To a solution of piperidin-4-ol (5 g, 49.43 mmol) and 2-chloropyrimidine (5.66 g, 49.43 mmol) in CH$_3$CN (50 mL) was added N-ethyl-N-isopropyl-propan-2-amine (19.17 g, 148.30 mmol) at 25° C. The reaction mixture was stirred at 80° C. for 18h then diluted with H$_2$O (50 mL) and extracted with EtOAc (100 mL×3). The organic layers were combined and concentrated. The residue was purified via silica gel chromatography (EtOAc:PE=2:1) to provide 1-pyrimidin-2-ylpiperidin-4-ol (8.6 g, 97% yield) as a light-yellow solid. $^1$H NMR (500 MHz, MeOD-d$_4$) δ 8.27 (d, J=4.8 Hz, 2H), 6.52 (t, J=4.8 Hz, 1H), 4.37 (dt, J=13.6, 4.0 Hz, 2H), 3.87-3.80 (m, 1H), 3.23 (ddd, J=13.4, 10.3, 3.1 Hz, 2H), 1.87 (ddd, J=12.6, 7.4, 3.6 Hz, 2H), 1.48-1.35 (m, 2H).

Step 2: 2-[tert-butyl(diphenyl)silyl]oxyethyl trifluoromethanesulfonate. To solution of 2-[tert-butyl(diphenyl)silyl]oxyethanol (15 g, 49.92 mmol) and N-ethyl-N-isopropyl-propan-2-amine (19.36 g, 149.77 mmol) in DCM (100 mL) at 0° C. under N$_2$ was added Tf$_2$O (16.90 g, 59.91 mmol) and the mixture was stirred at 0° C. for 2 h. The mixture was diluted with DCM (50 mL), washed with NaHCO$_3$ (150 mL), water (150 mL) and brine (150 mL). The organic layer was dried over Na$_2$SO$_4$, filtered and concentrated to provide 2-[tert-butyl(diphenyl)silyl]oxyethyl trifluoromethanesulfonate (20 g, 93% yield) as a brown oil. This was used without further purification. 1H NMR (400 MHz, CDCl3) δ 7.67 (dd, J=7.9, 1.5 Hz, 2H), 7.64-7.34 (m, 3H), 4.60-4.53 (m, 1H), 3.94-3.86 (m, 1H), 1.08 (d, J=8.7 Hz, 5H).

Step 3: tert-butyl-diphenyl-[2-[(1-pyrimidin-2-yl-4-piperidyl) oxy]ethoxy]silane. To a solution of 1-pyrimidin-2-ylpiperidin-4-ol (208 mg, 1.16 mmol) and 2-[tert-butyl (diphenyl)silyl]oxyethyl trifluoromethanesulfonate (0.5 g, 1.16 mmol) in toluene (5 mL) was added N-ethyl-N-isopropyl-propan-2-amine (450 mg, 3.48 mmol) and the reaction stirred at 60° C. for 16 h. The reaction was then diluted with H₂O (20 mL) and extracted with EtOAc (40 mL×3). The combined organic layers were dried over Na₂SO₄, filtered and concentrated. The residue was purified via silica gel chromatography (EtOAc:PE=1:2) to provide tert-butyl-diphenyl-[2-[(1-pyrimidin-2-yl-4-piperidyl)oxy]ethoxy]silane (150 mg, 28% yield) as a light-yellow oil. ESI-MS (EI+, m/z): 462.0 [M+H]+.

Step 4: 2-[(1-pyrimidin-2-yl-4-piperidyl) oxy]ethanol. To a solution of tert-butyl-diphenyl-[2-[(1-pyrimidin-2-yl-4-piperidyl) oxy]ethoxy]silane (3 g, 6.5 mmol) in THF (30 mL) was added Py.HF (1.93 g, 19.49 mmol) at rt and the reaction was stirred at rt for 3 h. The reaction mixture was diluted was H₂O (50 mL), extracted with EtOAc (50 mL×2). The combined organic layer was dried over Na₂SO₄, filtered and concentrated. The residue was purified via reverse phase chromatography (40% CH₃CN in water) to provide 2-[(1-pyrimidin-2-yl-4-piperidyl) oxy]ethanol (1 g, 69% yield) as a white solid. ¹HNMR (400 MHz, D₂O) δ 8.19 (dd, J=4.9, 1.3 Hz, 2H), 6.58 (dd, J=6.9, 3.1 Hz, 1H), 4.04 (d, J=13.7 Hz, 2H), 3.79-3.49 (m, 5H), 3.11 (t, J=12.0 Hz, 2H), 2.02-1.79 (m, 2H), 1.37 (d, J=9.7 Hz, 2H).

Step 5: (28E,30E,32E,33E,38R,39S,40R,41R,44S,46S,49S,50R,51R,60R)-50,60-dihydroxy-49-[(1R)-2-[(1S,3R,4R)-4-hydroxy-3-methoxy-cyclohexyl]-1-methyl-ethyl]-51-methoxy-38,39,40,41,52,53-hexamethyl-48-[2-[(1-pyrimidin-2-yl-4-piperidyl)oxy]ethoxy]-73,74-dioxa-64-azatricyclohexatriaconta-28,30,32(52),33(53)-tetraene-54,55,56,57,58-pentone (I-104). To a solution of (22E,24E,26E,27E,29R,30S,31R,32R,34S,36S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (200 mg, 0.2 mmol) in THF (5 mL) was added 4-methylbenzenesulfonic acid (188 mg, 1.09 mmol) at rt and the reaction was lowly warmed to 60° C. and stirred for 16 h then concentrated and purified via reverse-phase chromatography (75% CH₃CN in water) to provide the titled compound (45 mg, 19% yield) as a white solid. ESI-MS (EI+, m/z): 1105.2 [M+H]+. ¹HNMR (400 MHz, CDCl₃) δ 8.29 (d, J=4.6 Hz, 2H), 6.52-5.91 (m, 7H), 5.64-5.06 (m, 7H), 4.77-3.71 (m, 9H), 3.64-3.55 (m, 3H), 3.41-3.35 (m, 9H), 2.68 (ddd, J=54.3, 23.6, 7.4 Hz, 8H), 2.37-2.18 (m, 3H), 1.95 (dd, J=25.1, 10.9 Hz, 7H), 1.75-1.70 (m, 11H), 1.46 (s, 5H), 1.25 (s, 5H), 1.05-0.91 (m, 15H), 0.65 (d, J=11.5 Hz, 1H).

Example 53: Synthesis of (24E,26E,28E,29E,31R,32S,33R,34R,36S,38S,43S,44R,45R,56R)-42-[[(7R,8aS)-1,4-dioxo-2,3,6,7,8,8a-hexahydropyrrolo[1,2-a]pyrazin-7-yl]oxy]-44,56-dihydroxy-43-[(1R)-2-[(1S,3R,4R)-4-hydroxy-3-methoxy-cyclohexyl]-1-methyl-ethyl]-45-methoxy-31,32,33,34,46,47-hexamethyl-70,71-dioxa-58-azatricyclohexatriaconta-24,26,28(46),29(47)-tetraene-48,50,51,53,54-pentone (I-156), (24E,26E,28E,29E,31R,32S,33R,34R,36S,38S,42S,43S,44R,45R,56R)-42-[[(7R,8aS)-1,4-dioxo-2,3,6,7,8,8a-hexahydropyrrolo[1,2-a]pyrazin-7-yl]oxy]-44,56-dihydroxy-43-[(1R)-2-[(1S,3R,4R)-4-hydroxy-3-methoxy-cyclohexyl]-1-methyl-ethyl]-45-methoxy-31,32,33,34,46,47-hexamethyl-70,71-dioxa-58-azatricyclohexatriaconta-24,26,28(46),29(47)-tetraene-48,50,51,53,54-pentone (I-106) and (24E,26E,28E,29E,31R,32S,33R,34R,36S,38S,42S,43S,44R,45R,56R)-42-[[(7R,8aS)-1,4-dioxo-2,3,6,7,8,8a-hexahydropyrrolo[1,2-a]pyrazin-7-yl]oxy]-44,56-dihydroxy-43-[(1R)-2-[(1S,3R,4R)-4-hydroxy-3-methoxy-cyclohexyl]-1-methyl-ethyl]-45-methoxy-31,32,33,34,46,47-hexamethyl-70,71-dioxa-58-azatricyclohexatriaconta-24,26,28(46),29(47)-tetraene-48,50,51,53,54-pentone (I-114)

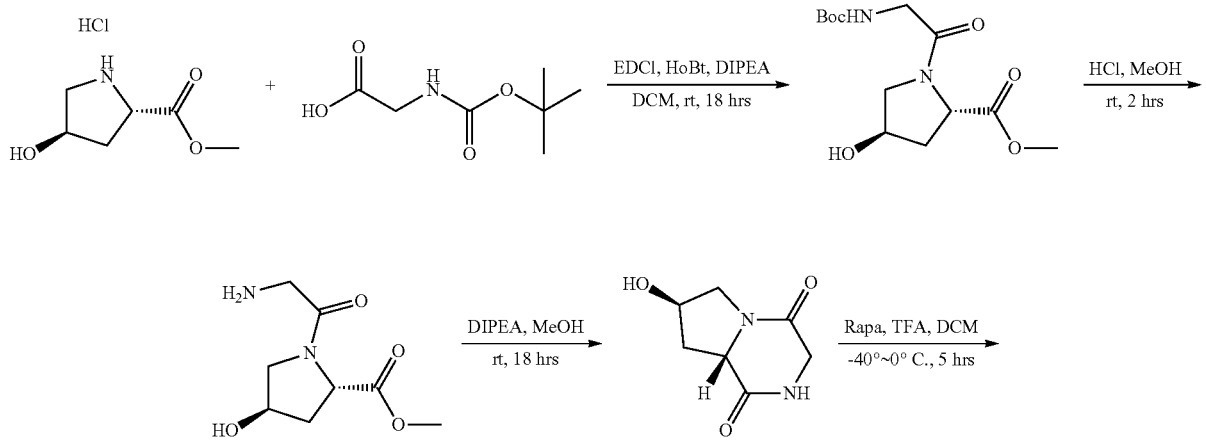

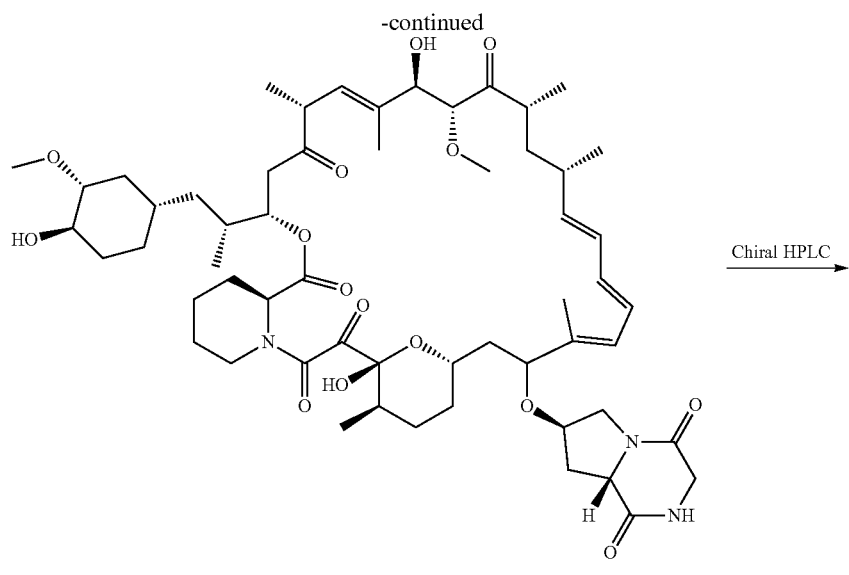
I-156
Chiral HPLC →
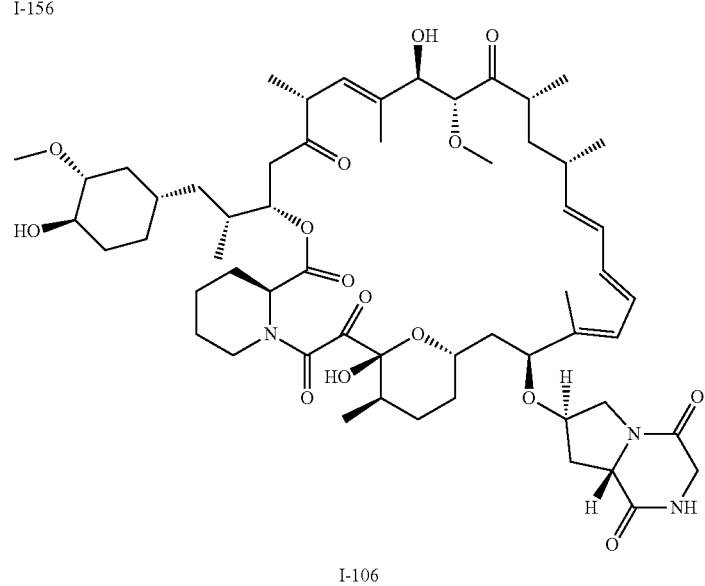
I-106
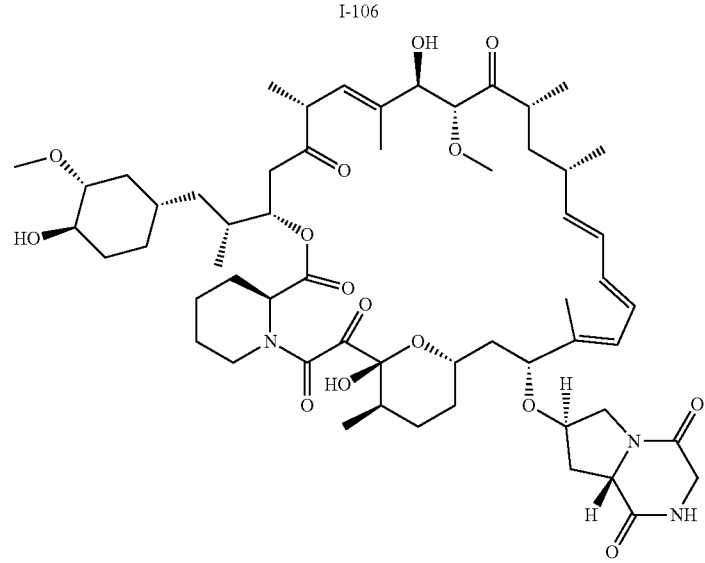
I-114

Step 1: methyl (2S,4R)-1-[2-(tert-butoxycarbonylamino) acetyl]-4-hydroxy-pyrrolidine-2-carboxylate. A solution of methyl (2S,4R)-4-hydroxypyrrolidine-2-carboxylate (10 g, 55.06 mmol), 2-(tert-butoxycarbonylamino)acetic acid (9.65 g, 55.06 mmol), EDCI (11.6 g, 60.57 mmol), 1-hydroxy-benzotriazole (9.67 g, 71.58 mmol) and N-ethyl-N-isopropyl-propan-2-amine (35.58 g, 275.3 mmol) in DCM (100 mL) was stirred at 15° C. for 18 h. The reaction was washed with H$_2$O (100 mL×2) then the combined organic layers were concentrated. The residue was purified via silica gel chromatography (DCM:MeOH=10:1) to provide methyl (2S,4R)-1-[2-(tert-butoxycarbonylamino) acetyl]-4-hydroxy-pyrrolidine-2-carboxylate (9 g, 54% yield) as a clear oil. ESI-MS (EI$^+$, m/z): 325.0 [M+Na]$^+$.

Step 2: methyl (2S,4R)-1-(2-aminoacetyl)-4-hydroxy-pyrrolidine-2-carboxylate. A solution of methyl (2S,4R)-1-[2-(tert-butoxycarbonylamino)acetyl]-4-hydroxy-pyrrolidine-2-carboxylate (9 g, 29.77 mmol) in HCl in MeOH (4 M, 37.21 mL) was stirred at room temperature for 2 h. The reaction was concentrated under reduced pressure and the residue was used without further purification. ESI-MS (EI$^+$, m/z): 203.1 [M+H]$^+$.

Step 3: (7R,8aS)-7-hydroxy-2,3,6,7,8,8a-hexahydropyrrolo[1,2-a]pyrazine-1,4-dione. To a solution of methyl (2S,4R)-1-(2-aminoacetyl)-4-hydroxy-pyrrolidine-2-carboxylate (6 g, 29.67 mmol) in MeOH (100 mL) was added N-ethyl-N-isopropyl-propan-2-amine (3.83 g, 29.67 mmol, 5.17 mL) followed by addition of DIPEA (5 mL) and the resulting solution was stirred at room temperature overnight. The reaction was concentrated then redissolved in DCM, cooled then filtered and dried under vacuum to provide (7R,8aS)-7-hydroxy-2,3,6,7,8,8a-hexahydropyrrolo[1,2-a]pyrazine-1,4-dione (4 g, 79% yield) as a white solid. ESI-MS (EI$^+$, m/z): 170.9 [M+H]$^+$. $^1$HNMR (400 MHz, DMSO-d$_6$) δ 8.09 (d, J=3.5 Hz, 1H), 5.13 (s, 1H), 4.42-4.21 (m, 2H), 4.04 (d, J=16.4 Hz, 1H), 3.59-3.45 (m, 2H), 3.20 (t, J=11.7 Hz, 1H), 2.05 (dd, J=13.0, 6.4 Hz, 1H), 1.95-1.83 (m, 1H).

Step 4: (24E,26E,28E,29E,31R,32S,33R,34R,36S,38S,43S,44R,45R,56R)-42-[[(7R,8aS)-1,4-dioxo-2,3,6,7,8,8a-hexahydropyrrolo[1,2-a]pyrazin-7-yl]oxy]-44,56-dihydroxy-43-[(1R)-2-[(1S,3R,4R)-4-hydroxy-3-methoxy-cyclohexyl]-1-methyl-ethyl]-45-methoxy-31,32,33,34,46,47-hexamethyl-70,71-dioxa-58-azatricyclohexatriaconta-24,26,28(46),29(47)-tetraene-48,50,51,53,54-pentone (I-156). To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (250 mg, 0.27 mmol) in DCM (8 mL) was added 2,2,2-trifluoroacetic acid (312 mg, 2.73 mmol) at −40° C. The mixture was stirred at −40° C. for 10 minutes. (7R,8aS)-7-hydroxy-2,3,6,7,8,8a-hexahydropyrrolo[1,2-a]pyrazine-1,4-dione (233 mg, 1.37 mmol) in DCM (3 mL) was added and the mixture was stirred at −40° C. for 5 h. The reaction was then treated with aqueous NaHCO$_3$ (30 mL) and extracted with EtOAc (30 mL×2). The combined organic layers were concentrated and purified via reverse-phase chromatography (55% CH$_3$CN in water) to provide the titled compound (15 mg, 5% yield) as a white solid. ESI-MS (EI$^+$, m/z): 1074.7 [M+Na]$^+$. $^1$HNMR (400 MHz, CDCl$_3$): δ 8.11-8.17 (m, 1H), 6.08-6.57 (m, 4H), 4.90-5.52 (m, 4H), 4.58-4.65 (m, 1H), 3.84-4.30 (m, 6H), 3.43-3.67 (m, 3H), 3.08-3.33 (m, 9H), 2.65-2.88 (m, 3H), 1.83-2.43 (m, 8H), 1.47-1.80 (m, 14H), 1.08-1.46 (m, 9H), 0.66-1.08 (m, 18H), 0.52-0.65 (m, 1H).

Step 5: (24E,26E,28E,29E,31R,32S,33R,34R,36S,38S,42S,43S,44R,45R,56R)-42-[[(7R,8aS)-1,4-dioxo-2,3,6,7,8,8a-hexahydropyrrolo[1,2-a]pyrazin-7-yl]oxy]-44,56-dihydroxy-43-[(1R)-2-[(1S,3R,4R)-4-hydroxy-3-methoxy-cyclohexyl]-1-methyl-ethyl]-45-methoxy-31,32,33,34,46,47-hexamethyl-70,71-dioxa-58-azatricyclohexatriaconta-24,26,28(46),29(47)-tetraene-48,50,51,53,54-pentone (I-106) and (24E,26E,28E,29E,31R,32S,33R,34R,36S,38S,42R,43S,44R,45R,56R)-42-[[(7R,8aS)-1,4-dioxo-2,3,6,7,8,8a-hexahydropyrrolo[1,2-a]pyrazin-7-yl]oxy]-44,56-dihydroxy-43-[(1R)-2-[(1S,3R,4R)-4-hydroxy-3-methoxy-cyclohexyl]-1-methyl-ethyl]-45-methoxy-31,32,33,34,46,47-hexamethyl-70,71-dioxa-58-azatricyclohexatriaconta-24,26,28(46),29(47)-tetraene-48,50,51,53,54-pentone (I-114). 146 mg of the mixture was mixture was separated via chiral HPLC to provide the titled compound (I-106: 26.3 mg, 18% yield) and (I-114: 18.1 mg, 12% yield) as white solids.

Chiral Separation Method:

| Column: | CHIRALPAK IC |
|---|---|
| Column size: | 5.0 cm I.D. × 25 cm L, 10 μm |
| Sample solution: | 1.4 mg/ml in Mobile phase: |
| Injection: | 10 ml |
| Mobile phase: | EtOH = 100% |
| Flow rate: | 14 ml/min |
| Wave length: | UV 254 nm |
| Temperature: | 35° C. |

I-106: ESI-MS (EI$^+$, m/z): 1074.4 [M+Na]$^+$. $^1$H NMR (500 MHz, CDCl$_3$) δ 6.41-5.89 (m, 5H), 5.64-4.88 (m, 5H), 4.49-3.56 (m, 11H), 3.52-3.26 (m, 11H), 3.01-2.54 (m, 5H), 2.42-1.72 (m, 16H), 1.38 (ddd, J=65.4, 25.5, 11.4 Hz, 13H), 1.16-0.79 (m, 19H), 0.72-0.63 (m, 1H).

I-114: ESI-MS (EI$^+$, m/z): 1074.4 [M+Na]$^+$. $^1$H NMR (500 MHz, CDCl$_3$) δ 6.43-5.95 (m, 5H), 5.80-5.66 (m, 1H), 5.49 (dd, J=28.7, 10.0 Hz, 1H), 5.27 (dd, J=30.2, 26.1 Hz, 2H), 4.45 (dd, J=26.5, 20.1 Hz, 2H), 4.35-4.25 (m, 1H), 4.18 (d, J=16.7 Hz, 1H), 4.09-3.97 (m, 2H), 3.96-3.48 (m, 6H), 3.33 (ddd, J=24.0, 21.0, 10.3 Hz, 9H), 2.90 (d, J=13.1 Hz, 2H), 2.77-2.49 (m, 4H), 2.45-1.88 (m, 7H), 1.74 (dd, J=33.3, 9.6 Hz, 10H), 1.39 (ddd, J=59.4, 35.0, 10.8 Hz, 13H), 1.21-0.85 (m, 18H), 0.71-0.61 (m, 1H).

Example 54: Synthesis of (28E,30E,32E,33E,36R, 37S,38R,39R,42S,44S,46S,47S,48R,49R,58R)-48, 58-dihydroxy-47-[(1R)-2-[(1S,3R,4R)-4-hydroxy-3-methoxy-cyclohexyl]-1-methyl-ethyl]-49-methoxy-36,37,38,39,50,51-hexamethyl-46-[(1-pyrimidin-2-yl-4-piperidyl)oxy]-71,72-dioxa-62-azatricyclohexatriaconta-28,30,32(50),33(51)-tetraene-52,53,54,55,56-pentone (I-107) and (28E, 30E,32E,33E,36R,37S,38R,39R,42S,44S,46R,47S, 48R,49R,58R)-48,58-dihydroxy-47-[(1R)-2-[(1S,3R, 4R)-4-hydroxy-3-methoxy-cyclohexyl]-1-methyl-ethyl]-49-methoxy-36,37,38,39,50,51-hexamethyl-46-[(1-pyrimidin-2-yl-4-piperidyl)oxy]-71,72-dioxa-62-azatricyclohexatriaconta-28,30,32(50),33(51)-tetraene-52,53,54,55,56-pentone (I-112)

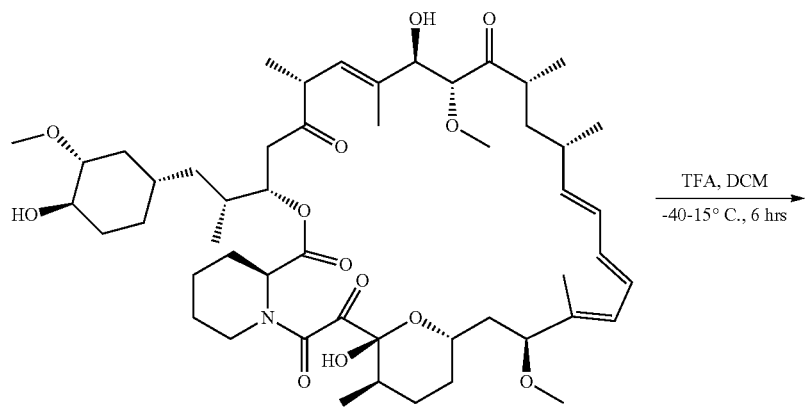

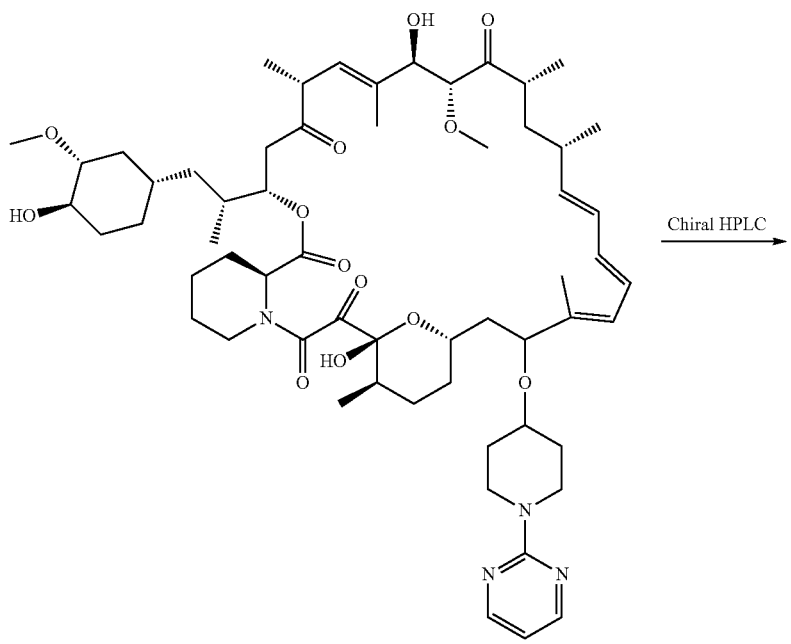

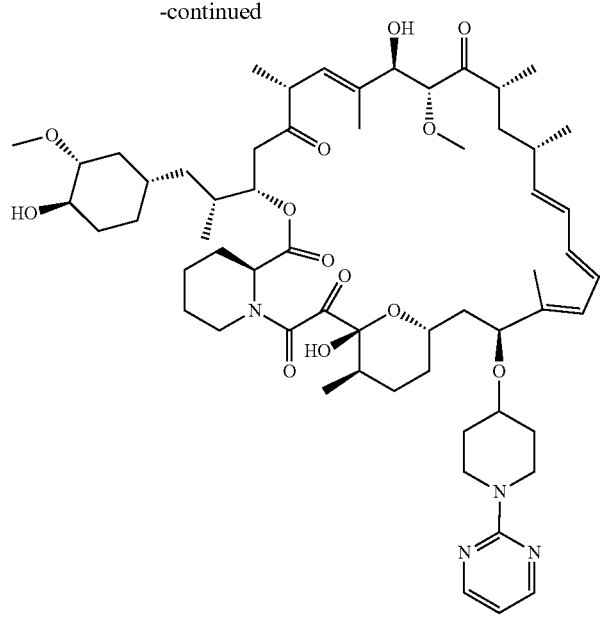

I-107

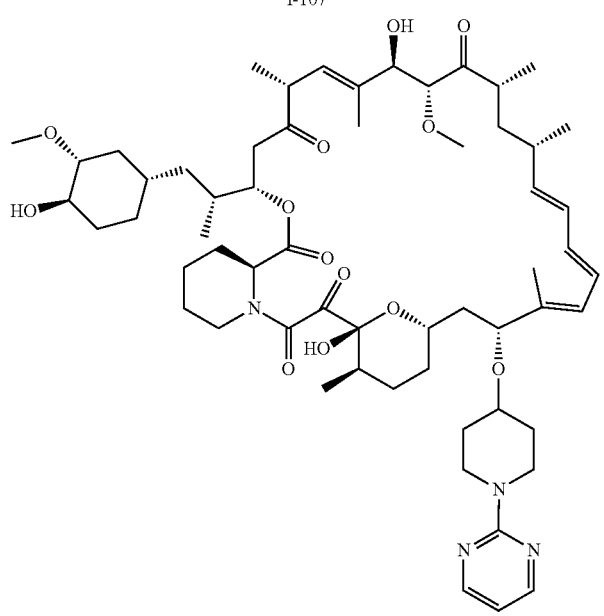

I-112

Step 1: (28E,30E,32E,33E,36R,37S,38R,39R,42S,44S, 47S,48R,49R,58R)-48,58-dihydroxy-47-[(1R)-2-[(1S,3R, 4R)-4-hydroxy-3-methoxy-cyclohexyl]-1-methyl-ethyl]-49-methoxy-36,37,38,39,50,51-hexamethyl-46-[(1-pyrimidin-2-yl-4-piperidyl)oxy]-71,72-dioxa-62-azatricyclohexatriaconta-28,30,32(50),33(51)-tetraene-52, 53,54,55,56-pentone. To a solution of (22E,24E,26E,27E, 29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32, 42,43-hexamethyl-60,61-dioxa-51-azatricyclohexatriaconta-22,24,26(42),27(43)-tetraene-44, 45,46,47,48-pentone (300 mg, 0.33 mmol) in DCM (15 mL) was added CF$_3$COOH (748 mg, 6.56 mmol) and 1-pyrimidin-2-ylpiperidin-4-ol (471 mg, 2.63 mmol) at −40° C. under N2. The mixture was slowly warmed to 15° C. over 6 h. The reaction was poured into ice cold NaHCO$_3$ aqueous solution and extracted with EtOAc. The organic layer was washed with water and brine, dried over Na$_2$SO$_4$, filtered and concentrated. The residue was purified by reverse-phase chromatography (70% CH$_3$CN in water), then via silica gel chromatography (MeOH:DCM=1:20), then via prep-TLC to provide the titled compound (30 mg, 8% yield) as a white solid. ESI-MS (EI$^+$, m/z): 1061.2 [M+H]$^+$.

Step 2: (28E,30E,32E,33E,36R,37S,38R,39R,42S,44S, 46S,47S,48R,49R,58R)-48,58-dihydroxy-47-[(1R)-2-[(1S, 3R,4R)-4-hydroxy-3-methoxy-cyclohexyl]-1-methyl-ethyl]-49-methoxy-36,37,38,39,50,51-hexamethyl-46-[(1-pyrimidin-2-yl-4-piperidyl)oxy]-71,72-dioxa-62-azatricyclohexatriaconta-28,30,32(50),33(51)-tetraene-52, 53,54,55,56-pentone (I-107) and (28E,30E,32E,33E,36R, 37S,38R,39R,42S,44S,46R,47S,48R,49R,58R)-48,58- dihydroxy-47-[(1R)-2-[(1S,3R,4R)-4-hydroxy-3-methoxy-cyclohexyl]-1-methyl-ethyl]-49-methoxy-36,37,38,39,50,51-hexamethyl-46-[(1-pyrimidin-2-yl-4-piperidyl)oxy]-71,72-dioxa-62-azatricyclohexatriaconta-28,30,32(50),33(51)-tetraene-52,53,54,55,56-pentone (I-112). 130 mg of the mixture was separated via chiral HPLC and then purified by silica gel chromatography (hexane:DCM:EtOAc:MeOH from 3:3:1:0 to 3:3:1:0.7) to obtain the titled compound (I-107: 32.9 mg, 25% yield) and (I-112: 23.1 mg, 18% yield) as white solids.

Chiral Separation Method:

| | |
|---|---|
| Column: | CHIRALPAK IC |
| Column size: | 5.0 cm I.D. × 25 cm L, 10 μm |
| Sample solution: | 1.3 mg/ml in Mobile phase: |
| Injection: | 5 ml |
| Mobile phase: | Hexane/EtOH = 50/50(V/V) |
| Flow rate: | 20 ml/min |
| Wave length: | UV 254 nm |
| Temperature: | 35° C. |

I-107: ESI-MS (EI$^+$, m/z): 1061.6 [M+H]$^+$, 1083.6 [M+Na]$^+$. $^1$H NMR (500 MHz, CDCl$_3$) δ 8.39-8.19 (m, 2H), 6.52-6.08 (m, 4H), 5.93 (dd, J=34.3, 10.7 Hz, 1H), 5.55-5.03 (m, 4H), 4.36-4.13 (m, 3H), 4.02-3.80 (m, 2H), 3.71 (dd, J=10.9, 6.1 Hz, 1H), 3.58 (d, J=14.1 Hz, 1H), 3.52-3.20 (m, 13H), 2.97-2.53 (m, 5H), 2.25-1.88 (m, 7H), 1.84-1.57 (m, 16H), 1.55-1.18 (m, 10H), 1.16-0.83 (m, 18H), 0.71-0.63 (m, 1H).

I-112: ESI-MS (EI$^+$, m/z): 1061.6 [M+H]$^+$, 1083.6 [M+Na]$^+$. $^1$H NMR (500 MHz, CDCl$_3$) δ 8.29 (t, J=4.2 Hz, 2H), 6.53-5.88 (m, 5H), 5.77-5.02 (m, 4H), 4.38-3.81 (m, 6H), 3.61-3.03 (m, 13H), 2.97-1.94 (m, 12H), 1.92-1.58 (m, 17H), 1.57-1.19 (m, 10H), 1.18-0.81 (m, 18H), 0.75-0.61 (m, 1H).

Example 55: Synthesis of (23E,25E,27E,28E,32R,33S,34R,35R,37S,39S,41S,42S,47R,48R,57R)-41-[[(3S,3aR,6R,6aR)-3-(2-hydroxyethoxy)-2,3,3a,5,6,6a-hexahydrofuro[3,2-b]furan-6-yl]oxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-109) and (23E,25E,27E,28E,32R,33S,34R,35R,37S,39S,41R,42S,47R,48R,57R)-41-[[(3S,3aR,6R,6aR)-3-(2-hydroxyethoxy)-2,3,3a,5,6,6a-hexahydrofuro[3,2-b]furan-6-yl]oxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-110)

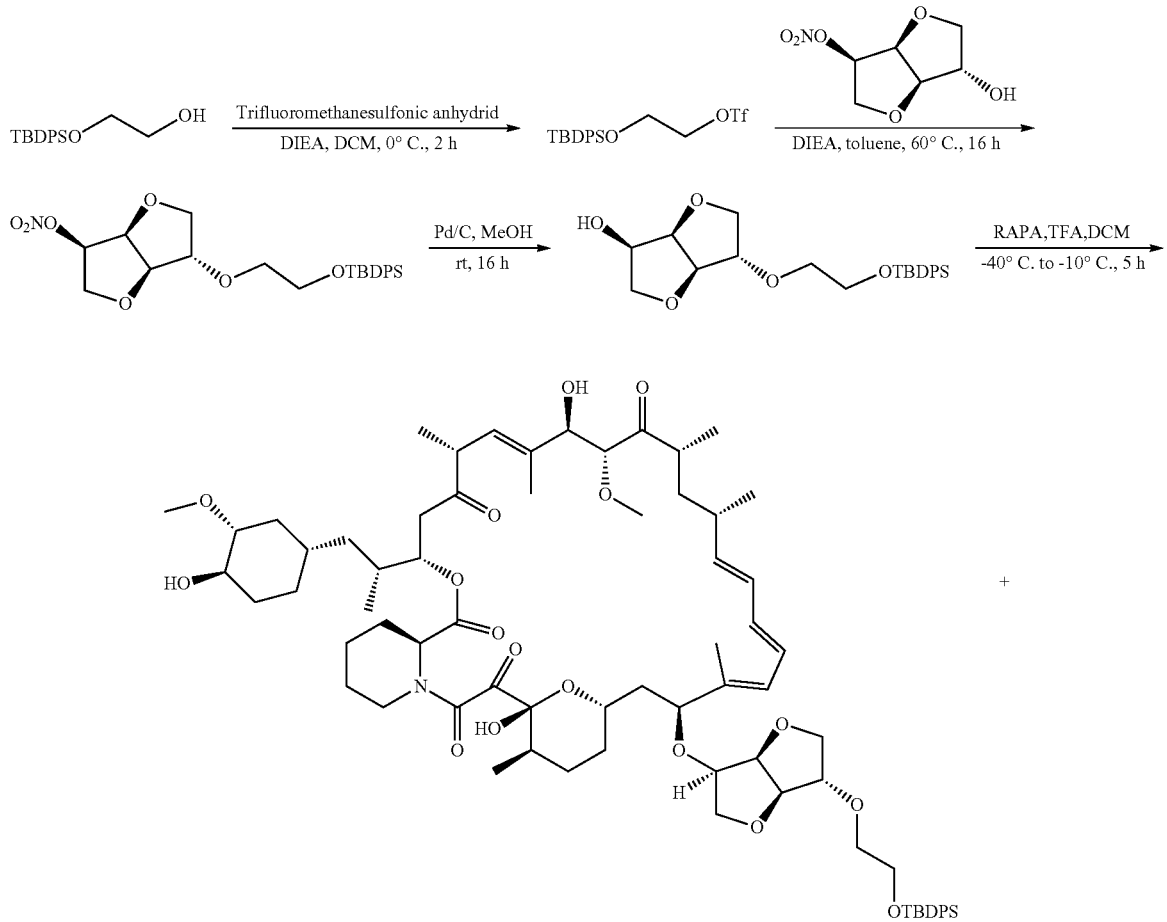

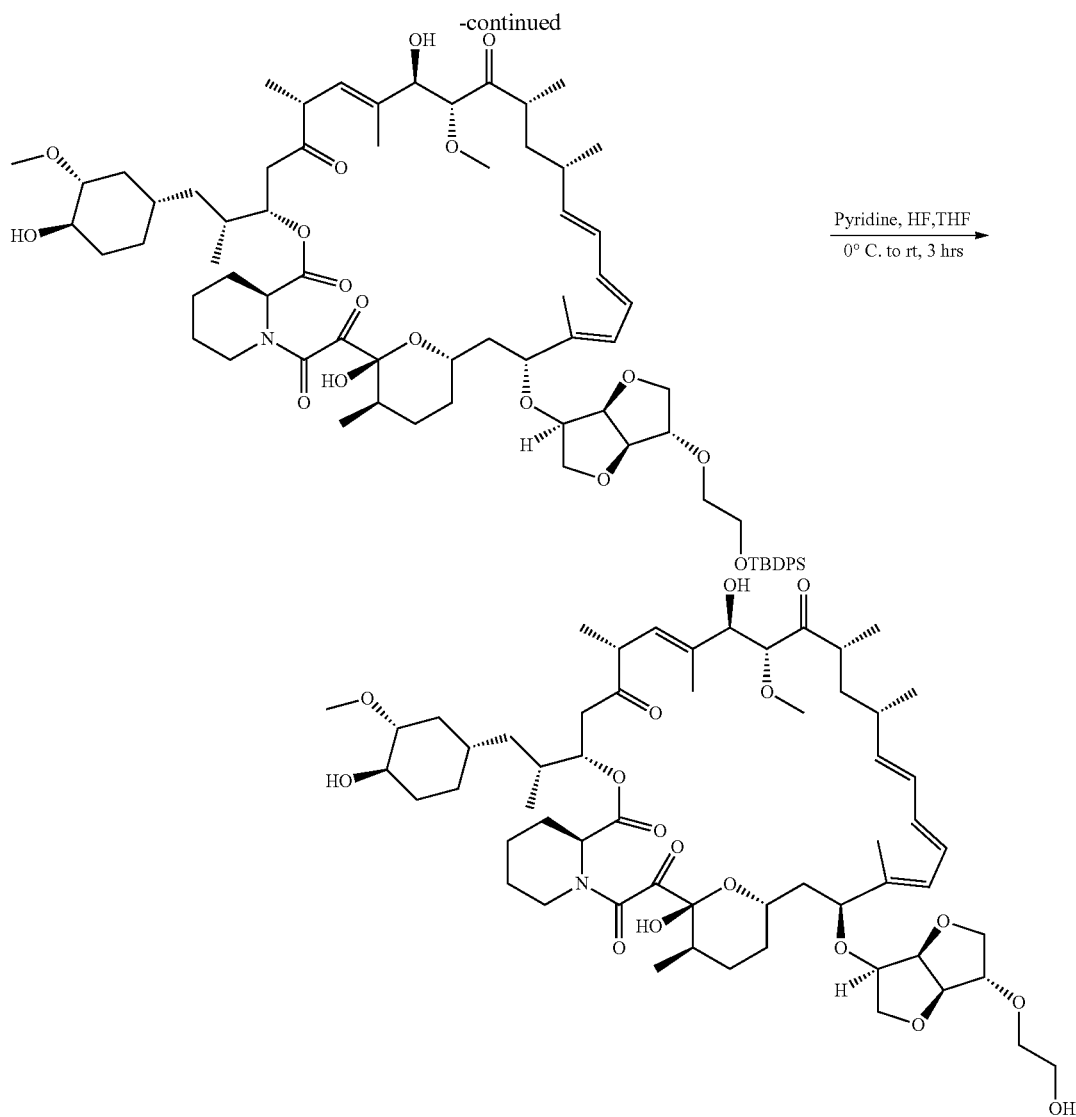
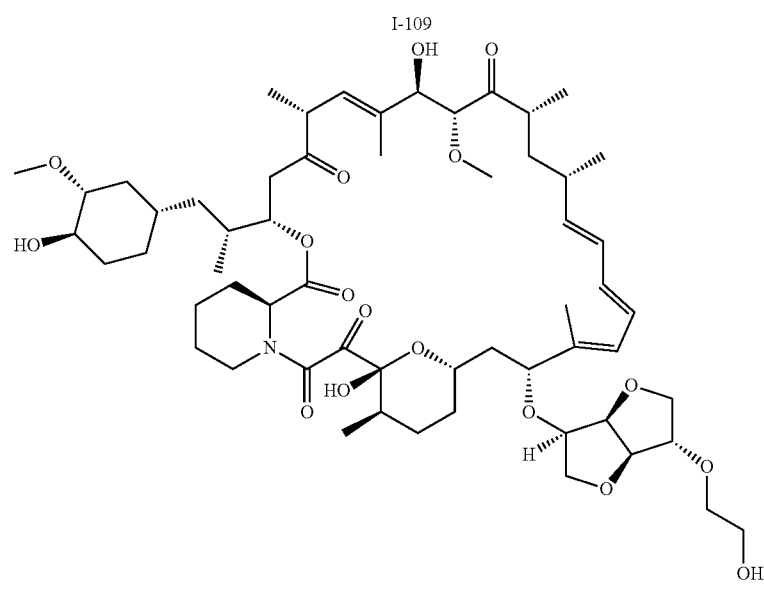
I-110

Step 1: 2-[tert-butyl (diphenyl) silyl]oxyethyl trifluoromethanesulfonate. A solution of 2-[tert-butyl(diphenyl)silyl]oxyethanol (1.1 g, 3.66 mmol) and DIEA (710 mg, 5.49 mmol) in DCM (240 mL) was cooled to 0° C. under $N_2$. $Tf_2O$ (1.14 g, 4.03 mmol) was added and the mixture was stirred at 0° C. for 2h. The reaction was diluted with DCM (150 mL), washed with saturated $NaHCO_3$ (150 mL), water (150 mL) and brine (150 mL). The organic layer was dried over $Na_2SO_4$, filtered and concentrated to provide 2-[tert-butyl(diphenyl)silyl]oxyethyl trifluoromethanesulfonate (1.4 g, 88% yield) as brown oil. The crude was used in the next step without further purification. $^1$H NMR (400 MHz, $CDCl_3$): δ 7.67-7.65 (m, 4H), 7.45-7.38 (m, 6H), 4.56 (t, J=4.4 Hz, 2H), 3.90 (t, J=4.4 Hz, 2H).

Step 2: [(3S,3aR,6R,6aS)-3-[2-[tert-butyl(diphenyl)silyl]oxyethoxy]-2,3,3a,5,6,6a-hexahydrofuro[3,2-b]furan-6-yl] nitrate. A solution of [(3S,3aR,6R,6aS)-3-hydroxy-2,3,3a,5,6,6a-hexahydrofuro[3,2-b]furan-6-yl] nitrate (7 g, 36.62 mmol), 2-[tert-butyl(diphenyl)silyl]oxyethyl trifluoromethanesulfonate (47.52 g, 109.87 mmol) and N-ethyl-N-isopropyl-propan-2-amine (23.67 g, 183.11 mmol) in toluene (50 mL) was stirred at 60° C. for 16 h. The reaction was diluted with EtOAc (100 mL) and washed with $H_2O$ (80 mL) and brine (80 mL). The organic layer was dried over $Na_2SO_4$, filtered and concentrated. The residue was purified via reverse phase chromatography (70% $CH_3CN$ in water) to provide [(3S,3aR,6R,6aS)-3-[2-[tert-butyl(diphenyl)silyl]oxyethoxy]-2,3,3a,5,6,6a-hexahydrofuro[3,2-b]furan-6-yl] nitrate (1.6 g, 9% yield) as a yellow oil. ESI-MS (EI+, m/z): 496.0 [M+Na]$^+$. $^1$H NMR (500 MHz, $CDCl_3$): δ 7.67-7.66 (m, 4H), 7.44-7.36 (m, 6H), 5.30 (q, J=2.5 Hz, 1H), 4.88 (t, J=5.0 Hz, 1H), 4.46 (d, J=4.5 Hz, 1H), 4.06-3.95 (m, 3H), 3.88-3.83 (m, 2H), 3.79-3.77 (m, 2H), 3.61-3.59 (m, 2H), 1.05 (s, 9H).

Step 3: (3R,3aR,6S,6aR)-6-[2-[tert-butyl(diphenyl)silyl]oxyethoxy]-2,3,3a,5,6,6a-hexahydrofuro[3,2-b]furan-3-ol: To a solution of [(3S,3aR,6R,6aS)-3-[2-[tert-butyl(diphenyl)silyl]oxyethoxy]-2,3,3a,5,6,6a-hexahydrofuro[3,2-b]furan-6-yl] nitrate (1.6 g, 3.38 mmol) in MeOH (150 mL) was added Pd/C (0.8 g) and the reaction was stirred at 20° C. under $H_2$ for 16 h. The mixture was then filtered, concentrated and purified via reverse phase chromatography (60% $CH_3CN$ in water) to provide (3R,3aR,6S,6aR)-6-[2-[tert-butyl(diphenyl)silyl]oxyethoxy]-2,3,3a,5,6,6a-hexahydrofuro[3,2-b]furan-3-ol (1.0 g, 69% yield) as a clear oil. ESI-MS (EI+, m/z): 451.0 [M+Na]$^+$. $^1$H NMR (500 MHz, $CDCl_3$): δ 7.68-7.67 (m, 4H), 7.44-7.36 (m, 6H), 4.56 (t, J=5.0 Hz, 1H), 4.45 (d, J=4.5 Hz, 1H), 4.25 (q, J=5.5 Hz, 1H), 4.07-4.02 (m, 2H), 3.87-3.82 (m, 2H), 3.80-3.78 (m, 2H), 3.63-3.61 (m, 2H), 3.57-3.54 (m, 1H), 2.65 (d, J=7.0 Hz, 1H), 1.05 (s, 9H).

Step 4: Synthesis of (36E,38E,40E,41E,47R,48S,49R,50R,52S,54S,57S,62R,63R,72R)-56-[[(3S,3aR,6R,6aR)-3-[2-[tert-butyl(diphenyl)silyl]oxyethoxy]-2,3,3a,5,6,6a-hexahydrofuro[3,2-b]furan-6-yl]oxy]-62,72-dihydroxy-57-[(1R)-2-[(1S,3R,4R)-4-hydroxy-3-methoxy-cyclohexyl]-1-methyl-ethyl]-63-methoxy-47,48,49,50,64,65-hexamethyl-85,86-dioxa-74-azatricyclohexatriaconta-36,38,40(64),41(65)-tetraene-66,67,68,69,70-pentone. To a solution of (22E,24E,26E,27E,29R,30S,31R,32R,34S,36S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (0.5 g, 0.55 mmol) in DCM (5 mL) was added 2,2,2-trifluoroacetic acid (0.499 g, 4.38 mmol) at −40° C. under argon. The solution was stirred at −40° C. for 10 min, then (3R,3aR,6S,6aR)-6-[2-[tert-butyl(diphenyl)silyl]oxyethoxy]-2,3,3a,5,6,6a-hexahydrofuro[3,2-b]furan-3-ol (586 mg, 1.37 mmol) was added. The reaction mixture was stirred at −10° C. for 5 h under argon then quenched with ice cold aqueous $NaHCO_3$ (20 mL) and extracted with DCM (50 mL×2). The combined organic layers were washed with brine (50 mL), dried over $Na_2SO_4$, filtered and concentrated. The residue was purified via reverse phase chromatography (100% $CH_3CN$) to provide the titled compound (70 mg, 10% yield) as a white solid and the titled compound (100 mg, 14% yield) as a white solid. ESI-MS (EI+, m/z): 1332.2 [M+Na]$^+$.

Step 5: (23E,25E,27E,28E,32R,33S,34R,35R,37S,39S,41S,42S,47R,48R,57R)-41-[[(3S,3aR,6R,6aR)-3-(2-hydroxyethoxy)-2,3,3a,5,6,6a-hexahydrofuro[3,2-b]furan-6-yl]oxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-109) and (23E,25E,27E,28E,32R,33S,34R,35R,37S,39S,41S,42S,47R,48R,57R)-41-[[(3S,3aR,6R,6aR)-3-(2-hydroxyethoxy)-2,3,3a,5,6,6a-hexahydrofuro[3,2-b]furan-6-yl]oxy]-47,57-dihydroxy-42-[(1R)-2-[(1S,3R,4R)-4-hydroxy-3-methoxy-cyclohexyl]-1-methyl-ethyl]-48-methoxy-32,33,34,35,49,50-hexamethyl-70,71-dioxa-58-azatricyclohexatriaconta-23,25,27(49),28(50)-tetraene-51,52,53,54,55-pentone (I-110). To a solution of (36E,38E,40E,41E,47R,48S,49R,50R,52S,54S,56S,57S,62R,63R,72R)-56-[[(3S,3aR,6R,6aR)-3-[2-[tert-butyl(diphenyl)silyl]oxyethoxy]-2,3,3a,5,6,6a-hexahydrofuro[3,2-b]furan-6-yl]oxy]-62,72-dihydroxy-57-[(1R)-2-[(1S,3R,4R)-4-hydroxy-3-methoxy-cyclohexyl]-1-methyl-ethyl]-63-methoxy-47,48,49,50,64,65-hexamethyl-85,86-dioxa-74-azatricyclohexatriaconta-36,38,40(64),41(65)-tetraene-66,67,68,69,70-pentone (170 mg, 0.13 mmol) in THF (8 mL) was added Py.HF (129 mg, 1.3 mmol) at 0° C. The reaction was stirred at 10° C. for 3 h then at rt overnight. Saturated $NaHCO_3$ solution (80 mL) was added then the mixture was extracted with EtOAc (60 mL). The organic layer was washed with brine (30 mL), dried and concentrated. The residue was purified via reverse phase chromatography (48% $CH_3CN$ in water) to provide the titled compound (I-109: 29.2 mg, 21% yield) as a white solid. ESI-MS (EI+, m/z): 1094.2 [M+Na]$^+$. $^1$H NMR (400 MHz, $CDCl_3$): δ 6.42-5.95 (m, 4H), 5.57-5.14 (m, 4H), 4.50-4.15 (m, 4H), 4.01-3.28 (m, 23H), 2.97-2.91 (m, 2H), 2.79-2.51 (m, 4H), 2.38-2.31 (m, 2H), 2.18-1.88 (m, 6H), 1.78-1.72 (m, 6H), 1.64-1.31 (m, 12H), 1.28-0.79 (m, 21H), 0.72-0.66 (m, 1H). To a solution of (36E,38E,40E,41E,47R,48S,49R,50R,52S,54S,56R,57S,62R,63R,72R)-56-[[(3S,3aR,6R,6aR)-3-[2-[tert-butyl(diphenyl)silyl]oxyethoxy]-2,3,3a,5,6,6a-hexahydrofuro[3,2-b]furan-6-yl]oxy]-62,72-dihydroxy-57-[(1R)-2-[(1S,3R,4R)-4-hydroxy-3-methoxy-cyclohexyl]-1-methyl-ethyl]-63-methoxy-47,48,49,50,64,65-hexamethyl-85,86-dioxa-74-azatricyclohexatriaconta-36,38,40(64),41(65)-tetraene-66,67,68,69,70-pentone (200 mg, 0.153 mmol) in THF (10 mL) was added Py.HF (151 mg, 1.53 mmol, 2 mL) at 0° C. The solution was stirred at 10° C. for 3 h then at rt overnight. Saturated $NaHCO_3$ solution (80 mL) was added then the mixture was extracted with EtOAc (60 mL). The organic layer was washed with brine (30 mL), dried and concentrated. The residue was purified via reverse phase chromatography (50% $CH_3CN$ in water) to provide the titled compound (I-110: 45.7 mg, 28% yield) as a white solid. ESI-MS (EI+, m/z): 1118.5 [M+Na]$^+$. $^1$H NMR (400 MHz, $CDCl_3$): δ 6.37-5.97 (m, 4H), 5.78-5.05 (m, 4H), 4.71-4.56 (m, 2H), 4.44-3.44 (m, 15H), 3.41-3.28 (m, 10H), 3.04-2.81 (m, 3H), 2.72-2.51 (m, 5H), 2.40-1.96 (m, 7H), 1.92-1.79 (m, 7H), 1.49-1.15 (m, 13H), 1.12-0.88 (m, 18H), 0.76-0.62 (m, 1H).

Example 56: Synthesis of (24E,26E,28E,29E,31R, 32S,33R,34R,36S,38S,40S,41S,42R,43R,52R)-41-[(1R)-2-[(1S,3R,4R)-3,4-dimethoxycyclohexyl]-1-methyl-ethyl]-52-hydroxy-40,42,43-trimethoxy-31,32,33,34,44,45-hexamethyl-60,61-dioxa-53-azatricyclohexatriaconta-24,26,28(44),29(45)-tetraene-46,47,48,49,50-pentone (Intermediate A), (24E,26E,28E,29E,35R,36S,37R,38R,40S,42S,45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethoxy)ethoxy]-35,36,37,38,48,49-hexamethyl-64,65-dioxa-57-azatricyclohexatriaconta-24,26,28(48),29(49)-tetraene-50,51,52,53,54-pentone (I-116), (24E,26E,28E,29E,35R,36S,37R,38R,40S,42S,44S,45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethoxy)ethoxy]-35,36,37,38,48,49-hexamethyl-64,65-dioxa-57-azatricyclohexatriaconta-24,26,28(48),29(49)-tetraene-50,51,52,53,54-pentone (I-118) and (24E,26E,28E,29E,35R,36S,37R,38R,40S,42S,44R,45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethoxy)ethoxy]-35,36,37,38,48,49-hexamethyl-64,65-dioxa-57-azatricyclohexatriaconta-24,26,28(48),29(49)-tetraene-50,51,52,53,54-pentone (I-119)

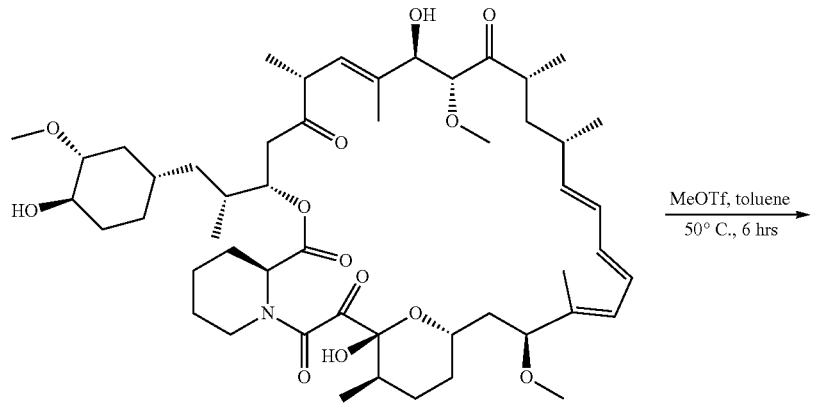

MeOTf, toluene
50° C., 6 hrs

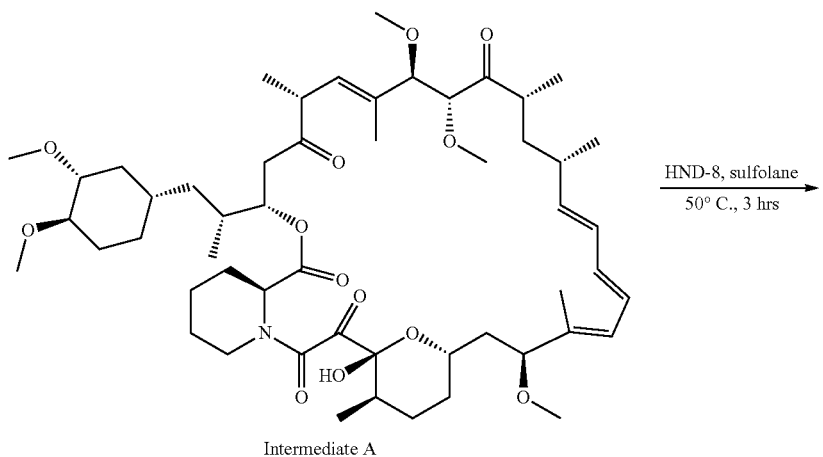

Intermediate A

HND-8, sulfolane
50° C., 3 hrs

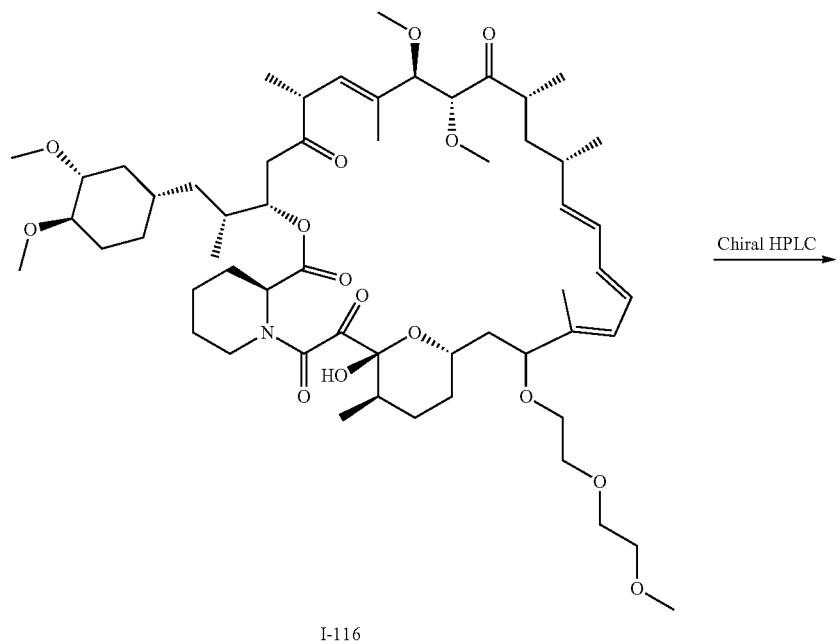
I-116
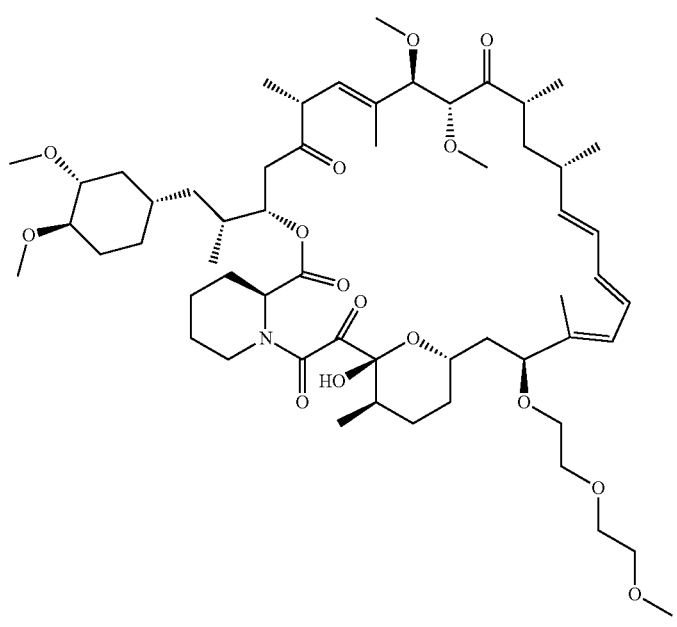
I-118

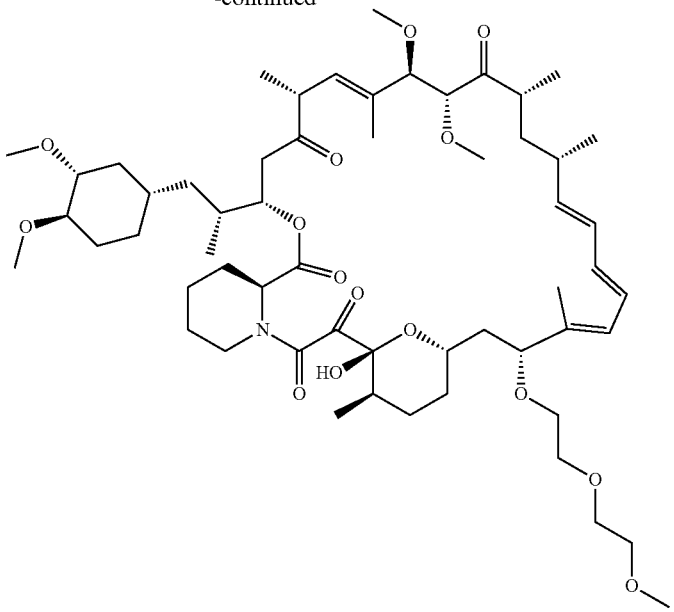

I-119

Step 1: (24E,26E,28E,29E,31R,32S,33R,34R,36S,38S, 40S,41S,42R,43R,52R)-41-[(1R)-2-[(1S,3R,4R)-3,4-dimethoxycyclohexyl]-1-methyl-ethyl]-52-hydroxy-40,42,43-trimethoxy-31,32,33,34,44,45-hexamethyl-60,61-dioxa-53-azatricyclohexatriaconta-24,26,28(44),29(45)-tetraene-46, 47,48,49,50-pentone (Intermediate A). To a solution of (22E, 24E,26E,27E,29R,30S,31R,32R,34S,36S,38S,39S,40R, 41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44, 45,46,47,48-pentone (200 mg, 0.22 mmol) in toluene (5 mL) was added proton sponge (938 mg, 4.38 mmol) and methyl trifluoromethanesulfonate (539 mg, 3.28 mmol). The mixture was stirred at 50° C. for 6 h. Upon cooling the reaction was concentrated and purified via silica gel chromatography then reverse-phase chromatography (85% CH$_3$CN in water) to provide the titled compound (50 mg, 24% yield) as a white solid. ESI-MS (EI$^+$, m/z): 964.2 [M+Na]$^+$. $^1$H NMR (400 MHz, CDCl$_3$) δ 6.50-5.80 (m, 4H), 5.62 (ddd, J=22.9, 14.5, 7.9 Hz, 1H), 5.32 (dt, J=11.6, 7.7 Hz, 2H), 5.18-5.03 (m, 1H), 4.68 (s, 1H), 3.95-3.54 (m, 5H), 3.50-3.33 (m, 7H), 3.32-3.21 (m, 3H), 3.18-2.92 (m, 8H), 2.83-2.48 (m, 3H), 2.25 (dd, J=30.1, 10.7 Hz, 2H), 2.02 (ddd, J=34.0, 26.3, 9.6 Hz, 4H), 1.88-1.56 (m, 14H), 1.51-1.16 (m, 9H), 1.15-0.82 (m, 18H), 0.79-0.68 (m, 1H).

Step 2: (24E,26E,28E,29E,35R,36S,37R,38R,40S,42S, 45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethoxy)ethoxy]-35,36,37,38,48,49-hexamethyl-64,65-dioxa-57-azatricyclohexatriaconta-24, 26,28(48),29(49)-tetraene-50,51,52,53,54-pentone (I-116). To a solution of (24E,26E,28E,29E,31R,32S,33R,34R,36S, 38S,40S,41S,42R,43R,52R)-41-[(1R)-2-[(1S,3R,4R)-3,4-dimethoxycyclohexyl]-1-methyl-ethyl]-52-hydroxy-40,42, 43-trimethoxy-31,32,33,34,44,45-hexamethyl-60,61-dioxa-53-azatricyclohexatriaconta-24,26,28(44),29(45)-tetraene-46,47,48,49,50-pentone (170 mg, 180.42 umol) and 2-(2-methoxyethoxy)ethanol (434 mg, 3.61 mmol) in sulfolane (5 mL) was added HND-8 (35 mg) at 50° C. under N$_2$ and the mixture stirred at 50° C. for 3 h. The reaction was filtered, concentrated and purified via reverse phase chromatography (85% CH$_3$CN in water) to provide the titled compound (65 mg, 35% yield) as a white solid. ESI-MS (EI$^+$, m/z): 1052.5 [M+Na]$^+$. H NMR (500 MHz, CDCl$_3$) δ 6.46-5.81 (m, 4H), 5.74-5.03 (m, 4H), 4.68-4.15 (m, 2H), 3.99-3.52 (m, 11H), 3.50-3.22 (m, 16H), 3.21-2.98 (m, 6H), 2.94-2.44 (m, 3H), 2.37-1.89 (m, 7H), 1.86-1.69 (m, 7H), 1.52-1.24 (m, 9H), 1.22-0.84 (m, 21H), 0.74 (dd, J=22.3, 10.9 Hz, 1H).

Step 3: (24E,26E,28E,29E,35R,36S,37R,38R,40S,42S, 44S,45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethoxy)ethoxy]-35,36,37,38,48,49-hexamethyl-64,65-dioxa-57-azatricyclohexatriaconta-24, 26,28(48),29(49)-tetraene-50,51,52,53,54-pentone (I-118) and (24E,26E,28E,29E,35R,36S,37R,38R,40S,42S,44R, 45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethoxy)ethoxy]-35,36,37,38,48,49-hexamethyl-64,65-dioxa-57-azatricyclohexatriaconta-24, 26,28(48),29(49)-tetraene-50,51,52,53,54-pentone (I-119). 130 mg of the mixture was separated via chiral HPLC and then purified by silica gel chromatography (hexane:DCM: EtOAc:MeOH from 3:3:1:0 to 3:3:1:0.4) to provide the titled compound (I-118: 45 mg, 35% yield) and (I-119: 40 mg, 31% yield) as white solids.

Chiral Separation Method:

| Column: | CHIRALPAK IC |
|---|---|
| Column size: | 5.0 cm I.D. × 25 cm L, 10 μm |
| Sample solution: | 1.4 mg/ml in Mobile phase: |
| Injection: | 15 ml |
| Mobile phase: | Hexane/EtOH = 50/50(V/V) |
| Flow rate: | 60 ml/min |
| Wave length: | UV 254 nm |
| Temperature: | 35° C. |

I-118: ESI-MS (EI$^+$, m/z): 1052.1 [M+Na]$^+$. $^1$H NMR (400 MHz, CDCl$_3$) δ 6.51-5.82 (m, 4H), 5.76-5.03 (m, 4H), 4.51 (dd, J=56.0, 27.4 Hz, 1H), 4.35-4.06 (m, 1H), 4-3.20 (m, 26H), 3.19-2.98 (m, 5H), 2.88-2.48 (m, 3H), 2.40-1.85 (m, 7H), 1.82-1.65 (m, 11H), 1.38 (ddd, J=37.8, 31.6, 21.3 Hz, 10H), 1.21-0.83 (m, 18H), 0.79-0.68 (m, 1H).

I-119: ESI-MS (EI+, m/z): 1052.2 [M+Na]+. 1H NMR (400 MHz, CDCl3) δ 6.52-5.81 (m, 4H), 5.77-5.04 (m, 5H), 4.70-4.14 (m, 2H), 4.01-2.97 (m, 31H), 2.64 (dd, J=50.7, 36.3 Hz, 3H), 2.42-1.68 (m, 16H), 1.50-0.61 (m, 30H).

Example 57: Synthesis of (23E,25E,27E,28E,32R, 33S,34R,35R,37S,39S,44S,45R,46R,57R)-43-[[(7aS)-2-(2-hydroxyethyl)-1,3-dioxo-5,6,7,7a-tetrahydropyrrolo[1,2-c]imidazol-6-yl]oxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-72,73-dioxa-58-azatricyclohexatriaconta-23,25,27(47),28(48)-tetraene-49,50,51,53,54-pentone (I-117), (23E,25E, 27E,28E,32R,33S,34R,35R,37S,39S,43S,44S,45R, 46R,57R)-43-[[(6R,7aS)-2-(2-hydroxyethyl)-1,3-dioxo-5,6,7,7a-tetrahydropyrrolo[1,2-c]imidazol-6-yl]oxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-72,73-dioxa-58-azatricyclohexatriaconta-23,25,27(47),28 (48)-tetraene-49,50,51,53,54-pentone (I-123) and (23E,25E,27E,28E,32R,33S,34R,35R,37S,39S,43R, 44S,45R,46R,57R)-43-[[(6R,7aS)-2-(2-hydroxyethyl)-1,3-dioxo-5,6,7,7a-tetrahydropyrrolo[1,2-c]imidazol-6-yl]oxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-72,73-dioxa-58-azatricyclohexatriaconta-23,25,27(47),28(48)-tetraene-49,50,51,53,54-pentone (I-124)

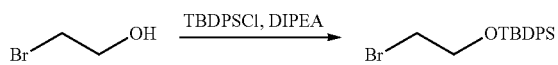

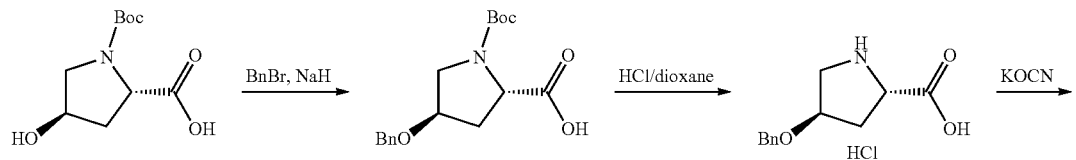

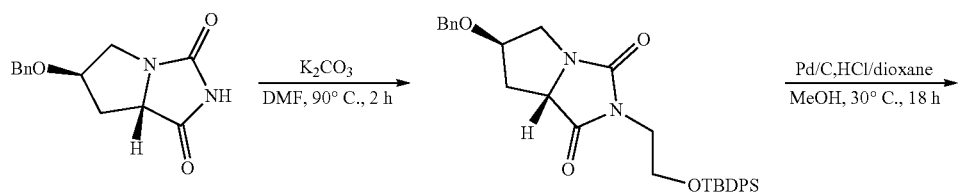

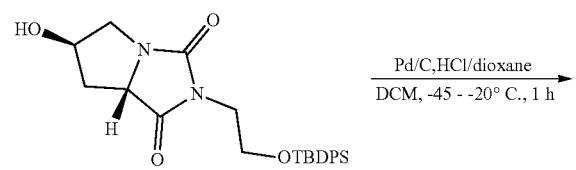

-continued
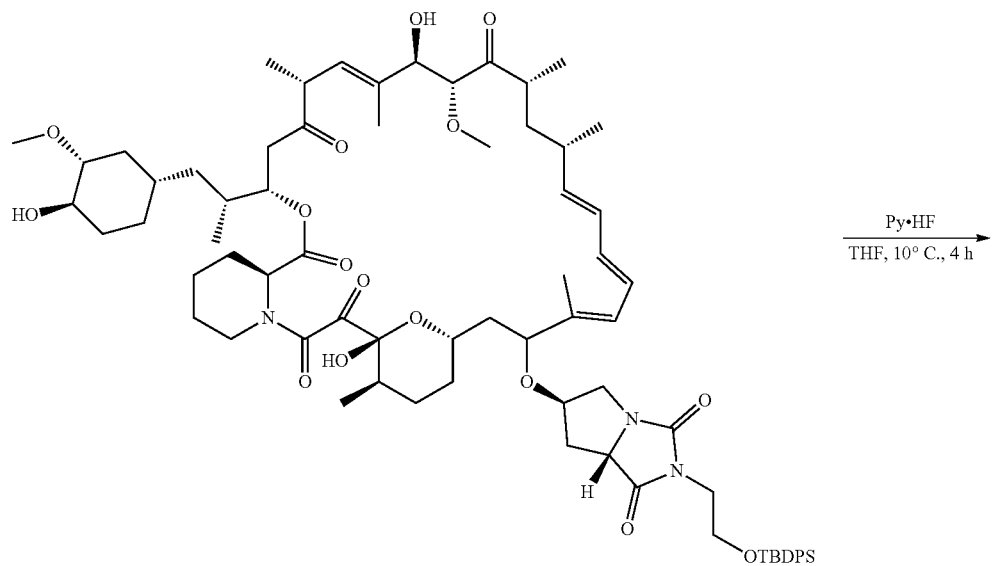
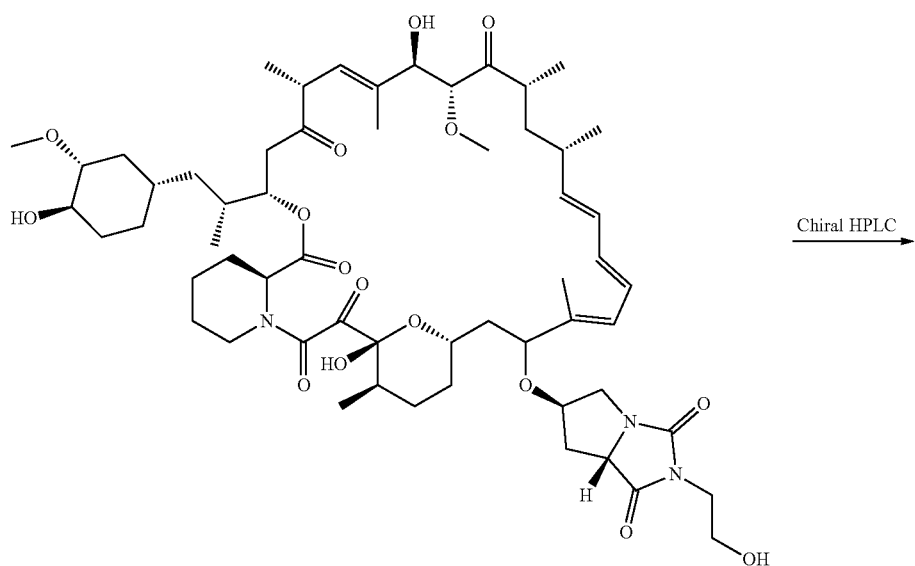
I-117

-continued

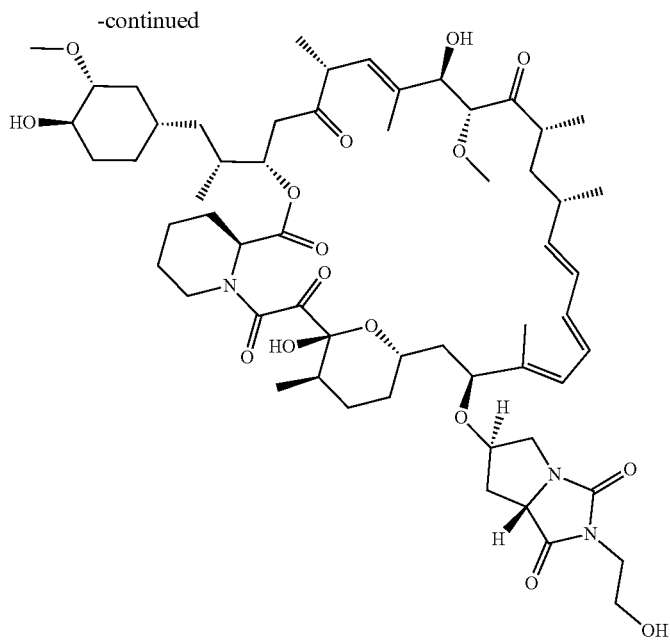

I-123

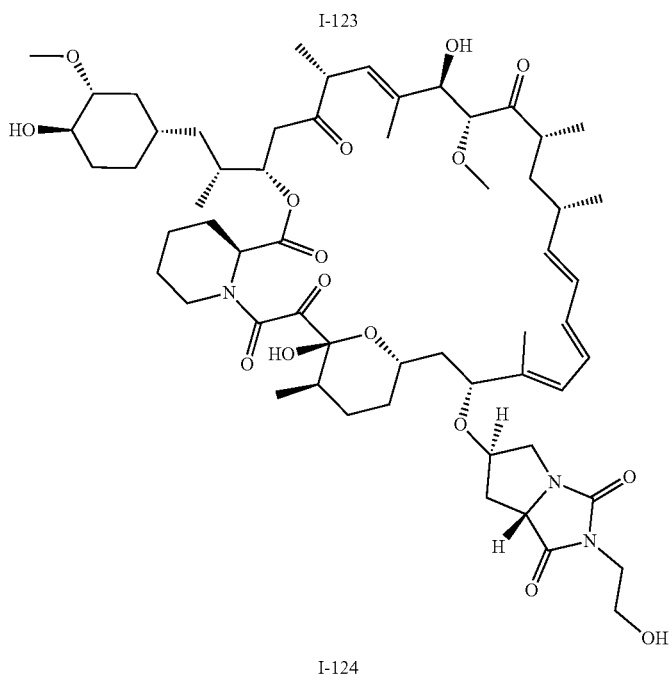

I-124

Step 1: (2-bromoethoxy) (tert-butyl)diphenylsilane. To a solution of 2-bromoethanol (50 g, 400 mmol) in DMF (120 mL) was added tert-butyl-chloro-diphenyl-silane (131.97 g, 480 mmol) and TEA (121.46 g, 1.20 mol) at 0° C. The reaction mixture was stirred at rt for 16 h then diluted with 200 mL EtOAc and washed with $H_2O$ and brine. The organic layer was dried over $Na_2SO_4$, filtered and concentrated. The residue was purified via silica gel chromatography (PE: EtOAc=99:1) to provide 2-bromoethoxy-tert-butyl-diphenyl-silane (15.7 g, 11% yield) as a colorless oil. ESI-MS (EI+, m/z): 280.0 [M+H]+.

Step 2: (2S,4R)-4-(benzyloxy)-1-(tert-butoxycarbonyl) pyrrolidine-2-carboxylic acid. To a solution of (2S,4R)-1-tert-butoxycarbonyl-4-hydroxy-pyrrolidine-2-carboxylic acid (20 g, 86.49 mmol) in THF (200 mL) was added sodium hydride (9.69 g, 242.17 mmol, 60% purity) at 0° C. The mixture was stirred for 0.5 h at 0° C. under $N_2$ then bromomethylbenzene (19.23 g, 112.43 mmol) was added and stirring continued for an additional 16 h at rt. The reaction was quenched by adding water (50 mL) at 0° C., then 6 M HCl was added to adjust the pH to 4. The mixture was extracted with EtOAc (100 mL×3) and the combined organic layers washed with water (100 mL×3), and brine (100 mL×3), dried over anhydrous sodium sulfate, filtered and concentrated. The residue was purified via silica gel chromatography (eluting with 50% EtOAc in PE) to provide (2S,4R)-4-benzyloxy-1-tert-butoxycarbonyl-pyrrolidine-2-carboxylic acid (4 g, 14% yield) as a yellow oil. ESI-MS (EI+, m/z): 344.1 [M+Na]+. $^1$H NMR (400 MHz, CDCl$_3$): δ 8.43-8.62 (br, 1H), 7.37-7.28 (m, 5H), 4.56-4.35 (m, 3H), 4.20-4.17 (m, 1H), 3.75-3.51 (m, 2H), 2.49-2.43 (m, 0.5H), 2.35-2.30 (m, 1H), 2.16-2.09 (m, 0.5H), 1.45 (d, J=21.6 Hz, 9H).

Step 3: (2S,4R)-4-(benzyloxy) pyrrolidine-2-carboxylic acid hydrochloride. A solution of (2S,4R)-4-benzyloxy-1-tert-butoxycarbonyl-pyrrolidine-2-carboxylic acid (6.7 g, 20.85 mmol) in HCl in dioxane (4 M, 36.57 mL) was stirred for 16 h at 25° C. The reaction mixture was concentrated under vacuum to provide (2S,4R)-4-benzyloxypyrrolidine-2-carboxylic acid (5.3 g, 99% yield) as a yellow solid. The product was used without further purification. ESI-MS (EI+, m/z): 222 [M+H]+.

Step 4: (6R,7aS)-6-(benzyloxy)tetrahydro-1H-pyrrolo[1,2-c]imidazole-1,3(2H)-dione A solution of (2S,4R)-4-benzyloxypyrrolidine-2-carboxylic acid (5.3 g, 23.95 mmol, HCl salt) and potassium cyanate (3.89 g, 47.91 mmol) in water (50 mL) was stirred at 95° C. for 4 h. The reaction was cooled to rt and 1M HCl (120 mL) was added. The reaction was then stirred at 95° C. for a further 5 h. The reaction mixture was extracted with EtOAc (100 mL×3) and the combined organic layers washed with brine (100 mL×3), dried over anhydrous sodium sulfate, filtered and concentrated. The residue was purified via silica gel chromatography (eluting with 65% EtOAc in PE) then by reverse phase chromatography (eluting with 35% CH$_3$CN in water with 0.01% HCOOH) to provide the titled compound (2.5 g, 42% yield) as a white solid. ESI-MS (EI+, m/z): 247.1 [M+H]+. $^1$H NMR (400 MHz, CDCl$_3$) δ 8.32 (s, 1H), 7.43-7.25 (m, 5H), 4.59-4.48 (m, 2H), 4.46-4.33 (m, 2H), 3.87 (dd, J=12.4, 5.4 Hz, 1H), 3.33 (d, J=12.4 Hz, 1H), 2.45 (dd, J=13.3, 6.6 Hz, 1H), 1.78 (ddd, J=13.3, 10.8, 5.1 Hz, 2H).

Step 5: (6R,7aS)-6-(benzyloxy)-2-(2-(tert-butyldiphenylsilyloxy) ethyl) tetrahydro-1H-pyrrolo[1,2-c]imidazole-1,3(2H)-dione. To a solution of (6R,7aS)-6-benzyloxy-5,6,7,7a-tetrahydropyrrolo[1,2-c]imidazole-1,3-dione (0.5 g, 2.03 mmol) and 2-bromoethoxy-tert-butyl-diphenyl-silane (1.48 g, 4.06 mmol) in DMF (20 mL) was added potassium carbonate (0.42 g, 3.05 mmol). The mixture was stirred for 2 h at 100° C. under N$_2$ then cooled rt and quenched by adding water. The mixture was extracted with EtOAc (50 mL×2) and the combined organic layers washed with brine (50 mL×2), dried over anhydrous sodium sulfate, filtered and concentrated. The residue was purified via silica gel chromatography (eluting with 20% EtOAc in PE) to provide the titled compound (0.88 g, 82% yield) as a colorless oil. ESI-MS (EI+, m/z): 551.0[M+Na]+. $^1$H NMR (400 MHz, CDCl$_3$): δ 7.65-7.62 (m, 4H), 7.44-7.35 (m, 8H), 7.32-7.29 (m, 3H), 4.55-4.47 (m, 2H), 4.35-4.30 (m, 2H), 3.87-3.81 (m, 3H), 3.67-3.63 (m, 2H), 3.37-3.33 (m, 1H), 2.46-2.40 (m, 1H), 1.66-1.59 (m, 1H), 1.01 (s, 9H).

Step 6: (6R,7aS)-2-(2-(tert-butyldiphenylsilyloxy) ethyl)-6-hydroxytetrahydro-1H-pyrrolo[1,2-c]imidazole-1,3(2H)-dione. To a solution of (6R,7aS)-6-benzyloxy-2-[2-[tert-butyl(diphenyl)silyl]oxyethyl]-5,6,7,7a-tetrahydropyrrolo[1,2-c]imidazole-1,3-dione (0.8 g, 1.51 mmol) in MeOH (20 mL) was added palladium on carbon (1.84 g, 1.73 mmol) and hydrogen chloride (4 M, 756.55 uL) under N$_2$. The mixture was stirred for 18 h at 30° C. under H$_2$. The reaction was filtered and concentrated. The residue was purified by reverse phase chromatography (eluting with 65% CH$_3$CN in water) to provide the titled compound (0.55 g, 83% yield) as a white solid. ESI-MS (EI+, m/z): 461.1 [M+Na]+. $^1$H NMR (400 MHz, DMSO-d$_6$) δ 7.58 (d, J=6.7 Hz, 4H), 7.50-7.31 (m, 6H), 5.31 (s, 1H), 4.45 (s, 1H), 4.32 (dd, J=10.5, 6.7 Hz, 1H), 3.83-3.70 (m, 2H), 3.64 (dd, J=11.5, 4.9 Hz, 1H), 3.53 (dd, J=17.2, 11.7 Hz, 2H), 3.01 (d, J=11.6 Hz, 1H), 1.99 (dd, J=12.4, 6.8 Hz, 1H), 1.76-1.63 (m, 1H), 0.95 (s, 9H).

Step 7: (36E,38E,40E,41E,47R,48S,49R,50R,52S,54S,59S,60R,61R,72R)-58-[[(6R,7aS)-2-[2-[tert-butyl(diphenyl)silyl]oxyethyl]-1,3-dioxo-5,6,7,7a-tetrahydropyrrolo[1,2-c]imidazol-6-yl]oxy]-60,72-dihydroxy-59-[(1R)-2-[(1S,3R,4R)-4-hydroxy-3-methoxy-cyclohexyl]-1-methyl-ethyl]-61-methoxy-47,48,49,50,62,63-hexamethyl-87,88-dioxa-74-azatricyclohexatriaconta-36,38,40(62),41(63)-tetraene-64,65,66,68,69-pentone. To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (1.1 g, 1.1 mmol) in DCM (80 mL) was added TFA (2.74 g, 24.07 mmol) at –45° C. The reaction was stirred at the same temperature for 10 minutes then (6R,7aS)-2-[2-[tert-butyl(diphenyl)silyl]oxyethyl]-6-hydroxy-5,6,7,7a-tetrahydropyrrolo[1,2-c]imidazole-1,3-dione (2.7 g, 5.68 mmol) in DCM (20 mL) was added and the mixture was allowed to warm to –20° C. over 1 h. The reaction mixture was quenched with aqueous saturated NaHCO$_3$ (60 mL) and extracted with DCM (60 mL). The organic layer was washed with water (100 mL×2) and brine (100 mL×2), dried over anhydrous sodium sulfate, filtered and concentrated. The residue was purified via reverse phase chromatography (eluting with 95% CH$_3$CN in water) to provide the titled compound (185 mg, 12%) as a white solid. ESI-MS (EI+, m/z): P1:1343.2[M+Na]+. P2:1343.1 [M+Na]+.

Step 8: (23E,25E,27E,28E,32R,33S,34R,35R,37S,39S,44S,45R,46R,57R)-43-[[(7aS)-2-(2-hydroxyethyl)-1,3-dioxo-5,6,7,7a-tetrahydropyrrolo[1,2-c]imidazol-6-yl]oxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-72,73-dioxa-58-azatricyclohexatriaconta-23,25,27(47),28(48)-tetraene-49,50,51,53,54-pentone (I-117). To a solution of (36E,38E,40E,41E,47R,48S,49R,50R,52S,54S,59S,60R,61R,72R)-58-[[(7aS)-2-[2-[tert-butyl(diphenyl)silyl]oxyethyl]-1,3-dioxo-5,6,7,7a-tetrahydropyrrolo[1,2-c]imidazol-6-yl]oxy]-60,72-dihydroxy-59-[(1R)-2-[(1S,3R,4R)-4-hydroxy-3-methoxy-cyclohexyl]-1-methyl-ethyl]-61-methoxy-47,48,49,50,62,63-hexamethyl-87,88-dioxa-74-azatricyclohexatriaconta-36,38,40(62),41(63)-tetraene-64,65,66,68,69-pentone (0.35 g, 0.265 mmol) in THF (35 mL) was added pyridine hydrofluoride (2.1 g, 14.84 mmol) and the resulting solution stirred at rt for 4h. Saturated aqueous NaHCO$_3$ solution was added to the reaction, bringing the pH to 7 and the mixture extracted with DCM (120 mL). The organic layer was washed with brine (100 mL×2), dried over anhydrous sodium sulfate, filtered and concentrated. The residue was purified via prep-HPLC (eluting with 60% CH$_3$CN in water) to provide the titled compound (0.12 g, 42% yield) as a white solid. ESI-MS (EI+, m/z): 1104.1 [M+Na]+. 1H NMR (400 MHz, CDCl3) δ 6.28-5.88 (m, 4H), 5.50-4.82 (m, 5H), 4.34-4.05 (m, 4H), 3.84-3.52 (m, 9H), 3.34-3.18 (m, 10H), 3.14-3.10 (m, 1H), 2.95-2.83 (m, 2H), 2.70-2.47 (m, 5H), 2.32-2.05 (m, 5H), 1.95-1.91 (m, 3H), 1.67-1.46 (m, 26H), 1.34-1.13 (m, 17H), 1.16-0.73 (m, 22H), 0.65-0.55 (m, 1H).

Step 9: (23E,25E,27E,28E,32R,33S,34R,35R,37S,39S,43S,44S,45R,46R,57R)-43-[[(6R,7aS)-2-(2-hydroxyethyl)-1,3-dioxo-5,6,7,7a-tetrahydropyrrolo[1,2-c]imidazol-6-yl]oxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-72,73-dioxa-58-azatricyclohexatriaconta-23,25,27(47),28(48)-tetraene-49,50,51,53,54-pentone (I-123) and (23E,25E,27E,28E,32R, 33S,34R,35R,37S,39S,43R,44S,45R,46R,57R)-43-[[(6R,7aS)-2-(2-hydroxyethyl)-1,3-dioxo-5,6,7,7a-tetrahydropyrrolo[1,2-c]imidazol-6-yl]oxy]-45,57-dihydroxy-44-[(1R)-2-[(1S,3R,4R)-4-hydroxy-3-methoxy-cyclohexyl]-1-methyl-ethyl]-46-methoxy-32,33,34,35,47,48-hexamethyl-72,73-dioxa-58-azatricyclohexatriaconta-23,25,27(47),28(48)-tetraene-49,50,51,53,54-pentone (I-124). 110 mg of the mixture was separated via chiral HPLC and then purified via silica gel chromatography (hexane:DCM:EtOAc:MeOH from 3:3:1:0 to 3:3:1:0.6) to provide the titled compound (I-123:35 mg, 32% yield) and (I-124: 26 mg, 24% yield) as white solids.

Chiral Separation Method:

| | |
|---|---|
| Column: | CHIRALPAK IC |
| Column size: | 5.0 cm I.D. × 25 cm L, 10 μm |
| Sample solution: | 1.2 mg/ml in Mobile phase: |
| Injection: | 15 ml |
| Mobile phase: | Hexane/EtOH = 30/70(V/V) |
| Flow rate: | 60 ml/min |
| Wave length: | UV 254 nm |
| Temperature: | 35° C. |

I-123: ESI-MS (EI$^+$, m/z): 1104.1 [M+Na]$^+$. $^1$H NMR (400 MHz, CDCl$_3$) δ 6.41-6.25 (m, 2H), 6.19-6.08 (m, 1H), 6.03-5.88 (m, 1H), 5.60-5.24 (m, 3H), 5.10 (dt, J=43.0, 5.7 Hz, 1H), 4.89 (s, 1H), 4.37-4.11 (m, 4H), 3.90-3.57 (m, 9H), 3.52-3.27 (m, 10H), 3.19 (d, J=12.3 Hz, 1H), 3.04-2.47 (m, 7H), 2.42-1.78 (m, 11H), 1.68-1.21 (m, 17H), 1.16-0.78 (m, 18H), 0.76-0.55 (m, 1H).

I-124: ESI-MS (EI$^+$, m/z): 1104.1 [M+Na]$^+$. $^1$H NMR (400 MHz, CDCl$_3$) δ 6.50-5.88 (m, 4H), 5.77-5.09 (m, 4H), 4.54-4.04 (m, 5H), 3.97-3.56 (m, 8H), 3.53-3.15 (m, 11H), 2.68 (ddd, J=59.1, 24.7, 11.3 Hz, 8H), 2.44-1.94 (m, 7H), 1.91-1.62 (m, 10H), 1.53-1.28 (m, 11H), 1.15-0.81 (m, 18H), 0.79-0.52 (m, 1H).

Example 58: Synthesis of (25E,27E,29E,30E,36R,37S,38R,39R,41S,43S,46S,47R,48R,57R)-46-[(1R)-2-[(1S,3R,4R)-4-dimethylphosphoryloxy-3-methoxy-cyclohexyl]-1-methyl-ethyl]-57-hydroxy-47,48-dimethoxy-45-[2-(2-methoxyethoxy)ethoxy]-36,37,38,39,49,50-hexamethyl-66,67-dioxa-58-azatricyclohexatriaconta-25,27,29(49),30(50)-tetraene-51,52,53,54,55-pentone (I-120), (25E,27E,29E,30E,36R,37S,38R,39R,41S,43S,45S,46S,47R,48R,57R)-46-[(1R)-2-[(1S,3R,4R)-4-dimethylphosphoryloxy-3-methoxy-cyclohexyl]-1-methyl-ethyl]-57-hydroxy-47,48-dimethoxy-45-[2-(2-methoxyethoxy)ethoxy]-36,37,38,39,49,50-hexamethyl-66,67-dioxa-58-azatricyclohexatriaconta-25,27,29(49),30(50)-tetraene-51,52,53,54,55-pentone (I-125) and (25E,27E,29E,30E,36R,37S,38R,39R,41S,43S,45R,46S,47R,48R,57R)-46-[(1R)-2-[(1S,3R,4R)-4-dimethylphosphoryloxy-3-methoxy-cyclohexyl]-1-methyl-ethyl]-57-hydroxy-47,48-dimethoxy-45-[2-(2-methoxyethoxy)ethoxy]-36,37,38,39,49,50-hexamethyl-66,67-dioxa-58-azatricyclohexatriaconta-25,27,29(49),30(50)-tetraene-51,52,53,54,55-pentone (I-126)

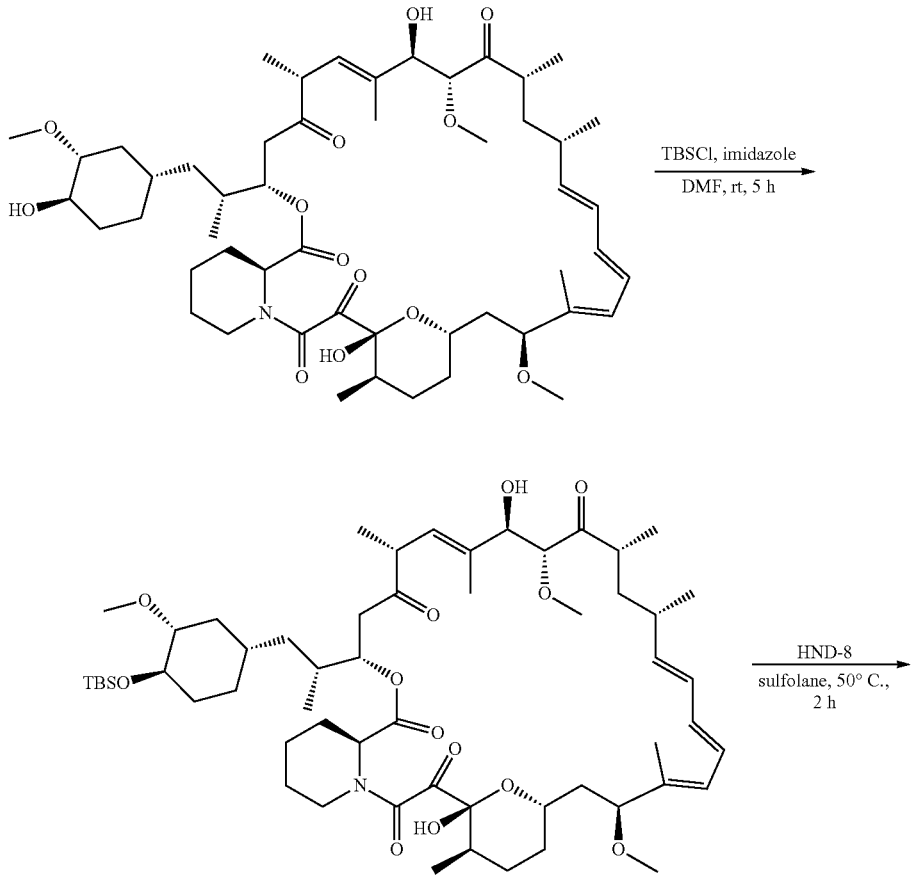

-continued
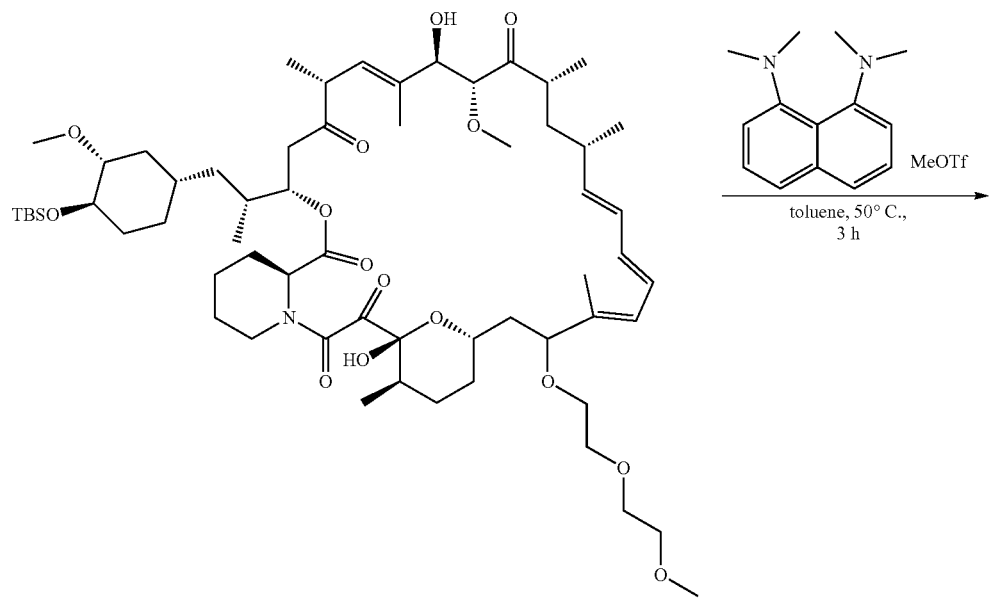
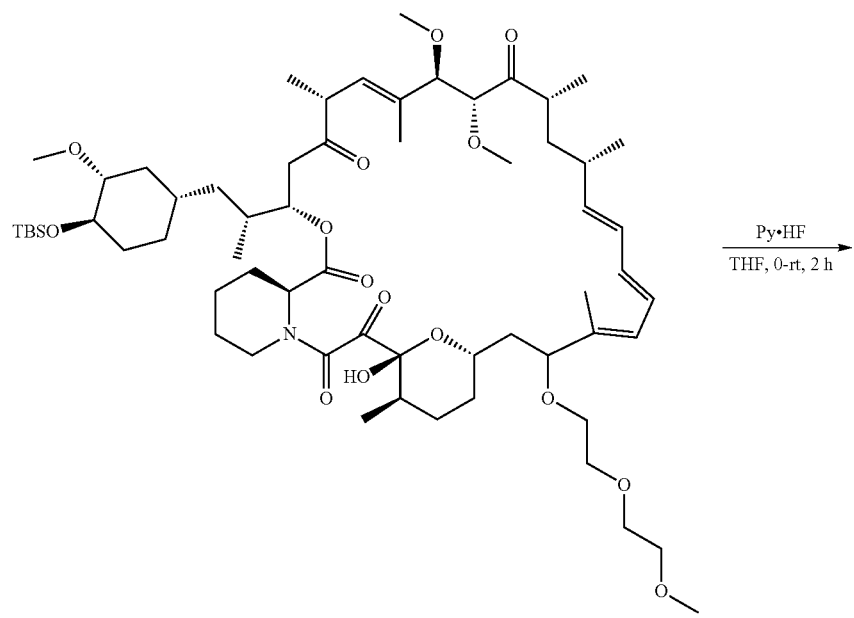

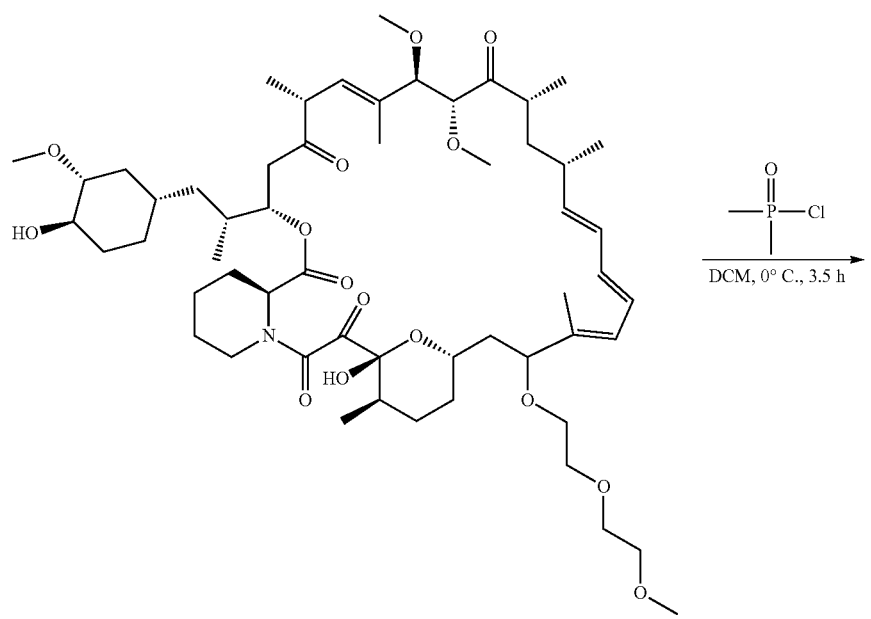
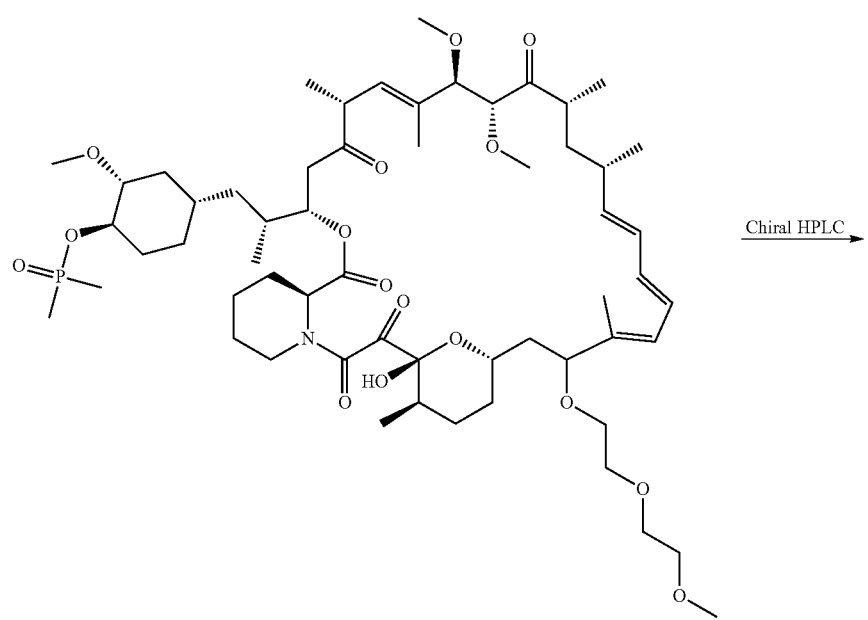
I-120

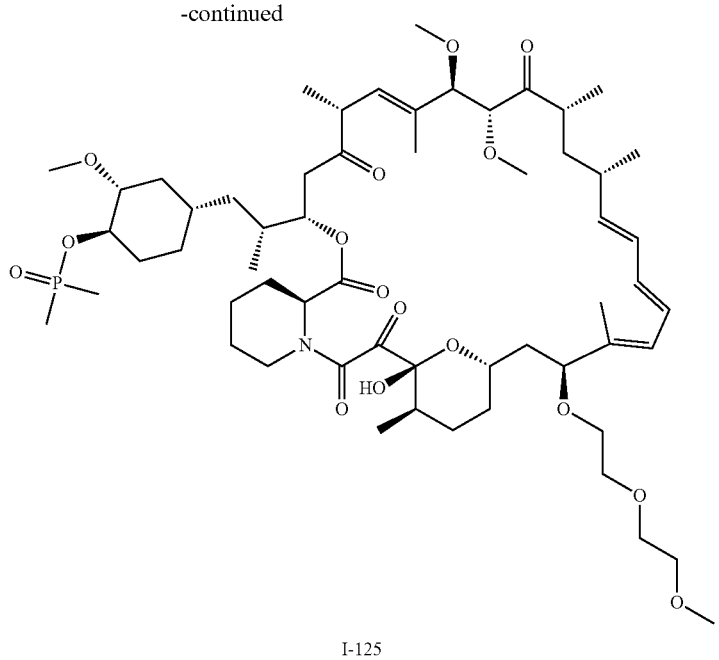

I-125

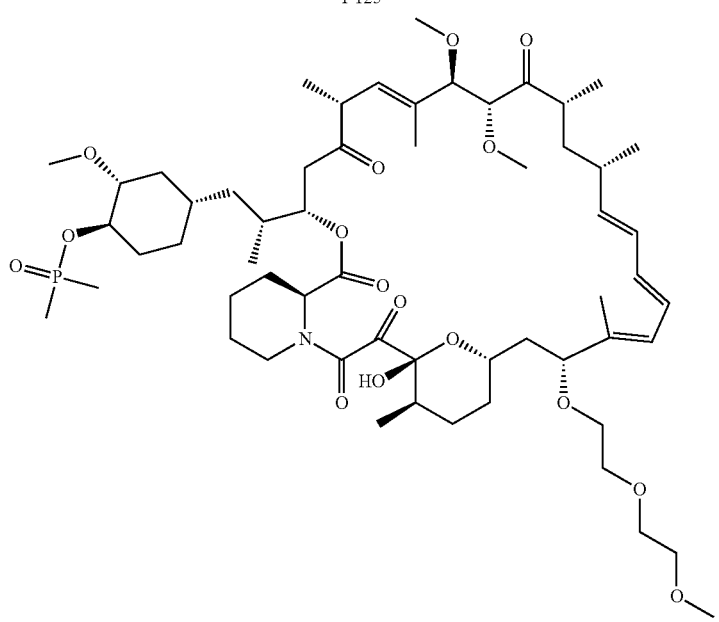

I-126

Step 1: (27E,29E,31E,32E,34R,35S,36R,37R,39S,41S,43S,44S,45R,46R,55R)-44-[(1R)-2-[(1S,3R,4R)-4-[tert-butyl(dimethyl)silyl]oxy-3-methoxy-cyclohexyl]-1-methyl-ethyl]-45,55-dihydroxy-43,46-dimethoxy-34,35,36,37,47,48-hexamethyl-65,66-dioxa-57-azatricyclohexatriaconta-27,29,31(47),32(48)-tetraene-49,50,51,52,53-pentone. To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (2 g, 2.19 mmol) in DMF (15 mL) was added imidazole (298 mg, 4.38 mmol) at rt, followed immediately by the addition of a solution of tert-butyl-chloro-dimethyl-silane (495 mg, 3.28 mmol). The mixture was stirred at 20° C. for 5 h then poured into ice cold saturated aqueous NH$_4$Cl (10 mL) and Et$_2$O: petroleum ether (300 mL, 2:1). The organic layer was washed with saturated NH$_4$Cl solution (100 mL), water (100 mL), brine (100 mL), dried over Na$_2$SO$_4$, filtered and concentrated. The residue was purified via silica gel chromatography (EtOAc in PE from 10% to 50%) to provide the titled compound (1.85 g, 82% yield) as a white solid. ESI-MS (EI$^+$, m/z): 1050.2 [M+Na]$^+$. $^1$H NMR (400 MHz, CDCl$_3$) δ 6.44-5.83 (m, 4H), 5.60-5.07 (m, 4H), 4.32-4.04 (m, 2H), 3.79 (d, J=13.4 Hz, 1H), 3.70 (d, J=6.1 Hz, 1H), 3.65 (dd, J=9.8, 5.5 Hz, 1H), 3.62-3.53 (m, 1H), 3.43-3.28 (m, 8H), 3.13 (s, 3H), 2.94-2.81 (m, 1H), 2.73 (dd, J=16.8, 5.9 Hz, 2H), 2.63-2.47 (m, 1H), 2.33 (d, J=12.7 Hz, 2H), 2.07-1.89 (m, 4H), 1.89-1.40 (m, 19H), 1.38-1.02 (m, 15H), 1.02-0.76 (m, 18H), 0.69 (s, 1H), 0.05 (dd, J=8.2, 5.1 Hz, 6H).

Step 2: (27E,29E,31E,32E,38R,39S,40R,41R,43S,45S, 48S,49R,50R,59R)-48-[(1R)-2-[(1S,3R,4R)-4-[tert-butyl (dimethyl)silyl]oxy-3-methoxy-cyclohexyl]-1-methyl-ethyl]-49,59-dihydroxy-50-methoxy-47-[2-(2-methoxyethoxy)ethoxy]-38,39,40,41,51,52-hexamethyl-69,70-dioxa-61-azatricyclohexatriaconta-27,29,31(51),32(52)-tetraene-53,54,55,56,57-pentone. To a solution of (27E,29E,31E,32E,34R,35S,36R,37R,39S,41S,43S,44S,45R,46R,55R)-44-[(1R)-2-[(1S,3R,4R)-4-[tert-butyl(dimethyl)silyl]oxy-3-methoxy-cyclohexyl]-1-methyl-ethyl]-45,55-dihydroxy-43,46-dimethoxy-34,35,36,37,47,48-hexamethyl-65,66-dioxa-57-azatricyclohexatriaconta-27,29,31(47),32(48)-tetraene-49,50,51,52,53-pentone (1.7 g, 1.65 mmol) and 2-(2-methoxyethoxy)ethanol (3.97 g, 33.06 mmol) in sulfolane (20 mL) was added HND-8 (255 mg) at 50° C. under $N_2$. The reaction was stirred at 50° C. for 2 h then poured into water and extracted with EtOAc. The organic layer was washed with water and brine, dried over $Na_2SO_4$, filtered and concentrated. The residue was purified by silica gel chromatography (50% EtOAc in PE) and then by reverse phase chromatography (85% $CH_3CN$ in water) to provide the titled compound (950 mg, 52% yield) as a white solid. ESI-MS (EI$^+$, m/z): 1138.2 [M+Na]$^+$.

Step 3: (28E,30E,32E,33E,39R,40S,41R,42R,44S,46S, 49S,50R,51R,60R)-49-[(1R)-2-[(1S,3R,4R)-4-[tert-butyl (dimethyl)silyl]oxy-3-methoxy-cyclohexyl]-1-methyl-ethyl]-60-hydroxy-50,51-dimethoxy-48-[2-(2-methoxyethoxy)ethoxy]-39,40,41,42,52,53-hexamethyl-69,70-dioxa-62-azatricyclohexatriaconta-28,30,32(52),33(53)-tetraene-54,55,56,57,58-pentone. To a solution of (27E,29E,31E,32E,38R,39S,40R,41R,43S,45S,48S,49R,50R,59R)-48-[(1R)-2-[(1S,3R,4R)-4-[tert- butyl(dimethyl)silyl]oxy-3-methoxy-cyclohexyl]-1-methyl-ethyl]-49,59-dihydroxy-50-methoxy-47-[2-(2-methoxyethoxy)ethoxy]-38,39,40,41,51,52-hexamethyl-69,70-dioxa-61-azatricyclohexatriaconta-27,29,31(51),32(52)-tetraene-53,54,55,56,57-pentone (0.5 g, 0.448 mmol) in toluene (15 mL) was added N1,N1,N8,N8-tetramethylnaphthalene-1,8-diamine (1.92 g, 8.96 mmol) and methyl trifluoromethanesulfonate (1.10 g, 6.72 mmol). The reaction was stirred at 50° C. for 3 h then filtered and concentrated. The residue was purified via silica gel chromatography (eluting with EtOAc in PE from 0% to 50%) and reverse phase chromatography ($CH_3CN$ in water from 0% to 100%) to provide the titled compound (160 mg, 32% yield) as a light yellow solid. ESI-MS (EI$^+$, m/z): 1152.2 [M+Na]$^+$.

Step 4: (23E,25E,27E,28E,34R,35S,36R,37R,39S,41S, 44S,45R,46R,55R)-55-hydroxy-44-[(1R)-2-[(1S,3R,4R)-4-hydroxy-3-methoxy-cyclohexyl]-1-methyl-ethyl]-45,46-dimethoxy-43-[2-(2-methoxyethoxy)ethoxy]-34,35,36,37,47,48-hexamethyl-64,65-dioxa-56-azatricyclohexatriaconta-23,25,27(47),28(48)-tetraene-49,50,51,52,53-pentone. To a solution of (28E,30E,32E,33E,39R,40S,41R,42R,44S,46S,49S,50R,51R,60R)-49-[(1R)-2-[(1S,3R,4R)-4-[tert- butyl (dimethyl)silyl]oxy-3-methoxy-cyclohexyl]-1-methyl-ethyl]-60-hydroxy-50,51-dimethoxy-48-[2-(2-methoxyethoxy)ethoxy]-39,40,41,42,52,53-hexamethyl-69,70-dioxa-62-azatricyclohexatriaconta-28,30,32(52),33(53)-tetraene-54,55,56,57,58-pentone (580 mg, 0.513 mmol) in THF (20 mL) was added Py.HF (2.54 g, 25.65 mmol) at 0° C. The reaction was stirred at rt for 3 h then diluted with DCM and aqueous $NaHCO_3$ solution, washed with water and brine, dried over $Na_2SO_4$, filtered and concentrated. The residue was purified via reverse phase chromatography (75% $CH_3CN$ in water) to provide the titled compound (200 mg, 39% yield) as a white solid. ESI-MS (EI$^+$, m/z): 1038.1 [M+Na]$^+$. $^1$H NMR (400 MHz, CDCl$_3$) δ 6.49-5.79 (m, 4H), 5.69-5.03 (m, 4H), 4.62 (d, J=13.2 Hz, 1H), 4-3.07 (m, 28H), 3.02-2.47 (m, 6H), 2.41-1.68 (m, 16H), 1.54-1.21 (m, 11H), 1.17-0.82 (m, 18H), 0.79-0.55 (m, 1H).

Step 5: (25E,27E,29E,30E,36R,37S,38R,39R,41S,43S, 46S,47R,48R,57R)-46-[(1R)-2-[(1S,3R,4R)-4-dimethylphosphoryloxy-3-methoxy-cyclohexyl]-1-methyl-ethyl]-57-hydroxy-47,48-dimethoxy-45-[2-(2-methoxyethoxy)ethoxy]-36,37,38,39,49,50-hexamethyl-66,67-dioxa-58-azatricyclohexatriaconta-25,27,29(49),30(50)-tetraene-51,52,53,54,55-pentone (I-120). To a solution of (23E,25E,27E,28E,34R,35S,36R,37R,39S,41S,44S,45R,46R,55R)-55-hydroxy-44-[(1R)-2-[(1S,3R,4R)-4-hydroxy-3-methoxy-cyclohexyl]-1-methyl-ethyl]-45,46-dimethoxy-43-[2-(2-methoxyethoxy)ethoxy]-34,35,36,37,47,48-hexamethyl-64,65-dioxa-56-azatricyclohexatriaconta-23,25,27(47),28(48)-tetraene-49,50,51,52,53-pentone (180 mg, 0.177 mmol) in DCM (3 mL) was added 2,6-di-tert-butyl-4-methylpyridine (273 mg, 1.33 mmol) and dimethylphosphinic chloride (100 mg, 0.89 mmol, dissolved in 0.5 mL of DCM) at 0° C. The resulting solution was stirred at 0° C. for 3.5 h, then diluted with EtOAc, washed with $NaHCO_3$, water and brine. The organic layer was dried over $Na_2SO_4$, filtered and concentrated. The residue was purified via reverse phase chromatography ($CH_3CN$ in water) to provide the titled compound (90 mg, 47% yield) as a white solid. ESI-MS (EI$^+$, m/z): 1114.1 [M+Na]$^+$. $^1$H NMR (500 MHz, CDCl$_3$) δ 6.49-5.81 (m, 4H), 5.74-4.96 (m, 4H), 4.67-4.03 (m, 2H), 4-3.01 (m, 29H), 2.99-2.46 (m, 4H), 2.44-1.73 (m, 17H), 1.59-1.22 (m, 15H), 1.19-0.83 (m, 18H), 0.82-0.59 (m, 1H).

Step 6: (25E,27E,29E,30E,36R,37S,38R,39R,41S,43S, 45S,46S,47R,48R,57R)-46-[(1R)-2-[(1S,3R,4R)-4-dimethylphosphoryloxy-3-methoxy-cyclohexyl]-1-methyl-ethyl]-57-hydroxy-47,48-dimethoxy-45-[2-(2-methoxyethoxy)ethoxy]-36,37,38,39,49,50-hexamethyl-66,67-dioxa-58-azatricyclohexatriaconta-25,27,29(49),30(50)-tetraene-51,52,53,54,55-pentone (I-125) and (25E,27E,29E,30E,36R,37S,38R,39R,41S,43S,45S,46R,47R,48R,57R)-46-[(1R)-2-[(1S,3R,4R)-4-dimethylphosphoryloxy-3-methoxy-cyclohexyl]-1-methyl-ethyl]-57-hydroxy-47,48-dimethoxy-45-[2-(2-methoxyethoxy)ethoxy]-36,37,38,39,49,50-hexamethyl-66,67-dioxa-58-azatricyclohexatriaconta-25,27,29(49),30(50)-tetraene-51,52,53,54,55-pentone (I-126). 125 mg of the mixture was separated via chiral HPLC and then purified via silica gel chromatography (hexane:DCM:EtOAc:MeOH from 3:3:1:0 to 3:3:1:0.3) to obtain the titled compound (I-125: 25 mg, 20% yield) and (I-126: 15 mg, 12% yield) as a white solid.

Chiral Separation Method:

| | |
|---|---|
| Column: | CHIRALPAK IC |
| Column size: | 5.0 cm I.D. × 25 cm L, 10 μm |
| Sample solution: | 1.2 mg/ml in Mobile phase: |
| Injection: | 10 ml |
| Mobile phase: | Hexane/EtOH = 40/60(V/V) |
| Flow rate: | 25 ml/min |
| Wave length: | UV 254 nm |
| Temperature: | 35° C. |

I-125: ESI-MS (EI$^+$, m/z): 1114.1 [M+Na]$^+$. $^1$H NMR (500 MHz, CDCl$_3$) δ 6.41-6.01 (m, 3H), 5.87 (dd, J=83.6, 10.7 Hz, 1H), 5.57-5.40 (m, 1H), 5.38-4.97 (m, 3H), 4.57 (s, 1H), 4.02 (d, J=20.9 Hz, 1H), 3.92-3.62 (m, 3H), 3.61-2.94 (m, 26H), 2.78-2.40 (m, 3H), 2.29-1.79 (m, 9H), 1.60-1.38 (m, 15H), 1.36-1.11 (m, 9H), 1.08-0.76 (m, 18H), 0.75-0.64 (m, 1H).

I-126: ESI-MS (EI$^+$, m/z): 1114.1 [M+Na]$^+$. $^1$H NMR (500 MHz, CDCl$_3$) δ 6.48-5.79 (m, 4H), 5.63-5.02 (m, 4H), 4.56 (d, J=62.6 Hz, 1H), 3.99-3.09 (m, 28H), 3.01-2.49 (m, 5H), 2.40-1.72 (m, 18H), 1.54-1.19 (m, 14H), 1.18-0.81 (m, 19H), 0.78-0.59 (m, 1H).

Example 59: Synthesis of (23E,25E,27E,28E,34R, 35S,36R,37R,39S,41S,43S,44S,45R,46R,55R)-55-hydroxy-44-[(1R)-2-[(1S,3R,4R)-4-hydroxy-3-methoxy-cyclohexyl]-1-methyl-ethyl]-45,46-dimethoxy-43-[2-(2-methoxyethoxy)ethoxy]-34,35, 36,37,47,48-hexamethyl-64,65-dioxa-56-azatricyclohexatriaconta-23,25,27(47),28(48)-tetraene-49,50,51,52,53-pentone (I-121) and (23E, 25E,27E,28E,34R,35S,36R,37R,39S,41S,43R,44S, 45R,46R,55R)-55-hydroxy-44-[(1R)-2-[(1S,3R,4R)-4-hydroxy-3-methoxy-cyclohexyl]-1-methyl-ethyl]-45,46-dimethoxy-43-[2-(2-methoxyethoxy)ethoxy]-34,35,36,37,47,48-hexamethyl-64,65-dioxa-56-azatricyclohexatriaconta-23,25,27(47),28(48)-tetraene-49,50,51,52,53-pentone (I-122)

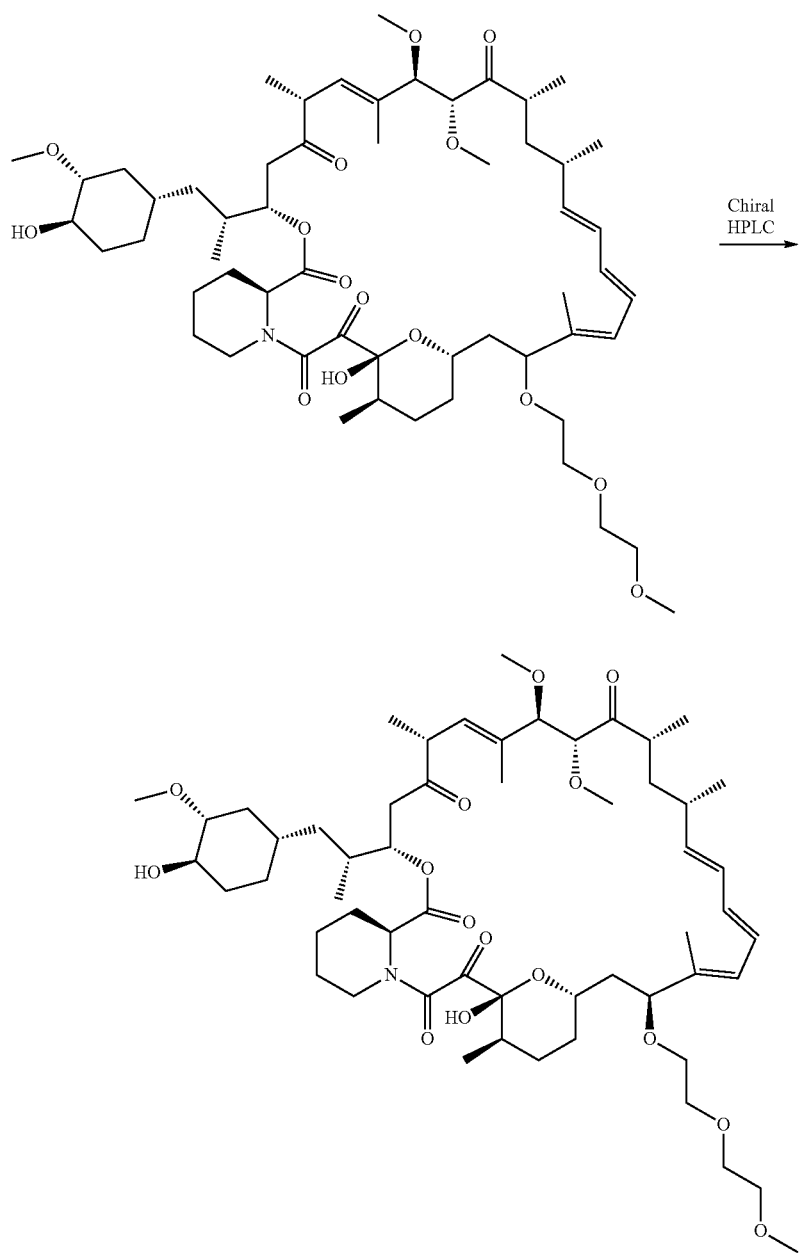

I-121

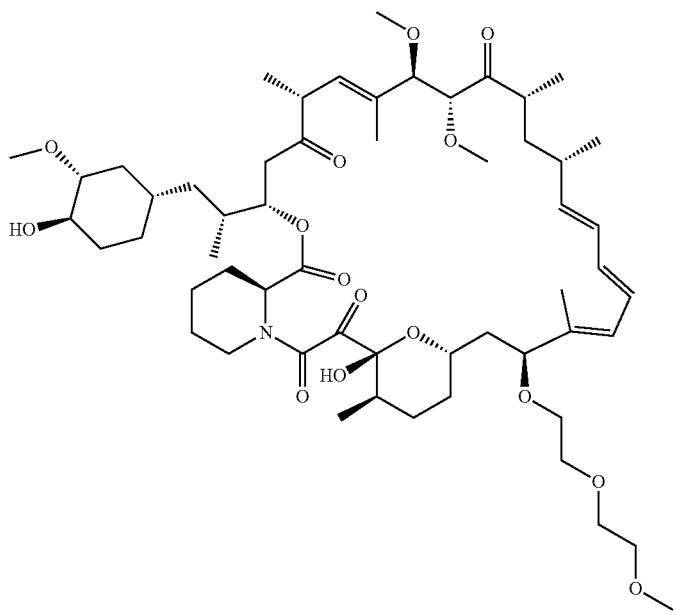

I-122

Step 1: (23E,25E,27E,28E,34R,35S,36R,37R,39S,41S,43S,44S,45R,46R,55R)-55-hydroxy-44-[(1R)-2-[(1S,3R,4R)-4-hydroxy-3-methoxy-cyclohexyl]-1-methyl-ethyl]-45,46-dimethoxy-43-[2-(2-methoxyethoxy)ethoxy]-34,35,36,37,47,48-hexamethyl-64,65-dioxa-56-azatricyclohexatriaconta-23,25,27(47),28(48)-tetraene-49,50,51,52,53-pentone (I-121) and (23E,25E,27E,28E,34R,35S,36R,37R,39S,41S,43R,44S,45R,46R,55R)-55-hydroxy-44-[(1R)-2-[(1S,3R,4R)-4-hydroxy-3-methoxy-cyclohexyl]-1-methyl-ethyl]-45,46-dimethoxy-43-[2-(2-methoxyethoxy)ethoxy]-34,35,36,37,47,48-hexamethyl-64,65-dioxa-56-azatricyclohexatriaconta-23,25,27(47),28(48)-tetraene-49,50,51,52,53-pentone (I-122). 116 mg of the mixture was separated via chiral HPLC and then purified via silica gel chromatography (hexane:DCM:EtOAc:MeOH=3:3:1:0.4) to obtain the titled compounds (I-121:40 mg, 35% yield) and (I-122: 35 mg, 30% yield) as white solids.

Chiral Separation Method:

| Column: | CHIRALPAK IC |
|---|---|
| Column size: | 5.0 cm I.D. × 25 cm L, 10 μm |
| Sample solution: | 0.7 mg/ml in Mobile phase: |
| Injection: | 18 ml |
| Mobile phase: | Hexane/EtOH = 60/40(V/V) |
| Flow rate: | 60 ml/min |
| Wave length: | UV 254 nm |
| Temperature: | 35° C. |

I-121: ESI-MS (EI$^+$, m/z): 1038.1 [M+Na]$^+$. $^1$H NMR (400 MHz, CDCl$_3$) δ 6.46-5.81 (m, 4H), 5.75-5.02 (m, 4H), 4.61 (d, J=16.7 Hz, 1H), 3.99-3.21 (m, 25H), 3.21-3.06 (m, 3H), 3.01-2.50 (m, 5H), 2.41-1.68 (m, 14H), 1.63-1.19 (m, 14H), 1.17-0.82 (m, 18H), 0.77-0.64 (m, 1H).

I-122: ESI-MS (EI$^+$, m/z): 1038.1 [M+Na]$^+$. $^1$H NMR (400 MHz, CDCl$_3$) δ 6.62-5.87 (m, 4H), 5.77-5.02 (m, 4H), 4.72-4.27 (m, 1H), 3.99-3.06 (m, 28H), 3-2.47 (m, 6H), 2.43-1.70 (m, 15H), 1.52-1.20 (m, 12H), 1.18-0.79 (m, 18H), 0.69 (d, J=11.7 Hz, 1H).

Example 60: Synthesis of (25E,27E,29E,30E,34R, 35S,36R,37R,39S,41S,43S,44S,46R,47R,56R)-44-[(1R)-2-[(1S,3R,4R)-3,4-dimethoxycyclohexyl]-1-methyl-ethyl]-56-hydroxy-46,47-dimethoxy-34,35, 36,37,48,49-hexamethyl-43-[2-(oxetan-3-yloxy) ethoxy]-65,66-dioxa-57-azatricyclohexatriaconta-25, 27,29(48),30(49)-tetraene-50,51,52,53,54-penton (I-127), (25E,27E,29E,30E,34R,35S,36R,37R,39S, 41S,43S,44S,46R,47R,56R)-44-[(1R)-2-[(1S,3R, 4R)-3,4-dimethoxycyclohexyl]-1-methyl-ethyl]-56-hydroxy-46,47-dimethoxy-34,35,36,37,48,49-hexamethyl-43-[2-(oxetan-3-yloxy)ethoxy]-65,66-dioxa-57-azatricyclohexatriaconta-25,27,29(48),30 (49)-tetraene-50,51,52,53,54-pentone (I-130) and (25E,27E,29E,30E,34R,35S,36R,37R,39S,41S,43R, 44S,46R,47R,56R)-44-[(1R)-2-[(1S,3R,4R)-3,4-dimethoxycyclohexyl]-1-methyl-ethyl]-56-hydroxy-46,47-dimethoxy-34,35,36,37,48,49-hexamethyl-43-[2-(oxetan-3-yloxy)ethoxy]-65,66-dioxa-57-azatricyclohexatriaconta-25,27,29(48),30(49)-tetraene-50,51,52,53,54-pentone (I-131)

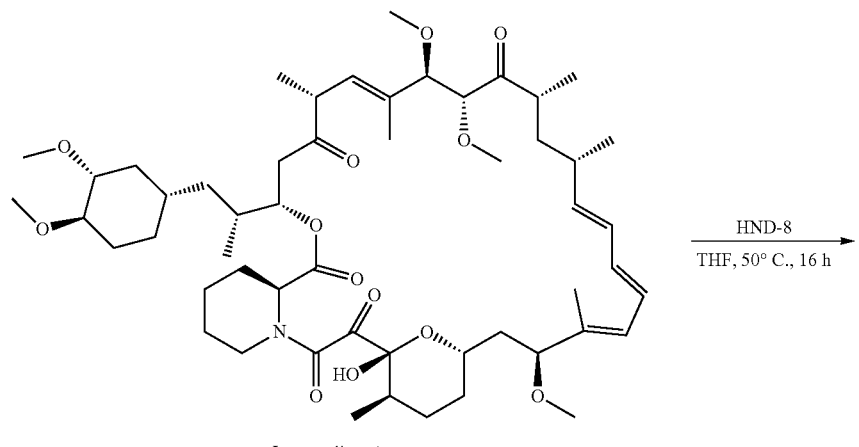

Intermediate A

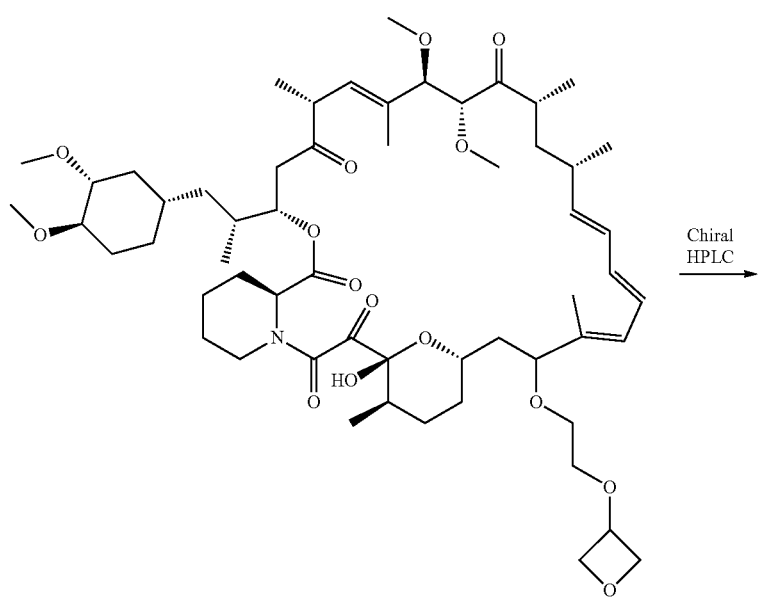

I-127

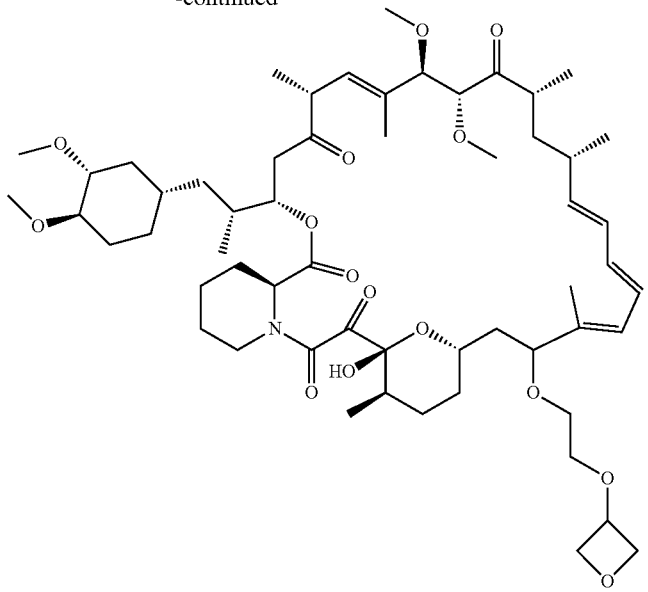

I-130

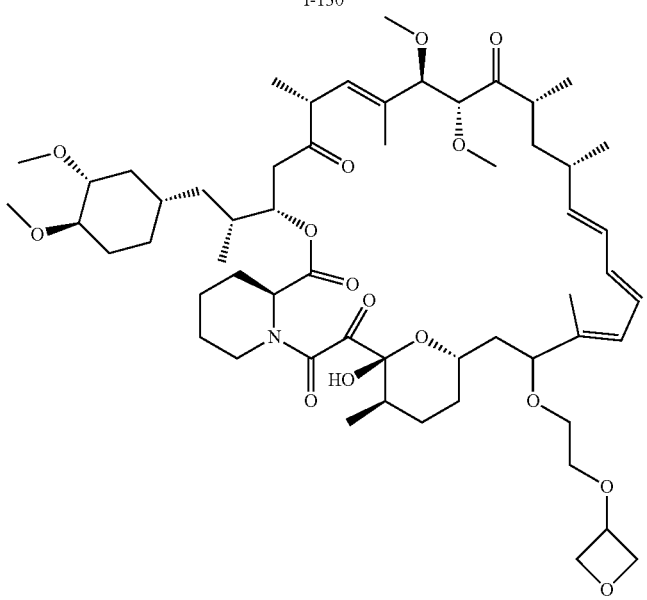

I-131

Step 1: (25E,27E,29E,30E,34R,35S,36R,37R,39S,41S,43S,44S,46R,47R,56R)-44-[(1R)-2-[(1S,3R,4R)-3,4-dimethoxycyclohexyl]-1-methyl-ethyl]-56-hydroxy-46,47-dimethoxy-34,35,36,37,48,49-hexamethyl-43-[2-(oxetan-3-yloxy)ethoxy]-65,66-dioxa-57-azatricyclohexatriaconta-25,27,29(48),30(49)-tetraene-50,51,52,53,54-pentone (I-127). To a solution of Intermediate A (0.05 g, 0.05 mmol) and 2-(oxetan-3-yloxy)ethanol (125 mg, 1.06 mmol) in THF (5 mL) was added HND-8 (0.02 g) at 50° C. under $N_2$. The reaction mixture was stirred for 16 h at 50° C. Upon cooling the reaction was filtered, concentrated and purified via reverse phase chromatography (eluting with 80% CH3CN in water) to provide the titled compound (0.019 g, 35% yield) as a white solid. ESI-MS (EI+, m/z): 1050.1 [M+Na]$^+$. $^1$HNMR (400 MHz, CDCl3) δ 6.44-5.98 (m, 4H), 5.69-5.01 (m, 4H), 4.66-4.27 (m, 2H), 3.89-3.56 (m, 9H), 3.44-3.31 (m, 10H), 3.28-3.21 (m, 3H), 3.07-2.96 (m, 7H), 2.95-2.51 (m, 4H), 2.34-1.82 (m, 7H), 1.77-1.48 (m, 27H), 1.44-1.22 (m, 8H), 1.20-1.01 (m, 13H), 1.01-0.88 (m, 8H), 0.85-0.65 (m, 2H).

Step 2: (25E,27E,29E,30E,34R,35S,36R,37R,39S,41S,43S,44S,46R,47R,56R)-44-[(1R)-2-[(1S,3R,4R)-3,4-dimethoxycyclohexyl]-1-methyl-ethyl]-56-hydroxy-46,47-dimethoxy-34,35,36,37,48,49-hexamethyl-43-[2-(oxetan-3-yloxy)ethoxy]-65,66-dioxa-57-azatricyclohexatriaconta-25,27,29(48),30(49)-tetraene-50,51,52,53,54-pentone (I-130) and (25E,27E,29E,30E,34R,35S,36R,37R,39S,41S,43R,44S,46R,47R,56R)-44-[(1R)-2-[(1S,3R,4R)-3,4-dimethoxycyclohexyl]-1-methyl-ethyl]-56-hydroxy-46,47-dimethoxy-34,35,36,37,48,49-hexamethyl-43-[2-(oxetan-3-yloxy)ethoxy]-65,66-dioxa-57-azatricyclohexatriaconta-25,27,29(48),30(49)-tetraene-50,51,52,53,54-pentone (I-131).

140 mg of the mixture was separated via chiral HPLC to obtain the titled compound (I-130: 36.6 mg, 26% yield) and (I-131:17.2 mg, 12% yield) as white solids.

Chiral Separation Method:

| | |
|---|---|
| Column: | CHIRALPAK IC |
| Column size: | 5.0 cm I.D. × 25 cm L, 10 μm |
| Sample solution: | 2 mg/ml in Mobile phase: |
| Injection: | 5 ml |
| Mobile phase: | Hexane/EtOH = 70/30(V/V) |
| Flow rate: | 30 ml/min |
| Wave length: | UV 254 nm |
| Temperature: | 38° C. |

I-130: ESI-MS (EI$^+$, m/z): 1049.8 [M+Na]$^+$. $^1$H NMR (500 MHz, CDCl$_3$) δ 6.47-5.80 (m, 4H), 5.75-5.50 (m, 1H), 5.49-5.04 (m, 3H), 4.69-4.41 (m, 1H), 4.36-4.11 (m, 1H), 3.91-3.50 (m, 10H), 3.48-2.99 (m, 19H), 2.79-2.51 (m, 2H), 2.38-1.85 (m, 7H), 1.83-1.58 (m, 12H), 1.53-1.17 (m, 10H), 1.14-0.84 (m, 18H), 0.75 (d, J=10.9 Hz, 1H).

I-131: ESI-MS (EI$^+$, m/z): 1049.8 [M+Na]$^+$. $^1$H NMR (500 MHz, CDCl$_3$) δ 6.60-5.70 (m, 4H), 5.66-5.01 (m, 4H), 4.72-4.14 (m, 2H), 4.10-3.50 (m, 9H), 3.49-2.98 (m, 18H), 2.59 (dd, J=79.6, 49.4 Hz, 3H), 2.40-1.64 (m, 19H), 1.52-1.20 (m, 10H), 1.19-0.65 (m, 20H).

Example 61: Synthesis of (24E,26E,28E,29E,35R,36S,37R,38R,40S,42S,45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethylsulfonyl)ethoxy]-35,36,37,38,48,49-hexamethyl-66,67-dioxa-57-azatricyclohexatriaconta-24,26,28(48),29(49)-tetraene-50,51,52,53,54-pentone (I-128), (24E,26E,28E,29E,35R,36S,37R,38R,40S,42S,44S,45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethylsulfonyl)ethoxy]-35,36,37,38,48,49-hexamethyl-66,67-dioxa-57-azatricyclohexatriaconta-24,26,28(48),29(49)-tetraene-50,51,52,53,54-pentone (I-134) and (24E,26E,28E,29E,35R,36S,37R,38R,40S,42S,44R,45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethylsulfonyl)ethoxy]-35,36,37,38,48,49-hexamethyl-66,67-dioxa-57-azatricyclohexatriaconta-24,26,28(48),29(49)-tetraene-50,51,52,53,54-pentone (I-135)

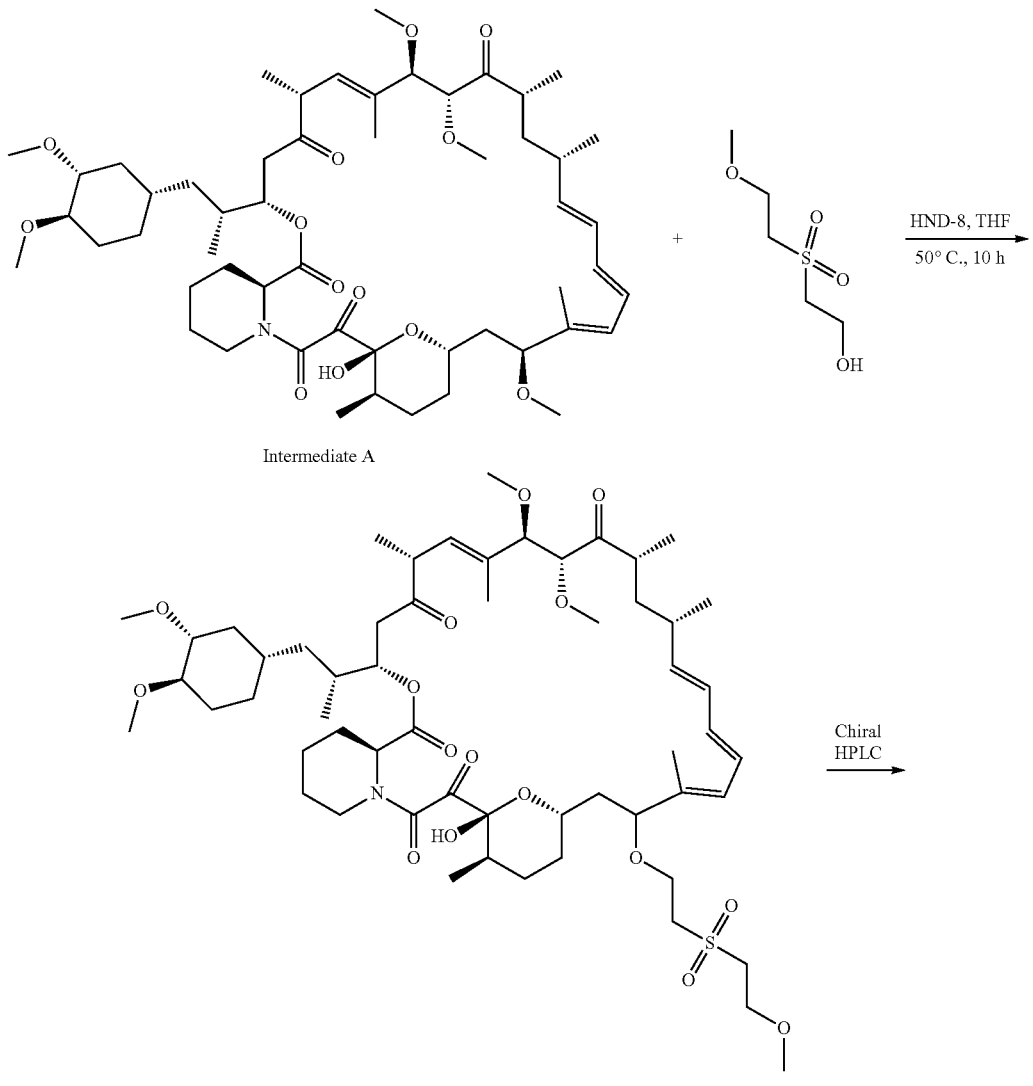

Intermediate A

I-128

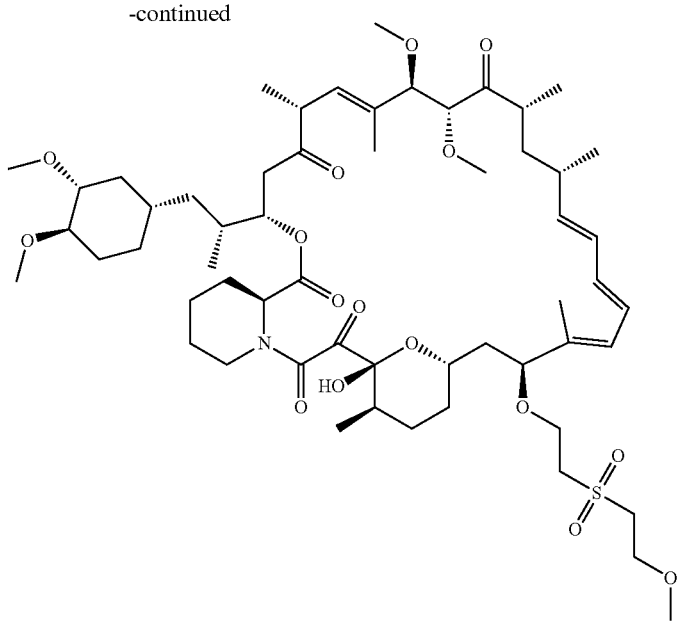

I-134

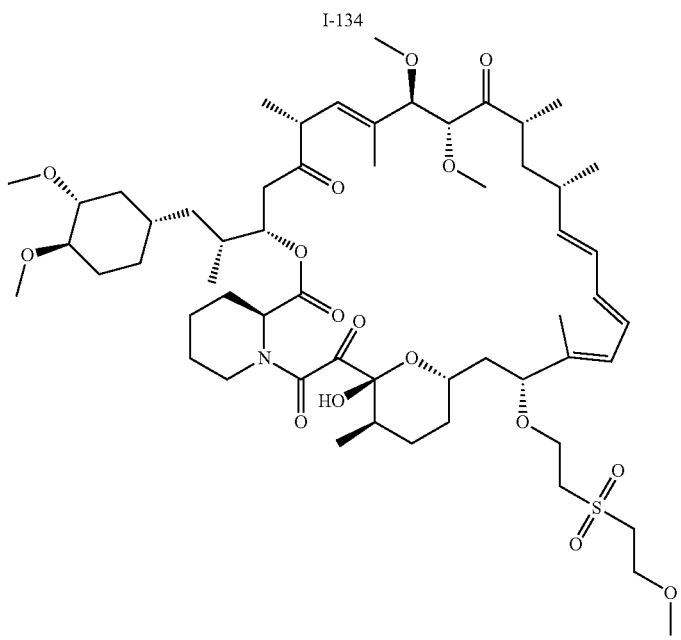

I-135

Step 1: (24E,26E,28E,29E,35R,36S,37R,38R,40S,42S, 45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethylsulfonyl)ethoxy]-35,36,37,38, 48,49-hexamethyl-66,67-dioxa-57-azatricyclohexatriaconta-24,26,28(48),29(49)-tetraene-50, 51,52,53,54-pentone (I-128). To a solution of Intermediate A (150 mg, 0.16 mmol) and 2-(2-methoxyethylsulfonyl)ethanol (268 mg, 1.59 mmol) in THF (5 mL) was added HND-8 (50 mg) at 0° C. The mixture was stirred at 50° C. for 10 h then quenched by adding sat. NaHCO$_3$ (aq.) (20 mL) and extracted with EtOAc (30 mL) at 0° C. The organic layer was washed with water (20 mL) and brine (20 mL), dried over anhydrous sodium sulfate, filtered and concentrated. The residue was purified via reverse-phase chromatography (85% CH$_3$CN in water) to provide the titled compound (44 mg, 25.6% yield) as a white solid. ESI-MS (EI$^+$, m/z): 1100.0 [M+Na]$^+$. $^1$HNMR (400 MHz, CDCl$_3$) δ 6.50-5.96 (m, 4H), 5.80-5.02 (m, 4H), 4.83-4.75 (m, 1H), 4.76-4.39 (m, 1H), 3.85-3.80 (m, 2H), 3.75-3.53 (m, 4H), 3.45-3.10 (m, 17H), 3.09-2.85 (m, 3H), 2.81-2.48 (m, 3H), 2.35-1.85 (m, 7H), 1.76-1.57 (m, 21H), 1.39-1.22 (m, 5H), 1.17-0.83 (m, 18H), 0.79-0.66 (m, 1H).

Step 2: (24E,26E,28E,29E,35R,36S,37R,38R,40S,42S, 44S,45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethylsulfonyl)ethoxy]-35,36,37,38, 48,49-hexamethyl-66,67-dioxa-57-azatricyclohexatriaconta-24,26,28(48),29(49)-tetraene-50, 51,52,53,54-pentone (I-134) and (24E,26E,28E,29E,35R, 36S,37R,38R,40S,42S,44R,45S,46R,47R,56R)-45-[(1R)-2-[(1S,3R,4R)-3,4-dimethoxycyclohexyl]-1-methyl-ethyl]-56-hydroxy-46,47-dimethoxy-44-[2-(2-methoxyethylsulfonyl)ethoxy]-35,36,37,38,48,49-hexamethyl-66,67-dioxa-57-azatricyclohexatriaconta-24,26,28(48),29(49)-tetraene-50,51,52,53,54-pentone (I-135). 140 mg of the mixture was separated via chiral HPLC to provide the titled compound (I-134: 18 mg, 20% yield) and (I-135: 26 mg, 29% yield) as a white solid.

Chiral Separation Method:

| | |
|---|---|
| Column: | CHIRALPAK IC |
| Column size: | 5.0 cm I.D. × 25 cm L, 10 μm |
| Sample solution: | 2.5 mg/ml in Mobile phase: |
| Injection: | 8 ml |
| Mobile phase: | Hexane/EtOH = 50/50(V/V) |
| Flow rate: | 40 ml/min |
| Wave length: | UV 254 nm |
| Temperature: | 35° C. |

I-134: ESI-MS (EI+, m/z): 1099.7 [M+Na]+. 1H NMR (400 MHz, CDCl3) δ 6.48-5.83 (m, 4H), 5.56 (dd, J=14.8, 8.1 Hz, 1H), 5.49-5.02 (m, 3H), 4.75 (s, 1H), 3.91-3.51 (m, 9H), 3.46-3.18 (m, 18H), 3.16-2.98 (m, 6H), 2.96-2.45 (m, 3H), 2.38-1.66 (m, 17H), 1.54-1.16 (m, 13H), 1.25-0.65 (m, 19H).

I-135: ESI-MS (EI+, m/z): 1100.0 [M+Na]+. 1H NMR (400 MHz, CDCl3) δ 6.65-5.86 (m, 4H), 5.75-5.02 (m, 5H), 4.81-4.31 (m, 2H), 4.08-2.99 (m, 34H), 2.97-2.49 (m, 4H), 2.45-1.65 (m, 17H), 1.51-0.53 (m, 25H).

Example 62: Synthesis of (25E,27E,29E,30E,35R,36S,37R,38R,40S,42S,45S,46R,47R,56R)-45-[(1R)-2-[(1S,3R,4R)-3,4-dimethoxycyclohexyl]-1-methyl-ethyl]-56-hydroxy-46,47-dimethoxy-35,36,37,38,48,49-hexamethyl-44-[3-(1,2,4-triazol-4-yl)propoxy]-67,68-dioxa-60-azatricyclohexatriaconta-25,27,29(48),30(49)-tetraene-50,51,52,53,54-pentone (I-129)

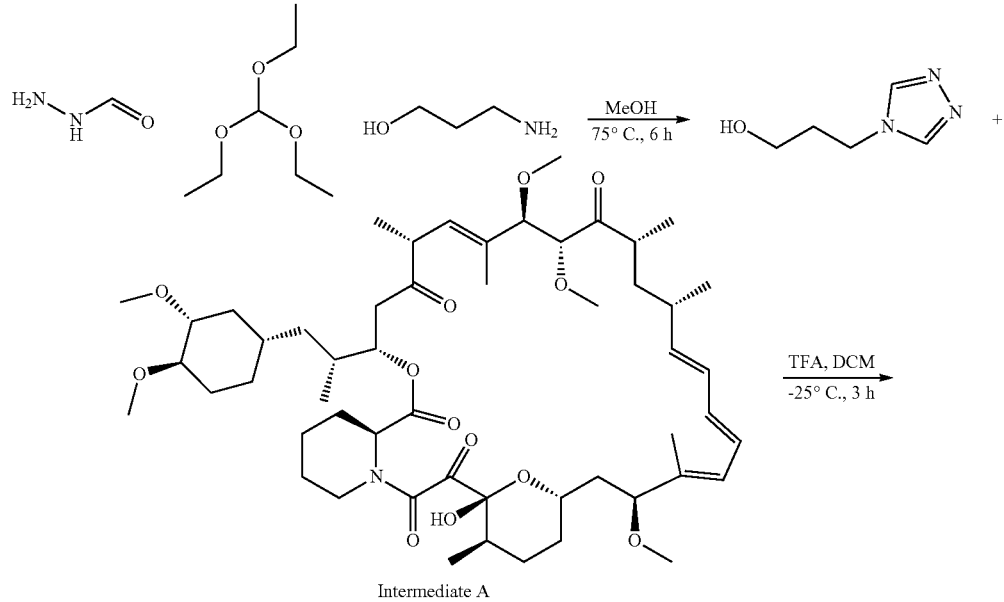

Intermediate A

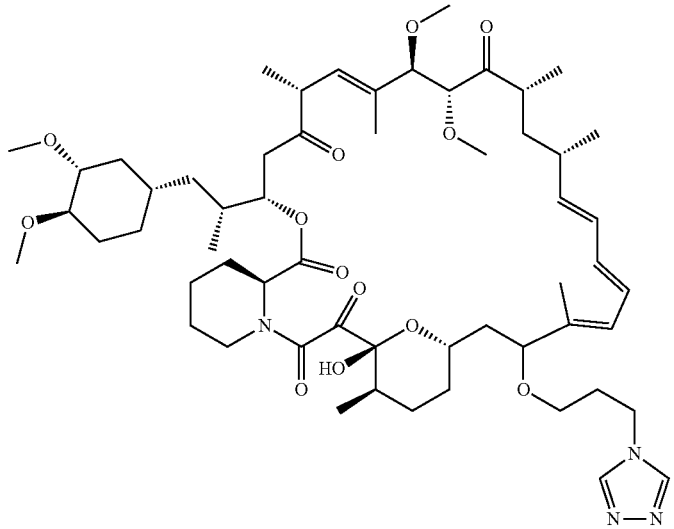

I-129

Step 1: 3-(1,2,4-triazol-4-yl) propan-1-ol. A mixture of formohydrazide (10 g, 166.51 mmol) and diethoxymethoxyethane (29.61 g, 199.82 mmol) in methanol (200 mL) was heated to reflux for 2 h then 3-aminopropan-1-ol (12.51 g, 166.51 mmol) was added dropwise, and the mixture was kept at reflux for another 4 h. The reaction was cooled, concentrated and purified via reverse-phase chromatography (10% $CH_3CN$ in water) and then purified via silica gel chromatography ($DCM:CH_3OH=12:1$) to provide 3-(1,2,4-triazol-4-yl) propan-1-ol (20.6 g, 97% yield) as light pink solid. ESI-MS (EI+, m/z): 128.1 [M+H]+, T=0.189 min. $^1$H NMR (400 MHz, MeOD-$d_4$) δ 8.49 (s, 2H), 4.18 (t, J=7.0 Hz, 2H), 3.48 (t, J=5.9 Hz, 2H), 2-1.90 (m, 2H).

Step 2: (25E,27E,29E,30E,35R,36S,37R,38R,40S,42S, 45S,46R,47R,56R)-45-[(1R)-2-[(1S,3R,4R)-3,4-dimethoxycyclohexyl]-1-methyl-ethyl]-56-hydroxy-46,47-dimethoxy-35,36,37,38,48,49-hexamethyl-44-[3-(1,2,4-triazol-4-yl)propoxy]-67,68-dioxa-60-azatricyclohexatriaconta-25,27,29(48),30(49)-tetraene-50,51,52,53,54-pentone (I-129). To a solution of Intermediate A (330 mg, 350.24 umol) and TFA (479 mg, 4.20 mmol) in DCM (20 mL) was added 3-(1,2,4-triazol-4-yl)propan-1-ol (223 mg, 1.75 mmol) and the reaction was stirred at −30° C. for 3 h. Saturated aqueous $NaHCO_3$ was added then the organic layer was washed with water (2×), brine then concentrated. The residue was purified via reverse phase chromatography followed by silica gel chromatography (MeOH:DCM=1:15) to provide the titled compound (60 mg, 16.5% yield). ESI-MS (EI+, m/z): 1038.3 [M+H]+. $^1$H NMR (400 MHz, $CDCl_3$) δ 8.36-7.82 (m, 1H), 6.49-5.92 (m, 4H), 5.75-4.96 (m, 5H), 4.51-3.92 (m, 2H), 3.64 (ddd, J=34.7, 33.2, 24.8 Hz, 4H), 3.48-3.20 (m, 11H), 3.08 (dd, J=38.8, 18.3 Hz, 7H), 2.92-2.42 (m, 5H), 2.25 (dd, J=76.9, 68.3 Hz, 8H), 1.94-1.46 (m, 19H), 1.44-0.96 (m, 20H), 0.96-0.62 (m, 9H).

Example 63: Synthesis of (23E,25E,27E,28E,36R, 37S,38R,39R,41S,43S,46S,47R,48R,57R)-57-hydroxy-46-[(1R)-2-[(1S,3R,4R)-4-(2-hydroxyethoxy)-3-methoxy-cyclohexyl]-1-methyl-ethyl]-47,48-dimethoxy-45-[2-(2-methoxyethoxy)ethoxy]-36,37, 38,39,49,50-hexamethyl-66,67-dioxa-58-azatricyclohexatriaconta-23,25,27(49),28(50)-tetraene-51,52,53,54,55-pentone (I-132), (23E,25E, 27E,28E,36R,37S,38R,39R,41S,43S,45S,46S,47R, 48R,57R)-57-hydroxy-46-[(1R)-2-[(1S,3R,4R)-4-(2-hydroxyethoxy)-3-methoxy-cyclohexyl]-1-methyl-ethyl]-47,48-dimethoxy-45-[2-(2-methoxyethoxy) ethoxy]-36,37,38,39,49,50-hexamethyl-66,67-dioxa-58-azatricyclohexatriaconta-23,25,27(49),28(50)-tetraene-51,52,53,54,55-pentone (I-138) and (23E, 25E,27E,28E,36R,37S,38R,39R,41S,43S,45R,46S, 47R,48R,57R)-57-hydroxy-46-[(1R)-2-[(1S,3R,4R)-4-(2-hydroxyethoxy)-3-methoxy-cyclohexyl]-1-methyl-ethyl]-47,48-dimethoxy-45-[2-(2-methoxyethoxy)ethoxy]-36,37,38,39,49,50-hexamethyl-66,67-dioxa-58-azatricyclohexatriaconta-23,25,27(49),28(50)-tetraene-51,52,53,54,55-pentone (I-139)

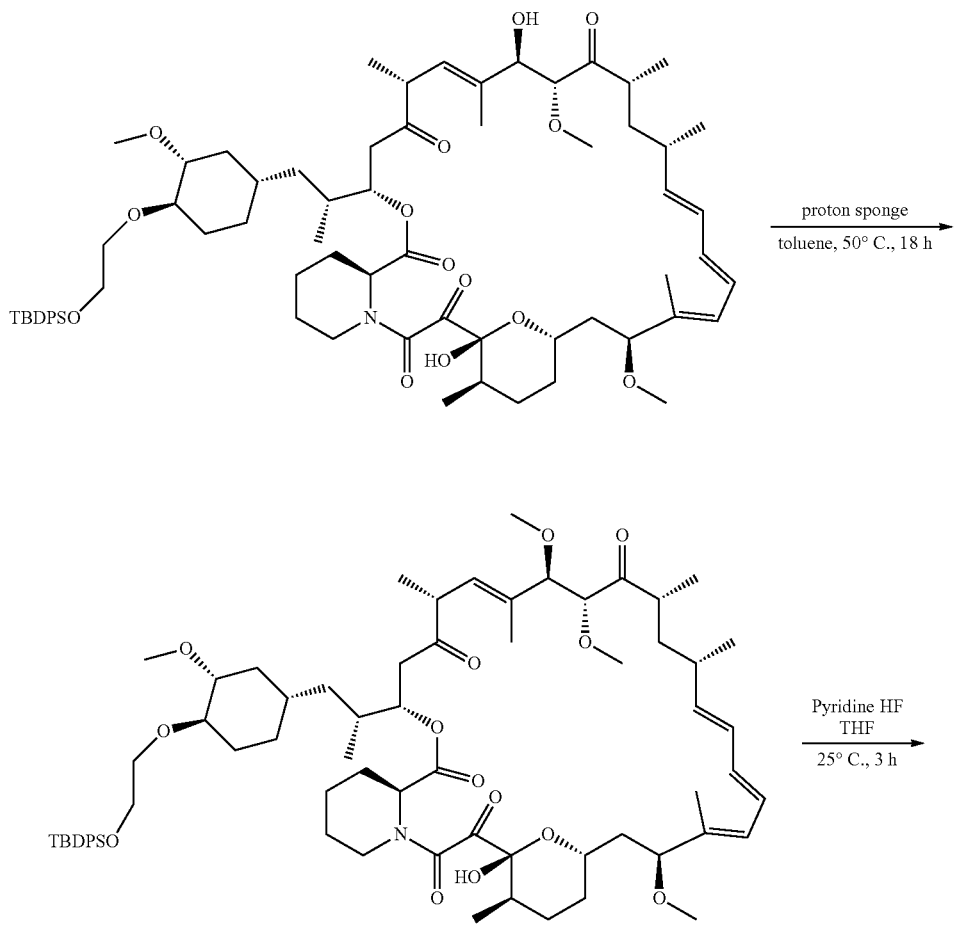

-continued
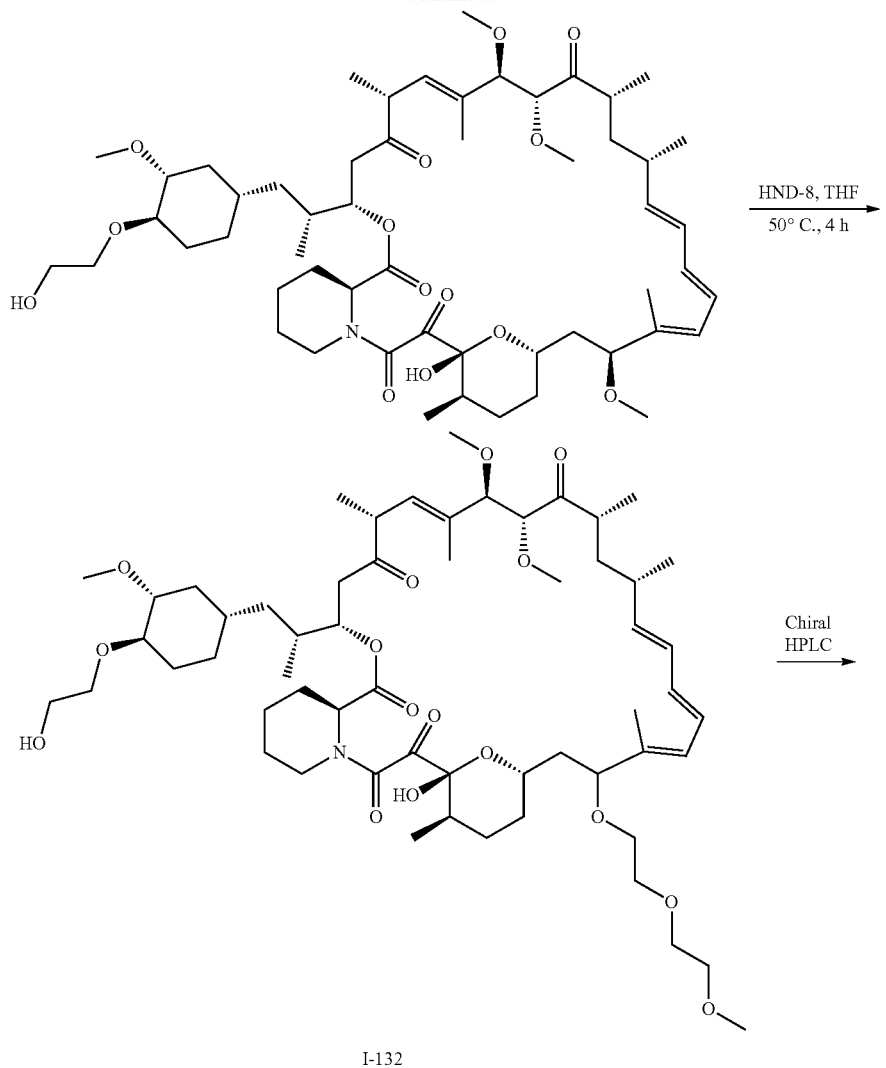
I-132
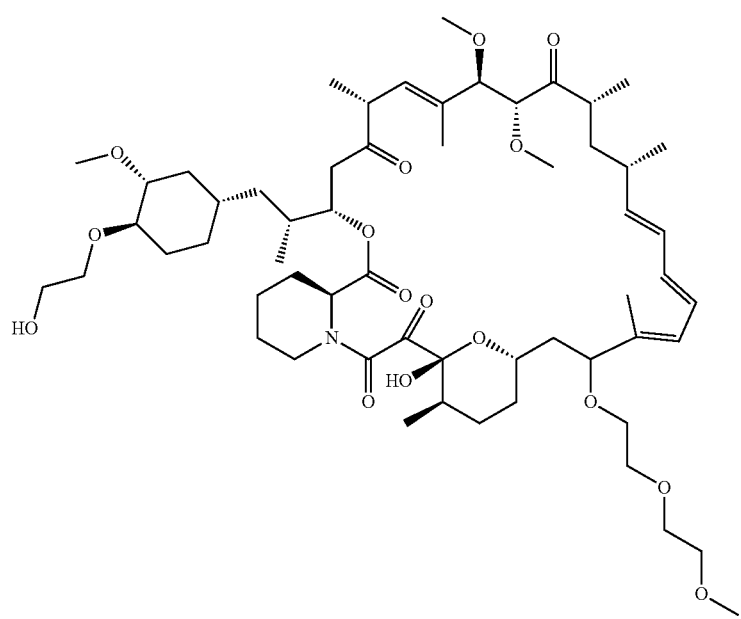
I-138

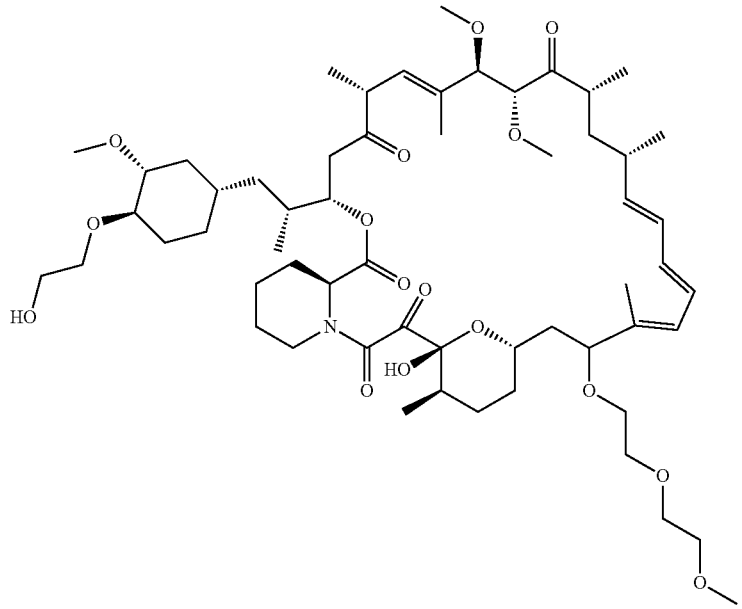

I-139

Step 1: (36E,38E,40E,41E,47R,48S,49R,50R,52S,54S, 56S,57S,58R,59R,68R)-57-[(1R)-2-[(1S,3R,4R)-4-[2-[tert-butyl(diphenyl)silyl]oxyethoxy]-3-methoxy-cyclohexyl]-1-methyl-ethyl]-68-hydroxy-56,58,59-trimethoxy-47,48,49, 50,60,61-hexamethyl-77,78-dioxa-70-azatricyclohexatriaconta-36,38,40(60),41(61)-tetraene-62, 63,64,65,66-pentone. To a suspension of (35E,37E,39E,40E, 46R,47S,48R,49R,51S,53S,55S,56S,57R,58R,67R)-56-[(1R)-2-[(1S,3R,4R)-4-[2-[tert-butyl(diphenyl)silyl] oxyethoxy]-3-methoxy-cyclohexyl]-1-methyl-ethyl]-57,67-dihydroxy-55,58-dimethoxy-46,47,48,49,59,60-hexamethyl-77,78-dioxa-69-azatricyclohexatriaconta-35, 37,39(59),40(60)-tetraene-61,62,63,64,65-pentone (1.8 g, 1.5 mmol) and 1,8-bis(dimethylamino)napthalene (6.45 g, 30.08 mmol) in toluene (40 mL) was added methyl trifluoromethanesulfonate (3.70 g, 22.56 mmol,) dropwise at rt under $N_2$. The reaction was then heated to 50° C. for 5 h. Upon cooling the mixture was quenched by adding water (50 mL) and extracted with EtOAc (50 mL) at 0° C. The organic layer was washed with water (50 mL×3) and brine (50 mL×3), dried over anhydrous sodium sulfate, filtered and concentrated. The residue was purified via silica gel chromatography (PE:EtOAc=3:1) to provide the titled compound (700 mg, 38% yield) as a light yellow solid. ESI-MS (EI$^+$, m/z): 1232.2 [M+Na]$^+$. $^1$HNMR (400 MHz, CDCl$_3$) δ 7.70-7.68 (m, 4H), 7.43-7.26 (m, 6H), 6.40-5.87 (m, 4H), 5.68-5.07 (m, 4H), 4.67 (s, 1H), 4.48-4.13 (m, 1H), 3.81-3.57 (m, 7H), 3.47-3.33 (m, 5H), 3.20-3.08 (m, 7H), 3.07-2.97 (m, 1H), 2.71-2.50 (m, 2H), 2.35-2.20 (m, 2H), 2.09-1.97 (m, 3H), 1.70-1.66 (m, 6H), 1.61-1.58 (m, 11H), 1.38-1.20 (m, 10H), 1.15-1.10 (m, 5H), 1.09-1.05 (m, 10H), 0.98-0.73 (m, 13H), 0.71-0.66 (m, 1H).

Step 2: (23E,25E,27E,28E,32R,33S,34R,35R,37S,39S, 41S,42S,43R,44R,53R)-53-hydroxy-42-[(1R)-2-[(1S,3R, 4R)-4-(2-hydroxyethoxy)-3-methoxy-cyclohexyl]-1-methyl-ethyl]-41,43,44-trimethoxy-32,33,34,35,45,46-hexamethyl-62,63-dioxa-54-azatricyclohexatriaconta-23, 25,27(45),28(46)-tetraene-47,48,49,50,51-pentone. To a solution of (36E,38E,40E,41E,47R,48S,49R,50R,52S,54S, 56S,57S,58R,59R,68R)-57-[(1R)-2-[(1S,3R,4R)-4-[2-[tert-butyl(diphenyl)silyl]oxyethoxy]-3-methoxy-cyclohexyl]-1-methyl-ethyl]-68-hydroxy-56,58,59-trimethoxy-47,48,49, 50,60,61-hexamethyl-77,78-dioxa-70-azatricyclohexatriaconta-36,38,40(60),41(61)-tetraene-62, 63,64,65,66-pentone (700 mg, 0.578 mmol) in THF (7 mL) was added Py.HF (457 mg, 5.78 mmol) at 0° C. The mixture was stirred at 30° C. for 3 h then quenched by adding saturated NaHCO$_3$ (aq.) (20 mL) and extracted with EtOAc (30 mL) at 0° C. The organic layer was washed with water (20 mL) and brine (20 mL), dried over anhydrous sodium sulfate, filtered and concentrated. The residue was purified via silica gel chromatography (PE:acetone=3:1) to provide the titled compound (250 mg, 45% yield) as a light yellow solid. ESI-MS (EI$^+$, m/z): 995.0 [M+Na]$^+$. $^1$HNMR (400 MHz, CDCl$_3$) δ6.48-6.01 (m, 4H), 5.71-5.08 (m, 4H), 4.68 (s, 1H), 4.50-4.08 (m, 1H), 3.83-3.55 (m, 7H), 3.45-3.08 (m, 17H), 3-2.51 (m, 2H), 2.40-2.32 (m, 2H), 2.16-1.97 (m, 3H), 1.75-1.58 (m, 15H), 1.30-1.24 (m, 6H), 1.15-1.10 (m, 5H), 0.98-0.82 (m, 17H), 0.78-0.68 (m, 1H).

Step 3: (23E,25E,27E,28E,36R,37S,38R,39R,41S,43S, 46S,47R,48R,57R)-57-hydroxy-46-[(1R)-2-[(1S,3R,4R)-4-(2-hydroxyethoxy)-3-methoxy-cyclohexyl]-1-methyl-ethyl]-47,48-dimethoxy-45-[2-(2-methoxyethoxy)ethoxy]-36,37,38,39,49,50-hexamethyl-66,67-dioxa-58-azatricyclohexatriaconta-23,25,27(49),28(50)-tetraene-51, 52,53,54,55-pentone (I-132). To a solution of (23E,25E,27E, 28E,32R,33S,34R,35R,37S,39S,41S,42S,43R,44R,53R)-53-hydroxy-42-[(1R)-2-[(1S,3R,4R)-4-(2-hydroxyethoxy)-3-methoxy-cyclohexyl]-1-methyl-ethyl]-41,43,44-trimethoxy-32,33,34,35,45,46-hexamethyl-62,63-dioxa-54-azatricyclohexatriaconta-23,25,27(45),28(46)-tetraene-47, 48,49,50,51-pentone (250 mg, 0.257 mmol) and 2-(2- methoxyethoxy)ethanol (618 mg, 5.14 mmol) in THF (4 mL) was added HND-8 (80 mg) at 0° C. The mixture was stirred at 50° C. for 4 h then quenched by adding saturated NaHCO₃ (20 mL) and extracted with EtOAc (30 mL) at 0° C. The organic layer was washed with water (20 mL) and brine (20 mL), dried over anhydrous sodium sulfate, filtered and the filtrate was concentrated. The residue was purified via reverse phase chromatography (85% CH₃CN in water) to provide the titled compound (120 mg, 44% yield) as a white solid. ESI-MS (EI⁺, m/z): 1082.8 [M+Na]⁺. ¹HNMR (400 MHz, CDCl₃) δ6.42-5.98 (m, 4H), 5.85-5.08 (m, 4H), 4.72-4.65 (m, 1H), 4.51-4.10 (m, 1H), 3.83-3.75 (m, 2H), 3.65-3.55 (m, 7H), 3.40-3.06 (m, 17H), 2.71-2.46 (m, 2H), 2.40-2.20 (m, 2H), 2.15-1.88 (m, 3H), 1.75-1.58 (m, 21H), 1.42-1.30 (m, 5H), 1.19-1(m, 13H), 0.97-0.82 (m, 10H), 0.78-0.68 (m, 1H).

Step 4: (23E,25E,27E,28E,36R,37S,38R,39R,41S,43S,45S,46S,47R,48R,57R)-57-hydroxy-46-[(1R)-2-[(1S,3R,4R)-4-(2-hydroxyethoxy)-3-methoxy-cyclohexyl]-1-methyl-ethyl]-47,48-dimethoxy-45-[2-(2-methoxyethoxy)ethoxy]-36,37,38,39,49,50-hexamethyl-66,67-dioxa-58-azatricyclohexatriaconta-23,25,27(49),28(50)-tetraene-51,52,53,54,55-pentone (I-138) and (23E,25E,27E,28E,36R,37S,38R,39R,41S,43S,45R,46S,47R,48R,57R)-57-hydroxy-46-[(1R)-2-[(1S,3R,4R)-4-(2-hydroxyethoxy)-3-methoxy-cyclohexyl]-1-methyl-ethyl]-47,48-dimethoxy-45-[2-(2-methoxyethoxy)ethoxy]-36,37,38,39,49,50-hexamethyl-66,67-dioxa-58-azatricyclohexatriaconta-23,25,27(49),28(50)-tetraene-51,52,53,54,55-pentone (I-139). 140 mg of the mixture was separated via chiral HPLC to provide the titled compounds (I-138: 30 mg, 30% yield) and (I-139: 30 mg, 30% yield) as white solids.

Chiral Separation Method:

| Column: | CHIRALPAK IC |
|---|---|
| Column size: | 5.0 cm I.D. × 25 cm L, 10 μm |

| Sample solution: | 4 mg/ml in Mobile phase: |
|---|---|
| Injection: | 5 ml |
| Mobile phase: | Hexane/EtOH = 70/30(V/V) |
| Flow rate: | 30 ml/min |
| Wave length: | UV 254 nm |
| Temperature: | 38° C. |

I-138: ESI-MS (EI⁺, m/z): 1081.7 [M+Na]⁺. ¹H NMR (400 MHz, CDCl₃) δ 6.52-6.10 (m, 3H), 5.96 (dd, J=62.3, 11.6 Hz, 1H), 5.62 (ddd, J=40.8, 14.6, 7.8 Hz, 1H), 5.24 (ddd, J=66.7, 18.2, 10.9 Hz, 3H), 4.68 (s, 1H), 3.93-3.52 (m, 9H), 3.51-3.03 (m, 17H), 3.01-2.49 (m, 3H), 2.40-1.63 (m, 24H), 1.53-1.18 (m, 12H), 1.18-0.81 (m, 18H), 0.78-0.62 (m, 1H).

I-139: ESI-MS (EI⁺, m/z): 1081.7 [M+Na]⁺. ¹H NMR (400 MHz, CDCl₃) δ 6.56-5.81 (m, 4H), 5.75-5.15 (m, 4H), 4.01-3.51 (m, 16H), 3.51-3.06 (m, 20H), 2.85-2.49 (m, 2H), 2.45-1.64 (m, 18H), 1.47-1.19 (m, 10H), 1.17-0.61 (m, 19H).

Example 64: Synthesis of (24E,26E,28E,29E,37R,38S,39R,40R,42S,44S,47S,48R,49R,58R)-58-hydroxy-48,49-dimethoxy-46-[2-(2-methoxyethoxy)ethoxy]-47-[(1R)-2-[(1S,3R,4R)-3-methoxy-4-(2-methoxyethoxy)cyclohexyl]-1-methyl-ethyl]-37,38,39,40,50,51-hexamethyl-66,67-dioxa-59-azatricyclohexatriaconta-24,26,28(50),29(51)-tetraene-52,53,54,55,56-pentone (I-133) and (24E,26E,28E,29E,37R,38S,39R,40R,42S,44S,46S,47S,48R,49R,58R)-58-hydroxy-48,49-dimethoxy-46-[2-(2-methoxyethoxy)ethoxy]-47-[(1R)-2-[(1S,3R,4R)-3-methoxy-4-(2-methoxyethoxy)cyclohexyl]-1-methyl-ethyl]-37,38,39,40,50,51-hexamethyl-66,67-dioxa-59-azatricyclohexatriaconta-24,26,28(50),29(51)-tetraene-52,53,54,55,56-pentone (I-151)

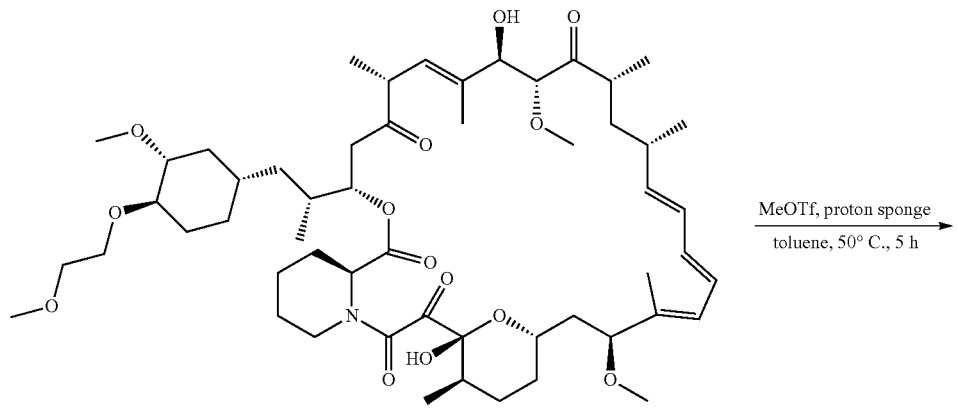

-continued
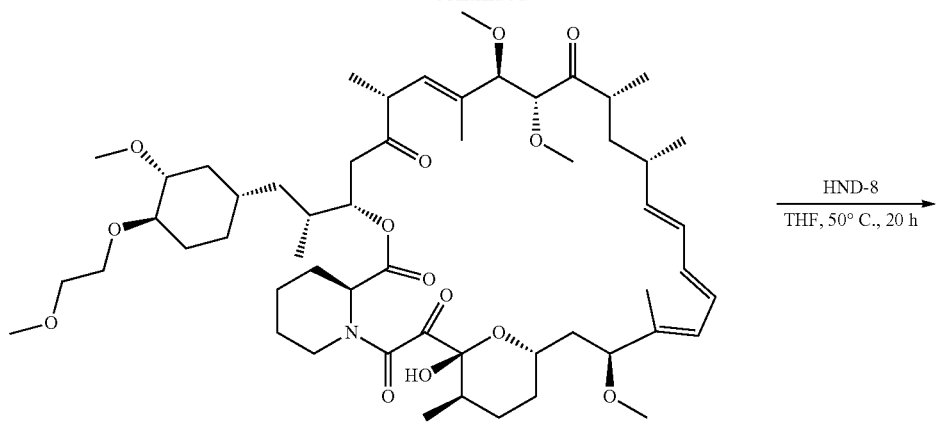
I-133
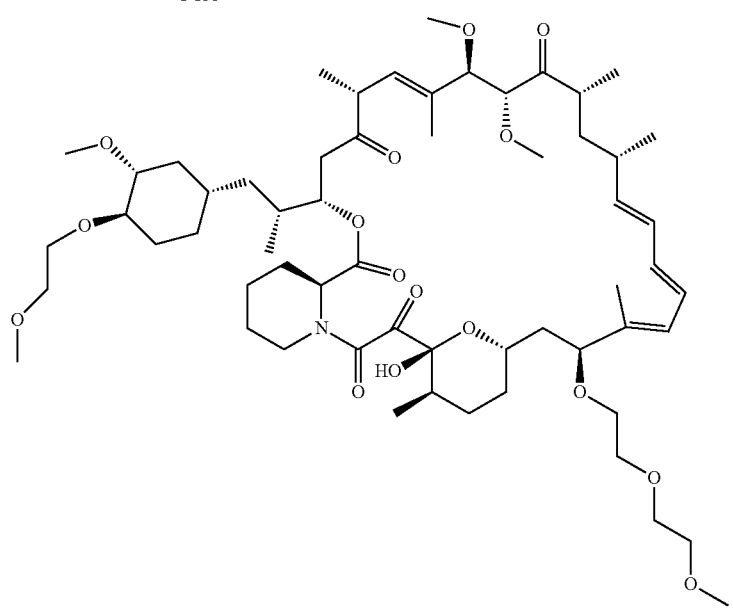
I-151

Step 1: (24E,26E,28E,29E,31R,32S,33R,34R,36S,38S, 40S,41S,42R,43R,52R)-41-[(1R)-2-[(1S,3R,4R)-3,4-dimethoxycyclohexyl]-1-methyl-ethyl]-52-hydroxy-40,42,43-trimethoxy-31,32,33,34,44,45-hexamethyl-60,61-dioxa-53-azatricyclohexatriaconta-24,26,28(44),29(45)-tetraene-46, 47,48,49,50-pentone. To a suspension of (23E,25E,27E,28E, 32R,33S,34R,35R,37S,39S,41S,42S,43R,44R,53R)-43,53-dihydroxy-41,44-dimethoxy-42-[(1R)-2-[(1S,3R,4R)-3-methoxy-4-(2-methoxyethoxy)cyclohexyl]-1-methyl-ethyl]-32,33,34,35,45,46-hexamethyl-62,63-dioxa-54-azatricyclohexatriaconta-23,25,27(45),28(46)-tetraene-47, 48,49,50,51-pentone (1.4 g, 1.44 mmol) and 1,8-bis(dimethylamino)naphthalene (4.63 g, 21.6 mmol) in toluene (24 mL) was added methyl trifluoromethanesulfonate (2.36 g, 14.4 mmol, 1.58 mL) dropwise at rt under $N_2$. The reaction mixture was then heated to 50° C. for 3 h, filtered and the filtrate diluted with EtOAc (60 mL), washed with sat. $NH_4Cl$ (aq.) (60 mL×2), water (60 mL) and brine (60 mL). The organic layer was dried over anhydrous sodium sulfate, filtered and concentrated. The residue was purified via silica gel chromatography (PE:EtOAc=7:3) and reverse phase chromatography eluting with 80% $CH_3CN$ in water to provide the titled compound (0.22 g, 15.5% yield) as a white solid. ESI-MS (EI+, m/z): 1009.5 $[M+Na]^+$.

Step 2: (24E,26E,28E,29E,37R,38S,39R,40R,42S,44S, 47S,48R,49R,58R)-58-hydroxy-48,49-dimethoxy-46-[2-(2-methoxyethoxy)ethoxy]-47-[(1R)-2-[(1S,3R,4R)-3-methoxy-4-(2-methoxyethoxy)cyclohexyl]-1-methyl-ethyl]-37,38,39,40,50,51-hexamethyl-66,67-dioxa-59-azatricyclohexatriaconta-24,26,28(50),29(51)-tetraene-52, 53,54,55,56-pentone (I-133). To a solution of (24E,26E,28E, 29E,33R,34S,35R,36R,38S,40S,42S,43S,44R,45R,54R)-54-hydroxy-42,44,45-trimethoxy-43-[(1R)-2-[(1S,3R,4R)-3-methoxy-4-(2-methoxyethoxy)cyclohexyl]-1-methyl-ethyl]-33,34,35,36,46,47-hexamethyl-62,63-dioxa-55-azatricyclohexatriaconta-24,26,28(46),29(47)-tetraene-48, 49,50,51,52-pentone (0.1 g, 0.01 mmol) and 2-(2-methoxyethoxy)ethanol (244 mg, 2.03 mmol) in THF (10 mL) was added HND-8 (0.04 g) at 50° C. under $N_2$. The reaction mixture was stirred for 20 h at 50° C. then cooled and filtered. The filtrate diluted with saturated aqueous $NaHCO_3$ (20 mL) at 0° C. and extracted with EtOAc (15 mL). The organic layer was washed with water (15 mL) and brine (15 mL), dried over anhydrous sodium sulfate, filtered and concentrated. The residue was purified via silica gel chromatography (EtOAc:PE=4:1) then by reverse phase chromatography eluting with 65% $CH_3CN$ in water to provide the titled compound (0.065 g, 60% yield) as a white solid. ESI-MS (EI+, m/z): 1095.8 $[M+Na]^+$. $^1$HNMR (400 MHz, $CDCl_3$) δ 6.43-5.84 (m, 4H), 5.72-5.06 (m, 4H), 4.84-4.17 (m, 2H), 3.96-3.73 (m, 4H), 3.70-3.52 (m, 10H), 3.50-3.43 (m, 4H), 3.41-3.30 (m, 8H), 3.29-3.20 (m, 3H), 3.18-2.99 (m, 5H), 2.96-2.50 (m, 4H), 2.35-2.14 (m, 3H), 2.05-1.84 (m, 5H), 1.80-1.56 (m, 21H), 1.55-1.23 (m, 10H), 1.16-1 (m, 11H), 0.97-0.84 (m, 9H), 0.81-0.69 (m, 1H).

Step 3: (24E,26E,28E,29E,37R,38S,39R,40R,42S,44S, 46S,47S,48R,49R,58R)-58-hydroxy-48,49-dimethoxy-46-[2-(2-methoxyethoxy)ethoxy]-47-[(1R)-2-[(1S,3R,4R)-3-methoxy-4-(2-methoxyethoxy)cyclohexyl]-1-methyl-ethyl]-37,38,39,40,50,51-hexamethyl-66,67-dioxa-59-azatricyclohexatriaconta-24,26,28(50),29(51)-tetraene-52, 53,54,55,56-pentone (I-151). 50 mg of the mixture was separated via chiral HPLC and then purified via silica gel chromatography (PE:DCM:EtOAc:MeOH=3:3:1:0.2) to provide the titled compound (13 mg, 26% yield) as a white solid.

Chiral Separation Method:

| | |
|---|---|
| Column: | CHIRALPAK IC |
| Column size: | 5.0 cm I.D. × 25 cm L, 10 μm |
| Sample solution: | 0.55 mg/ml in Mobile phase: |
| Injection: | 15 ml |
| Mobile phase: | Hexane/EtOH = 70/30(V/V) |
| Flow rate: | 30 ml/min |
| Wave length: | UV 254 nm |
| Temperature: | 38° C. |

I-151: ESI-MS (EI+, m/z): 1095.8 $[M+Na]^+$. $^1$H NMR (400 MHz, $CDCl_3$) δ 6.44-5.72 (m, 4H), 5.72-4.98 (m, 4H), 3.96-3.14 (m, 32H), 3.05 (d, J=7.9 Hz, 5H), 2.76-2.42 (m, 3H), 2.37-1.57 (m, 22H), 1.46-1.17 (m, 16H), 1.14-0.77 (m, 18H), 0.73-0.61 (m, 1H).

Example 65: Synthesis of (24E,26E,28E,29E,37R, 38S,39R,40R,42S,44S,47S,48R,49R,58R)-47-[(1R)-2-[(1S,3R,4R)-3,4-dimethoxycyclohexyl]-1-methyl-ethyl]-58-hydroxy-48,49-dimethoxy-46-[2-[2-(2-methoxyethoxy)ethoxy]ethoxy]-37,38,39,40,50,51-hexamethyl-66,67-dioxa-59-azatricyclohexatriaconta-24,26,28(50),29(51)-tetraene-52,53,54,55,56-pentone (I-136)

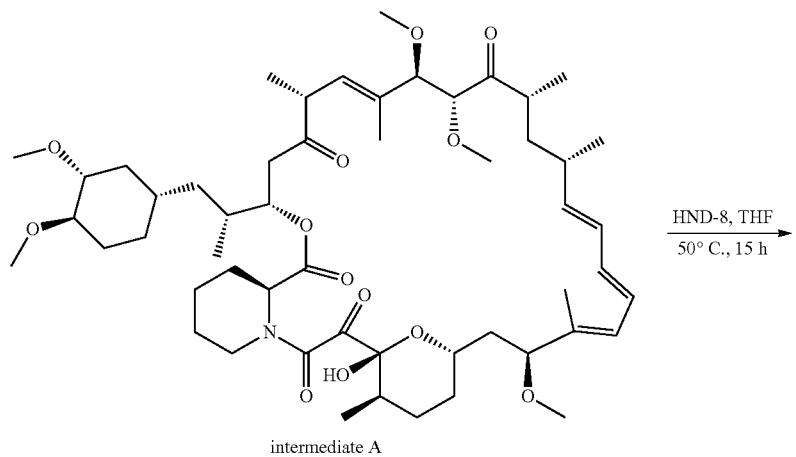

intermediate A

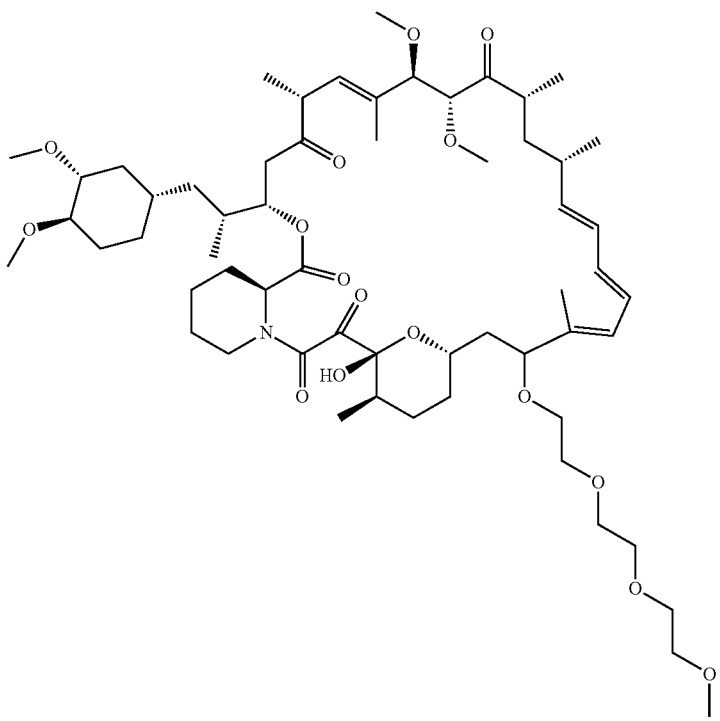

I-136

To a solution of (24E,26E,28E,29E,31R,32S,33R,34R, 36S,38S,40S,41S,42R,43R,52R)-41-[(1R)-2-[(1S,3R,4R)-3,4-dimethoxycyclohexyl]-1-methyl-ethyl]-52-hydroxy-40,42,43-trimethoxy-31,32,33,34,44,45-hexamethyl-60,61-dioxa-53-azatricyclohexatriaconta-24,26,28(44),29(45)-tetraene-46,47,48,49,50-pentone (200 mg, 0.212 mmol) and 2-[2-(2-methoxyethoxy)ethoxy]ethanol (349 mg, 2.12 mmol) in THF (5 mL) was added HND-8 (50 mg) under $N_2$ at 50° C. The reaction was stirred at 50° C. for a further 15 h then diluted with EtOAc and filtered. The organic filtrate was washed with water and brine, dried over $Na_2SO_4$, filtered and concentrated. The residue was purified via silica gel chromatography (EtOAc:PE=1:0.8) and reverse-phase chromatography (85% $CH_3CN$ in water) to provide the titled compound (40 mg, 18% yield) as a light yellow solid. ESI-MS (EI$^+$, m/z): 1095.8 [M+Na]$^+$. $^1$HNMR (400 MHz, CDCl$_3$) δ 6.60-5.79 (m, 4H), 5.76-5.06 (m, 4H), 3.93-2.97 (m, 33H), 2.92-2.49 (m, 3H), 2.47-1.75 (m, 22H), 1.51-0.63 (m, 29H).

Example 66: Synthesis of (23E,25E,27E,28E,34R, 35S,36R,37R,39S,41S,44S,45R,46R,55R)-44-[(1R)- 2-[(1S,3R,4R)-3,4-dimethoxycyclohexyl]-1-methyl- ethyl]-45,55-dihydroxy-46-methoxy-43-[2-(2- methoxyethoxy)ethoxy]-34,35,36,37,47,48- hexamethyl-64,65-dioxa-56- azatricyclohexatriaconta-23,25,27(47),28(48)- tetraene-49,50,51,52,53-pentone (I-137), (23E,25E, 27E,28E,34R,35S,36R,37R,39S,41S,43S,44S,45R, 46R,55R)-44-[(1R)-2-[(1S,3R,4R)-3,4- dimethoxycyclohexyl]-1-methyl-ethyl]-45,55- dihydroxy-46-methoxy-43-[2-(2-methoxyethoxy) ethoxy]-34,35,36,37,47,48-hexamethyl-64,65-dioxa- 56-azatricyclohexatriaconta-23,25,27(47),28(48)- tetraene-49,50,51,52,53-pentone (I-141) and (23E, 25E,27E,28E,34R,35S,36R,37R,39S,41S,43R,44S, 45R,46R,55R)-44-[(1R)-2-[(1S,3R,4R)-3,4- dimethoxycyclohexyl]-1-methyl-ethyl]-45,55- dihydroxy-46-methoxy-43-[2-(2-methoxyethoxy) ethoxy]-34,35,36,37,47,48-hexamethyl-64,65-dioxa- 56-azatricyclohexatriaconta-23,25,27(47),28(48)- tetraene-49,50,51,52,53-pentone (I-142)

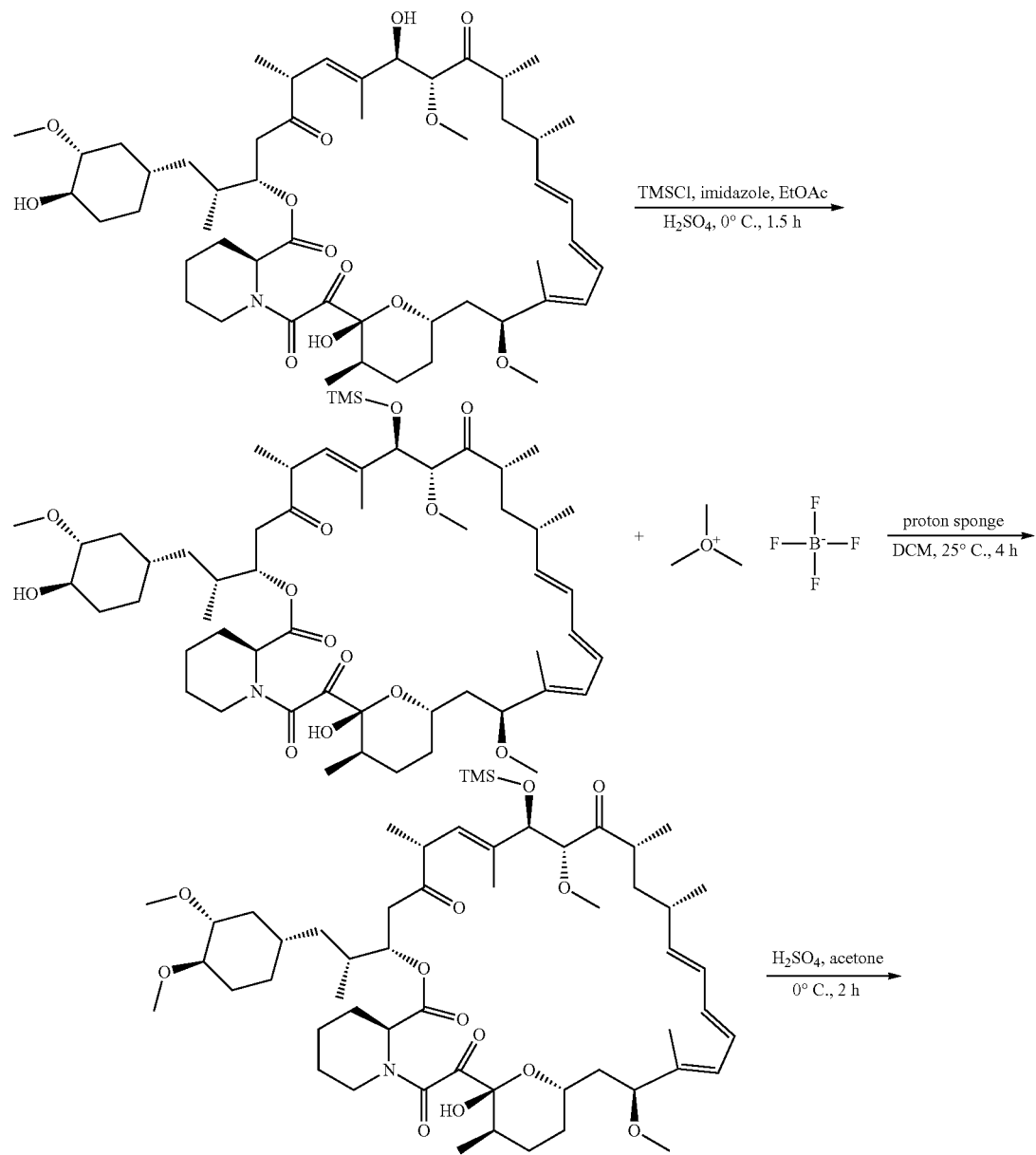

-continued
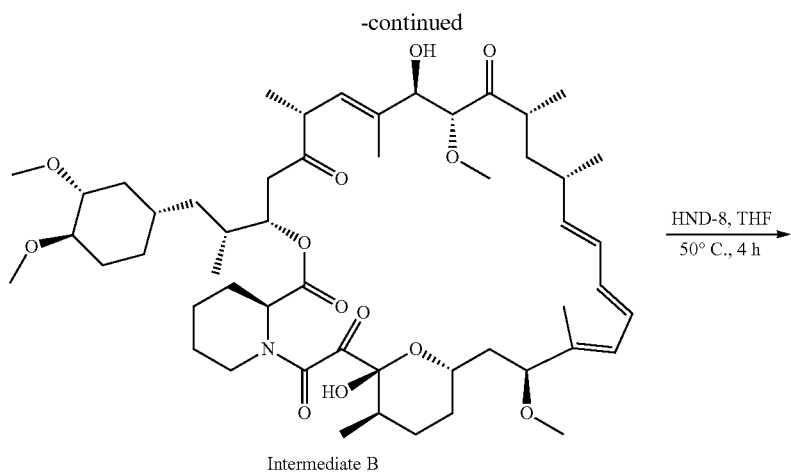
Intermediate B
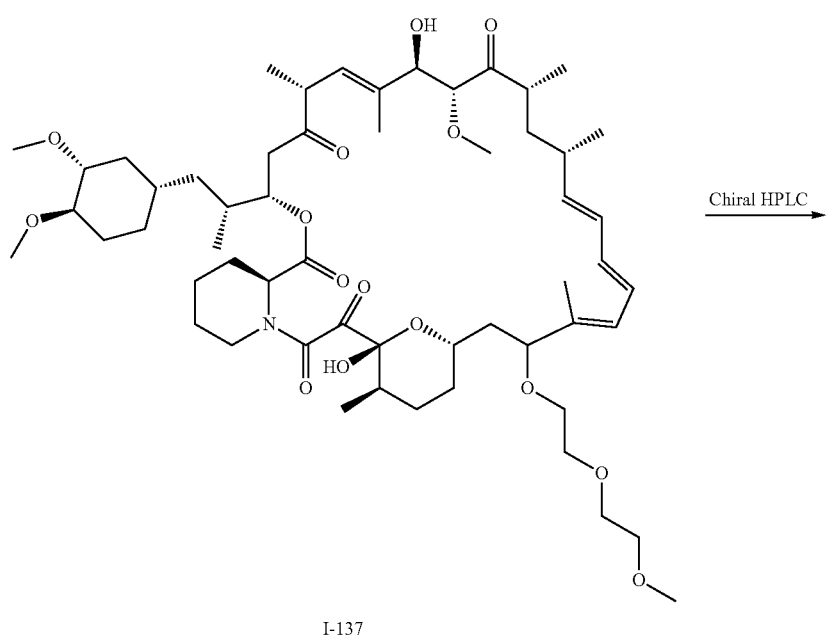
I-137
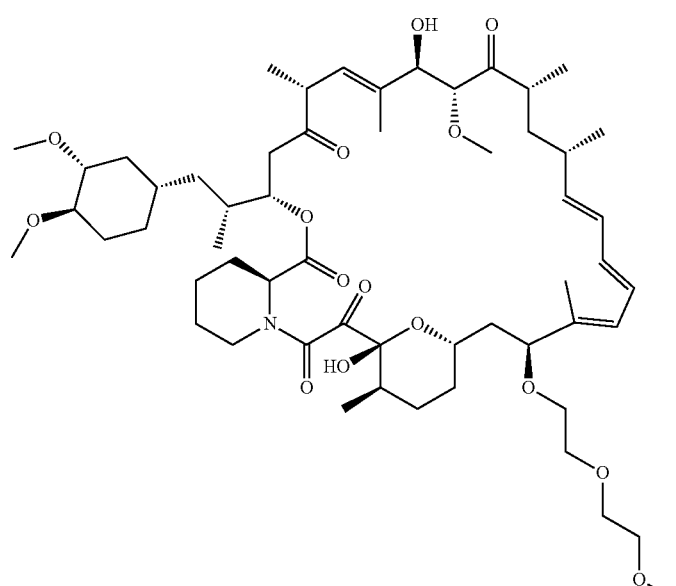
I-141

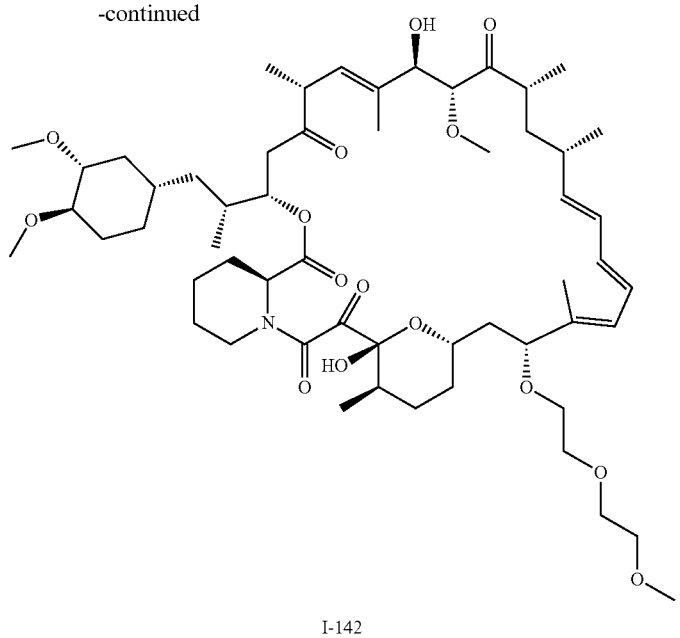

I-142

Step 1: (25E,27E,29E,30E,32R,33S,34R,35R,37S,39S, 41S,42S,43R,44R,53R)-53-hydroxy-42-[(1R)-2-[(1S,3R, 4R)-4-hydroxy-3-methoxy-cyclohexyl]-1-methyl-ethyl]-41, 44-dimethoxy-32,33,34,35,45,46-hexamethyl-43-trimethylsilyloxy-62,63-dioxa-54-azatricyclohexatriaconta-25,27,29(45),30(46)-tetraene-47,48,49,50,51-pentone. To a solution of (22E,24E,26E,27E,29R,30S,31R,32R,34S,36S, 38S,39S,40R,41R,50R)-40,50-dihydroxy-39-[(1R)-2-[(1S, 3R,4R)-4-hydroxy-3-methoxy-cyclohexyl]-1-methyl-ethyl]-38,41-dimethoxy-29,30,31,32,42,43-hexamethyl-60, 61-dioxa-51-azatricyclohexatriaconta-22,24,26(42),27(43)-tetraene-44,45,46,47,48-pentone (5 g, 5.47 mmol) in EtOAc (30 mL) was added imidazole (2.98 g, 43.76 mmol) and chloro(trimethyl)silane (4.75 g, 43.76 mmol) at 0° C. The mixture was stirred at rt for 0.5 h then cooled with ice bath $H_2SO_4$ (22 mL) added dropwise. The reaction was then stirred at 0° C. for 1.5 h, quenched by water and extracted with EtOAc (100 mL×3). The combined organic layers were washed with water and brine, dried over anhydrous $Na_2SO_4$, filtered and concentrated. The crude was purified via silica gel chromatography (EtOAc:PE=1:2) to provide the titled compound (4.2 g, 78% yield) as a white solid. ESI-MS (EI+, m/z): 1008.6 [M+Na]+. 1HNMR (400 MHz, CDCl3) δ 6.42-6.03 (m, 4H), 5.59-5.54 (m, 1H), 5.31-5.03 (m, 3H), 4.72-4.71 (d, J=0.8 Hz, 1H), 3.86-3.64 (m, 4H), 3.43-3.12 (m, 12H), 2.95-2.92 (m, 1H), 2.74-2.59 (m, 3H), 2.41-2.08 (m, 4H), 2-1.96 (m, 3H), 1.83-1.53 (m, 17H), 1.49-1.28 (m, 7H), 1.13-0.85 (m, 17H), 0.73-0.64 (m, 1H), 0.01 (s, 9H).

Step 2: (26E,28E,30E,31E,33R,34S,35R,36R,38S,40S, 42S,43S,44R,45R,54R)-43-[(1R)-2-[(1S,3R,4R)-3,4-dimethoxycyclohexyl]-1-methyl-ethyl]-54-hydroxy-42,45-dimethoxy-33,34,35,36,46,47-hexamethyl-44-trimethylsilyloxy-62,63-dioxa-55-azatricyclohexatriaconta-26,28,30(46),31 (47)-tetraene-48,49,50,51,52-pentone. To a solution of (25E, 27E,29E,30E,32R,33S,34R,35R,37S,39S,41S,42S,43R, 44R,53R)-53-hydroxy-42-[(1R)-2-[(1S,3R,4R)-4-hydroxy-3-methoxy-cyclohexyl]-1-methyl-ethyl]-41,44-dimethoxy-32,33,34,35,45,46-hexamethyl-43-trimethylsilyloxy-62,63-dioxa-54-azatricyclohexatriaconta-25,27,29(45),30(46)-tetraene-47,48,49,50,51-pentone (2 g, 2.03 mmol) in DCM (40 mL) at rt was added proton sponge (5.21 g, 24.33 mmol) and trimethyloxonium tetrafluoroborate (3 g, 20.28 mmol).

The mixture was stirred at 0° C. for 3 h then poured into ice cold saturated $NaHCO_3$ (50 mL), washed with water (50 mL×3), brine (50 mL), dried over anhydrous $Na_2SO_4$, filtered and concentrated. The crude was purified via silica gel chromatography (PE:EtOAc=3:1) to provide the titled compound (400 mg, 20% yield) as a white solid. ESI MS (EI+, m/z): 1022.6 [M+Na]+. 1H NMR (400 MHz, CDCl3) δ 6.45-6.03 (m, 4H), 5.60-5.55 (m, 1H), 5.30-5.02 (m, 3H), 4.72-4.71 (d, J=0.8 Hz, 1H), 4.12-4.07 (m, 1H), 3.88-3.61 (m, 4H), 3.43-3.13 (m, 12H), 3.09-2.96 (m, 2H), 2.64-2.19 (m, 4H), 2.16-1.89 (m, 4H), 1.78-1.53 (m, 18H), 1.39-1.12 (m, 8H), 1.11-1.02 (m, 10H), 0.96-0.84 (m, 7H), 0.80-0.69 (m, 1H), 0.01 (s, 9H).

Step 3: (23E,25E,27E,28E,30R,31S,32R,33R,35S,37S, 39S,40S,41R,42R,51R)-40-[(1R)-2-[(1S,3R)-3,4-dimethoxycyclohexyl]-1-methyl-ethyl]-41,51-dihydroxy-39,42-dimethoxy-30,31,32,33,43,44-hexamethyl-60,61-dioxa-52-azatricyclohexatriaconta-23,25,27(43),28(44)-tetraene-45, 46,47,48,49-pentone (Intermediate B). To a solution of (26E, 28E,30E,31E,33R,34S,35R,36R,38S,40S,42S,43S,44R, 45R,54R)-43-[(1R)-2-[(1S,3R)-3,4-dimethoxycyclohexyl]-1-methyl-ethyl]-54-hydroxy-42,45-dimethoxy-33,34,35,36, 46,47-hexamethyl-44-trimethylsilyloxy-62,63-dioxa-55-azatricyclohexatriaconta-26,28,30(46),31(47)-tetraene-48, 49,50,51,52-pentone (1.2 g, 1.20 mmol) in acetone (10 mL) was added $H_2SO_4$ (10 mL) at 0° C. The reaction was stirred at 0° C. for 2 h then quenched with saturated aqueous $NaHCO_3$ and extracted with EtOAc (50 mL×3). The combined organic layers were washed with water and brine, dried over anhydrous $Na_2SO_4$, filtered and concentrated. The residue was purified via reserve phase chromatography (80% $CH_3CN$ in water) to provide the titled compound (0.45 g, 40.4% yield) as a white solid. ESI-MS (EI+, m/z): 950.6 [M+Na]+. 1HNMR (400 MHz, CDCl3) δ 6.41-5.95 (m, 4H), 5.57-5.15 (m, 4H), 4.81 (s, 1H), 4.28-4.17 (m, 1H), 3.90-3.56 (m, 4H), 3.45-3.30 (m, 11H), 3.18-3.12 (m, 3H), 3.06-2.85 (m, 2H), 2.90-2.56 (m, 3H), 2.35-2.30 (m, 2H), 2.12-1.90 (m, 4H), 1.88-1.55 (m, 17H), 1.53-1.25 (m, 7H), 1.25-0.82 (m, 17H), 0.76-0.65 (m, 1H).

Step 4: (23E,25E,27E,28E,34R,35S,36R,37R,39S,41S, 44S,45R,46R,55R)-44-[(1R)-2-[(1S,3R,4R)-3,4-dimethoxycyclohexyl]-1-methyl-ethyl]-45,55-dihydroxy-46- methoxy-43-[2-(2-methoxyethoxy)ethoxy]-34,35,36,37,47,48-hexamethyl-64,65-dioxa-56-azatricyclohexatriaconta-23,25,27(47),28(48)-tetraene-49,50,51,52,53-pentone (I-137). To a solution of (23E,25E,27E,28E,30R,31S,32R,33R,35S,37S,39S,40S,41R,42R,51R)-40-[(1R)-2-[(1S,3R,4R)-3,4-dimethoxycyclohexyl]-1-methyl-ethyl]-41,51-dihydroxy-39,42-dimethoxy-30,31,32,33,43,44-hexamethyl-60,61-dioxa-52-azatricyclohexatriaconta-23,25,27(43),28(44)-tetraene-45,46,47,48,49-pentone (200 mg, 0.22 mmol) and 2-(2-methoxyethoxy)ethanol (518 mg, 4.31 mmol) in THF (5 mL) was added HND-8 (80 mg) at 20° C. The mixture was stirred at 50° C. for 4 h then quenched with saturated aqueous $NaHCO_3$ (20 mL) and extracted with EtOAc (30 mL) at 0° C. The organic layer was washed with water (20 mL) and brine (20 mL), dried over anhydrous sodium sulfate, filtered and concentrated. The residue was purified via reverse-phase chromatography (85% $CH_3CN$ in water) to obtain the titled compound (140 mg, 64% yield) as a white solid. ESI-MS (EI$^+$, m/z): 1038.6 [M+Na]$^+$. $^1$H NMR (400 MHz, CDCl$_3$) δ 6.40-5.96 (m, 4H), 5.58-5.14 (m, 4H), 4.83-4.75 (d, J=16.0 Hz, 1H), 4.59-4.13 (m, 2H), 4.01-3.71 (m, 2H), 3.68-3.52 (m, 6H), 3.45-3.31 (m, 13H), 3.29-2.97 (m, 4H), 2.93-2.42 (m, 4H), 2.41-2.25 (m, 2H), 2.18-1.91 (m, 4H), 1.71-1.57 (m, 17H), 1.55-1.43 (m, 3H), 1.25-1.12 (m, 4H), 1.10-0.83 (m, 18H), 0.79-0.66 (m, 1H).

Step 5: (23E,25E,27E,28E,34R,35S,36R,37R,39S,41S,43S,44S,45R,46R,55R)-44-[(1R)-2-[(1S,3R,4R)-3,4-dimethoxycyclohexyl]-1-methyl-ethyl]-45,55-dihydroxy-46-methoxy-43-[2-(2-methoxyethoxy)ethoxy]-34,35,36,37,47,48-hexamethyl-64,65-dioxa-56-azatricyclohexatriaconta-23,25,27(47),28(48)-tetraene-49,50,51,52,53-pentone (I-141) and (23E,25E,27E,28E,34R,35S,36R,37R,39S,41S,43R,44S,45R,46R,55R)-44-[(1R)-2-[(1S,3R,4R)-3,4-dimethoxycyclohexyl]-1-methyl-ethyl]-45,55-dihydroxy-46-methoxy-43-[2-(2-methoxyethoxy)ethoxy]-34,35,36,37,47,48-hexamethyl-64,65-dioxa-56-azatricyclohexatriaconta-23,25,27(47),28(48)-tetraene-49,50,51,52,53-pentone (I-142). 200 mg of the mixture was separated via chiral HPLC and then purified via silica gel chromatography (hexane:DCM:EtOAc:MeOH=3:3:1:0.5) to provide the titled compounds (I-141:45 mg, 23% yield) and (I-142: 38 mg, 19% yield) as white solids.

Chiral Separation Method:

| Column: | CHIRALPAK IC |
|---|---|
| Column size: | 5.0 cm I.D. × 25 cm L, 10 μm |
| Sample solution: | 5 mg/ml in Mobile phase: |
| Injection: | 3 ml |
| Mobile phase: | Hexane/EtOH = 70/30(V/V) |
| Flow rate: | 30 ml/min |
| Wave length: | UV 254 nm |
| Temperature: | 38° C. |

I-141: ESI-MS (EI$^+$, m/z): 1037.8 [M+Na]$^+$. $^1$HNMR (500 MHz, CDCl$_3$) δ 6.41-6.09 (m, 3H), 5.91 (dd, J=41.4, 10.9 Hz, 1H), 5.48 (ddd, J=34.3, 19.9, 9.4 Hz, 2H), 5.19 (ddd, J=19.1, 14.4, 7.3 Hz, 2H), 4.76 (s, 1H), 4.19 (t, J=9.1 Hz, 1H), 3.92-3.52 (m, 10H), 3.50-3.25 (m, 18H), 3.04 (dt, J=10.2, 6.5 Hz, 2H), 2.88-2.52 (m, 3H), 2.39-1.87 (m, 8H), 1.84-1.68 (m, 9H), 1.55-1.11 (m, 10H), 1.10-0.81 (m, 18H), 0.72 (dt, J=21.2, 10.8 Hz, 1H).

I-142: ESI-MS (EI$^+$, m/z): 1037.8 [M+Na]$^+$. $^1$HNMR (500 MHz, CDCl$_3$) δ 6.44-5.90 (m, 4H), 5.71-5.09 (m, 4H), 4.28 (s, 1H), 4.03-3.73 (m, 2H), 3.71-3.46 (m, 8H), 3.46-3.17 (m, 15H), 3.09-2.42 (m, 7H), 2.41-1.67 (m, 19H), 1.57-1.20 (m, 10H), 1.19-0.82 (m, 18H), 0.76-0.64 (m, 1H).

Example 67: Synthesis of (24E,26E,28E,29E,33R,34S,35R,36R,38S,40S,43S,45R,46R,55R)-43-[(1R)-2-[(1S,3R,4R)-3,4-dimethoxycyclohexyl]-1-methyl-ethyl]-45,55-dihydroxy-46-methoxy-33,34,35,36,47,48-hexamethyl-42-[2-(oxetan-3-yloxy)ethoxy]-65,66-dioxa-56-azatricyclohexatriaconta-24,26,28(47),29(48)-tetraene-49,50,51,52,53-pentone (I-140), (24E,26E,28E,29E,33R,34S,35R,36R,38S,40S,42S,43S,45R,46R,55R)-43-[(1R)-2-[(1S,3R,4R)-3,4-dimethoxycyclohexyl]-1-methyl-ethyl]-45,55-dihydroxy-46-methoxy-33,34,35,36,47,48-hexamethyl-42-[2-(oxetan-3-yloxy)ethoxy]-65,66-dioxa-56-azatricyclohexatriaconta-24,26,28(47),29(48)-tetraene-49,50,51,52,53-pentone (I-145) and (24E,26E,28E,29E,33R,34S,35R,36R,38S,40S,42R,43S,45R,46R,55R)-43-[(1R)-2-[(1S,3R,4R)-3,4-dimethoxycyclohexyl]-1-methyl-ethyl]-45,55-dihydroxy-46-methoxy-33,34,35,36,47,48-hexamethyl-42-[2-(oxetan-3-yloxy)ethoxy]-65,66-dioxa-56-azatricyclohexatriaconta-24,26,28(47),29(48)-tetraene-49,50,51,52,53-pentone (I-146)

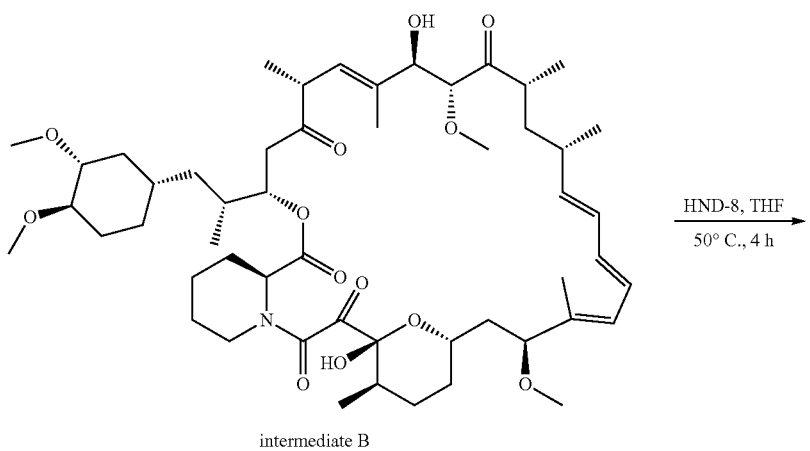

intermediate B

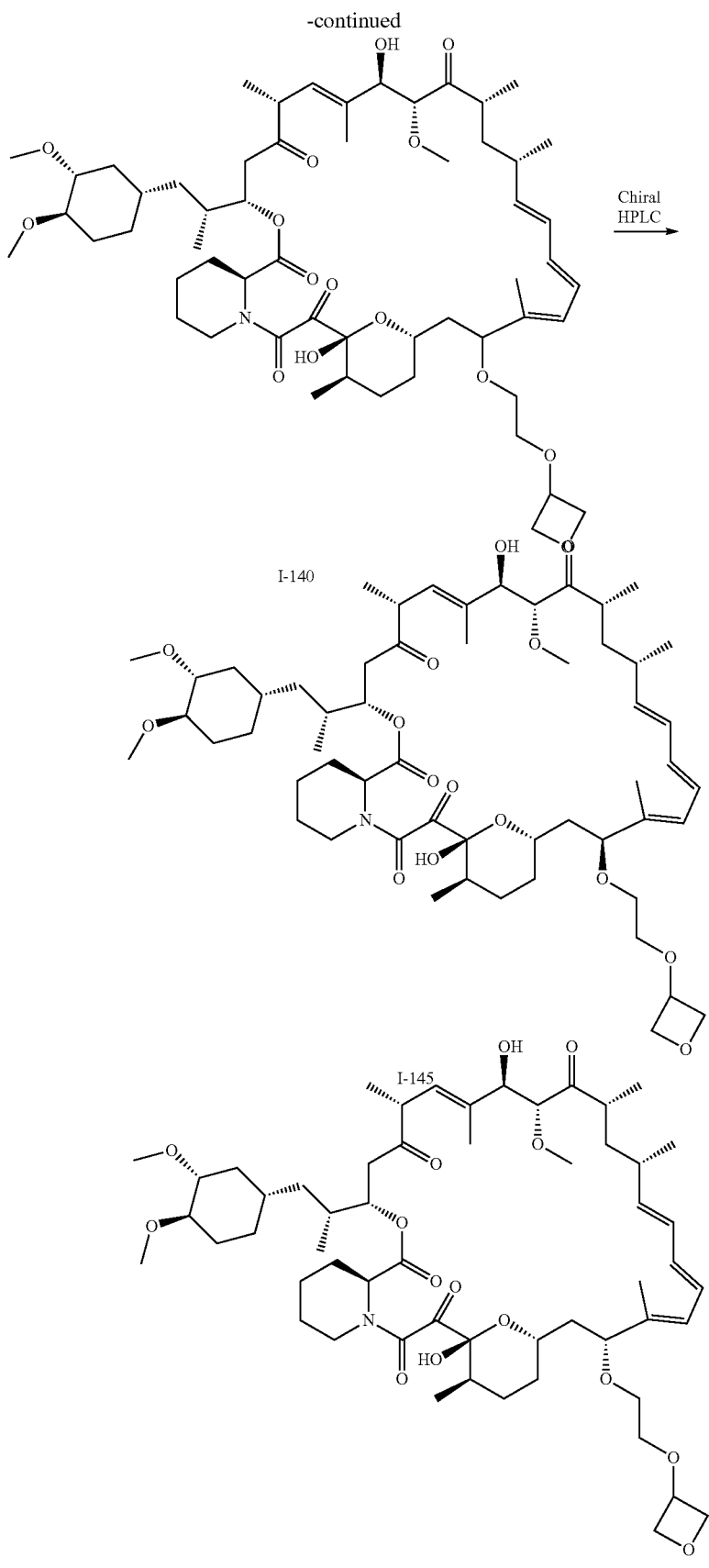

Step 1: (24E,26E,28E,29E,33R,34S,35R,36R,38S,40S, 43S,45R,46R,55R)-43-[(1R)-2-[(1S,3R,4R)-3,4-dimethoxycyclohexyl]-1-methyl-ethyl]-45,55-dihydroxy-46-methoxy-33,34,35,36,47,48-hexamethyl-42-[2-(oxetan-3-yloxy)ethoxy]-65,66-dioxa-56-azatricyclohexatriaconta-24, 26,28(47),29(48)-tetraene-49,50,51,52,53-pentone (I-140). To a solution of Intermediate B (200 mg, 0.22 mmol) and 2-(oxetan-3-yloxy)ethanol (509 mg, 4.31 mmol) in THF (5 mL) was added HND-8 (80 mg) at 50° C. The mixture was stirred at 50° C. for 14 h then quenched with saturated aqueous NaHCO$_3$ (20 mL) and extracted with EtOAc (30 mL) at 0° C. The organic layer was washed with water (20 mL) and brine (20 mL), dried over anhydrous sodium sulfate, filtered and the filtrate was concentrated. The residue was purified via reverse-phase (85% CH$_3$CN in water) to provide the titled compound (20 mg, 9% yield) as a white solid. ESI-MS (EI$^+$, m/z): 1036.5 [M+Na]$^+$. $^1$H NMR (400 MHz, CDCl$_3$) δ 6.39-5.96 (m, 4H), 5.56-5.14 (m, 4H), 4.83-4.75 (d, J=16 Hz, 1H), 4.59-4.39 (m, 1H), 4.31-3.95 (m, 2H), 3.92-3.66 (m, 7H), 3.65-3.53 (m, 2H), 3.47-3.31 (m, 13H), 3.29-2.97 (m, 5H), 2.93-2.53 (m, 3H), 2.41-2.25 (m, 2H), 2.18-1.91 (m, 4H), 1.71-1.56 (m, 14H), 1.55-1.43 (m, 3H), 1.25-1.12 (m, 4H), 1.10-0.83 (m, 17H), 0.79-0.66 (m, 1H).

Step 2: (24E,26E,28E,29E,33R,34S,35R,36R,38S,40S, 42S,43S,45R,46R,55R)-43-[(1R)-2-[(1S,3R,4R)-3,4-dimethoxycyclohexyl]-1-methyl-ethyl]-45,55-dihydroxy-46-methoxy-33,34,35,36,47,48-hexamethyl-42-[2-(oxetan-3-yloxy)ethoxy]-65,66-dioxa-56-azatricyclohexatriaconta-24, 26,28(47),29(48)-tetraene-49,50,51,52,53-pentone (I-145) and (24E,26E,28E,29E,33R,34S,35R,36R,38S,40S,42R, 43S,45R,46R,55R)-43-[(1R)-2-[(1S,3R,4R)-3,4-dimethoxycyclohexyl]-1-methyl-ethyl]-45,55-dihydroxy-46-methoxy-33,34,35,36,47,48-hexamethyl-42-[2-(oxetan-3-yloxy)ethoxy]-65,66-dioxa-56-azatricyclohexatriaconta-24, 26,28(47),29(48)-tetraene-49,50,51,52,53-pentone (I-146). 95 mg of the mixture was separated via chiral HPLC and then purified via silica gel chromatography (PE:DCM:EtOAc:MeOH=3:3: 1:0.5) to provide the titled compounds (I-145: 35 mg, 37% yield) and (I-146: 20 mg, 21% yield) as white solids.

Chiral Separation Method:

| | |
|---|---|
| Column: | CHIRALPAK IC |
| Column size: | 5.0 cm I.D. × 25 cm L, 10 μm |
| Sample solution: | 3 mg/ml in Mobile phase: |
| Injection: | 5 ml |
| Mobile phase: | Hexane/EtOH = 60/40(V/V) |
| Flow rate: | 30 ml/min |
| Wave length: | UV 254 nm |
| Temperature: | 35° C. |

I-145: ESI-MS (EI$^+$, m/z): 1035.7 [M+Na]$^+$. $^1$H NMR (500 MHz, CDCl$_3$) δ 6.43-6.06 (m, 3H), 5.90 (dd, J=37.6, 10.2 Hz, 1H), 5.59-5.09 (m, 4H), 4.79 (d, J=22.1 Hz, 1H), 4.17 (s, 1H), 3.91-3.52 (m, 10H), 3.51-3.29 (m, 15H), 3.28-2.93 (m, 4H), 2.90-2.54 (m, 3H), 2.41-1.86 (m, 8H), 1.83-1.63 (m, 8H), 1.55-1.17 (m, 10H), 1.15-0.80 (m, 18H), 0.78-0.65 (m, 1H).

I-146: ESI-MS (EI$^+$, m/z): 1035.7 [M+Na]$^+$. $^1$H NMR (500 MHz, CDCl$_3$) δ 6.43-5.75 (m, 4H), 5.69-4.86 (m, 5H), 4.09 (ddd, J=46.0, 21.7, 9.5 Hz, 3H), 3.88-3.57 (m, 7H), 3.54-3.10 (m, 15H), 3.10-2.28 (m, 9H), 2.20-1.59 (m, 25H), 1.17-0.51 (m, 19H).

Example 68: Synthesis of (23E,25E,27E,28E,36R, 37S,38R,39R,41S,43S,46S,47R,48R,57R)-57-hydroxy-46-[(1R)-2-[(1S,3R,4R)-4-hydroxy-3-methoxy-cyclohexyl]-1-methyl-ethyl]-47,48-dimethoxy-45-[2-[2-(2-methoxyethoxy)ethoxy] ethoxy]-36,37,38,39,49,50-hexamethyl-66,67-dioxa-58-azatricyclohexatriaconta-23,25,27(49),28(50)-tetraene-51,52,53,54,55-pentone (I-143)

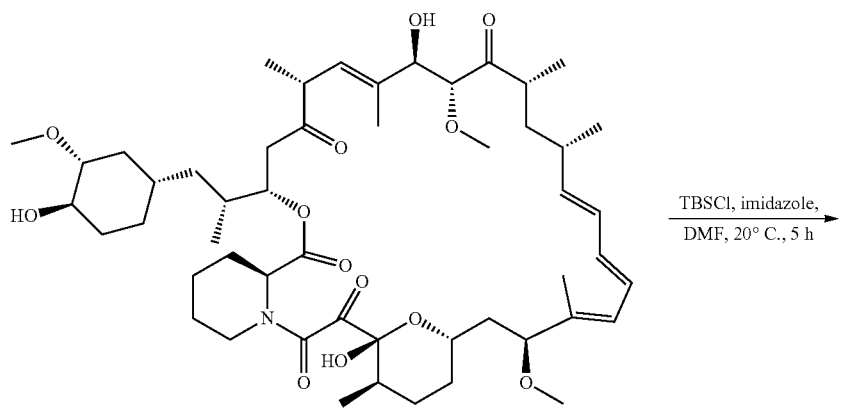

-continued
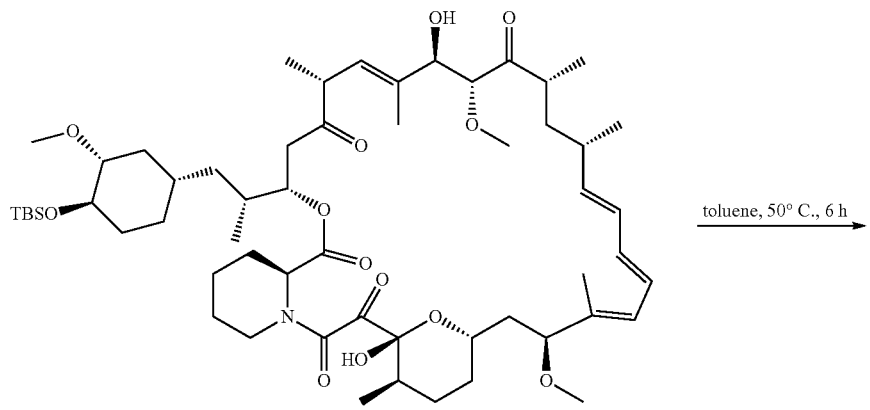
toluene, 50° C., 6 h
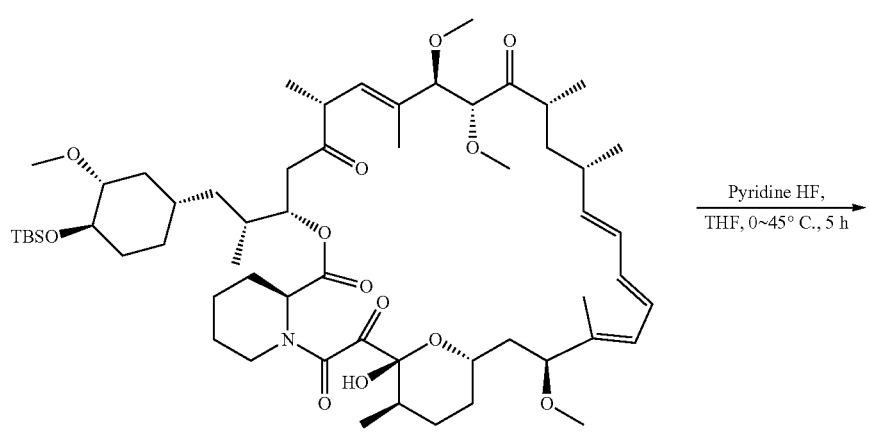
Pyridine HF,
THF, 0~45° C., 5 h
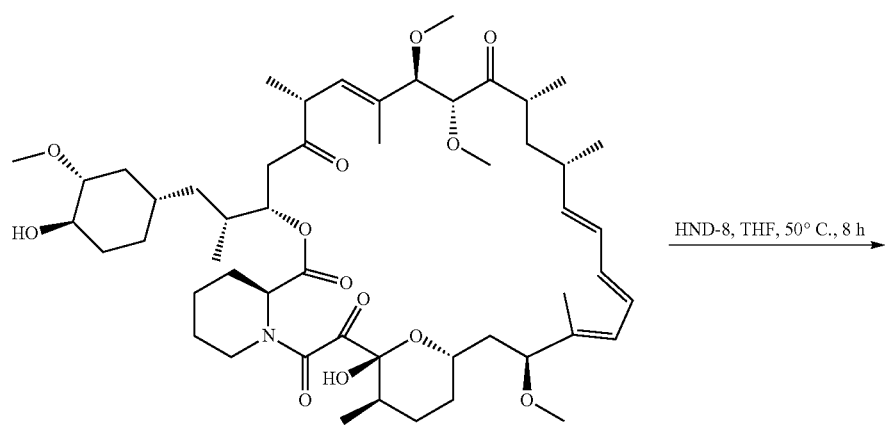
HND-8, THF, 50° C., 8 h -continued

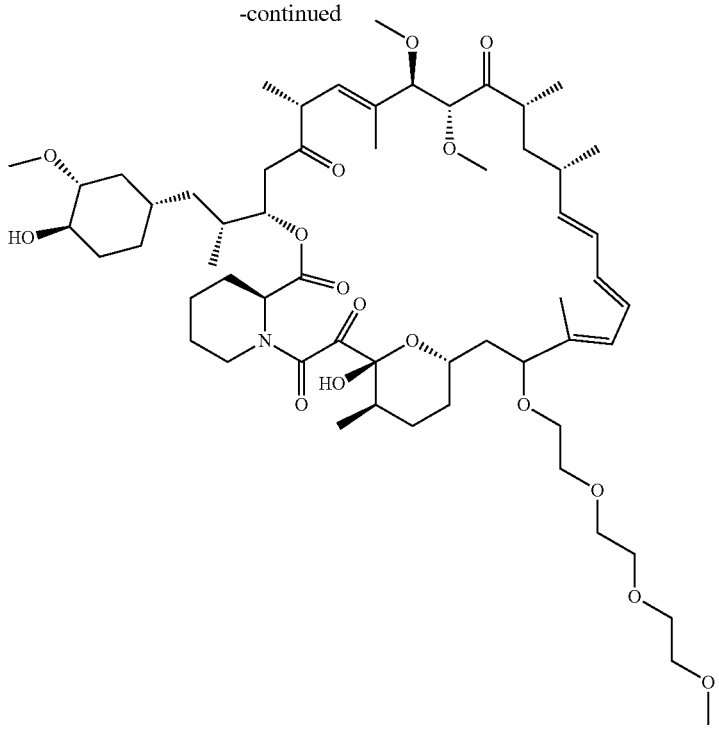

I-143

Step 1: (27E,29E,31E,32E,34R,35S,36R,37R,39S,41S, 43S,44S,45R,46R,55R)-44-[(1R)-2-[(1S,3R,4R)-4-[tert-butyl(dimethyl)silyl]oxy-3-methoxy-cyclohexyl]-1-methyl-ethyl]-45,55-dihydroxy-43,46-dimethoxy-34,35,36,37,47, 48-hexamethyl-65,66-dioxa-57-azatricyclohexatriaconta-27,29,31(47),32(48)-tetraene-49,50,51,52,53-pentone. To a solution of (22E,24E,26E,27E,29R,30S,31R,32R,34S,36S, 38S,39S,40R,41R,50R)-40,50-dihydroxy-39-[(1R)-2-[(1S, 3R,4R)-4-hydroxy-3-methoxy-cyclohexyl]-1-methyl-ethyl]-38,41-dimethoxy-29,30,31,32,42,43-hexamethyl-60, 61-dioxa-51-azatricyclohexatriaconta-22,24,26(42),27(43)-tetraene-44,45,46,47,48-pentone (2 g, 2.19 mmol) in DMF (30 mL) at rt was added imidazole (596 mg, 8.75 mmol) and tert-butyl-chloro-dimethyl-silane (989 mg, 6.56 mmol). The reaction was stirred at 20° C. for 5 h then poured into ice cold saturated aqueous NH$_4$Cl (40 mL) and Et$_2$O:PE (60 mL, 2:1). The organic layer was washed with saturated aqueous NH$_4$Cl (20 mL), water (20 mL) and brine (20 mL), dried over Na$_2$SO$_4$, filtered and concentrated. The residue was purified via silica gel chromatography (EtOAc in PE from 10% to 50%) to provide the titled compound (1.5 g, 67% yield) as a white solid. ESI-MS (EI+, m/z): 1049.8 [M+Na]$^+$.

Step 2: (28E,30E,32E,33E,35R,36S,37R,38R,40S,42S, 44S,45S,46R,47R,56R)-45-[(1R)-2-[(1S,3R,4R)-4-[tert-butyl(dimethyl)silyl]oxy-3-methoxy-cyclohexyl]-1-methyl-ethyl]-56-hydroxy-44,46,47-trimethoxy-35,36,37,38,48,49-hexamethyl-65,66-dioxa-58-azatricyclohexatriaconta-28, 30,32(48),33(49)-tetraene-50,51,52,53,54-pentone. To a suspension of (27E,29E,31E,32E,34R,35S,36R,37R,39S, 41S,43S,44S,45R,46R,55R)-44-[(1R)-2-[(1S,3R,4R)-4-[tert-butyl(dimethyl)silyl]oxy-3-methoxy-cyclohexyl]-1-methyl-ethyl]-45,55-dihydroxy-43,46-dimethoxy-34,35,36, 37,47,48-hexamethyl-65,66-dioxa-57-azatricyclohexatriaconta-27,29,31(47),32(48)-tetraene-49, 50,51,52,53-pentone (600 mg, 0.58 mmol) and 1,8-bis (dimethylamino)napthalene (1.5 g, 7 mmol) in toluene (20 mL) was added methyl trifluoromethanesulfonate (957 mg, 5.83 mmol) dropwise at rt under N$_2$. Upon completion, the mixture was heated to 50° C. for 6 h then cooled and filtered. The filtrate was concentrated and purified via silica gel chromatography (EtOAc:PE=4:1) to provide the titled compound (240 mg, 40% yield) as a white solid. ESI-MS (EI+, m/z): 1063.8 [M+Na]$^+$.

Step 3: (23E,25E,27E,28E,30R,31S,32R,33R,35S,37S, 39S,40S,41R,42R,51R)-51-hydroxy-40-[(1R)-2-[(1S,3R, 4R)-4-hydroxy-3-methoxy-cyclohexyl]-1-methyl-ethyl]-39, 41,42-trimethoxy-30,31,32,33,43,44-hexamethyl-60,61-dioxa-52-azatricyclohexatriaconta-23,25,27(43),28(44)-tetraene-45,46,47,48,49-pentone. To a solution of (28E,30E, 32E,33E,35R,36S,37R,38R,40S,42S,44S,45S,46R,47R, 56R)-45-[(1R)-2-[(1S,3R,4R)-4-[tert-butyl(dimethyl)silyl] oxy-3-methoxy-cyclohexyl]-1-methyl-ethyl]-56-hydroxy-44,46,47-trimethoxy-35,36,37,38,48,49-hexamethyl-65,66-dioxa-58-azatricyclohexatriaconta-28,30,32(48),33(49)-tetraene-50,51,52,53,54-pentone (240 mg, 0.23 mmol) in THF (10 mL) at 0° C. was added pyridine hydrofluoride (2.28 g, 23 mmol, 2 mL). This was stirred at 45° C. for 5 h then diluted with DCM and aqueous NaHCO$_3$ solution, washed with water and brine, dried over Na$_2$SO$_4$, filtered and concentrated. The residue was purified via reverse phase chromatography (78% CH$_3$CN in water) to provide the titled compound (105 mg, 49% yield) as a white solid. ESI-MS (EI+, m/z): 949.7 [M+Na]$^+$.

Step 4: (23E,25E,27E,28E,36R,37S,38R,39R,41S,43S, 46S,47R,48R,57R)-57-hydroxy-46-[(1R)-2-[(1S,3R,4R)-4-hydroxy-3-methoxy-cyclohexyl]-1-methyl-ethyl]-47,48-di-methoxy-45-[2-[2-(2-methoxyethoxy)ethoxy]ethoxy]-36, 37,38,39,49,50-hexamethyl-66,67-dioxa-58-azatricyclohexatriaconta-23,25,27(49),28(50)-tetraene-51, 52,53,54,55-pentone (I-143). To a solution of (23E,25E,27E, 28E,30R,31S,32R,33R,35S,37S,39S,40S,41R,42R,51R)-51-hydroxy-40-[(1R)-2-[(1S,3R,4R)-4-hydroxy-3-methoxy-cyclohexyl]-1-methyl-ethyl]-39,41,42-trimethoxy-30,31,32,33,43,44-hexamethyl-60,61-dioxa-52-azatricyclohexatriaconta-23,25,27(43),28(44)-tetraene-45,46,47,48,49-pentone (150 mg, 0.16 mmol) in THF (15 mL) at 0° C. under nitrogen was added 2-(2-(2-methoxyethoxy)ethoxy)ethanol (265 mg, 1.62 mmol) and HND-8 (300 mg) and the mixture was stirred at 50° C. for 8 h. The reaction mixture was filtered, concentrated and purified via reverse phase chromatography (eluting with 80% CH3CN in water) and then by prep-TLC (Petroleum ether: Ethyl acetate=1:2) to provide the titled compound (36.5 mg, 21% yield) as a white solid. ESI-MS (EI+, m/z): 1035.8 [M+Na]+. ¹HNMR (500 MHz, CDCl₃): ¹H NMR (400 MHz, CDCl₃) δ 6.59-5.88 (m, 3H), 5.85-4.93 (m, 4H), 4.72-4.18 (m, 1H), 4.15-3.76 (m, 2H), 3.74-3.52 (m, 8H), 3.50-3.30 (m, 8H), 3.29-3.03 (m, 5H), 3.03-2.47 (m, 5H), 2.45-1.89 (m, 6H), 1.90-1.52 (m, 21H), 1.32 (ddd, J=28.1, 22.9, 5.8 Hz, 9H), 1.19-0.78 (m, 14H), 0.69 (d, J=12.0 Hz, 1H).

Example 69: Synthesis of (24E,26E,28E,29E,33R, 34S,35R,36R,38S,40S,43S,45R,46R,55R)-55-hydroxy-43-[(1R)-2-[(1S,3R,4R)-4-hydroxy-3-methoxy-cyclohexyl]-1-methyl-ethyl]-45,46-dimethoxy-33,34,35,36,47,48-hexamethyl-42-[2-(oxetan-3-yloxy)ethoxy]-65,66-dioxa-56-azatricyclohexatriaconta-24,26,28(47),29(48)-tetraene-49,50,51,52,53-pentone (I-144) and (24E, 26E,28E,29E,33R,34S,35R,36R,38S,40S,42S,43S, 45R,46R,55R)-55-hydroxy-43-[(1R)-2-[(1S,3R,4R)-4-hydroxy-3-methoxy-cyclohexyl]-1-methyl-ethyl]-45,46-dimethoxy-33,34,35,36,47,48-hexamethyl-42-[2-(oxetan-3-yloxy)ethoxy]-65,66-dioxa-56-azatricyclohexatriaconta-24,26,28(47),29(48)-tetraene-49,50,51,52,53-pentone (I-148)

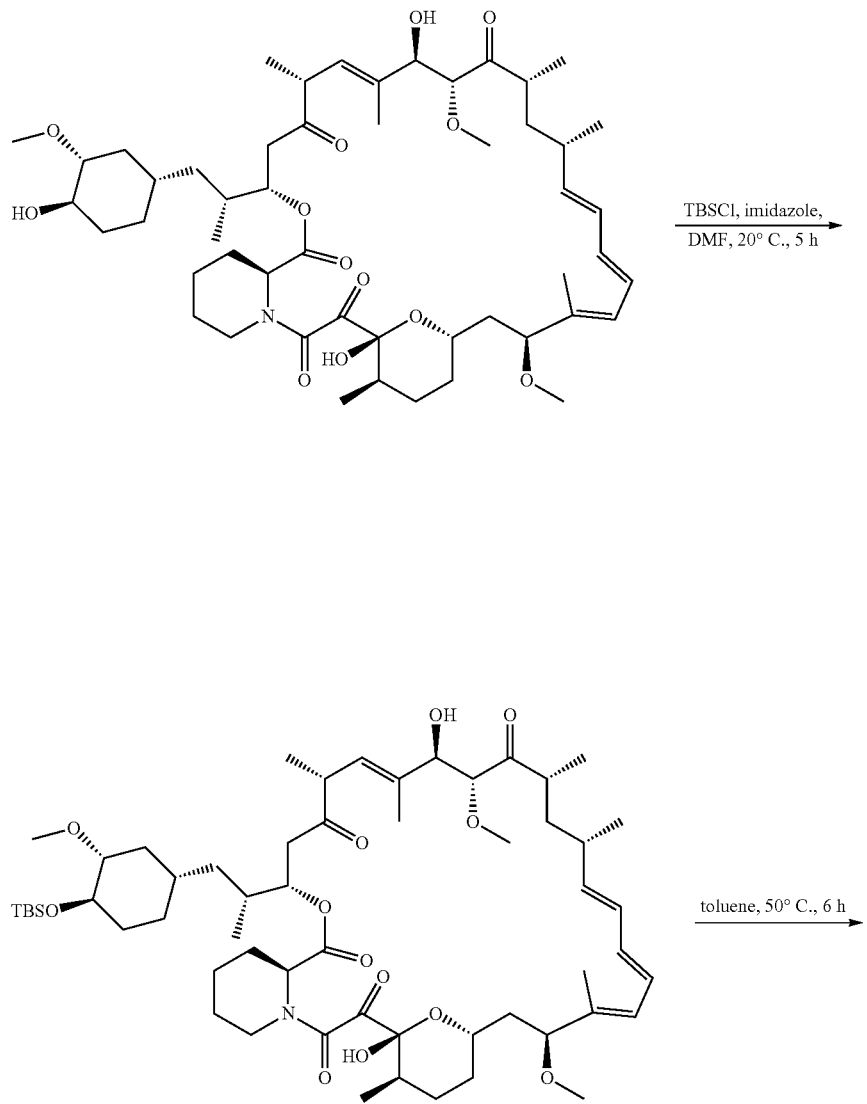

-continued
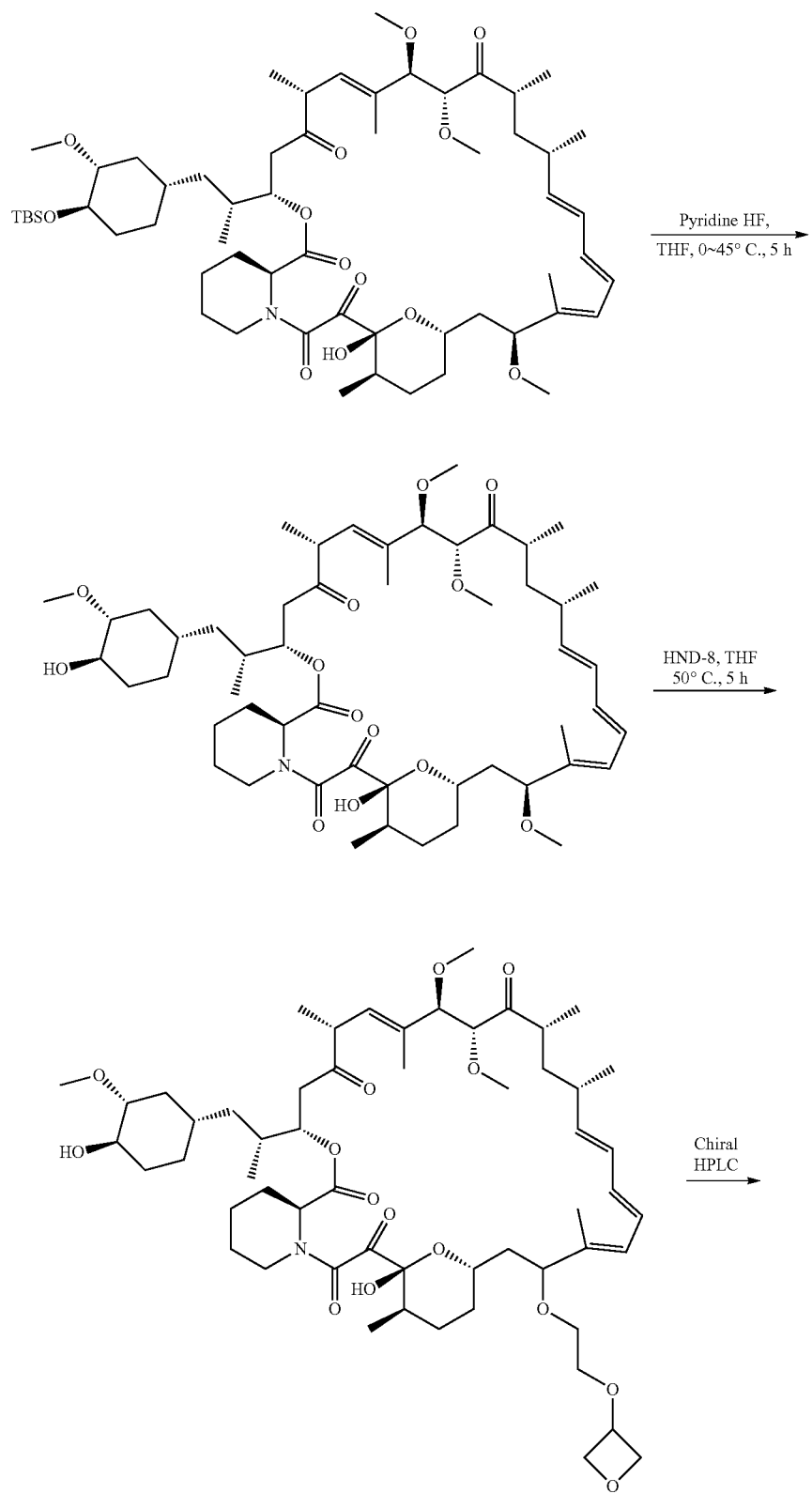
I-144

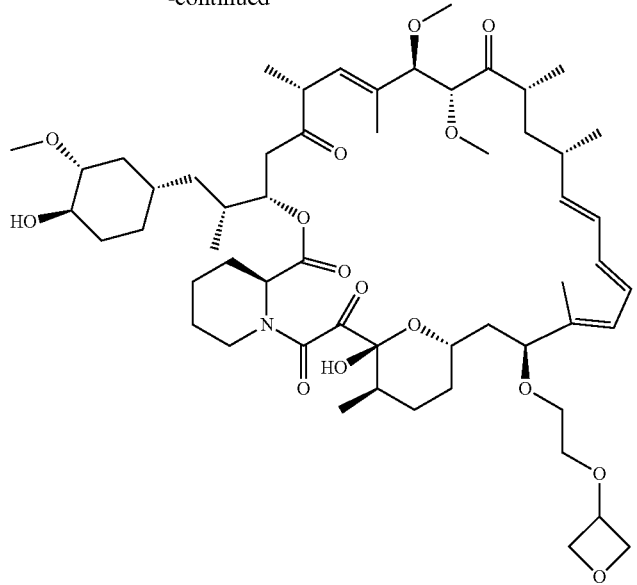

I-148

Step 1: (27E,29E,31E,32E,34R,35S,36R,37R,39S,41S,43S,44S,45R,46R,55R)-44-[(1R)-2-[(1S,3R,4R)-4-[tert-butyl(dimethyl)silyl]oxy-3-1-methoxy-cyclohexyl]-1-methyl-ethyl]-45,55-dihydroxy-43,46-dimethoxy-34,35,36,37,47,48-hexamethyl-65,66-dioxa-57-azatricyclohexatriaconta-27,29,31(47),32(48)-tetraene-49,50,51,52,53-pentone. To a solution of (22E,24E,26E,27E,29R,30S,31R,32R,34S,36S,38S,39S,40R,41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (2 g, 2.19 mmol) in DMF (30 mL) at rt was added imidazole (0.6 g, 8.75 mmol) and tert-butyl-chloro-dimethyl-silane (0.99 g, 6.56 mmol). The reaction was stirred at 20° C. for 5 h then poured into ice cold saturated aqueous $NH_4Cl$ (40 mL) and $Et_2O$:PE (60 mL, 2:1). The organic layer was washed with saturated aqueous $NH_4Cl$ (20 mL), washed with water (20 mL) and brine (20 mL), dried over $Na_2SO_4$, filtered and concentrated. The residue was purified via silica gel chromatography (EtOAc in PE from 10% to 50%) to provide the titled compound (1.5 g, 67% yield) as a white solid. ESI-MS (EI+, m/z): 1049.8 [M+Na]$^+$.

Step 2: (28E,30E,32E,33E,35R,36S,37R,38R,40S,42S,44S,45S,46R,47R,56R)-45-[(1R)-2-[(1S,3R,4R)-4-[tert-butyl(dimethyl)silyl]oxy-3-methoxy-cyclohexyl]-1-methyl-ethyl]-56-hydroxy-44,46,47-trimethoxy-35,36,37,38,48,49-hexamethyl-65,66-dioxa-58-azatricyclohexatriaconta-28,30,32(48),33(49)-tetraene-50,51,52,53,54-pentone: To a suspension of (27E,29E,31E,32E,34E,35S,36R,37R,39S,41S,43S,44S,45R,46R,55R)-44-[(1R)-2-[(1S,3R,4R)-4-[tert-butyl(dimethyl)silyl]oxy-3-methoxy-cyclohexyl]-1-methyl-ethyl]-45,55-dihydroxy-43,46-dimethoxy-34,35,36,37,47,48-hexamethyl-65,66-dioxa-57-azatricyclohexatriaconta-27,29,31(47),32(48)-tetraene-49,50,51,52,53-pentone (600 mg, 0.58 mmol) and 1,8-bis(dimethylamino)napthalene (1.5 g, 7 mmol) in toluene (20 mL) was added methyl trifluoromethanesulfonate (0.96 g, 5.83 mmol) dropwise at rt under $N_2$. The reaction was then heated to 50° C. for 6 h, cooled and filtered. The filtrate was concentrated and purified via silica gel chromatography (EtOAc:PE=4:1) to obtain the titled compound (285 mg, 47% yield) as a white solid. ESI-MS (EI+, m/z): 1063.8 [M+Na]$^+$.

Step 3: (23E,25E,27E,28E,30R,31S,32R,33R,35S,37S,39S,40S,41R,42R,51R)-51-hydroxy-40-[(1R)-2-[(1S,3R,4R)-4-hydroxy-3-methoxy-cyclohexyl]-1-methyl-ethyl]-39,41,42-trimethoxy-30,31,32,33,43,44-hexamethyl-60,61-dioxa-52-azatricyclohexatriaconta-23,25,27(43),28(44)-tetraene-45,46,47,48,49-pentone. To a solution of (28E,30E,32E,33E,35R,36S,37R,38R,40S,42S,44S,45S,46R,47R,56R)-45-[(1R)-2-[(1S,3R,4R)-4-[tert-butyl(dimethyl)silyl]oxy-3-methoxy-cyclohexyl]-1-methyl-ethyl]-56-hydroxy-44,46,47-trimethoxy-35,36,37,38,48,49-hexamethyl-65,66-dioxa-58-azatricyclohexatriaconta-28,30,32(48),33(49)-tetraene-50,51,52,53,54-pentone (240 mg, 0.23 mmol) in THF (10 mL) at 0° C. was added pyridine hydrofluoride (2.28 g, 23 mmol). The reaction was stirred at 45° C. for 5 h then diluted with DCM and aqueous $NaHCO_3$ solution, washed with water and brine, dried over $Na_2SO_4$, filtered and concentrated. The residue was purified via reverse phase chromatography (85% $CH_3CN$ in water) to obtain the titled compound (104 mg, 49% yield) as a white solid. ESI-MS (EI+, m/z): 949.7 [M+Na]$^+$.

Step 4: (24E,26E,28E,29E,33R,34S,35R,36R,38S,40S,43S,45R,46R,55R)-55-hydroxy-43-[(1R)-2-[(1S,3R,4R)-4-hydroxy-3-methoxy-cyclohexyl]-1-methyl-ethyl]-45,46-dimethoxy-33,34,35,36,47,48-hexamethyl-42-[2-(oxetan-3-yloxy)ethoxy]-65,66-dioxa-56-azatricyclohexatriaconta-24,26,28(47),29(48)-tetraene-49,50,51,52,53-pentone (I-144). To a solution of (23E,25E,27E,28E,30R,31S,32R,33R,35S,37S,39S,40S,41R,42R,51R)-51-hydroxy-40-[(1R)-2-[(1S,3R,4R)-4-hydroxy-3-methoxy-cyclohexyl]-1-methyl-ethyl]-39,41,42-trimethoxy-30,31,32,33,43,44-hexamethyl-60,61-dioxa-52-azatricyclohexatriaconta-23,25,27(43),28(44)-tetraene-45,46,47,48,49-pentone (312 mg, 0.34 mmol) in THF (15 mL) under nitrogen at 0° C. was added 2-(oxetan-3-yloxy)ethanol (397 mg, 3.36 mmol) and HND-8 (624 mg). The reaction was stirred at 50° C. for 5 h then cooled, concentrated and purified via reverse phase chromatography eluting with 80% CH$_3$CN in water and by prep-TLC (PE:EtOAc=1:2) to provide the titled compound (30 mg, 9% yield) as a white solid. ESI-MS (EI+, m/z): 1035.8 [M+Na]$^+$. $^1$H NMR (500 MHz, CDCl$_3$): $^1$H NMR (500 MHz, CDCl$_3$) δ 6.57-5.90 (m, 3H), 5.71-5 (m, 3H), 4.72-4.10 (m, 1H), 3.91-3.52 (m, 7H), 3.38 (dd, J=22.8, 12.9 Hz, 5H), 3.30-3.15 (m, 3H), 3.16-3.02 (m, 3H), 3-2.46 (m, 4H), 2.15 (dd, J=97.2, 37.0 Hz, 5H), 1.85-1.53 (m, 23H), 1.52-1.21 (m, 9H), 1.19-0.82 (m, 14H), 0.69 (d, J=11.9 Hz, 1H).

Step 5: (24E,26E,28E,29E,33R,34S,35R,36R,38S,40S, 42S,43S,45R,46R,55R)-55-hydroxy-43-[(1R)-2-[(1S,3R, 4R)-4-hydroxy-3-methoxy-cyclohexyl]-1-methyl-ethyl]-45, 46-dimethoxy-33,34,35,36,47,48-hexamethyl-42-[2-(oxetan-3-yloxy)ethoxy]-65,66-dioxa-56-azatricyclohexatriaconta-24,26,28(47),29(48)-tetraene-49, 50,51,52,53-pentone (I-148). 85 mg of the mixture was separated via chiral HPLC and then purified via silica gel chromatography (hexane:DCM:EtOAc:MeOH=3:3:1:0.3) to obtain the titled compound (25 mg, 29% yield) as a white solid.

Chiral Separation Method:

| Column: | CHIRALPAK IC |
|---|---|
| Column size: | 5.0 cm I.D. × 25 cm L, 10 μm |
| Sample solution: | 0.3 mg/ml in Mobile phase: |
| Injection: | 3 ml |
| Mobile phase: | Hexane/EtOH = 70/30(V/V) |

| | |
|---|---|
| Flow rate: | 25 ml/min |
| Wave length: | UV 254 nm |
| Temperature: | 35° C. |

I-148: ESI-MS (EI$^+$, m/z): 1036.4 [M+Na]$^+$. $^1$H NMR (400 MHz, CDCl$_3$) δ 6.44-5.80 (m, 4H), 5.65-5.01 (m, 4H), 4.64 (d, J=15.9 Hz, 1H), 3.99-3.52 (m, 11H), 3.47-3.02 (m, 16H), 3.02-2.46 (m, 5H), 2.43-1.85 (m, 8H), 1.83-1.64 (m, 9H), 1.46-1.19 (m, 10H), 1.16-0.83 (m, 18H), 0.79-0.59 (m, 1H).

Example 70: Synthesis of (23E,25E,27E,28E,36R, 37S,38R,39R,41S,43S,46S,47R,48R,57R)-46-[(1R)-2-[(1S,3R,4R)-3,4-dimethoxycyclohexyl]-1-methylethyl]-47,57-dihydroxy-48-methoxy-45-[2-[2-(2-methoxyethoxy)ethoxy]ethoxy]-36,37,38,39,49,50-hexamethyl-66,67-dioxa-58-azatricyclohexatriaconta-23,25,27(49),28(50)-tetraene-51,52,53,54,55-pentone (I-147), (23E,25E, 27E,28E,36R,37S,38R,39R,41S,43S,45S,46S,47R, 48R,57R)-46-[(1R)-2-[(1S,3R,4R)-3,4-dimethoxycyclohexyl]-1-methyl-ethyl]-47,57-dihydroxy-48-methoxy-45-[2-[2-(2-methoxyethoxy)ethoxy]ethoxy]-36,37,38,39,49,50-hexamethyl-66, 67-dioxa-58-azatricyclohexatriaconta-23,25,27(49), 28(50)-tetraene-51,52,53,54,55-pentone (I-149) and (23E,25E,27E,28E,36R,37S,38R,39R,41S,43S,45R, 46S,47R,48R,57R)-46-[(1R)-2-[(1S,3R,4R)-3,4-dimethoxycyclohexyl]-1-methyl-ethyl]-47,57-dihydroxy-48-methoxy-45-[2-[2-(2-methoxyethoxy)ethoxy]ethoxy]-36,37,38,39,49,50-hexamethyl-66, 67-dioxa-58-azatricyclohexatriaconta-23,25,27(49), 28(50)-tetraene-51,52,53,54,55-pentone (I-150)

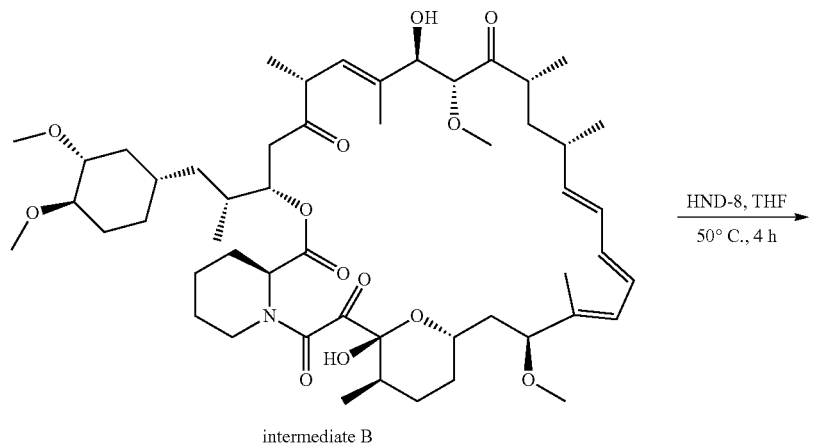

intermediate B

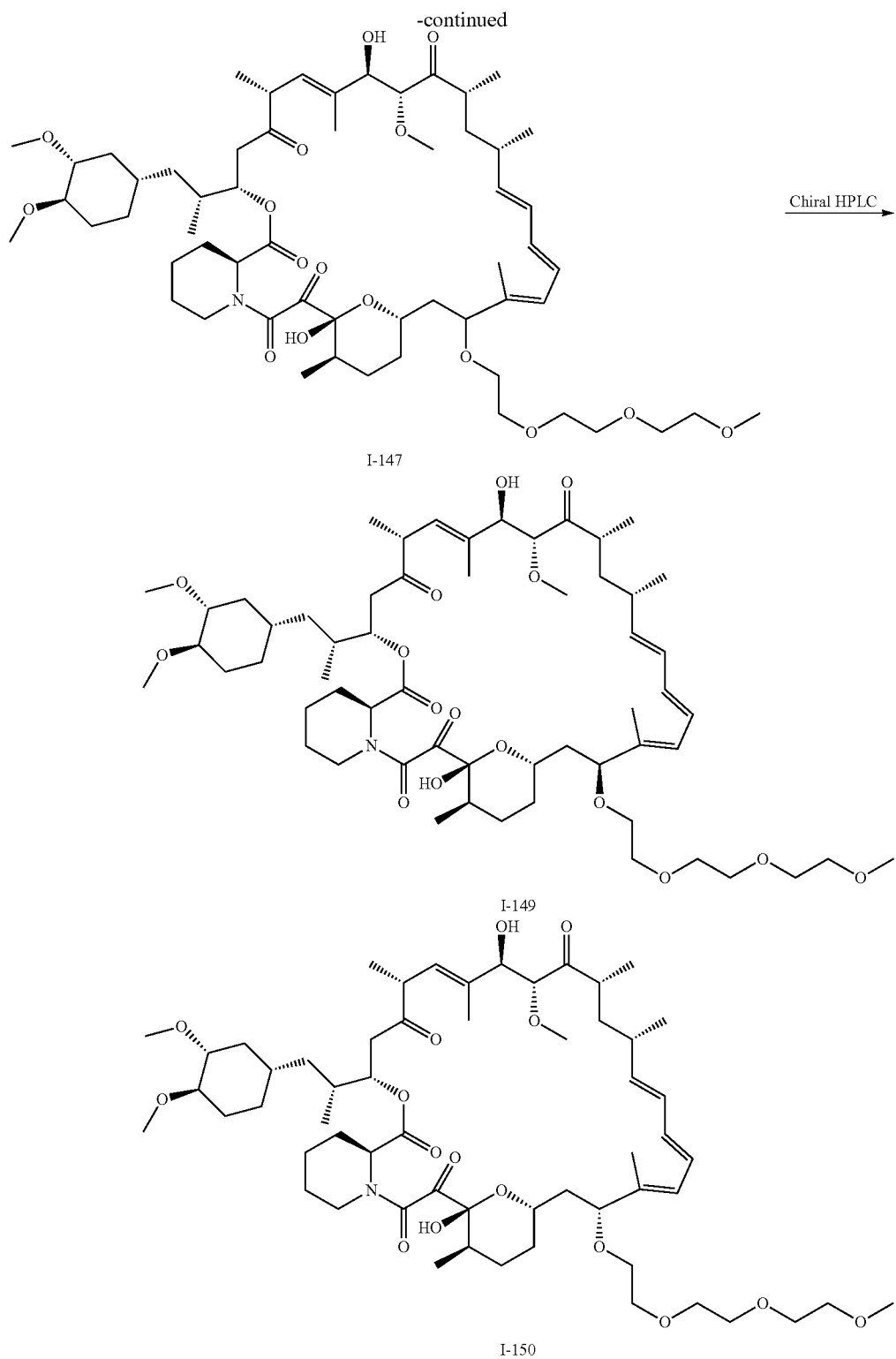

I-147

I-149

I-150

Step 1: (23E,25E,27E,28E,36R,37S,38R,39R,41S,43S, 46S,47R,48R,57R)-46-[(1R)-2-[(1S,3R,4R)-3,4-dimethoxycyclohexyl]-1-methyl-ethyl]-47,57-dihydroxy-48-methoxy-45-[2-[2-(2-methoxyethoxy)ethoxy]ethoxy]-36, 37,38,39,49,50-hexamethyl-66,67-dioxa-58-azatricyclohexatriaconta-23,25,27(49),28(50)-tetraene-51, 52,53,54,55-pentone (I-147). To a solution of Intermediate B (200 mg, 0.2 mol) and 2-[2-(2-methoxyethoxy)ethoxy]ethanol (0.71 g, 4.31 mmol) in THF (5 mL) at 50° C. was added HND-8 (60 mg). The reaction was stirred at 50° C. for 4 h then quenched with saturated aqueous NaHCO₃ (20 mL) and extracted with EtOAc (30 mL) at 0° C. The organic layer was washed with water (20 mL) and brine (20 mL), dried over anhydrous sodium sulfate, filtered and concentrated. The residue was purified via reverse phase chromatography (80% CH$_3$CN in water) to provide the titled compound (31 mg, 14% yield) as a white solid. ESI-MS (EI$^+$, m/z): 1082.6 [M+Na]$^+$. H NMR (400 MHz, CDCl$_3$) δ 6.39-5.95 (m, 4H), 5.56-5.14 (m, 4H), 4.77 (s, 1H), 4.31-3.98 (m, 2H), 3.92-3.72 (m, 2H), 3.70-3.51 (m, 10H), 3.49-3.21 (m, 17H), 3.07-2.97 (m, 2H), 2.78-2.42 (m, 3H), 2.41-2.22 (m, 2H), 2.18-2(m, 3H), 1.65-1.56 (m, 17H), 1.55-1.43 (m, 3H), 1.25-1.12 (m, 4H), 1.10-0.83 (m, 18H), 0.79-0.66 (m, 1H).

Step 2: (23E,25E,27E,28E,36R,37S,38R,39R,41S,43S,45S,46S,47R,48R,57R)-46-[(1R)-2-[(1S,3R,4R)-3,4-dimethoxycyclohexyl]-1-methyl-ethyl]-47,57-dihydroxy-48-methoxy-45-[2-[2-(2-methoxyethoxy)ethoxy]ethoxy]-36,37,38,39,49,50-hexamethyl-66,67-dioxa-58-azatricyclohexatriaconta-23,25,27(49),28(50)-tetraene-51,52,53,54,55-pentone (I-149) and (23E,25E,27E,28E,36R,37S,38R,39R,41S,43S,45R,46S,47R,48R,57R)-46-[(1R)-2-[(1S,3R,4R)-3,4-dimethoxycyclohexyl]-1-methyl-ethyl]-47,57-dihydroxy-48-methoxy-45-[2-[2-(2-methoxyethoxy)ethoxy]ethoxy]-36,37,38,39,49,50-hexamethyl-66,67-dioxa-58-azatricyclohexatriaconta-23,25,27(49),28(50)-tetraene-51,52,53,54,55-pentone (I-150). 200 mg of the mixture was separated via chiral HPLC and then purified via silica gel chromatography (hexane:DCM:EtOAc:MeOH=3:3:1:0.3) to obtain the titled compounds (I-149: 55 mg, 28% yield) and (I-150: 23 mg, 12% yield) as white solids.

Chiral Separation Method:

| Column: | CHIRALPAK IC |
|---|---|
| Column size: | 5.0 cm I.D. × 25 cm L, 10 μm |
| Sample solution: | 1 mg/ml in Mobile phase: |
| Injection: | 10 ml |
| Mobile phase: | Hexane/EtOH = 60/40(V/V) |
| Flow rate: | 30 ml/min |
| Wave length: | UV 254 nm |
| Temperature: | 35° C. |

I-149: ESI-MS (EI$^+$, m/z): 1081.9 [M+Na]$^+$. $^1$H NMR (400 MHz, CDCl$_3$) δ 6.42-6.08 (m, 3H), 5.91 (dd, J=33.4, 10.7 Hz, 1H), 5.55-5.39 (m, 2H), 5.32-5.09 (m, 2H), 4.77 (s, 1H), 4.19 (t, J=7.8 Hz, 1H), 3.95-3.52 (m, 14H), 3.50-3.23 (m, 16H), 3.11-2.92 (m, 2H), 2.92-2.53 (m, 3H), 2.40-1.87 (m, 7H), 1.84-1.57 (m, 12H), 1.54-1.18 (m, 10H), 1.15-0.82 (m, 18H), 0.73 (dd, J=23.1, 12.1 Hz, 1H).

I-150: ESI-MS (EI$^+$, m/z): 1081.9 [M+Na]$^+$. $^1$H NMR (400 MHz, CDCl$_3$) δ 6.48-5.80 (m, 4H), 5.74-5.10 (m, 4H), 4.70 (s, 1H), 4.20 (dd, J=51.2, 9.1 Hz, 2H), 3.99 (d, J=3.9 Hz, 1H), 3.94-3.18 (m, 27H), 3.11-1.96 (m, 13H), 1.93-1.73 (m, 8H), 1.57-1.20 (m, 13H), 1.19-0.82 (m, 19H), 0.69 (dd, J=23.4, 11.8 Hz, 1H).

Example 71: Synthesis of (25E,27E,29E,30E,34R,35S,36R,37R,39S,41S,44S,46R,47R,56R)-44-[(1R)-2-[(1S,3R,4R)-4-dimethylphosphoryloxy-3-methoxy-cyclohexyl]-1-methyl-ethyl]-46,56-dihydroxy-47-methoxy-34,35,36,37,48,49-hexamethyl-43-[2-(oxetan-3-yloxy)ethoxy]-67,68-dioxa-57-azatricyclohexatriaconta-25,27,29(48),30(49)-tetraene-50,51,52,53,54-pentone (I-152)

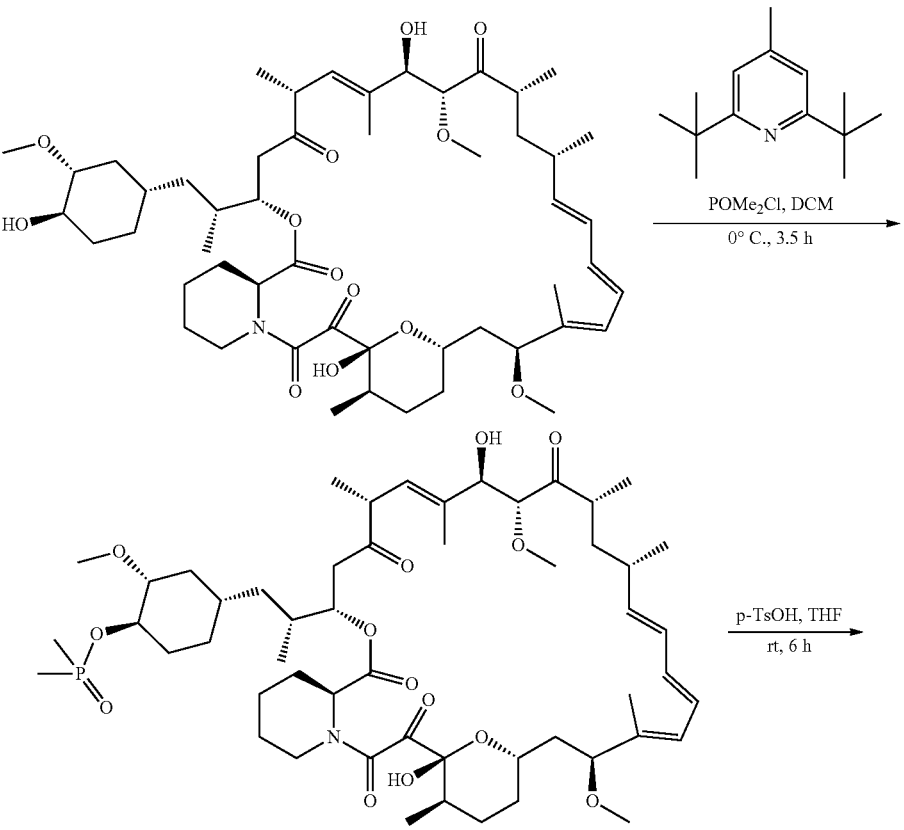

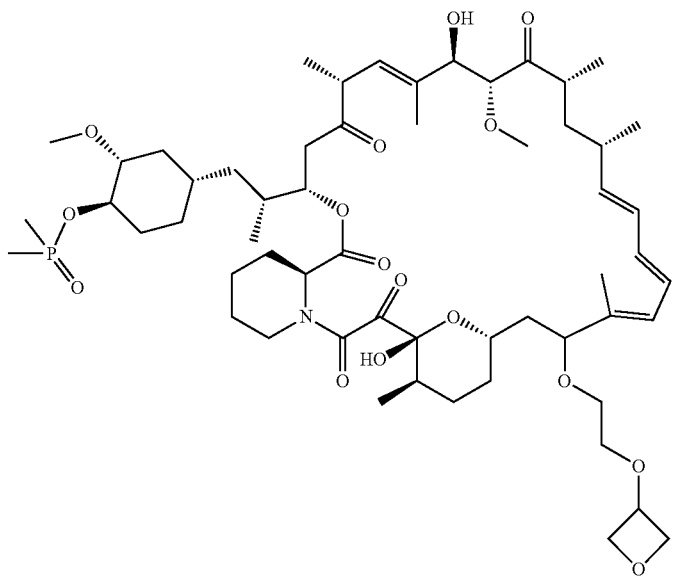

I-152

Step 1: (24E,26E,28E,29E,31R,32S,33R,34R,36S,38S, 40S,41S,42R,43R,52R)-41-[(1R)-2-[(1S,3R,4R)-4-dimethylphosphoryloxy-3-methoxy-cyclohexyl]-1-methyl-ethyl]-42,52-dihydroxy-40,43-dimethoxy-31,32,33,34,44,45-hexamethyl-62,63-dioxa-53-azatricyclohexatriaconta-24, 26,28(44),29(45)-tetraene-46,47,48,49,50-pentone. To a solution of (22E,24E,26E,27E,29R,30S,31R,32R,34S,36S, 38S,39S,40R,41R,50R)-40,50-dihydroxy-39-[(1R)-2-[(1S, 3R,4R)-4-hydroxy-3-methoxy-cyclohexyl]-1-methyl-ethyl]-38,41-dimethoxy-29,30,31,32,42,43-hexamethyl-60, 61-dioxa-51-azatricyclohexatriaconta-22,24,26(42),27(43)-tetraene-44,45,46,47,48-pentone (0.5 g, 0.547 mmol) in DCM (9 mL) at 0° C. under $N_2$ was added 2,6-ditert-butyl-4-methyl-pyridine (840 mg, 4.09 mmol) and [chloro(methyl)phosphoryl]methane (308 mg, 2.73 mmol) in DCM (1 mL). The mixture was stirred at 0° C. for 3.5 h then diluted with 20 ml EtOAc and poured into ice cold (100 mL) and EtOAc (100 mL). The organic layer was washed with ice cold 1N HCl aqueous solution (100 mL), washed with saturated aqueous $NaHCO_3$(100 mL) and brine (100 mL), dried over $Na_2SO_4$, filtered and concentrated. The residue was purified via silica gel chromatography (MeOH:DCM: EtOAc:PE=1:10:3:3) to provide the titled compound (0.5 g, 92% yield) as a white solid. ESI-MS (EI$^+$, m/z): 1012.1 [M+Na]$^+$. $^1$H NMR (500 MHz, CDCl$_3$) δ 6.48-5.82 (m, 4H), 5.58-5.05 (m, 4H), 4.79 (d, J=15.3 Hz, 1H), 4.26-4.13 (m, 1H), 3.95-3.54 (m, 4H), 3.50-3.28 (m, 9H), 3.27-3.10 (m, 4H), 3.08-2.54 (m, 5H), 2.40-1.78 (m, 12H), 1.71-1.45 (m, 13H), 1.43-1.20 (m, 8H), 1.15-0.81 (m, 18H), 0.80-0.63 (m, 1H).

Step 2: (25E,27E,29E,30E,34R,35S,36R,37R,39S,41S, 44S,46R,47R,56R)-44-[(1R)-2-[(1S,3R,4R)-4-dimethylphosphoryloxy-3-methoxy-cyclohexyl]-1-methyl-ethyl]-46,56-dihydroxy-47-methoxy-34,35,36,37,48,49-hexamethyl-43-[2-(oxetan-3-yloxy)ethoxy]-67,68-dioxa-57-azatricyclohexatriaconta-25,27,29(48),30(49)-tetraene-50,51,52,53,54-pentone (I-152). To a solution of (24E,26E, 28E,29E,31R,32S,33R,34R,36S,38S,40S,41S,42R,43R, 52R)-41-[(1R)-2-[(1S,3R,4R)-4-dimethylphosphoryloxy-3-methoxy-cyclohexyl]-1-methyl-ethyl]-42,52-dihydroxy-40, 43-dimethoxy-31,32,33,34,44,45-hexamethyl-62,63-dioxa-53-azatricyclohexatriaconta-24,26,28(44),29(45)-tetraene-46,47,48,49,50-pentone (170 mg, 0.17 mmol) and 4-methylbenzenesulfonic acid hydrate (163 mg, 858.41 μmol) in THF (5 mL) under argon at 25° C. was added 2-(oxetan-3-yloxy)ethanol (203 mg, 1.72 mmol). The reaction was stirred at this temperature for 6 h then poured into ice water and washed with aqueous $NaHCO_3$, water, brine, dried over $Na_2SO_4$, filtered and concentrated. The residue was purified by reverse phase chromatography (75% $CH_3CN$ in water) to provide the titled compound (30 mg, 16% yield) as a white solid. ESI-MS (EI$^+$, m/z): 1098.4 [M+Na]$^+$. $^1$H NMR (400 MHz, CDCl$_3$) δ 6.48-5.83 (m, 4H), 5.58-5.05 (m, 4H), 4.35-3.96 (m, 2H), 3.94-3.51 (m, 7H), 3.51-2.99 (m, 15H), 2.95-2.45 (m, 3H), 2.40-1.67 (m, 15H), 1.55-1.21 (m, 21H), 1.17-0.65 (m, 19H).

Example 72: Synthesis of (21E,23E,25E,26E,35R, 36S,37R,38R,40S,42S,45S,46R,47R,56R)-46,56-dihydroxy-45-[(1R)-2-[(1S,3R,4R)-4-(2-hydroxy-ethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy]ethoxy]-67,68-dioxa-58-azatricyclohexatriaconta-21,23,25(48),26(49)-tetraene-50,51,52,53,54-pentone (I-157), (21E,23E,25E,26E,35R,36S,37R,38R,40S,42S,44S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy]ethoxy]-67,68-dioxa-58-azatricyclohexatriaconta-21,23,25(48),26(49)-tetraene-50,51,52,53,54-pentone (I-153), and (21E,23E,25E,26E,35R,36S,37R,38R,40S,42S,44R,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy]ethoxy]-67,68-dioxa-58-azatricyclohexatriaconta-21,23,25(48),26(49)-tetraene-50,51,52,53,54-pentone (I-154)

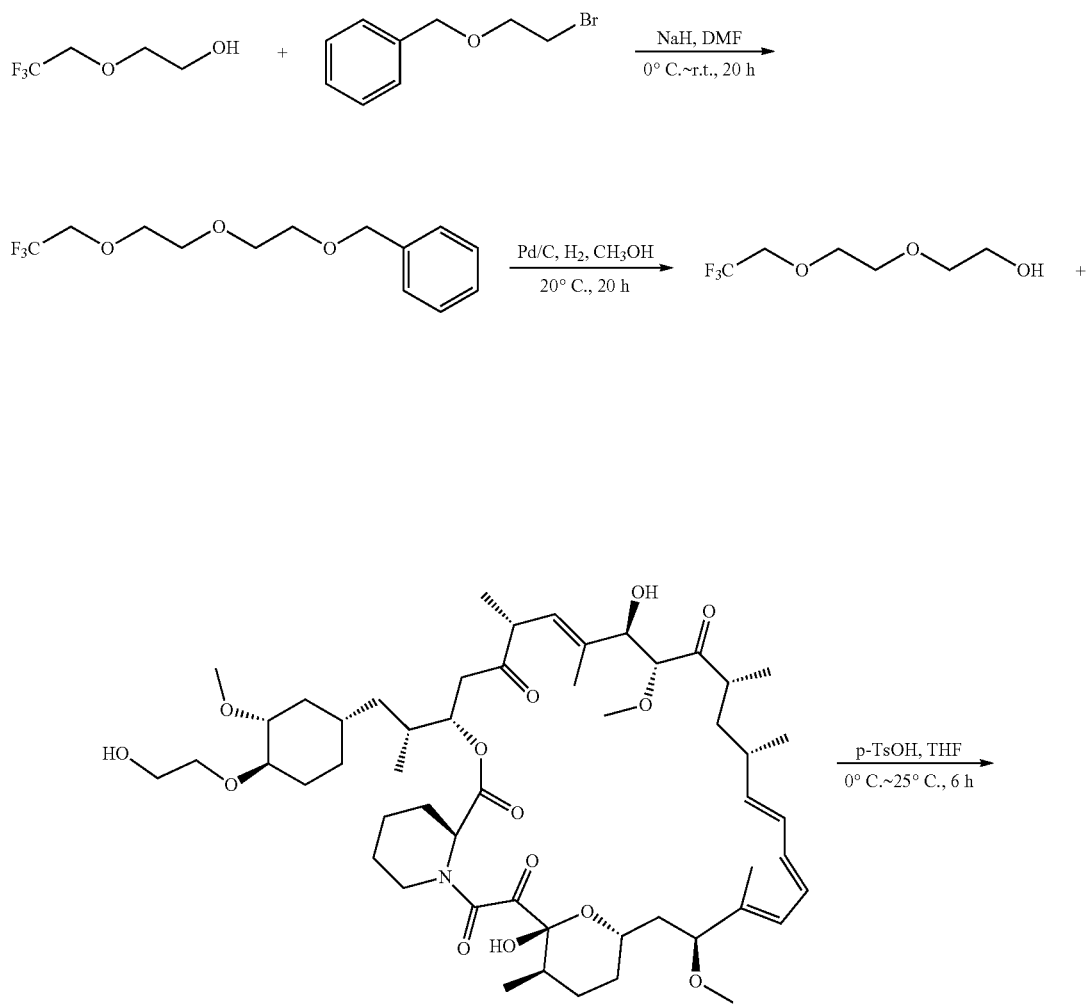

-continued
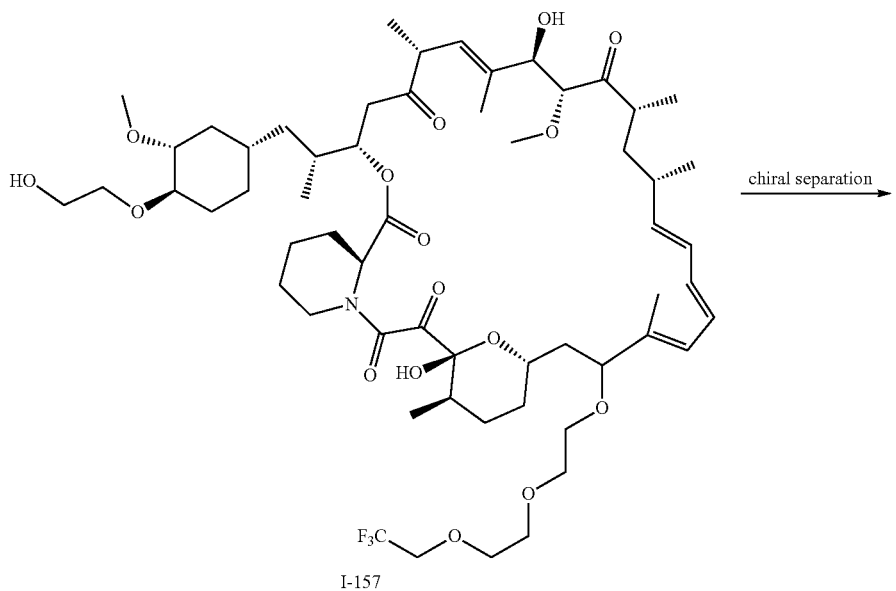
I-157
chiral separation →
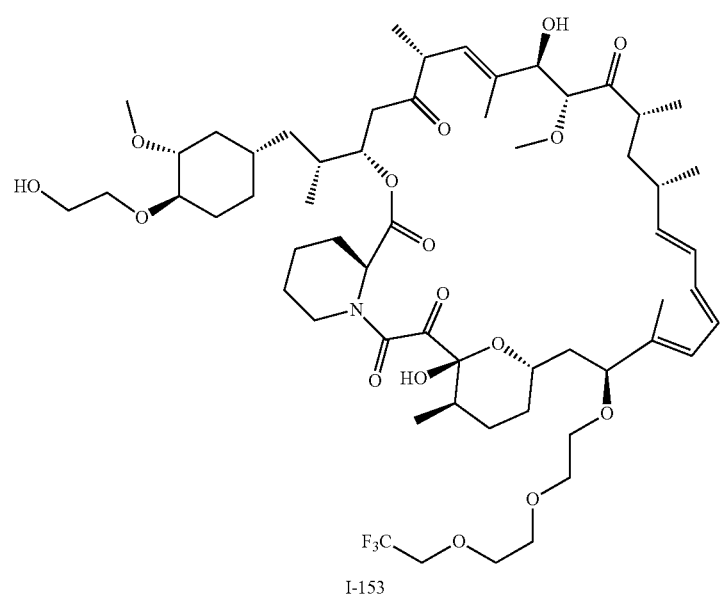
I-153

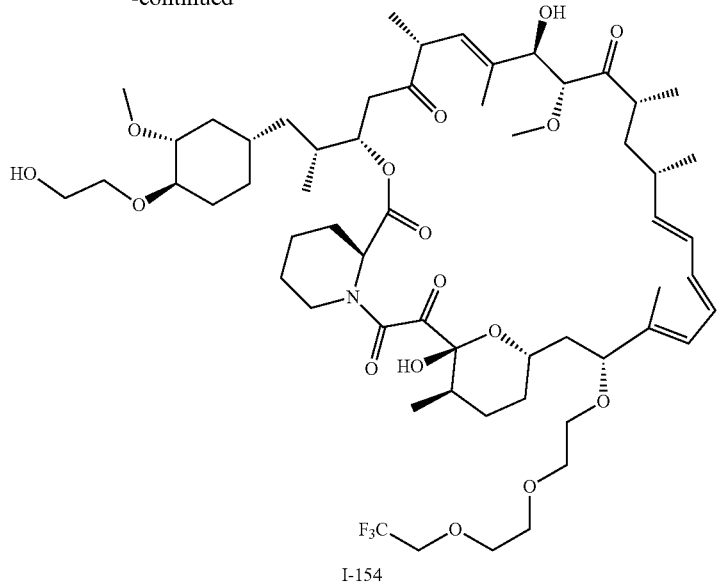

I-154

Step 1: Synthesis of 2-[2-(2, 2, 2-trifluoroethoxy) ethoxy] ethoxymethylbenzene. To a mixture of sodium hydride (12.49 g, 520.5 mmol) in DMF (150 mL) was added 2-(2, 2,2-trifluoroethoxy) ethanol (5 g, 34.7 mmol) in DMF (10 mL) under $N_2$ at 0° C. The mixture was stirred at 0° C. for 1h then 2-bromoethoxymethylbenzene (18.66 g, 86.75 mmol) was added dropwise. The reaction was stirred at room temperature for 20 h then quenched with water (50 mL) and extracted with EtOAc (80 mL). The organic layer was washed with water (50 mL×3), brine (50 mL), dried over anhydrous $Na_2SO_4$, filtered and concentrated. The residue was purified via silica gel chromatography (PE:EtOAc=25:1 to 20:1) to provide 2-[2-(2, 2,2-trifluoroethoxy) ethoxy]ethoxymethylbenzene (8.1 g, 84%) as a colorless liquid. $^1$H NMR (400 MHz, $CDCl_3$): δ 7.37-7.26 (m, 5H), 4.57 (s, 2H), 3.90 (q, J=8.8 Hz, 2H), 3.79 (dd, J=5.6, 3.5 Hz, 2H), 3.71-3.61 (m, 6H).

Step 2: Synthesis of 2-[2-(2, 2,2-trifluoroethoxy) ethoxy]. To a mixture of 2-[2-(2, 2,2-trifluoroethoxy) ethoxy] ethoxymethylbenzene (0.5 g, 1.80 mmol) in $CH_3OH$ (10 mL) was added Pd/C (0.44 g). The reaction was stirred under $H_2$ at rt for 20 h then filtered, concentrated and purified via silica gel chromatography ($DCM:CH_3OH$=50:1) to provide 2-[2-(2,2,2-trifluoroethoxy)ethoxy]ethanol (0.30 g, 89%) as a colorless oil. $^1$H NMR (400 MHz, $CDCl_3$) δ 3.91 (q, J=8.7 Hz, 2H), 3.80 (dd, J=5.6, 3.4 Hz, 2H), 3.75 (d, J=4.0 Hz, 2H), 3.70 (dd, J=5.5, 3.5 Hz, 2H), 3.62 (dd, J=5.2, 3.9 Hz, 2H), 2.23 (t, J=5.7 Hz, 1H). $^{19}$F NMR (376 MHz, $CDCl_3$, (trifluoromethyl) benzene as standard) δ −74.33 (t, J=8.8 Hz).

Step 3: Synthesis of (21E,23E,25E,26E,35R,36S,37R, 38R,40S,42S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy] ethoxy]-67,68-dioxa-58-azatricyclohexatriaconta-21,23,25 (48),26(49)-tetraene-50,51,52,53,54-pentone (I-157). To a solution of everolimus (0.5 g, 0.52 mmol) in THF (5 mL) 0° C. under $N_2$ was added p-toluenesulfonic acid (0.45 g, 2.61 mmol) and 2-[2-(2,2,2-trifluoroethoxy)ethoxy]ethanol (0.98 g, 5.22 mmol). The reaction was stirred at 0° C. for 0.5 h then at 23° C. for 6 h. The solution was poured into saturated aqueous $NaHCO_3$ (40 mL) and extracted with EtOAc (30 mL). The organic layer was washed with water (30 mL×2), brine (40 mL), dried over anhydrous $Na_2SO_4$, filtered and concentrated. The residue was purified via reverse phase chromatography ($CH_3CN:H_2O$ from 0% to 70%) to provide the titled compound (0.08 g, 14%) as a white solid. ESI-MS (EI$^+$, m/z): 1136.5 [M+Na]$^+$. $^1$H NMR (400 MHz, $CDCl_3$): δ 6.44-5.88 (m, 4H), 5.73-5.06 (m, 4H), 4.52-4.32 (m, 1H), 4.22-4.12 (m, 1H), 3.91-3.81 (m, 2H), 3.71-3.51 (m, 6H), 3.42-3.21 (m, 16H), 3.13-2.98 (m, 4H), 2.63-2.42 (m, 4H), 2.32-2.14 (m, 2H), 2.05-1.93 (m, 3H), 1.86-1.55 (m, 16H), 1.44-1.35 (m, 4H), 1.24-1.15 (m, 5H), 1.06-0.78 (m, 17H), 0.65-0.51 (m, 1H).

Step 4: Synthesis of (21E,23E,25E,26E,35R,36S,37R, 38R,40S,42S,44S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy] ethoxy]-67,68-dioxa-58-azatricyclohexatriaconta-21,23,25 (48),26(49)-tetraene-50,51,52,53,54-pentone (I-153) and (21E,23E,25E,26E,35R,36S,37R,38R,40S,42S,44R,45S, 46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy]ethoxy]-67,68-dioxa-58-azatricyclohexatriaconta-21,23,25(48),26(49)-tetraene-50, 51,52,53,54-pentone (I-154). 100 mg of the mixture was separated via chiral HPLC to provide the titled compounds (I-153:14.3 mg, 14% yield) and (I-154: 10.4 mg, 10% yield) as white solids.

Chiral Separation Method:

| | |
|---|---|
| Column: | CHIRALPAK IC |
| Column size: | 5.0 cm I.D. × 25 cm L |
| Solution conc.: | 2.4 mg/ml |
| Injection: | 5 ml |
| Mobile phase: | Hexane/EtOH = 70/30(V/V) |
| Flow rate: | 30 ml/min |

-continued

| Wave length: | UV 254 nm |
|---|---|
| Temperature: | 35° C. |

I-153: ESI-MS (EI+, m/z): 1136.4 [M+Na]+. $^1$H NMR (400 MHz, CDCl3) δ 6.42-6.06 (m, 3H), 5.92 (dd, J=30.3, 10.3 Hz, 1H), 5.56-5.06 (m, 5H), 4.74 (s, 1H), 4.18 (d, J=5.7 Hz, 1H), 3.94-3.83 (m, 2H), 3.82-3.51 (m, 12H), 3.49-3.25 (m, 11H), 3.22-3.03 (m, 2H), 2.72 (dd, J=16.6, 5.5 Hz, 2H), 2.57 (dd, J=17.0, 6.5 Hz, 1H), 2.34 (d, J=12.4 Hz, 2H), 2.25-2.18 (m, 1H), 2.13-1.85 (m, 5H), 1.69 (dd, J=35.2, 8.9 Hz, 10H), 1.47 (dd, J=20.5, 13.6 Hz, 5H), 1.26 (s, 7H), 1.15-0.81 (m, 18H), 0.71 (dd, J=23.9, 12.0 Hz, 1H).

I-154: ESI-MS (EI+, m/z): 1136.4 [M+Na]+. $^1$H NMR (400 MHz, CDCl$_3$) δ 6.46-5.90 (m, 4H), 5.74-5.09 (m, 5H), 4.20 (dd, J=40.4, 12.5 Hz, 2H), 4.03-3.01 (m, 28H), 2.93-1.69 (m, 25H), 1.55-1.20 (m, 11H), 1.16-0.82 (m, 18H), 0.79-0.54 (m, 1H).

Example 73: Synthesis of (24E,26E,28E,29E,35R, 36S,37R,38R,40S,42S,45S,47R,48R,57R)-47,57-dihydroxy-48-methoxy-45-[(1R)-2-[(1S,3R,4R)-3-methoxy-4-(2-methoxyethoxy)cyclohexyl]-1-methyl-ethyl]-35,36,37,38,49,50-hexamethyl-44-[2-(oxetan-3-yloxy)ethoxy]-67,68-dioxa-58-azatricyclohexatriaconta-24,26,28(49),29(50)-tetraene-51,52,53,54,55-pentone (I-155)

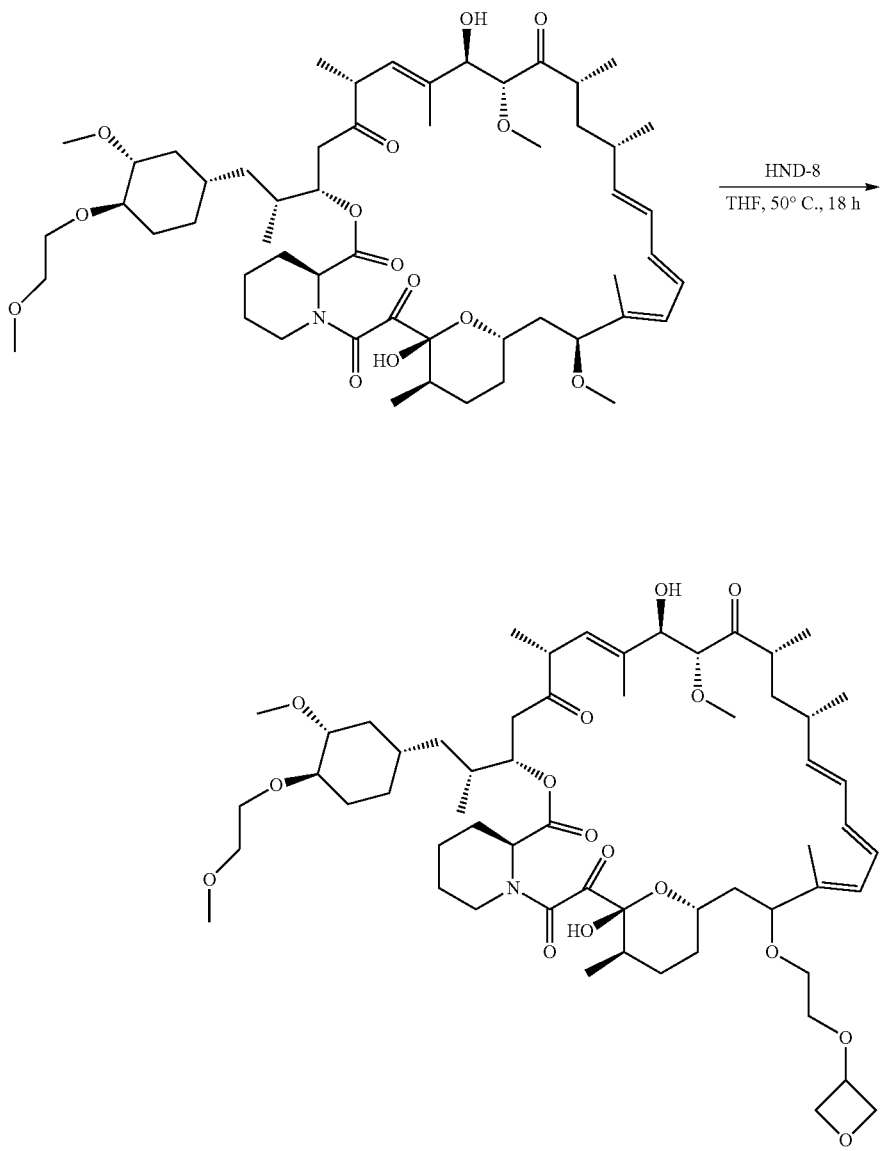

I-155

To a solution of (23E,25E,27E,28E,32R,33S,34R,35R, 37S,39S,41S,42S,43R,44R,53R)-43,53-dihydroxy-41,44-dimethoxy-42-[(1R)-2-[(1S,3R,4R)-3-methoxy-4-(2-methoxyethoxy)cyclohexyl]-1-methyl-ethyl]-32,33,34,35, 45,46-hexamethyl-62,63-dioxa-54-azatricyclohexatriaconta-23,25,27(45),28(46)-tetraene-47, 48,49,50,51-pentone (0.2 g, 0.2 mmol) and 2-(oxetan-3-yloxy)ethanol (0.8 g, 6.77 mmol) in THF (10 mL) at 50° C. under $N_2$ was added HND-8 (0.09 g). The reaction was stirred for 18 h at 50° C. then cooled, filtered, poured into saturated aqueous $NaHCO_3$ (4 mL) at 0° C. and extracted with EA (30 mL). The organic layer was washed with water (30 mL) and brine (30 mL), dried over anhydrous sodium sulfate, filtered and concentrated. The residue was purified via silica gel chromatography (EtOAc 100%) and reverse phase chromatography (eluting with 60% $CH_3CN$ in water) to provide the titled compound (0.015 g, 7% yield) as a white solid. ESI-MS (EI+, m/z): 1080.6 $[M+Na]^+$. 1H NMR (400 MHz, CDCl3) δ 6.39-5.93 (m, 4H), 5.66-4.76 (m, 5H), 4.31-3.96 (m, 2H), 3.84-3.67 (m, 9H), 3.65-3.51 (m, 4H), 3.46-3.28 (m, 12H), 3.26-2.96 (m, 5H), 2.86-2.55 (m, 3H), 2.35-2.19 (m, 2H), 2.05-1.83 (m, 4H), 1.77-1.54 (m, 24H), 1.55-1.20 (m, 11H), 1.14-0.79 (m, 18H), 0.80-0.65 (m, 1H).

Example 74: AlphaLISA Ultra pS6K1 Assay

Assay Protocol:
1. Seed MCF-7 cells in Corning 3701 plate and incubate for 20~24 hour. 12,000~16,000 cells will be seeded in 36 μL medium per well.
2. Change the culture medium with fresh medium and incubate for another 2 hours.
3. Add 12 μL (4×) compounds into the cell plate by HAMILTON. Final DMSO concentration is 0.5%. Incubate for 90 minutes.
4. Aspirate 38 μL by HAMILTON, 10 μL rest per well.
5. Add 10 μL 2× lysis buffer using HAMILTON; total volume in wells is 20 μL. Allow cells to shake for 30 min. Cover plate by plastic foil and store plate at −80° C. up to analysis.
6. Thaw cell lysate at RT and transfer 10 μL lysate to assay plate (Optiplate-384).
7. Add 5 μL acceptor beads into assay plate and incubation for 2 hours
8. Add 5 μL donor beads and incubation for 2 hours
9. Count the plate by EnSpire Multimode Plate Reader

TABLE 2

Key Reagents/Supplies

| Reagents/materials | Vendor | Cat. No. | Lot. No. |
|---|---|---|---|
| MCF-7 | ATCC | HTB-22 | 5105360 |
| DMEM | Invitrogen | 12430-054 | 1677193 |
| FBS | Invitrogen | 10099-141 | 1660516 |
| 0.25% Trypsin-EDTA | Invitrogen | 25200-072 | 1638603 |
| 384 well plate, tissue culture treated | Corning | CLS3701 | 29214010 |
| Corning 384 well storage plates | Corning | CLS3656 | 29514036 |
| Torin1 | Selleck | S2827 | 01 |
| OptiPlate-384, White Opaque 384-well MicroPlate | PerkinElmer | 6007299 | 8210-14501 |
| AlphaLISA SureFire Ultra p-p70 S6 Kinase (Thr389) Assay Kit | PerkinElmer | ALSU-PP70-A10K | U0381 |

Example 75: AlphaLISA Ultra pAKT Assay

Assay Protocol:
1. MCF-7 cells in Corning 3701 plate and incubate for 2024 hour. 16,000~20,000 cells will be seeded in 36 μL medium per well.
2. Change the culture medium with fresh medium and incubate for another 90 minutes.
3. Add 12 μL (4×) compounds into the cell plate by HAMILTON. Final DMSO concentration is 0.5%. Incubate for 2 hours.
4. Aspirate 38 μL by HAMILTON, 10 μL rest per well.
5. Add 10 μL 2× lysis buffer using HAMILTON; total volume in wells is 20 μL. Allow cells to shake for 30 min. Cover plate by plastic foil and store plate at −80° C. up to analysis.
6. Thaw cell lysate at RT and transfer 10 μL lysate to assay plate (Optiplate-384).
7. Add 5 μL acceptor beads into assay plate and incubation for 2 hours
8. Add 5 μL donor beads and incubation for 2 hours
9. Count the plate by EnSpire Multimode Plate Reader

TABLE 3

Key Reagents/Supplies

| Reagents/materials | Vendor | Cat. No. | Lot. No. |
|---|---|---|---|
| MCF-7 | ATCC | HTB-22 | 5105360 |
| DMEM | Invitrogen | 12430-054 | 1677193 |
| FBS | Invitrogen | 10099-141 | 1660516 |
| 0.25% Trypsin-EDTA | Invitrogen | 25200-072 | 1638603 |
| 384 well plate, tissue culture treated | Corning | CLS3701 | 29214010 |
| Corning 384 well storage plates | Corning | CLS3656 | 29514036 |
| Torin1 | Selleck | S2827 | 01 |
| OptiPlate-384, White Opaque 384-well MicroPlate | PerkinElmer | 6007299 | 8210-14501 |
| AlphaLISA SureFire Ultra p-Akt 1/2/3 (Ser473) Assay Kits | PerkinElmer | ALSU-PAKT-B10K | U0329 |

Example 76: Western Blot Based pS6K1 and pAKT Assay at 24 and 48 Hour Timepoints Assay Protocol:
1. Seed six well plate with 500,000 PC3 cells per well and incubate for 2024 hour.
2. Add compounds into the cell plate. Incubate for 24 to 48 hours.
4. Plate is placed on ice and the media is removed via aspiration. The wells are washed with 1 mL of 1×PBS and then fully aspirated.
5. 110 μL of 1% Triton Lysis Buffer is added and each well is scraped vigorously.
6. Cell homogenates are transferred to 1.5 mL eppendorf tubes on ice and spun down at 4° C. for 10 minutes at 10,000 rpm.
7. Protein concentration of resulting cell lysates were quantified utilizing a Bradford assay and the samples run analyzed via Western blot on 4-12% Bis/Tris gels with 1×MES buffer.
8. The gels were transferred onto membranes at 50V for 100 minutes, blocked with Odyssey Blocking buffer for 30 minutes then incubated overnight with primary antibody (pS6K1 T389 Rabbit or pAkt S473 Rabbit) overnight at 4° C. on a rotator.

9. The membranes were washed 3× with TBS-T with a 5 minute incubation between each wash then incubated with secondary antibody (LiCor IRDye 800 Donkey Anti Rabbit) for at least 30 minutes.

10. The membranes were washed 3× with TBS-T with a 5 minute incubation between each wash.

11. The gels were then incubated for 5 minutes with PBS at room temperature then imaged using a Li-Cor.

Results for a representative Western blot are summarized in FIG. 1. PC3 cells were treated with everolimus (0.1 µM, 0.01 µM, and 0.001 µM) or I-9 (1 M, 0.1 µM, 0.01 µM, and 0.001 µM) for 24 hours. Blots show a reduction in pS6K1 for both everolimus and I-9 at 24 hours, indicating inhibition of the mTORC1 pathway. Importantly, I-9 did not reduce the levels of pAkt at 24 hours. In contrast, everolimus exhibited inhibition of S6K1 phosphorylation ($S^{473}$), indicative of mTORC2 pathway inhibition.

Figure 2:
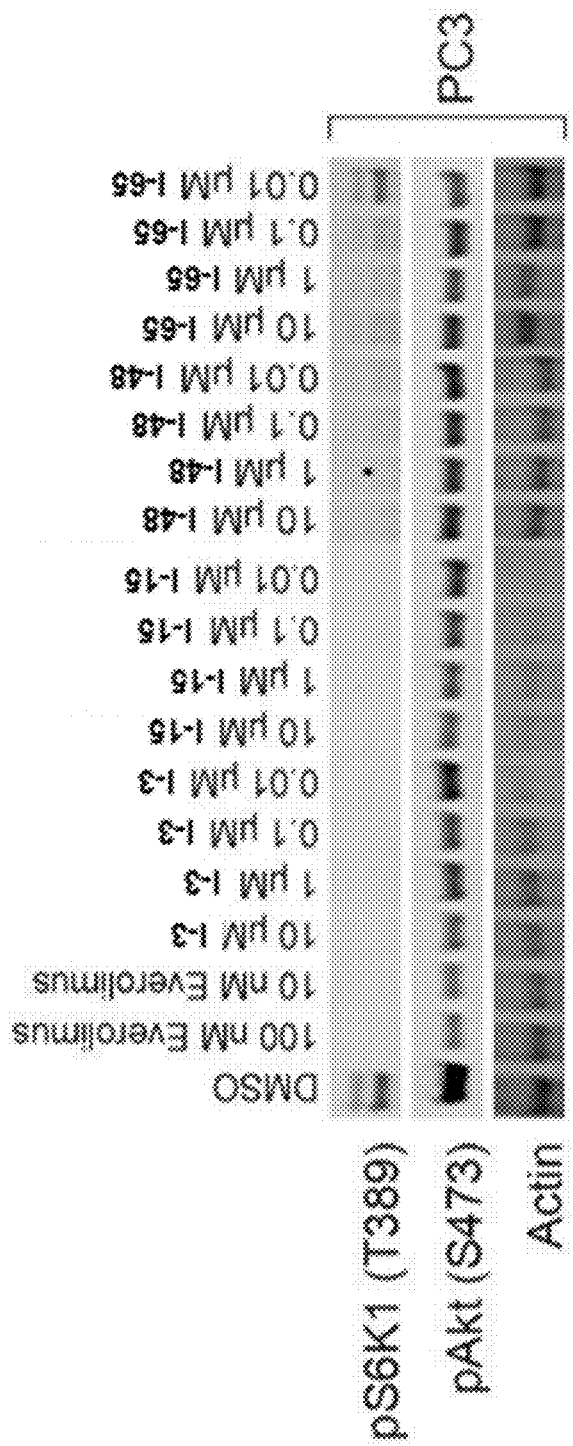
FIG. 2 shows a Western blot performed after treating PC3 cells with everolimus, or a compound of the present invention (I-3, I-15, I-48, and I-65) for 24 hours. Staining indicates strong inhibition of the mTORC1 pathway for everolimus, and strong inhibition of the mTORC1 pathway for both I-3, I-15, I-48, and I-65. Significantly, these results demonstrate that compounds of the present invention do not inhibit mTORC2, as demonstrated by the lack of Akt phosphorylation inhibition.

Results for additional representative Western blots, and the compounds evaluated therein, are summarized in FIG. 2. The methods employed were substantially similar to those described above. Compounds were evaluated in PC3 cells. Additional cell lines that may be used include Jurkat cells, wild-type mouse embryotic fibroblast (MEF) cells, tuberous sclerosis 2 (TSC2) negative (TSC−/−) MEF cells, and tuberous sclerosis 2 (TSC2) positive (TSC+/+) MEF cells. Cells are incubated with compounds of the present invention for various time periods (e.g., 5 minutes, 15 minutes, 30 minutes, 90 minutes, 24 hours, or 48 hours), and evaluated according to known methodologies, such as those herein described.

Table 4 shows the inhibitory activity ($IC_{50}$) of selected compounds of this invention in the pS6K1 and pAKT assays, and their solubility in 100 mM phosphate buffer (pH 7.4). The compound numbers correspond to the compound numbers in Table 1.

Compounds of the present invention that selectively inhibit mTORC1 over mTORC2—and retain selectivity for at least 24 hours— are indicated by "YES" in the "mTORC1 selective @ 24 hrs" column of Table 4. Compounds that are not selective at the 24 hrs mark are indicated by "NO" in the "mTORC1 selective @ 24 hrs" column of Table 4. Compounds that partially retain selectivity for mTORC1 inhibition over mTORC2 are indicated by "Partial" in the "mTORC1 selective @ 24 hrs" column of Table 4.

Compounds denoted "A" exhibited an $IC_{50}$ lower than 0.1 nM (x<0.1 nM). Compounds denoted "B" exhibited an $IC_{50}$ greater than or equal to 0.1 nM and less than 1 nM (0.1 nM≤x<1.0 nM). Compounds denoted "C" exhibited an $IC_{50}$ greater than or equal to 1.0 nM and less than 10 nM (1.0 nM≤x<10 nM). Compounds denoted "D" exhibited an $IC_{50}$ greater than or equal to 10 nM and less than 100 nM (10 nM≤x<100 nM). Compounds denoted "E" exhibited an $IC_{50}$ greater than or equal to 100 nM (100 nM≤x).

TABLE 4

Assay Data for Exemplary Compounds

| I-# | pS6K1 in MCF7 @ 90 min ($IC_{50}$) | mTORC1 selective @ 24 hrs |
|---|---|---|
| I-5 | A | — |
| I-6 | C | — |
| I-7 | C | Yes |
| I-8 | C | — |
| I-9 | B | Yes |
| I-10 | C | — |
| I-11 | A | — |
| I-12 | B | — |
| I-13 | C | — |
| I-14 | B | — |
| I-24 | C | — |
| I-25 | B | — |
| I-26 | B | — |
| I-27 | D | — |
| I-28 | D | — |
| I-30 | E | — |
| I-31 | C | — |
| I-32 | C | — |
| I-33 | C | — |
| I-34 | B | — |
| I-35 | B | Yes |
| I-36 | B | Yes |
| I-37 | E | — |
| I-38 | D | — |

We claim:

1. A compound of Formula I:

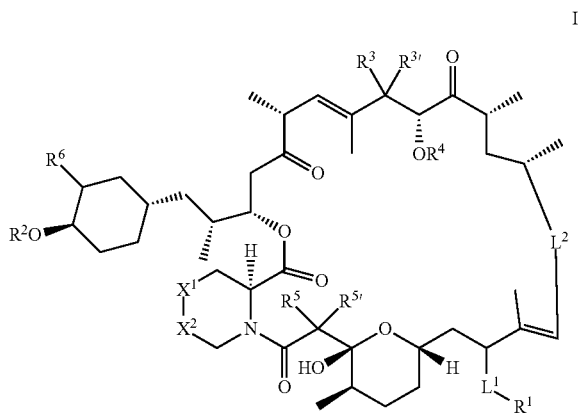

I or a pharmaceutically acceptable salt thereof, wherein:

$L^1$ is a covalent bond, or a $C_{1-30}$ bivalent straight or branched saturated or unsaturated hydrocarbon chain, wherein 1-10 methylene units of the chain are independently and optionally replaced with -Cy$_1$-, —O—, —S—, —S(O)$_2$—, —C(O)—, —CF$_2$—, —Si(R)$_2$—, or —NR—;

each -Cy$_1$- is independently an optionally substituted bivalent ring selected from phenylene, 4-7 membered saturated or partially unsaturated heterocyclylene having 1-2 heteroatoms independently selected from nitrogen, oxygen, and sulfur, or 5-6 membered heteroarylene having 1-4 heteroatoms independently selected from nitrogen, oxygen, and sulfur;

each R is independently hydrogen or optionally substituted $C_{1-6}$ aliphatic;

$L^2$ is

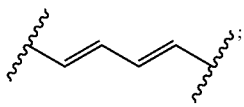

$R^1$ is hydrogen, halogen, —OR, —CN, —NO₂, —NR₂, or an optionally substituted group selected from a $C_{1-6}$ aliphatic, a 3-8 membered saturated or partially unsaturated monocyclic carbocyclic ring, a phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 7-10 membered saturated or partially unsaturated bicyclic heterocyclic ring having 1-3 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur, wherein -L¹-R¹ taken together do not form —OMe;

$R^2$ is methyl,

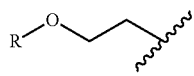

or

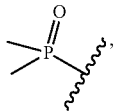

$R^3$ is —OH or —OMe;
$R^{3'}$ is hydrogen;
$R^4$ is hydrogen or $C_{1-6}$ aliphatic;
$R^5$ and $R^{5'}$ are taken together to form =O;
$R^6$ is —OMe; and
$X^1$ and $X^2$ are each —CH₂—.

2. The compound of claim 1, wherein said compound is selected from any one of the following formulae:

I-y-4

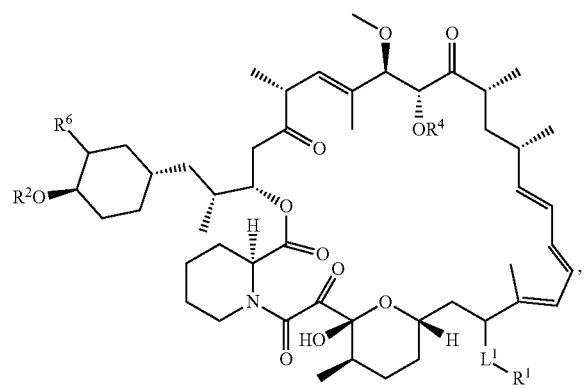

I-y-5

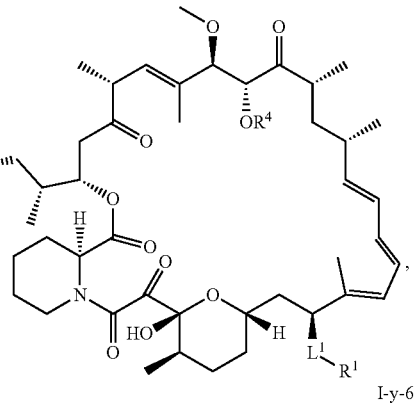

I-y-6

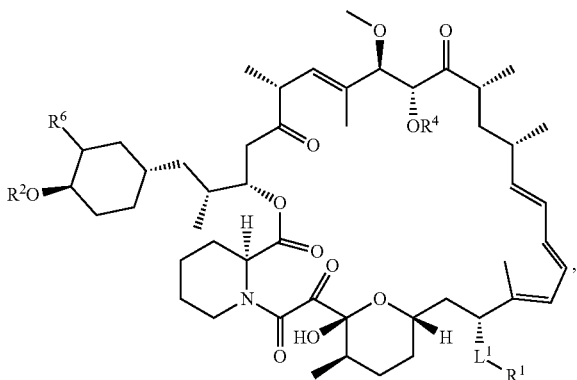

I-z-4

I-z-5

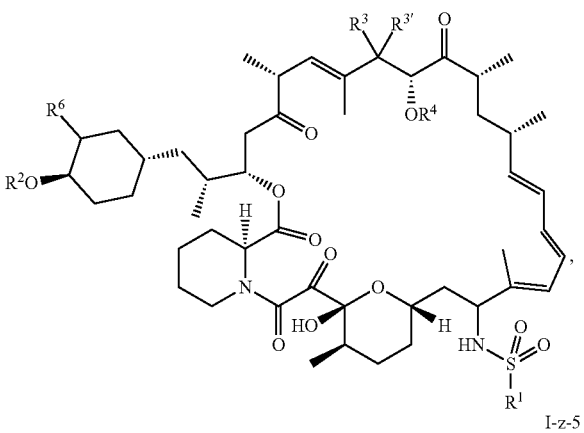

-continued

I-z-6

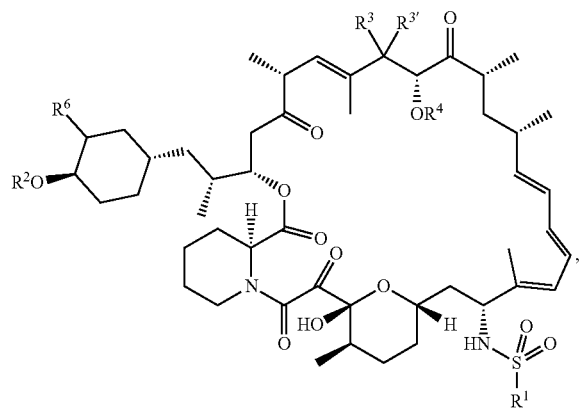

or a pharmaceutically acceptable salt thereof.

3. The compound of claim 1, wherein $L^1$ is a $C_{1-30}$ bivalent straight or branched saturated or unsaturated hydrocarbon chain wherein 1-10 methylene units of the chain are independently and optionally replaced with -Cy$_1$-, —O—, —S—, —S(O)$_2$—, —C(O)—, —CF$_2$—, —Si(R)$_2$—, or —NR—.

4. The compound of claim 1, wherein $L^1$ is selected from —O—, —NH—, —O—CH$_2$—, —O—(CH$_2$)$_2$—, —O—(CH$_2$)$_3$—, —O—(CH$_2$)$_4$—, —O—(CH$_2$)$_5$—, —O—(CH$_2$)$_2$—O—, —O—(CH$_2$)$_2$—O—(CH$_2$)$_2$—, —NH—CH$_2$—, —NH—C(O)—, —NH—C(O)O—, —NH—SO$_2$—, —NH—SO$_2$—(CH$_2$)$_2$—, —NH—SO$_2$—(CH$_2$)$_2$—O—(CH$_2$)$_2$—, —O—(CH$_2$)$_2$—SO$_2$—(CH$_2$)$_2$—, —O—(CH$_2$)$_2$—SO$_2$—(CH$_2$)$_2$—SO$_2$—, —O—(CH$_2$)$_2$—O—(CH$_2$)$_2$—O—(CH$_2$)$_2$—, and

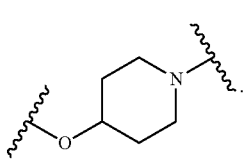 [SMILES: *OC1CCN(*)CC1]

5. The compound of claim 1, wherein $L^1$ is a covalent bond.

6. The compound of claim 1, wherein each R is independently hydrogen or $C_{1-6}$ aliphatic.

7. The compound of claim 1, wherein $R^1$ is selected from hydrogen, halogen, —OR, —CN, —NO$_2$, or an optionally substituted group selected from a $C_{1-6}$ aliphatic, a 3-8 membered saturated or partially unsaturated monocyclic carbocyclic ring, a phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur.

8. The compound of claim 1, wherein $R^1$ is selected from hydrogen, halogen, —OR, and —NR$_2$.

9. The compound of claim 1, wherein $R^1$ is an optionally substituted group selected from: a $C_{1-6}$ aliphatic, a 3-8 membered saturated or partially unsaturated monocyclic carbocyclic ring, a phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfurs, and an 8-10 membered bicyclic heteroaromatic ring having 1-5 heteroatoms independently selected from nitrogen, oxygen, and sulfur.

10. The compound of claim 1, wherein $R^1$ is selected from —OMe, —(CH$_2$)$_2$—OH, —(CH$_2$)$_2$—OMe, —SO$_2$—NH$_2$, —C(O)NH$_2$, —C(O)NMe$_2$, —OC(O)NHMe, —CO$_2$H,

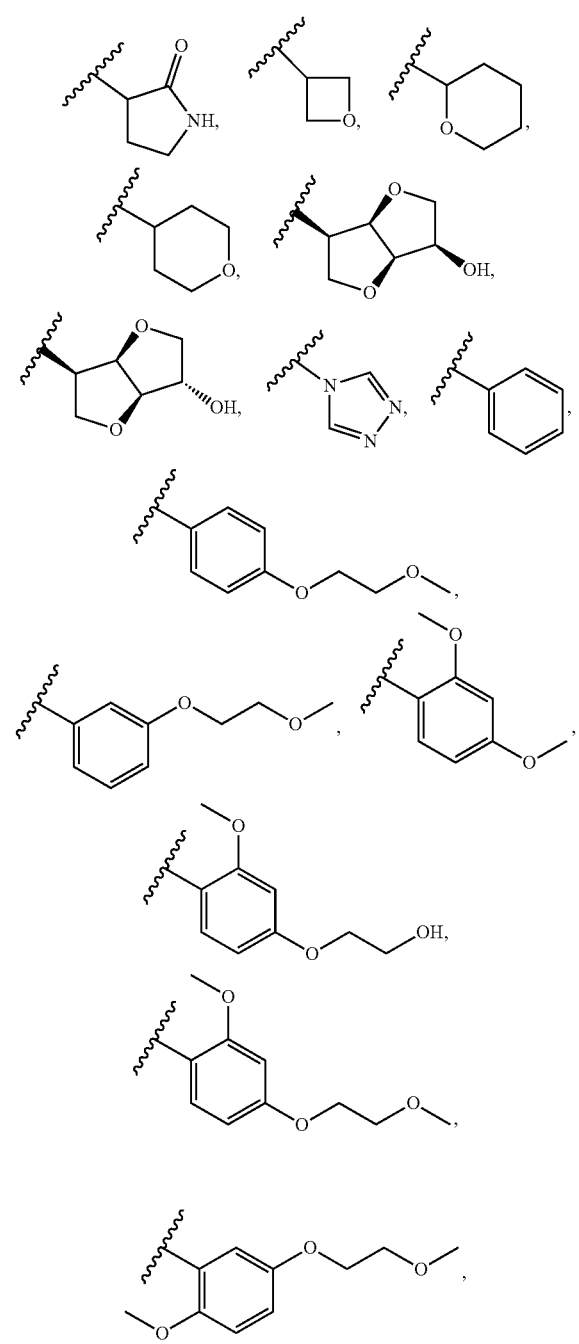

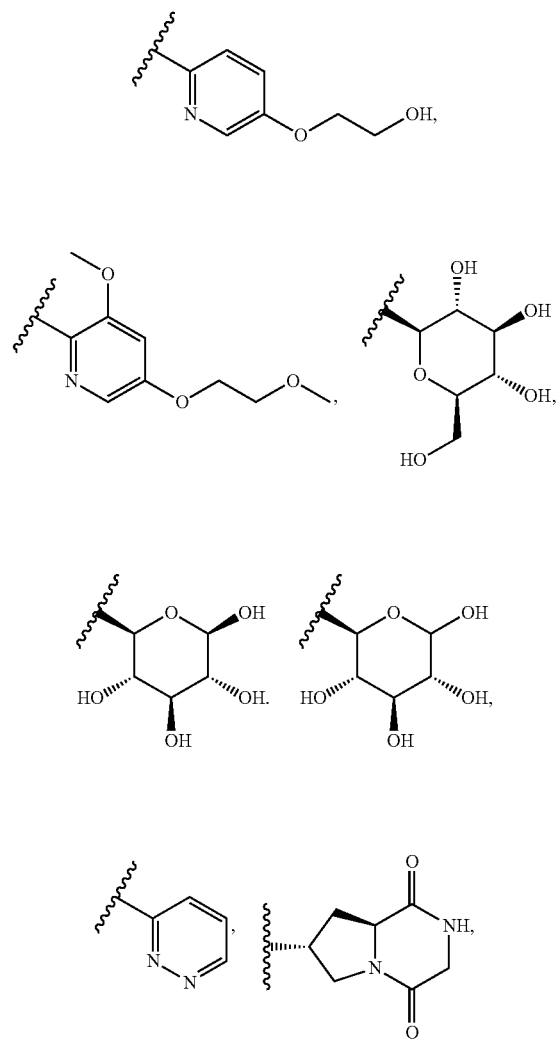
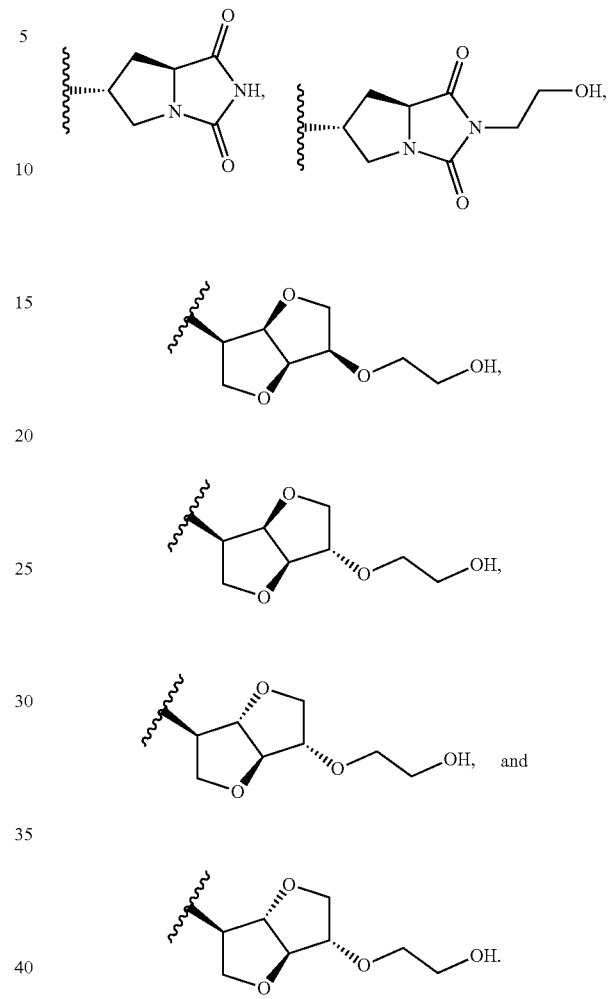
11. The compound of claim 1, wherein said compound is selected any one of the following:
I-2
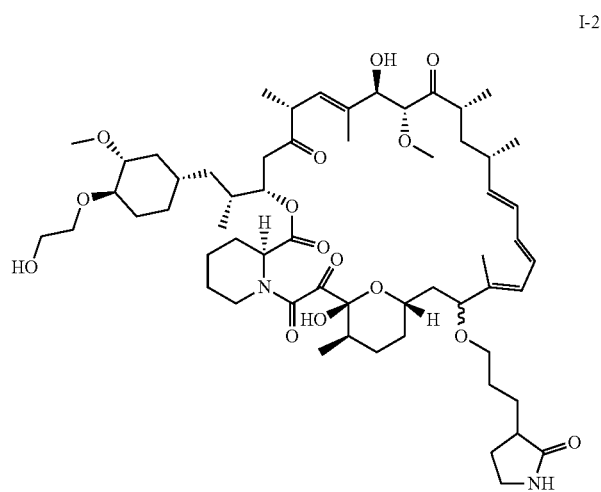

I-3
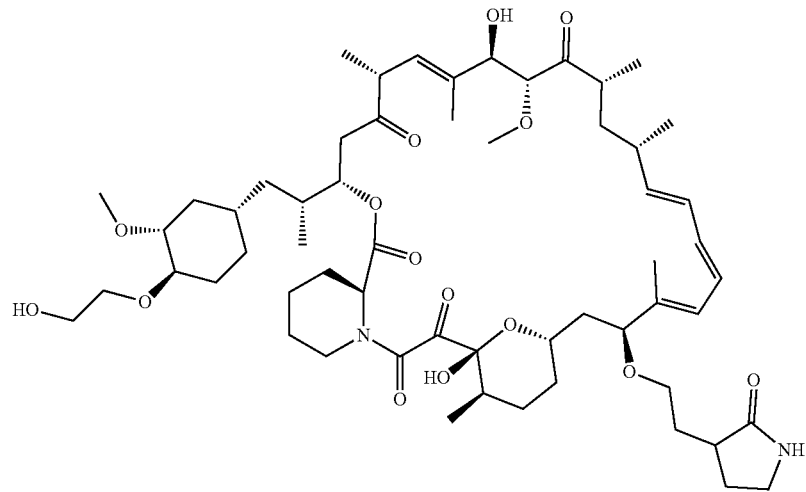
I-6
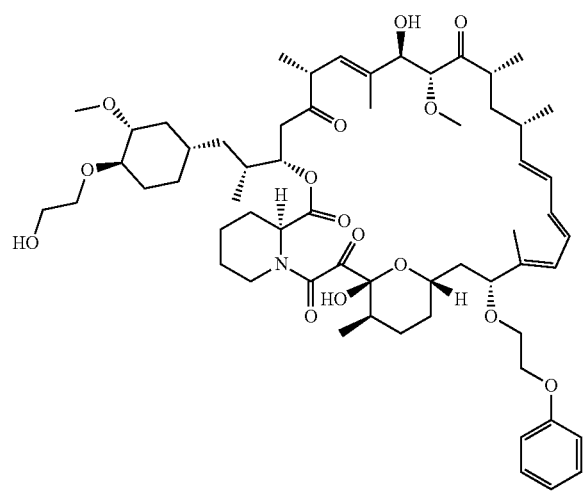
I-7
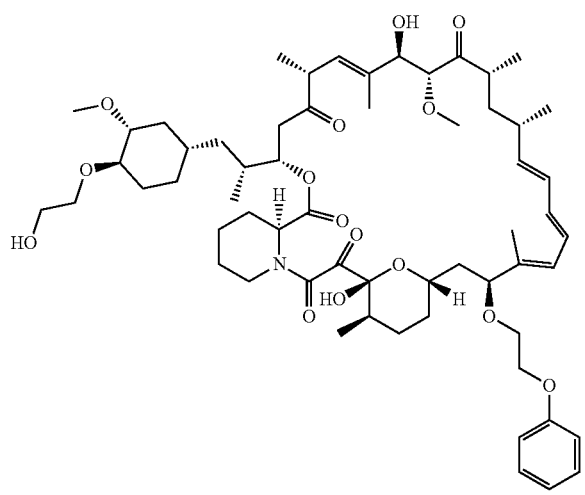
I-8
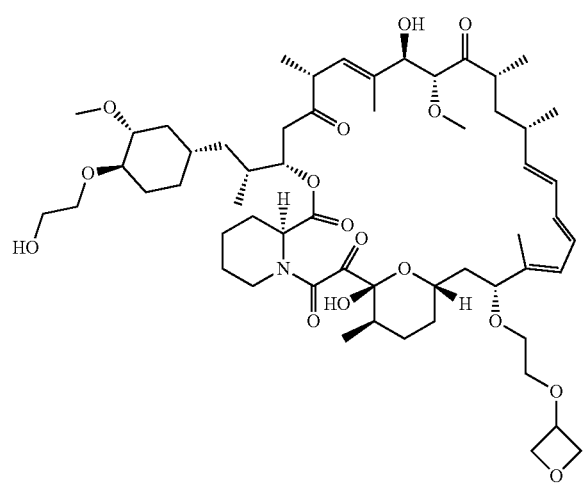
I-9
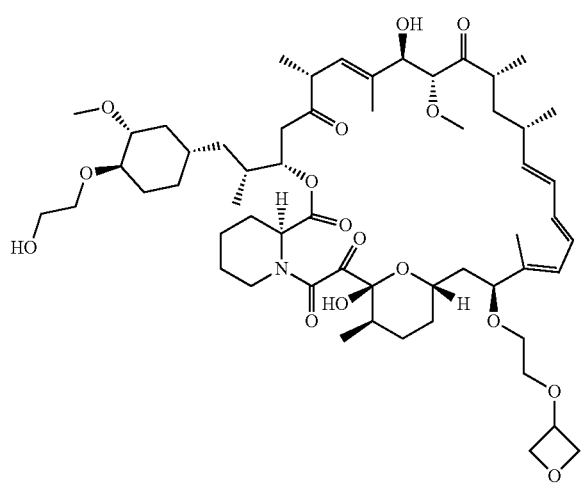

-continued
I-10
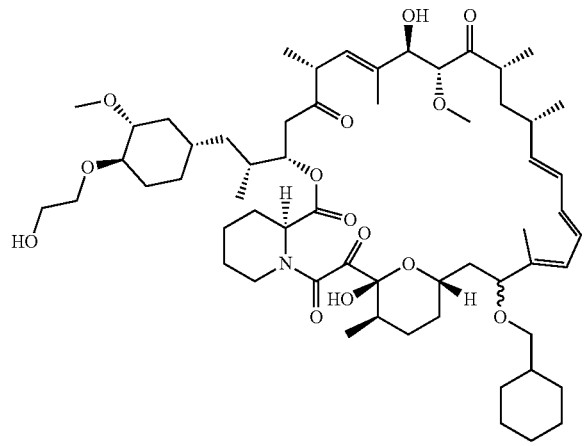
I-11
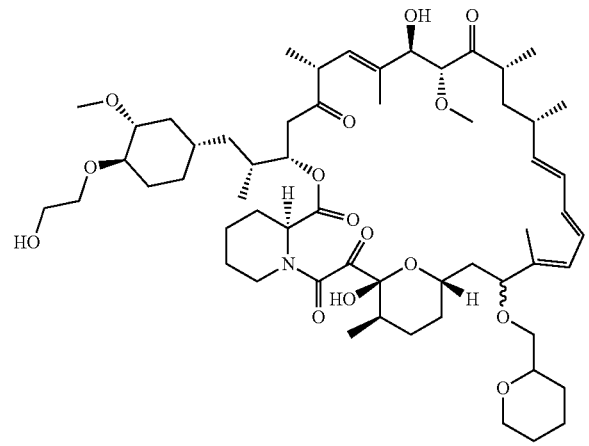
I-12
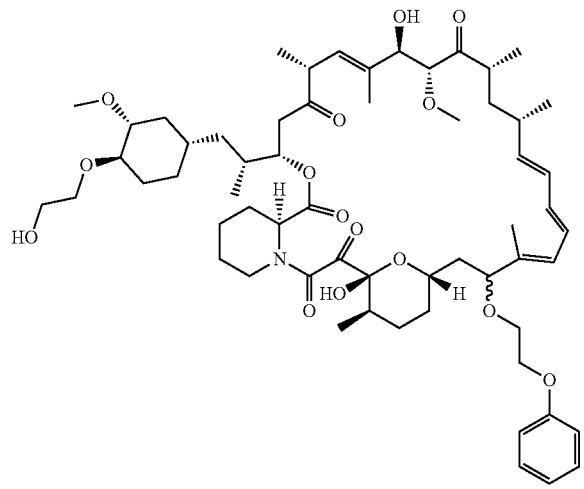
I-13
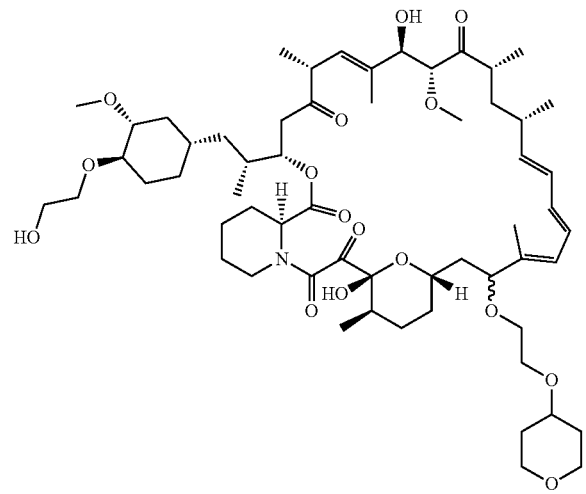
I-14
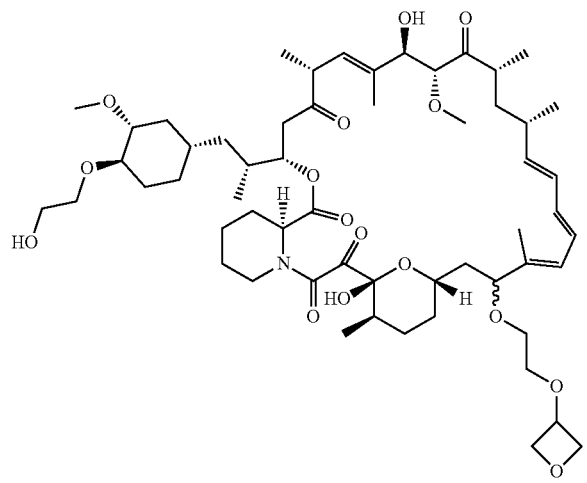
I-15
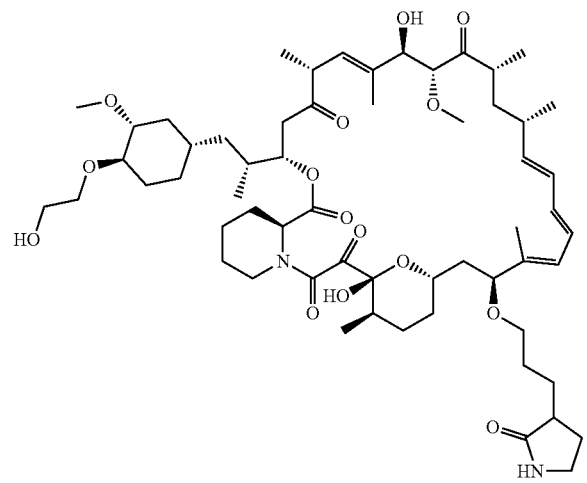

I-19
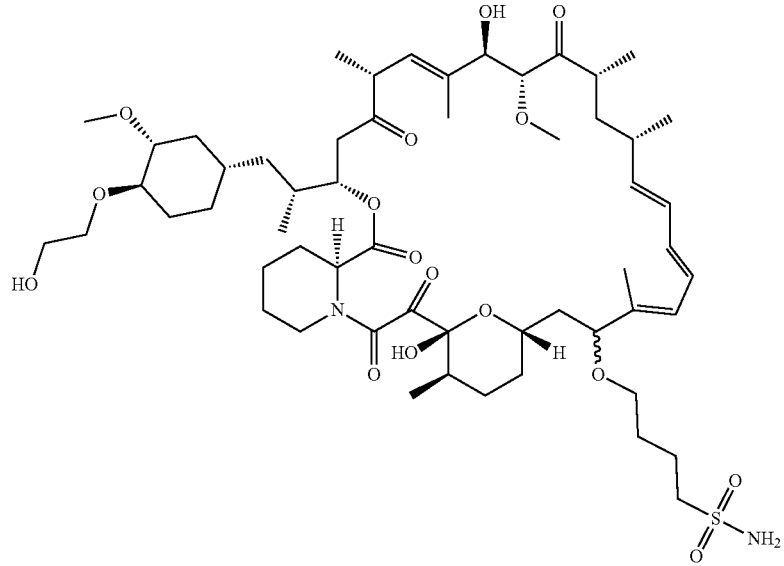
I-25
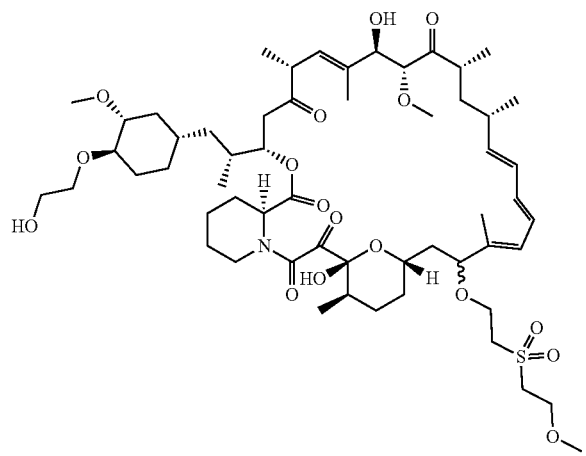
I-28
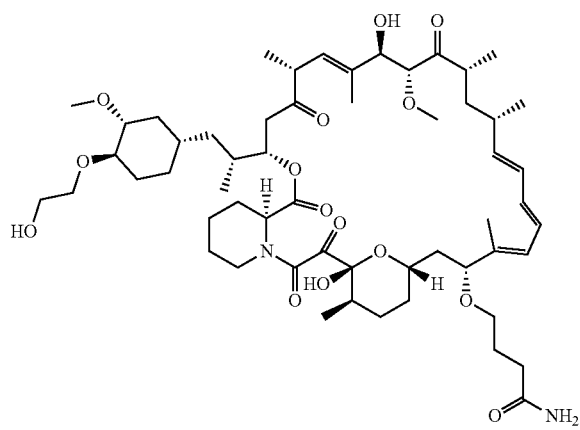
I-29
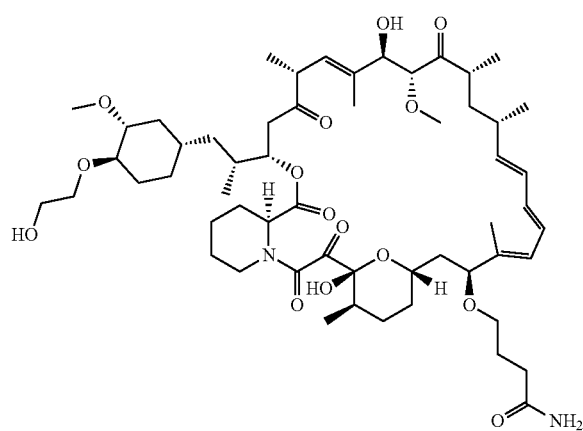
I-30
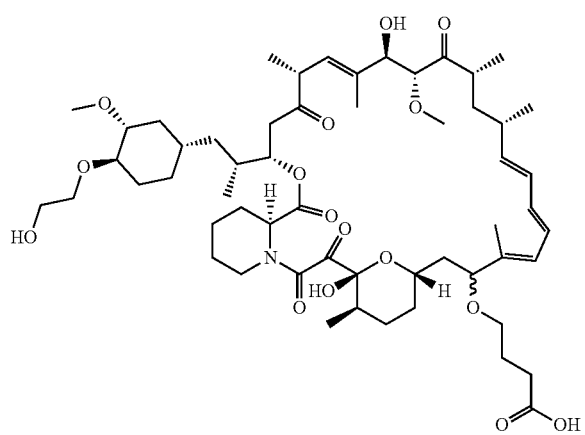

I-39
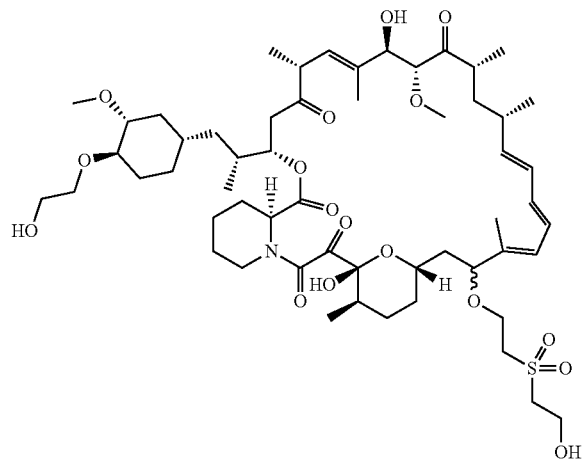
I-45
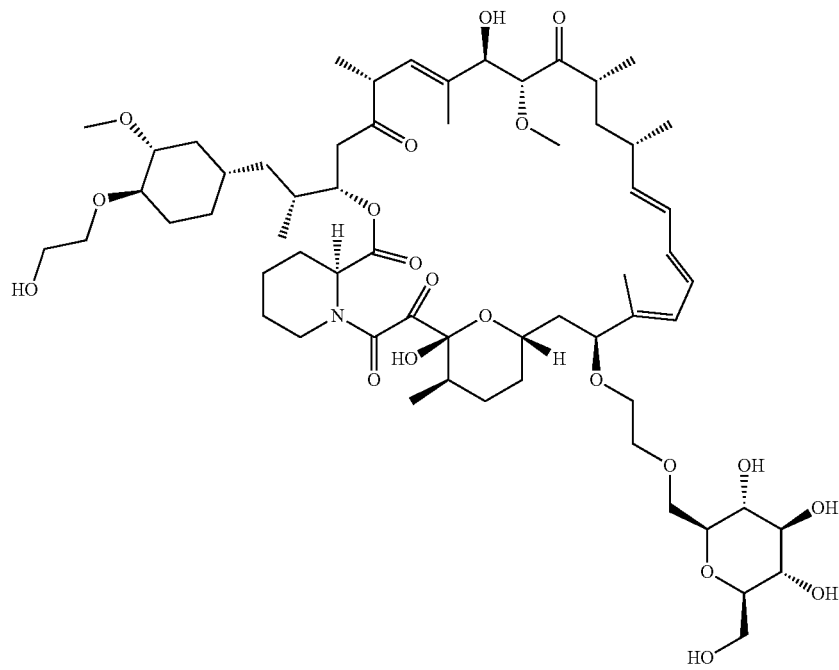
I-46
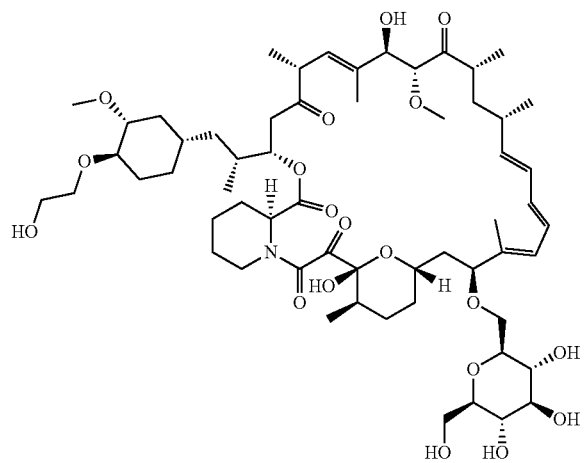
I-47
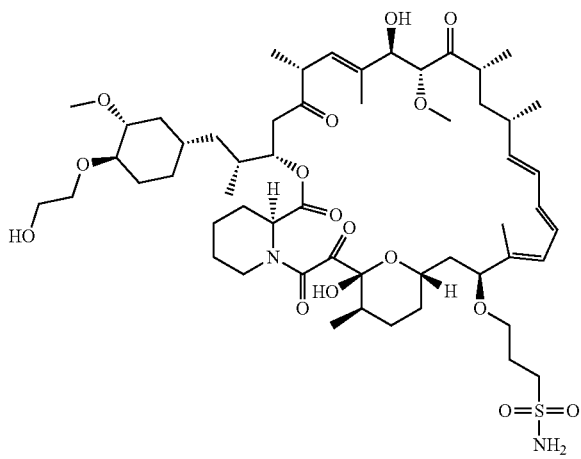

I-48
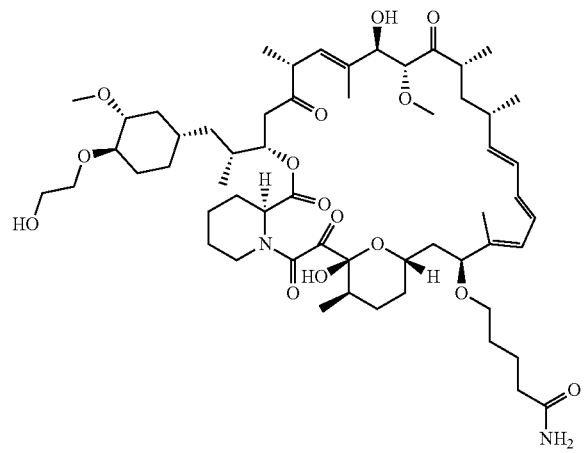
I-63
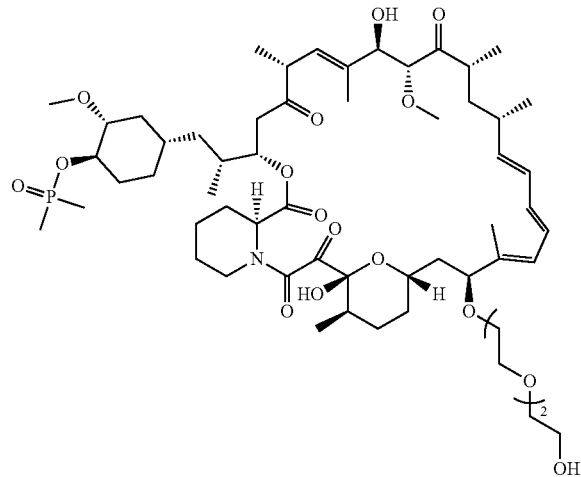
I-64
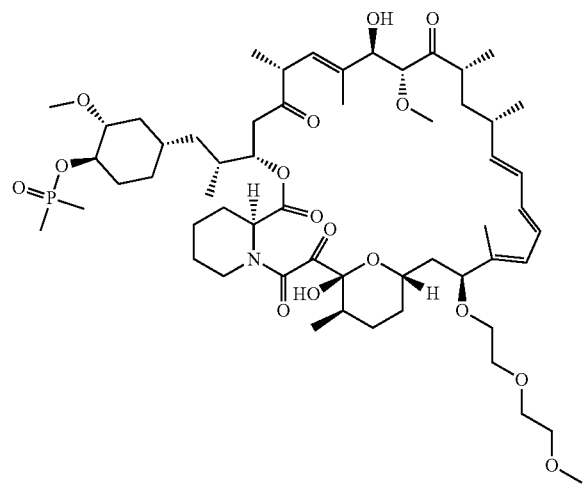
I-69
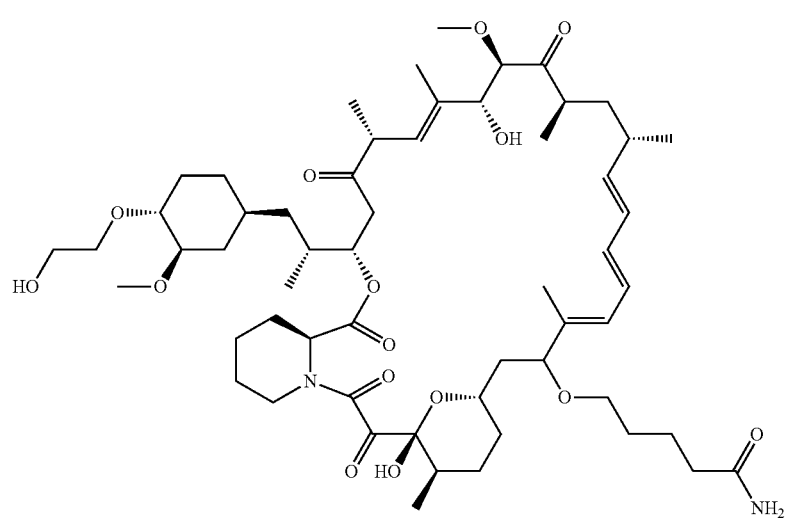

I-78
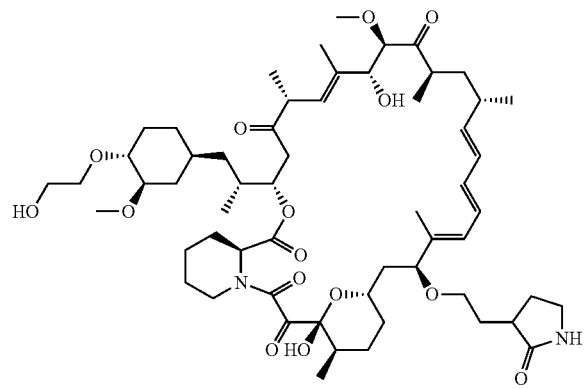
I-79
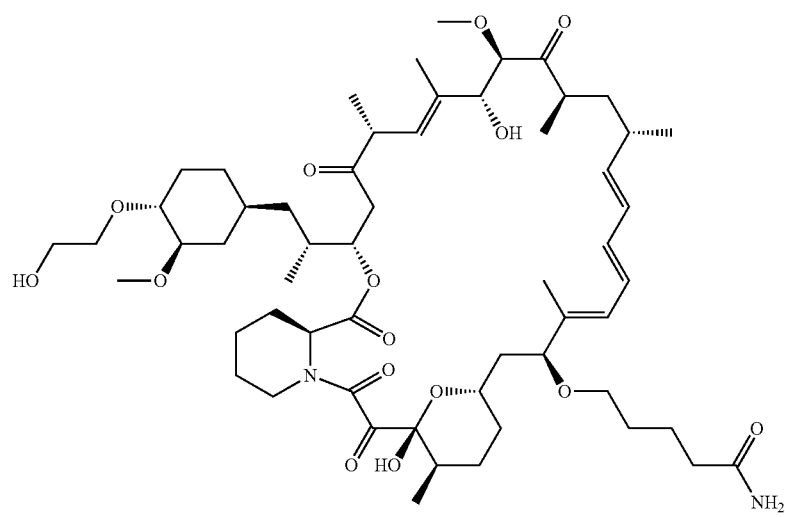
I-80
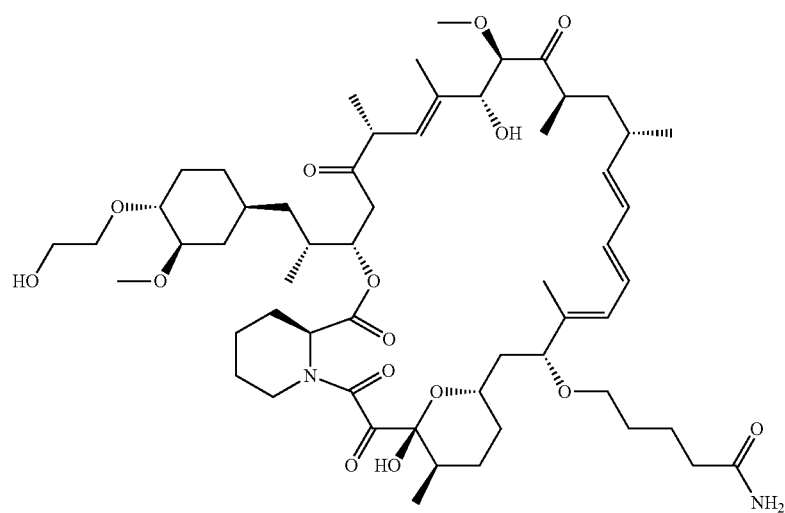

I-92
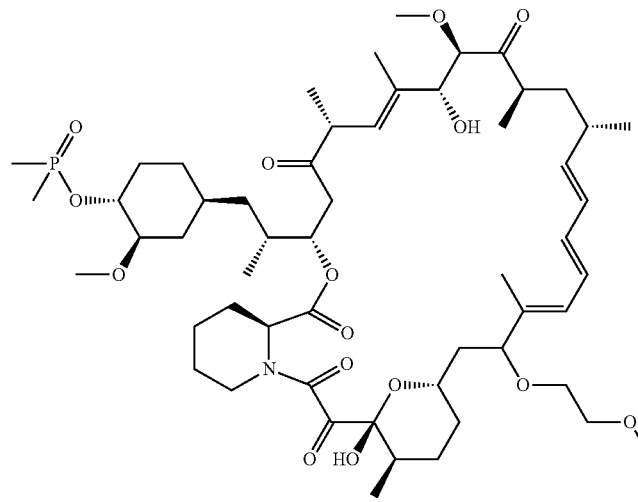
I-99
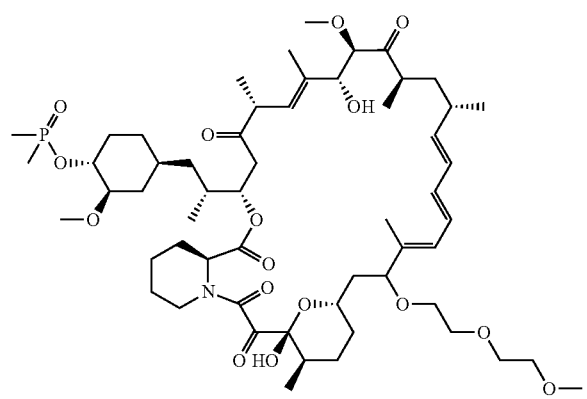
I-116
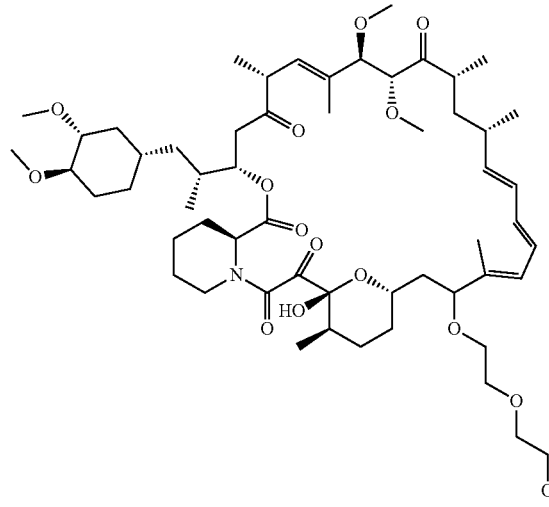
I-118
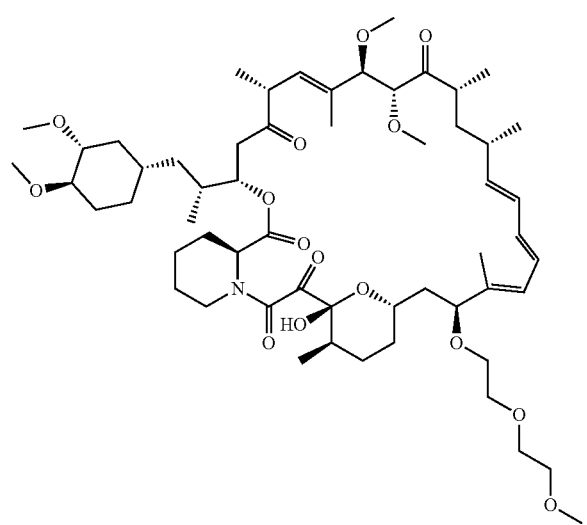
I-119
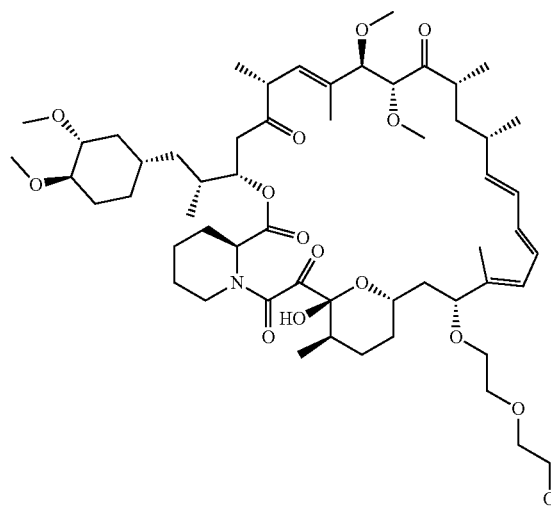

-continued
I-120
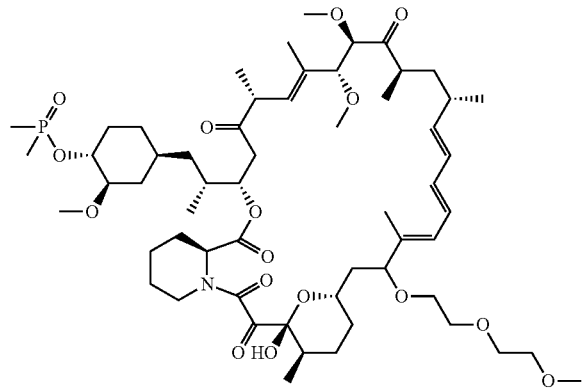
I-125
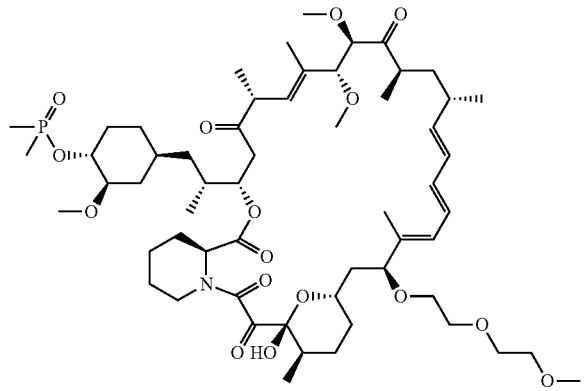
I-126
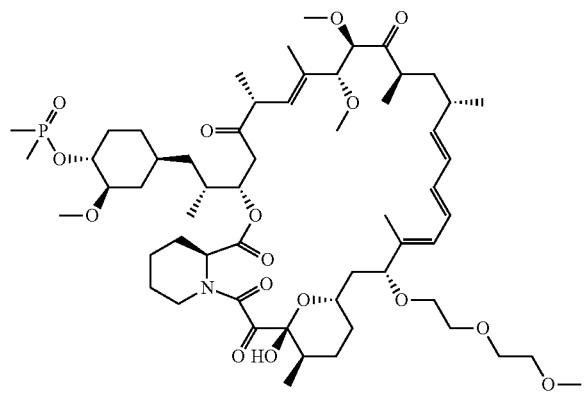
I-127
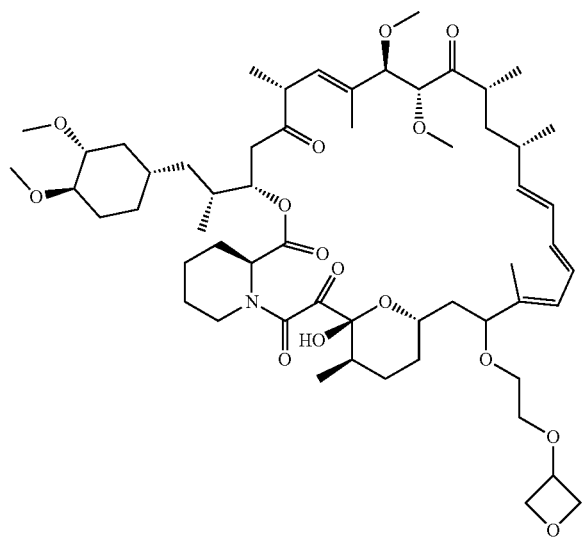
I-128
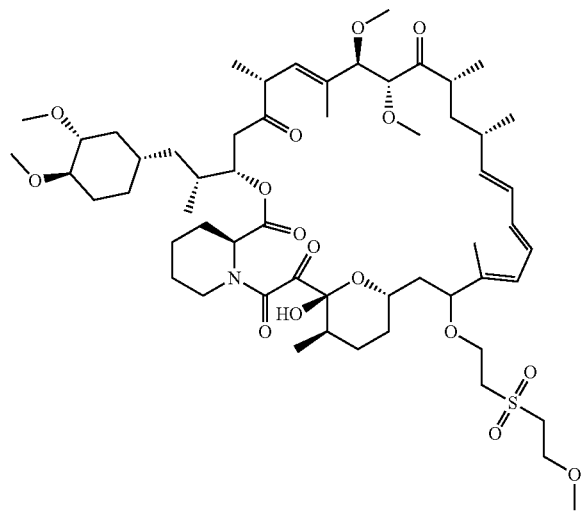
I-129
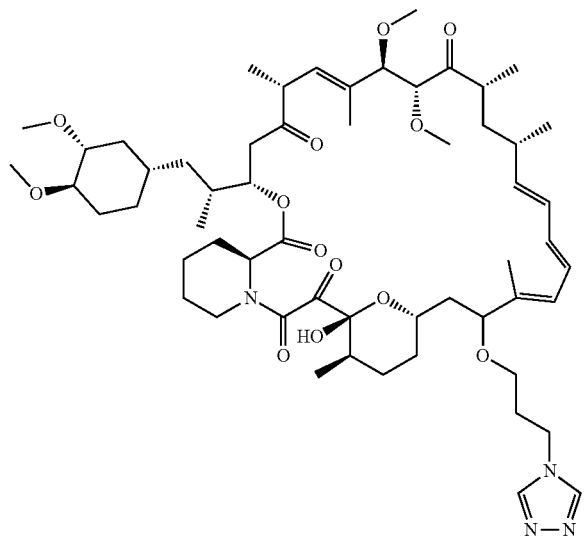

I-130
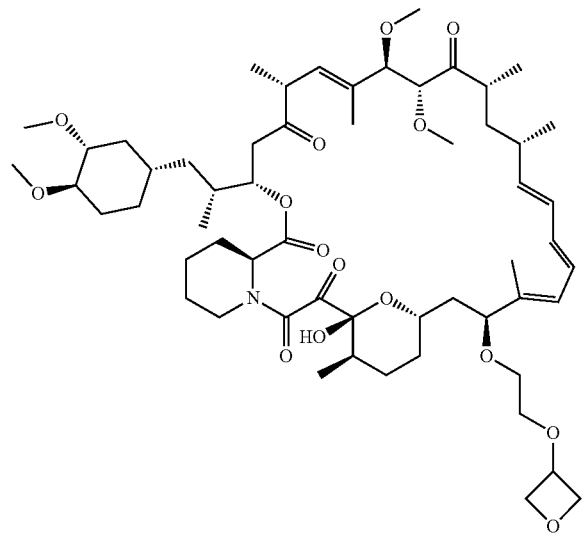
I-131
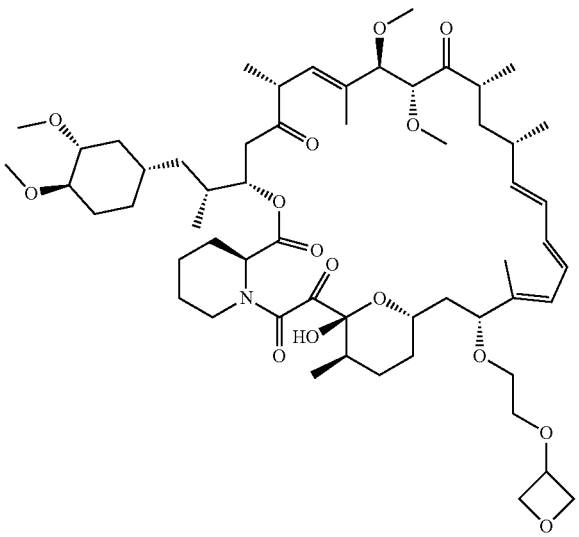
I-132
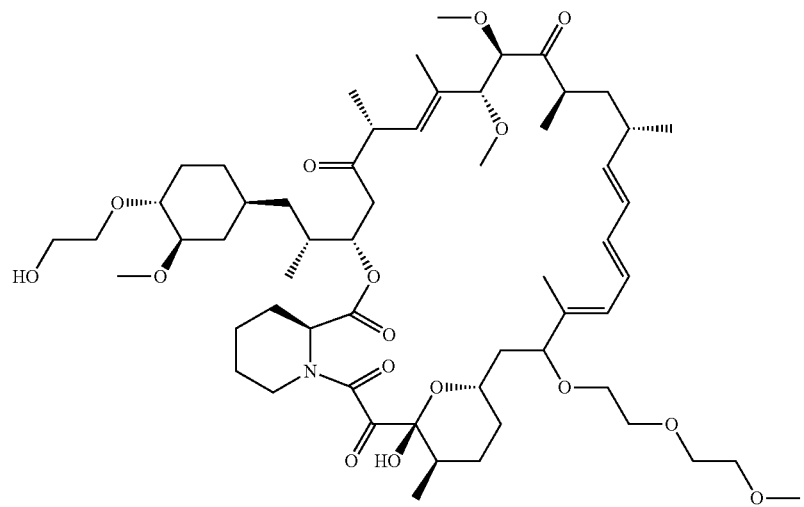
I-133
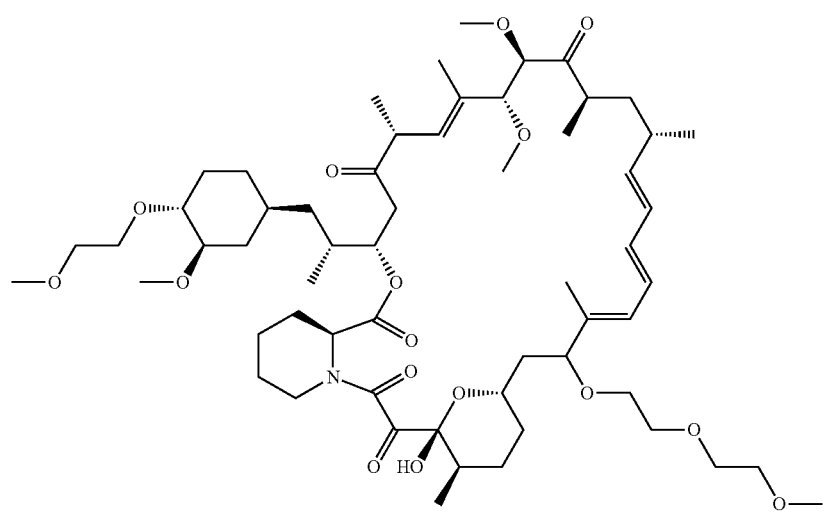

-continued
I-134
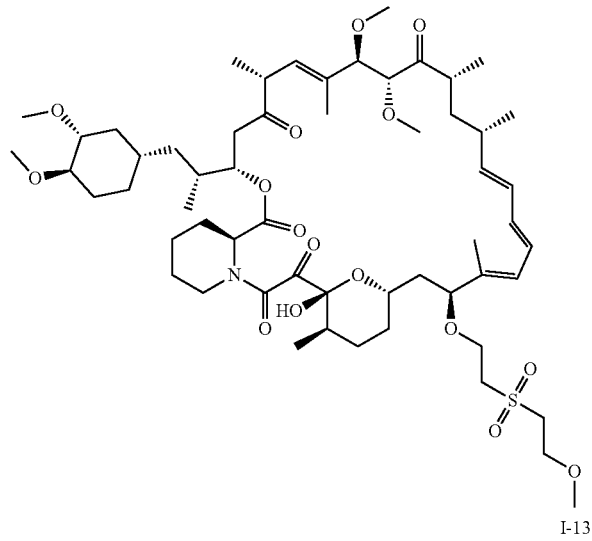
I-135
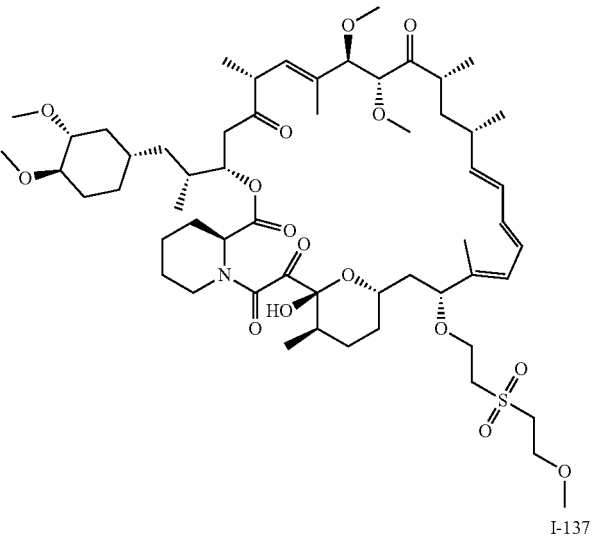
I-136
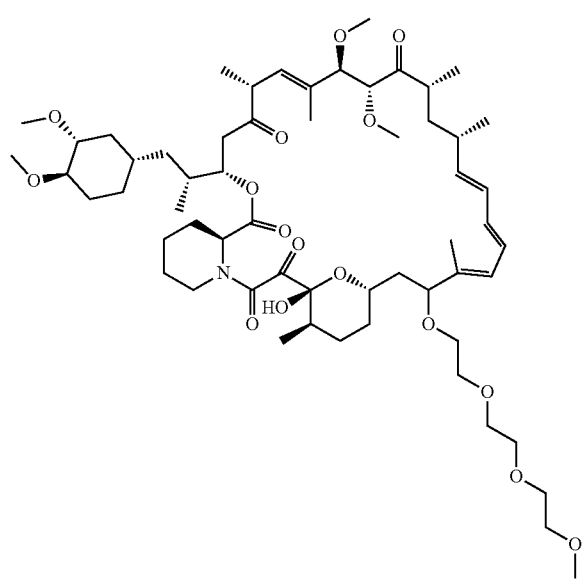
I-137
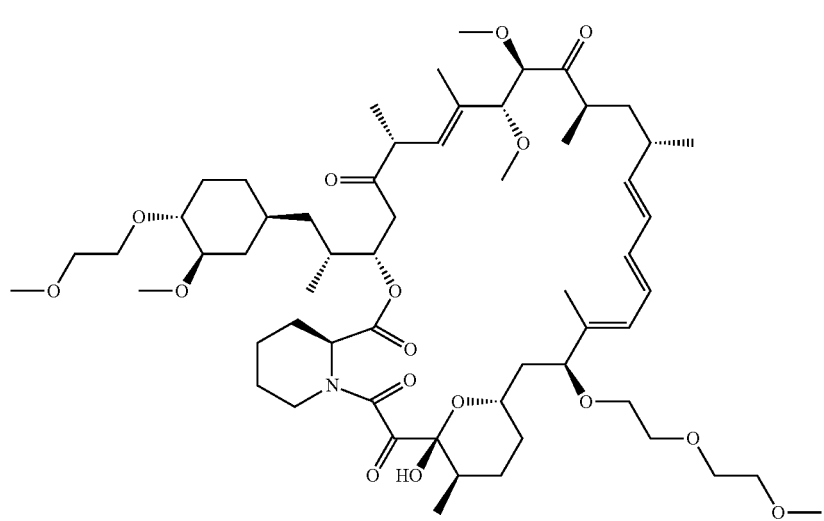
I-138

I-139
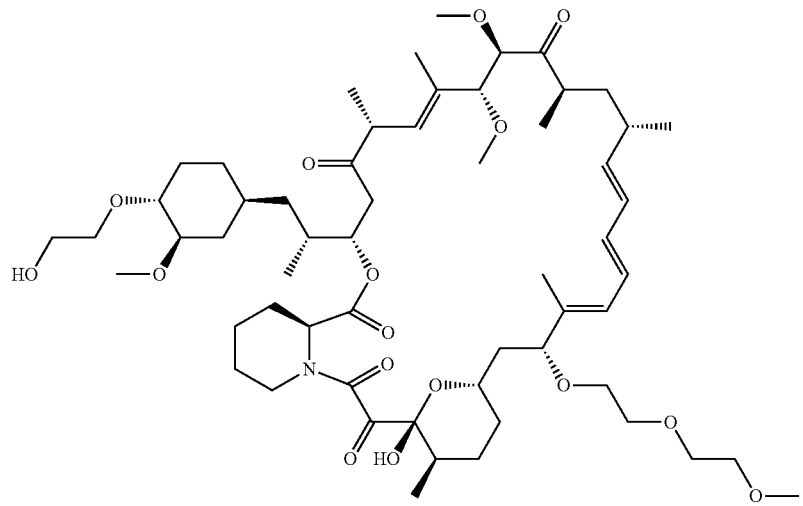
I-140 I-141
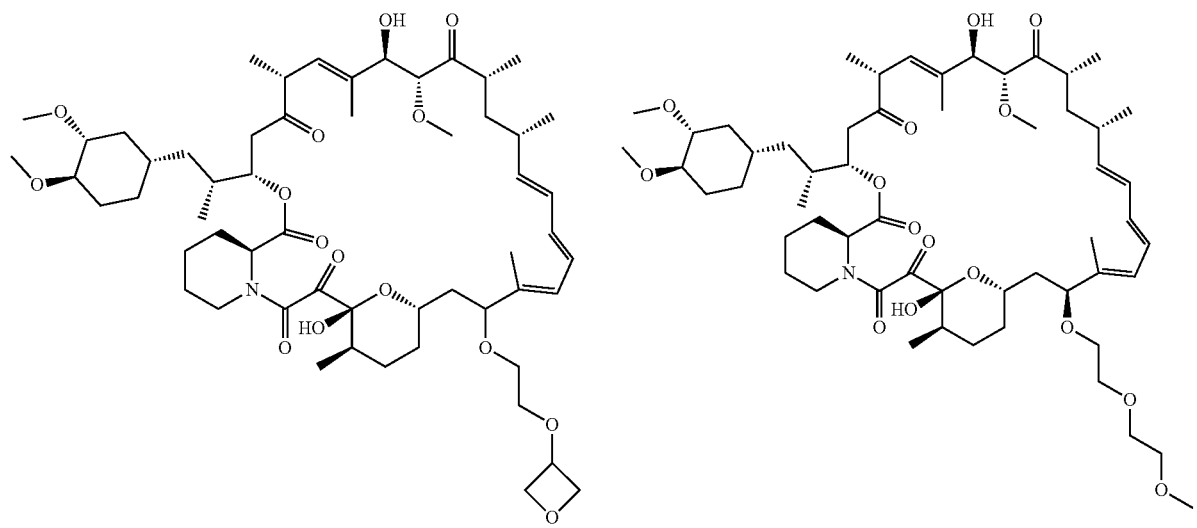
I-142 I-145
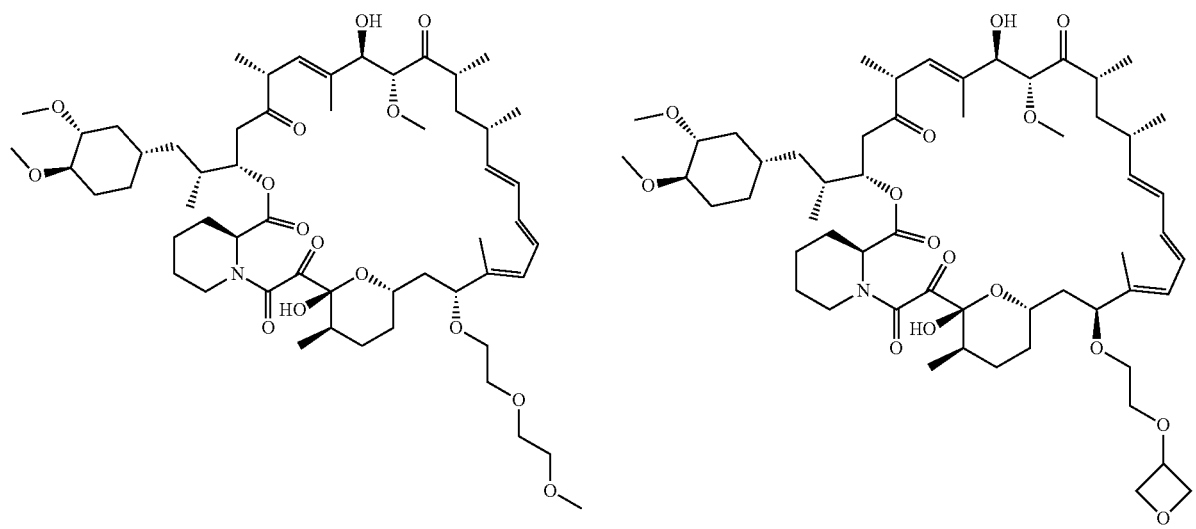

I-146
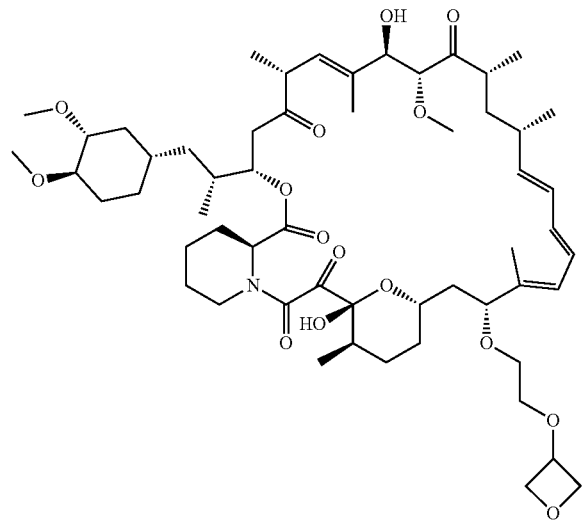
I-147
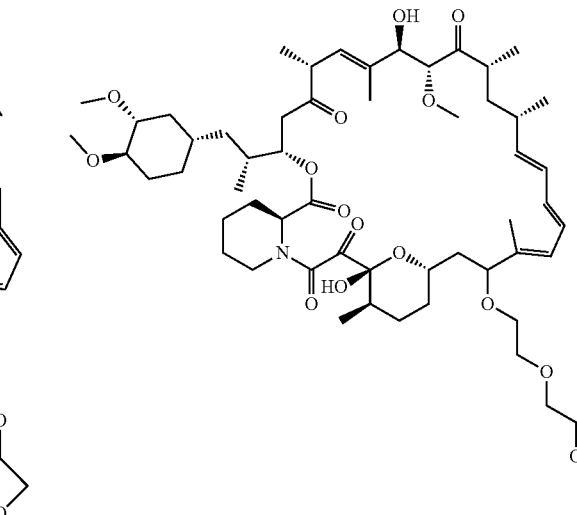
I-149
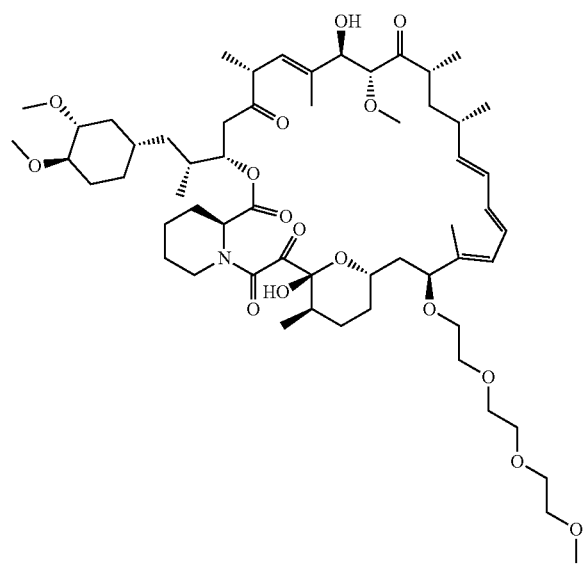
I-150
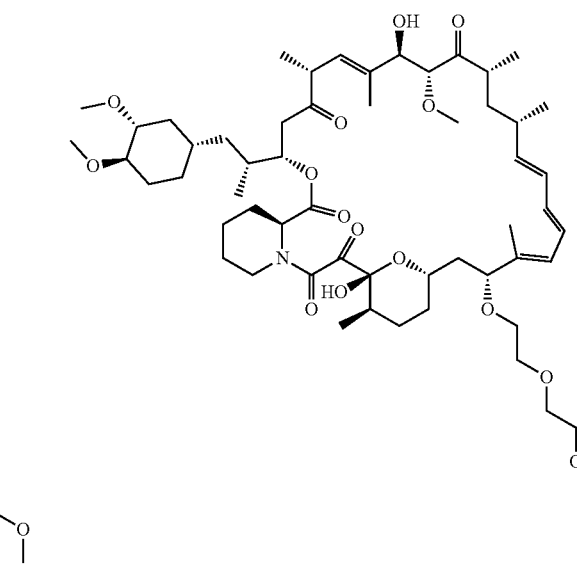
I-151
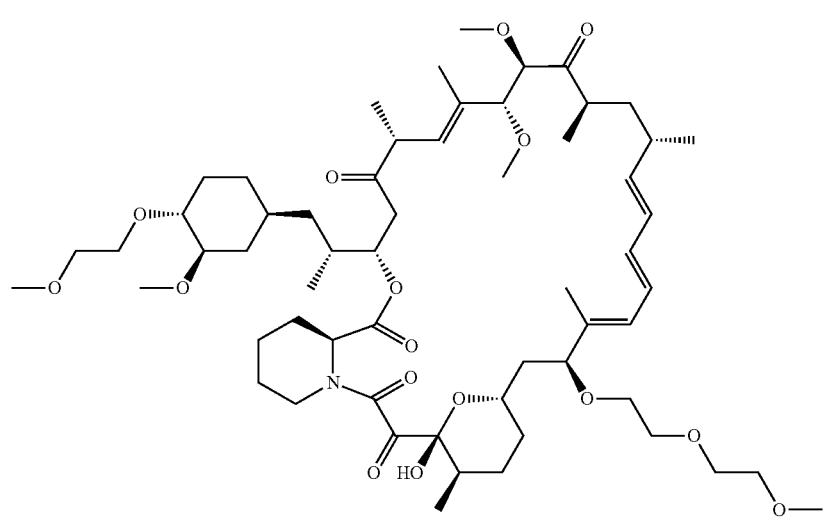

I-152
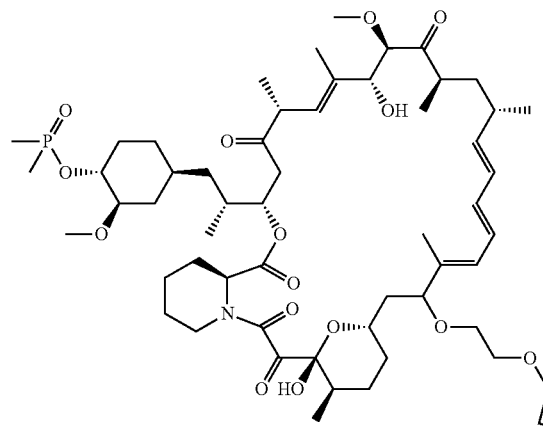
I-153
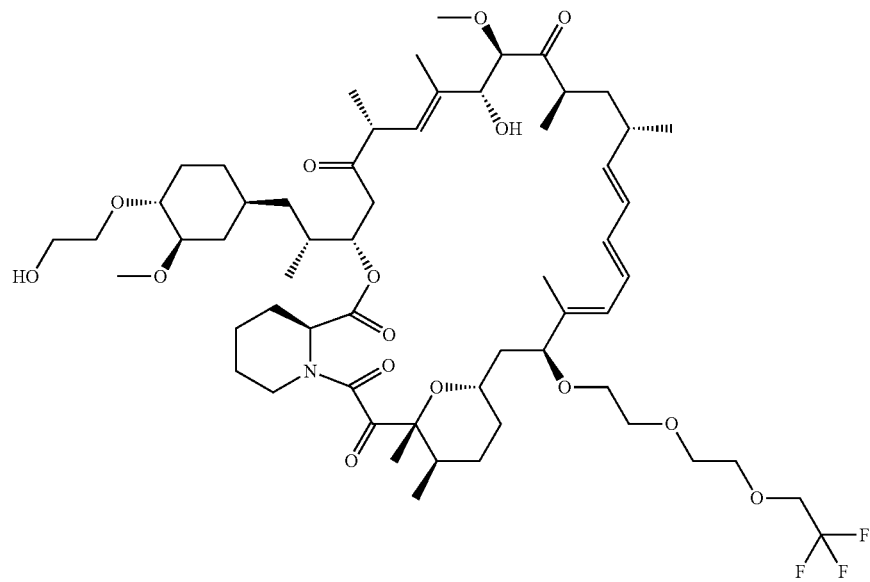
I-154
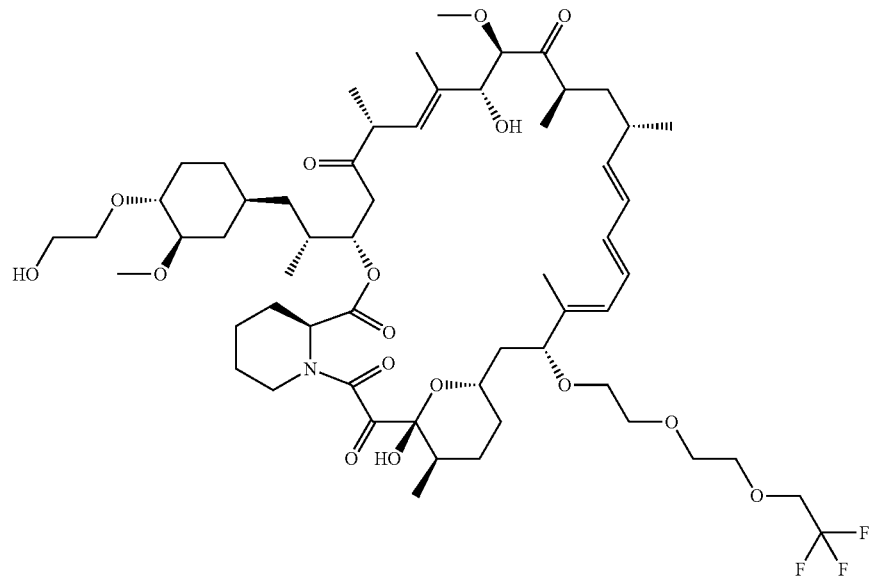

-continued
I-155
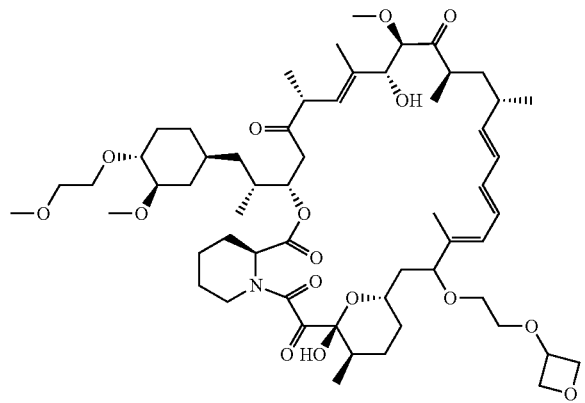
I-157
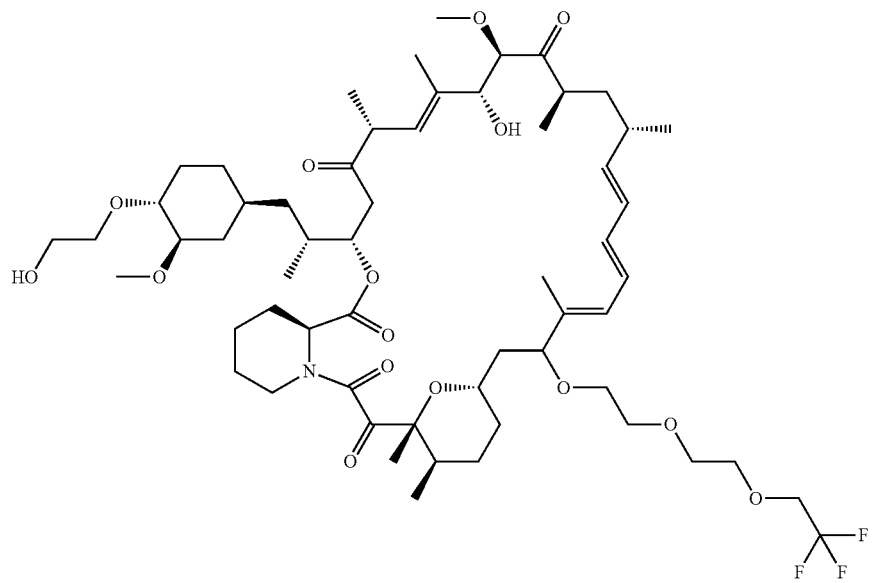
or a pharmaceutically acceptable salt thereof.
12. A pharmaceutically acceptable composition comprising a compound of claim 1, and a pharmaceutically acceptable carrier, adjuvant, or vehicle.
* * * * *